US009175003B2

(12) United States Patent
Mjalli et al.

(10) Patent No.: US 9,175,003 B2
(45) Date of Patent: Nov. 3, 2015

(54) SUBSTITUTED AZOANTHRACENE DERIVATIVES AND INTERMEDIATES FOR PREPARATION THEREOF

(71) Applicant: TransTech Pharma, LLC, High Point, NC (US)

(72) Inventors: Adnan M. M. Mjalli, Oak Ridge, NC (US); Christopher Behme, Jamestown, NC (US); Daniel P. Christen, Jamestown, NC (US); Devi Reddy Gohimukkula, Jamestown, NC (US); Dharma Rao Polisetti, High Point, NC (US); James C. Quada, Jr., Hight Point, NC (US); Jennifer L. R. Freeman, Winston-Salem, NC (US); Muralidhar Bondlela, Greensboro, NC (US); Mustafa Guzel, Jamestown, NC (US); Ravindra Reddy Yarragunta, Greensboro, NC (US); Robert Carl Andrews, Jamestown, NC (US); Santhosh Kalpathy, Jamestown, NC (US); Stephen Thomas Davis, Durham, NC (US); Thomas Scott Yokum, Greensboro, NC (US)

(73) Assignee: vTv Therapeutics LLC, High Point, NC (US)

( * ) Notice: Subject to any disclaimer, the term of this patent is extended or adjusted under 35 U.S.C. 154(b) by 0 days.

(21) Appl. No.: 14/603,556

(22) Filed: Jan. 23, 2015

(65) Prior Publication Data
US 2015/0148539 A1 May 28, 2015

Related U.S. Application Data

(60) Continuation of application No. 13/707,265, filed on Dec. 6, 2012, now Pat. No. 8,987,295, which is a division of application No. 12/825,631, filed on Jun. 29, 2010, now Pat. No. 8,383,644, which is a continuation of application No. PCT/US2010/029172, filed on Mar. 30, 2010.

(60) Provisional application No. 61/164,523, filed on Mar. 30, 2009, provisional application No. 61/309,348, filed on Mar. 1, 2010.

(51) Int. Cl.
C07D 491/056 (2006.01)
C07D 319/20 (2006.01)
C07D 491/06 (2006.01)

(52) U.S. Cl.
CPC .......... C07D 491/056 (2013.01); C07D 319/20 (2013.01); C07D 491/06 (2013.01)

(58) Field of Classification Search
CPC .............. C07D 491/056; C07D 319/20
USPC ............................. 546/90; 549/362
See application file for complete search history.

(56) References Cited

U.S. PATENT DOCUMENTS

| 3,865,832 | A | * | 2/1975 | Boschman et al. ............. 546/90 |
|---|---|---|---|---|
| 4,789,675 | A | | 12/1988 | Meguro et al. |
| 5,756,532 | A | | 5/1998 | Stack et al. |
| 7,727,983 | B2 | | 6/2010 | Mjalli et al. |
| 7,790,714 | B2 | | 9/2010 | Mjalli et al. |
| 7,906,507 | B2 | | 3/2011 | Mjalli et al. |
| 2006/0178515 | A1 | | 8/2006 | Aissaoui et al. |
| 2010/0324033 | A1 | | 12/2010 | Mjalli et al. |
| 2011/0028335 | A1 | | 2/2011 | Rao |

FOREIGN PATENT DOCUMENTS

| RU | 2284325 | | 1/2002 |
|---|---|---|---|
| RU | 2178416 | | 9/2006 |
| WO | WO 00/42026 | | 7/2000 |
| WO | WO 02/076979 | | 10/2002 |
| WO | WO 03/033496 | | 4/2003 |
| WO | WO 2005/014532 | | 2/2005 |
| WO | WO 03/055482 | | 9/2006 |
| WO | WO2008118935 | * | 10/2008 |
| WO | WO 2009/111700 | | 9/2009 |
| WO | WO 2009/126709 | | 10/2009 |
| WO | WO 2010/114824 | | 10/2010 |
| WO | WO 2011/156655 | | 12/2011 |

OTHER PUBLICATIONS

Dorwald, F.A., Side Reactions in Organic Synthesis, 2005, Wiley: VCH, Weinheim p. IX of Preface.
Eurasian Search Report for Patent Application No. 201171197 dated Apr. 24, 2012.
European Search Report for Patent Application No. 10779665.8 dated Jul. 19, 2012.
Freeman, Jennifer L.R. et al., "TTP3859: Identification of a Non-Peptide GLP-1 Receptor Agonist That Enhances Glycemic Control in vivo," 4th G Protein-Coupled Receptors: An ASPET Colloquium, Apr. 24-25, 2013, abstract, p. 51 (2013).
Freeman, Jennifer L.R. et al., "TTP3859: Identification of a Non-Peptide GLP-1 Receptor Agonist That Enhances Glycemic in vivo," 4th G Protein-Coupled Receptors: An ASPET Colloquium, Apr. 24-25, 2013, poster 61 (2013).
Garber, Alan, "Long-Acting Glucagon-Like Peptide 1 Receptor Agonists" Diabetes Care, 25(Supp. 2): S279-S284 (2011).
Gustavson, S.M, Burstein, A., Valcarce, C., Grimes, I.M., Mjalli, A. Abstract—TTP273, an Orally-Available Glucagon-Like Peptide-1 (GLP-1) Agonist, Notably Reduces Glycemia in Subjects with Type 2 Diabetes Mellitus (T2DM). Jun. 2014. ADA 74th Scientific Sessions. (155-OR).

(Continued)

Primary Examiner — Rita Desai
(74) Attorney, Agent, or Firm — Samuel B. Rollins

(57) ABSTRACT

The present invention relates to substituted azoanthracene derivatives and intermediates for the preparation thereof. The substituted azoanthracene derivatives and associated intermediates may be useful for the preparation of pharmaceutical compositions for the treatment or prevention of diseases, disorders, and conditions wherein modulation of the human GLP-1 receptor is beneficial.

11 Claims, No Drawings

(56) References Cited

OTHER PUBLICATIONS

Gustavson, S.M, Burstein, A., Valcarce, C., Grimes, I.M., Mjalli, A. TTP273, an Orally-Available Glucagon-Like Peptide-1 (GLP-1) Agonist, Notably Reduces Glycemia in Subjects with Type 2 Diabetes Mellitus (T2DM). Jun. 2014. ADA 74th Scientific Sessions. (155-OR).

Naslund et al., GLP-1 slows solid gastric emptying and inhibits insulin, glucagon, and PYY release in humans (1999).

PCT International Searh Report for Application No. PCT/US2010/029172 dated May 13, 2010.

PCT Written Opinion for Application No. PCT/US2010/029172 dated May 13, 2010.

Wettergren et al, Truncated GLP-1 (Proglucagon 78-107-Amide) Inhibits Gastric and Pancreatic Functions in Man, 1993.

Wootten, Denise et al., "Differential Activation and Modulation of the Glucagon-Like Peptide-1 Receptor by Small Molecule Ligands" Molecular Pharmacology, vol. 83, pp. 822-834 (2013).

\* cited by examiner

SUBSTITUTED AZOANTHRACENE DERIVATIVES AND INTERMEDIATES FOR PREPARATION THEREOF

BACKGROUND OF THE INVENTION

1. Field of Invention

The present invention relates to substituted azoanthracene derivatives and intermediates for the preparation thereof. The substituted azoanthracene derivatives and associated intermediates may be useful for the preparation of pharmaceutical compositions for the treatment or prevention of diseases, disorders, and conditions wherein modulation of the human GLP-1 receptor is beneficial.

2. Description of Related Art

Diabetes mellitus type 2 is a metabolic disorder where the disease progression may be characterized by one or more of peripheral tissue insulin resistance, hyperglycemia, islet b-cell compensation, hyperinsulinemia, dyslipidemia, increased liver gluconeogenesis, and ultimate loss of b-cell mass and function. The pathophysiological consequences of aberrant glucose and lipid metabolism are toxicity to organs such as the kidney, eye, peripheral neurons, vasculature and heart. Thus, there is a need for agents that may delay disease progression by improving glycemic control and by improving b-cell mass and function.

Glucagon-like peptide-1 (GLP-1) is a member of the incretin family of neuroendocrine peptide hormones secreted from L-cells of the intestine in response to food ingestion. GLP-1 has multiple metabolic effects that are attractive for an anti-diabetic agent. A key function of GLP-1 is to activate its receptor, GLP-1R, on the pancreatic b-cell to enhance glucose-dependent insulin secretion. Positive metabolic benefits of GLP-1 may include, but are not limited to, suppression of excessive glucagon production, decreased food intake, delayed gastric emptying, and improvement of b-cell mass and function. The positive effects of GLP-1 on b-cell mass and function offers the prospect that GLP-1-based therapies may delay early-stage disease progression. In addition, a GLP-1 agonist may also be useful in combination therapies, such as with insulin in patients with type I diabetes. Unfortunately, the rapid proteolysis of GLP-1 into an inactive metabolite limits its use as a therapeutic agent.

Validation of GLP-1R agonists as a therapeutic modality was achieved by Exendin-4 (Byetta® (Amylin Pharmaceuticals, Inc.)), a peptide GLP-1 receptor agonist recently approved in some countries for the treatment of diabetes mellitus type 2. Dosing of Exendin-4 by subcutaneous administration lowers blood glucose and decreases HbA1c levels, which are important biomarker measurements for disease control. Thus, an oral GLP-1 receptor agonist should provide glycemic control while offering the convenience of oral dosing.

GLP-1R belongs to the class B receptor sub-class of the G protein-coupled receptor (GPCR) superfamily that regulates important physiological and pathophysiological processes. In addition to the seven transmembrane domains characteristic of all GPCR family members, class B GPCRs contain a relatively large N-terminal domain. It is believed that the binding and activation of these receptors by large natural peptide ligands require both the N-terminal domain and the transmembrane domain of the receptor. The identification of low molecular weight non-peptide molecules that bind and activate class B GPCRs has proven to be difficult.

Because peptides, such as GLP-1, may lack sufficient oral bioavailability for consideration as oral drug agents, small molecule modulators of GLP-1R with oral bioavailability are desired. The present invention describes a class of compounds that modulate GLP-1R.

BRIEF SUMMARY OF THE INVENTION

The present invention provides substituted azoanthracene derivatives that modulate GLP-1R, and that may be useful in the treatment and/or prevention of disorders, diseases, or conditions wherein modulation of the human GLP-1 receptor is beneficial. Particularly, the invention provides substituted azoanthracene derivatives of Formula (I)

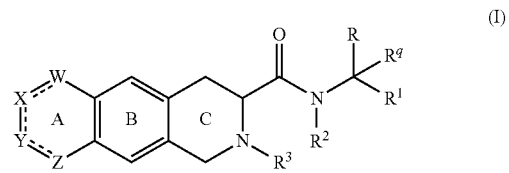

or a pharmaceutically acceptable salt thereof, as described in detail below.

The invention is also directed to pharmaceutical compositions comprising one or more substituted azoanthracene derivatives and the use of these compounds and pharmaceutical compositions in the treatment of diseases, disorders, or conditions in which modulation of the human GLP-1 receptor is beneficial.

In one aspect, the present invention provides novel substituted azoanthracene derivatives, where such compounds include compounds of Formula (I) or pharmaceutically acceptable salts of compounds of Formula (I), as described below. In another aspect, the present invention provides methods for the preparation of compounds of Formula (I) or the pharmaceutically acceptable salts thereof.

In another aspect, the present invention provides pharmaceutical compositions comprising a compound of Formula (I) or a pharmaceutically acceptable salt thereof. In an embodiment, the pharmaceutical composition comprises a compound of Formula (I), or a pharmaceutically acceptable salt thereof, and a pharmaceutically acceptable carrier, excipient, diluent, or mixture thereof. In another aspect, the present invention provides a method for the preparation of a pharmaceutical composition comprising a compound of Formula (I) or a pharmaceutically acceptable salt thereof.

In another aspect, the present invention provides methods of treatment comprising administering a compound of Formula (I), or a pharmaceutically acceptable salt thereof, or a pharmaceutical composition comprising a compound of Formula (I), or a pharmaceutically acceptable salt thereof, to a subject having a disease, disorder, or condition in which modulation of the human GLP-1 receptor is beneficial.

In another aspect, the present invention provides methods of treatment comprising administering a compound of Formula (I), or a pharmaceutically acceptable salt thereof, or a pharmaceutical composition comprising a compound of Formula (I), or a pharmaceutically acceptable salt thereof, to a subject having a disease, disorder, or condition or a subject at risk for having a disease, disorder, or condition, wherein the disease, disorder, or condition is selected from: metabolic syndrome, glucose intolerance, hyperglycaemia, dyslipidemia, diabetes mellitus type 1, diabetes mellitus type 2, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders that where activation of the GLP-1 receptor is beneficial, and complications resulting from or associated with diabetes, including, but not limited to, neuropathy, retinopathy, nephropathy, and impaired wound healing.

Additional features of the present invention are described hereinafter.

BRIEF DESCRIPTION OF DRAWINGS

Not applicable.

DETAILED DESCRIPTION

The following definitions are meant to clarify the meaning of the terms defined. If terms used herein are not specifically defined, such terms should not be considered to be indefinite. Rather, such undefined terms are to be construed in accordance with their plain and ordinary meaning to skilled artisans in the field(s) of art to which the invention is directed.

As used herein the term "alkyl" refers to a straight or branched chain saturated hydrocarbon having one to twelve carbon atoms, which may be optionally substituted, as herein further described, with multiple degrees of substitution being allowed. Examples of "alkyl" as used herein include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl.

As used throughout this specification, the number carbon atoms in an alkyl group will be represented by the phrase "$C_{x\text{-}y}$ alkyl," which refers to an alkyl group, as herein defined, containing from x to y, inclusive, carbon atoms. Thus, $C_{1\text{-}6}$ alkyl represents an alkyl chain having from 1 to 6 carbons as described above, and for example, includes, but is not limited to, methyl, ethyl, n-propyl, isopropyl, isobutyl, n-butyl, sec-butyl, tert-butyl, isopentyl, n-pentyl, neopentyl, and n-hexyl.

As used herein the term "alkenyl" refers to a straight or branched chain aliphatic hydrocarbon having two to twelve carbon atoms and containing one or more carbon-to-carbon double bonds, which may be optionally substituted as herein further described, with multiple degrees of substitution being allowed. Examples of "alkenyl" as used herein include, but are not limited to, vinyl, allyl, and 1-propen-1-yl.

As used throughout this specification, the number carbon atoms in an alkenyl group will be represented by the phrase "$C_{x\text{-}y}$ alkenyl," which refers to an alkenyl group, as herein defined, containing from x to y, inclusive, carbon atoms. Thus, $C_{2\text{-}6}$ alkenyl represents an alkenyl chain having from 2 to 6 carbons as described above, and for example, includes, but is not limited to, vinyl, allyl, and 1-propen-1-yl.

As used herein the term "alkynyl" refers to a straight or branched chain aliphatic hydrocarbon having two to twelve carbon atoms and containing one or more carbon-to-carbon triple bonds, which may be optionally substituted as herein further described, with multiple degrees of substitution being allowed. Examples of "alkynyl" as used herein include, but are not limited to, acetylenyl and 2-propyn-1-yl.

As used throughout this specification, the number carbon atoms in an alkynyl group will be represented by the phrase "$C_{x\text{-}y}$ alkynyl," which refers to an alkynyl group, as herein defined, containing from x to y, inclusive, carbon atoms. Thus, $C_{2\text{-}6}$ alkynyl represents an alkynyl chain having from 2 to 6 carbons as described above, and for example, includes, but is not limited to, acetylenyl and 2-propyn-1-yl.

As used herein, the term "alkylene" refers to a straight or branched chain divalent hydrocarbon radical having from one to ten carbon atoms, which may be optionally substituted as herein further described, with multiple degrees of substitution being allowed. Examples of "alkylene" as used herein include, but are not limited to, methylene, ethylene, n-propylene, 1-methylethylene, 2-methylethylene, dimethylmethylene, n-butylene, 1-methyl-n-propylene, and 2-methyl-n-propylene.

As used throughout this specification, the number of carbon atoms in an alkylene group will be represented by the phrase "$C_{x\text{-}y}$ alkylene," which refers to an alkylene group, as herein defined, containing from x to y, inclusive, carbon atoms. Thus, $C_{1\text{-}4}$ alkylene represents an alkylene chain having from 1 to 4 carbons as described above, and for example, includes, but is not limited to, methylene, ethylene, n-propylene, 1-methylethylene, 2-methylethylene, dimethylmethylene, n-butylene, 1-methyl-n-propylene, and 2-methyl-n-propylene.

As used herein, the term "alkenylene" refers to a straight or branched chain divalent hydrocarbon radical having from two to ten carbon atoms and containing one or more carbon-to-carbon double bonds, which may be optionally substituted as herein further described, with multiple degrees of substitution being allowed. Examples of "alkenylene" as used herein include, but are not limited to, vinylene, allylene, and 2-butenylene.

As used throughout this specification, the number of carbon atoms in an alkenylene group will be represented by the phrase "$C_{x\text{-}y}$ alkenylene," which refers to an alkenylene group, as herein defined, containing from x to y, inclusive, carbon atoms. Thus, $C_{2\text{-}4}$ alkenylene represents an alkenylene chain having from 2 to 4 carbons as described above, and for example, includes, but is not limited to, vinylene, allylene, and 2-butenylene.

As used herein, the term "alkynylene" refers to a straight or branched chain divalent hydrocarbon radical having from two to ten carbon atoms and containing one or more carbon-to-carbon triple bonds, which may be optionally substituted as herein further described, with multiple degrees of substitution being allowed. Examples of "alkynylene" as used herein include, but are not limited to, ethynylene and 2-butynylene.

As used throughout this specification, the number of carbon atoms in an alkynylene group will be represented by the phrase "$C_{x\text{-}y}$ alkynylene," which refers to an alkynylene group, as herein defined, containing from x to y, inclusive, carbon atoms. Thus, $C_{2\text{-}4}$ alkynylene represents an alkynylene chain having from 2 to 4 carbons as described above, and for example, includes, but is not limited to, ethynylene and 2-butynylene.

As used herein, the term "cycloalkyl" refers to a three- to twelve-membered, cyclic non-aromatic hydrocarbon ring, which may be optionally substituted as herein further described, with multiple degrees of substitution being allowed. Such "cycloalkyl" groups can contain one or more degrees of unsaturation. Examples of "cycloalkyl" groups as used herein include, but are not limited to, cyclopropyl, cyclobutyl, cyclopentyl, cyclohexyl, cycloheptyl, 1-norbornyl, 2-norbornyl, 7-norbornyl, 1-adamantyl, 2-adamantyl, cyclopropenyl, cyclobutenyl, cyclopentenyl, cyclohexenyl, and cycloheptenyl.

As used throughout this specification, the number of carbon atoms in a cycloalkyl group will be represented by the phrase "$C_{x\text{-}y}$ cycloalkyl," which refers to a cycloalkyl group, as herein defined, containing from x to y, inclusive, carbon atoms. Thus, $C_{3\text{-}10}$ cycloalkyl represents a cycloalkyl group having from 3 to 10 carbons as described above, and for example, includes, but is not limited to, cyclopropyl, cyclobutyl, cyclopentyl, cyclohexyl, cycloheptyl, 1-norbornyl, 2-norbornyl, 7-norbornyl, 1-adamantyl, and 2-adamantyl.

As used herein, the term "cycloalkylene" refers to a divalent three- to twelve-membered, cyclic non-aromatic hydrocarbon ring, which may be optionally substituted as herein further described, with multiple degrees of substitution being allowed. Examples of "cycloalkyl" groups as used herein include, but are not limited to, cyclopropylene, cyclobutylene, cyclopentylene, cyclohexylene, and cycloheptylene. As used herein, the term "cycloalkylene" can include divalent rings having different points of attachment as well as a common point of attachment, which connecting atom may be referred to as a "spiroatom."

As used throughout this specification, the number of carbon atoms in a cycloalkylene group will be represented by the phrase "$C_{x-y}$ cycloalkylene," which refers to a cycloalkylene group, as herein defined, containing from x to y, inclusive, carbon atoms. Thus, $C_{3-10}$ cycloalkylene represents a cycloalkylene group having from 3 to 10 carbons as described above, and for example, includes, but is not limited to, cyclopropylene, cyclobutylene, cyclopentylene, cyclohexylene, and cycloheptylene.

As used herein, the term "heterocycle" or "heterocyclyl" refers to an optionally substituted univalent non-aromatic mono- or polycyclic ring system, optionally containing one or more degrees of unsaturation, and containing one or more heteroatoms selected from the group consisting of nitrogen, oxygen, and sulfur. Such "heterocycle" or "heterocyclyl" groups may be optionally oxidized, or may also be optionally substituted as herein further described, with multiple degrees of substitution being allowed. The term "heterocycle" or "heterocyclyl," as used herein, includes ring systems that are fully saturated or that have one or more degrees of unsaturation. Typically, the ring is three- to twelve-membered. Such rings may be optionally fused to one or more of another heterocyclic ring(s), cycloalkyl ring(s), aryl group(s), or heteroaryl group(s), as defined herein. Examples of "heterocyclic" groups as used herein include, but are not limited to, tetrahydrofuran, tetrahydropyran, 1,4-dioxane, 1,3-dioxane, piperidine, pyrrolidine, morpholine, tetrahydrothiopyran, and tetrahydrothiophene, where attachment can occur at any point on said rings, as long as attachment is chemically feasible.

As used herein, when "heterocycle" or "heterocyclyl" is recited as a possible substituent, the "heterocycle" or "heterocyclyl" group can attach through either a carbon atom or any heteroatom, to the extent that attachment at that point is chemically feasible. For example, "heterocyclyl" would include pyrrolidin-1-yl, pyrrolidin-2-yl, and pyrrolidin-3-yl. When "heterocycle" or "heterocyclyl" groups contain a nitrogen atom in the ring, attachment through the nitrogen atom can alternatively be indicated by using an "-ino" suffix with the ring name. For example, pyrrolidino refers to pyrrolidin-1-yl.

As used herein, the term "heterocyclylene" refers to an optionally substituted divalent non-aromatic ring system, optionally containing one or more degrees of unsaturation, and containing one or more heteroatoms selected from the group consisting of nitrogen, oxygen, and sulfur. Such "heterocyclylene" groups may be optionally oxidized, or may also be optionally substituted as herein further described, with multiple degrees of substitution being allowed. The term "heterocyclylene," as used herein, includes ring systems that are fully saturated or that have one or more degrees of unsaturation. Typically, the ring is three- to twelve-membered. Such rings may be optionally fused to one or more of another heterocyclic ring(s), cycloalkyl ring(s), aryl group(s), or heteroaryl group(s), as defined herein. Examples of "heterocyclylene" groups as used herein include, but are not limited to, tetrahydrofuran-2,5-diyl and morpholin-2,4-diyl.

As used herein, the term "aryl" refers to an aromatic hydrocarbon ring, which may be optionally substituted as herein further described, with multiple degrees of substitution being allowed. The term "aryl" can also include polycyclic fused ring systems having up to three rings, where each ring in the ring system has from 3 to 7 atoms. Examples of "aryl" groups as used herein include, but are not limited to, phenyl, 1-naphthyl, 2-naphthyl, anthracene, phenanthrene, and indene. In one embodiment, "aryl" refers to a phenyl group, which may be substituted as herein further described.

As used herein, the term "arylene" refers to a divalent aromatic hydrocarbon ring, which may be optionally substituted as herein further described, with multiple degrees of substitution being allowed. The term "arylene" can also include polycyclic fused ring systems having up to three rings, where each ring in the ring system has from 3 to 7 atoms. Examples of "aryl" groups as used herein include, but are not limited to, 1,4-phenylene and 1,3-phenylene.

As used herein, the term "heteroaryl" refers to a monocyclic five- to seven-membered aromatic ring, or to a fused bicyclic aromatic ring system comprising two of such aromatic rings, which may be optionally substituted as herein further described, with multiple degrees of substitution being allowed. These "heteroaryl" rings contain one or more of nitrogen, sulfur, and/or oxygen atoms, where N-oxides, sulfur oxides, and dioxides are permissible heteroatom substitutions. Examples of "heteroaryl" groups, as used herein include, but are not limited to, furyl, thiophenyl, pyrrolyl, oxazolyl, thiazolyl, imidazolyl, isoxazolyl, isothiazolyl, 1,2,4-triazolyl, pyrazolyl, pyridinyl, pyridazinyl, pyrimidinyl, indolyl, isoindolyl, benzo[b]thiophenyl, benzimidazolyl, benzothiazolyl, pteridinyl, and phenazinyl.

As used herein, the term "heteroarylene" refers to a monocyclic five- to seven-membered aromatic ring diradical, or to a fused bicyclic ring system comprising two such rings, which may be optionally substituted as herein further described, with multiple degrees of substitution being allowed. These heteroaryl rings contain one or more nitrogen, sulfur, and/or oxygen atoms, where N-oxides, sulfur oxides, and dioxides are permissible heteroatom substitutions. Examples of "heteroarylene" as used herein include, but are not limited to, furan-2,5-diyl, thiophene-2,4-diyl, and pyridine-2,4-diyl.

As used herein, the term "fused cycloalkylaryl" refers to one or two cycloalkyl groups fused to an aryl group, the aryl and cycloalkyl groups having two atoms in common, and wherein the aryl group is the point of substitution. Examples of "fused cycloalkylaryl" used herein include 5-indanyl, and 5,6,7,8-tetrahydro-2-naphthyl

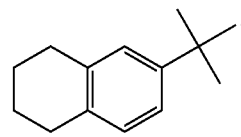

As used herein, the term "fused cycloalkylarylene" refers to a fused cycloalkylaryl, wherein the aryl group is divalent. Examples include

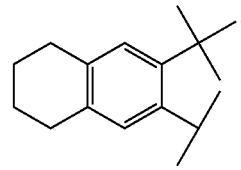

As used herein, the term "fused arylcycloalkyl" refers to one or two aryl groups fused to a cycloalkyl group, the cycloalkyl and aryl groups having two atoms in common, and wherein the cycloalkyl group is the point of substitution. Examples of "fused arylcycloalkyl" used herein include 1-indanyl, 2-indanyl, 9-fluorenyl, 1-(1,2,3,4-tetrahydronaphthyl) and

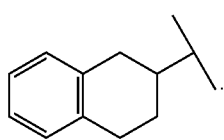

As used herein, the term "fused arylcycloalkylene" refers to a fused arylcycloalkyl, wherein the cycloalkyl group is divalent. Examples include 9,1-fluorenylene

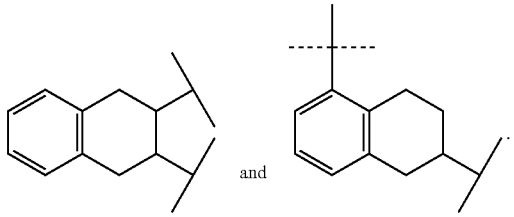 and

As used herein, the term "fused heterocyclylaryl" refers to one or two heterocyclyl groups fused to an aryl group, the aryl and heterocyclyl groups having two atoms in common, and wherein the aryl group is the point of substitution. Examples of "fused heterocyclylaryl" used herein include 3,4-methylenedioxy-1-phenyl and

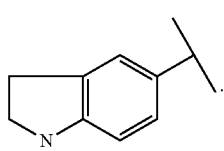

As used herein, the term "fused heterocyclylarylene" refers to a fused heterocyclylaryl, wherein the aryl group is divalent. Examples include

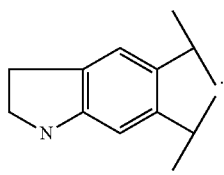

As used herein, the term "fused arylheterocyclyl" refers to one or two aryl groups fused to a heterocyclyl group, the heterocyclyl and aryl groups having two atoms in common, and wherein the heterocyclyl group is the point of substitution. Examples of "fused arylheterocyclyl" used herein include 2-(1,3-benzodioxolyl) and

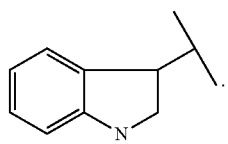

As used herein, the term "fused arylheterocyclylene" refers to a fused arylheterocyclyl, wherein the heterocyclyl group is divalent. Examples include

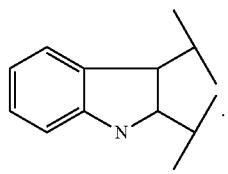

As used herein, the term "fused cycloalkylheteroaryl" refers to one or two cycloalkyl groups fused to a heteroaryl group, the heteroaryl and cycloalkyl groups having two atoms in common, and wherein the heteroaryl group is the point of substitution. Examples of "fused cycloalkylheteroaryl" used herein include 5-aza-6-indanyl and

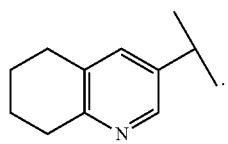

As used herein, the term "fused cycloalkylheteroarylene" refers to a fused cycloalkylheteroaryl, wherein the heteroaryl group is divalent. Examples include

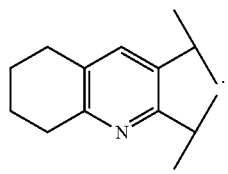 [SMILES: CC(C)c1cc2c(nc1C(C)C)CCCC2]

As used herein, the term "fused heteroarylcycloalkyl" refers to one or two heteroaryl groups fused to a cycloalkyl group, the cycloalkyl and heteroaryl groups having two atoms in common, and wherein the cycloalkyl group is the point of substitution. Examples of "fused heteroarylcycloalkyl" used herein include 5-aza-1-indanyl and

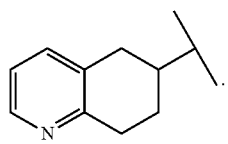

As used herein, the term "fused heteroarylcycloalkylene" refers to a fused heteroarylcycloalkyl, wherein the cycloalkyl group is divalent. Examples include

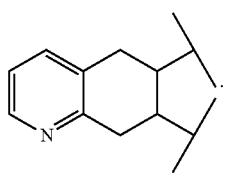 [SMILES: CC(C)C1Cc2cccnc2CC1C(C)C]

As used herein, the term "fused heterocyclylheteroaryl" refers to one or two heterocyclyl groups fused to a heteroaryl group, the heteroaryl and heterocyclyl groups having two atoms in common, and wherein the heteroaryl group is the point of substitution. Examples of "fused heterocyclylheteroaryl" used herein include 1,2,3,4-tetrahydro-beta-carbolin-8-yl and

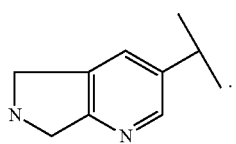

As used herein, the term "fused heterocyclylheteroarylene" refers to a fused heterocyclylheteroaryl, wherein the heteroaryl group is divalent. Examples include

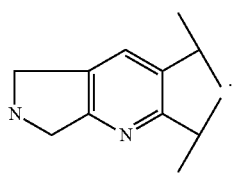

As used herein, the term "fused heteroarylheterocyclyl" refers to one or two heteroaryl groups fused to a heterocyclyl group, the heterocyclyl and heteroaryl groups having two atoms in common, and wherein the heterocyclyl group is the point of substitution. Examples of "fused heteroarylheterocyclyl" used herein include -5-aza-2,3-dihydrobenzofuran-2-yl and

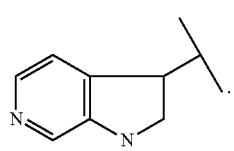

As used herein, the term "fused heteroarylheterocyclylene" refers to a fused heteroarylheterocyclyl, wherein the heterocyclyl group is divalent. Examples include

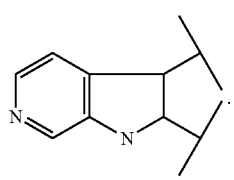

As used herein the term "halogen" refers to fluorine, chlorine, bromine, or iodine.

As used herein, the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include groups such as —$CF_3$, —$CH_2$—$CF_3$, and —$CF_2Cl$.

As used herein, the term "haloalkylene" refers to a straight or branched chain divalent hydrocarbon radical, substituted with at least one halogen. The term should be interpreted to include perfluoroalkylene groups such as —$CF_2$—.

As used herein, the term "alkoxy" refers to $R^vO$—, where $R^v$ is alkyl.

As used herein, the term "alkenyloxy" refers to $R^vO$—, where $R^v$ is alkenyl.

As used herein, the term "alkynyloxy" refers to $R^vO$—, where $R^v$ is alkynyl.

As used herein the term "nitro" refers to —$NO_2$.

As used herein the term "cyano" refers to —CN.

As used herein the term "azido" refers to —$N_3$.

As used herein, the term "alkylsulfanyl" refers to $R^vS$—, where $R^v$ is alkyl.

As used herein, the term "alkenylsulfanyl" refers to $R^vS$—, where $R^v$ is alkenyl.

As used herein, the term "alkynylsulfanyl" refers to $R^vS$—, where $R^v$ is alkynyl.

As used herein, the term "alkylsulfinyl" refers to $R^vS(O)$—, where $R^v$ is alkyl.

As used herein, the term "alkenylsulfinyl" refers to $R^vS(O)$—, where $R^v$ is alkenyl.

As used herein, the term "alkynylsulfinyl" refers to $R^vS(O)$—, where $R^v$ is alkynyl.

As used herein, the term "alkylsulfonyl" refers to $R^vSO_2$—, where $R^v$ is alkyl.

As used herein, the term "alkenylsulfonyl" refers to $R^vSO_2$—, where $R^v$ is alkenyl.

As used herein, the term "alkynylsulfonyl" refers to $R^vSO_2$—, where $R^v$ is alkynyl.

As used herein, the term "haloalkoxy" refers to —$OR^v$, where $R^v$ is haloalkyl, as herein defined. A haloalkoxy group includes, but is not limited to, —$O(CH_2)F$, —$O(CH)F_2$, and —$OCF_3$.

As used herein, the term "amide" refers to —$C(O)NR^vR^w$ or —$NR^vC(O)$—, where each $R^v$ and $R^w$ individually is hydrogen, alkyl, alkenyl, alkynyl, cycloalkyl, aryl, heterocylcyl, or heteroaryl.

As used herein, the term "amino" refers to —$NR^vR^w$, where each of $R^v$ and $R^w$ individually is hydrogen, alkyl, alkenyl, alkynyl, cycloalkyl, aryl, heterocylcyl, or heteroaryl. As used herein, when either $R^v$ or $R^w$ is other than hydrogen, such a group may be referred to as a "substituted amino" or, for example if $R^v$ is H and $R^w$ is alkyl, as an "alkylamino."

As used herein, the term "oxo" refers to the substituent =O, and is available as a substituent on carbon atoms that have at least two hydrogens available for substitution and on heteroatoms such as nitrogen and sulfur where the heteroatom may be oxidized.

As used herein, the terms "hydroxyl" and "hydroxyl" each refer to —OH.

As used herein, the term "aminosulfonyl" refers to —$SO_2NH_2$.

As used herein, the term "mercapto" refers to —SH.

As used herein, the terms "carboxy" and "carboxyl" each refer to —COOH.

As used herein, the term "carbamoyl" refers to —C(O)NH$_2$.

As used herein, the term "sulfanyl" refers to —S—.

As used herein, the term "sulfinyl" refers to —S(O)—.

As used herein, the term "sulfonyl" refers to —S(O)$_2$—.

As used herein, the term "acid isostere" refers to a substituent group which will ionize at physiological pH to bear a net negative charge. Examples of such "acid isosteres" include, but are not limited to, isoxazol-3-ol-5-yl, 1H-tetrazole-5-yl, 2H-tetrazole-5-yl, imidazolidin-2,4-dione-5-yl, imidazolidin-2,4-dione-1-yl, 1,3-thiazolidin-2,4-dione-5-yl, 5-hydroxy-4H-pyran-4-one-2-yl, 1,2,5-thiadiazolidin-3-one-1,1-dioxide-4-yl, and 1,2,5-thiadiazolidin-3-one-1,1-dioxide-5-yl.

As used herein, the term "optionally" means that the subsequently described event(s) may or may not occur.

As used herein, the term "direct bond", where recited as part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined. A direct joining of the substituents flanking the variable taken as a direct bond may be joined with a single bond, a double bond or a triple bond, provided that at least one of the bonds between the variable taken as the direct bond and the flanking substituents is a single bond, a double bond or a triple bond, respectively. For example, the structure G-J=K, when J is a direct bond, includes the structures G-K and G=K, so long as both structures are chemically feasible structures.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . ." and "substituted one or more times . . ." refer to a number of substituents that equals from one to the maximum number of substituents possible based on the number of available bonding sites, provided that the above conditions of stability and chemical feasibility are met. As used herein, the phrases "substituted with one to four . . ." and "substituted one to four times . . ." and "substituted 1-4 times" and "substituted with 1-4 . . ." refer to a number of substituents that equals from one to a maximum number of four substituents or up to the maximum possible of substituents based on the number of available bonding sites, provided that the above conditions of stability and chemical feasibility are met.

As used herein, the various functional groups represented will be understood to have a point of attachment at the functional group having the hyphen or dash (-) or an asterisk (*). In other words, in the case of —CH$_2$CH$_2$CH$_3$, it will be understood that the point of attachment is the CH$_2$ group at the far left. If a group is recited without an asterisk or a dash, then the attachment point is indicated by the plain and ordinary meaning of the recited group.

When any variable occurs more than one time in any one constituent (e.g., R$^a$), or multiple constituents, its definition on each occurrence is independent of its definition on every other occurrence.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

As used herein, "treat" or "treating" or "treatment" can refer to one or more of delaying the progress of a disease, disorder, or condition, controlling a disease, disorder, or condition, delaying the onset of a disease, disorder, or condition, ameliorating one or more symptoms characteristic of a disease, disorder, or condition, or delaying the recurrence of a disease, disorder, or condition or characteristic symptoms thereof, depending on the nature of a disease, disorder, or condition and its characteristic symptoms.

As used herein, "subject" refers to any mammal such as, but not limited to, humans, horses, cows, sheep, pigs, mice, rats, dogs, cats, and primates such as chimpanzees, gorillas, and rhesus monkeys. In an embodiment, the "subject" is a human. In another embodiment, the "subject" is a human who exhibits one or more symptoms characteristic of a disease, disorder, or condition. In another embodiment, the "subject" is a human in need of activation of GLP-1R. The term "subject" does not require one to have any particular status with respect to a hospital, clinic, or research facility (e.g., as an admitted patient, a study participant, or the like).

As used herein the terms "pharmaceutically acceptable carrier", "pharmaceutically acceptable diluent", and "pharmaceutically acceptable excipient" mean that the carrier, diluent or excipient must be compatible with the other ingredients of the formulation and not deleterious to the recipient thereof.

As used herein the term "therapeutically effective amount" as used herein means that amount of active compound or pharmaceutical agent that elicits the biological or medicinal response in a tissue, system, animal, human, or subject that is being sought by a researcher, veterinarian, medical doctor, patient or other clinician, which includes reduction or alleviation of the symptoms of the disease being treated. When the active compound (i.e., active ingredient) is administered as the salt, references to the amount of active ingredient are to the free acid or free base form of the compound.

As used herein, "substituted azoanthracene derivatives" refers to compounds encompassed by Formula (I), described below.

As used herein, the phrases such as "the compound of embodiment 1" or "the compound of claim 1" are intended to refer to any free acids, free bases, and/or pharmaceutically acceptable salts thereof that are encompassed by the recited claim(s) or embodiment(s).

As used herein, the term "pharmaceutical composition" is used to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

In a first aspect, the present invention provides substituted azoanthracene derivatives or pharmaceutically acceptable salts thereof. Such substituted azoanthracene derivatives or pharmaceutically acceptable salts thereof are useful in the activation of GLP-1R.

In a first embodiment (i.e., embodiment 1), the present invention provides a compound of Formula (I), or a pharmaceutically acceptable salt thereof:

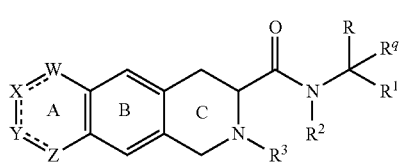

(I)

wherein
----- represents the presence or absence of a bond;
W, X, Y and Z are independently selected from the group consisting of:
  a) a direct bond,
  b) a nitrogen atom,
  c) —N($R^a$)—,
  d) —N(H)—,
  e) =C($R^4$)—,
  f) —C($R^4$)($R^4$)—,
  g) =C($R^5$)—,
  h) —C($R^4$)($R^5$)—,
  i) =C(H)—,
  j) —CH$_2$—,
  k) —C(=O)—,
  l) a sulfur atom,
  m) —SO$_2$—,
  n) =S(O)—, and
  o) an oxygen atom;
wherein
  $R^4$ is H or $R^b$;
  $R^5$ is -$G^3$-$L^2$-$Q^2$-$L^3$-$G^4$, wherein
    $L^2$ and $L^3$ are independently selected from the group consisting of: a direct bond, —CH$_2$—, —O—, —N($R^{26}$)—, —C(O)—, —CON($R^{26}$)—, —N($R^{26}$)C(O)—, —N($R^{26}$)CON($R^{27}$)—, —N($R^{26}$)C(O)O—, —OC(O)N($R^{26}$)—, —N($R^{26}$)SO$_2$—, —SO$_2$N($R^{26}$)—, —C(O)—O—, —O—C(O)—, —S—, —S(O)—, —S(O)$_2$—, and —N($R^{26}$)SO$_2$N($R^{27}$)—, wherein
      $R^{26}$ and $R^{27}$ are independently selected from the group consisting of: hydrogen, -alkyl, -aryl, and -alkylene-aryl, wherein $R^{26}$ and $R^{27}$ are optionally substituted 1-4 times with $R^c$; or $R^{26}$ and $R^{27}$ are taken together with the atoms to which they are attached to form a heterocyclic ring of 5 to 7 members containing 0-2 additional heteroatoms independently selected from oxygen, nitrogen, and sulfur;
    $Q^2$ is selected from the group consisting of: a direct bond, $C_{1-10}$ alkylene, $C_{2-10}$ alkenylene, and $C_{2-10}$ alkynylene,
    $G^3$ is selected from the group consisting of: arylene, cycloalkylene, heterocyclylene, heteroarylene, fused arylcycloalkylene, fused cycloalkylarylene, fused cycloalkylheteroarylene, fused heterocyclylarylene, and fused heterocyclylheteroarylene, wherein
    $G^3$ is optionally substituted 1-4 times with substituents independently selected from $R^8$, wherein $R^8$ is selected from $R^b$,
    $G^4$ is selected from the group consisting of: aryl, cycloalkyl, heterocyclyl, heteroaryl, fused arylcycloalkyl, fused cycloalkylaryl, fused cycloalkylheteroaryl, fused heterocyclylaryl, and fused heterocyclylheteroaryl, wherein
    $G^4$ is optionally substituted 1-4 times with substituents independently selected from $R^9$, wherein $R^9$ is selected from $R^b$; or
    $G^4$ is —$C_{1-8}$ alkyl, —$C_{2-8}$ alkenyl, —$C_{2-8}$ alkynyl, —$C_{1-6}$ alkylene-$G^5$, —$C_{2-6}$ alkenylene-$G^5$, —$C_{2-6}$ alkynylene-$G^5$, or —$C_{3-10}$ cycloalkylene-$G^5$, where the alkyl, alkenyl, alkynyl, alkylene, alkenylene, alkynylene and cycloalkylene groups are optionally substituted one or more times with substituents independently selected from $R^y$;
    $G^5$ is -phenyl, —$C_{3-10}$ cycloalkyl, -heterocyclyl, -heteroaryl, -fused arylcycloalkyl, -fused cycloalkylaryl, -fused cycloalkyl-heteroaryl, -fused heterocyclylaryl, and -fused heterocyclyl-heteroaryl, wherein each member of $G^5$ is optionally substituted one or more times with substituents independently selected from $R^y$;
R is —(CH$_2$)$_p$-$G^1$-$L^1$-$G^2$, wherein
  $L^1$ is selected from the group consisting of: a direct bond, —CH$_2$—, —O—, —N($R^{16}$)—, —C(O)—, —CON($R^{16}$)—, —N($R^{16}$)C(O)—, —N($R^{16}$)SO$_2$—, —SO$_2$N($R^{16}$)—, —C(O)—O—, —O—C(O)—, —S—, —S(O)—, —S(O)$_2$—, and —C≡C—, wherein
    $R^{16}$ is selected from the group consisting of: -hydrogen, -alkyl, -aryl, and -alkylene-aryl;
  $G^1$ is selected from the group consisting of: alkynylene, arylene, heteroarylene, fused arylcycloalkylene, fused cycloalkylarylene, fused cycloalkylheteroarylene, fused heterocyclylarylene, and fused heterocyclylheteroarylene, wherein $G^1$ is optionally substituted 1-4 times with substituents independently selected from $R^{10}$, wherein
    $R^{10}$ is $R^b$,
  $G^2$ is selected from the group consisting of: -aryl, -heteroaryl, -fused arylcycloalkyl, -fused cycloalkylaryl, -fused cycloalkylheteroaryl, -fused heterocyclylaryl, and -fused heterocyclylheteroaryl, wherein $G^2$ is optionally substituted 1-4 times with substituents independently selected from $R^{11}$, wherein
    $R^{11}$ is $R^b$,
$R^1$ is selected from the group consisting of: —CO$_2$H, —CO$_2$R$^{12}$, —C(O)NH$_2$, —C(O)NHR$^{12}$, -tetrazole, and acid isostere, wherein
  $R^{12}$ is selected from the group consisting of: —$C_{1-10}$ alkyl, -cycloalkyl, and -aryl, wherein $R^{12}$ is optionally substituted 1-4 times with a group independently selected from $R^c$;
$R^2$ is selected from the group consisting of: -hydrogen, -alkyl, -phenyl, -cycloalkyl, -alkylene-cycloalkyl, and -alkylene-phenyl, wherein the alkyl, phenyl, and cycloalkyl groups are optionally substituted 1-4 times with a group independently selected from $R^c$;
$R^3$ is —H, $R^a$, or $R^h$;
$R^q$ is hydrogen or methyl;

Rings B and C are optionally substituted 1-4 times with substituents independently selected from the group consisting of $R^b$;

$R^a$ is selected from the group consisting of:
  a) —S(O)$_m$R$^d$,
  b) —S(O)$_2$OR$^d$,
  c) —S(O)$_m$NR$^d$R$^e$,
  d) —C(O)R$^d$,
  e) —CO$_2$R$^d$,
  f) —C(O)NR$^d$R$^e$,
  g) -haloalkyl,
  h) -cycloalkyl,
  i) -heterocyclyl,
  j) —C$_{1-10}$ alkyl,
  k) —C$_{2-10}$ alkenyl,
  l) —C$_{2-10}$ alkynyl,
  m) -aryl,
  n) -heteroaryl,
  o) —C$_{1-10}$ alkylene-aryl,
  p) —C$_{2-10}$ alkynylene-aryl,
  q) —C$_{1-10}$ alkylene-heteroaryl, and
  r) —C$_{2-10}$ alkynylene-heteroaryl,
   wherein the alkyl, alkenyl, alkynyl, aryl, heterocyclyl, heteroaryl, and cycloalkyl groups are optionally substituted 1-4 times with a group independently selected from R$^c$;

$R^b$ is selected from the group consisting of:
  a) -cycloalkyl,
  b) -cyano,
  c) —OR$^d$,
  d) —NO$_2$,
  e) -halogen,
  f) —S(O)$_m$R$^d$,
  g) —SR$^d$,
  h) —S(O)$_2$OR$^d$,
  i) —S(O)$_m$NR$^d$R$^e$,
  j) —NR$^d$R$^e$,
  k) —O(CR$^f$R$^g$)$_n$NR$^d$R$^e$,
  l) —C(O)R$^d$,
  m) —CO$_2$R$^d$,
  n) —CO$_2$(CR$^f$R$^g$)$_n$CONR$^d$R$^e$,
  o) —OC(O)R$^d$,
  p) —C(O)NR$^d$R$^e$,
  q) —NR$^d$C(O)R$^e$,
  r) —OC(O)NR$^d$R$^e$,
  s) —NR$^d$C(O)OR$^e$,
  t) —NR$^d$C(O)NR$^d$R$^e$,
  u) —CF$_3$,
  v) —OCF$_3$,
  w) -haloalkyl,
  x) -haloalkoxy,
  y) —C$_{1-10}$ alkyl,
  z) —C$_{2-10}$ alkenyl,
  aa) —C$_{2-10}$ alkynyl,
  bb) —C$_{1-10}$ alkylene-aryl,
  cc) —C$_{1-10}$ alkylene-heteroaryl, and
  dd) -heteroaryl,
   wherein the alkyl, alkenyl, alkynyl, aryl, heteroaryl, and cycloalkyl groups are optionally substituted 1-4 times with a group independently selected from R$^c$;

$R^c$ is selected from the group consisting of:
  a) -halogen,
  b) -amino,
  c) -carboxy,
  d) -cyano,
  e) —C$_{1-4}$ alkyl,
  f) —O—C$_{1-4}$ alkyl,
  g) —O—CF$_3$,
  h) -cycloalkyl,
  i) —O-cycloalkyl,
  j) -aryl,
  k) —C$_{1-4}$ alkylene-aryl,
  l) -hydroxy,
  m) —CF$_3$,
  n) -haloalkyl,
  o) -haloalkoxy,
  p) —O-aryl,
  q) -heteroaryl,
  r) -heteroarylene-C$_{1-10}$ alkyl,
  s) -heterocyclyl,
  t) —CO$_2$—C$_{1-10}$ alkyl,
  u) —CO$_2$—C$_{1-10}$ alkyl-aryl,
  v) fused arylcycloalkyl,
  w) -alkynylene-heteroaryl,
  x) -alkylene-aryl, and
  y) -alkynylene-aryl;

$R^d$ and $R^e$ are independently selected from the group consisting of: hydrogen, C$_{1-10}$ alkyl, C$_{2-10}$ alkenyl, C$_{2-10}$ alkynyl, cycloalkyl, —C$_{1-10}$ alkylene-cycloalkyl, aryl, heteroaryl, and heterocyclyl, wherein alkyl, alkenyl, alkynyl, cycloalkyl, aryl, heteroaryl, heterocyclyl groups are optionally substituted with one to four substituents independently selected from R$^c$; or R$^d$ and R$^e$ together with the atoms to which they are attached form a heterocyclic ring of 5 to 7 members containing 0-2 additional heteroatoms independently selected from oxygen, sulfur and nitrogen and optionally substituted with 1-3 times with R$^c$, $R^f$ and $R^g$ are independently selected from the group consisting of: hydrogen, C$_{1-10}$ alkyl, cycloalkyl, —C$_{1-10}$ alkylene-cycloalkyl, and aryl, wherein alkyl, cycloalkyl, and aryl groups are optionally substituted with one to four substituents independently selected from R$^c$; or R$^f$ and R$^g$ together with the carbon to which they are attached form a ring of 5 to 7 members containing 0-2 heteroatoms independently selected from oxygen, sulfur and nitrogen optionally substituted with 1-3 times with R$^c$;

$R^h$ is selected from the group consisting of:
  a) —S(O)$_m$R$^j$,
  b) —S(O)$_2$OR$^j$,
  c) —S(O)$_m$NR$^j$R$^k$,
  d) —C(O)R$^j$,
  e) —CO$_2$R$^j$,
  f) —C(O)NR$^j$R$^k$,
  g) —C$_{3-10}$ cycloalkyl,
  h) -heterocyclyl,
  i) —C$_{1-10}$ alkyl,
  j) —C$_{2-10}$ alkenyl,
  k) —C$_{2-10}$ alkynyl,
  l) -aryl,
  m) -heteroaryl,
  n) —C$_{1-10}$ alkylene-C$_{3-10}$ cycloaklyl,
  o) —C$_{2-10}$ alkynylene-C$_{3-10}$ cycloalkyl,
  p) —C$_{1-10}$ alkylene-heterocyclyl,
  q) —C$_{2-10}$ alkynylene-heterocyclyl,
  r) —C$_{1-10}$ alkylene-aryl,
  s) —C$_{2-10}$ alkynylene-aryl,
  t) —C$_{1-10}$ alkylene-heteroaryl,
  u) —C$_{2-10}$ alkynylene-heteroaryl,
  v) -1,4-phenylene-phenyl,
  w) -1,3-phenylene-phenyl,
  x) -1,4-phenylene-heteroaryl, and
  y) -1,3-phenylene-heteroaryl,
   wherein the alkyl, alkenyl, alkynyl, cycloalkyl, heterocyclyl, aryl, phenyl, heteroaryl, alkylene, alkynylene, and phenylene groups are optionally substituted one or more times with substituents independently selected from $R^x$;

$R^j$ and $R^k$ are independently selected from hydrogen, —$C_{1-6}$ alkyl, —$C_{3-10}$ cycloalkyl, heterocyclyl, phenyl, heteroaryl, —$C_{1-6}$ alkylene-$C_{3-10}$ cycloalkyl, —$C_{1-6}$ alkylene-heterocyclyl, —$C_{1-6}$ alkylene-phenyl, and —$C_{1-6}$ alkylene-heteroaryl, where the alkyl, alkylene, cycloalkyl, heterocyclyl, phenyl, and heteroaryl groups are optionally substituted one or more times with substituents independently selected from $R^x$; or, if $R^j$ and $R^k$ are both attached to the same nitrogen atom, together with that nitrogen atom may optionally form a heterocyclic ring selected from azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from $R^x$;

$R^m$ and $R^n$ are independently selected from hydrogen, —$C_{1-6}$ alkyl, —$C_{3-10}$ cycloalkyl, heterocyclyl, phenyl, heteroaryl, —$C_{1-4}$ alkylene-$C_{3-10}$ cycloalkyl, —$C_{1-4}$ alkylene-heterocyclyl, —$C_{1-4}$ alkylene-phenyl, and —$C_{1-4}$ alkylene-heteroaryl, where the alkyl, alkylene, cycloalkyl, heterocyclyl, phenyl, and heteroaryl groups are optionally substituted one or more times with substituents independently selected from $R^y$; or, if $R^m$ and $R^n$ are both attached to the same nitrogen atom, together with that nitrogen atom may optionally form a heterocyclic ring selected from azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from $R^y$;

$R^s$ and $R^t$ are independently selected from hydrogen, —$C_{1-6}$ alkyl, —$C_{3-10}$ cycloalkyl, heterocyclyl, phenyl, heteroaryl, —$C_{1-4}$ alkylene-$C_{3-10}$ cycloalkyl, —$C_{1-4}$ alkylene-heterocyclyl, —$C_{1-4}$ alkylene-phenyl, and —$C_{1-4}$ alkylene-heteroaryl, where the alkyl, alkylene, cycloalkyl, heterocyclyl, phenyl, and heteroaryl groups are optionally substituted one or more times with substituents independently selected from $R^z$; or, if $R^s$ and $R^t$ are both attached to the same nitrogen atom, together with that nitrogen atom may optionally form a heterocyclic ring selected from azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from $R^z$;

$R^x$ is:
a) -halogen,
b) —$C_{1-6}$ alkyl,
c) —$C_{3-10}$ cycloalkyl,
d) —$C_{1-4}$ alkylene-$C_{3-10}$ cycloalkyl,
e) -heterocyclyl,
f) —$C_{1-4}$ alkylene-heterocyclyl,
g) -phenyl,
h) —$C_{1-4}$ alkylene-phenyl,
i) -heteroaryl,
j) —$C_{1-4}$ alkylene-heteroaryl,
k) -cyano,
l) —$CF_3$,
m) —$OCF_3$,
n) —O—$R^m$,
o) —$S(O)_w$—$R^m$,
p) —$S(O)_2$O—$R^m$,
q) —$NR^m R^n$,
r) —C(O)—$R^m$,
s) —C(O)—O—$R^m$,
t) —OC(O)—$R^m$,
u) —C(O)$NR^m R^n$,
v) —$NR^m$C(O)$R^n$,
w) —OC(O)$NR^m R^n$,
x) —$NR^m$C(O)O$R^n$,
y) —$NR^m$C(O)$NR^m R^n$, or
z) —$NO_2$, where the alkyl, alkylene, cycloalkyl, heterocyclyl, phenyl, and heteroaryl groups are optionally substituted one or more times with substituents independently selected from $R^y$;

$R^y$ is
a) -halogen,
b) —$NR^s R^t$,
c) —O—$R^s$,
d) —S—$R^s$,
e) —$S(O)_2$—$R^s$,
f) —CN,
g) —C(O)—$R^s$,
h) —C(O)—O—$R^s$,
i) —C(O)$NR^s R^t$,
j) —$NR^s$—C(O)—$R^t$,
k) —$NR^s$—C(O)—$NR^s R^t$,
l) —$NR^s$—C(O)—O—$R^t$,
m) —$C_{1-6}$ alkyl,
n) -heterocyclyl,
o) —$C_{3-10}$ cycloalkyl,
p) —$CF_3$,
q) —$OCF_3$,
r) -phenyl, or
s) -heteroaryl;

where the alkyl, cycloalkyl, heterocyclyl, phenyl, and heteroaryl groups are optionally substituted one or more times with substituents independently selected from $R^z$;

$R^z$ is selected from the group consisting of halogen, methyl, ethyl, isopropyl, —$CF_3$, —$NH_2$, —NH($CH_3$), —NH($CH_2CH_3$), —N($CH_3$)$_2$, —N($CH_3$)($CH_2CH_3$), —N($CH_2CH_3$)$_2$, —$OCH_3$, —$OCF_3$, —$OCH_2CH_3$, —$OCH_2CF_3$, —$OCH(CH_3)_2$, —OH, —$S(O)_2CH_3$, and —CN;

m is an integer from 1 to 2;
n is an integer from 1 to 10;
p is an integer from 0 to 2; and w is an integer from 0 to 2;

provided that when W is —N(R$^a$)—, X is not —C(O)— and Y is not —C(R$^5$)— and Z is not an oxygen atom.

Embodiment 2: A compound according to embodiment 1, wherein
G$^4$ is selected from the group consisting of: -aryl, -cycloalkyl, -heterocyclyl, -heteroaryl, -fused arylcycloalkyl, -fused cycloalkylaryl, -fused cycloalkyl-heteroaryl, -fused heterocyclylaryl, and -fused heterocyclylheteroaryl; wherein G$^4$ is optionally substituted 1-4 times with substituents independently selected from R$^9$, wherein R$^9$ is selected from R$^b$; R$^3$ is R$^a$; and R$^q$ is hydrogen.

Embodiment 3: A compound according to embodiment 1 or 2, wherein
the compound of Formula (I) is represented by Formula (I-A):

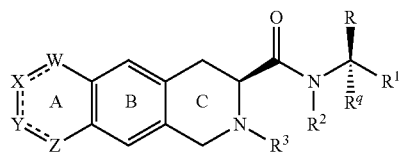

Formula (I-A)

wherein the variables are as defined in embodiment 1 or 2, or a pharmaceutically acceptable salt thereof.

Embodiment 4: A compound according to embodiment 1 or 2, wherein
the compound of Formula (I) is represented by Formula (I—B):

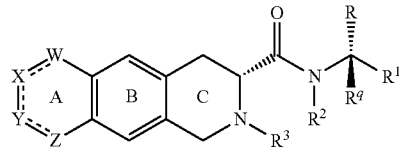

Formula (I-B)

wherein the variables are as defined in embodiment 1 or 2, or a pharmaceutically acceptable salt thereof.

Embodiment 5: A compound according to embodiment 1 or 2, wherein
the compound of Formula (I) is represented by Formula (I—C):

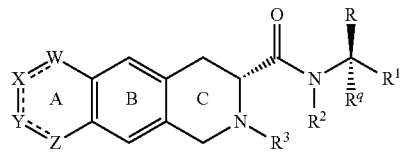

Formula (I-C)

wherein the variables are as defined in embodiment 1 or 2, or a pharmaceutically acceptable salt thereof.

Embodiment 6: A compound according to embodiment 1 or 2, wherein
the compound of Formula (I) is represented by Formula (I-D):

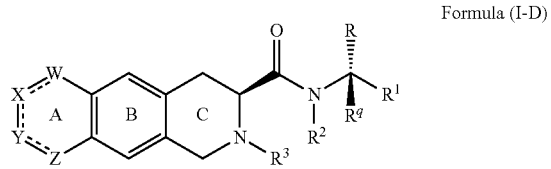

Formula (I-D)

wherein the variables are as defined in embodiment 1 or 2, or a pharmaceutically acceptable salt thereof.

Embodiment 7: A compound according to any one of embodiments 1 to 6, wherein
the compound of Formula (I) is represented by Formula (I-E):

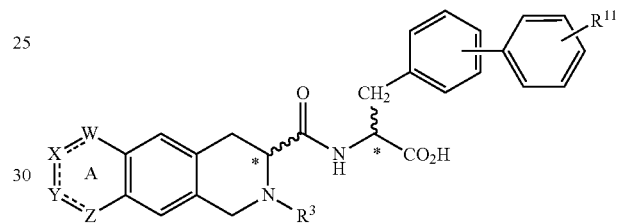

Formula (I-E)

wherein * indicates the presence of a chiral center which may be in the R- or S-configuration and wherein the variables are as defined in any one of embodiments 1 to 6, or a pharmaceutically acceptable salt thereof.

Embodiment 8: A compound according to any one of embodiments 1 to 7, wherein ring A is selected from the group consisting of

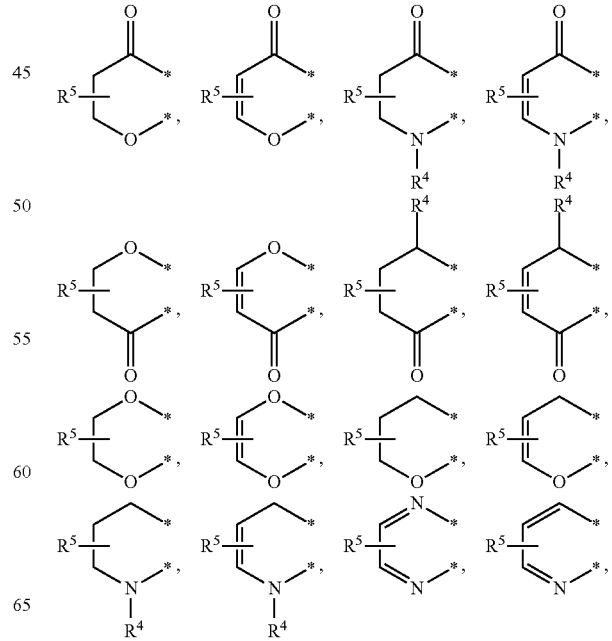

-continued

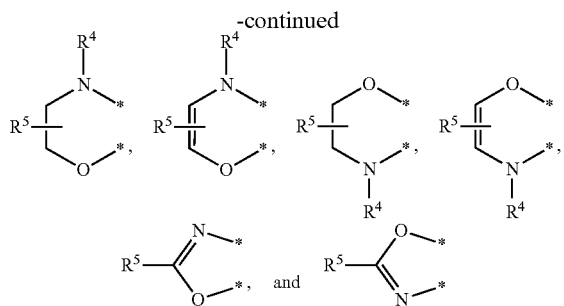

wherein $R^5$ is as described in any one of embodiments 1 to 7.

Embodiment 9: A compound according to any one of embodiments 1 to 7, wherein
ring A is selected from the group consisting of

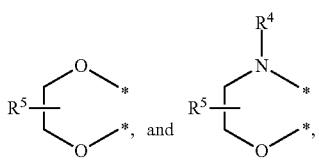

wherein $R^4$ and $R^5$ are as described in any one of embodiments 1 to 7.

Embodiment 10: A compound according to any one of embodiments 1 to 9, wherein
ring B and ring C contain no further substitutions.

Embodiment 11: A compound according to any one of embodiments 1 to 10, wherein
each aryl group is a phenyl group.

Embodiment 12: A compound according to any one of embodiments 1 to 11, wherein
each heteroaryl group is selected from the group consisting of pyridinyl, pyridazinyl, pyrimidinyl, pyrazinyl, furanyl, pyrrolyl, pyranyl, thiophenyl, isoxazolyl, oxazolyl, thiazolyl, isothiazolyl, imidazolyl, pyrazolyl, indolyl, benzofuranyl, benzothiophenyl, and quinolinyl.

Embodiment 13: A compound according to any one of embodiments 1 to 12, wherein
each heterocyclyl group is selected from the group consisting of piperdinyl, piperazinyl, morpholinyl, dioxanyl, pyrrolidinyl, tetrahydrofuranyl, dioxolanyl, imidazolidinyl and pyrazolidinyl.

Embodiment 14: A compound according to any one of embodiments 1 to 13, wherein
$R^1$ is selected from the group consisting of: —$CO_2H$ and —$CO_2R^{12}$.

Embodiment 15: A compound according to any one of embodiments 1 to 14, wherein
$R^1$ is —$CO_2H$.

Embodiment 16: A compound according to any one of embodiments 1 to 15, wherein
$R^2$ is selected from the group consisting of: hydrogen and —$C_{1-10}$ alkyl.

Embodiment 17: A compound according to any one of embodiments 1 to 16, wherein
$R^2$ is hydrogen.

Embodiment 18: A compound according to any one of embodiments 1 to 17, wherein
p is 1.

Embodiment 19: A compound according to any one of embodiments 1 to 18, wherein
$L^1$ is a direct bond.

Embodiment 20: A compound according to any one of embodiments 1 to 17, wherein
p is 1; $G^1$ is a substituted or unsubstituted phenyl; $L^1$ is selected from the group consisting of a direct bond, —O—, and —N(H)C(O)—; $G^2$ is a phenyl group substituted 1-4 times with substituents independently selected from $R^{11}$, and $G^2$ is substituted with at least one substituent selected from the group consisting of:
a) —$C_{1-10}$ alkyl,
b) -haloalkyl,
c) -haloalkoxy,
d) —$CF_3$,
e) —$OCF_3$,
f) -halogen,
g) —O—$R^d$,
h) -cyano,
i) —$C(O)R^d$,
j) —$NR^dR^e$,
k) -cycloalkyl, and
l) —$CO_2R^d$;
wherein the alkyl and cycloalkyl groups are optionally substituted 1-4 times with a group independently selected from $R^c$.

Embodiment 21: A compound according to any one of embodiments 1 to 17, wherein
p is 1; $G^1$ is a $C_{2-10}$ alkylene; $L^1$ is a direct bond; and $G^2$ is a substituted or unsubstituted phenyl group.

Embodiment 22: A compound according to any one of embodiments 1 to 17, wherein
p is 1; $G^1$ is —C≡C—; $L^1$ is a direct bond; and $G^2$ is a phenyl group substituted 1-4 times with substituents independently selected from $R^{11}$, where at least one of said substituents is selected from the group consisting of:
a) —$C_{1-10}$ alkyl,
b) -haloalkyl,
c) -haloalkoxy,
d) —$CF_3$,
e) —$OCF_3$,
f) -halogen,
g) —O—$R^d$,
h) -cyano,
i) —$C(O)R^d$,
j) —$NR^dR^e$,
k) -cycloalkyl, and
l) —$CO_2R^d$,
wherein the alkyl and cycloalkyl groups are optionally substituted 1-4 times with a group independently selected from $R^c$.

Embodiment 23: A compound according to any one of embodiments 1 to 17, wherein
p is 1; $G^1$ is a substituted or unsubstituted phenyl; $L^1$ is a direct bond; and $G^2$ is selected from the group consisting of: indole, pyridine, pyrimidine, quinoline, and isoxazole, wherein
$G^2$ is optionally substituted or unsubstituted.

Embodiment 24: A compound according to any one of embodiments 1 to 23, wherein
$R^3$ is selected from the group consisting of:
a) —$C_{1-10}$ alkyl,
b) -phenyl,
c) -thiopheneyl,
d) -furanyl,
e) -pyridyl, f) —$C_{1-10}$ alkylene-pyridyl,
g) —$C_{1-10}$ alkylene-aminothiazolyl,
h) —$C_{1-10}$ alkylene-imidazolyl,
i) —$C_{1-10}$ alkylene-oxazolyl,
j) —$C_{1-10}$ alkylene-thiopheneyl,
k) —$C_{2-10}$ alkynylene-phenyl,
l) —$C_{2-10}$ alkynlene-thiopheneyl,
m) —$C_{2-10}$ alkynylene-pyridyl,
n) —$C_{2-10}$ alkynylene-pyrimidinyl,
o) —$SO_2$-phenyl,
p) —$CO_2$—$C_{1-10}$ alkyl,
q) —$CO_2$-cycloalkyl,
r) —$CO_2$-tetrahydrofuranyl,
s) —$CO_2$-tetrahydropyranyl,
t) —$CO_2$—$C_{1-10}$ alkylene-cycloalkyl,
u) —$CO_2$—$C_{2-10}$-alkynyl,
v) —$CO_2$—$CH_2$—C≡C-phenyl,
w) —C(O)—$C_{1-10}$ alkyl,
x) —C(O)-phenyl,
y) —C(O)-naphthyl,
z) —C(O)-cycloalkyl,
aa) —C(O)-furanyl,
bb) —C(O)-thiopheneyl,
cc) —C(O)-isoxazolyl,
dd) —C(O)—$C_{1-10}$ alkylene-cycloalkyl,
bb) —C(O)—NH—$C_{1-10}$ alkyl,
ff) —C(O)—NH-phenyl, and
gg) —C(O)—N(cycloalkyl)-$C_{1-10}$ phenyl,
wherein the alkyl, alkynyl, cycloalkyl, tetrahydrofuranyl, tetrahydropyranyl, phenyl, naphthyl, thiopheneyl, furanyl, pyridyl, pyrimidinyl, thiazolyl, imidazolyl, oxazolyl, and isoxazolyl groups are optionally substituted 1-4 times with a group independently selected from $R^c$.

Embodiment 25: A compound according to any one of embodiments 1 to 23, wherein
$R^3$ is selected from the group consisting of:
a) —$CO_2$-tert-butyl,
b) —$CO_2$-n-hexyl,
c) —$CO_2$-isopropyl,
d) —$CO_2$-(tert-butylcyclohexyl)
e) —$CO_2$-tetrahydrofuran-2-yl,
f) —$CO_2$-tetrahydropyran-4-yl,
g) —$CO_2$—$CH_2$-cyclopropyl,
h) —C(O)NH-(tert-butylphenyl),
i) —C(O)-piperidin-2-yl,
j) —C(O)—NH-(trifluoromethoxyphenyl),
k) —C(O)—NH-(1,1-diphenylmethyl),
l) —C(O)-isopropy,
m) —C(O)-phenyl,
n) —C(O)-(fluorophenyl),
o) —C(O)-(chlorophenyl),
p) —C(O)-(cyanophenyl),
q) —C(O)-pyridin-2-yl,
r) —C(O)-pyrimidin-4-yl,
s) —C(O)-furan-2-yl,
t) —C(O)-cyclobutyl,
u) —C(O)-cyclopentyl,
v) —C(O)-cyclohexyl,
w) —C(O)-thiophene-2-yl,
x) —C(O)-benzyl,
y) —C(O)-(fluorobenzyl),
z) —C(O)-(chlorobenzyl),
aa) —C(O)-(cyanobenzyl),
bb) —C(O)-(2,5-dimethyl-oxazol-4-yl),
cc) —$CH_2$-oxazol-2-yl,
dd) —$CH_2$-(1-methylimdiazol-2-yl),
ee) —$CH_2$-pyridin-2-yl,
ff) —$CH_2$-furan-2-yl,
gg) —$CH_2$-thiazol-2-yl,
hh) —$CH_2$—C≡C-pyrimidin-2-yl,
ii) —$CH_2$—C≡C-phenyl,
jj) —$CH_2$-thiophene-2-yl,
kk) —(R)-1-(phenyl)-propyl, and
ll) —(S)-1-(phenyl)-propyl.

Embodiment 26: A compound according to any one of embodiments 1 to 25, wherein
$R^4$ is selected from the group consisting of: hydrogen, $C_{1-10}$ alkyl, $C_{2-10}$ alkenyl, $C_{2-10}$ alkynyl, cycloalkyl, —$C_{1-10}$ alkylene-cycloalkyl, aryl, heteroaryl, and heterocyclyl, wherein the alkyl, alkenyl, alkynyl, cycloalkyl, aryl, heteroaryl, heterocyclyl groups are optionally substituted with one to four substituents independently selected from $R^c$.

Embodiment 27: A compound according to any one of embodiments 1 to 25, wherein
$R^4$ is selected from the group consisting of: hydrogen, —$C_{1-6}$ alkyl and —C(O)—$C_{1-6}$ alkyl.

Embodiment 28: A compound according to any one of embodiments 1 to 27, wherein
$R^5$ is -$G^3$-$L^2$-$Q^2$-$L^3$-$G^4$, wherein $L^2$ is selected from the group consisting of: a direct bond, —$CH_2$—, —O—, —N($R_{26}$)—, —C(O)—, —CON($R_{26}$)—, —N($R^{26}$)C(O)—, —N($R_{26}$)CON($R_{27}$)—, —N($R_{26}$)C(O)O—, —OC(O)N($R_{26}$)—, —N($R_{26}$)$SO_2$—, —$SO_2$N($R_{26}$)—, —C(O)—O—, —O—C(O)—, —S—, —S(O)—, —S(O)$_2$—, and —N($R_{26}$)$SO_2$N($R_{27}$)—, wherein $R^{26}$ and $R^{27}$ are independently selected from the group consisting of: hydrogen, -alkyl, -aryl, and -alkylene-aryl, wherein $R^{26}$ and $R^{27}$ are optionally substituted 1-4 times with $R^c$ or $R^{26}$ and $R^{27}$ are taken together with the atoms to which they are attached to form a heterocyclic ring of 5 to 7 members containing 0-2 additional heteroatoms independently selected from oxygen, nitrogen, and sulfur; $L^3$ is a direct bond; $Q^2$ is selected from the group consisting of: a direct bond, $C_{1-10}$ alkylene, $C_{2-10}$ alkenylene, and $C_{2-10}$ alkynylene; $G^3$ is a phenylene group, wherein $G^3$ is optionally substituted 1-4 times with substituents independently selected from $R^8$, wherein $R^8$ is selected from $R^b$; and $G^4$ is selected from the group consisting of: aryl, cycloalkyl, heterocyclyl, heteroaryl, fused arylcycloalkyl, fused cycloalkylaryl, fused cycloalkyl-heteroaryl, fused heterocyclylaryl, and fused heterocyclylheteroaryl, wherein $G^4$ is optionally substituted 1-4 times with substituents independently selected from $R^9$, wherein $R^9$ is selected from $R^b$.

Embodiment 29: A compound according to any one of embodiments 1 to 28, wherein
$R^5$ is -$G^3$-$L^2$-$Q^2$-$L^3$-$G^4$, wherein $L^2$ is selected from the group consisting of: —$CH_2$—, —O—, —N($R^{26}$)—, and —C(O)—, wherein $R^{26}$ is selected from the group consisting of: hydrogen, -alkyl, -aryl, and -alkylene-aryl; $L^3$ is a direct bond; $Q^2$ is a $C_{1-10}$ alkylene group; $G^3$ is a phenylene group, wherein $G^3$ is optionally substituted 1-4 times with substituents independently selected from $R^8$, wherein $R^8$ is selected from $R^b$; and $G^4$ is selected from the group consisting of: cycloalkyl, phenyl, pyridinyl, benzothiopheneyl, benzothiazolyl, where $G^4$ is optionally substituted 1-4 times with substituents independently selected from $R^9$, wherein $R^9$ is selected from $R^b$.

Embodiment 30: A compound according to any one of embodiments 1 to 29, wherein
$R^5$ is -$G^3$-$L^2$-$Q^2$-$L^3$-$G^4$, wherein $L^2$ is selected from the group consisting of: —$CH_2$—, —O—, —N($R^{26}$)—, and —C(O)—, wherein $R^{26}$ is selected from the group consisting of: hydrogen, -alkyl, -aryl, and -alkylene-aryl; $L^3$ is a direct bond; $Q^2$ is selected from the group consisting of: a direct bond and a $C_{1-10}$ alkylene group; $G^3$ is a phenylene group, wherein $G^3$ is optionally substituted 1-4 times with substituents independently selected from $R^8$, wherein $R^8$ is selected from $R^b$; and $G^4$ is a phenyl group, wherein $G^4$ is substituted 1-4 times with substituents independently selected from $R^9$, wherein $R^9$ is selected from $R^b$, and wherein $G^4$ is substituted with at least one substituent selected from the group consisting of:
a) —$C_{1-6}$ alkyl,
b) -haloalkyl,
c) -halogen,
d) -alkoxy,
e) -haloalkoxy,
f) —$CF_3$, and
g) —O—$CF_3$.

Embodiment 31: A compound according to any one of embodiments 1 to 30, wherein
ring A is

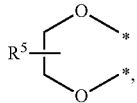

wherein $R^5$ is as described in any one of embodiments 1 to 30.

Embodiment 32: A compound according to any one of embodiments 1 to 30, wherein
W and Z are an oxygen atom; X is —C($R^4$)($R^4$)—; and Y is —C($R^4$)($R^5$)—.

Embodiment 33: A compound according to any one of embodiments 1 to 30, wherein
W and Z are an oxygen atom; X is —$CH_2$—; and Y is —CH($R^5$)—.

Embodiment 34: A compound according to any one of embodiments 1 to 30, wherein
W is —NH—, —N($CH_3$)—, —N($CH_2CH_3$)—, —N(CH($CH_3$)$_2$)—, —N(C(O)$CH_3$)—, —N(C(O)$CH_2CH_3$)—, or —N(C(O)CH($CH_3$)$_2$); Z is an oxygen atom; X is —C($R^4$)($R^4$)—; and Y is —C($R^4$)($R^5$).

Embodiment 35: A compound according to any one of embodiments 1 to 30, wherein
W is —NH—, —N($CH_3$)—, or —N(C(O)$CH_3$)—; Z is an oxygen atom; X is —$CH_2$—; and Y is —CH($R^5$)—.

Embodiment 36: A compound according to embodiment 33 or 35, wherein
Y is —CH($R^5$)—, where the stereocenter on the —CH($R^5$)— carbon has an (R) configuration.

Embodiment 37: A compound according to embodiment 33 or 35, wherein
Y is —CH($R^5$)—, where the stereocenter on the —CH($R^5$)— carbon has an (S) configuration.

Embodiment 38: A compound according to any one of embodiments 1 to 37, wherein
$G^3$ is 1,4-phenylene optionally substituted 1 to 4 times with substituents independently selected from halogen, methyl, ethyl, isopropyl, —$CF_3$, —$CH_2CF_3$, —CN, —$OCH_3$, —$OCH_2CH_3$, —OCH($CH_3$)$_2$, —$OCF_3$, —$OCH_2CF_3$, —S(O)$_2$—$CH_3$, —NH—$CH_3$, —NH—$CH_2CH_3$, —N($CH_3$)$_2$, —N($CH_3$)($CH_2CH_3$), —N($CH_2CH_3$)$_2$, and —C(O)—$CH_3$.

Embodiment 39: A compound according to any one of embodiments 1 to 37, wherein
$G^3$ is 1,3-phenylene optionally substituted 1 to 4 times with substituents independently selected from halogen, methyl, ethyl, isopropyl, —$CF_3$, —$CH_2CF_3$, —CN, —$OCH_3$, —$OCH_2CH_3$, —OCH($CH_3$)$_2$, —$OCF_3$, —$OCH_2CF_3$, —S(O)$_2$—$CH_3$, —NH—$CH_3$, —NH—$CH_2CH_3$, —N($CH_3$)$_2$, —N($CH_3$)($CH_2CH_3$), —N($CH_2CH_3$)$_2$, and —C(O)—$CH_3$.

Embodiment 40: A compound according to any one of embodiments 1 to 39, wherein
$L^2$ is a direct bond; $L^3$ is a direct bond; and $Q^2$ is a direct bond.

Embodiment 41: A compound according to any one of embodiments 1 to 39, wherein
$L^2$ is —O—; $L^3$ is a direct bond; and $Q^2$ is a direct bond.

Embodiment 42: A compound according to any one of embodiments 1 to 39, wherein
$L^2$ is —NH—; $L^3$ is —C(O)—; and $Q^2$ is a direct bond.

Embodiment 43: A compound according to any one of embodiments 1 to 39, wherein
$L^2$ is —O—; $L^3$ is —$CH_2$—; and $Q^2$ is a direct bond.

Embodiment 44: A compound according to any one of embodiments 1 to 39, wherein
$L^2$ is —N($CH_3$)—; $L^3$ is —C(O)—; and $Q^2$ is a direct bond.

Embodiment 45: A compound according to any one of embodiments 1 to 39, wherein
$L^2$ is —O—; $L^3$ is a direct bond; and $Q^2$ is —$CH_2$—.

Embodiment 46: A compound according to any one of embodiments 1 to 39, wherein
$L^2$ is —O—; $L^3$ is a direct bond; and $Q^2$ is —$CH_2CH_2$—.

Embodiment 47: A compound according to any one of embodiments 1 to 46, wherein
$G^4$ is -phenyl optionally substituted 1-4 times with substituents independently selected from $R^9$.

Embodiment 48: A compound according to any one of embodiments 1 to 47, wherein
$G^4$ is phenyl optionally substituted 1 to 4 times with substituents independently selected from halogen, methyl, ethyl, isopropyl, —$CF_3$, —$CH_2CF_3$, —CN, —$OCH_3$, —$OCH_2CH_3$, —OCH($CH_3$)$_2$, —$OCF_3$, —$OCH_2CF_3$, —S(O)$_2$—$CH_3$, —NH—$CH_3$, —NH—$CH_2CH_3$, —N($CH_3$)$_2$, —N($CH_3$)($CH_2CH_3$), —N($CH_2CH_3$)$_2$, and —C(O)—$CH_3$.

Embodiment 49: A compound according to any one of embodiments 1 to 48, wherein
$G^4$ is phenyl optionally substituted 1 to 4 times with substituents independently selected from fluoro, chloro, methyl, —$CF_3$, —$OCH_3$, and —$OCF_3$.

Embodiment 50: A compound according to any one of embodiments 1 to 46, wherein
$G^4$ is -heteroaryl optionally substituted 1-4 times with substituents independently selected from $R^9$.

Embodiment 51: A compound according to any one of embodiments 1 to 46, wherein
$G^4$ is pyridin-2-yl, pyridin-3-yl, pyridin-4-yl, pyrimidin-2-yl, pyrimidin-4-yl, pyrimidin-5-yl, pyridazin-3-yl, pyridazin-4-yl, or pyrazin-2-yl, where each is optionally substituted 1 to 4 times with substituents independently selected from halogen, methyl, ethyl, isopropyl, —$CF_3$, —$CH_2CF_3$, —CN, —$OCH_3$, —$OCH_2CH_3$, —OCH($CH_3$)$_2$, —$OCF_3$, —$OCH_2CF_3$, —S(O)$_2$—$CH_3$, —NH—$CH_3$, —NH—$CH_2CH_3$, —N($CH_3$)$_2$, —N($CH_3$)($CH_2CH_3$), —N($CH_2CH_3$)$_2$, and —C(O)—$CH_3$.

Embodiment 52: A compound according to any one of embodiments 1 to 46, wherein
G⁴ is pyridin-2-yl or pyridin-3-yl, where each is optionally substituted 1 to 4 times with substituents independently selected from fluoro, chloro, methyl, —CF₃, —OCH₃, and —OCF₃.

Embodiment 53: A compound according to any one of embodiments 1 to 46, wherein
G⁴ is -cycloalkyl optionally substituted 1-4 times with substituents independently selected from R⁹.

Embodiment 54: A compound according to any one of embodiments 1 to 46, wherein
G⁴ is cyclopropyl, cyclobutyl, cyclopentyl, cyclohexyl, cyclopentyl, norborn-1-yl, norborn-2-yl, norborn-7-yl, adamant-1-yl, or adamant-2-yl, where each is optionally substituted 1 to 4 times with substituents independently selected from halogen, methyl, ethyl, isopropyl, —CF₃, —CH₂CF₃, —CN, —OCH₃, —OCH₂CH₃, —OCH(CH₃)₂, —OCF₃, —OCH₂CF₃, —S(O)₂—CH₃, —NH—CH₃, —NH—CH₂CH₃, —N(CH₃)₂, —N(CH₃)(CH₂CH₃), —N(CH₂CH₃)₂, and —C(O)—CH₃.

Embodiment 55: A compound according to any one of embodiments 1 to 46, wherein
G⁴ is cyclopentyl, cyclohexyl, or norborn-1-yl, where each is optionally substituted 1 to 4 times with substituents independently selected from fluoro, chloro, methyl, —CF₃, —OCH₃, and —OCF₃.

Embodiment 56: A compound according to any one of embodiments 1 to 46, wherein
G⁴ is cyclohexyl optionally substituted 1 to 4 times with substituents independently selected from fluoro, chloro, methyl, ethyl, isopropyl, n-propyl, sec-butyl, isobutyl, tert-butyl, —CF₃, —CH₂CF₃, —OCH₃, —OCH₂CH₃, —OCH(CH₃)₂, —OC(CH₃)₃, —OCF₃, and —OCH₂CF₃.

Embodiment 57: A compound according to any one of embodiments 1 to 46, wherein
G⁴ is cyclopentyl optionally substituted 1 to 4 times with substituents independently selected from fluoro, chloro, methyl, ethyl, isopropyl, n-propyl, sec-butyl, isobutyl, tert-butyl, —CF₃, —CH₂CF₃, —OCH₃, —OCH₂CH₃, —OCH(CH₃)₂, —OC(CH₃)₃, —OCF₃, and —OCH₂CF₃.

Embodiment 58: A compound according to any one of embodiments 1 to 46, wherein
G⁴ is selected from the group consisting of: aryl, cycloalkyl, heterocyclyl, heteroaryl, fused arylcycloalkyl, fused cycloalkylaryl, fused cycloalkylheteroaryl, fused heterocyclylaryl, and fused heterocyclyl-heteroaryl, wherein G⁴ is optionally substituted 1-4 times with substituents independently selected from R⁹, wherein R⁹ is selected from R^b;
or G⁴ is —C₁₋₈ alkyl, —C₂₋₈ alkenyl, —C₂₋₆ alkynyl, —C₁₋₆ alkylene-G⁵, —C₂₋₆ alkenylene-G⁵, or —C₂₋₆ alkynylene-G⁵, where the alkyl, alkenyl, alkynyl, alkylene, alkenylene, and alkynylene groups are optionally substituted one or more times with substituents independently selected from R^y; and G⁵ is -phenyl, —C₃₋₁₀ cycloalkyl, -heterocyclyl, -heteroaryl, -fused arylcycloalkyl, -fused cycloalkylaryl, -fused cycloalkyl-heteroaryl, -fused heterocyclylaryl, and -fused heterocyclyl-heteroaryl, wherein each member of G⁵ is optionally substituted one or more times with substituents independently selected from R^y.

Embodiment 59: A compound according to any one of embodiments 1 to 46, wherein
G⁴ is —C₁₋₈ alkyl optionally substituted one or more times with substituents independently selected from R^y.

Embodiment 60: A compound according to any one of embodiments 1 to 46, wherein
G⁴ is methyl, ethyl, n-propyl, isopropyl, n-butyl, isobutyl, sec-butyl, tert-butyl, neopentyl, or 2,2-dimethylbut-4-yl, where each is optionally substituted one or more times with substituents independently selected from halogen, —CF₃, —CN, —OCH₃, —OCH₂CH₃, —OCH(CH₃)₂, —OCF₃, —OCH₂CF₃, —S(O)₂—CH₃, —NH—CH₃, —NH—CH₂CH₃, —N(CH₃)₂, —N(CH₃)(CH₂CH₃), —N(CH₂CH₃)₂, and —C(O)—CH₃.

Embodiment 61: A compound according to any one of embodiments 1 to 46, wherein
G⁴ is (—(CH₂)₁₋₄—R^y, —CH(CH₃)—R^y, —CH₂CH(CH₃)—R^y, —CH(CH₃)—CH₂—R^y, —CH₂CH₂CH(CH₃)—R^y, or —(CH₂)₁₋₃—C(CH₃)₂—(CH₂)₀₋₁R^y.

Embodiment 62: A compound according to embodiment 61, wherein
R^y is selected from halogen, —CF₃, —CN, —OCH₃, —OCH₂CH₃, —OCH(CH₃)₂, —OCF₃, —OCH₂CF₃, —S(O)₂—CH₃, —NH—CH₃, —NH—CH₂CH₃, —N(CH₃)₂, —N(CH₃)(CH₂CH₃), —N(CH₂CH₃)₂, and —C(O)—CH₃.

Embodiment 63: A compound according to any one of embodiments 1 to 46, wherein
G⁴ is methyl, ethyl, n-propyl, isopropyl, n-butyl, isobutyl, sec-butyl, tert-butyl, neopentyl, or 2,2-dimethylbut-4-yl.

Embodiment 64: A compound according to any one of embodiments 1 to 46, wherein
G⁴ is —C₃₋₁₀ cycloalkylene-G⁵, where the cycloalkynylene group is optionally substituted one or more times with substituents independently selected from R^y; and G⁵ is -phenyl, —C₃₋₁₀ cycloalkyl, -heterocyclyl, -heteroaryl, -fused arylcycloalkyl, -fused cycloalkylaryl, -fused cycloalkyl-heteroaryl, -fused heterocyclylaryl, and -fused heterocyclyl-heteroaryl, wherein each member of G⁵ is optionally substituted one or more times with substituents independently selected from R^y.

Embodiment 65: A compound according to embodiment 64, wherein
G⁴ is

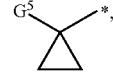

where G⁵ is phenyl optionally substituted one or more times with substituents independently selected from R^y.

Embodiment 66: A compound according to any one of embodiments 1 to 65, wherein
R² is hydrogen.

Embodiment 67: A compound according to any one of embodiments 1 to 65, wherein
R² is methyl.

Embodiment 68: A compound according to any one of embodiments 1 to 67, wherein
R¹ is —CO₂H.

Embodiment 69: A compound according to any one of embodiments 1 to 67, wherein
R¹ is —CO₂CH₃.

Embodiment 70: A compound according to any one of embodiments 1 to 67, wherein
R¹ is —CONH₂.

Embodiment 71: A compound according to any one of embodiments 1 to 67, wherein
R¹ is —CONH—CH₃.

Embodiment 72: A compound according to any one of embodiments 1 to 67, wherein
R¹ is isoxazol-3-ol-5-yl, 1H-tetrazole-5-yl, 2H-tetrazole-5-yl, imidazolidine-2,4-dione-5-yl, imidazolidine-2,4-dione-1-yl, 1,3-thiazolidine-2,4-dione-5-yl, 5-hydroxy-4H-pyran-4-on-2-yl, 1,2,5-thiadiazolidin-3-one-1,1-dioxide-4-yl, or 1,2-5-thiadiazolidin-3-one-1,1-dioxide-5-yl.

Embodiment 73: A compound according to any one of embodiments 1 to 72, wherein
$R^q$ is hydrogen.

Embodiment 74: A compound according to any one of embodiments 1 to 72, wherein
$R^q$ is methyl.

Embodiment 75: A compound according to any one of embodiments 1 to 74, wherein
p is 1.

Embodiment 76: A compound according to any one of embodiments 1 to 74, wherein
p is 2.

Embodiment 77: A compound according to any one of embodiments 1 to 76, wherein
L¹ is a direct bond.

Embodiment 78: A compound according to any one of embodiments 1 to 76, wherein
L¹ is —O—.

Embodiment 79: A compound according to any one of embodiments 1 to 76, wherein
L¹ is —C≡C—.

Embodiment 80: A compound according to any one of embodiments 1 to 79, wherein
G¹ is 1,4-phenylene optionally substituted 1 to 4 times with substituents independently selected from halogen, methyl, ethyl, isopropyl, —CF₃, —CH₂CF₃, —CN, —OCH₃, —OCH₂CH₃, —OCH(CH₃)₂, —OCF₃, —OCH₂CF₃, —S(O)₂—CH₃, —NH—CH₃, —NH—CH₂CH₃, —N(CH₃)₂, —N(CH₃)(CH₂CH₃), —N(CH₂CH₃)₂, and —C(O)—CH₃.

Embodiment 81: A compound according to any one of embodiments 1 to 79, wherein
G¹ is thiophen-2,5-diyl optionally substituted 1 to 4 times with substituents independently selected from halogen, methyl, ethyl, isopropyl, —CF₃, —CH₂CF₃, —CN, —OCH₃, —OCH₂CH₃, —OCH(CH₃)₂, —OCF₃, —OCH₂CF₃, —S(O)₂—CH₃, —NH—CH₃, —NH—CH₂CH₃, —N(CH₃)₂, —N(CH₃)(CH₂CH₃), —N(CH₂CH₃)₂, and —C(O)—CH₃.

Embodiment 82: A compound according to any one of embodiments 1 to 79, wherein
G¹ is furan-2,5-diyl optionally substituted 1 to 4 times with substituents independently selected from halogen, methyl, ethyl, isopropyl, —CF₃, —CH₂CF₃, —CN, —OCH₃, —OCH₂CH₃, —OCH(CH₃)₂, —OCF₃, —OCH₂CF₃, —S(O)₂—CH₃, —NH—CH₃, —NH—CH₂CH₃, —N(CH₃)₂, —N(CH₃)(CH₂CH₃), —N(CH₂CH₃)₂, and —C(O)—CH₃.

Embodiment 83: A compound according to any one of embodiments 1 to 82, wherein
G² is phenyl optionally substituted 1 to 4 times with substituents independently selected from halogen, methyl, ethyl, isopropyl, n-propyl, —CF₃, —CH₂CF₃, —CN, —OH, —OCH₃, —OCH₂CH₃, —OCH(CH₃)₂, —OCF₃, —OCH₂CF₃, —S(O)₂—CH₃, —NH₂, —NH—CH₃, —NH—CH₂CH₃, —N(CH₃)₂, —N(CH₃)(CH₂CH₃), —N(CH₂CH₃)₂, —CH₂OH, —CH₂F, and —C(O)—CH₃.

Embodiment 84: A compound according to any one of embodiments 1 to 82, wherein
G² is pyridin-2-yl optionally substituted 1 to 4 times with substituents independently selected from R¹¹.

Embodiment 85: A compound according to any one of embodiments 1 to 82, wherein
G² is pyridin-3-yl optionally substituted 1 to 4 times with substituents independently selected from R¹¹.

Embodiment 86: A compound according to any one of embodiments 1 to 82, wherein
G² is pyridin-4-yl optionally substituted 1 to 4 times with substituents independently selected from R¹¹.

Embodiment 87: A compound according to any one of embodiments 1 to 82, wherein
G² is pyridazin-3-yl optionally substituted 1 to 3 times with substituents independently selected from R¹¹.

Embodiment 88: A compound according to any one of embodiments 1 to 82, wherein
G² is pyridazin-4-yl optionally substituted 1 to 3 times with substituents independently selected from R¹¹.

Embodiment 89: A compound according to any one of embodiments 1 to 82, wherein
G² is pyrimidin-2-yl optionally substituted 1 to 3 times with substituents independently selected from R¹¹.

Embodiment 90: A compound according to any one of embodiments 1 to 82, wherein
G² is pyrimidin-4-yl optionally substituted 1 to 3 times with substituents independently selected from R¹¹.

Embodiment 91: A compound according to any one of embodiments 1 to 82, wherein
G² is pyrimidin-5-yl optionally substituted 1 to 3 times with substituents independently selected R¹¹.

Embodiment 92: A compound according to any one of embodiments 1 to 82, wherein
G² is pyrazin-2-yl optionally substituted 1 to 3 times with substituents independently selected from R¹¹.

Embodiment 93: A compound according to any one of embodiments 1 to 82, wherein
G² is 2H-pyrazol-3-yl or 2H-pyrazol-4-yl, where each is optionally substituted 1 to 3 times with substituents independently selected from halogen, methyl, ethyl, isopropyl, n-propyl, —CF₃, —CH₂CF₃, —CN, —OH, —OCH₃, —OCH₂CH₃, —OCH(CH₃)₂, —OCF₃, —OCH₂CF₃, —S(O)₂—CH₃, —NH₂, —NH—CH₃, —NH—CH₂CH₃, —N(CH₃)₂, —N(CH₃)(CH₂CH₃), —N(CH₂CH₃)₂, —CH₂OH, —CH₂F, and —C(O)—CH₃.

Embodiment 94: A compound according to any one of embodiments 1 to 82, wherein
G² is

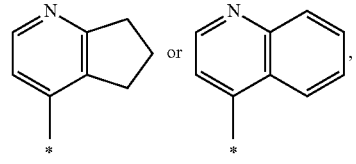

where each is optionally substituted 1 to 4 times with substituents independently selected from halogen, methyl, ethyl, isopropyl, n-propyl, —CF₃, —CH₂CF₃, —CN, —OH, —OCH₃, —OCH₂CH₃, —OCH(CH₃)₂, —OCF₃, —OCH₂CF₃, —S(O)₂—CH₃, —NH₂, —NH—CH₃, —NH—CH₂CH₃, —N(CH₃)₂, —N(CH₃)(CH₂CH₃), —N(CH₂CH₃)₂, —CH₂OH, —CH₂F, and —C(O)—CH₃.

Embodiment 95: A compound according to any one of embodiments 1 to 94, wherein
R³ is —H.

Embodiment 96: A compound according to any one of embodiments 1 to 94, wherein
R³ is Rᵃ.

Embodiment 97: A compound according to any one of embodiments 1 to 94, wherein
R³ is Rʰ.

Embodiment 98: A compound according to embodiment 96, wherein
R³ is —S(O)₂—Rᵈ.

Embodiment 99: A compound according to embodiment 97, wherein
R³ is —S(O)₂—Rʲ.

Embodiment 100: A compound according to embodiment 96, wherein
R³ is —S(O)₂-phenyl, where the phenyl group is optionally substituted one to four times with substituents independently selected from halogen, —NH₂, —NH-alkyl, —N(alkyl)₂, —CN, —C₁₋₄ alkyl, —O—C₁₋₄ alkyl, —O—CF₃, cycloalkyl, —OH, —CF₃, -haloalkyl, -haloalkoxy, -heteroaryl, and -aryl.

Embodiment 101: A compound according to embodiment 96, wherein
R³ is —S(O)₂-phenyl, where the phenyl group is optionally substituted one to four times with substituents independently selected from halogen, —NH₂, —NH—CH₃, —NH—CH₂CH₃, —N(CH₃)₂, —N(CH₃)—CH₂CH₃, —N(CH₂CH₃)₂, —CN, methyl, ethyl, isopropyl, isobutyl, sec-butyl, tert-butyl, —O—CH₃, —O—CH₂CH₃, —O—CH(CH₃)₂, —O—CF₃, —O—CH₂CF₃, —CF₃, —O—CH₂CF₃, thiazol-5-yl, and 2-methyl-thiazol-5-yl.

Embodiment 102: A compound according to embodiment 97, wherein
R³ is —S(O)₂-phenyl, where the phenyl group is optionally substituted one or more times with substituents independently selected from Rˣ.

Embodiment 103: A compound according to embodiment 97, wherein
R³ is —S(O)₂-phenyl, where the phenyl group is optionally substituted one or more times with substituents independently selected from halogen, —NH₂, —NH—CH₃, —NH—CH₂CH₃, —N(CH₃)₂, —N(CH₃)—CH₂CH₃, —N(CH₂CH₃)₂, —CN, —NO₂, methyl, ethyl, isopropyl, isobutyl, sec-butyl, tert-butyl, —S(O)₂—CH₃, —O—CH₃, —O—CH₂CH₃, —O—CH(CH₃)₂, —O—CF₃, —O—CH₂CF₃, —CF₃, —O—CH₂CF₃, —NH—C(O)—CH₃, —NH—C(O)—CH₂CH₃, —N(CH₃)—C(O)—CH₃, —N(CH₃)—C(O)—CH₂CH₁, thiazol-4-yl, thiazol-5-yl, 2-methyl-thiazol-5-yl

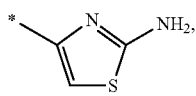

and

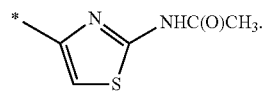

Embodiment 104: A compound according to embodiment 96, wherein
R³ is —S(O)₂-heteroaryl, where the heteroaryl group is optionally substituted one to four times with substituents independently selected from Rᶜ.

Embodiment 105: A compound according to embodiment 96, wherein
R³ is —S(O)₂-heteroaryl, where the heteroaryl group is optionally substituted one to four times with substituents independently selected from methyl, ethyl, isopropyl, isobutyl, sec-butyl, tert-butyl, —NH₂, —NH—(CH₂)₀₋₄—CH₃, —NH—(CH₂)₀₋₂—CH(CH₃)₂, —NH—(CH₂)₀₋₂—C(CH₃)₃, —NH-cyclopropyl, —NH-cyclobutyl, —NH-cyclopentyl, —NH-cyclohexyl, —CF₃, —CH₂CF₃, —O—CH₃, —OCH₂CH₃, —O—CH(CH₃)₂, —O—CF₃, —O—CH₂CF₃, -phenyl, —(CH₂)₁₋₂-phenyl, —CH(CH₃)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl.

Embodiment 106: A compound according to embodiment 96, wherein
R³ is —S(O)₂-(furan-2-yl), —S(O)₂-(furan-3-yl), —S(O)₂-(thiophen-2-yl), —S(O)₂-(thiophen-3-yl), —S(O)₂-(1H-pyrrol-1-yl), —S(O)₂-(1H-pyrrol-2-yl), —S(O)₂-(1H-pyrrol-3-yl), —S(O)₂-(oxazol-2-yl), —S(O)₂-(oxazol-4-yl), —S(O)₂-(oxazol-5-yl), —S(O)₂-(isoxazol-3-yl), —S(O)₂-(isoxazol-4-yl), —S(O)₂-(isoxazol-5-yl), —S(O)₂-(thiazol-2-yl), —S(O)₂-(thiazol-4-yl), —S(O)₂-(thiazol-5-yl), —S(O)₂-(isothiazol-3-yl), —S(O)₂-(isothiazol-4-yl), —S(O)₂-(isothiazol-5-yl), —S(O)₂-(1H-imidazol-1-yl), —S(O)₂-(1H-imidazol-2-yl), —S(O)₂-(1H-imidazol-4-yl), —S(O)₂-(1H-imidazol-5-yl), —S(O)₂-(1H-pyrazol-1-yl), —S(O)₂-(1H-pyrazol-3-yl), —S(O)₂-(1H-pyrazol-4-yl), —S(O)₂-(1H-pyrazol-5-yl), —S(O)₂-(2-pyridyl), —S(O)₂-(3-pyridyl), —S(O)₂-(4-pyridyl), —S(O)₂-(pyridazin-3-yl), —S(O)₂-(pyridazin-4-yl), —S(O)₂-(pyrimidin-2-yl), —S(O)₂-(pyrimidin-4-yl), —S(O)₂-(pyrimidin-5-yl), or —S(O)₂-(pyrazin-2-yl), where each named heteroaryl ring is optionally substituted one to four times with substituents independently selected from Rᶜ.

Embodiment 107: A compound according to embodiment 96, wherein
R³ is —S(O)₂-(thiazol-5-yl), where the thiazole ring is optionally substituted one to two times with substituents independently selected from methyl, ethyl, isopropyl, isobutyl, sec-butyl, tert-butyl, —NH₂, —NH—(CH₂)₀₋₄—CH₃, —NH—(CH₂)₀₋₂—CH(CH₃)₂, —NH—(CH₂)₀₋₂—C(CH₃)₃, —NH-cyclopropyl, —NH-cyclobutyl, —NH-cyclopentyl, —NH-cyclohexyl, —CF₃, —CH₂CF₃, —O—CH₃, —OCH₂CH₃, —O—CH(CH₃)₂, —O—CF₃, —O—CH₂CF₃, -phenyl, —(CH₂)₁₋₂-phenyl, —CH(CH₃)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl.

Embodiment 108: A compound according to embodiment 96, wherein
R³ is —S(O)₂-(oxazol-4-yl), where the oxazole ring is optionally substituted one to two times with substituents independently selected from methyl, ethyl, isopropyl, isobutyl, sec-butyl, tert-butyl, —NH₂, —NH—(CH₂)₀₋₄—CH₃, —NH—(CH₂)₀₋₂—CH(CH₃)₂, —NH—(CH₂)₀₋₂—C(CH₃)₃, —NH-cyclopropyl, —NH-cyclobutyl, —NH-cyclopentyl, —NH-cyclohexyl, —CF₃, —CH₂CF₃, —O—CH₃, —OCH₂CH₃, —O—CH(CH₃)₂, —O—CF₃, —O—CH₂CF₃, -phenyl, —(CH₂)₁₋₂-phenyl, —CH(CH₃)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl.

Embodiment 109: A compound according to embodiment 96, wherein
R³ is —S(O)₂-(isoxazol-4-yl), where the isoxazole ring is optionally substituted one to four times with substituents independently selected from methyl, ethyl, isopropyl, isobutyl, sec-butyl, tert-butyl, —NH₂, —NH—(CH₂)₀₋₄—CH₃, —NH—(CH₂)₀₋₂—CH(CH₃)₂, —NH—(CH₂)₀₋₂—C(CH₃)₃, —NH-cyclopropyl, —NH-cyclobutyl, —NH-cyclopentyl, —NH-cyclohexyl, —CF₃, —CH₂CF₃, —O—CH₃, —OCH₂CH₃, —O—CH(CH₃)₂, —O—CF₃, —O—CH₂CF₃, -phenyl, —(CH₂)₁₋₂-phenyl, —CH(CH₃)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl.

Embodiment 110: A compound according to embodiment 96, wherein
R³ is —S(O)₂-(3-pyridyl), where the pyridine ring is optionally substituted one to two times with substituents independently selected from methyl, ethyl, isopropyl, isobutyl, sec-butyl, tert-butyl, —NH₂, —NH—(CH₂)₀₋₄—CH₃, —NH—(CH₂)₀₋₂—CH(CH₃)₂, —NH—(CH₂)₀₋₂—C(CH₃)₃, —NH-cyclopropyl, —NH-cyclobutyl, —NH-cyclopentyl, —NH-cyclohexyl, —CF₃, —CH₂CF₃, —O—CH₃, —OCH₂CH₃, —O—CH(CH₃)₂, —O—CF₃, —O—CH₂CF₃, -phenyl, —(CH₂)₁₋₂-phenyl, —CH(CH₃)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl.

Embodiment 111: A compound according to embodiment 96, wherein
R³ is —S(O)₂-(thiazol-4-yl), where the thiazole ring is optionally substituted one to two times with substituents independently selected from R$^c$.

Embodiment 112: A compound according to embodiment 97, wherein
R³ is —S(O)₂-heteroaryl, where the heteroaryl group is optionally substituted one or more times with substituents independently selected from R$^x$.

Embodiment 113: A compound according to embodiment 97, wherein
R³ is —S(O)₂-heteroaryl, where the heteroaryl group is optionally substituted one or more times with substituents independently selected from methyl, ethyl, isopropyl, isobutyl, sec-butyl, tert-butyl, —S(O)₂—CH₃, —NH₂, —NH—(CH₂)₀₋₄—CH₃, —NH—(CH₂)₀₋₂—CH(CH₃)₂, —NH—(CH₂)₀₋₂—C(CH₃)₃, —NH-cyclopropyl, —NH-cyclobutyl, —NH-cyclopentyl, —NH-cyclohexyl, —CF₃, —CH₂CF₃, —O—CH₃, —OCH₂CH₃, —O—CH(CH₃)₂, —O—CF₃, —O—CH₂CF₃, -phenyl, —(CH₂)₁₋₂-phenyl, —CH(CH₃)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, 2-oxo-piperazin-1-yl, —NH—C(O)—(CH₂)₀₋₂—CH₃, —NH—C(O)—(CH₂)₀₋₁—CH(CH₃)₂, —NH—C(O)—(CH₂)₀₋₁—CF₃, —NH—C(O)-phenyl, —NH—C(O)-cyclopropyl, —NH—C(O)-cyclobutyl, —NH—C(O)—cyclopentyl, —NH—C(O)-cyclohexyl, —NH—C(O)-(pyrrolidin-2-yl), NH—C(O)-(1-methyl-pyrrolidin-2-yl), NH—C(O)-(1-tert-butoxycarbonyl-pyrrolidin-2-yl), —NH—C(O)-(piperazin-1-yl), NH—C(O)-(4-methyl-piperazin-1-yl), NH—C(O)-(4-tert-butoxycarbonyl-piperazin-1-yl), —NH—C(O)-(piperidin-4-yl), NH—C(O)-(1-methyl-piperidin-4-yl), NH—C(O)-(1-tert-butoxycarbonyl-piperidin-4-yl), —NH—C(O)-(tetrahydropyran-4-yl), —NH—(CH₂)₁₋₂-phenyl, —NH—(CH₂)₁₋₂-cyclopropyl, —NH—(CH₂)₁₋₂-cyclobutyl, —NH—(CH₂)₁₋₂-cyclopentyl, —NH—(CH₂)₁₋₂-cyclohexyl, —NH—(CH₂)₁₋₂—O—CH₃, —NH—(CH₂)₁₋₂—O—CH₂CH₃, —NH—(CH₂)₁₋₂—O—CF₃, —NH—(CH₂)₁₋₂—N(CH₃)₂, —NH—C(O)—NH—(CH₂)₀₋₁—CH₃, —NH—C(O)—NH—(CH₂)₀₋₁-cyclopropyl, —NH—C(O)—NH—(CH₂)₀₋₁-cyclobutyl, —NH—C(O)—NH—(CH₂)₀₋₁-cyclopentyl, and —NH—C(O)—NH—(CH₂)₀₋₁-cyclohexyl.

Embodiment 114: A compound according to embodiment 97, wherein
R³ is —S(O)₂-(furan-2-yl), —S(O)₂-(furan-3-yl), —S(O)₂-(thiophen-2-yl), —S(O)₂-(thiophen-3-yl), —S(O)₂-(1H-pyrrol-1-yl), —S(O)₂-(1H-pyrrol-2-yl), —S(O)₂-(1H-pyrrol-3-yl), —S(O)₂-(oxazol-2-yl), —S(O)₂-(oxazol-4-yl), —S(O)₂-(oxazol-5-yl), —S(O)₂-(isoxazol-3-yl), —S(O)₂-(isoxazol-4-yl), —S(O)₂-(isoxazol-5-yl), —S(O)₂-(thiazol-2-yl), —S(O)₂-(thiazol-4-yl), —S(O)₂-(thiazol-5-yl), —S(O)₂-(isothiazol-3-yl), —S(O)₂-(isothiazol-4-yl), —S(O)₂-(isothiazol-5-yl), —S(O)₂-(1H-imidazol-1-yl), —S(O)₂-(1H-imidazol-2-yl), —S(O)₂-(1H-imidazol-4-yl), —S(O)₂-(1H-imidazol-5-yl), —S(O)₂-(1H-pyrazol-1-yl), —S(O)₂-(1H-pyrazol-3-yl), —S(O)₂-(1H-pyrazol-4-yl), —S(O)₂-(1H-pyrazol-5-yl), —S(O)₂-(2-pyridyl), —S(O)₂-(3-pyridyl), —S(O)₂-(4-pyridyl), —S(O)₂-(pyridazin-3-yl), —S(O)₂-(pyridazin-4-yl), —S(O)₂-(pyrimidin-2-yl), —S(O)₂-(pyrimidin-4-yl), —S(O)₂-(pyrimidin-5-yl), or —S(O)₂-(pyrazin-2-yl), where each named heteroaryl ring is optionally substituted one or more times with substituents independently selected from R$^x$.

Embodiment 115: A compound according to embodiment 97, wherein
R³ is —S(O)₂-(thiazol-5-yl), where the thiazole ring is optionally substituted one or more times with substituents independently selected from methyl, ethyl, isopropyl, isobutyl, sec-butyl, tert-butyl, —S(O)₂—CH₃, —NH₂, —NH—(CH₂)₀₋₄—CH₃, —NH—(CH₂)₀₋₂—CH(CH₃)₂, —NH—(CH₂)₀₋₂—C(CH₃)₃, —NH-cyclopropyl, —NH-cyclobutyl, —NH-cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl, —NH—C(O)—(CH$_2$)$_{0-2}$—CH$_3$, —NH—C(O)—(CH$_2$)$_{0-1}$—CH(CH$_3$)$_2$, —NH—C(O)—(CH$_2$)$_{0-1}$—CF$_3$, —NH—C(O)-phenyl, —NH—C(O)-cyclopropyl, —NH—C(O)-cyclobutyl, —NH—C(O)-cyclopentyl, —NH—C(O)-cyclohexyl, —NH—C(O)-(pyrrolidin-2-yl), —NH—C(O)-(1-methyl-pyrrolidin-2-yl), —NH—C(O)-(1-tert-butoxycarbonyl-pyrrolidin-2-yl), —NH—C(O)-(piperazin-1-yl), —NH—C(O)-(4-methyl-piperazin-1-yl), —NH—C(O)-(4-tert-butoxycarbonyl-piperazin-1-yl), —NH—C(O)-(piperidin-4-yl), NH—C(O)-(1-methyl-piperidin-4-yl), NH—C(O)-(1-tert-butoxy-carbonyl-piperidin-4-yl), —NH—C(O)-(tetrahydropyran-4-yl), —NH—(CH$_2$)$_{1-2}$-phenyl, —NH—(CH$_2$)$_{1-2}$-cyclopropyl, —NH—(CH$_2$)$_{1-2}$-cyclobutyl, —NH—(CH$_2$)$_{1-2}$-cyclopentyl, —NH—(CH$_2$)$_{1-2}$-cyclohexyl, —NH—(CH$_2$)$_{1-2}$—O—CH$_3$, —NH—(CH$_2$)$_{1-2}$—O—CH$_2$CH$_3$, —NH—(CH$_2$)$_{1-2}$—O—CF$_3$, —NH—(CH$_2$)$_{1-2}$—N(CH$_3$)$_2$, —NH—C(O)—NH—(CH$_2$)$_{0-1}$—CH$_3$, —NH—C(O)—NH—(CH$_2$)$_{0-1}$-cyclopropyl, —NH—C(O)—NH—(CH$_2$)$_{0-1}$-cyclobutyl, —NH—C(O)—NH—(CH$_2$)$_{0-1}$-cyclopentyl, and —NH—C(O)—NH—(CH$_2$)$_{0-1}$-cyclohexyl.

Embodiment 116: A compound according to embodiment 97, wherein

R$^3$ is —S(O)$_2$-(oxazol-4-yl), where the oxazole ring is optionally substituted one or more times with substituents independently selected from methyl, ethyl, isopropyl, isobutyl, sec-butyl, tert-butyl, —S(O)$_2$—CH$_3$, —NH$_2$, —NH—(CH$_2$)$_{0-4}$—CH$_3$, —NH—(CH$_2$)$_{0-2}$—CH(CH$_3$)$_2$, —NH—(CH$_2$)$_{0-2}$—C(CH$_3$)$_3$, —NH-cyclopropyl, —NH-cyclobutyl, —NH-cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl, —NH—C(O)—(CH$_2$)$_{0-2}$—CH$_3$, —NH—C(O)—(CH$_2$)$_{0-1}$—CH(CH$_3$)$_2$, —NH—C(O)—(CH$_2$)$_{0-1}$—CF$_3$, —NH—C(O)-phenyl, —NH—C(O)-cyclopropyl, —NH—C(O)-cyclobutyl, —NH—C(O)-cyclopentyl, —NH—C(O)-cyclohexyl, —NH—C(O)-(pyrrolidin-2-yl), —NH—C(O)-(1-methyl-pyrrolidin-2-yl), —NH—C(O)-(1-tert-butoxycarbonyl-pyrrolidin-2-yl), —NH—C(O)-(piperazin-1-yl), —NH—C(O)-(4-methyl-piperazin-1-yl), —NH—C(O)-(4-tert-butoxycarbonyl-piperazin-1-yl), —NH—C(O)-(piperidin-4-yl), NH—C(O)-(1-methyl-piperidin-4-yl), NH—C(O)-(1-tert-butoxy-carbonyl-piperidin-4-yl), —NH—C(O)-(tetrahydropyran-4-yl), —NH—(CH$_2$)$_{1-2}$-phenyl, —NH—(CH$_2$)$_{1-2}$-cyclopropyl, —NH—(CH$_2$)$_{1-2}$-cyclobutyl, —NH—(CH$_2$)$_{1-2}$-cyclopentyl, —NH—(CH$_2$)$_{1-2}$-cyclohexyl, —NH—(CH$_2$)$_{1-2}$—O—CH$_3$, —NH—(CH$_2$)$_{1-2}$—O—CH$_2$CH$_3$, —NH—(CH$_2$)$_{1-2}$—O—CF$_3$, —NH—(CH$_2$)$_{1-2}$—N(CH$_3$)$_2$, —NH—C(O)—NH—(CH$_2$)$_{0-1}$—CH$_3$, —NH—C(O)—NH—(CH$_2$)$_{0-1}$-cyclopropyl, —NH—C(O)—NH—(CH$_2$)$_{0-1}$-cyclobutyl, —NH—C(O)—NH—(CH$_2$)$_{0-1}$-cyclopentyl, and —NH—C(O)—NH—(CH$_2$)$_{0-1}$-cyclohexyl.

Embodiment 117: A compound according to embodiment 97, wherein

R$^3$ is —S(O)$_2$-(isoxazol-4-yl), where the isoxazole ring is optionally substituted one or more times with substituents independently selected from methyl, ethyl, isopropyl, isobutyl, sec-butyl, tert-butyl, —S(O)$_2$—CH$_3$, —NH$_2$, —NH—(CH$_2$)$_{0-4}$—CH$_3$, —NH—(CH$_2$)$_{0-2}$—CH(CH$_3$)$_2$, —NH—(CH$_2$)$_{0-2}$—C(CH$_3$)$_3$, —NH-cyclopropyl, —NH-cyclobutyl, —NH-cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl, —NH—C(O)—(CH$_2$)$_{0-2}$—CH$_3$, —NH—C(O)—(CH$_2$)$_{0-1}$—CH(CH$_3$)$_2$, —NH—C(O)—(CH$_2$)$_{0-1}$—CF$_3$, —NH—C(O)-phenyl, —NH—C(O)-cyclopropyl, —NH—C(O)-cyclobutyl, —NH—C(O)-cyclopentyl, —NH—C(O)-cyclohexyl, —NH—C(O)-(pyrrolidin-2-yl), —NH—C(O)-(1-methyl-pyrrolidin-2-yl), —NH—C(O)-(1-tert-butoxycarbonyl-pyrrolidin-2-yl), —NH—C(O)-(piperazin-1-yl), —NH—C(O)-(4-methyl-piperazin-1-yl), —NH—C(O)-(4-tert-butoxycarbonyl-piperazin-1-yl), —NH—C(O)-(piperidin-4-yl), NH—C(O)-(1-methyl-piperidin-4-yl), NH—C(O)-(1-tert-butoxy-carbonyl-piperidin-4-yl), —NH—C(O)-(tetrahydropyran-4-yl), —NH—(CH$_2$)$_{1-2}$-phenyl, —NH—(CH$_2$)$_{1-2}$-cyclopropyl, —NH—(CH$_2$)$_{1-2}$-cyclobutyl, —NH—(CH$_2$)$_{1-2}$-cyclopentyl, —NH—(CH$_2$)$_{1-2}$-cyclohexyl, —NH—(CH$_2$)$_{1-2}$—O—CH$_3$, —NH—(CH$_2$)$_{1-2}$—O—CH$_2$CH$_3$, —NH—(CH$_2$)$_{1-2}$—O—CF$_3$, —NH—(CH$_2$)$_{1-2}$—N(CH$_3$)$_2$, —NH—C(O)—NH—(CH$_2$)$_{0-1}$—CH$_3$, —NH—C(O)—NH—(CH$_2$)$_{0-1}$-cyclopropyl, —NH—C(O)—NH—(CH$_2$)$_{0-1}$-cyclobutyl, —NH—C(O)—NH—(CH$_2$)$_{0-1}$-cyclopentyl, and —NH—C(O)—NH—(CH$_2$)$_{0-1}$-cyclohexyl.

Embodiment 118: A compound according to embodiment 97, wherein

R$^3$ is —S(O)$_2$-(3-pyridyl), where the pyridine ring is optionally substituted one or more times with substituents independently selected from methyl, ethyl, isopropyl, isobutyl, sec-butyl, tert-butyl, —S(O)$_2$—CH$_3$, —NH$_2$, —NH—(CH$_2$)$_{0-4}$—CH$_3$, —NH—(CH$_2$)$_{0-2}$—CH(CH$_3$)$_2$, —NH—(CH$_2$)$_{0-2}$—C(CH$_3$)$_3$, —NH-cyclopropyl, —NH-cyclobutyl, —NH-cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl, —NH—C(O)—(CH$_2$)$_{0-2}$—CH$_3$, —NH—C(O)—(CH$_2$)$_{0-1}$—CH(CH$_3$)$_2$, —NH—C(O)—(CH$_2$)$_{0-1}$—CF$_3$, —NH—C(O)-phenyl, —NH—C(O)-cyclopropyl, —NH—C(O)-cyclobutyl, —NH—C(O)-cyclopentyl, —NH—C(O)-cyclohexyl, —NH—C(O)-(pyrrolidin-2-yl), —NH—C(O)-(1-methylpyrrolidin-2-yl), —NH—C(O)-(1-tert-butoxycarbonyl-pyrrolidin-2-yl), —NH—C(O)-(piperazin-1-yl), —NH—C(O)-(4-methyl-piperazin-1-yl), —NH—C(O)-(4-tert-butoxycarbonyl-piperazin-1-yl), —NH—C(O)-(piperidin-4-yl), NH—C(O)-(1-methyl-piperidin-4-yl), NH—C(O)-(1-tert-butoxy-carbonyl-piperidin-4-yl), —NH—C(O)-(tetrahydropyran-4-yl), —NH—(CH$_2$)$_{1-2}$-phenyl, —NH—(CH$_2$)$_{1-2}$-cyclopropyl, —NH—(CH$_2$)$_{1-2}$-cyclobutyl, —NH—(CH$_2$)$_{1-2}$-cyclopentyl, —NH—(CH$_2$)$_{1-2}$-cyclohexyl, —NH—(CH$_2$)$_{1-2}$—O—CH$_3$, —NH—(CH$_2$)$_{1-2}$—O—CH$_2$CH$_3$, —NH—(CH$_2$)$_{1-2}$—O—CF$_3$, —NH—(CH$_2$)$_{1-2}$—N(CH$_3$)$_2$, —NH—C(O)—NH—(CH$_2$)$_{0-1}$—CH$_3$, —NH—C(O)—NH—(CH$_2$)$_{0-1}$-cyclopropyl, —NH—C(O)—NH—(CH$_2$)$_{0-1}$-cyclobutyl, —NH—C(O)—NH—(CH$_2$)$_{0-1}$-cyclopentyl, and —NH—C(O)—NH—(CH$_2$)$_{0-1}$-cyclohexyl.

Embodiment 119: A compound according to embodiment 97, wherein
R$^3$ is —S(O)$_2$-(thiazol-4-yl), where the thiazole ring is optionally substituted one or more times with substituents independently selected from R$^x$.

Embodiment 120: A compound according to embodiment 96, wherein
R$^3$ is —S(O)$_2$—C$_{1-10}$ alkyl, where the alkyl group is optionally substituted one to four times with substituents independently selected from R$^c$.

Embodiment 121: A compound according to embodiment 97, wherein
R$^3$ is —S(O)$_2$—C$_{1-10}$ alkyl, where the alkyl is optionally substituted one or more times with substituents independently selected from R$^x$.

Embodiment 122: A compound according to embodiment 96, wherein
R$^3$ is —C(O)—R$^d$.

Embodiment 123: A compound according to embodiment 97, wherein
R$^3$ is —C(O)—R$^j$.

Embodiment 124: A compound according to embodiment 96, wherein
R$^3$ is —C(O)-phenyl, where the phenyl group is optionally substituted one to four times with substituents independently selected from R$^c$.

Embodiment 125: A compound according to embodiment 96, wherein
R$^3$ is —C(O)-phenyl, where the phenyl group is optionally substituted one to four times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, methyl, ethyl, isopropyl, isobutyl, sec-butyl, tert-butyl, —O—CH$_3$, —O—CH$_2$CH$_3$, —O—CH(CH$_3$)$_2$, —O—CF$_3$, —O—CH$_2$CF$_3$, —CF$_3$, —OCH$_2$CF$_3$, thiazol-5-yl, and 2-methyl-thiazol-5-yl.

Embodiment 126: A compound according to embodiment 97, wherein
R$^3$ is —C(O)-phenyl, where the phenyl group is optionally substituted one or more times with substituents independently selected from R$^c$.

Embodiment 127: A compound according to embodiment 97, wherein
R$^3$ is —C(O)-phenyl, where the phenyl group is optionally substituted one or more times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, —NO$_2$, methyl, ethyl, isopropyl, isobutyl, sec-butyl, tert-butyl, —S(O)$_2$—CH$_3$, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, —NH—C(O)—CH$_3$, —NH—C(O)—CH$_2$CH$_3$, —N(CH$_3$)—C(O)—CH$_3$, —N(CH$_3$)—C(O)—CH$_2$CH$_3$, thiazol-4-yl, thiazol-5-yl, and 2-methyl-thiazol-5-yl,

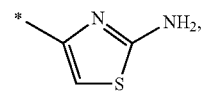

and

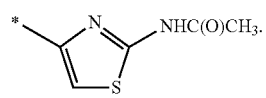

Embodiment 128: A compound according to embodiment 96, wherein
R$^3$ is —C(O)-heteroaryl, where the heteroaryl group is optionally substituted one to four times with substituents independently selected from R$^c$.

Embodiment 129: A compound according to embodiment 96, wherein
R$^3$ is —C(O)-heteroaryl, where the heteroaryl group is optionally substituted one to four times with substituents independently selected from methyl, ethyl, isopropyl, isobutyl, sec-butyl, tert-butyl, —NH$_2$, —NH—(CH$_2$)$_{0-4}$—CH$_3$, —NH—(CH$_2$)$_{0-2}$—CH(CH$_3$)$_2$, —NH—(CH$_2$)$_{0-2}$—C(CH$_3$)$_3$, —NH-cyclopropyl, —NH-cyclobutyl, —NH-cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl.

Embodiment 130: A compound according to embodiment 96, wherein
R$^3$ is —C(O)-(furan-2-yl), —C(O)-(furan-3-yl), —C(O)-(thiophen-2-yl), —C(O)-(thiophen-2-yl), —C(O)-(1H-pyrrol-1-yl), —C(O)-(1H-pyrrol-2-yl), —C(O)-(1H-pyrrol-3-yl), —C(O)-(oxazol-2-yl), —C(O)-(oxazol-4-yl), —C(O)-(oxazol-5-yl), —C(O)-(isoxazol-3-yl), —C(O)-(isoxazol-4-yl), —C(O)-(isoxazol-5-yl), —C(O)-(thiazol-2-yl), —C(O)-(thiazol-4-yl), —C(O)-(thiazol-5-yl), —C(O)-(isothiazol-3-yl), —C(O)-(isothiazol-4-yl), —C(O)-(isothiazol-5-yl), —C(O)-(1H-imidazol-1-yl), —C(O)-(1H-imidazol-2-yl), —C(O)-(1H-imidazol-4-yl), —C(O)-(1H-imidazol-5-yl), —C(O)-(1H-pyrazol-1-yl), —C(O)-(1H-pyrazol-3-yl), —C(O)-(1H-pyrazol-4-yl), —C(O)-(1H-pyrazol-5-yl), —C(O)-(2-pyridyl), —C(O)-(3-pyridyl), —C(O)-(4-pyridyl), —C(O)-(pyridazin-3-yl), —C(O)-(pyridazin-4-yl), —C(O)-(pyrimidin-2-yl), —C(O)-(pyrimidin-4-yl), —C(O)-(pyrimidin-5-yl), or —C(O)-(pyrazin-2-yl), where each named heteroaryl ring is optionally substituted one to four times with substituents independently selected from R$^c$.

Embodiment 131: A compound according to embodiment 96, wherein
R$^3$ is —C(O)-(furan-2-yl), —C(O)-(furan-3-yl), —C(O)-(thiophen-2-yl), —C(O)-(thiophen-3-yl), —C(O)-(oxazol-2-yl), —C(O)-(oxazol-4-yl), —C(O)-(oxazol-5-yl), —C(O)-(isoxazol-3-yl), —C(O)-(isoxazol-4-yl), —C(O)-(isoxazol-5-yl), —C(O)-(thiazol-2-yl), —C(O)-(thiazol-4-yl), —C(O)-(thiazol-5-yl), —C(O)-(isothiazol-3-yl), —C(O)-(isothiazol-4-yl), —C(O)-(isothiazol-5-yl), —C(O)-(1H-pyrazol-3-yl), —C(O)-(1H-pyrazol-4-yl), —C(O)-(1H-pyrazol-5-yl), —C(O)-(2-pyridyl), —C(O)-(3-pyridyl), —C(O)-(4-pyridyl), or —C(O)-(pyrazin-2-yl), where the heteroaryl ring is optionally substituted one to four times with substituents independently selected from methyl, ethyl, isopropyl, isobutyl, sec-butyl, tert-butyl, —NH$_2$, —NH—(CH$_2$)$_{0-4}$—CH$_3$, —NH—(CH$_2$)$_{0-2}$—CH(CH$_3$)$_2$, —NH—(CH$_2$)$_{0-2}$—C(CH$_3$)$_3$, —NH-cyclopropyl, —NH-cyclobutyl, —NH— cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl.

Embodiment 132: A compound according to embodiment 96, wherein
R$^3$ is —C(O)-(oxazol-4-yl), where the oxazole ring is optionally substituted one to two times with substituents independently selected from methyl, ethyl, isopropyl, isobutyl, sec-butyl, tert-butyl, —NH$_2$, —NH—(CH$_2$)$_{0-4}$—CH$_3$, —NH—(CH$_2$)$_{0-2}$—CH(CH$_3$)$_2$, —NH—(CH$_2$)$_{0-2}$—C(CH$_3$)$_3$, —NH-cyclopropyl, —NH-cyclobutyl, —NH-cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl.

Embodiment 133: A compound according to embodiment 96, wherein
R$^3$ is —C(O)-(oxazol-4-yl), where the oxazole ring is optionally substituted one to two times with substituents independently selected from R$^c$.

Embodiment 134: A compound according to embodiment 96, wherein
R$^3$ is —C(O)-(oxazol-5-yl), where the oxazole ring is optionally substituted one to two times with substituents independently selected from R$^c$.

Embodiment 135: A compound according to embodiment 96, wherein
R$^3$ is —C(O)-(isoxazol-4-yl), where the isoxazole ring is optionally substituted one to two times with substituents independently selected from R$^c$.

Embodiment 136: A compound according to embodiment 96, wherein
R$^3$ is —C(O)-(imidazol-2-yl), where the imidazole ring is optionally substituted one to two times with substituents independently selected from R$^c$.

Embodiment 137: A compound according to embodiment 96, wherein
R$^3$ is —C(O)-(pyrazol-3-yl), where the pyrazole ring is optionally substituted one to two times with substituents independently selected from R$^c$.

Embodiment 138: A compound according to embodiment 96, wherein
R$^3$ is —C(O)-(thiophen-2-yl), where the thiophene ring is optionally substituted one to two times with substituents independently selected from R$^c$.

Embodiment 139: A compound according to embodiment 96, wherein
R$^3$ is —C(O)-(pyrazin-2-yl), where the pyrazine ring is optionally substituted one to three times with substituents independently selected from R$^c$.

Embodiment 140: A compound according to embodiment 96, wherein
R$^3$ is —C(O)-(2-pyridyl), where the pyridine ring is optionally substituted one to three times with substituents independently selected from R$^c$.

Embodiment 141: A compound according to embodiment 96, wherein
R$^3$ is —C(O)-(1,2,3-triazol-4-yl), where the triazole ring is optionally substituted one to two times with substituents independently selected from R$^c$.

Embodiment 142: A compound according to embodiment 96, wherein
R$^3$ is —C(O)-(benzofuran-2-yl), where the benzofuran ring is optionally substituted one to four times with substituents independently selected from R$^c$.

Embodiment 143: A compound according to embodiment 96, wherein
R$^3$ is —C(O)-(benzothiazol-2-yl), where the benzothiazole ring is optionally substituted one to four times with substituents independently selected from R$^c$.

Embodiment 144: A compound according to embodiment 96, wherein
R$^3$ is —C(O)-(1,2,4-triazol-5-yl), where the triazole ring is optionally substituted one to two times with substituents independently selected from R$^c$.

Embodiment 145: A compound according to embodiment 96, wherein
R$^3$ is —C(O)-(imidazo[1,2-a]pyridin-2-yl), where the imidazopyridine ring is optionally substituted one to four times with substituents independently selected from R$^c$.

Embodiment 146: A compound according to embodiment 96, wherein
R$^3$ is —C(O)-(2,5-dimethyl-oxazol-4-yl).

Embodiment 147: A compound according to embodiment 97, wherein
R$^3$ is —C(O)-heteroaryl, where the heteroaryl group is optionally substituted one or more times with substituents independently selected from R$^x$.

Embodiment 148: A compound according to embodiment 97, wherein
R$^3$ is —C(O)-heteroaryl, where the heteroaryl group is optionally substituted one or more times with substituents independently selected from methyl, ethyl, isopropyl, isobutyl, sec-butyl, tert-butyl, —S(O)$_2$—CH$_3$, —NH$_2$, —NH—(CH$_2$)$_{0-4}$—CH$_3$, —NH—(CH$_2$)$_{0-2}$—CH(CH$_3$)$_2$, —NH—(CH$_2$)$_{0-2}$—C(CH$_3$)$_3$, —NH-cyclopropyl, —NH-cyclobutyl, —NH-cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, 2-oxo-piperazin-1-yl, —NH—C(O)—(CH$_2$)$_{0-2}$—CH$_3$, —NH—C(O)—(CH$_2$)$_{0-1}$—CH(CH$_3$)$_2$, —NH—C(O)—(CH$_2$)$_{0-1}$—CF$_3$, —NH—C(O)-phenyl, —NH—C(O)-cyclopropyl, —NH—C(O)-cyclobutyl, —NH—C(O)—cyclopentyl, —NH—C(O)-cyclohexyl, —NH—C(O)-(pyrrolidin-2-yl), NH—C(O)-(1-methyl-pyrrolidin-2-yl), —NH—C(O)-(1-tert-butoxycarbonyl-pyrrolidin-2-yl), —NH—C(O)-(piperazin-1-yl), NH—C(O)-(4-methyl-piperazin-1-yl), NH—C(O)-(4-tert-butoxycarbonyl-piperazin-1-yl), —NH—C(O)-(piperidin-4-yl), NH—C(O)-(1-methyl-piperidin-4-yl), NH—C(O)-(1-tert-butoxycarbonyl-piperidin-4-yl), —NH—C(O)-(tetrahydropyran-4-yl), —NH—(CH$_2$)$_{1-2}$-phenyl, —NH—(CH$_2$)$_{1-2}$-cyclopropyl, —NH—(CH$_2$)$_{1-2}$-cyclobutyl, —NH—(CH$_2$)$_{1-2}$-cyclopentyl, —NH—(CH$_2$)$_{1-2}$-cyclohexyl, —NH—(CH$_2$)$_{1-2}$—O—CH$_3$, —NH—(CH$_2$)$_{1-2}$—O—CH$_2$CH$_3$, —NH—(CH$_2$)$_{1-2}$—O—CF$_3$, —NH—(CH$_2$)$_{1-2}$—N(CH$_3$)$_2$, —NH—C(O)—NH—(CH$_2$)$_{0-1}$—CH$_3$, —NH—C(O)—NH—(CH$_2$)$_{0-1}$-cyclopropyl, —NH—C(O)—NH—(CH$_2$)$_{0-1}$-cyclobutyl, —NH—C(O)—NH—(CH$_2$)$_{0-1}$-cyclopentyl, and —NH—C(O)—NH—(CH$_2$)$_{0-1}$-cyclohexyl.

Embodiment 149: A compound according to embodiment 97, wherein

R$^3$ is —C(O)-(furan-2-yl), —C(O)-(furan-3-yl), —C(O)-(thiophen-2-yl), —C(O)-(thiophen-2-yl), —C(O)-(1H-pyrrol-1-yl), —C(O)-(1H-pyrrol-2-yl), —C(O)-(1H-pyrrol-3-yl), —C(O)-(oxazol-2-yl), —C(O)-(oxazol-4-yl), —C(O)-(oxazol-5-yl), —C(O)-(isoxazol-3-yl), —C(O)-(isoxazol-4-yl), —C(O)-(isoxazol-5-yl), —C(O)-(thiazol-2-yl), —C(O)-(thiazol-4-yl), —C(O)-(thiazol-5-yl), —C(O)-(isothiazol-3-yl), —C(O)-(isothiazol-4-yl), —C(O)-(isothiazol-5-yl), —C(O)-(1H-imidazol-1-yl), —C(O)-(1H-imidazol-2-yl), —C(O)-(1H-imidazol-4-yl), —C(O)-(1H-imidazol-5-yl), —C(O)-(1H-pyrazol-1-yl), —C(O)-(1H-pyrazol-3-yl), —C(O)-(1H-pyrazol-4-yl), —C(O)-(1H-pyrazol-5-yl), —C(O)-(2-pyridyl), —C(O)-(3-pyridyl), —C(O)-(4-pyridyl), —C(O)-(pyridazin-3-yl), —C(O)-(pyridazin-4-yl), —C(O)-(pyrimidin-2-yl), —C(O)-(pyrimidin-4-yl), —C(O)-(pyrimidin-5-yl), or —C(O)-(pyrazin-2-yl), where each named heteroaryl ring is optionally substituted one or more times with substituents independently selected from R$^x$.

Embodiment 150: A compound according to embodiment 97, wherein

R$^3$ is —C(O)-(furan-2-yl), —C(O)-(furan-3-yl), —C(O)-(thiophen-2-yl), —C(O)-(thiophen-3-yl), —C(O)-(oxazol-2-yl), —C(O)-(oxazol-4-yl), —C(O)-(oxazol-5-yl), —C(O)-(isoxazol-3-yl), —C(O)-(isoxazol-4-yl), —C(O)-(isoxazol-5-yl), —C(O)-(thiazol-2-yl), —C(O)-(thiazol-4-yl), —C(O)-(thiazol-5-yl), —C(O)-(isothiazol-3-yl), —C(O)-(isothiazol-4-yl), —C(O)-(isothiazol-5-yl), —C(O)-(1H-pyrazol-3-yl), —C(O)-(1H-pyrazol-4-yl), —C(O)-(1H-pyrazol-5-yl), —C(O)-(2-pyridyl), —C(O)-(3-pyridyl), —C(O)-(4-pyridyl), or —C(O)-(pyrazin-2-yl), where each heteroaryl ring is optionally substituted one or more times with substituents independently selected from methyl, ethyl, isopropyl, isobutyl, sec-butyl, tert-butyl, —S(O)$_2$—CH$_3$, —NH$_2$, —NH—(CH$_2$)$_{0-4}$—CH$_3$, —NH—(CH$_2$)$_{0-2}$—CH(CH$_3$)$_2$, —NH—(CH$_2$)$_{0-2}$—C(CH$_3$)$_3$, —NH—cyclopropyl, —NH-cyclobutyl, —NH-cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl, —NH—C(O)—(CH$_2$)$_{0-2}$—CH$_3$, —NH—C(O)—(CH$_2$)$_{0-1}$—CH(CH$_3$)$_2$, —NH—C(O)—(CH$_2$)$_{0-1}$—CF$_3$, —NH—C(O)—phenyl, —NH—C(O)-cyclopropyl, —NH—C(O)-cyclobutyl, —NH—C(O)-cyclopentyl, —NH—C(O)—cyclohexyl, —NH—C(O)-(pyrrolidin-2-yl), —NH—C(O)-(1-methyl-pyrrolidin-2-yl), —NH—C(O)-(1-tert-butoxycarbonyl-pyrrolidin-2-yl), —NH—C(O)-(piperazin-1-yl), —NH—C(O)-(4-methyl-piperazin-1-yl), —NH—C(O)-(4-tert-butoxycarbonyl-piperazin-1-yl), —NH—C(O)-(piperidin-4-yl), NH—C(O)-(1-methyl-piperidin-4-yl), NH—C(O)-(1-tert-butoxy-carbonyl-piperidin-4-yl), —NH—C(O)-(tetrahydropyran-4-yl), —NH—(CH$_2$)$_{1-2}$-phenyl, —NH—(CH$_2$)$_{1-2}$-cyclopropyl, —NH—(CH$_2$)$_{1-2}$-cyclobutyl, —NH—(CH$_2$)$_{1-2}$-cyclopentyl, —NH—(CH$_2$)$_{1-2}$-cyclohexyl, —NH—(CH$_2$)$_{1-2}$—O—CH$_3$, —NH—(CH$_2$)$_{1-2}$—O—CH$_2$CH$_3$, —NH—(CH$_2$)$_{1-2}$—O—CF$_3$, —NH—(CH$_2$)$_{1-2}$—N(CH$_3$)$_2$, —NH—C(O)—NH—(CH$_2$)$_{0-1}$—CH$_3$, —NH—C(O)—NH—(CH$_2$)$_{0-1}$-cyclopropyl, —NH—C(O)—NH—(CH$_2$)$_{0-1}$-cyclobutyl, —NH—C(O)—NH—(CH$_2$)$_{0-1}$-cyclopentyl, and —NH—C(O)—NH—(CH$_2$)$_{0-1}$-cyclohexyl.

Embodiment 151: A compound according to embodiment 97, wherein

R$^3$ is —C(O)-(oxazol-4-yl), where the oxazole ring is optionally substituted one or more times with substituents independently selected from methyl, ethyl, isopropyl, isobutyl, sec-butyl, tert-butyl, —S(O)$_2$—CH$_3$, —NH$_2$, —NH—(CH$_2$)$_{0-4}$—CH$_3$, —NH—(CH$_2$)$_{0-2}$—CH(CH$_3$)$_2$, —NH—(CH$_2$)$_{0-2}$—C(CH$_3$)$_3$, —NH-cyclopropyl, —NH-cyclobutyl, —NH-cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl, —NH—C(O)—(CH$_2$)$_{0-2}$—CH$_3$, —NH—C(O)—(CH$_2$)$_{0-1}$—CH(CH$_3$)$_2$, —NH—C(O)—(CH$_2$)$_{0-1}$—CF$_3$, —NH—C(O)-phenyl, —NH—C(O)-cyclopropyl, —NH—C(O)-cyclobutyl, —NH—C(O)-cyclopentyl, —NH—C(O)-cyclohexyl, —NH—C(O)-(pyrrolidin-2-yl), —NH—C(O)-(1-methyl-pyrrolidin-2-yl), —NH—C(O)-(1-tert-butoxycarbonyl-pyrrolidin-2-yl), —NH—C(O)-(piperazin-1-yl), —NH—C(O)-(4-methyl-piperazin-1-yl), —NH—C(O)-(4-tert-butoxycarbonyl-piperazin-1-yl), —NH—C(O)-(piperidin-4-yl), NH—C(O)-(1-methyl-piperidin-4-yl), NH—C(O)-(1-tert-butoxy-carbonyl-piperidin-4-yl), —NH—C(O)-(tetrahydropyran-4-yl), —NH—(CH$_2$)$_{1-2}$-phenyl, —NH—(CH$_2$)$_{1-2}$-cyclopropyl, —NH—(CH$_2$)$_{1-2}$-cyclobutyl, —NH—(CH$_2$)$_{1-2}$-cyclopentyl, —NH—(CH$_2$)$_{1-2}$-cyclohexyl, —NH—(CH$_2$)$_{1-2}$—O—CH$_3$, —NH—(CH$_2$)$_{1-2}$—O—CH$_2$CH$_3$, —NH—(CH$_2$)$_{1-2}$—O—CF$_3$, —NH—(CH$_2$)$_{1-2}$—N(CH$_3$)$_2$, —NH—C(O)—NH—(CH$_2$)$_{0-1}$—CH$_3$, —NH—C(O)—NH—(CH$_2$)$_{0-1}$-cyclopropyl, —NH—C(O)—NH—(CH$_2$)$_{0-1}$-cyclobutyl, —NH—C(O)—NH—(CH$_2$)$_{0-1}$-cyclopentyl, and —NH—C(O)—NH—(CH$_2$)$_{0-1}$-cyclohexyl.

Embodiment 152: A compound according to embodiment 97, wherein
R$^3$ is —C(O)-(oxazol-4-yl), where the oxazole ring is optionally substituted one or more times with substituents independently selected from R$^x$.

Embodiment 153: A compound according to embodiment 97, wherein
R$^3$ is —C(O)-(oxazol-5-yl), where the oxazole ring is optionally substituted one or more times with substituents independently selected from R$^x$.

Embodiment 154: A compound according to embodiment 97, wherein
R$^3$ is —C(O)-(isoxazol-4-yl), where the isoxazole ring is optionally substituted one or more times with substituents independently selected from R$^x$.

Embodiment 155: A compound according to embodiment 97, wherein
R$^3$ is —C(O)-(imidazol-2-yl), where the imidazole ring is optionally substituted one or more times with substituents independently selected from R$^x$.

Embodiment 156: A compound according to embodiment 97, wherein
R$^3$ is —C(O)-(pyrazol-3-yl), where the pyrazole ring is optionally substituted one or more times with substituents independently selected from R$^x$.

Embodiment 157: A compound according to embodiment 97, wherein
R$^3$ is —C(O)-(thiophen-2-yl), where the thiophene ring is optionally substituted one or more times with substituents independently selected from R$^x$.

Embodiment 158: A compound according to embodiment 97, wherein
R$^3$ is —C(O)-(pyrazin-2-yl), where the pyrazine ring is optionally substituted one or more times with substituents independently selected from R$^x$.

Embodiment 159: A compound according to embodiment 97, wherein
R$^3$ is —C(O)-(2-pyridyl), where the pyridine ring is optionally substituted one or more times with substituents independently selected from R$^x$.

Embodiment 160: A compound according to embodiment 97, wherein
R$^3$ is —C(O)-(1,2,3-triazol-4-yl), where the triazole ring is optionally substituted one or more times with substituents independently selected from R$^x$.

Embodiment 161: A compound according to embodiment 97, wherein
R$^3$ is —C(O)-(benzofuran-2-yl), where the benzofuran ring is optionally substituted one or more times with substituents independently selected from R$^x$.

Embodiment 162: A compound according to embodiment 97, wherein
R$^3$ is —C(O)-(benzothiazol-2-yl), where the benzothiazole ring is optionally substituted one or more times with substituents independently selected from R$^x$.

Embodiment 163: A compound according to embodiment 97, wherein
R$^3$ is —C(O)-(1,2,4-triazol-5-yl), where the triazole ring is optionally substituted one or more times with substituents independently selected from R$^x$.

Embodiment 164: A compound according to embodiment 97, wherein
R$^3$ is —C(O)-(imidazo[1,2-a]pyridin-2-yl), where the imidazopyridine ring is optionally substituted one or more times with substituents independently selected from R$^x$.

Embodiment 165: A compound according to embodiment 97, wherein
R$^3$ is —C(O)-(2,5-dimethyl-oxazol-4-yl).

Embodiment 166: A compound according to embodiment 96, wherein
R$^3$ is —C(O)-cycloalkyl, where the cycloalkyl group is optionally substituted one to four times with substituents independently selected from R$^c$.

Embodiment 167: A compound according to embodiment 96, wherein
R$^3$ is —C(O)-cycloalkyl, where the cycloalkyl group is optionally substituted one to four times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, methyl, ethyl, isopropyl, isobutyl, sec-butyl, tert-butyl, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, thiazol-5-yl, and 2-methyl-thiazol-5-yl.

Embodiment 168: A compound according to embodiment 96, wherein
R$^3$ is —C(O)-cyclopropyl, —C(O)-cyclobutyl, —C(O)-cyclopentyl, —C(O)-cyclohexyl, where the cycloalkyl group is optionally substituted one to four times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, methyl, ethyl, isopropyl, isobutyl, sec-butyl, tert-butyl, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, thiazol-5-yl, and 2-methyl-thiazol-5-yl.

Embodiment 169: A compound according to embodiment 96, wherein
R$^3$ is —C(O)-cyclopentyl, where the cyclopentyl group is optionally substituted one to four times with substituents independently selected from R$^c$.

Embodiment 170: A compound according to embodiment 96, wherein
R$^3$ is —C(O)-cyclohexyl, where the cyclohexyl group is optionally substituted one to four times with substituents independently selected from R$^c$.

Embodiment 171: A compound according to embodiment 96, wherein
R$^3$ is —C(O)-indan-1-yl, where the indane group is optionally substituted one to four times with substituents independently selected from R$^c$.

Embodiment 172: A compound according to embodiment 96, wherein
R$^3$ is —C(O)-indan-2-yl, where the indane group is optionally substituted one to four times with substituents independently selected from R$^c$.

Embodiment 173: A compound according to embodiment 97, wherein
R$^3$ is —C(O)—C$_{3-10}$ cycloalkyl, where the cycloalkyl group is optionally substituted one or more times with substituents independently selected from R$^x$.

Embodiment 174: A compound according to embodiment 97, wherein
R$^3$ is —C(O)—C$_{3-10}$ cycloalkyl, where the cycloalkyl group is optionally substituted one or more times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, —NO$_2$, methyl, ethyl, isopropyl, isobutyl, sec-butyl, tert-butyl, —S(O)$_2$—CH$_3$, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, —NH—C(O)—CH$_3$, —NH—C(O)—CH$_2$CH$_3$, —N(CH$_3$)—C(O)—CH$_3$, —N(CH$_3$)—C(O)—CH$_2$CH$_3$, thiazol-5-yl, and 2-methyl-thiazol-5-yl.

Embodiment 175: A compound according to embodiment 97, wherein
R$^3$ is —C(O)-cyclopropyl, —C(O)-cyclobutyl, —C(O)-cyclopentyl, —C(O)-cyclohexyl, where the cycloalkyl group is optionally substituted one or more times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, —NO$_2$, methyl, ethyl, isopropyl, isobutyl, sec-butyl, tert-butyl, —S(O)$_2$—CH$_3$, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, —NH—C(O)—CH$_3$, —NH—C(O)—CH$_2$CH$_3$, —N(CH$_3$)—C(O)—CH$_3$, —N(CH$_3$)—C(O)—CH$_2$CH$_3$, thiazol-5-yl, and 2-methyl-thiazol-5-yl.

Embodiment 176: A compound according to embodiment 97, wherein
R$^3$ is —C(O)-cyclopentyl, where the cyclopentyl group is optionally substituted one or more times with substituents independently selected from R$^x$.

Embodiment 177: A compound according to embodiment 97, wherein
R$^3$ is —C(O)-cyclohexyl, where the cyclohexyl group is optionally substituted one or more times with substituents independently selected from R$^x$.

Embodiment 178: A compound according to embodiment 97, wherein
R$^3$ is —C(O)-indan-1-yl, where the indane group is optionally substituted one or more times with substituents independently selected from R$^x$.

Embodiment 179: A compound according to embodiment 97, wherein
R$^3$ is —C(O)-indan-2-yl, where the indane group is optionally substituted one or more times with substituents independently selected from R$^x$.

Embodiment 180: A compound according to embodiment 96, wherein
R$^3$ is —C(O)—CH$_2$-phenyl, where the phenyl group is optionally substituted one to four times with substituents independently selected from R$^c$.

Embodiment 181: A compound according to embodiment 96, wherein
R$^3$ is —C(O)—CH$_2$-phenyl, where the phenyl group is optionally substituted one to four times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, methyl, ethyl, isopropyl, isobutyl, sec-butyl, tert-butyl, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, thiazol-5-yl, and 2-methyl-thiazol-5-yl.

Embodiment 182: A compound according to embodiment 97, wherein
R$^3$ is —C(O)—CH$_2$-phenyl, where the phenyl group is optionally substituted one or more times with substituents independently selected from R$^x$.

Embodiment 183: A compound according to embodiment 97, wherein
R$^3$ is —C(O)—CH$_2$-phenyl, where the phenyl group is optionally substituted one or more times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, —NO$_2$, methyl, ethyl, isopropyl, isobutyl, sec-butyl, tert-butyl, —S(O)$_2$—CH$_3$, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, —NH—C(O)—CH$_3$, —NH—C(O)—CH$_2$CH$_3$, —N(CH$_3$)—C(O)—CH$_3$, —N(CH$_3$)—C(O)—CH$_2$CH$_3$, thiazol-5-yl, and 2-methyl-thiazol-5-yl.

Embodiment 184: A compound according to embodiment 96, wherein
R$^3$ is —C(O)-heterocyclyl, where the heterocyclyl group is optionally substituted one to four times with substituents independently selected from R$^c$.

Embodiment 185: A compound according to embodiment 96, wherein
R$^3$ is —C(O)-heterocyclyl, where the heterocyclyl group is optionally substituted one to four times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, methyl, ethyl, isopropyl, isobutyl, sec-butyl, tert-butyl, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, thiazol-5-yl, and 2-methyl-thiazol-5-yl.

Embodiment 186: A compound according to embodiment 96, wherein
R$^3$ is —C(O)-tetrahydrofuran-2-yl, —C(O)-tetrahydrofuran-3-yl-C(O)-tetrahydropyran-2-yl, —C(O)-tetrahydropyran-3-yl, or —C(O)-tetrahydropyran-4-yl, where each heterocyclyl group is optionally substituted one to four times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, methyl, ethyl, isopropyl, isobutyl, sec-butyl, tert-butyl, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, thiazol-5-yl, and 2-methyl-thiazol-5-yl.

Embodiment 187: A compound according to embodiment 96, wherein
R$^3$ is —C(O)-pyrrolidin-2-yl, where the pyrrolidine group is optionally substituted one to four times with substituents independently selected from R$^c$.

Embodiment 188: A compound according to embodiment 96, wherein
R$^3$ is —C(O)-pyrrolidin-3-yl, where the pyrrolidine group is optionally substituted one to four times with substituents independently selected from R$^c$.

Embodiment 189: A compound according to embodiment 96, wherein
R$^3$ is —C(O)-pyrrolidin-1-yl, where the pyrrolidine group is optionally substituted one to four times with substituents independently selected from R$^c$.

Embodiment 190: A compound according to embodiment 96, wherein
R$^3$ is —C(O)-piperidin-2-yl, where the piperidine group is optionally substituted one to four times with substituents independently selected from R$^c$.

Embodiment 191: A compound according to embodiment 96, wherein
R$^3$ is —C(O)-piperidin-3-yl, where the piperidine group is optionally substituted one to four times with substituents independently selected from R$^c$.

Embodiment 192: A compound according to embodiment 96, wherein
R$^3$ is —C(O)-piperidin-4-yl, where the piperidine group is optionally substituted one to four times with substituents independently selected from R$^c$.

Embodiment 193: A compound according to embodiment 96, wherein
R$^3$ is —C(O)-piperidin-1-yl, where the piperidine group is optionally substituted one to four times with substituents independently selected from R$^c$.

Embodiment 194: A compound according to embodiment 96, wherein
R$^3$ is —C(O)-(4-oxo-piperidin-1-yl), where the piperidine group is optionally substituted one to four times with substituents independently selected from R$^c$.

Embodiment 195: A compound according to embodiment 96, wherein
R$^3$ is —C(O)-morpholin-4-yl, where the morpholine group is optionally substituted one to four times with substituents independently selected from R$^c$.

Embodiment 196: A compound according to embodiment 96, wherein
R$^3$ is —C(O)-(2-oxo-imidazolidin-4-yl), where the imidazolidine group is optionally substituted one to four times with substituents independently selected from R$^c$.

Embodiment 197: A compound according to embodiment 97, wherein
R$^3$ is —C(O)-heterocyclyl, where the heterocyclyl group is optionally substituted one or more times with substituents independently selected from R$^x$.

Embodiment 198: A compound according to embodiment 97, wherein
R$^3$ is —C(O)-heterocyclyl, where the heterocyclyl group is optionally substituted one or more times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, —NO$_2$, methyl, ethyl, isopropyl, isobutyl, sec-butyl, tert-butyl, —S(O)$_2$—CH$_3$, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, —NH—C(O)—CH$_3$, —NH—C(O)—CH$_2$CH$_3$, —N(CH$_3$)—C(O)—CH$_3$, —N(CH$_3$)—C(O)—CH$_2$CH$_3$, thiazol-5-yl, and 2-methyl-thiazol-5-yl.

Embodiment 199: A compound according to embodiment 97, wherein
R$^3$ is —C(O)-tetrahydrofuran-2-yl, —C(O)-tetrahydrofuran-3-yl-C(O)-tetrahydropyran-2-yl, —C(O)-tetrahydropyran-3-yl, or —C(O)-tetrahydropyran-4-yl, where the heterocyclyl group is optionally substituted one or more times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, —NO$_2$, methyl, ethyl, isopropyl, isobutyl, sec-butyl, tert-butyl, —S(O)$_2$—CH$_3$, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, —NH—C(O)—CH$_3$, —NH—C(O)—CH$_2$CH$_3$, —N(CH$_3$)—C(O)—CH$_3$, and —N(CH$_3$)—C(O)—CH$_2$CH$_3$.

Embodiment 200: A compound according to embodiment 97, wherein
R$^3$ is —C(O)-pyrrolidin-2-yl, where the pyrrolidine group is optionally substituted one or more times with substituents independently selected from R$^x$.

Embodiment 201: A compound according to embodiment 97, wherein
R$^3$ is —C(O)-pyrrolidin-3-yl, where the pyrrolidine group is optionally substituted one or more times with substituents independently selected from R$^x$.

Embodiment 202: A compound according to embodiment 97, wherein
R$^3$ is —C(O)-pyrrolidin-1-yl, where the pyrrolidine group is optionally substituted one or more times with substituents independently selected from R$^x$.

Embodiment 203: A compound according to embodiment 97, wherein
R$^3$ is —C(O)-piperidin-2-yl, where the piperidine group is optionally substituted one or more times with substituents independently selected from R$^x$.

Embodiment 204: A compound according to embodiment 97, wherein
R$^3$ is —C(O)-piperidin-3-yl, where the piperidine group is optionally substituted one or more times with substituents independently selected from R$^x$.

Embodiment 205: A compound according to embodiment 97, wherein
R$^3$ is —C(O)-piperidin-4-yl, where the piperidine group is optionally substituted one or more times with substituents independently selected from R$^x$.

Embodiment 206: A compound according to embodiment 97, wherein
R$^3$ is —C(O)-piperidin-1-yl, where the piperidine group is optionally substituted one or more times with substituents independently selected from R$^x$.

Embodiment 207: A compound according to embodiment 97, wherein
R$^3$ is —C(O)-(4-oxo-piperidin-1-yl), where the piperidine group is optionally substituted one or more times with substituents independently selected from R$^x$.

Embodiment 208: A compound according to embodiment 97, wherein
R$^3$ is —C(O)-morpholin-4-yl, where the morpholine group is optionally substituted one or more times with substituents independently selected from R$^x$.

Embodiment 209: A compound according to embodiment 97, wherein
R$^3$ is —C(O)-(2-oxo-imidazolidin-4-yl), where the imidazolidine group is optionally substituted one or more times with substituents independently selected from R$^x$.

Embodiment 210: A compound according to embodiment 96, wherein
R$^3$ is —C(O)-alkyl, where the alkyl group is optionally substituted one to four times with substituents independently selected from R$^c$.

Embodiment 211: A compound according to embodiment 97, wherein
R$^3$ is —C(O)—C$_{1-6}$ alkyl, where the alkyl group is optionally substituted one or more times with substituents independently selected from R$^x$.

Embodiment 212: A compound according to embodiment 97, wherein
R$^3$ is —C(O)—CH$_3$, —C(O)—(CH$_2$)$_{1-3}$—CH$_3$—C(O)—CH(CH$_3$)$_2$, —C(O)—CH$_2$CH(CH$_3$)$_2$, —C(O)—CH(CH$_3$)—CH$_2$CH$_3$, or —C(O)—C(CH$_3$)$_3$, where each alkyl group is optionally substituted one or more times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, —NO$_2$, methyl, ethyl, isopropyl, isobutyl, sec-butyl, tert-butyl, —S(O)$_2$—CH$_3$, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, —NH—C(O)—CH$_3$, —NH—C(O)—CH$_2$CH$_3$, —N(CH$_3$)—C(O)—CH$_3$, and —N(CH$_3$)—C(O)—CH$_2$CH$_3$.

Embodiment 213: A compound according to embodiment 96 or 97, wherein
R$^3$ is —C(O)—CH$_3$, —C(O)—(CH$_2$)$_{1-3}$—CH$_3$—C(O)—CH(CH$_3$)$_2$, —C(O)—CH$_2$CH(CH$_3$)$_2$, —C(O)—CH(CH$_3$)—CH$_2$CH$_3$, or —C(O)—C(CH$_3$)$_3$.

Embodiment 214: A compound according to embodiment 96, wherein
R$^3$ is —CH$_2$-cycloalkyl, —CH$_2$-heterocyclyl, —CH$_2$-phenyl, or CH$_2$-heteroaryl, where the phenyl and heteroaryl groups are optionally substituted one to four times with substituents selected independently from $R^c$.

Embodiment 215: A compound according to embodiment 97, wherein
$R^3$ is —$CH_2$—$C_{3-10}$ cycloalkyl, —$CH_2$-heterocyclyl, —$CH_2$-phenyl, or $CH_2$-heteroaryl, where the aryl, heteroaryl, cycloalkyl, and heterocyclyl groups are optionally substituted one or more times with substituents selected independently from $R^x$.

Embodiment 216: A compound according to embodiment 96, wherein
$R^3$ is —$CH_2$-phenyl, where the phenyl group is optionally substituted one to four times with substituents independently selected from $R^c$.

Embodiment 217: A compound according to embodiment 96, wherein
$R^3$ is —$CH_2$-phenyl, where the phenyl group is optionally substituted one to four times with substituents independently selected from halogen, —$NH_2$, —NH—$CH_3$, —NH—$CH_2CH_3$, —$N(CH_3)_2$, —$N(CH_3)$—$CH_2CH_3$, —$N(CH_2CH_3)_2$, —CN, methyl, ethyl, isopropyl, isobutyl, sec-butyl, tert-butyl, —O—$CH_3$, —O—$CH_2CH_3$, —O—$CH(CH_3)_2$, —O—$CF_3$, —O—$CH_2CF_3$, —$CF_3$, —O—$CH_2CF_3$, thiazol-5-yl, and 2-methyl-thiazol-5-yl.

Embodiment 218: A compound according to embodiment 97, wherein
$R^3$ is —$CH_2$-phenyl, where the phenyl group is optionally substituted one or more times with substituents independently selected from $R^x$.

Embodiment 219: A compound according to embodiment 97, wherein
$R^3$ is —$CH_2$-phenyl, where the phenyl group is optionally substituted one or more times with substituents independently selected from halogen, —$NH_2$, —NH—$CH_3$, —NH—$CH_2CH_3$, —$N(CH_3)_2$, —$N(CH_3)$—$CH_2CH_3$, —$N(CH_2CH_3)_2$, —CN, —$NO_2$, methyl, ethyl, isopropyl, isobutyl, sec-butyl, tert-butyl, —$S(O)_2$—$CH_3$, —O—$CH_3$, —O—$CH_2CH_3$, —O—$CH(CH_3)_2$, —O—$CF_3$, —O—$CH_2CF_3$, —$CF_3$, —O—$CH_2CF_3$, —NH—C(O)—$CH_3$, —NH—C(O)—$CH_2CH_3$, —$N(CH_3)$—C(O)—$CH_3$, —$N(CH_3)$—C(O)—$CH_2CH_3$, thiazol-3-yl, thiazol-5-yl, and 2-methyl-thiazol-5-yl.

Embodiment 220: A compound according to embodiment 96, wherein
$R^3$ is —$CH_2$-heteroaryl, where the heteroaryl group is optionally substituted one to four times with substituents independently selected from $R^c$.

Embodiment 221: A compound according to embodiment 96, wherein
$R^3$ is —$CH_2$-heteroaryl, where the heteroaryl group is optionally substituted one to four times with substituents independently selected from methyl, ethyl, isopropyl, isobutyl, sec-butyl, tert-butyl, —$NH_2$, —NH—$(CH_2)_{04}$—$CH_3$, —NH—$(CH_2)_{0-2}$—$CH(CH_3)_2$, —NH—$(CH_2)_{0-2}$—$C(CH_3)_3$, —NH-cyclopropyl, —NH-cyclobutyl, —NH-cyclopentyl, —NH-cyclohexyl, —$CF_3$, —$CH_2CF_3$, —O—$CH_3$, —$OCH_2CH_3$, —O—$CH(CH_3)_2$, —O—$CF_3$, —O—$CH_2CF_3$, -phenyl, —$(CH_2)_{1-2}$-phenyl, —$CH(CH_3)$-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl.

Embodiment 222: A compound according to embodiment 96, wherein
$R^3$ is —$CH_2$-(furan-2-yl), —$CH_2$-(furan-3-yl), —$CH_2$-(thiophen-2-yl), —$CH_2$-(thiophen-2-yl), —$CH_2$-(1H-pyrrol-1-yl), —$CH_2$-(1H-pyrrol-2-yl), —$CH_2$-(1H-pyrrol-3-yl), —$CH_2$-(oxazol-2-yl), —$CH_2$-(oxazol-4-yl), —$CH_2$-(oxazol-5-yl), —$CH_2$-(isoxazol-3-yl), —$CH_2$-(isoxazol-4-yl), —$CH_2$-(isoxazol-5-yl), —$CH_2$-(thiazol-2-yl), —$CH_2$-(thiazol-4-yl), —$CH_2$-(thiazol-5-yl), —$CH_2$-(isothiazol-3-yl), —$CH_2$-(isothiazol-4-yl), —$CH_2$-(isothiazol-5-yl), —$CH_2$-(1H-imidazol-1-yl), —$CH_2$-(1H-imidazol-2-yl), —$CH_2$-(1H-imidazol-4-yl), —$CH_2$-(1H-imidazol-5-yl), —$CH_2$-(1H-pyrazol-1-yl), —$CH_2$-(1H-pyrazol-3-yl), —$CH_2$-(1H-pyrazol-4-yl), —$CH_2$-(1H-pyrazol-5-yl), —$CH_2$-(2-pyridyl), —$CH_2$-(3-pyridyl), —$CH_2$-(4-pyridyl), —$CH_2$-(pyridazin-3-yl), —$CH_2$-(pyridazin-4-yl), —$CH_2$-(pyrimidin-2-yl), —$CH_2$-(pyrimidin-4-yl), —$CH_2$-(pyrimidin-5-yl), or —$CH_2$-(pyrazin-2-yl), where each named heteroaryl ring is optionally substituted one to four times with substituents independently selected from $R^c$.

Embodiment 223: A compound according to embodiment 96, wherein
$R^3$ is —$CH_2$-(furan-2-yl), —$CH_2$-(furan-3-yl), —$CH_2$-(thiophen-2-yl), —$CH_2$-(thiophen-3-yl), —$CH_2$-(oxazol-2-yl), —$CH_2$-(oxazol-4-yl), —$CH_2$-(oxazol-5-yl), —$CH_2$-(isoxazol-3-yl), —$CH_2$-(isoxazol-4-yl), —$CH_2$-(isoxazol-5-yl), —$CH_2$-(thiazol-2-yl), —$CH_2$-(thiazol-4-yl), —$CH_2$-(thiazol-5-yl), —$CH_2$-(isothiazol-3-yl), —$CH_2$-(isothiazol-4-yl), —$CH_2$-(isothiazol-5-yl), —$CH_2$-(1H-pyrazol-3-yl), —$CH_2$-(1H-pyrazol-4-yl), —$CH_2$-(1H-pyrazol-5-yl), —$CH_2$-(2-pyridyl), —$CH_2$—(3-pyridyl), —$CH_2$-(4-pyridyl), or —$CH_2$-(pyrazin-2-yl), where the heteroaryl ring is optionally substituted one to four times with substituents independently selected from methyl, ethyl, isopropyl, isobutyl, sec-butyl, tert-butyl, —$NH_2$, —NH—$(CH_2)_{0-4}$—$CH_3$, —NH—$(CH_2)_{0-2}$—$CH(CH_3)_2$, —NH—$(CH_2)_{0-2}$—$C(CH_3)_3$, —NH-cyclopropyl, —NH-cyclobutyl, —NH-cyclopentyl, —NH-cyclohexyl, —$CF_3$, —$CH_2CF_3$, —O—$CH_3$, —$OCH_2CH_3$, —O—$CH(CH_3)_2$, —O—$CF_3$, —O—$CH_2CF_3$, -phenyl, —$(CH_2)_{1-2}$-phenyl, —$CH(CH_3)$-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl.

Embodiment 224: A compound according to embodiment 96, wherein
$R^3$ is —$CH_2$-(2-pyridyl), where the pyridine group is optionally substituted one to four times with substituents independently selected from $R^c$.

Embodiment 225: A compound according to embodiment 96, wherein
$R^3$ is —$CH_2$-(3-pyridyl), where the pyridine group is optionally substituted one to four times with substituents independently selected from $R^c$.

Embodiment 226: A compound according to embodiment 96, wherein
$R^3$ is —$CH_2$-(4-pyridyl), where the pyridine group is optionally substituted one to four times with substituents independently selected from $R^c$.

Embodiment 227: A compound according to embodiment 96, wherein
  $R^3$ is —CH$_2$-(imidazol-2-yl), where the imidazole group is optionally substituted one to four times with substituents independently selected from $R^c$.
Embodiment 228: A compound according to embodiment 96, wherein
  $R^3$ is —CH$_2$-(thiazol-2-yl), where the thiazole group is optionally substituted one to four times with substituents independently selected from $R^c$.
Embodiment 229: A compound according to embodiment 96, wherein
  $R^3$ is —CH$_2$-(oxazol-4-yl), where the oxazole group is optionally substituted one to four times with substituents independently selected from $R^c$.
Embodiment 230: A compound according to embodiment 97, wherein
  $R^3$ is —CH$_2$-heteroaryl, where the heteroaryl group is optionally substituted one or more times with substituents independently selected from $R^x$.
Embodiment 231: A compound according to embodiment 97, wherein
  $R^3$ is —CH$_2$-heteroaryl, where the heteroaryl group is optionally substituted one or more times with substituents independently selected from methyl, ethyl, isopropyl, isobutyl, sec-butyl, tert-butyl, —S(O)$_2$—CH$_3$, —NH$_2$, —NH—(CH$_2$)$_{0-4}$—CH$_3$, —NH—(CH$_2$)$_{0-2}$—CH(CH$_3$)$_2$, —NH—(CH$_2$)$_{0-2}$—C(CH$_3$)$_3$, —NH-cyclopropyl, —NH-cyclobutyl, —NH-cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, 2-oxo-piperazin-1-yl, —NH—C(O)—(CH$_2$)$_{0-2}$—CH$_3$, —NH—C(O)—(CH$_2$)$_{0-1}$—CH(CH$_3$)$_2$, —NH—C(O)—(CH$_2$)$_{0-1}$—CF$_3$, —NH—C(O)-phenyl, —NH—C(O)-cyclopropyl, —NH—C(O)-cyclobutyl, —NH—C(O)— cyclopentyl, —NH—C(O)-cyclohexyl, —NH—C(O)-(pyrrolidin-2-yl), NH—C(O)-(1-methyl-pyrrolidin-2-yl), NH—C(O)-(1-tert-butoxycarbonyl-pyrrolidin-2-yl), —NH—C(O)-(piperazin-1-yl), NH—C(O)-(4-methyl-piperazin-1-yl), NH—C(O)-(4-tert-butoxycarbonyl-piperazin-1-yl), —NH—C(O)-(piperidin-4-yl), NH—C(O)-(1-methyl-piperidin-4-yl), NH—C(O)-(1-tert-butoxycarbonyl-piperidin-4-yl), —NH—C(O)-(tetrahydropyran-4-yl), —NH—(CH$_2$)$_{1-2}$-phenyl, —NH—(CH$_2$)$_{1-2}$-cyclopropyl, —NH—(CH$_2$)$_{1-2}$-cyclobutyl, —NH—(CH$_2$)$_{1-2}$-cyclopentyl, —NH—(CH$_2$)$_{1-2}$-cyclohexyl, —NH—(CH$_2$)$_{1-2}$—O—CH$_3$, —NH—(CH$_2$)$_{1-2}$—O—CH$_2$CH$_3$, —NH—(CH$_2$)$_{1-2}$—O—CF$_3$, —NH—(CH$_2$)$_{1-2}$—N(CH$_3$)$_2$, —NH—C(O)—NH—(CH$_2$)$_{0-1}$—CH$_3$, —NH—C(O)—NH—(CH$_2$)$_{0-1}$-cyclopropyl, —NH—C(O)—NH—(CH$_2$)$_{0-1}$-cyclobutyl, —NH—C(O)—NH—(CH$_2$)$_{0-1}$-cyclopentyl, and —NH—C(O)—NH—(CH$_2$)$_{0-1}$-cyclohexyl.
Embodiment 232: A compound according to embodiment 97, wherein
  $R^3$ is —CH$_2$-(furan-2-yl), —CH$_2$-(furan-3-yl), —CH$_2$-(thiophen-2-yl), —CH$_2$-(thiophen-2-yl), —CH$_2$-(1H-pyrrol-1-yl), —CH$_2$-(1H-pyrrol-2-yl), —CH$_2$-(1H-pyrrol-3-yl), —CH$_2$-(oxazol-2-yl), —CH$_2$-(oxazol-4-yl), —CH$_2$-(oxazol-5-yl), —CH$_2$-(isoxazol-3-yl), —CH$_2$-(isoxazol-4-yl), —CH$_2$-(isoxazol-5-yl), —CH$_2$-(thiazol-2-yl), —CH$_2$-(thiazol-4-yl), —CH$_2$-(thiazol-5-yl), —CH$_2$-(isothiazol-3-yl), —CH$_2$-(isothiazol-4-yl), —CH$_2$-(isothiazol-5-yl), —CH$_2$-(1H-imidazol-1-yl), —CH$_2$-(1H-imidazol-2-yl), —CH$_2$-(1H-imidazol-4-yl), —CH$_2$-(1H-imidazol-5-yl), —CH$_2$-(1H-pyrazol-1-yl), —CH$_2$-(1H-pyrazol-3-yl), —CH$_2$-(1H-pyrazol-4-yl), —CH$_2$-(1H-pyrazol-5-yl), —CH$_2$-(2-pyridyl), —CH$_2$-(3-pyridyl), —CH$_2$-(4-pyridyl), —CH$_2$-(pyridazin-3-yl), —CH$_2$-(pyridazin-4-yl), —CH$_2$-(pyrimidin-2-yl), —CH$_2$-(pyrimidin-4-yl), —CH$_2$-(pyrimidin-5-yl), or —CH$_2$-(pyrazin-2-yl), where each named heteroaryl ring is optionally substituted one or more times with substituents independently selected from $R^x$.
Embodiment 233: A compound according to embodiment 97, wherein
  $R^3$ is —CH$_2$-(furan-2-yl), —CH$_2$-(furan-3-yl), —CH$_2$-(thiophen-2-yl), —CH$_2$-(thiophen-3-yl), —CH$_2$-(oxazol-2-yl), —CH$_2$-(oxazol-4-yl), —CH$_2$-(oxazol-5-yl), —CH$_2$-(isoxazol-3-yl), —CH$_2$-(isoxazol-4-yl), —CH$_2$-(isoxazol-5-yl), —CH$_2$-(thiazol-2-yl), —CH$_2$-(thiazol-4-yl), —CH$_2$-(thiazol-5-yl), —CH$_2$-(isothiazol-3-yl), —CH$_2$-(isothiazol-4-yl), —CH$_2$-(isothiazol-5-yl), —CH$_2$-(1H-pyrazol-3-yl), —CH$_2$-(1H-pyrazol-4-yl), —CH$_2$-(1H-pyrazol-5-yl), —CH$_2$-(2-pyridyl), —CH$_2$-(3-pyridyl), —CH$_2$-(4-pyridyl), or —CH$_2$-(pyrazin-2-yl), where each heteroaryl ring is optionally substituted one or more times with substituents independently selected from methyl, ethyl, isopropyl, isobutyl, sec-butyl, tert-butyl, —S(O)$_2$—CH$_3$, —NH$_2$, —NH—(CH$_2$)$_{0-4}$—CH$_3$, —NH—(CH$_2$)$_{0-2}$—CH(CH$_3$)$_2$, —NH—(CH$_2$)$_{0-2}$—C(CH$_3$)$_3$, —NH-cyclopropyl, —NH-cyclobutyl, —NH— cyclopentyl, —NH-cyclohexyl, —CF$_3$, —CH$_2$CF$_3$, —O—CH$_3$, —OCH$_2$CH$_3$, —O—CH(CH$_3$)$_2$, —O—CF$_3$, —O—CH$_2$CF$_3$, -phenyl, —(CH$_2$)$_{1-2}$-phenyl, —CH(CH$_3$)-phenyl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 2-oxo-pyrrolidin-1-yl, 2-oxo-piperidin-1-yl, and 2-oxo-piperazin-1-yl, —NH—C(O)—(CH$_2$)$_{0-2}$—CH$_3$, —NH—C(O)—(CH$_2$)$_{01}$—CH(CH$_3$)$_2$, —NH—C(O)—(CH$_2$)$_{0-1}$—CF$_3$, —NH—C(O)-phenyl, —NH—C(O)-cyclopropyl, —NH—C(O)— cyclobutyl, —NH—C(O)-cyclopentyl, —NH—C(O)-cyclohexyl, —NH—C(O)-(pyrrolidin-2-yl), —NH—C(O)-(1-methyl-pyrrolidin-2-yl), —NH—C(O)-(1-tert-butoxycarbonyl-pyrrolidin-2-yl), —NH—C(O)-(piperazin-1-yl), —NH—C(O)-(4-methyl-piperazin-1-yl), —NH—C(O)-(4-tert-butoxycarbonyl-piperazin-1-yl), —NH—C(O)-(piperidin-4-yl), NH—C(O)-(1-methyl-piperidin-4-yl), NH—C(O)-(1-tert-butoxycarbonyl-piperidin-4-yl), —NH—C(O)-(tetrahydropyran-4-yl), —NH—(CH$_2$)$_{1-2}$-phenyl, —NH—(CH$_2$)$_{1-2}$-cyclopropyl, —NH—(CH$_2$)$_{1-2}$-cyclobutyl, —NH—(CH$_2$)$_{1-2}$-cyclopentyl, —NH—(CH$_2$)$_{1-2}$-cyclohexyl, —NH—(CH$_2$)$_{1-2}$—O—CH$_3$, —NH—(CH$_2$)$_{1-2}$—O—CH$_2$CH$_3$, —NH—(CH$_2$)$_{1-2}$—O—CF$_3$, —NH—(CH$_2$)$_{1-2}$—N(CH$_3$)$_2$, —NH—C(O)—NH—(CH$_2$)$_{0-1}$—CH$_3$, —NH—C(O)—NH—(CH$_2$)$_{0-1}$- cyclopropyl, —NH—C(O)—NH—(CH$_2$)$_{0-1}$-cyclobutyl, —NH—C(O)—NH—(CH$_2$)$_{0-1}$-cyclopentyl, and —NH—C(O)—NH—(CH$_2$)$_{0-1}$-cyclohexyl.
Embodiment 234: A compound according to embodiment 97, wherein
  $R^3$ is —CH$_2$-(2-pyridyl), where the pyridine group is optionally substituted one or more times with substituents independently selected from $R^x$.

Embodiment 235: A compound according to embodiment 97, wherein
R$^3$ is —CH$_2$-(3-pyridyl), where the pyridine group is optionally substituted one or more times with substituents independently selected from R$^x$.

Embodiment 236: A compound according to embodiment 97, wherein
R$^3$ is —CH$_2$-(4-pyridyl), where the pyridine group is optionally substituted one or more times with substituents independently selected from R$^x$.

Embodiment 237: A compound according to embodiment 97, wherein
R$^3$ is —CH$_2$-(imidazol-2-yl), where the imidazole group is optionally substituted one or more times with substituents independently selected from R$^x$.

Embodiment 238: A compound according to embodiment 97, wherein
R$^3$ is —CH$_2$-(thiazol-2-yl), where the thiazole group is optionally substituted one or more times with substituents independently selected from R$^x$.

Embodiment 239: A compound according to embodiment 97, wherein
R$^3$ is —CH$_2$-(oxazol-4-yl), where the oxazole group is optionally substituted one or more times with substituents independently selected from R$^x$.

Embodiment 240: A compound according to embodiment 96, wherein
R$^3$ is —CH$_2$-cycloalkyl.

Embodiment 241: A compound according to embodiment 96, wherein
R$^3$ is —CH$_2$-cyclopropyl, —CH$_2$-cyclobutyl, —CH$_2$-cyclopentyl, or —CH$_2$-cyclohexyl.

Embodiment 242: A compound according to embodiment 97, wherein
R$^3$ is —CH$_2$—C$_{3-10}$ cycloalkyl, where the cycloalkyl group is optionally substituted one or more times with substituents independently selected from R$^x$.

Embodiment 243: A compound according to embodiment 97, wherein
R$^3$ is —CH$_2$—C$_{3-10}$ cycloalkyl, where the cycloalkyl group is optionally substituted one or more times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, —NO$_2$, methyl, ethyl, isopropyl, isobutyl, sec-butyl, tert-butyl, —S(O)$_2$—CH$_3$, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, —NH—C(O)—CH$_3$, —NH—C(O)—CH$_2$CH$_3$, —N(CH$_3$)—C(O)—CH$_3$, and —N(CH$_3$)—C(O)—CH$_2$CH$_3$.

Embodiment 244: A compound according to embodiment 97, wherein
R$^3$ is —CH$_2$-cyclopropyl, —CH$_2$-cyclobutyl, —CH$_2$-cyclopentyl, or —CH$_2$-cyclohexyl, where each cycloalkyl group is optionally substituted one or more times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, —NO$_2$, methyl, ethyl, isopropyl, isobutyl, sec-butyl, tert-butyl, —S(O)$_2$—CH$_3$, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, —NH—C(O)—CH$_3$, —NH—C(O)—CH$_2$CH$_3$, —N(CH$_3$)—C(O)—CH$_3$, and —N(CH$_3$)—C(O)—CH$_2$CH$_3$.

Embodiment 245: A compound according to embodiment 96, wherein
R$^3$ is —CH$_2$-heterocyclyl.

Embodiment 246: A compound according to embodiment 96, wherein
R$^3$ is —CH$_2$-tetrahydrofuran-2-yl, —CH$_2$-tetrahydrofuran-3-yl-CH$_2$-tetrahydropyran-2-yl, —CH$_2$-tetrahydropyran-3-yl, or —CH$_2$-tetrahydropyran-4-yl.

Embodiment 247: A compound according to embodiment 97, wherein
R$^3$ is —CH$_2$-heterocyclyl, where the heterocyclyl group is optionally substituted one or more times with substituents independently selected from R$^x$.

Embodiment 248: A compound according to embodiment 97, wherein
R$^3$ is —CH$_2$-heterocyclyl, where the heterocyclyl group is optionally substituted one or more times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, —NO$_2$, methyl, ethyl, isopropyl, isobutyl, sec-butyl, tert-butyl, —S(O)$_2$—CH$_3$, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, —NH—C(O)—CH$_3$, —NH—C(O)—CH$_2$CH$_3$, —N(CH$_3$)—C(O)—CH$_3$, and —N(CH$_3$)—C(O)—CH$_2$CH$_3$.

Embodiment 249: A compound according to embodiment 97, wherein
R$^3$ is —CH$_2$-tetrahydrofuran-2-yl, —CH$_2$-tetrahydrofuran-3-yl, —CH$_2$-tetrahydropyran-2-yl, —CH$_2$-tetrahydropyran-3-yl, or —CH$_2$-tetrahydropyran-4-yl, where the heterocyclyl group is optionally substituted one or more times with substituents independently selected from halogen, —NH$_2$, —NH—CH$_3$, —NH—CH$_2$CH$_3$, —N(CH$_3$)$_2$, —N(CH$_3$)—CH$_2$CH$_3$, —N(CH$_2$CH$_3$)$_2$, —CN, —NO$_2$, methyl, ethyl, isopropyl, isobutyl, sec-butyl, tert-butyl, —S(O)$_2$—CH$_3$, —O—CH$_3$, —O—CH$_2$CH$_3$, —O—CH(CH$_3$)$_2$, —O—CF$_3$, —O—CH$_2$CF$_3$, —CF$_3$, —O—CH$_2$CF$_3$, —NH—C(O)—CH$_3$, —NH—C(O)—CH$_2$CH$_3$, —N(CH$_3$)—C(O)—CH$_3$, and —N(CH$_3$)—C(O)—CH$_2$CH$_3$.

Embodiment 250: A compound according to embodiment 96 or 97, wherein
R$^3$ is methyl, ethyl, isopropyl, n-propyl, n-butyl, sec-butyl, isobutyl, tert-butyl, neopentyl, 1-ethyl-n-propyl, or 1-isopropyl-n-propyl.

Embodiment 251: A compound according to embodiment 96, wherein
R$^3$ is —CH(phenyl)-(CH$_2$)$_{0-2}$—CH$_3$, or —CH(phenyl)-CH(CH$_3$)$_2$, where the phenyl group is optionally substituted one to four times with substituents selected independently from R$^c$.

Embodiment 252: A compound according to embodiment 97, wherein
R$^3$ is —CH(phenyl)-(CH$_2$)$_{0-2}$—CH$_3$, or —CH(phenyl)-CH(CH$_3$)$_2$, where the phenyl group is
optionally substituted one or more times with substituents selected independently from R$^x$.

Embodiment 253: A compound according to embodiment 96, wherein
R$^3$ is —CH(2-pyridyl)-(CH$_2$)$_{0-2}$—CH$_3$, —CH(2-pyridyl)-CH(CH$_3$)$_2$, —CH(3-pyridyl)-(CH$_2$)$_{0-2}$—CH$_3$, —CH(3-pyridyl)-CH(CH$_3$)$_2$, —CH(4-pyridyl)-(CH$_2$)$_{0-2}$—CH$_3$, —CH(4-pyridyl)-CH(CH$_3$)$_2$, —CH(pyrimidin-2-yl)-(CH$_2$)$_{0-2}$—CH$_3$, —CH(pyrimidin-2-yl)-CH(CH$_3$)$_2$, —CH(pyrimidin-4-yl)-(CH$_2$)$_{0-2}$—CH$_3$, —CH(pyrimidin-4-yl)-CH(CH$_3$)$_2$, —CH(pyrimidin-5-yl)-(CH$_2$)$_{0-2}$—CH$_3$, —CH(pyrimidin-5-yl)-CH(CH$_3$)$_2$, —CH(pyridazin-3-yl)-(CH$_2$)$_{0-2}$—CH$_3$, —CH(pyridazin-3-yl)-CH(CH$_3$)$_2$, —CH(pyridazin-4-yl)-(CH$_2$)$_{0-2}$—CH$_3$, —CH(pyridazin-4-yl)-CH(CH$_3$)$_2$, —CH(pyrazin-2-yl)-(CH$_2$)$_{0-2}$—CH$_3$, or —CH(pyrazin-2-yl)-CH(CH$_3$)$_2$, where each heteroaryl group is optionally substituted one to four times with substituents selected independently from R$^c$.

Embodiment 254: A compound according to embodiment 97, wherein

R$^3$ is —CH(2-pyridyl)-(CH$_2$)$_{0-2}$—CH$_3$, —CH(2-pyridyl)-CH(CH$_3$)$_2$, —CH(3-pyridyl)-(CH$_2$)$_{0-2}$—CH$_3$, —CH(3-pyridyl)-CH(CH$_3$)$_2$, —CH(4-pyridyl)-(CH$_2$)$_{0-2}$—CH$_3$, —CH(4-pyridyl)-CH(CH$_3$)$_2$, —CH(pyrimidin-2-yl)-(CH$_2$)$_{0-2}$—CH$_3$, —CH(pyrimidin-2-yl)-CH(CH$_3$)$_2$, —CH(pyrimidin-4-yl)-(CH$_2$)$_{0-2}$—CH$_3$, —CH(pyrimidin-4-yl)-CH(CH$_3$)$_2$, —CH(pyrimidin-5-yl)-(CH$_2$)$_{0-2}$—CH$_3$, —CH(pyrimidin-5-yl)-CH(CH$_3$)$_2$, —CH(pyridazin-3-yl)-(CH$_2$)$_{0-2}$—CH$_3$, —CH(pyridazin-3-yl)-CH(CH$_3$)$_2$, —CH(pyridazin-4-yl)-(CH$_2$)$_{0-2}$—CH$_3$, —CH(pyridazin-4-yl)-CH(CH$_3$)$_2$, —CH(pyrazin-2-yl)-(CH$_2$)$_{0-2}$—CH$_3$, or —CH(pyrazin-2-yl)-CH(CH$_3$)$_2$, where each heteroaryl group is optionally substituted one or more times with substituents selected independently from R$^x$.

Embodiment 255: A compound according to embodiment 96, wherein

R$^3$ is —C≡C-phenyl, where the phenyl group is optionally substituted one to four times with substituents selected independently from R$^c$.

Embodiment 256: A compound according to embodiment 97, wherein

R$^3$ is —C≡C-phenyl, where the phenyl group is optionally substituted one or more times with substituents selected independently from R$^x$.

Embodiment 257: A compound according to embodiment 96, wherein

R$^3$ is

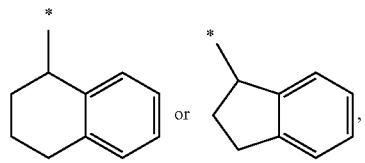

where each group is optionally substituted one to four times with substituents selected independently from R$^c$.

Embodiment 258: A compound according to embodiment 97, wherein

R$^3$

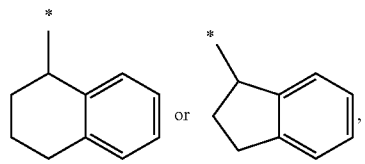

is where each group is optionally substituted one or more times with substituents selected independently from R$^x$.

Embodiment 259: A compound according to embodiment 96, wherein

R$^3$ is —C(O)NR$^d$R$^e$.

Embodiment 260: A compound according to embodiment 259, wherein

R$^e$ is hydrogen.

Embodiment 261: A compound according to embodiment 259, wherein

R$^e$ is methyl.

Embodiment 262: A compound according to any one of embodiments 259 to 261, wherein R$^d$ is phenyl optionally substituted with one to four substituents independently selected from R$^c$.

Embodiment 263: A compound according to any one of embodiments 259 to 261, wherein R$^d$ is 2-pyridyl, 3-pyridyl, 4-pyridyl, pyridazin-3-yl, pyridazin-4-yl, pyrimidine-2-yl, pyrimidin-4-yl, pyrimidin-5-yl, or pyrazin-2-yl, each of which is optionally substituted with one to four substituents independently selected from R$^c$.

Embodiment 264: A compound according to any one of embodiments 259 to 261, wherein R$^d$ is oxazol-4-yl, oxazol-5-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, imidazol-4-yl, or imidazol-5-yl, each of which is optionally substituted with one to four substituents independently selected from R$^c$.

Embodiment 265: A compound according to any one of embodiments 259 to 261, wherein R$^d$ is heterocyclyl optionally substituted one to four times with substituents independently selected from R$^c$.

Embodiment 266: A compound according to any one of embodiments 259 to 261, wherein R$^d$ is cycloalkyl optionally substituted one to four times with substituents independently selected from R$^c$.

Embodiment 267: A compound according to any one of embodiments 259 to 261, wherein R$^d$ is cyclopropyl, cyclobutyl, cyclopentyl, or cyclohexyl, where each is optionally substituted one to four times with substituents independently selected from R$^c$.

Embodiment 268: A compound according to any one of embodiments 259 to 261, wherein R$^d$ is indan-1-yl or indan-2-yl, where each is optionally substituted one to four times with substituents independently selected from R$^c$.

Embodiment 269: A compound according to any one of embodiments 259 to 261, wherein R$^d$ is alkylene-phenyl.

Embodiment 270: A compound according to any one of embodiments 259 to 261, wherein R$^d$ is —C$_{1-10}$ alkylene-2-pyridyl, —C$_{1-10}$ alkylene-3-pyridyl, —C$_{1-10}$ alkylene-4-pyridyl, alkylene-pyridazin-3-yl, —C$_{1-10}$ alkylene-pyridazin-4-yl, —C$_{1-10}$ alkylene-pyrimidin-2-yl, alkylene-pyrimidin-4-yl, —C$_{1-10}$ alkylene-pyrimidin-5-yl, or —C$_{1-10}$ alkylene-pyrazin-2-yl.

Embodiment 271: A compound according to any one of embodiments 259 to 261, wherein R$^d$ is C$_{1-10}$ alkyl optionally substituted with one to four times with substituents independently selected from R$^c$.

Embodiment 272: A compound according to embodiment 97, wherein

R$^3$ is —C(O)NR$^j$R$^k$.

Embodiment 273: A compound according to embodiment 272, wherein

R$^k$ is hydrogen.

Embodiment 274: A compound according to embodiment 272, wherein

R$^k$ is methyl.

Embodiment 275: A compound according to any one of embodiments 272 to 274,
wherein $R^j$ is phenyl optionally substituted one or more times with substituents independently selected from $R^x$.

Embodiment 276: A compound according to any one of embodiments 272 to 274,
wherein $R^j$ is 2-pyridyl, 3-pyridyl, 4-pyridyl, pyridazin-3-yl, pyridazin-4-yl, pyrimidin-2-yl, pyrimidin-4-yl, pyrimidin-5-yl, or pyrazin-2-yl, each of which is optionally substituted one or more times with substituents independently selected from $R^k$.

Embodiment 277: A compound according to any one of embodiments 272 to 274,
wherein $R^j$ is oxazol-4-yl, oxazol-5-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, imidazol-4-yl, or imidazol-5-yl, each of which is optionally substituted one or more times with substituents independently selected from $R^x$.

Embodiment 278: A compound according to any one of embodiments 272 to 274,
wherein $R^j$ is heterocyclyl optionally substituted with one or more times with substituents independently selected from $R^x$.

Embodiment 279: A compound according to any one of embodiments 272 to 274,
wherein $R^j$ is —$C_{3-10}$ cycloalkyl optionally substituted one or more times with substituents independently selected from $R^x$.

Embodiment 280: A compound according to any one of embodiments 272 to 274,
wherein $R^j$ is cyclopropyl, cyclobutyl, cyclopentyl, or cyclohexyl, where each is optionally substituted one or more times with substituents independently selected from $R^x$.

Embodiment 281: A compound according to any one of embodiments 272 to 274,
wherein $R^j$ is indan-1-yl or indan-2-yl, where each is optionally substituted one or more times with substituents independently selected from $R^x$.

Embodiment 282: A compound according to any one of embodiments 272 to 274,
wherein $R^j$ is —$C_{1-6}$ alkylene-phenyl, where the alkylene and phenyl groups are both optionally substituted one or more times with substituents independently selected from $R^x$ Embodiment 283: A compound according to any one of embodiments 272 to 274,
wherein $R^j$ is —$C_{1-6}$ alkylene-2-pyridyl, —$C_{1-6}$ alkylene-3-pyridyl, —$C_{1-6}$ alkylene-4-pyridyl, —$C_{1-6}$ alkylene-pyridazin-3-yl, —$C_{1-6}$ alkylene-pyridazin-4-yl, —$C_{1-6}$ alkylene-pyrimidin-2-yl, —$C_{1-6}$ alkylene-pyrimidin-4-yl, —$C_{1-6}$ alkylene-pyrimidin-5-yl, or —$C_{1-6}$ alkylene-pyrazin-2-yl, where the alkylene and heteroaryl groups are both optionally substituted one or more times with substituents independently selected from $R^x$.

Embodiment 284: A compound according to any one of embodiments 272 to 274,
wherein $R^j$ is $C_{1-6}$ alkyl optionally substituted one or more times with substituents independently selected from $R^x$.

Embodiment 285: A compound according to any one of embodiments 272 to 274,
wherein $R^j$ is heterocyclyl optionally substituted one or more times with substituents independently selected from $R^x$.

Embodiment 286: A compound according embodiment 259 or 272,
wherein $R^3$ is —C(O)N(CH$_3$)$_2$, —C(O)N(CH$_3$)(CH$_2$CH$_3$), —C(O)N(CH$_3$)(CH(CH$_3$)$_2$), —C(O)N(CH$_2$CH$_3$)$_2$, —C(O)(CH$_2$CH$_3$)(CH(CH$_3$)$_2$), or —C(O)N(CH(CH$_3$)$_2$)$_2$.

Embodiment 287: A compound according embodiment 259 or 272,
wherein $R^3$ is —C(O)-(pyrrolidin-1-yl), —C(O)-(piperidin-1-yl), —C(O)-(4-oxo-piperidin-1-yl), or —C(O)-(morpholin-4-yl).

Embodiment 288: A compound according to embodiment 96, wherein
$R^3$ is —C(O)OR$^d$.

Embodiment 289: A compound according to embodiment 288, wherein
wherein $R^d$ is phenyl optionally substituted one to four times with substituents independently selected from $R^c$.

Embodiment 290: A compound according to embodiment 288, wherein
$R^d$ is 2-pyridyl, 3-pyridyl, 4-pyridyl, pyridazin-3-yl, pyridazin-4-yl, pyrimidin-2-yl, pyrimidin-4-yl, pyrimidin-5-yl, or pyrazin-2-yl, each of which is optionally substituted with one to four substituents independently selected from $R^c$.

Embodiment 291: A compound according to embodiment 288, wherein
$R^d$ is oxazol-4-yl, thiazol-4-yl, or thiazol-5-yl, each of which is optionally substituted with one to four substituents independently selected from $R^c$.

Embodiment 292: A compound according to embodiment 288, wherein
$R^d$ is —$C_{1-10}$ alkyl optionally substituted with one to four substituents independently selected from $R^c$.

Embodiment 293: A compound according to embodiment 288, wherein
$R^d$ is —$C_{1-10}$ alkylene-phenyl.

Embodiment 294: A compound according to embodiment 288, wherein
$R^d$ is —$C_{1-10}$ alkylene-2-pyridyl, —$C_{1-10}$ alkylene-3-pyridyl, —$C_{1-10}$ alkylene-4-pyridyl, —$C_{1-10}$ alkylene-pyridazin-3-yl, alkylene-pyridazin-4-yl, —$C_{1-10}$ alkylene-pyrimidin-2-yl, alkylene-pyrimidin-4-yl, —$C_{1-10}$ alkylene-pyrimidin-5-yl, or —$C_{1-10}$ alkylene-pyrazin-2-yl.

Embodiment 295: A compound according to embodiment 97, wherein
$R^3$ is —C(O)—OR$^j$.

Embodiment 296: A compound according to embodiment 295, wherein
wherein $R^j$ is phenyl optionally substituted one or more times with substituents independently selected from $R^x$.

Embodiment 297: A compound according to embodiment 295, wherein
wherein $R^j$ is 2-pyridyl, 3-pyridyl, 4-pyridyl, pyridazin-3-yl, pyridazin-4-yl, pyrimidine-2-yl, pyrimidin-4-yl, pyrimidin-5-yl, or pyrazin-2-yl, each of which is optionally substituted one or more times with substituents independently selected from $R^x$.

Embodiment 298: A compound according to embodiment 295, wherein
$R^j$ is oxazol-4-yl, thiazol-4-yl, or thiazol-5-yl, each of which is optionally substituted with one or more substituents independently selected from $R^x$.

Embodiment 299: A compound according to embodiment 295, wherein
$R^j$ is —$C_{1-6}$ alkyl optionally substituted with one or more substituents independently selected from $R^x$.

Embodiment 300: A compound according to embodiment 295, wherein
wherein $R^j$ is $C_{1-6}$ alkylene-phenyl, where the alkylene and phenyl groups are both optionally substituted one or more times with substituents independently selected from $R^x$.

Embodiment 301: A compound according to embodiment 295, wherein
wherein $R^j$ is —$C_{1-6}$ alkylene-2-pyridyl, —$C_{1-6}$ alkylene-3-pyridyl, —$C_{1-6}$ alkylene-4-pyridyl, —$C_{1-6}$ alkylene-pyridazin-3-yl, —$C_{1-6}$ alkylene-pyridazin-4-yl, —$C_{1-6}$ alkylene-pyrimidine-2-yl, —$C_{1-6}$ alkylene-pyrimidin-4-yl, —$C_{1-6}$ alkylene-pyrimidin-5-yl, or —$C_{1-6}$ alkylene-pyrazin-2-yl, where the alkylene and heteroaryl groups are both optionally substituted one or more times with substituents independently selected from $R^x$.

Embodiment 302: A compound according to embodiment 288, wherein
wherein $R^d$ is heterocyclyl optionally substituted with one to four times with substituents independently selected from $R^c$.

Embodiment 303: A compound according to embodiment 295, wherein
wherein $R^j$ is heterocyclyl optionally substituted with one or more times with substituents independently selected from $R^c$.

Embodiment 304: A compound according to any one of embodiments 1 to 303, wherein
the compound is in its free (non-salted) form.

Embodiment 305: A compound according to any one of embodiments 1 to 303, wherein
the compound is in the form of a pharmaceutically acceptable salt.

Embodiment 306: A compound according to embodiment 305, wherein
the compound is in the form of a hydrochloride salt.

Embodiment 307: A compound according to any one of embodiments 1 to 306, wherein
any "heterocyclyl" group present in the compound is selected from the group consisting of: azetidin-1-yl, azetidin-2-yl, azetidin-3-yl, pyrrolidin-1-yl, pyrrolidin-2-yl, pyrrolidin-3-yl, tetrahydrofuran-2-yl, tetrahydrofuran-3-yl, tetrahydrothiophen-2-yl, tetrahydrothiophen-3-yl, pyrazolidin-1-yl, pyrazolidin-3-yl, pyrazolidin-4-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolodin-5-yl, isothiazolidin-2-yl, isothiazolidin-3-yl, isothiazolidin-4-yl, isothiazolodin-5-yl, 1,3-dioxolan-2-yl, 1,3-dioxolan-4-yl, 1,3-oxathiolan-2-yl, 1,3-oxathiolane-4-yl, 1,3-oxathiolan-5-yl, 1,2-dithiolan-3-yl, 1,2-dithiolan-4-yl, 1,3-dithiolan-2-yl, 1,3-dithiolan-4-yl, piperidin-1-yl, piperidin-2-yl, piperidin-3-yl, piperidin-4-yl, tetrahydropyran-2-yl, tetrahydropyran-3-yl, tetrahydropyran-4-yl, thian-2-yl, thian-3-yl, thian-4-yl, piperazin-1-yl, piperazin-2-yl, morpholin-2-yl, morpholin-3-yl, morpholin-4-yl, thiomorpholin-2-yl, thiomorpholin-3-yl, thiomorpholin-4-yl, 1,4-dioxan-2-yl, 1,3-dioxan-2-yl, 1,3-dioxan-4-yl, 1,3-dioxan-5-yl, 1,4-dithian-2-yl, 1,3-dithian-2-yl, 1,3-dithian-4-yl, 1,3-dithian-5-yl, 1,2-dithian-3-yl, 1,2-dithian-4-yl, azepan-1-yl, azepan-2-yl, azepan-3-yl, azepan-4-yl, and 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, and 2-oxo-azepan-1-yl, where each of these named rings may optionally be substituted one or more times with substituents independently selected from halogen, —$NH_2$, cyano, carboxy, $C_{1-4}$ alkyl, $C_{3-10}$ cycloalkyl, hydroxyl, thiol, —$CF_3$, —$OCF_3$, —O—$C_{1-4}$ alkyl, —NH—$C_{1-4}$ alkyl, —N($C_{1-4}$ alkyl)$_2$, —S—$C_{1-4}$ alkyl, —S(O)$_2$—$C_{1-4}$ alkyl, —C(O)—$C_{1-4}$ alkyl, —C(O)O—$C_{1-4}$ alkyl, —C(O)NH$_2$, —C(O)NH—$C_{1-4}$ alkyl, and —C(O)N($C_{1-4}$ alkyl)$_2$, and where any nitrogen atom in any of these named rings may optionally be oxidized when chemically feasible, and where any sulfur atom in any of these named rings may optionally be oxidized once or twice when chemically feasible.

Embodiment 308: A compound according to any one of embodiments 1 to 307, wherein
any "heteroaryl" group present in the compound is selected from the group consisting of: 1H-pyrrol-1-yl, 1H-pyrrol-2-yl, 1H-pyrrol-3-yl, furan-2-yl, furan-3-yl, thiophen-2-yl, thiophen-3-yl, 1H-imidazol-1-yl, 1H-imidazol-2-yl, 1H-imidazol-4-yl, 1H-imidazol-5-yl, 1H-pyrazol-1-yl, 1H-pyrazol-3-yl, 1H-pyrazol-4-yl, 1H-pyrazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl, 1H-1,2,4-triazol-5-yl, furazan-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1H-indol-1-yl, 1H-indol-2-yl, 1H-indol-3-yl, 2H-isoindol-1-yl, 2H-isoindol-2-yl, quinolin-2-yl, quinolin-3-yl, quinolin-4-yl, isoquinolin-1-yl, isoquinolin-3-yl, isoquinolin-4-yl, benzoxazol-2-yl, benzothiazol-2-yl, 1H-benzimidazol-1-yl, 1H-benzimidazol-2-yl, benzofuran-2-yl, benzofuran-3-yl, benzothiophen-2-yl, and benzothiophen-3-yl, where each of these named rings may optionally be substituted one or more times with substituents independently selected from halogen, —$NH_2$, cyano, carboxy, $C_{1-4}$ alkyl, $C_{3-10}$ cycloalkyl, hydroxyl, thiol, —$CF_3$, —$OCF_3$, —O—$C_{1-4}$ alkyl, —NH—$C_{1-4}$ alkyl, —N($C_{1-4}$ alkyl)$_2$, —S—$C_{1-4}$ alkyl, —S(O)$_2$—$C_{1-4}$ alkyl, —C(O)—$C_{1-4}$ alkyl, —C(O)O—$C_{1-4}$ alkyl, —C(O)NH$_2$, —C(O)NH—$C_{1-4}$ alkyl, —C(O)N($C_{1-4}$ alkyl)$_2$, and phenyl.

The routes in the Examples, listed below, illustrate methods of synthesizing compounds of Formula (I), or a pharmaceutically acceptable salt thereof. The skilled person will appreciate that the compounds or salts of the invention could be made by methods other than those specifically described herein, by adaptation of the methods described herein and/or adaptation thereof, for example by methods known in the art.

Examples of compounds of Formula (I) or pharmaceutically acceptable salts thereof of the present invention having potentially useful biological activity are listed by structure in Table 1. The ability of compounds of Formula (I) or a pharmaceutically acceptable salt thereof to function as agonists of GLP-1R was established with representative compounds of Formula (I) listed in Table 2 using the assays described below.

Examples of compounds of Formula (I) or pharmaceutically acceptable salts thereof, are shown in Table 1. The compound of each Example and its pharmaceutically acceptable salts is a separate embodiment of the invention. Further, the compound of each Example in its free (non-salted) form is a separate embodiment of the invention. Further, the pharmaceutically acceptable salts of each Example compound are separate embodiments of the invention. Further, the hydrochloride salts of each Example compound are separate embodiments of the invention. Table 1 also shows LC-MS data for each compound. The recorded m/z data are accurate to within about 1 amu. For some examples, proton NMR spectra were also recorded. Unless otherwise indicated, the chemical shifts in the proton NMR spectrum are given relative to tetramethyl silane (TMS).

The LCMS (m/z) data are obtained using gradient elution on a parallel MUX™ system, running four Waters® 1525 binary HPLC pumps, equipped with a Mux-UV 2488 multi-channel UV-Vis detector (recording at 215 and 254 nM) and a Leap Technologies HTS PAL Auto sampler using a Sepax GP-C18, 4.6×50 mm; 5 micron particle-size column. A three minute gradient is run from 25% B (97.5% acetonitrile, 2.5% water, 0.05% TFA) and 75% A (97.5% water, 2.5% acetonitrile, 0.05% TFA) to 100% B. The system is interfaced with a Waters Micromass ZQ mass spectrometer using electrospray ionization. MassLynx software is employed.

In all the compounds dislosed in this application, the compounds with structures and names provided below were named based on their chemical structure, using, at least in part, Autonom 2000 (Version 4.1, SP1, Elsevier MDL) plug-in for ISIS Draw and MDL Crossfire Commander AutoNom. In the event the nomenclature is in conflict with the structure, it shall be understood that the compound is defined by the structure.

Any incomplete valences for heteroatoms such as oxygen and nitrogen in the chemical structures listed in Table 1 are assumed to be completed by hydrogen.

Compounds in Table 1 having a basic group or acidic group are depicted and named as the free base or acid. Depending on the reaction conditions and purification conditions, various compounds in Table 1 having a basic group may have been isolated in either the free base form, as a salt (such as HCl salt), or in both forms.

For Examples in Table 1, if the structure does not indicate the absolute stereochemistry at a particular stereocenter, then the structure represents a mixture of epimers with respect to that stereocenter.

TABLE 1

| Ex | Structure | LCMS (m/z) |
|---|---|---|
| 1 | 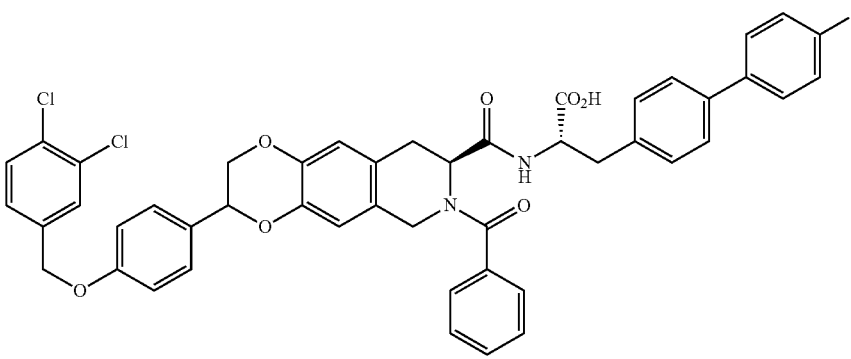 | 841 |
| 2 | 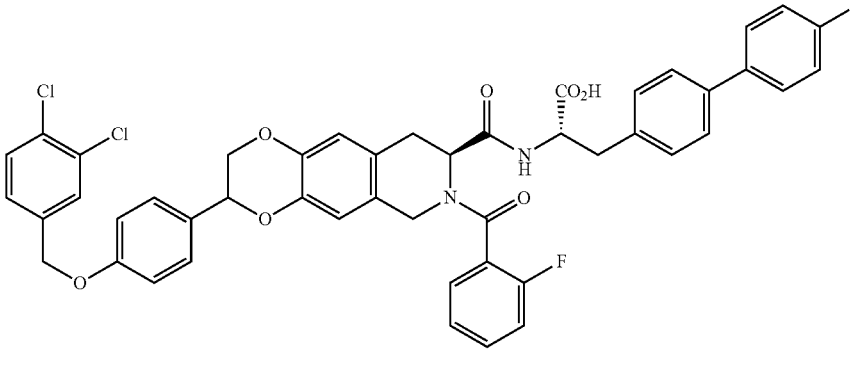 | 859 |
| 3 | 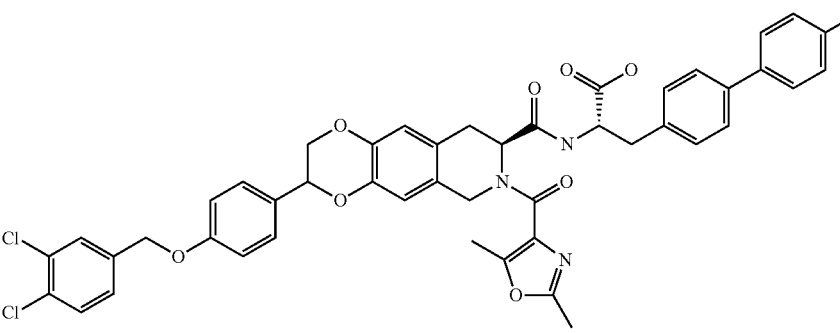 | 860 |

TABLE 1-continued

| Ex | Structure | LCMS (m/z) |
|---|---|---|
| 4 | 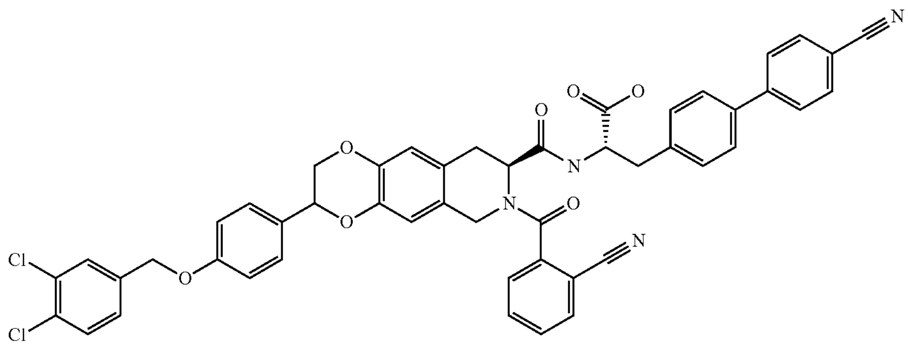 [SMILES: N#Cc1ccc(-c2ccc(C[C@H](NC(=O)[C@@H]3Cc4cc5c(cc4CN3C(=O)c3ccccc3C#N)OC(c3ccc(OCc4ccc(Cl)c(Cl)c4)cc3)CO5)C(=O)O)cc2)cc1] | 864 |
| 5 | 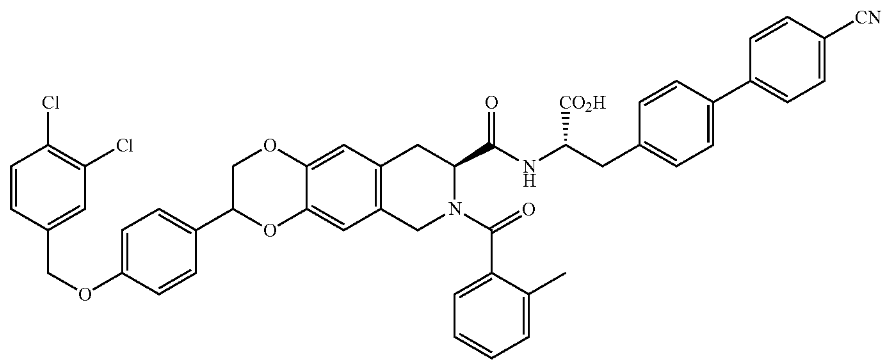 [SMILES: Cc1ccccc1C(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 853 |
| 6 | 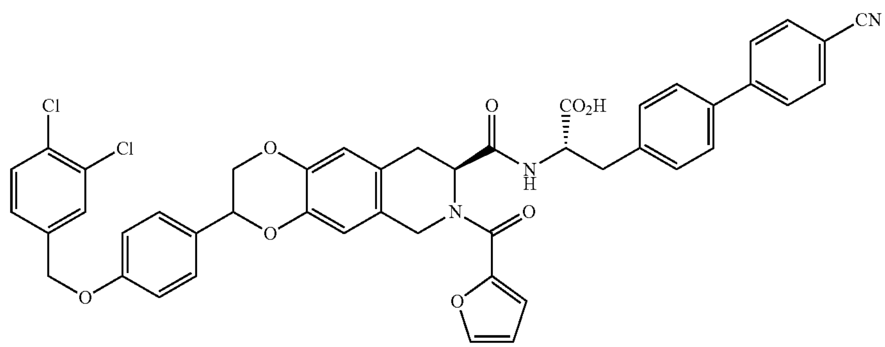 | 831 |
| 7 | 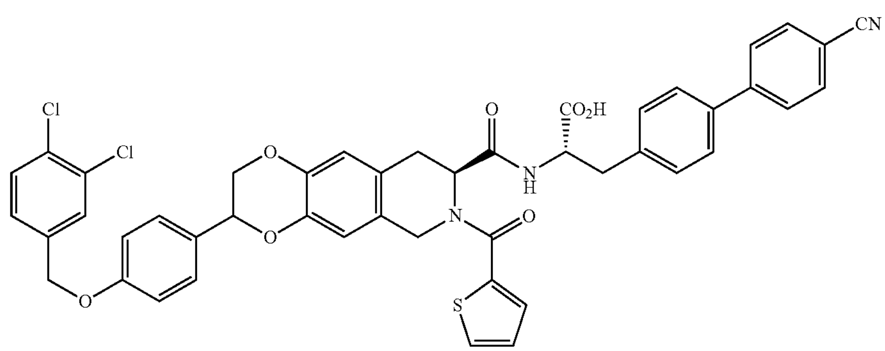 [SMILES: N#Cc1ccc(-c2ccc(C[C@H](NC(=O)[C@@H]3Cc4cc5c(cc4CN3C(=O)c3ccco3)OC(c3ccc(OCc4ccc(Cl)c(Cl)c4)cc3)CO5)C(=O)O)cc2)cc1] | 847 |

TABLE 1-continued

| Ex | Structure | LCMS (m/z) |
|---|---|---|
| 8 | 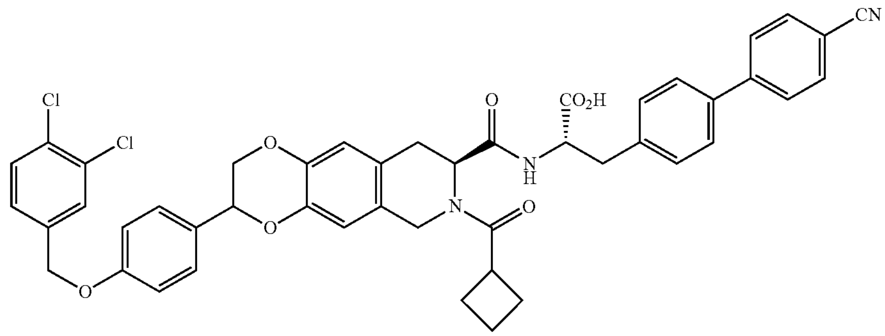 [SMILES: N#Cc1ccc(-c2ccc(C[C@H](NC(=O)[C@@H]3Cc4cc5c(cc4CN3C(=O)C3CCC3)OC(c3ccc(OCc4ccc(Cl)c(Cl)c4)cc3)CO5)C(=O)O)cc2)cc1] | 819 |
| 9 | 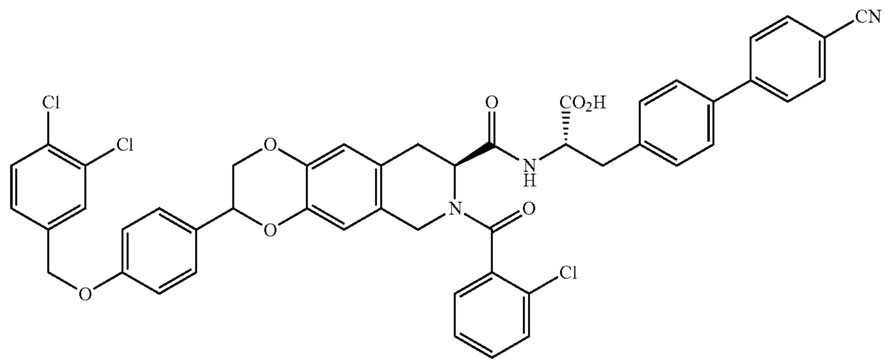 | 875 |
| 10 | 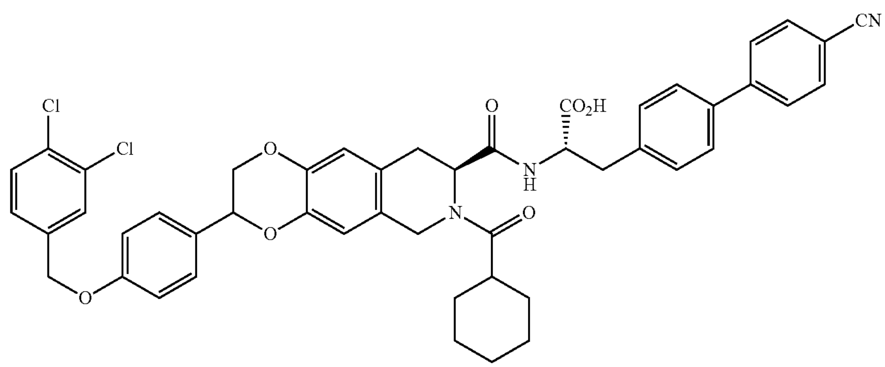 [SMILES: N#Cc1ccc(-c2ccc(C[C@H](NC(=O)[C@@H]3Cc4cc5c(cc4CN3C(=O)C3CCCCC3)OC(c3ccc(OCc4ccc(Cl)c(Cl)c4)cc3)CO5)C(=O)O)cc2)cc1] | 847 |
| 11 | 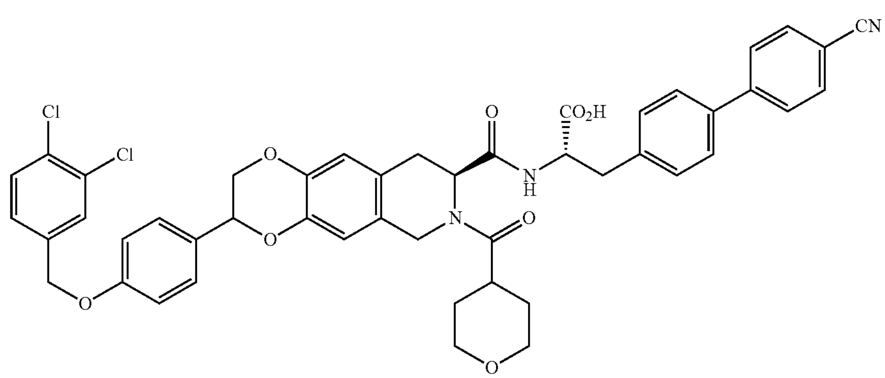 [SMILES: N#Cc1ccc(-c2ccc(C[C@H](NC(=O)[C@@H]3Cc4cc5c(cc4CN3C(=O)C3CCOCC3)OC(c3ccc(OCc4ccc(Cl)c(Cl)c4)cc3)CO5)C(=O)O)cc2)cc1] | 847 |

TABLE 1-continued

| Ex | Structure | LCMS (m/z) |
|---|---|---|
| 12 | 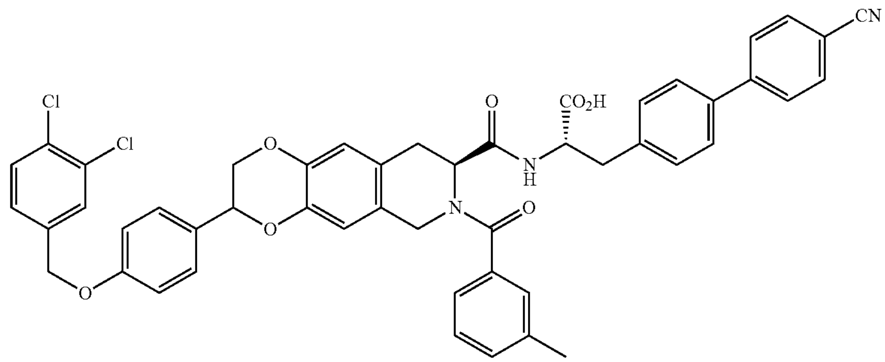 [SMILES: Cc1cccc(C(=O)N2Cc3cc4c(cc3C[C@H]2C(=O)N[C@@H](Cc2ccc(-c3ccc(C#N)cc3)cc2)C(=O)O)OCC(c2ccc(OCc3ccc(Cl)c(Cl)c3)cc2)O4)c1] | 855 |
| 13 | 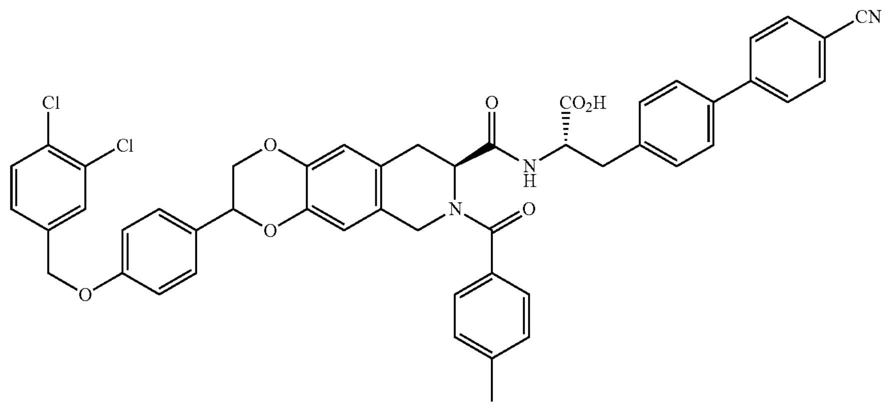 [SMILES: Cc1ccc(C(=O)N2Cc3cc4c(cc3C[C@H]2C(=O)N[C@@H](Cc2ccc(-c3ccc(C#N)cc3)cc2)C(=O)O)OCC(c2ccc(OCc3ccc(Cl)c(Cl)c3)cc2)O4)cc1] | 853 |
| 14 | 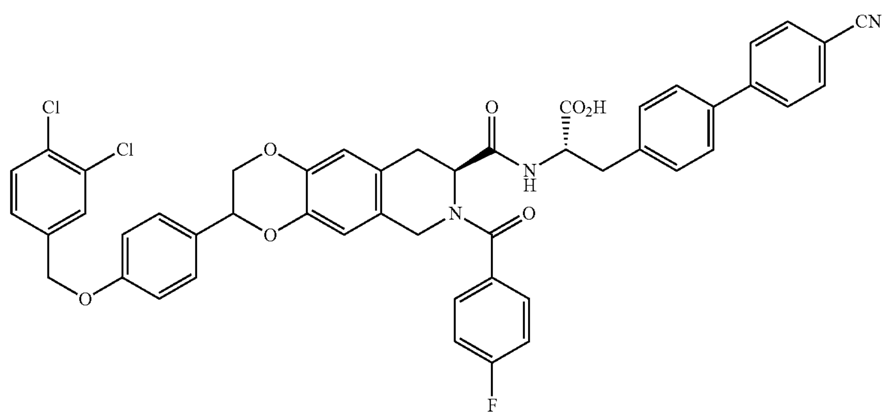 [SMILES: N#Cc1ccc(-c2ccc(C[C@H](NC(=O)[C@@H]3Cc4cc5c(cc4CN3C(=O)c3ccc(F)cc3)OC(c3ccc(OCc4ccc(Cl)c(Cl)c4)cc3)CO5)C(=O)O)cc2)cc1] | 857 |
| 15 | 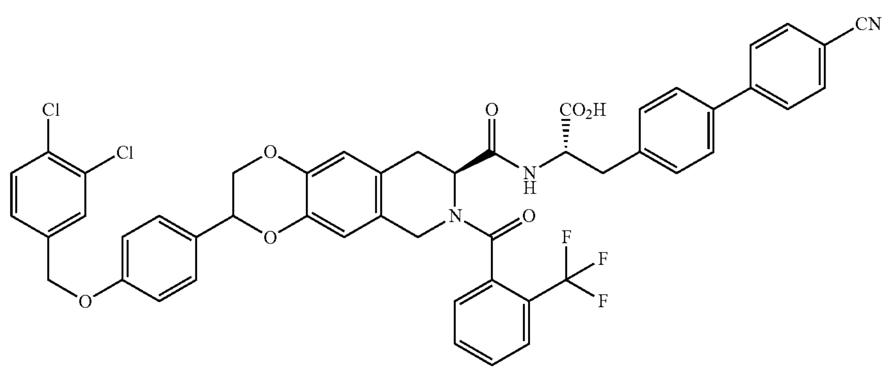 [SMILES: N#Cc1ccc(-c2ccc(C[C@H](NC(=O)[C@@H]3Cc4cc5c(cc4CN3C(=O)c3ccccc3C(F)(F)F)OC(c3ccc(OCc4ccc(Cl)c(Cl)c4)cc3)CO5)C(=O)O)cc2)cc1] | 907 |

TABLE 1-continued

| Ex | Structure | LCMS (m/z) |
|---|---|---|
| 16 | 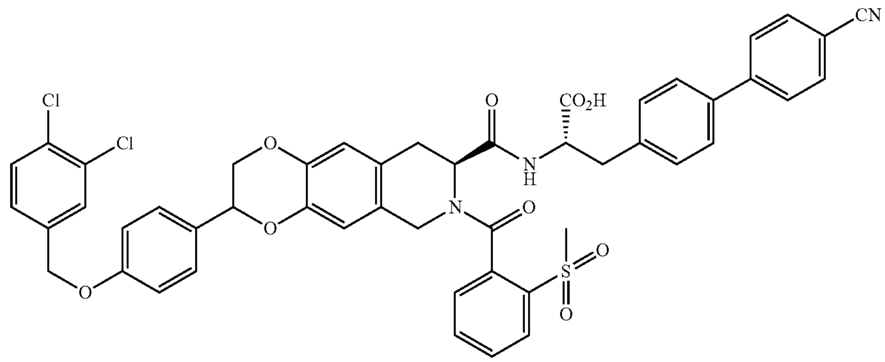 [SMILES: CS(=O)(=O)c1ccccc1C(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 919 |
| 17 | 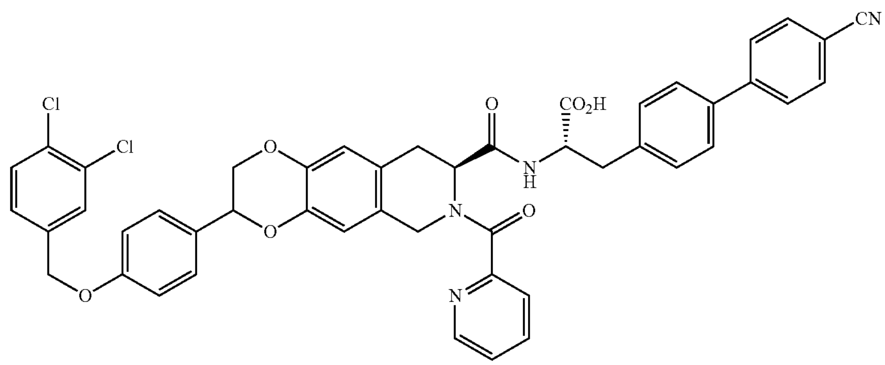 [SMILES: N#Cc1ccc(-c2ccc(C[C@H](NC(=O)[C@@H]3Cc4cc5c(cc4CN3C(=O)c3ccccn3)OC(c3ccc(OCc4ccc(Cl)c(Cl)c4)cc3)CO5)C(=O)O)cc2)cc1] | 842 |
| 18 | 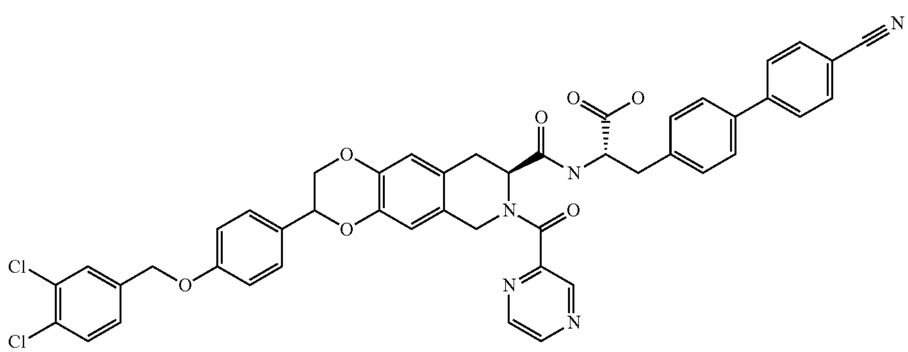 [SMILES: N#Cc1ccc(-c2ccc(C[C@H](NC(=O)[C@@H]3Cc4cc5c(cc4CN3C(=O)c3cnccn3)OC(c3ccc(OCc4ccc(Cl)c(Cl)c4)cc3)CO5)C(=O)O)cc2)cc1] | 841 |
| 19 | 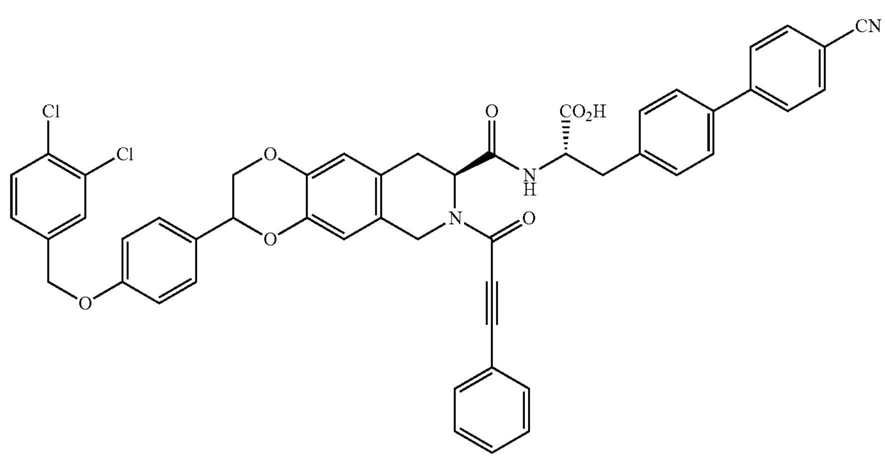 [SMILES: N#Cc1ccc(-c2ccc(C[C@H](NC(=O)[C@@H]3Cc4cc5c(cc4CN3C(=O)C#Cc3ccccc3)OC(c3ccc(OCc4ccc(Cl)c(Cl)c4)cc3)CO5)C(=O)O)cc2)cc1] | 863 |

TABLE 1-continued

| Ex | Structure | LCMS (m/z) |
|---|---|---|
| 20 | 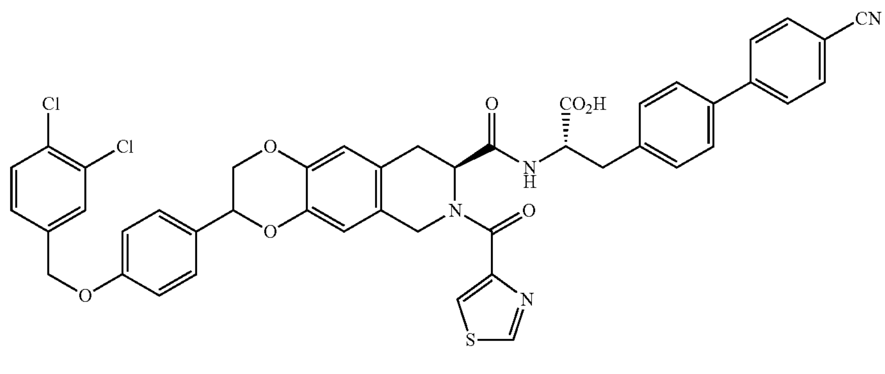 [SMILES: N#Cc1ccc(-c2ccc(C[C@H](NC(=O)[C@@H]3Cc4cc5c(cc4CN3C(=O)c3cscn3)OC(c3ccc(OCc4ccc(Cl)c(Cl)c4)cc3)CO5)C(=O)O)cc2)cc1] | 849 |
| 21 | 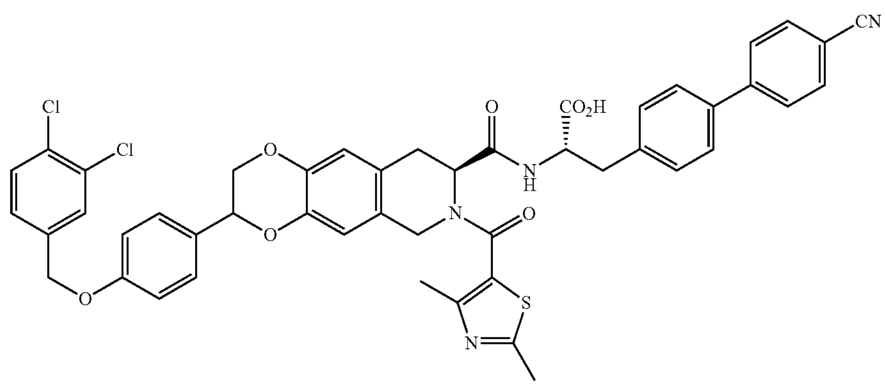 [SMILES: Cc1nc(C)c(C(=O)N2Cc3cc4c(cc3C[C@H]2C(=O)N[C@@H](Cc2ccc(-c3ccc(C#N)cc3)cc2)C(=O)O)OCC(c2ccc(OCc3ccc(Cl)c(Cl)c3)cc2)O4)s1] | 875 |
| 22 | 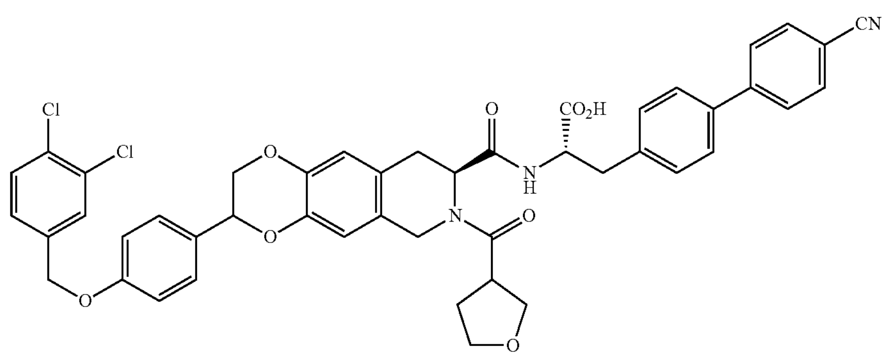 [SMILES: N#Cc1ccc(-c2ccc(C[C@H](NC(=O)[C@@H]3Cc4cc5c(cc4CN3C(=O)C3CCOC3)OC(c3ccc(OCc4ccc(Cl)c(Cl)c4)cc3)CO5)C(=O)O)cc2)cc1] | 835 |
| 23 | 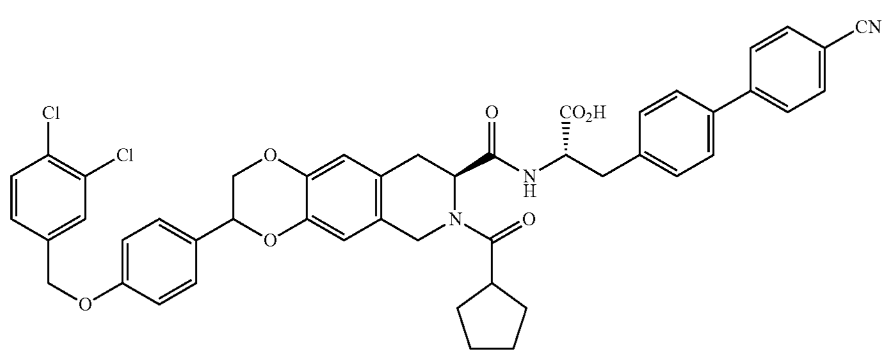 [SMILES: N#Cc1ccc(-c2ccc(C[C@H](NC(=O)[C@@H]3Cc4cc5c(cc4CN3C(=O)C3CCCC3)OC(c3ccc(OCc4ccc(Cl)c(Cl)c4)cc3)CO5)C(=O)O)cc2)cc1] | 830 |

TABLE 1-continued
| Ex | Structure | LCMS (m/z) |
|---|---|---|
| 24 | 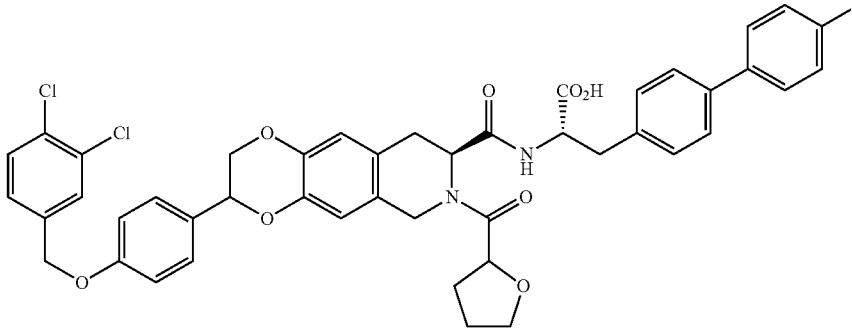 | 834 |
| 25 | 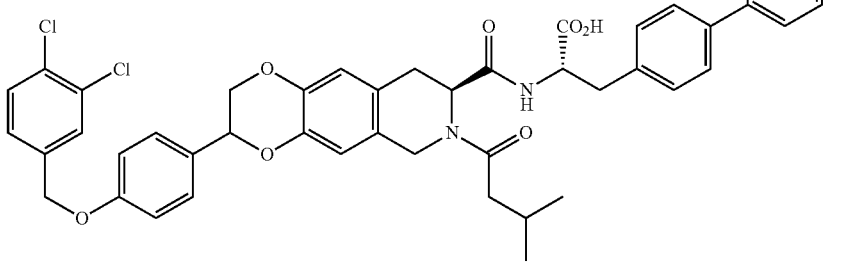 | 821 |
| 26 | 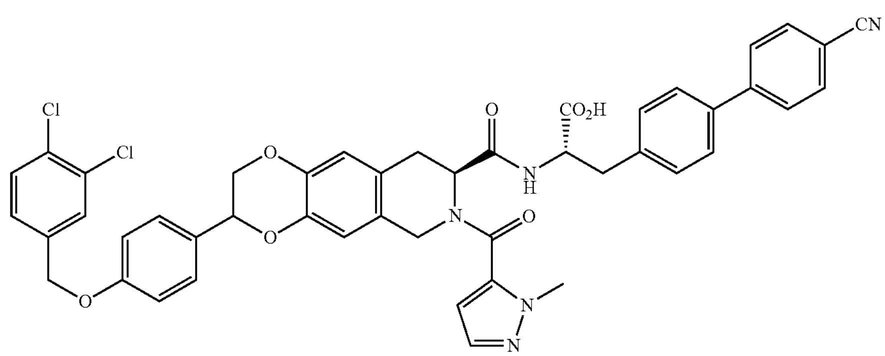 [SMILES: Cn1nccc1C(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 846 |
| 27 | 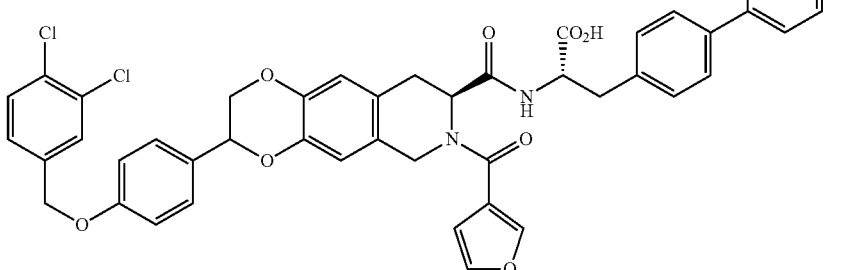 | 828 |

TABLE 1-continued
| Ex | Structure | LCMS (m/z) |
|---|---|---|
| 28 | 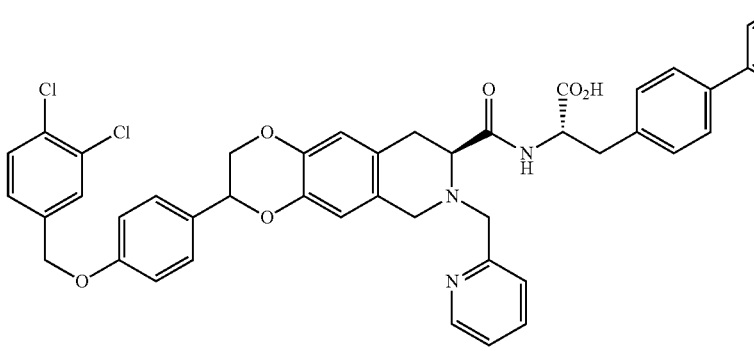 | 827 |
| 29 | 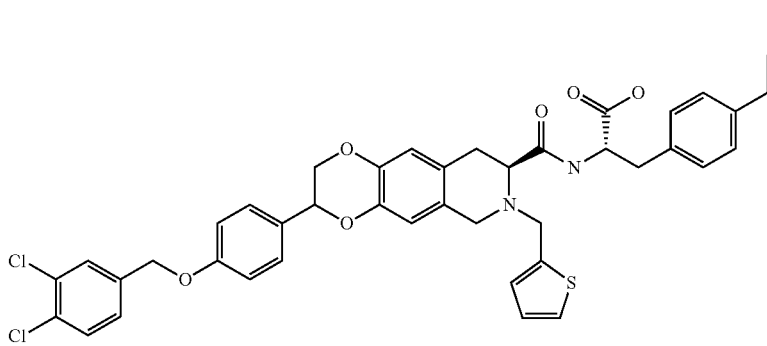 | 831 |
| 30 | 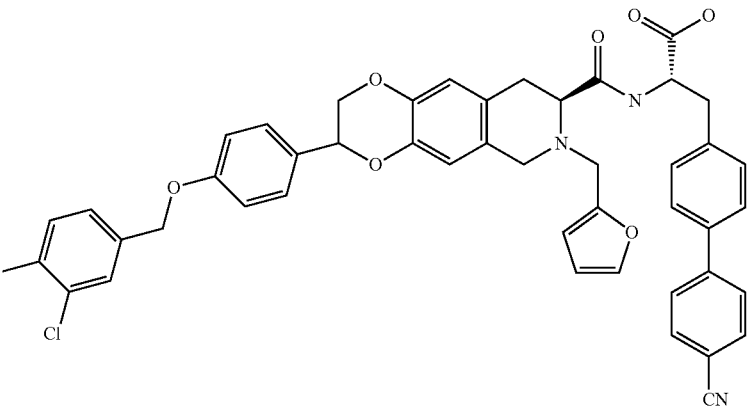 | 817 |
| 31 | 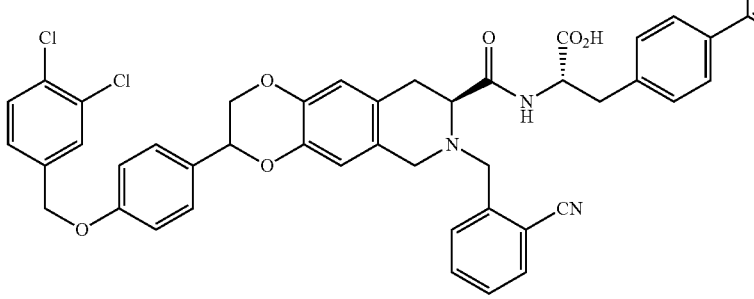 | 852 |

TABLE 1-continued
| Ex | Structure | LCMS (m/z) |
|---|---|---|
| 32 | 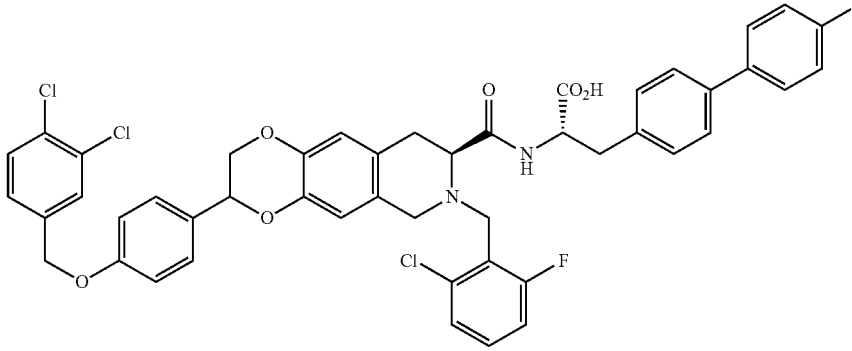 | 878 |
| 33 | 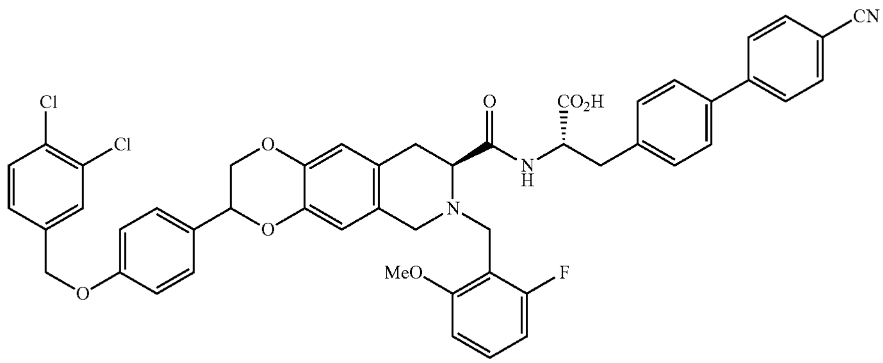 [SMILES: COc1cccc(F)c1CN1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 872 |
| 34 | 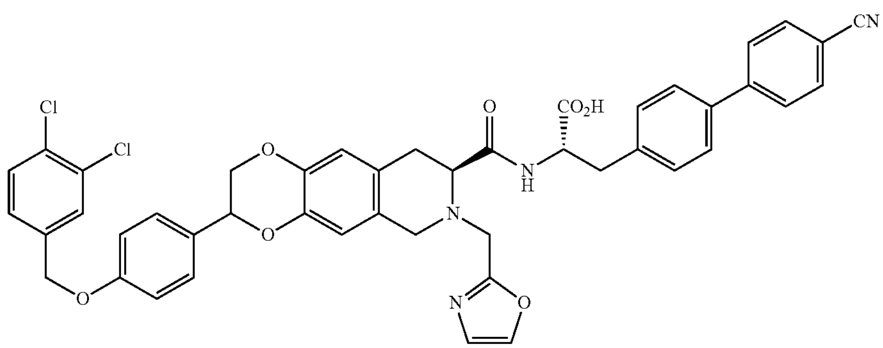 [SMILES: N#Cc1ccc(-c2ccc(C[C@H](NC(=O)[C@@H]3Cc4cc5c(cc4CN3Cc3ncco3)OC(c3ccc(OCc4ccc(Cl)c(Cl)c4)cc3)CO5)C(=O)O)cc2)cc1] | 817 |
| 35 | 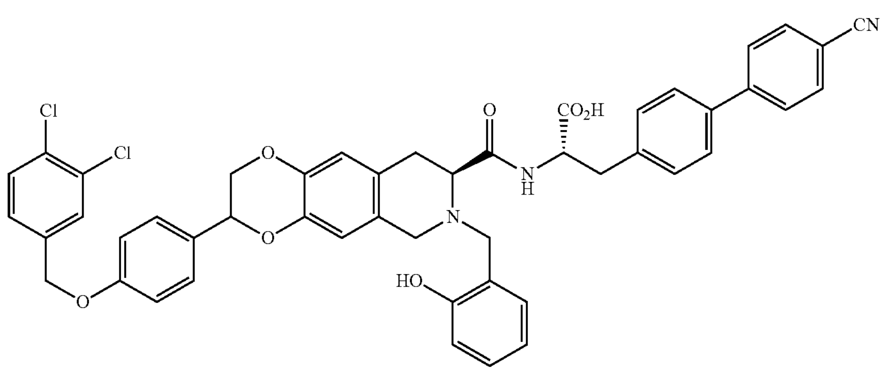 | 840 |

TABLE 1-continued

| Ex | Structure | LCMS (m/z) |
|---|---|---|
| 36 | 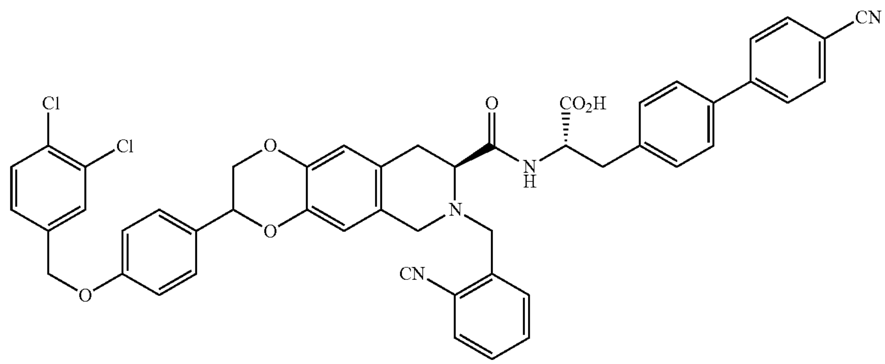 | 860 |
| 37 | 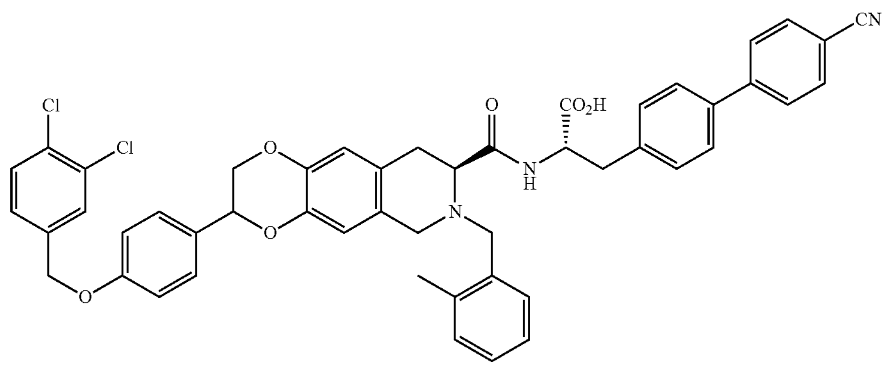 [SMILES: Cc1ccccc1CN1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 838 |
| 38 | 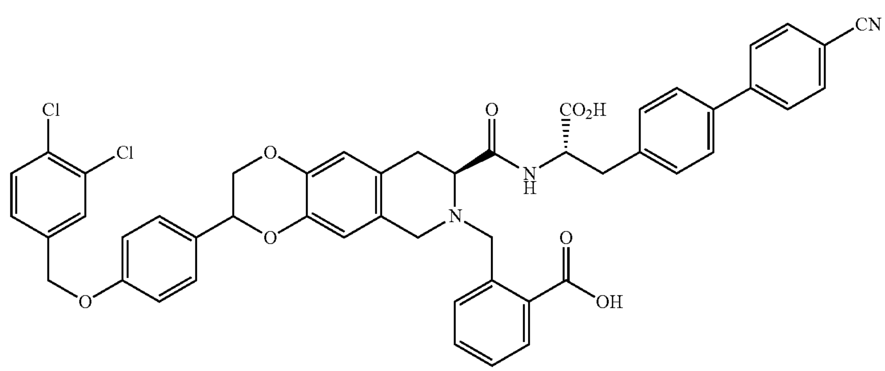 [SMILES: N#Cc1ccc(-c2ccc(C[C@H](NC(=O)[C@@H]3Cc4cc5c(cc4CN3Cc3ccccc3C(=O)O)OC(c3ccc(OCc4ccc(Cl)c(Cl)c4)cc3)CO5)C(=O)O)cc2)cc1] | 869 |
| 39 | 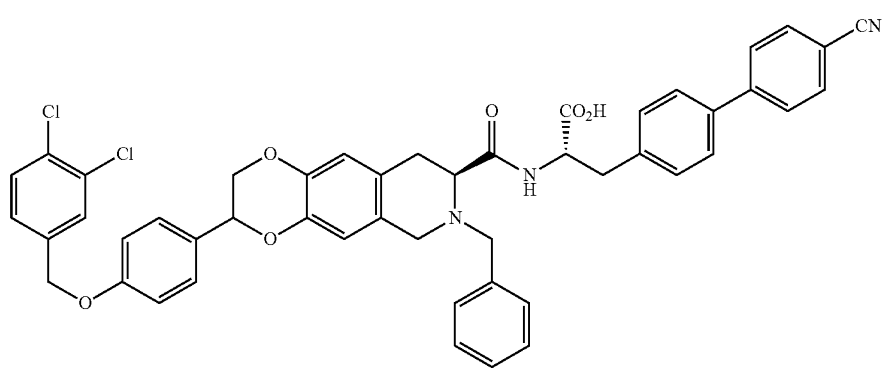 [SMILES: N#Cc1ccc(-c2ccc(C[C@H](NC(=O)[C@@H]3Cc4cc5c(cc4CN3Cc3ccccc3)OC(c3ccc(OCc4ccc(Cl)c(Cl)c4)cc3)CO5)C(=O)O)cc2)cc1] | 827 |

TABLE 1-continued
| Ex | Structure | LCMS (m/z) |
|---|---|---|
| 40 | 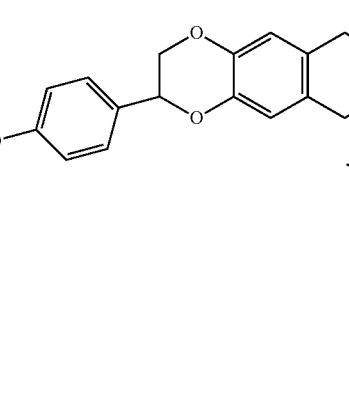 | 830 |
| 41 | 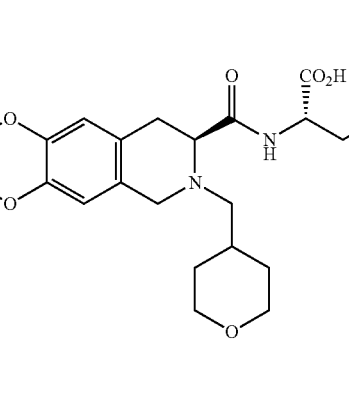 | 832 |
| 42 | 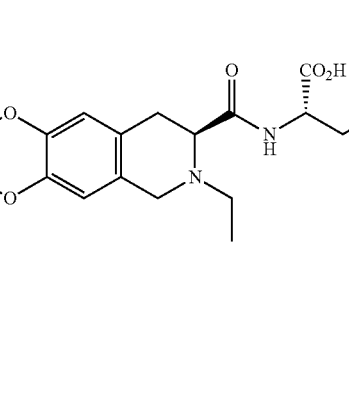 | 762 |
| 43 | 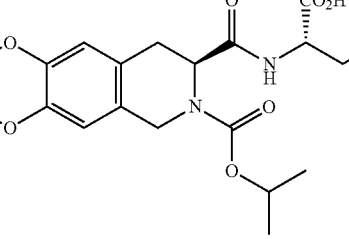 | 823 |

TABLE 1-continued
| Ex | Structure | LCMS (m/z) |
|---|---|---|
| 44 | 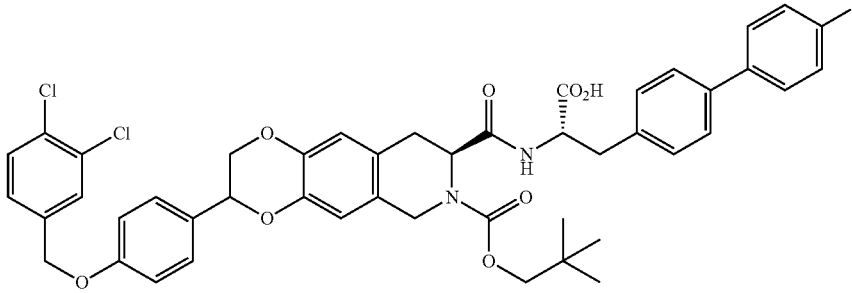 | 852 |
| 45 | 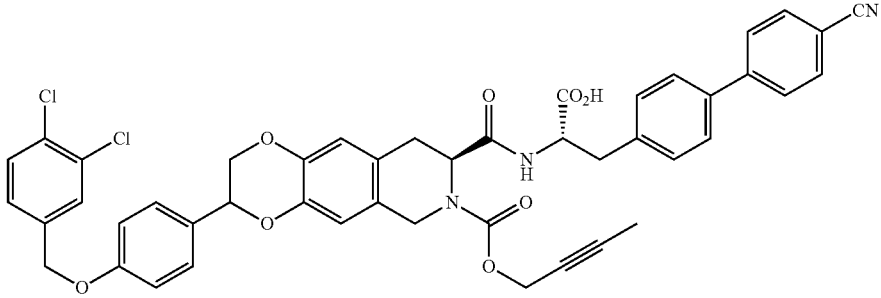 [SMILES: CC#CCOC(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 834 |
| 46 | 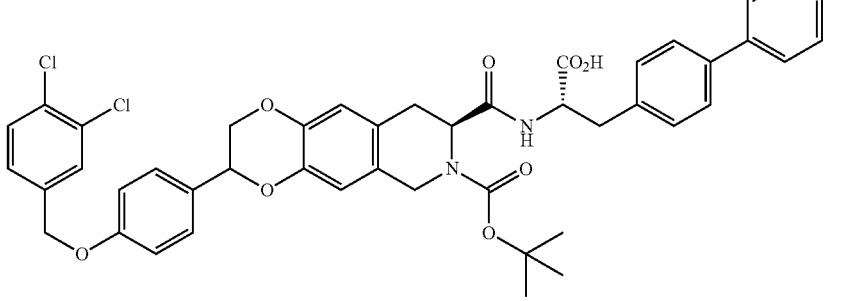 | 837 |
| 47 | 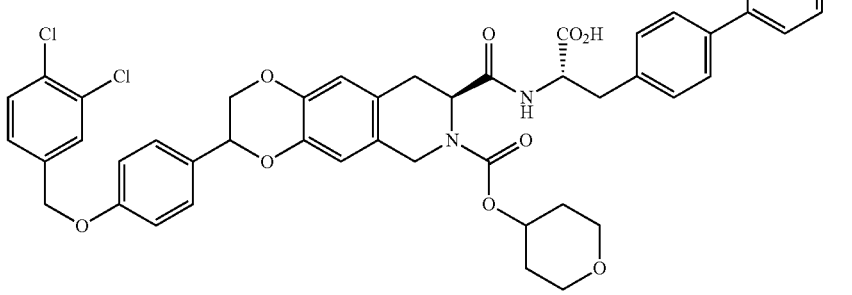 | 863 |

TABLE 1-continued

| Ex | Structure | LCMS (m/z) |
|---|---|---|
| 48 | 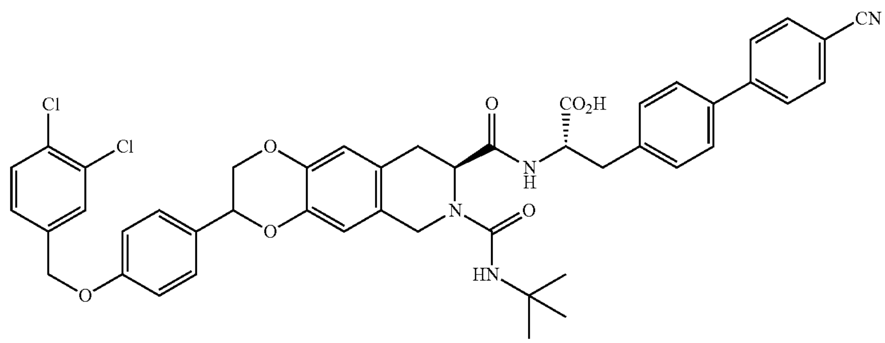 [SMILES: CC(C)(C)NC(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 837 |
| 49 | 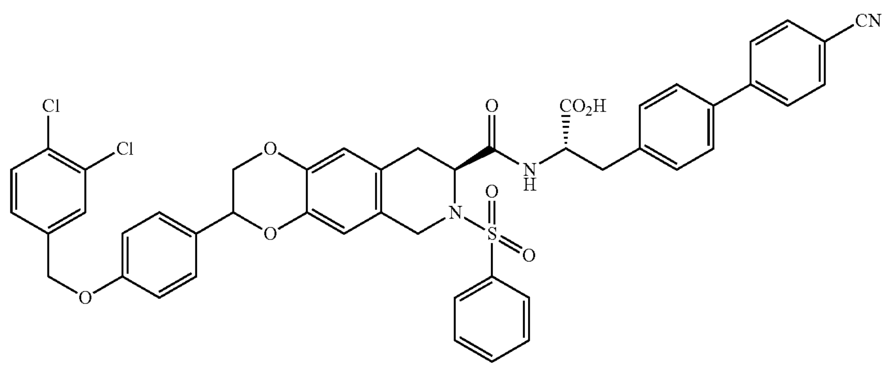 [SMILES: N#Cc1ccc(-c2ccc(C[C@H](NC(=O)[C@@H]3Cc4cc5c(cc4CN3S(=O)(=O)c3ccccc3)OC(c3ccc(OCc4ccc(Cl)c(Cl)c4)cc3)CO5)C(=O)O)cc2)cc1] | 879 |
| 50 | 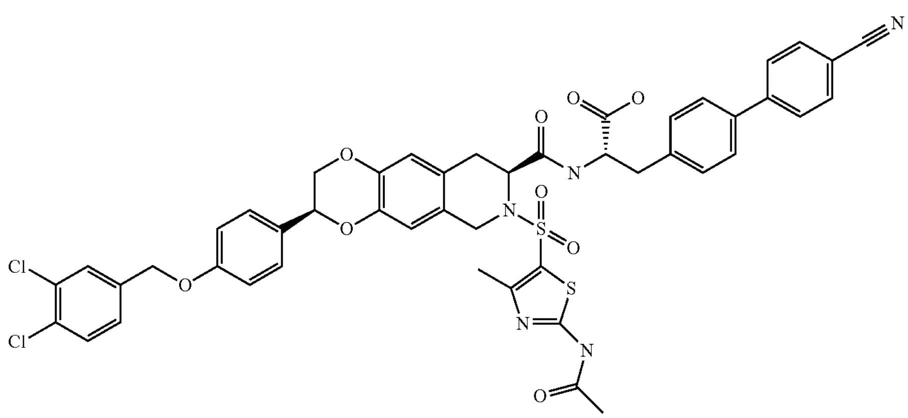 [SMILES: CC(=O)Nc1nc(C)c(S(=O)(=O)N2Cc3cc4c(cc3C[C@H]2C(=O)N[C@@H](Cc2ccc(-c3ccc(C#N)cc3)cc2)C(=O)O)OC[C@H](c2ccc(OCc3ccc(Cl)c(Cl)c3)cc2)O4)s1] | 952 |
| 51 | 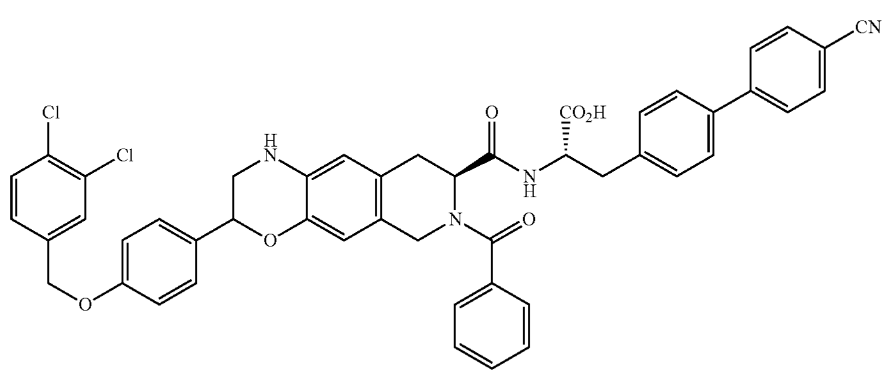 [SMILES: N#Cc1ccc(-c2ccc(C[C@H](NC(=O)[C@@H]3Cc4cc5c(cc4CN3C(=O)c3ccccc3)OC(c3ccc(OCc4ccc(Cl)c(Cl)c4)cc3)CN5)C(=O)O)cc2)cc1] | 840 |

TABLE 1-continued

| Ex | Structure | LCMS (m/z) |
|---|---|---|
| 52 | 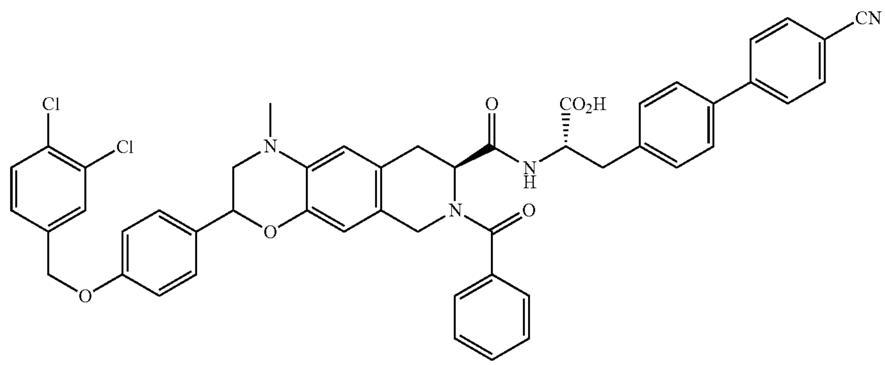 [SMILES: CN1CC(c2ccc(OCc3ccc(Cl)c(Cl)c3)cc2)Oc2cc3c(cc21)C[C@@H](C(=O)N[C@@H](Cc1ccc(-c2ccc(C#N)cc2)cc1)C(=O)O)N(C(=O)c1ccccc1)C3] | 851 |
| 53 | 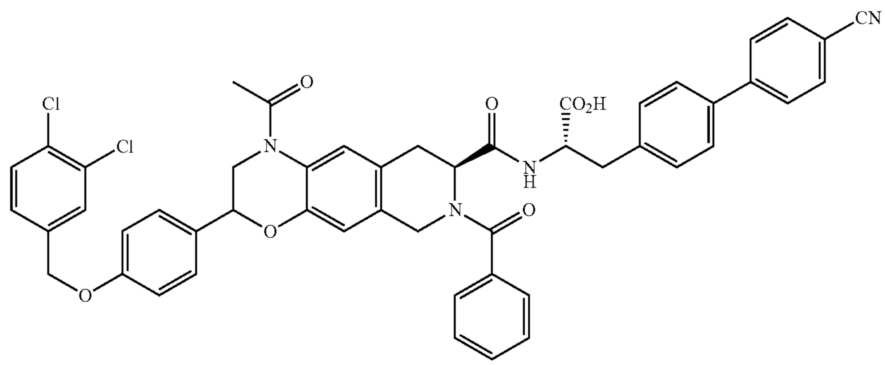 [SMILES: CC(=O)N1CC(c2ccc(OCc3ccc(Cl)c(Cl)c3)cc2)Oc2cc3c(cc21)C[C@@H](C(=O)N[C@@H](Cc1ccc(-c2ccc(C#N)cc2)cc1)C(=O)O)N(C(=O)c1ccccc1)C3] | 881 |
| 54 | 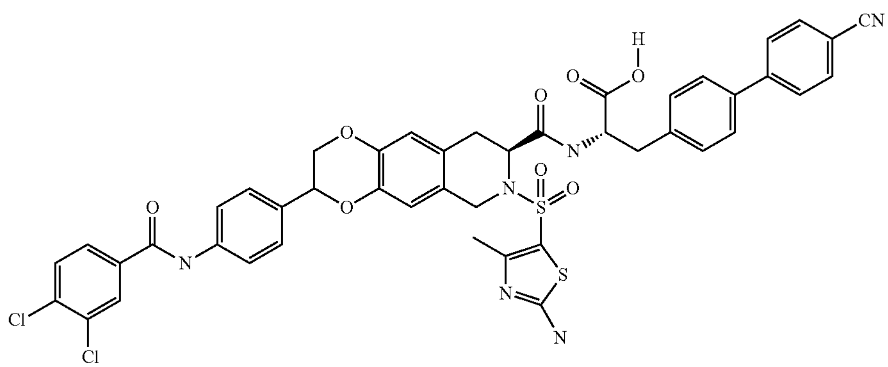 [SMILES: Cc1nc(N)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(NC(=O)c2ccc(Cl)c(Cl)c2)cc1)O3] | 924 |
| 55 | 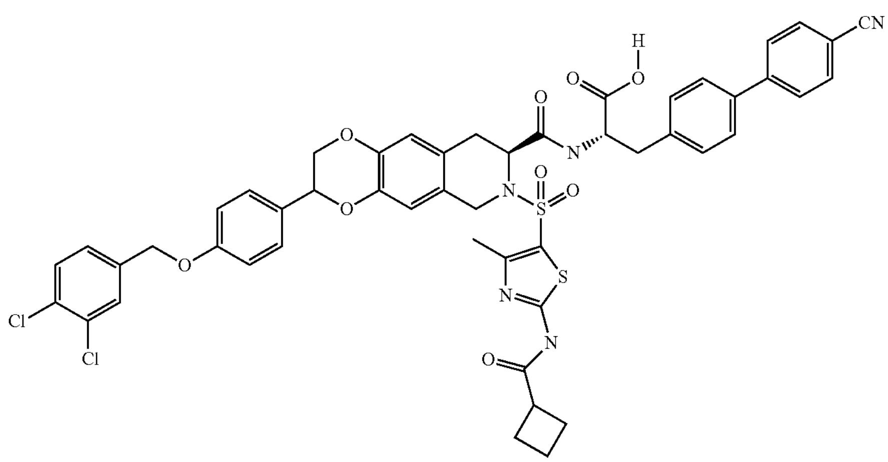 [SMILES: Cc1nc(NC(=O)C2CCC2)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 993 |

TABLE 1-continued

| Ex | Structure | LCMS (m/z) |
|---|---|---|
| 56 | 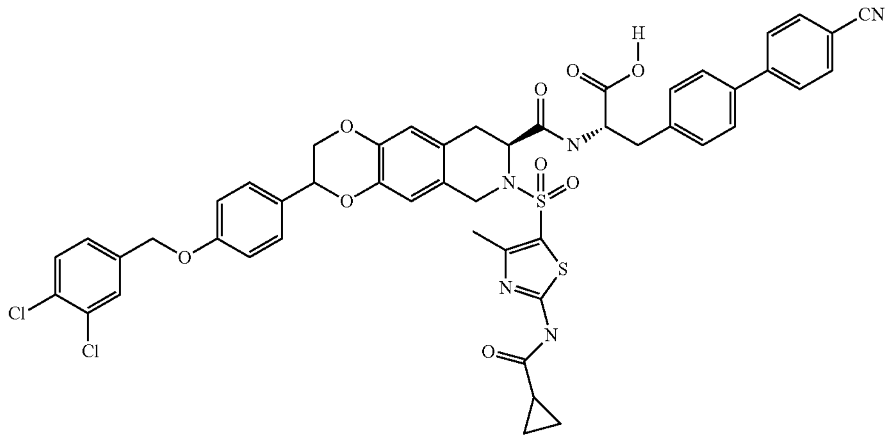 [SMILES: Cc1nc(NC(=O)C2CC2)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 979 |
| 57 | 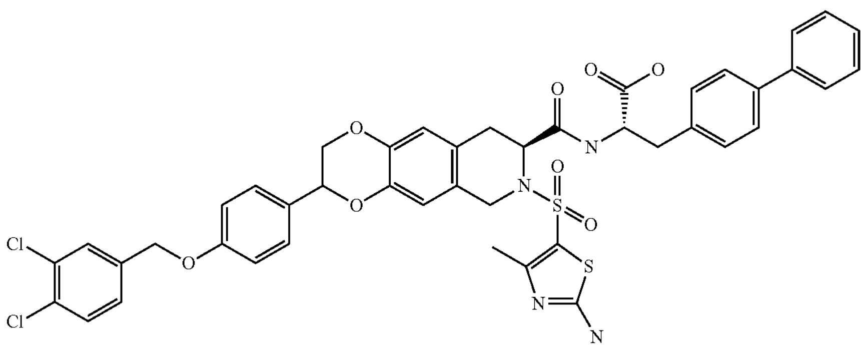 [SMILES: Cc1nc(N)sc1S(=O)(=O)N1Cc2cc3c(cc2C[C@H]1C(=O)N[C@@H](Cc1ccc(-c2ccccc2)cc1)C(=O)O)OCC(c1ccc(OCc2ccc(Cl)c(Cl)c2)cc1)O3] | 887 |
| 58 | 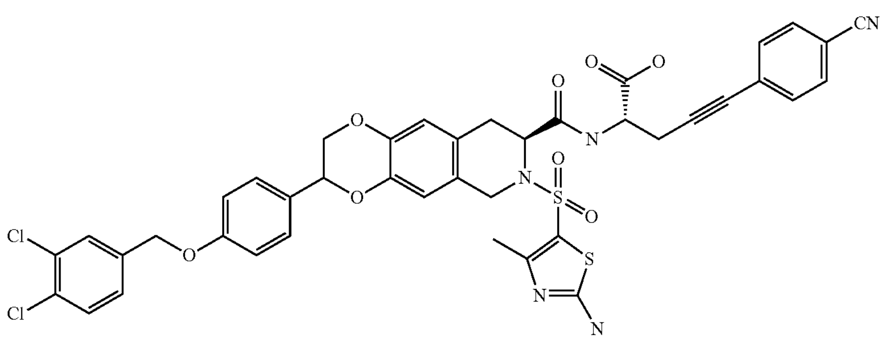 [SMILES: Cc1nc(N)sc1S(=O)(=O)N1Cc2cc3c(cc2C[C@H]1C(=O)N[C@@H](CC#Cc1ccc(C#N)cc1)C(=O)O)OCC(c1ccc(OCc2ccc(Cl)c(Cl)c2)cc1)O3] | 860 |
| 59 | 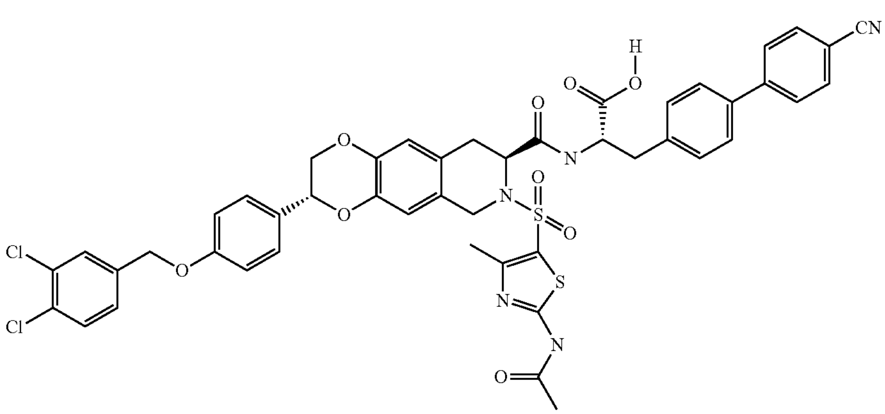 [SMILES: CC(=O)Nc1nc(C)c(S(=O)(=O)N2Cc3cc4c(cc3C[C@H]2C(=O)N[C@@H](Cc2ccc(-c3ccc(C#N)cc3)cc2)C(=O)O)OC[C@@H](c2ccc(OCc3ccc(Cl)c(Cl)c3)cc2)O4)s1] | 955 |

TABLE 1-continued

| Ex | Structure | LCMS (m/z) |
|---|---|---|
| 60 | 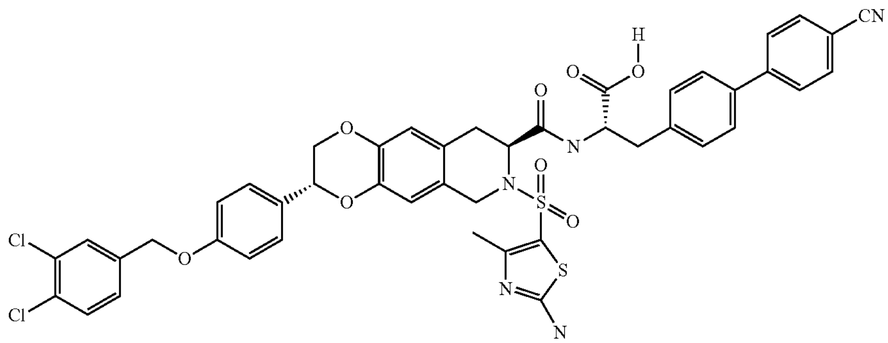 [SMILES: Cc1nc(N)sc1S(=O)(=O)N1Cc2cc3c(cc2C[C@H]1C(=O)N[C@@H](Cc1ccc(-c2ccc(C#N)cc2)cc1)C(=O)O)OC[C@@H](c1ccc(OCc2ccc(Cl)c(Cl)c2)cc1)O3] | 912 |
| 61 | 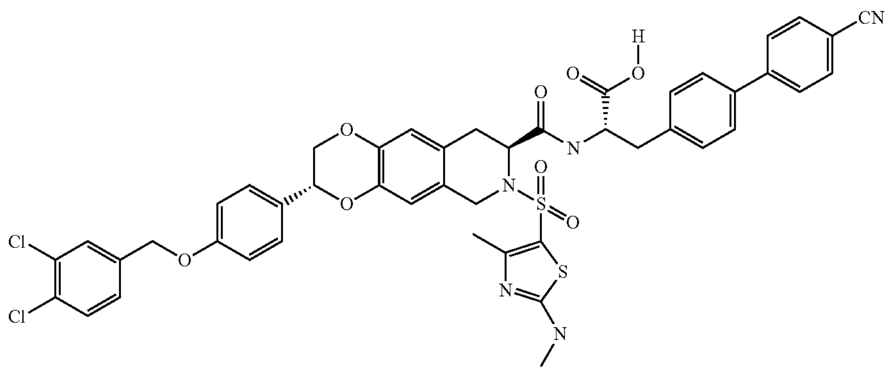 [SMILES: CNc1nc(C)c(S(=O)(=O)N2Cc3cc4c(cc3C[C@H]2C(=O)N[C@@H](Cc2ccc(-c3ccc(C#N)cc3)cc2)C(=O)O)OC[C@@H](c2ccc(OCc3ccc(Cl)c(Cl)c3)cc2)O4)s1] | 924 |
| 62 | 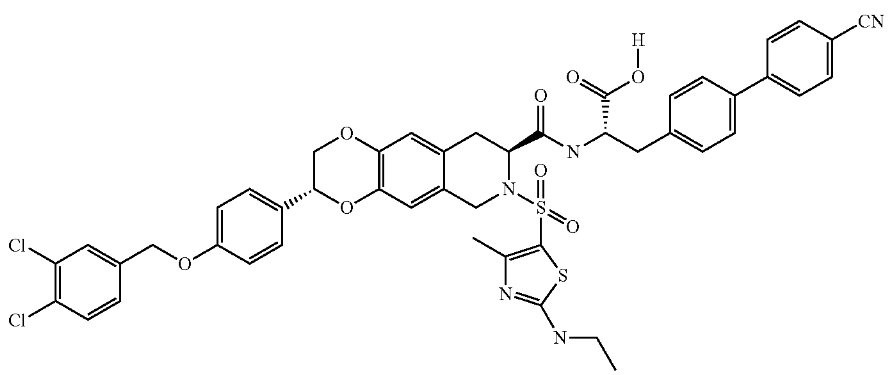 [SMILES: CCNc1nc(C)c(S(=O)(=O)N2Cc3cc4c(cc3C[C@H]2C(=O)N[C@@H](Cc2ccc(-c3ccc(C#N)cc3)cc2)C(=O)O)OC[C@@H](c2ccc(OCc3ccc(Cl)c(Cl)c3)cc2)O4)s1] | 938 |
| 63 | 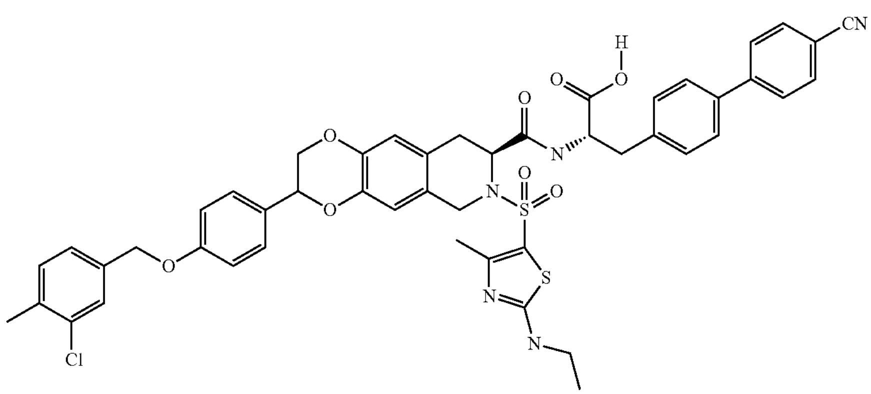 [SMILES: CCNc1nc(C)c(S(=O)(=O)N2Cc3cc4c(cc3C[C@H]2C(=O)N[C@@H](Cc2ccc(-c3ccc(C#N)cc3)cc2)C(=O)O)OCC(c2ccc(OCc3ccc(C)c(Cl)c3)cc2)O4)s1] | 918 |

TABLE 1-continued

| Ex | Structure | LCMS (m/z) |
|---|---|---|
| 64 | 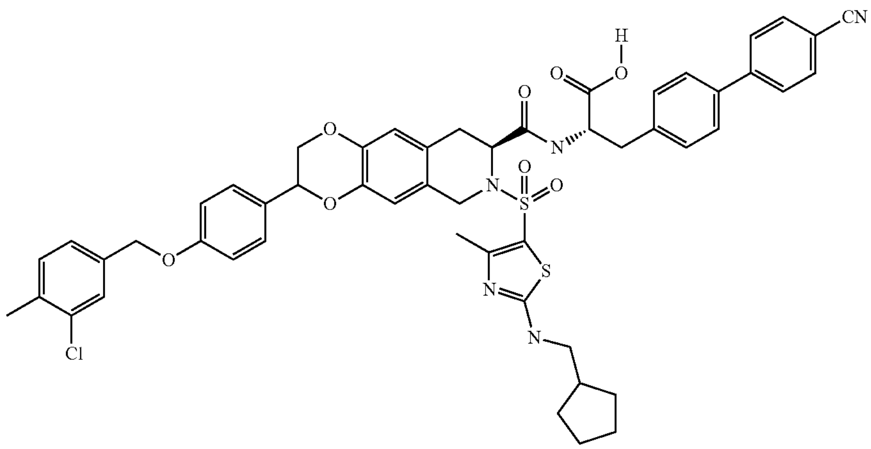 [SMILES: Cc1ccc(COc2ccc(C3COc4cc5c(cc4O3)CN(S(=O)(=O)c3sc(NCC4CCCC4)nc3C)[C@H](C(=O)N[C@@H](Cc3ccc(-c4ccc(C#N)cc4)cc3)C(=O)O)C5)cc2)cc1Cl] | 972 |
| 65 | 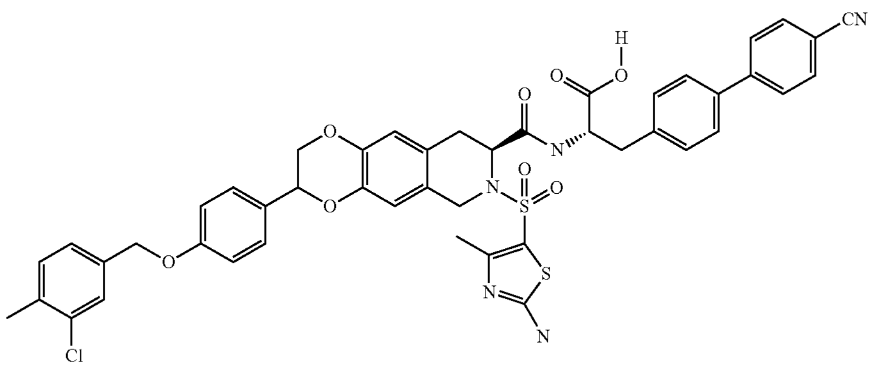 [SMILES: Cc1ccc(COc2ccc(C3COc4cc5c(cc4O3)CN(S(=O)(=O)c3sc(N)nc3C)[C@H](C(=O)N[C@@H](Cc3ccc(-c4ccc(C#N)cc4)cc3)C(=O)O)C5)cc2)cc1Cl] | 893 |
| 66 | 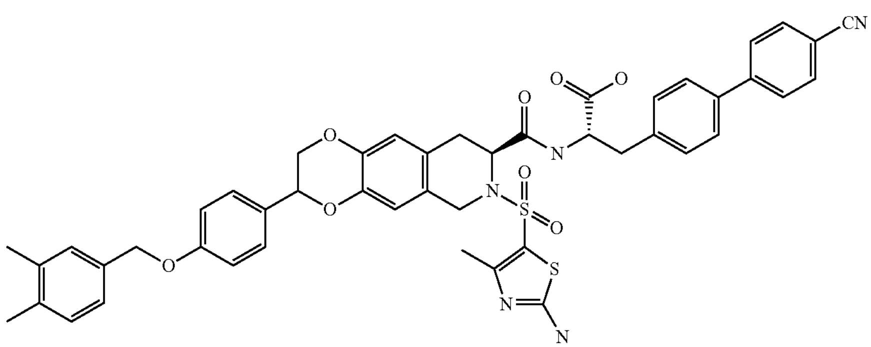 [SMILES: Cc1ccc(COc2ccc(C3COc4cc5c(cc4O3)CN(S(=O)(=O)c3sc(N)nc3C)[C@H](C(=O)N[C@@H](Cc3ccc(-c4ccc(C#N)cc4)cc3)C(=O)O)C5)cc2)cc1C] | 870 |
| 67 | 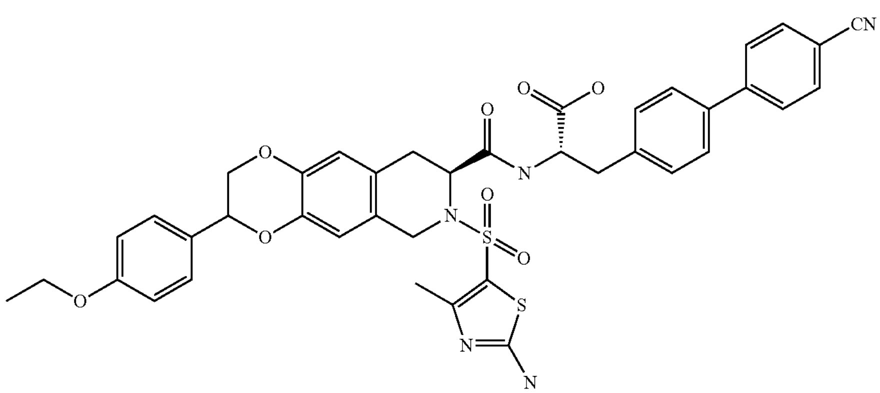 [SMILES: CCOc1ccc(C2COc3cc4c(cc3O2)CN(S(=O)(=O)c2sc(N)nc2C)[C@H](C(=O)N[C@@H](Cc2ccc(-c3ccc(C#N)cc3)cc2)C(=O)O)C4)cc1] | 783 |

TABLE 1-continued

| Ex | Structure | LCMS (m/z) |
|---|---|---|
| 68 | 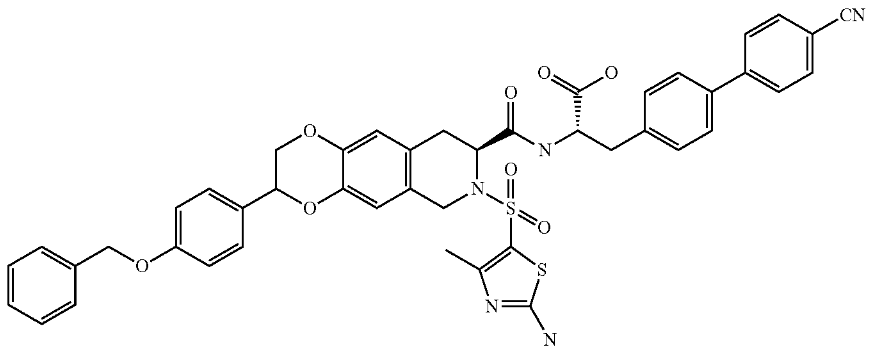 [SMILES: Cc1nc(N)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccccc2)cc1)O3] | 843 |
| 69 | 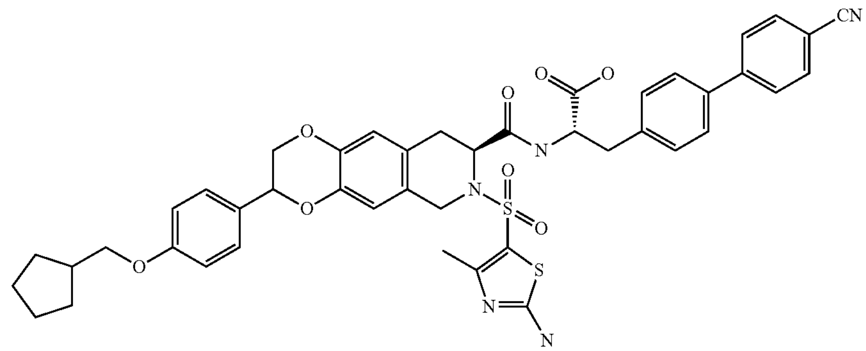 [SMILES: Cc1nc(N)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCC2CCCC2)cc1)O3] | 835 |
| 70 | 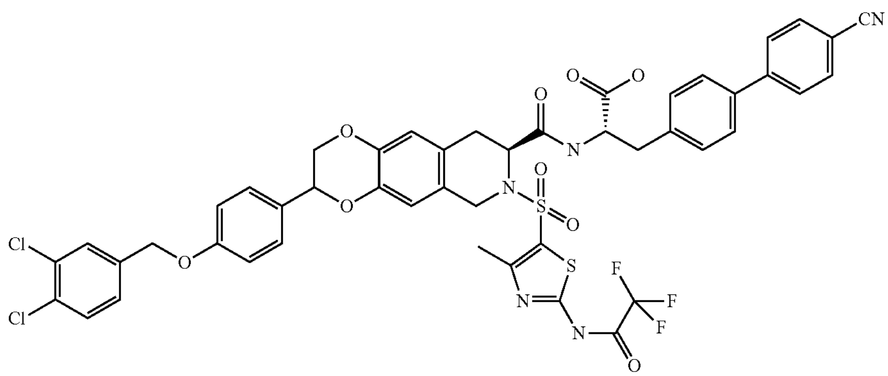 [SMILES: Cc1nc(NC(=O)C(F)(F)F)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 1007 |
| 71 | 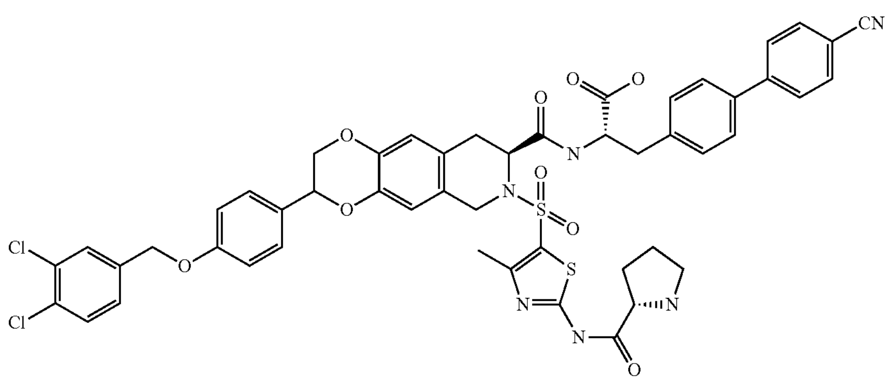 [SMILES: Cc1nc(NC(=O)[C@@H]2CCCN2)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 1008 |

TABLE 1-continued

| Ex | Structure | LCMS (m/z) |
|---|---|---|
| 72 | 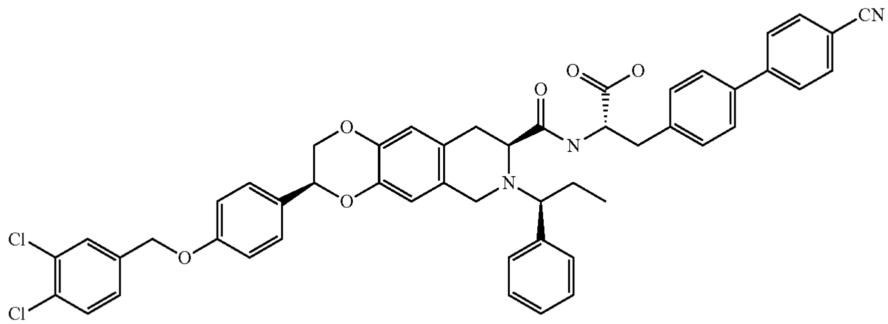 [SMILES: CC[C@@H](c1ccccc1)N1Cc2cc3c(cc2C[C@H]1C(=O)N[C@@H](Cc1ccc(-c2ccc(C#N)cc2)cc1)C(=O)O)OC[C@H](c1ccc(OCc2ccc(Cl)c(Cl)c2)cc1)O3] | 853 |
| 73 | 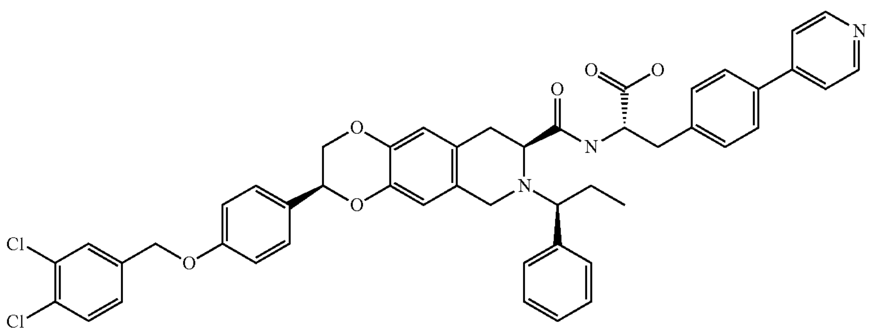 [SMILES: CC[C@@H](c1ccccc1)N1Cc2cc3c(cc2C[C@H]1C(=O)N[C@@H](Cc1ccc(-c2ccncc2)cc1)C(=O)O)OC[C@H](c1ccc(OCc2ccc(Cl)c(Cl)c2)cc1)O3] | 829 |
| 74 | 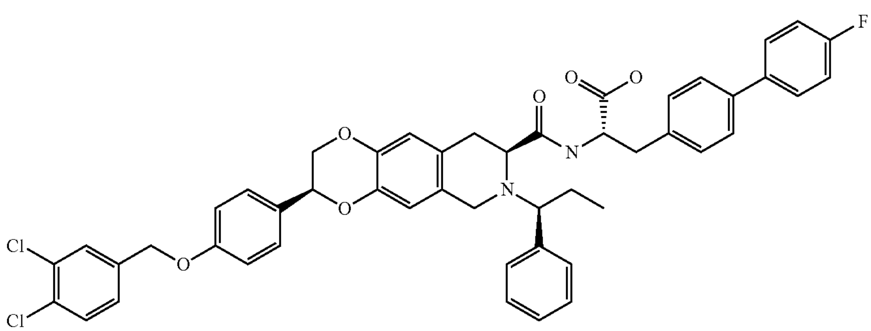 [SMILES: CC[C@@H](c1ccccc1)N1Cc2cc3c(cc2C[C@H]1C(=O)N[C@@H](Cc1ccc(-c2ccc(F)cc2)cc1)C(=O)O)OC[C@H](c1ccc(OCc2ccc(Cl)c(Cl)c2)cc1)O3] | 846 |
| 75 | 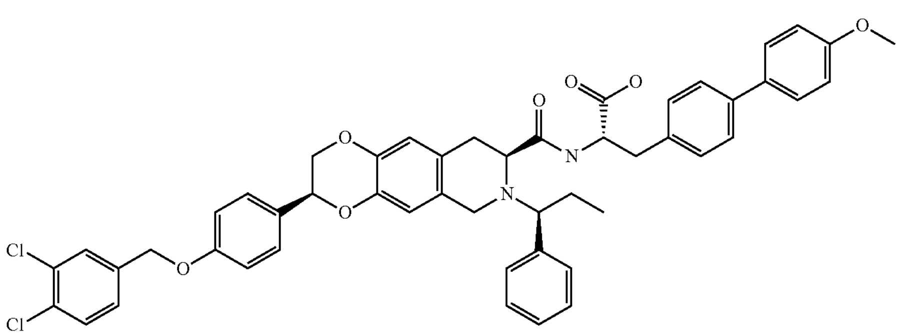 [SMILES: CC[C@@H](c1ccccc1)N1Cc2cc3c(cc2C[C@H]1C(=O)N[C@@H](Cc1ccc(-c2ccc(OC)cc2)cc1)C(=O)O)OC[C@H](c1ccc(OCc2ccc(Cl)c(Cl)c2)cc1)O3] | 858 |

TABLE 1-continued

| Ex | Structure | LCMS (m/z) |
|---|---|---|
| 76 | 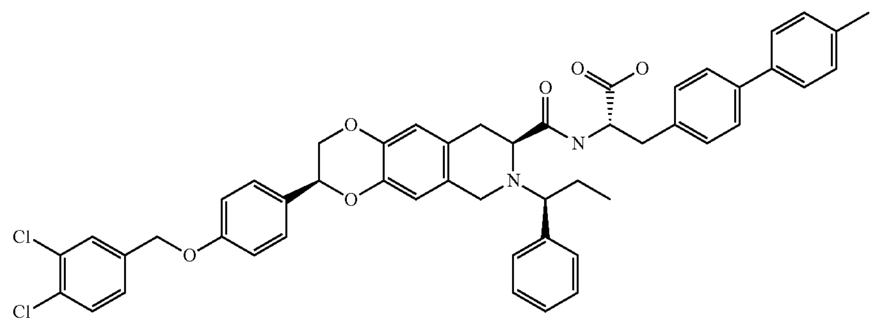 [SMILES: CC[C@@H](c1ccccc1)N1Cc2cc3c(cc2C[C@H]1C(=O)N[C@@H](Cc1ccc(-c2ccc(C)cc2)cc1)C(=O)O)OC[C@H](c1ccc(OCc2ccc(Cl)c(Cl)c2)cc1)O3] | 842 |
| 77 | 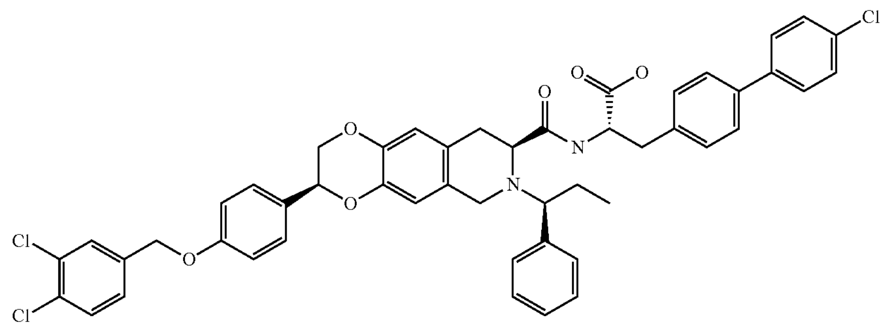 [SMILES: CC[C@@H](c1ccccc1)N1Cc2cc3c(cc2C[C@H]1C(=O)N[C@@H](Cc1ccc(-c2ccc(Cl)cc2)cc1)C(=O)O)OC[C@H](c1ccc(OCc2ccc(Cl)c(Cl)c2)cc1)O3] | 862 |
| 78 | 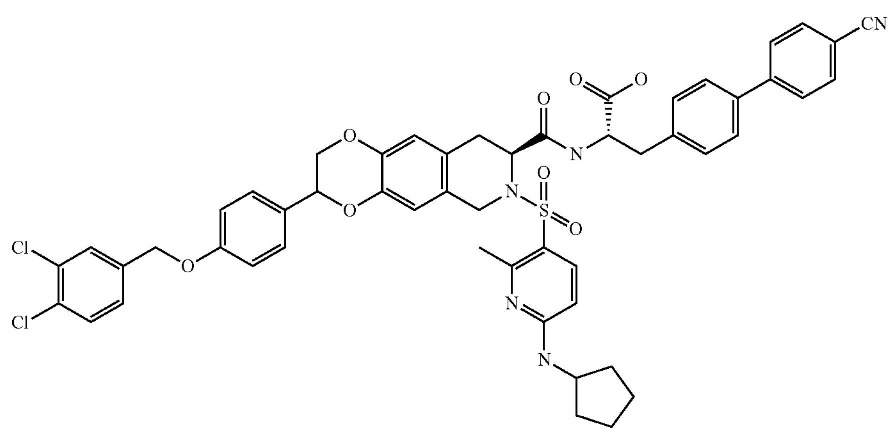 [SMILES: Cc1nc(NC2CCCC2)ccc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 974 |
| 79 | 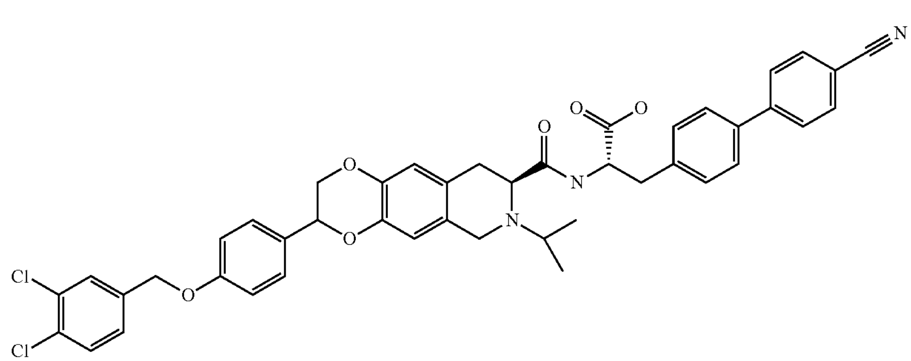 [SMILES: CC(C)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 777 |

TABLE 1-continued

| Ex | Structure | LCMS (m/z) |
|---|---|---|
| 80 | 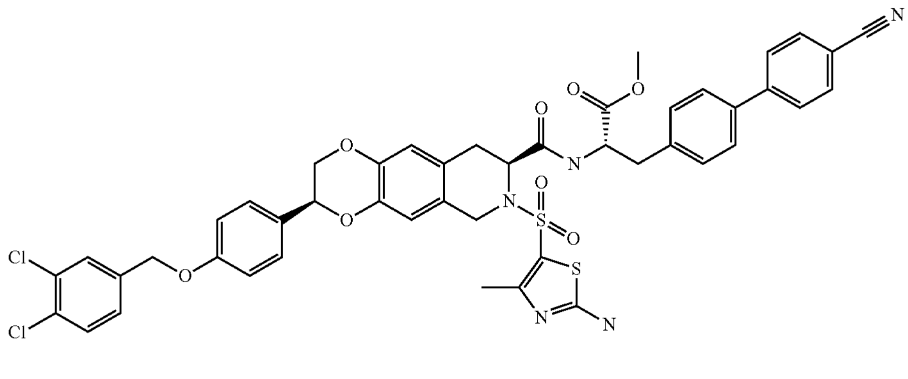 [SMILES: COC(=O)[C@H](Cc1ccc(-c2ccc(C#N)cc2)cc1)NC(=O)[C@@H]1Cc2cc3c(cc2CN1S(=O)(=O)c1sc(N)nc1C)O[C@@H](c1ccc(OCc2ccc(Cl)c(Cl)c2)cc1)CO3] | 926 |
| 81 | 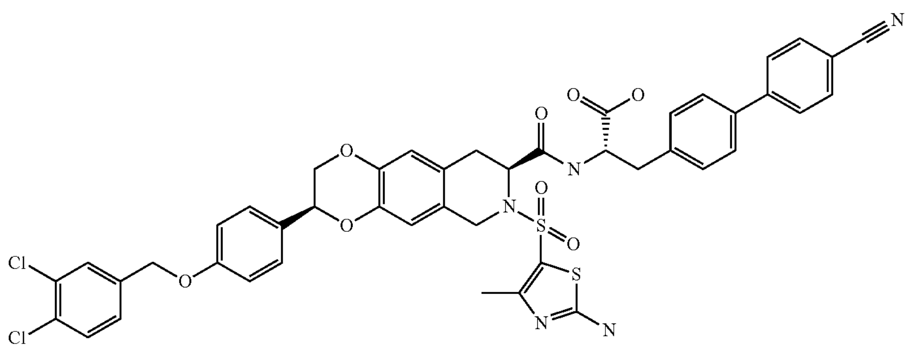 [SMILES: Cc1nc(N)sc1S(=O)(=O)N1Cc2cc3c(cc2C[C@H]1C(=O)N[C@@H](Cc1ccc(-c2ccc(C#N)cc2)cc1)C(=O)O)OC[C@H](c1ccc(OCc2ccc(Cl)c(Cl)c2)cc1)O3] | 910 |
| 82 | 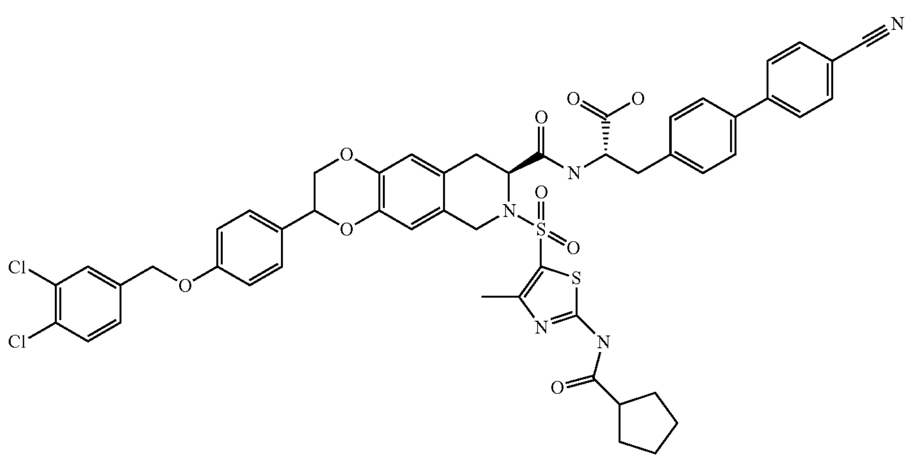 [SMILES: Cc1nc(NC(=O)C2CCCC2)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 1009 |

TABLE 1-continued

| Ex | Structure | LCMS (m/z) |
|---|---|---|
| 83 | 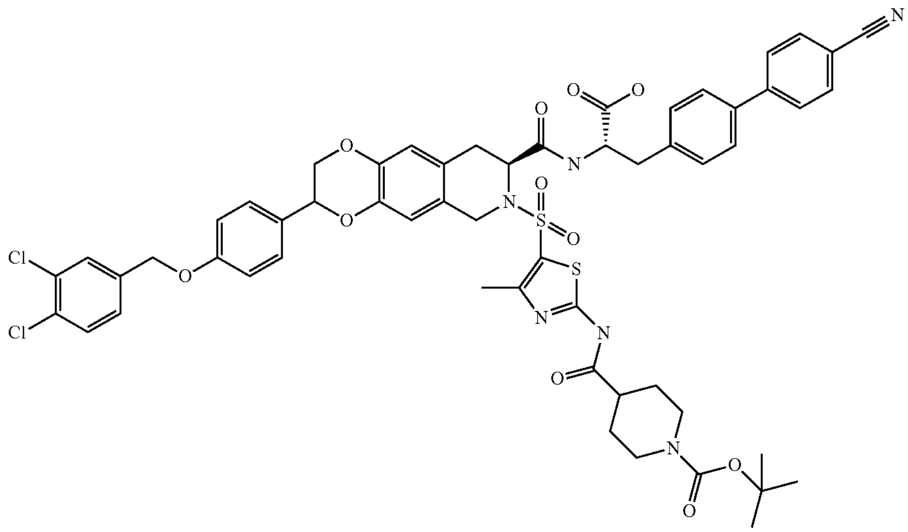 [SMILES: Cc1nc(NC(=O)C2CCN(C(=O)OC(C)(C)C)CC2)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 1023 |
| 84 | 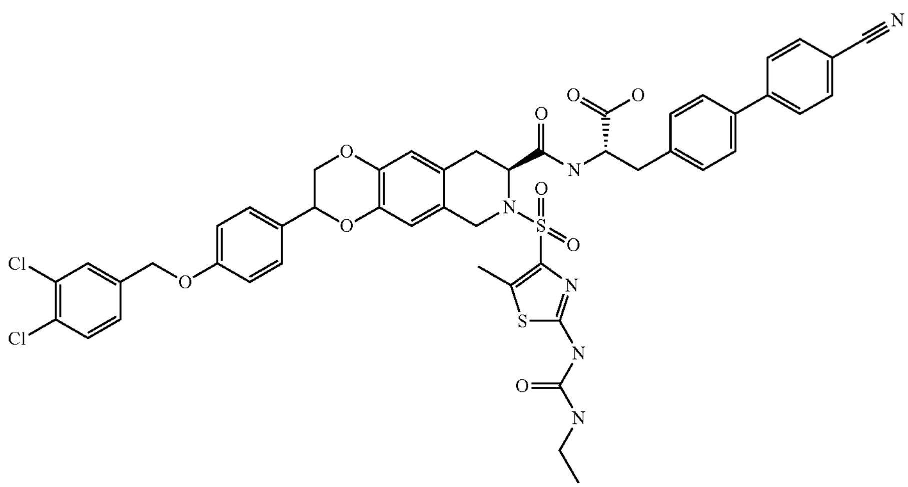 [SMILES: CCNC(=O)Nc1nc(S(=O)(=O)N2Cc3cc4c(cc3C[C@H]2C(=O)N[C@@H](Cc2ccc(-c3ccc(C#N)cc3)cc2)C(=O)O)OCC(c2ccc(OCc3ccc(Cl)c(Cl)c3)cc2)O4)c(C)s1] | 983 |
| 85 | 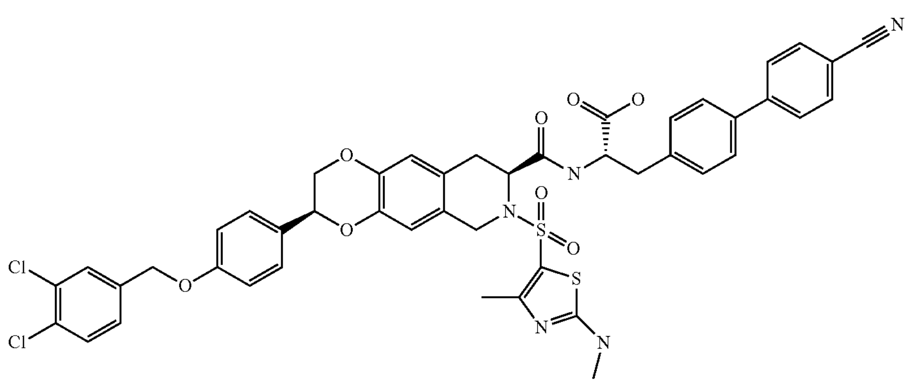 [SMILES: CNc1nc(C)c(S(=O)(=O)N2Cc3cc4c(cc3C[C@H]2C(=O)N[C@@H](Cc2ccc(-c3ccc(C#N)cc3)cc2)C(=O)O)OC[C@H](c2ccc(OCc3ccc(Cl)c(Cl)c3)cc2)O4)s1] | 924 |

TABLE 1-continued

| Ex | Structure | LCMS (m/z) |
|---|---|---|
| 86 | 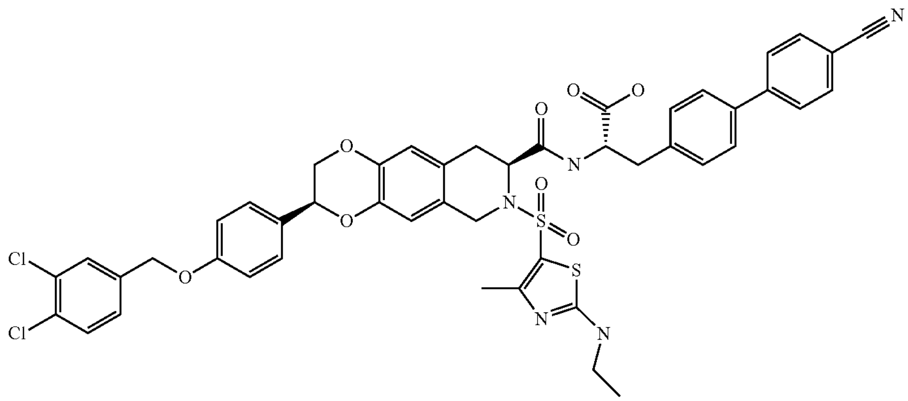 [SMILES: CCNc1nc(C)c(S(=O)(=O)N2Cc3cc4c(cc3C[C@H]2C(=O)N[C@@H](Cc2ccc(-c3ccc(C#N)cc3)cc2)C(=O)O)OC[C@H](c2ccc(OCc3ccc(Cl)c(Cl)c3)cc2)O4)s1] | 938 |
| 87 | 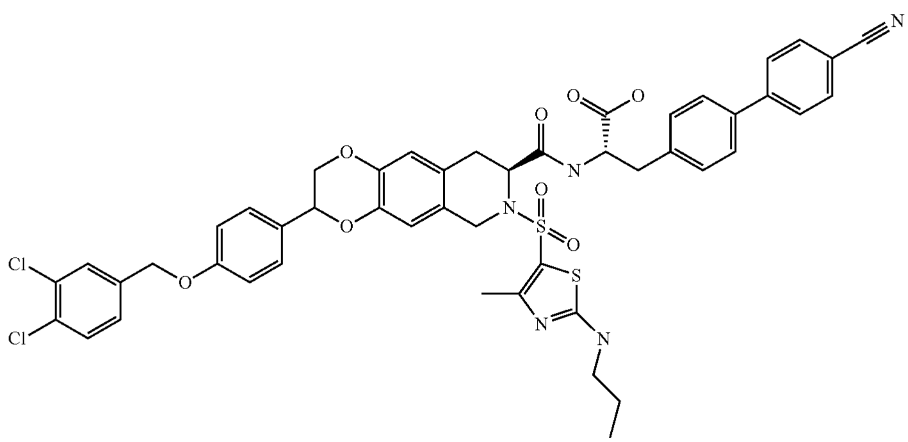 [SMILES: CCCNc1nc(C)c(S(=O)(=O)N2Cc3cc4c(cc3C[C@H]2C(=O)N[C@@H](Cc2ccc(-c3ccc(C#N)cc3)cc2)C(=O)O)OCC(c2ccc(OCc3ccc(Cl)c(Cl)c3)cc2)O4)s1] | 955 |
| 88 | 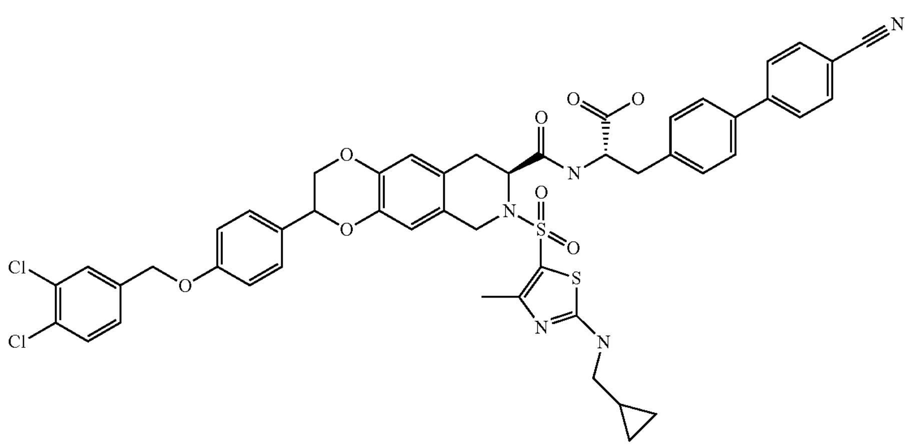 [SMILES: Cc1nc(NCC2CC2)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 970 |

TABLE 1-continued

| Ex | Structure | LCMS (m/z) |
|---|---|---|
| 89 | 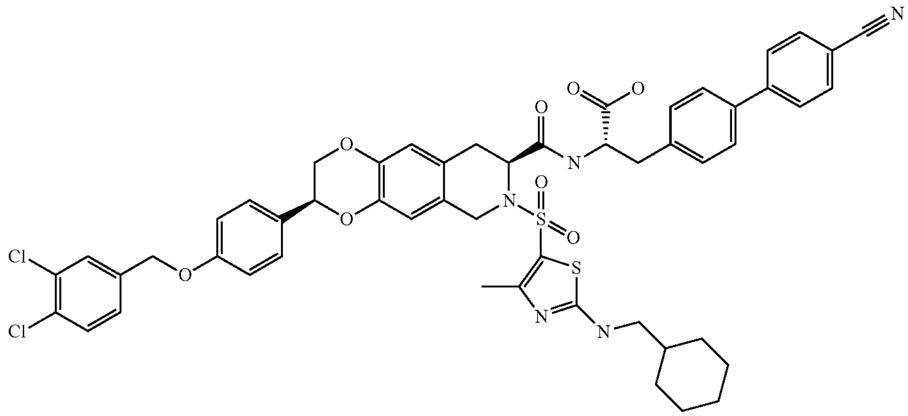 [SMILES: Cc1nc(NCC2CCCCC2)sc1S(=O)(=O)N1Cc2cc3c(cc2C[C@H]1C(=O)N[C@@H](Cc1ccc(-c2ccc(C#N)cc2)cc1)C(=O)O)OC[C@H](c1ccc(OCc2ccc(Cl)c(Cl)c2)cc1)O3] | 1009 |
| 90 | 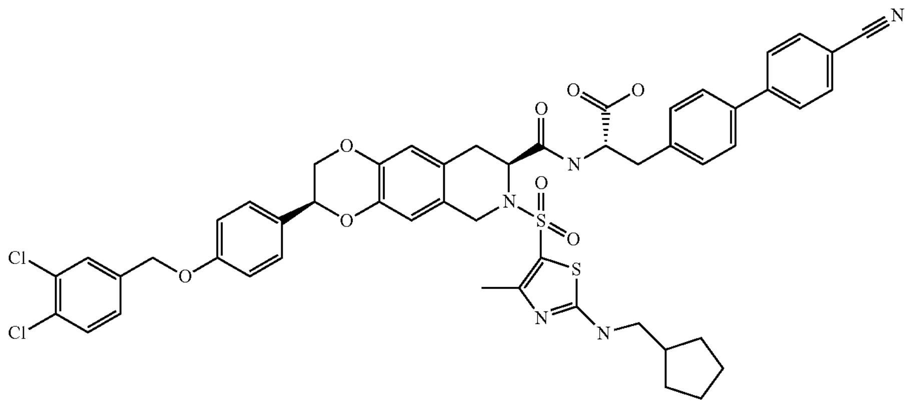 [SMILES: Cc1nc(NCC2CCCC2)sc1S(=O)(=O)N1Cc2cc3c(cc2C[C@H]1C(=O)N[C@@H](Cc1ccc(-c2ccc(C#N)cc2)cc1)C(=O)O)OC[C@H](c1ccc(OCc2ccc(Cl)c(Cl)c2)cc1)O3] | 992 |
| 91 | 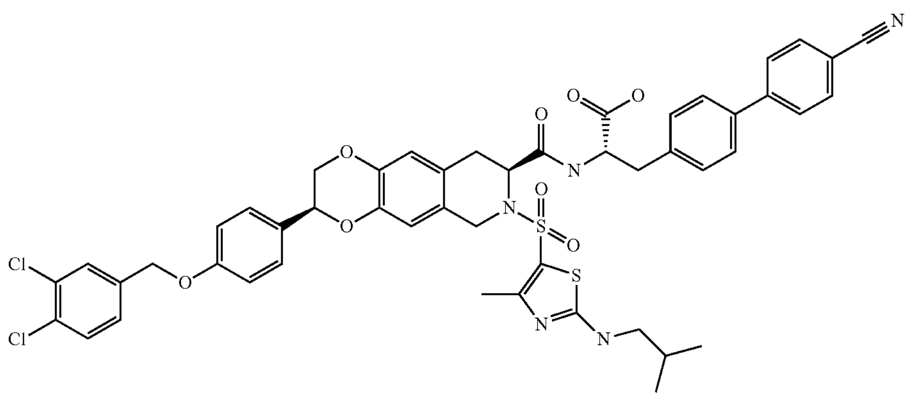 [SMILES: Cc1nc(NCC(C)C)sc1S(=O)(=O)N1Cc2cc3c(cc2C[C@H]1C(=O)N[C@@H](Cc1ccc(-c2ccc(C#N)cc2)cc1)C(=O)O)OC[C@H](c1ccc(OCc2ccc(Cl)c(Cl)c2)cc1)O3] | 966 |
| 92 | 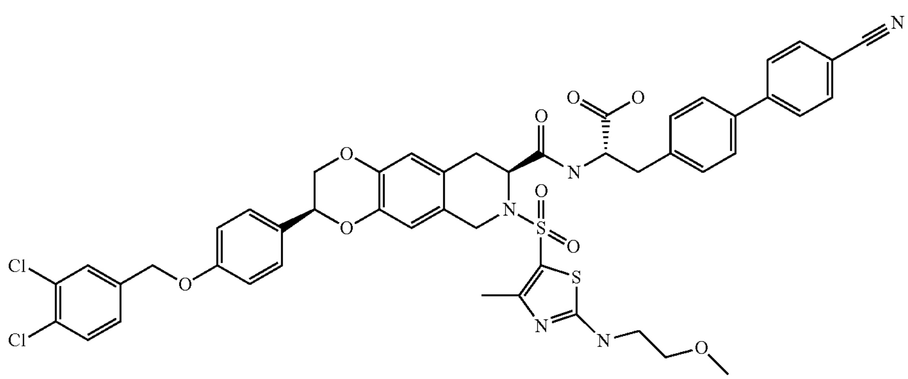 [SMILES: COCCNc1nc(C)c(S(=O)(=O)N2Cc3cc4c(cc3C[C@H]2C(=O)N[C@@H](Cc2ccc(-c3ccc(C#N)cc3)cc2)C(=O)O)OC[C@H](c2ccc(OCc3ccc(Cl)c(Cl)c3)cc2)O4)s1] | 969 |

TABLE 1-continued
| Ex | Structure | LCMS (m/z) |
|---|---|---|
| 93 | 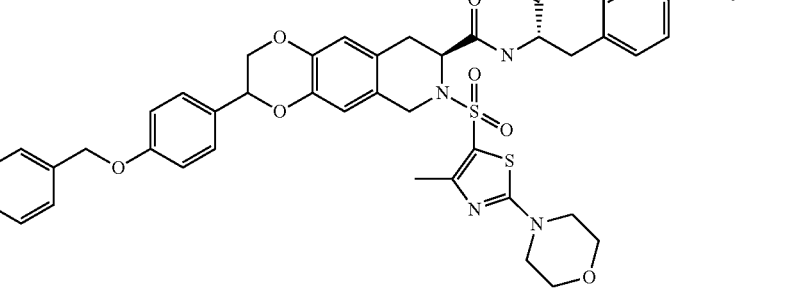 | 984 |
| 94 | 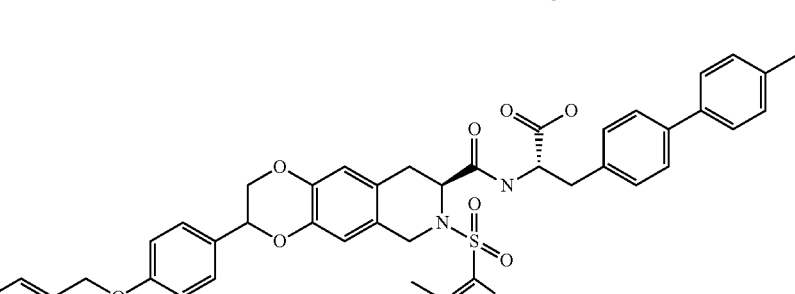 | 952 |
| 95 | 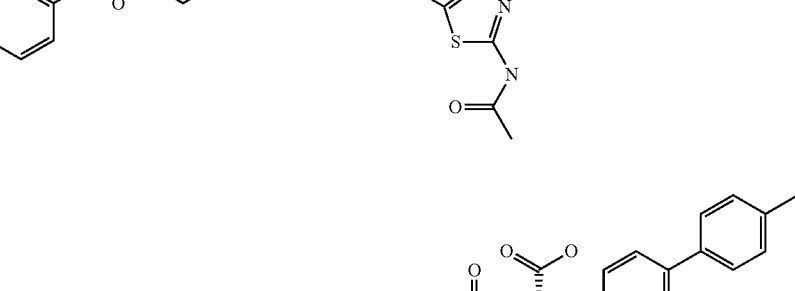 | 912 |
| 96 | 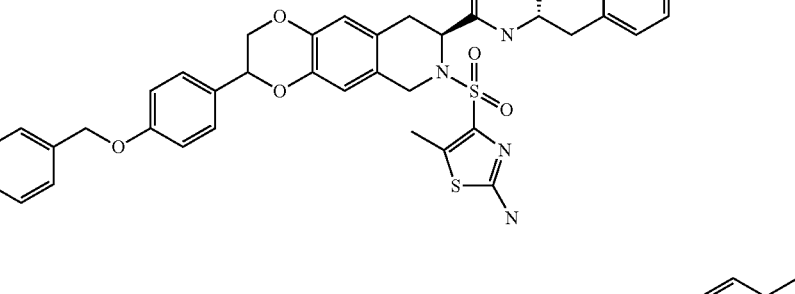 | 940 |

TABLE 1-continued

| Ex | Structure | LCMS (m/z) |
|---|---|---|
| 97 | 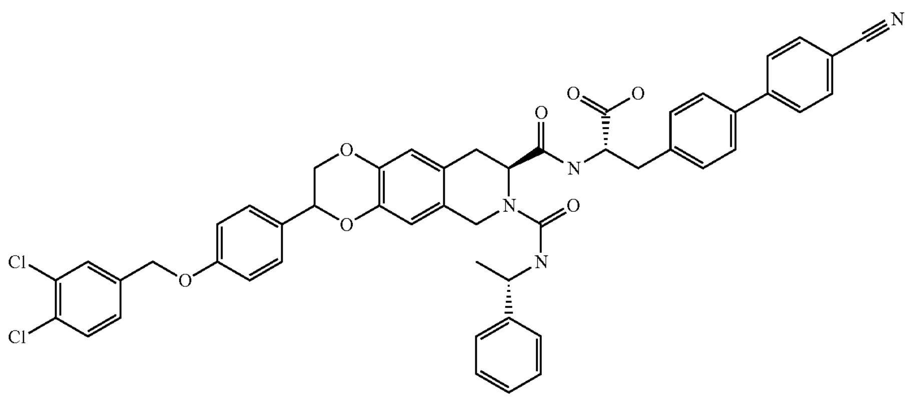 [SMILES: C[C@H](NC(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3)c1ccccc1] | 882 |
| 98 | 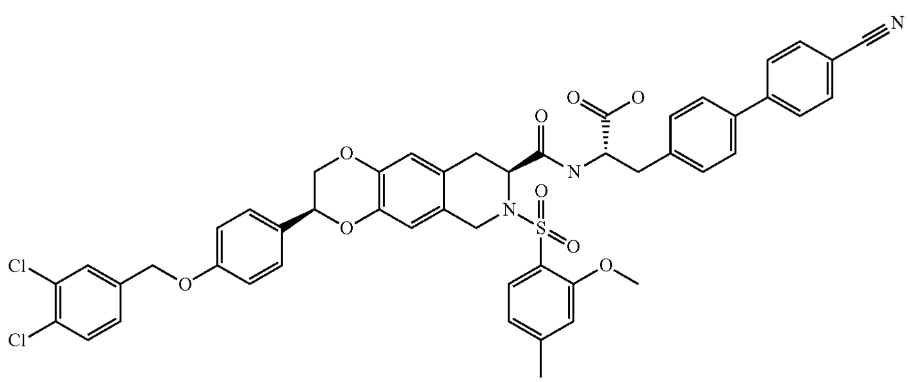 [SMILES: COc1cc(C)ccc1S(=O)(=O)N1Cc2cc3c(cc2C[C@H]1C(=O)N[C@@H](Cc1ccc(-c2ccc(C#N)cc2)cc1)C(=O)O)OC[C@H](c1ccc(OCc2ccc(Cl)c(Cl)c2)cc1)O3] | 919 |
| 99 | 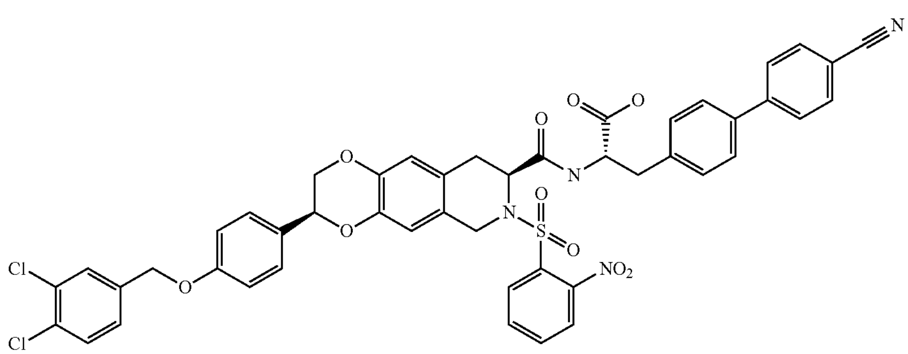 [SMILES: N#Cc1ccc(-c2ccc(C[C@H](NC(=O)[C@@H]3Cc4cc5c(cc4CN3S(=O)(=O)c3ccccc3[N+](=O)[O-])O[C@@H](c3ccc(OCc4ccc(Cl)c(Cl)c4)cc3)CO5)C(=O)O)cc2)cc1] | 919 |
| 100 | 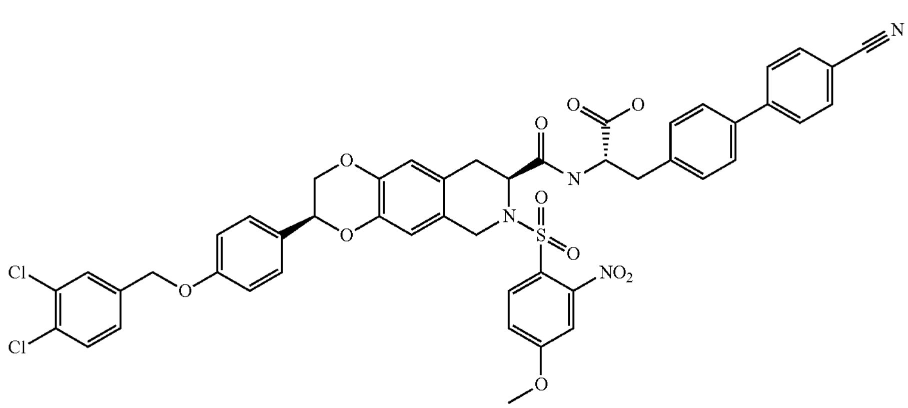 [SMILES: COc1ccc(S(=O)(=O)N2Cc3cc4c(cc3C[C@H]2C(=O)N[C@@H](Cc2ccc(-c3ccc(C#N)cc3)cc2)C(=O)O)OC[C@H](c2ccc(OCc3ccc(Cl)c(Cl)c3)cc2)O4)c([N+](=O)[O-])c1] | 951 |

TABLE 1-continued

| Ex | Structure | LCMS (m/z) |
|---|---|---|
| 101 | 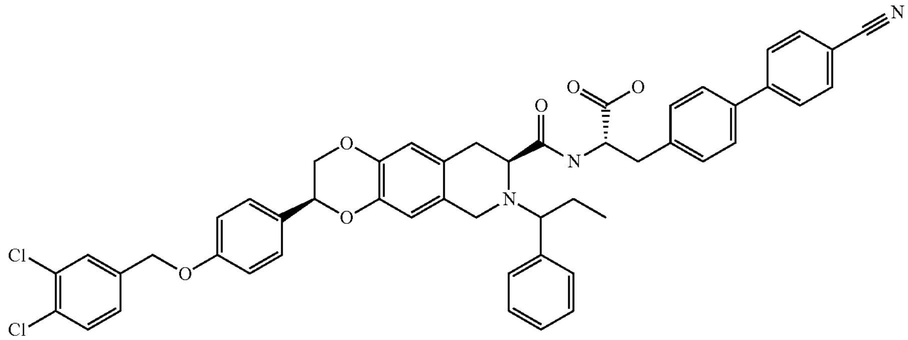 [SMILES: CCC(c1ccccc1)N1Cc2cc3c(cc2C[C@H]1C(=O)N[C@@H](Cc1ccc(-c2ccc(C#N)cc2)cc1)C(=O)O)OC[C@H](c1ccc(OCc2ccc(Cl)c(Cl)c2)cc1)O3] | 854 |
| 102 | 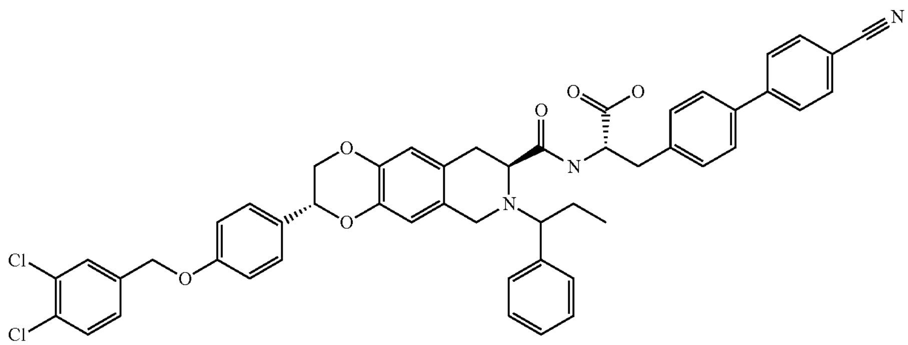 [SMILES: CCC(c1ccccc1)N1Cc2cc3c(cc2C[C@H]1C(=O)N[C@@H](Cc1ccc(-c2ccc(C#N)cc2)cc1)C(=O)O)OC[C@@H](c1ccc(OCc2ccc(Cl)c(Cl)c2)cc1)O3] | 852 |
| 103 | 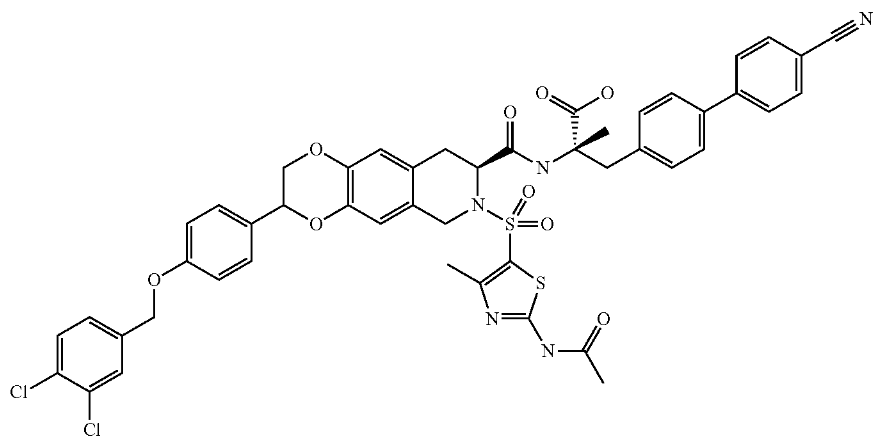 [SMILES: CC(=O)Nc1nc(C)c(S(=O)(=O)N2Cc3cc4c(cc3C[C@H]2C(=O)N[C@@](C)(Cc2ccc(-c3ccc(C#N)cc3)cc2)C(=O)O)OCC(c2ccc(OCc3ccc(Cl)c(Cl)c3)cc2)O4)s1] | 966 |
| 104 | 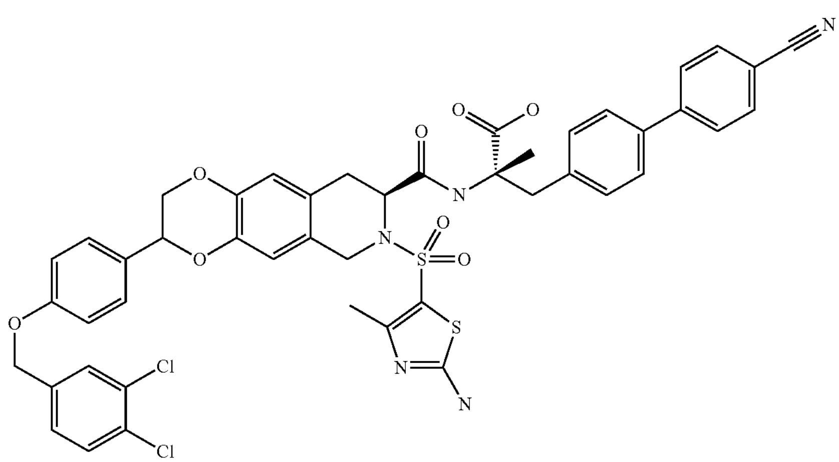 [SMILES: Cc1nc(N)sc1S(=O)(=O)N1Cc2cc3c(cc2C[C@H]1C(=O)N[C@@](C)(Cc1ccc(-c2ccc(C#N)cc2)cc1)C(=O)O)OCC(c1ccc(OCc2ccc(Cl)c(Cl)c2)cc1)O3] | 927 |

TABLE 1-continued

| Ex | Structure | LCMS (m/z) |
|---|---|---|
| 105 | 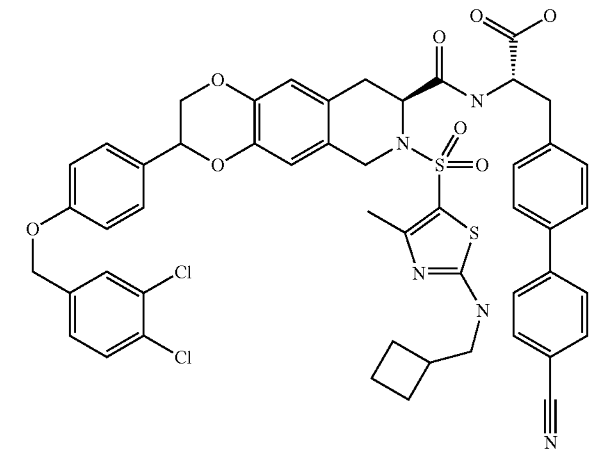 [SMILES: Cc1nc(NCC2CCC2)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 979 |
| 106 | 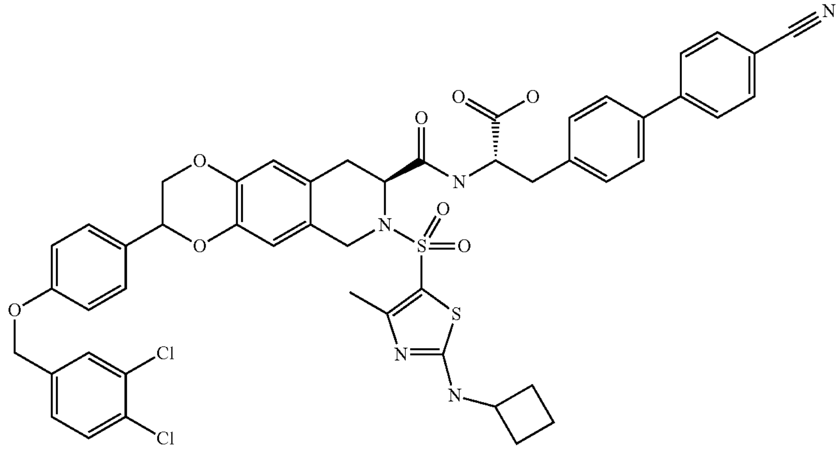 [SMILES: Cc1nc(NC2CCC2)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 964 |
| 107 | 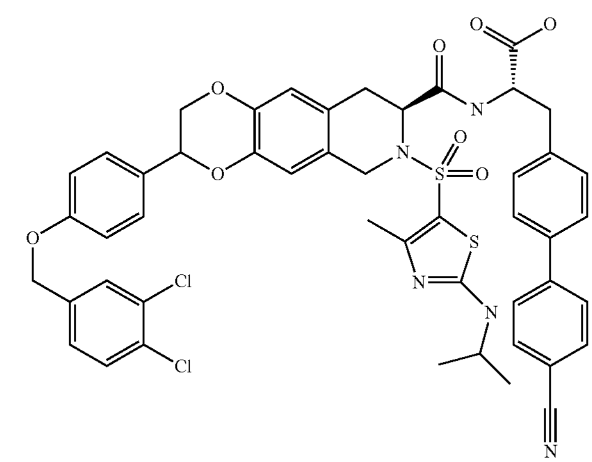 [SMILES: Cc1nc(NC(C)C)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 952 |

TABLE 1-continued

| Ex | Structure | LCMS (m/z) |
|---|---|---|
| 108 | 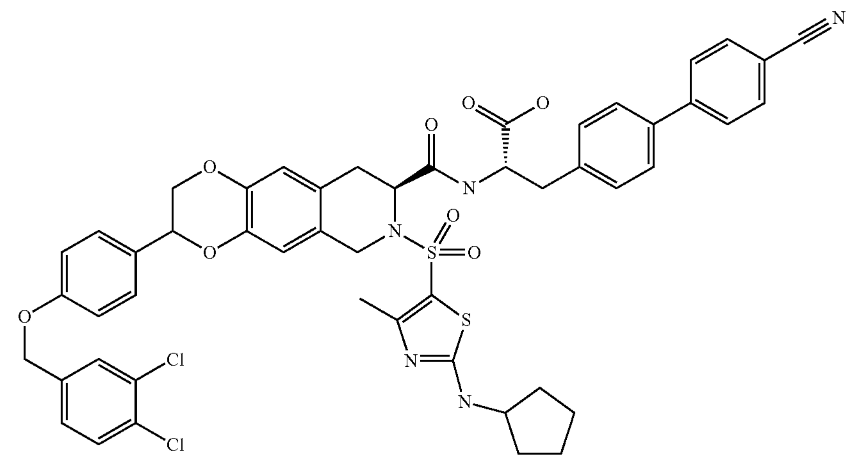 [SMILES: Cc1nc(NC2CCCC2)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 981 |
| 109 | 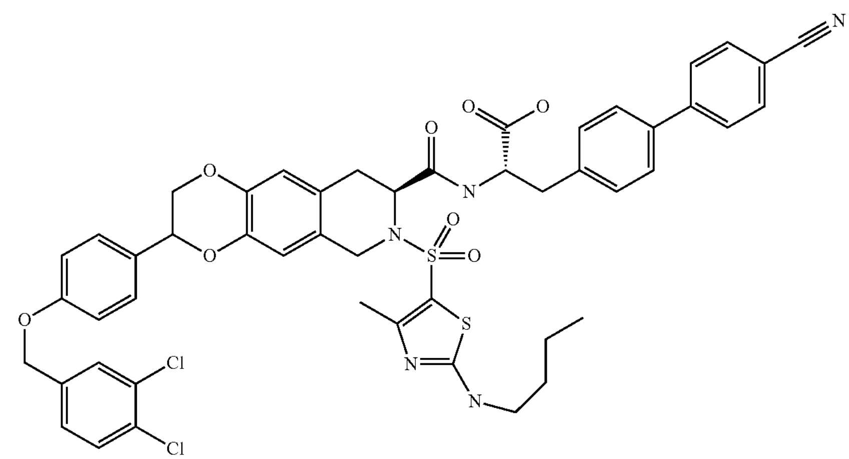 [SMILES: CCCCNc1nc(C)c(S(=O)(=O)N2Cc3cc4c(cc3C[C@H]2C(=O)N[C@@H](Cc2ccc(-c3ccc(C#N)cc3)cc2)C(=O)O)OCC(c2ccc(OCc3ccc(Cl)c(Cl)c3)cc2)O4)s1] | 968 |
| 110 | 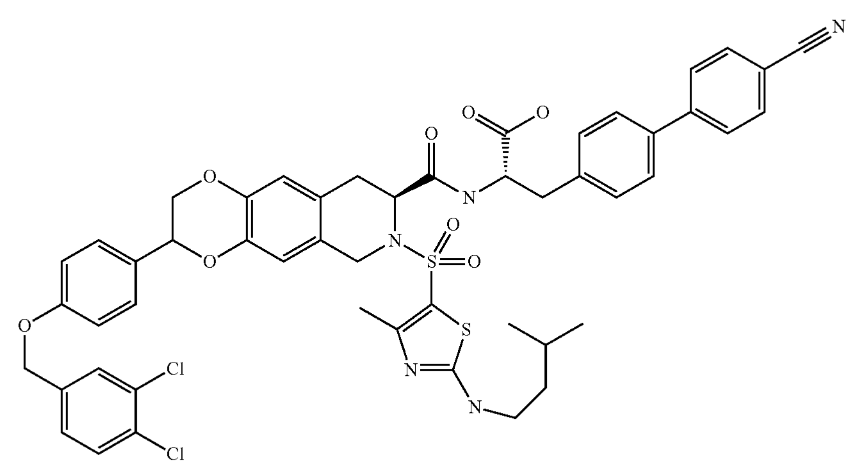 [SMILES: Cc1nc(NCCC(C)C)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 980 |

TABLE 1-continued
| Ex | Structure | LCMS (m/z) |
|---|---|---|
| 111 | 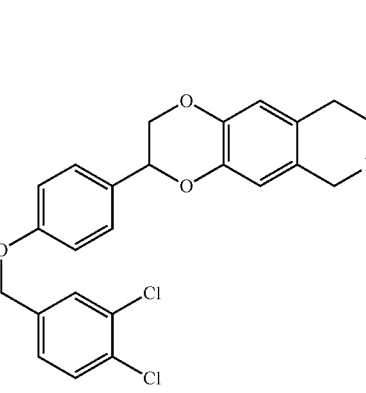 | 945 |
| 112 | 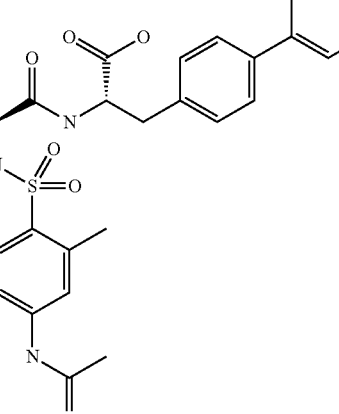 | 961 |
| 113 | 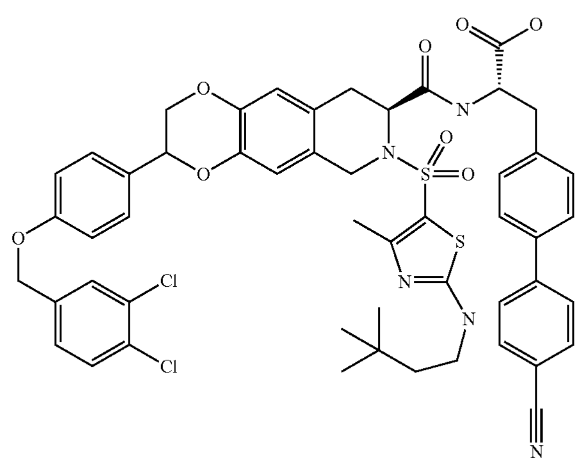 [SMILES: Cc1nc(NCCC(C)(C)C)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 996 |

TABLE 1-continued

| Ex | Structure | LCMS (m/z) |
|---|---|---|
| 114 | 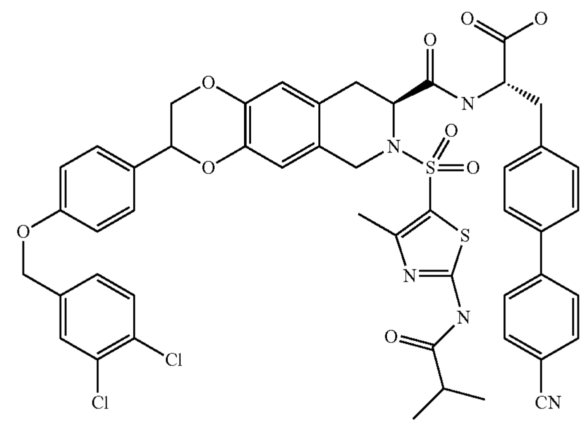 [SMILES: Cc1nc(NC(=O)C(C)C)sc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 980 |
| 115 | 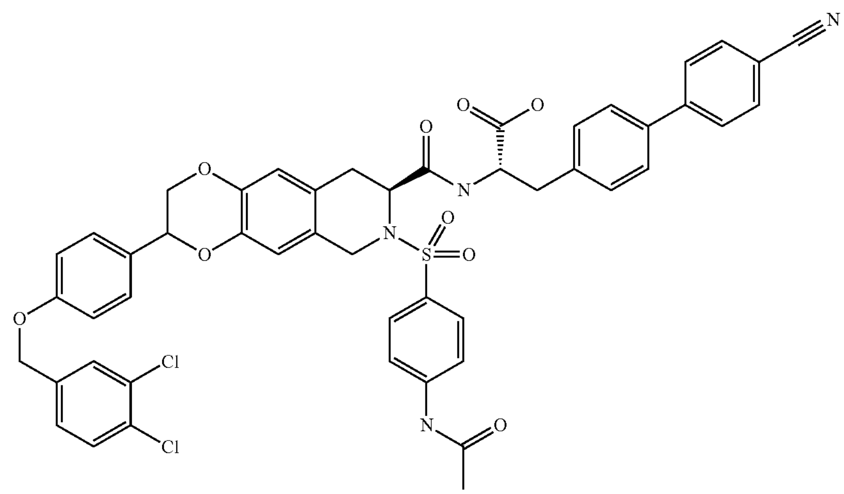 [SMILES: CC(=O)Nc1ccc(S(=O)(=O)N2Cc3cc4c(cc3C[C@H]2C(=O)N[C@@H](Cc2ccc(-c3ccc(C#N)cc3)cc2)C(=O)O)OCC(c2ccc(OCc3ccc(Cl)c(Cl)c3)cc2)O4)cc1] | 931 |
| 116 | 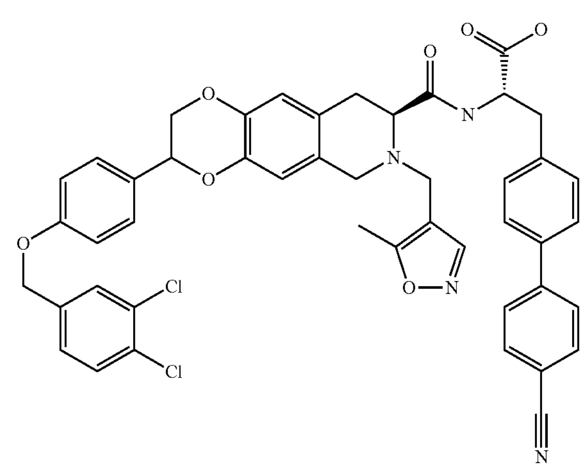 [SMILES: Cc1oncc1CN1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 830 |

TABLE 1-continued
| Ex | Structure | LCMS (m/z) |
|---|---|---|
| 117 | 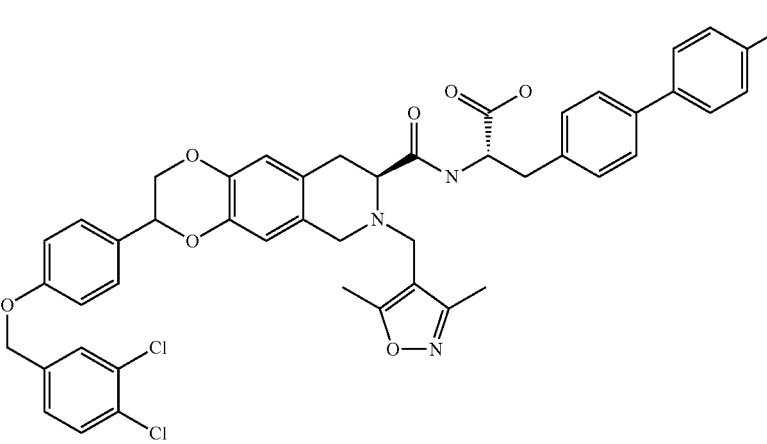 | 844 |
| 118 | 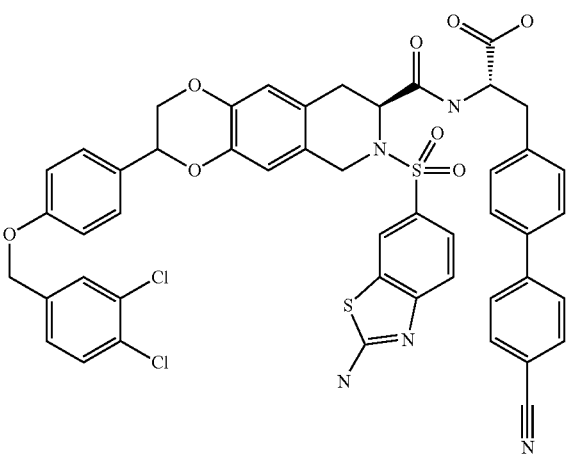 [SMILES: N#Cc1ccc(-c2ccc(C[C@H](NC(=O)[C@@H]3Cc4cc5c(cc4CN3S(=O)(=O)c3ccc4nc(N)sc4c3)OC(c3ccc(OCc4ccc(Cl)c(Cl)c4)cc3)CO5)C(=O)O)cc2)cc1] | 947 |
| 119 | 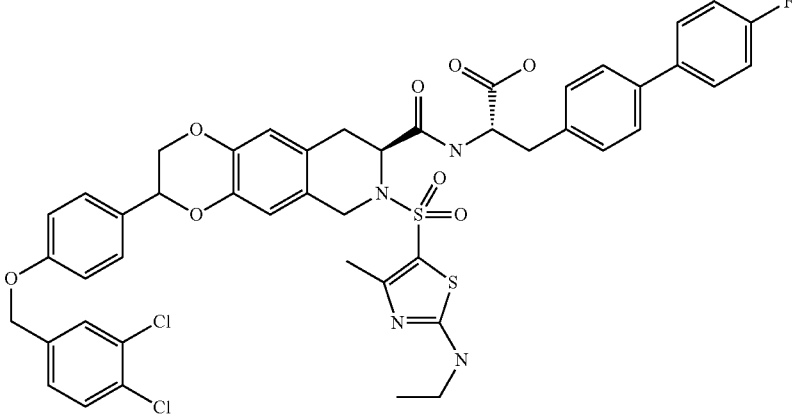 | 934 |

TABLE 1-continued

| Ex | Structure | LCMS (m/z) |
|---|---|---|
| 120 | 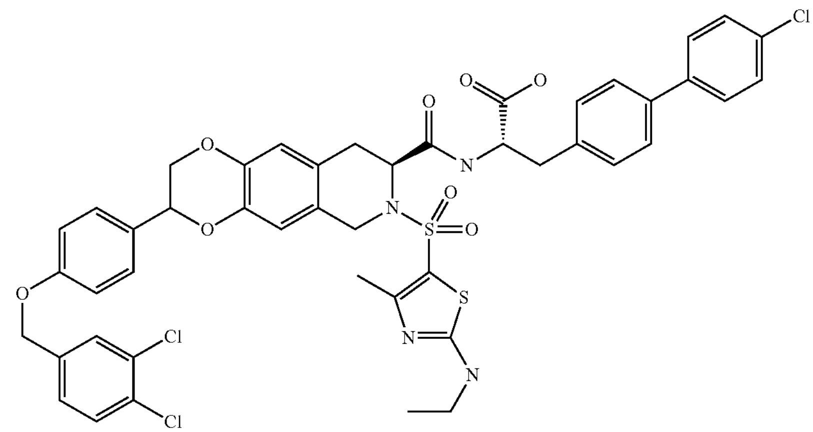 [SMILES: CCNc1nc(C)c(S(=O)(=O)N2Cc3cc4c(cc3C[C@H]2C(=O)N[C@@H](Cc2ccc(-c3ccc(Cl)cc3)cc2)C(=O)O)OCC(c2ccc(OCc3ccc(Cl)c(Cl)c3)cc2)O4)s1] | 950 |
| 121 | 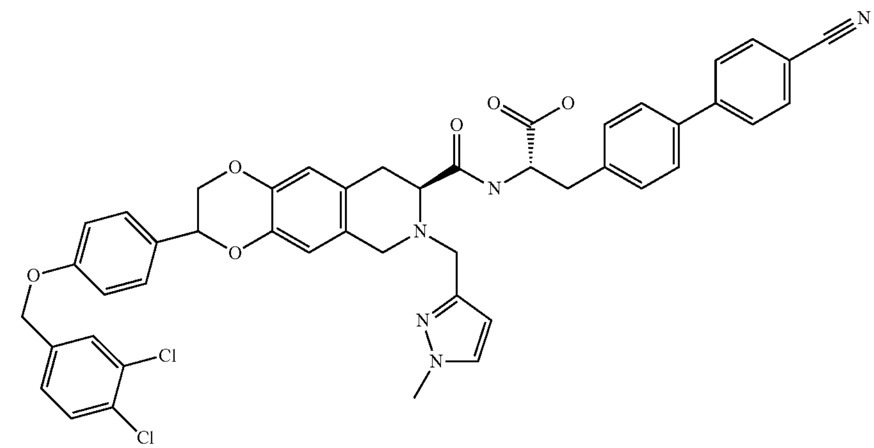 [SMILES: Cn1ccc(CN2Cc3cc4c(cc3C[C@H]2C(=O)N[C@@H](Cc2ccc(-c3ccc(C#N)cc3)cc2)C(=O)O)OCC(c2ccc(OCc3ccc(Cl)c(Cl)c3)cc2)O4)n1] | 830 |
| 122 | 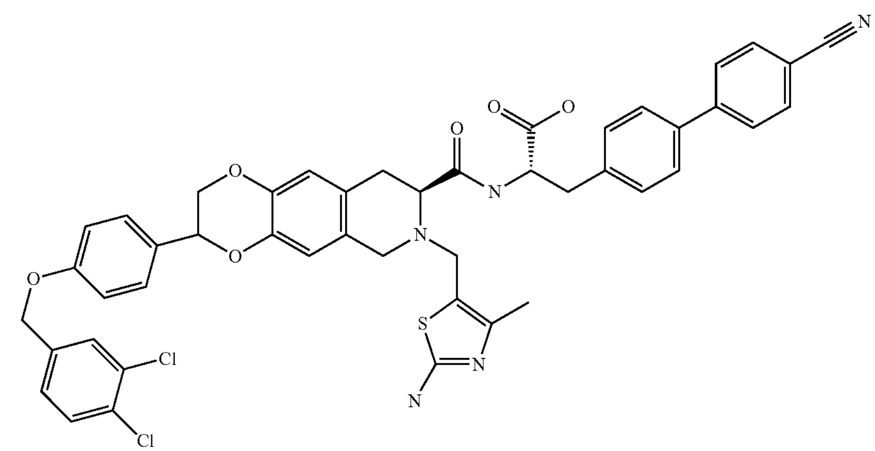 [SMILES: Cc1nc(N)sc1CN1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 862 |

TABLE 1-continued
| Ex | Structure | LCMS (m/z) |
|---|---|---|
| 123 | 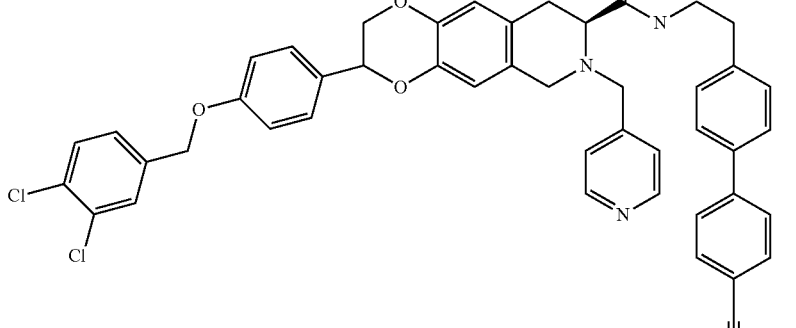 | 827 |
| 124 | 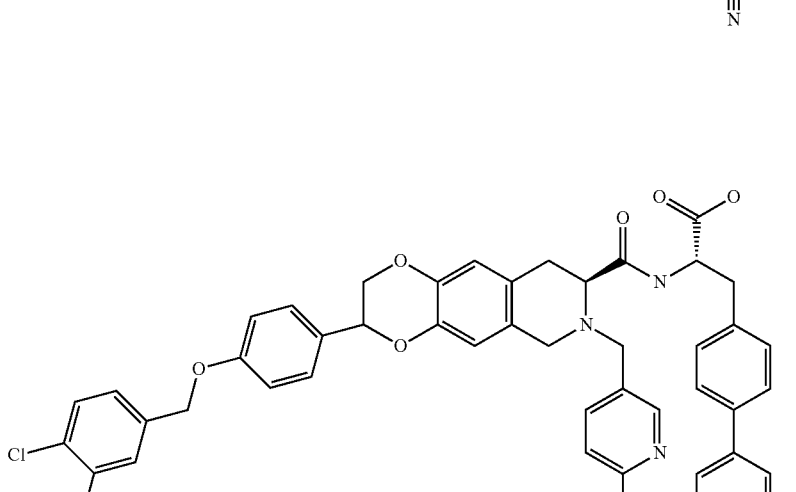 | 841 |
| 125 | 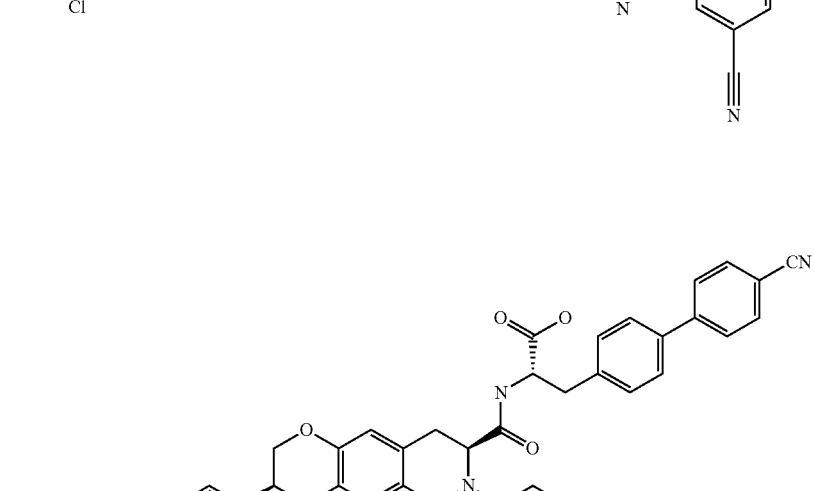 | 852 |

TABLE 1-continued
| Ex | Structure | LCMS (m/z) |
|---|---|---|
| 126 | 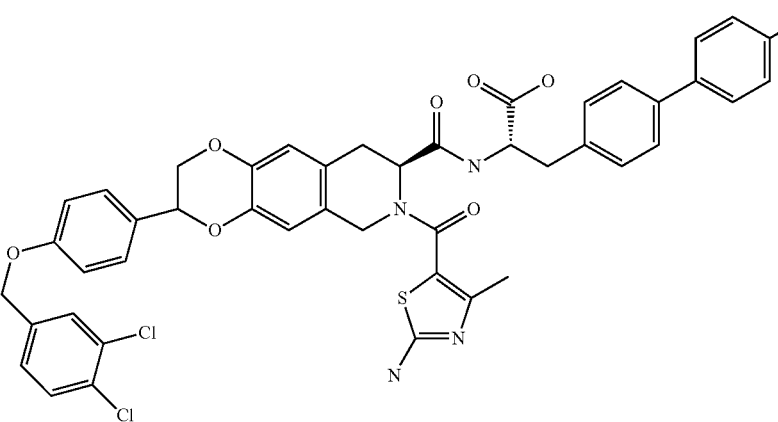 | 876 |
| 127 | 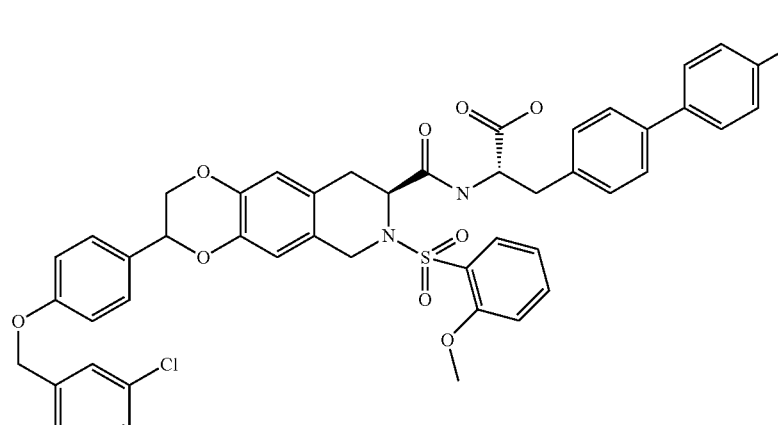 | 906 |
| 128 | 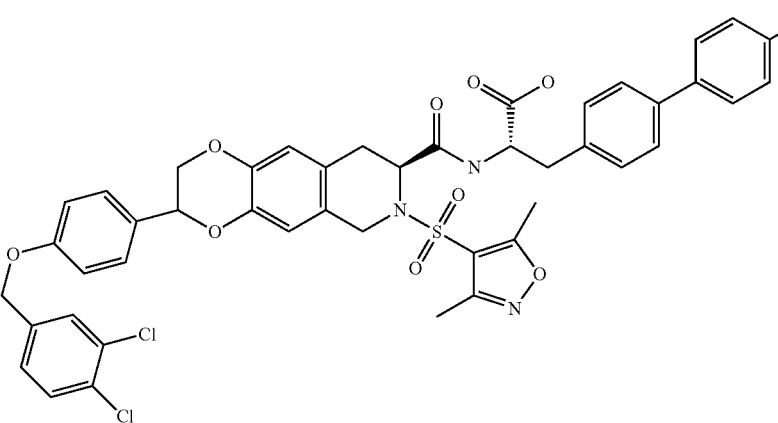 | 894 |

TABLE 1-continued
| Ex | Structure | LCMS (m/z) |
|---|---|---|
| 129 | 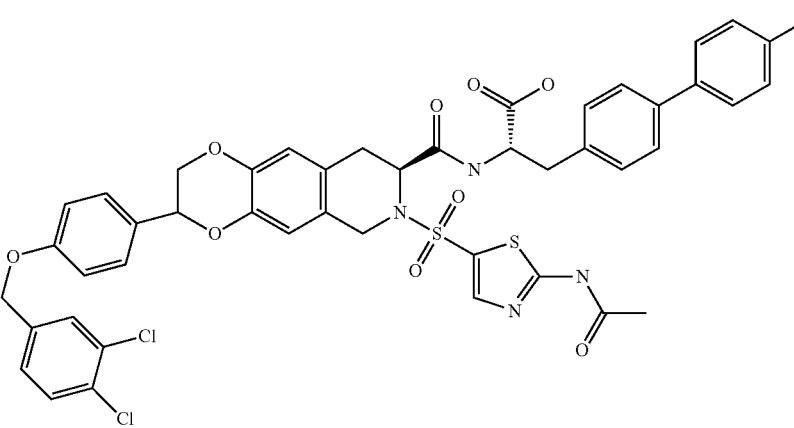 | 939 |
| 130 | 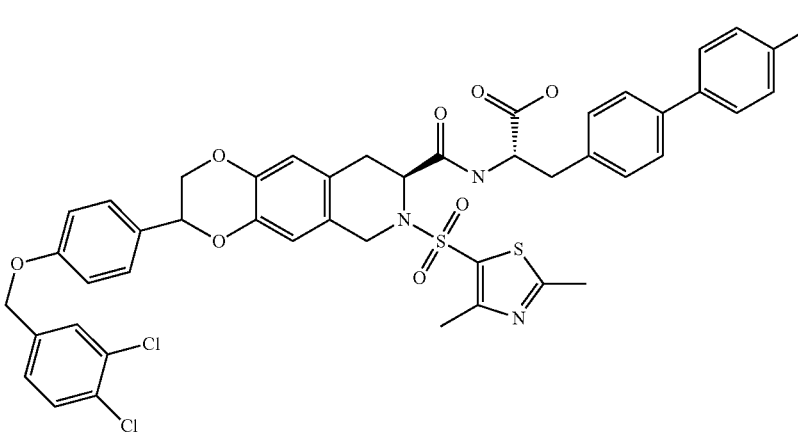 | 910 |
| 131 | 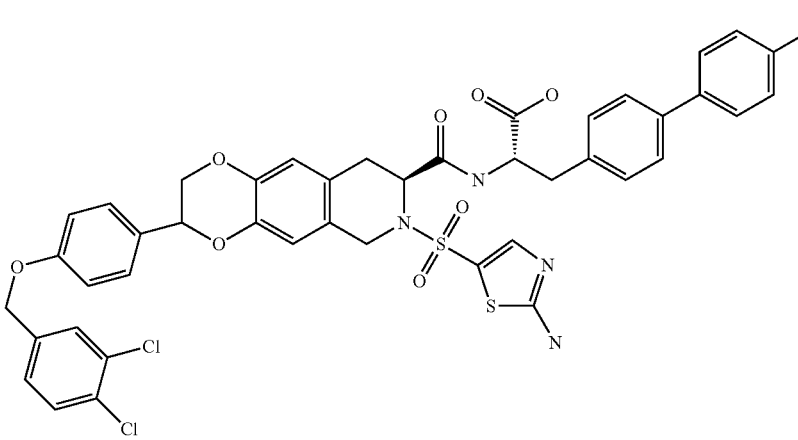 | 897 |

TABLE 1-continued

| Ex | Structure | LCMS (m/z) |
|----|-----------|------------|
| 132 | 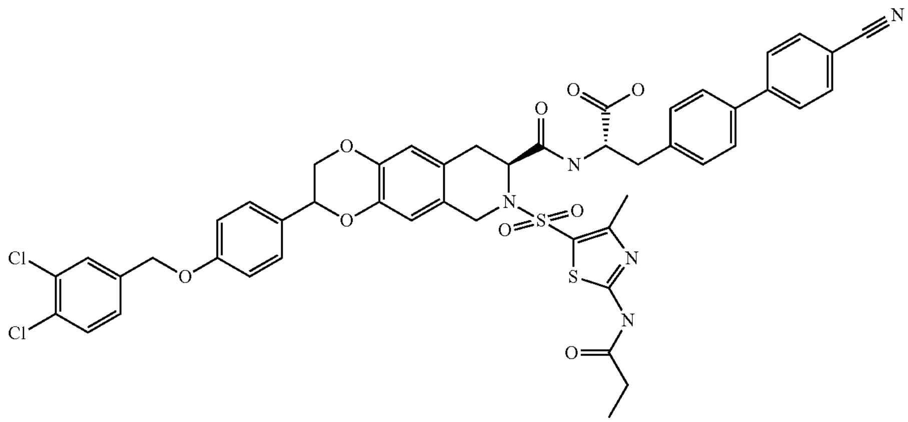 [SMILES: CCC(=O)Nc1nc(C)c(S(=O)(=O)N2Cc3cc4c(cc3C[C@H]2C(=O)N[C@@H](Cc2ccc(-c3ccc(C#N)cc3)cc2)C(=O)O)OCC(c2ccc(OCc3ccc(Cl)c(Cl)c3)cc2)O4)s1] | 967 |
| 133 | 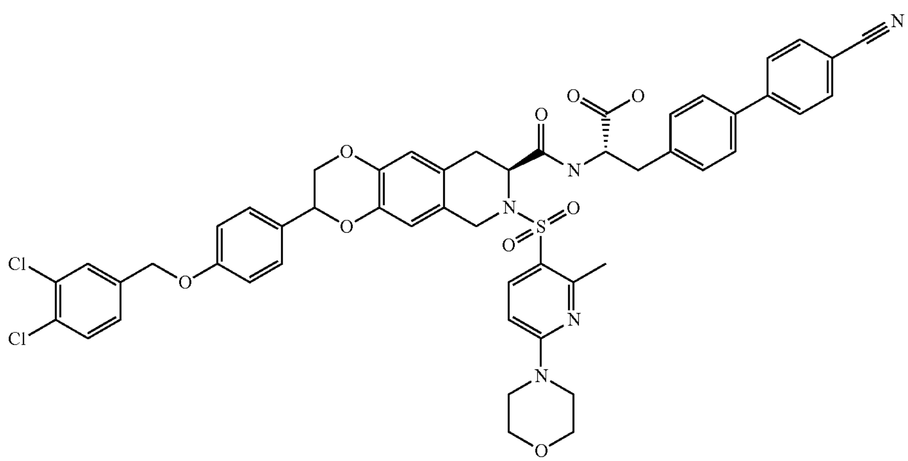 [SMILES: Cc1nc(N2CCOCC2)ccc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 975 |
| 134 | 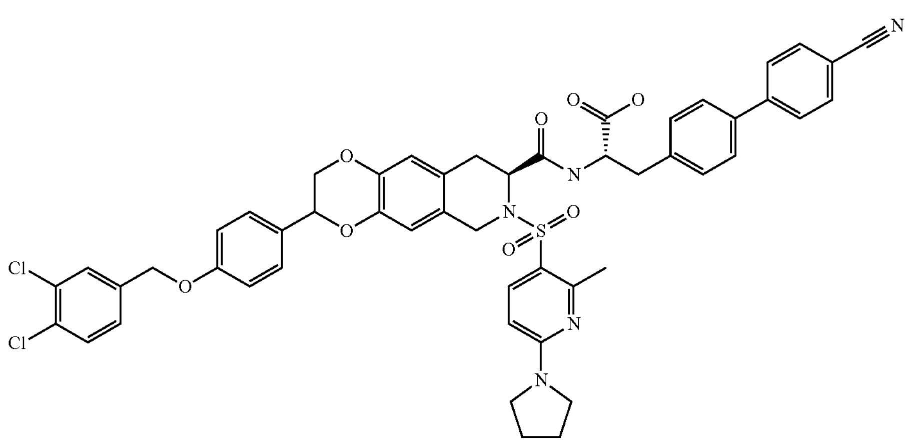 [SMILES: Cc1nc(N2CCCC2)ccc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 958 |

TABLE 1-continued

| Ex | Structure | LCMS (m/z) |
|---|---|---|
| 135 | 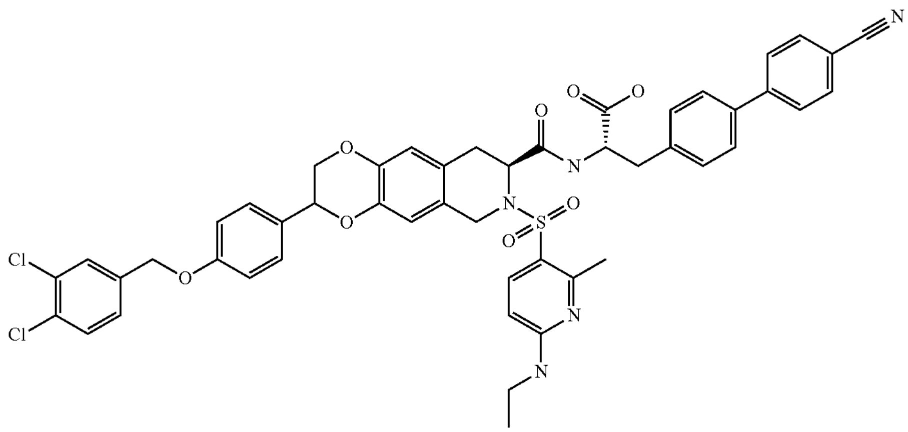 [SMILES: CCNc1ccc(S(=O)(=O)N2Cc3cc4c(cc3C[C@H]2C(=O)N[C@@H](Cc2ccc(-c3ccc(C#N)cc3)cc2)C(=O)O)OCC(c2ccc(OCc3ccc(Cl)c(Cl)c3)cc2)O4)c(C)n1] | 934 |
| 136 | 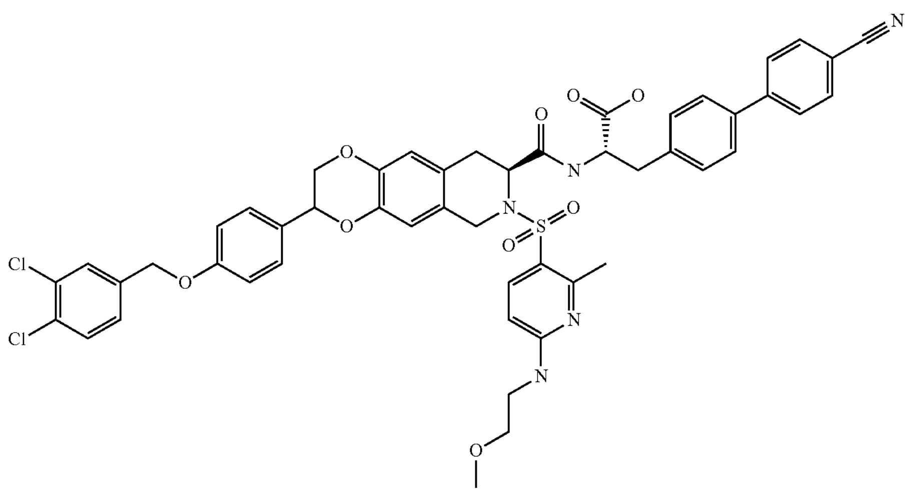 [SMILES: COCCNc1ccc(S(=O)(=O)N2Cc3cc4c(cc3C[C@H]2C(=O)N[C@@H](Cc2ccc(-c3ccc(C#N)cc3)cc2)C(=O)O)OCC(c2ccc(OCc3ccc(Cl)c(Cl)c3)cc2)O4)c(C)n1] | 962 |
| 137 | 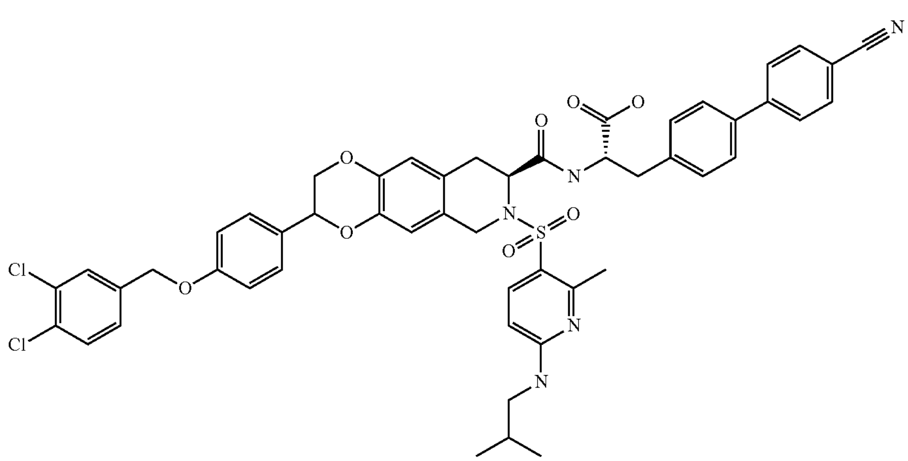 [SMILES: Cc1nc(NCC(C)C)ccc1S(=O)(=O)N1Cc2cc3c(cc2C[C@H]1C(=O)N[C@@H](Cc1ccc(-c2ccc(C#N)cc2)cc1)C(=O)O)OCC(c1ccc(OCc2ccc(Cl)c(Cl)c2)cc1)O3] | 960 |

TABLE 1-continued
| Ex | Structure | LCMS (m/z) |
|---|---|---|
| 138 | 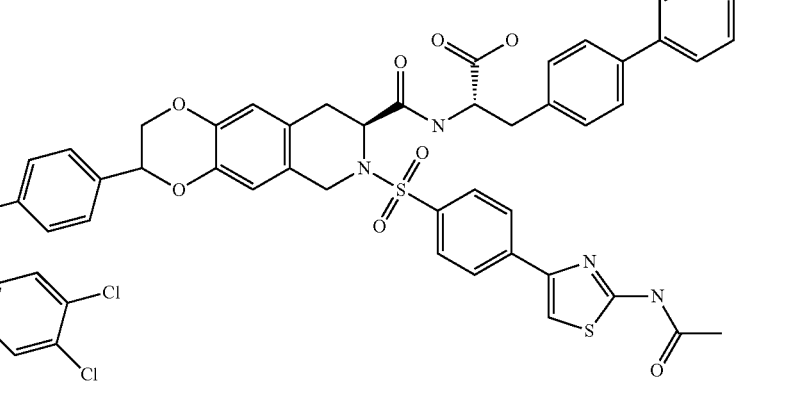 | 1014 |
| 139 | 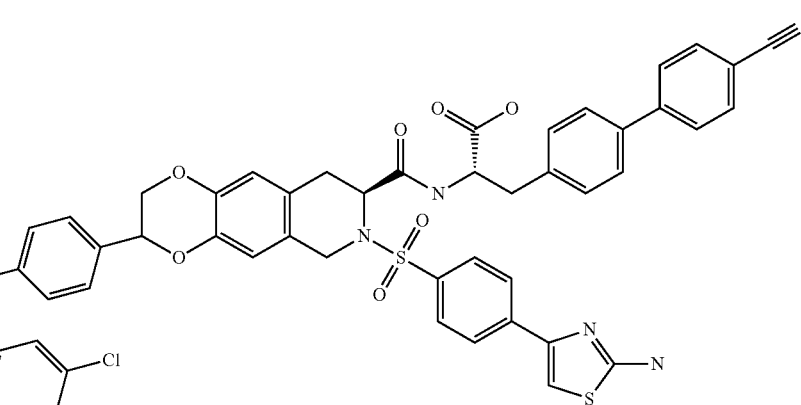 | 972 |
| 140 | 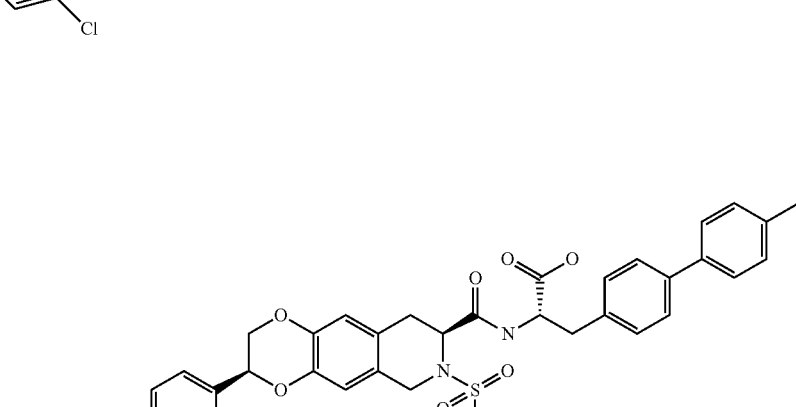 | 972 |

TABLE 1-continued

| Ex | Structure | LCMS (m/z) |
|---|---|---|
| 141 | 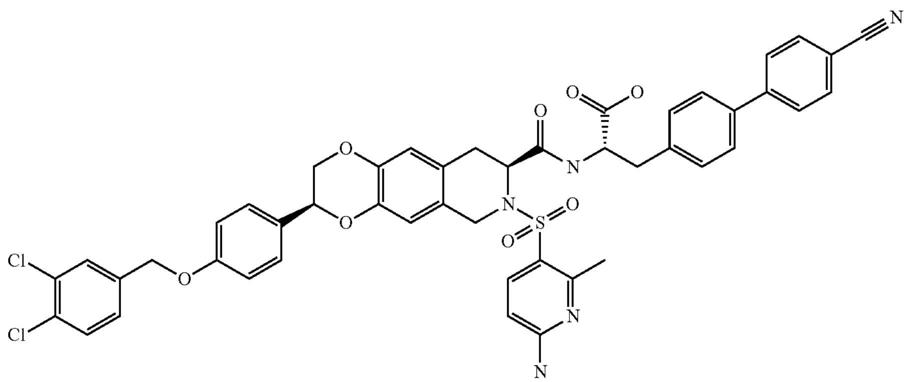 [SMILES: Cc1nc(N)ccc1S(=O)(=O)N1Cc2cc3c(cc2C[C@H]1C(=O)N[C@@H](Cc1ccc(-c2ccc(C#N)cc2)cc1)C(=O)O)OC[C@H](c1ccc(OCc2ccc(Cl)c(Cl)c2)cc1)O3] | 904 |
| 142 | 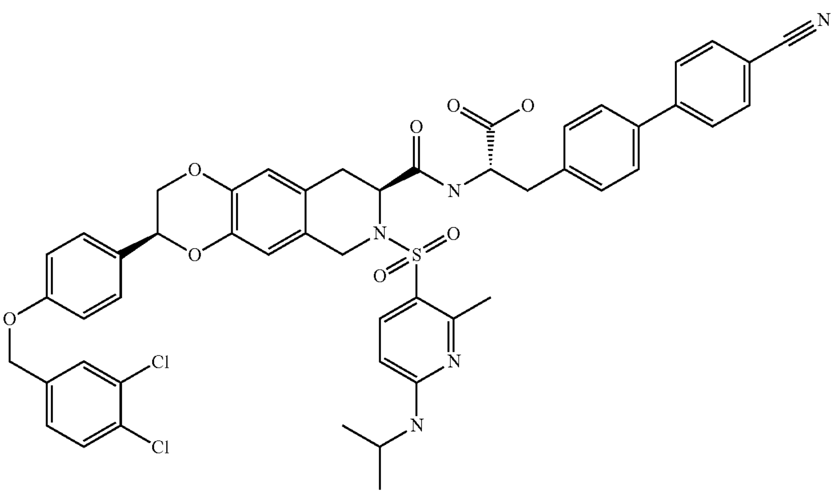 [SMILES: Cc1nc(NC(C)C)ccc1S(=O)(=O)N1Cc2cc3c(cc2C[C@H]1C(=O)N[C@@H](Cc1ccc(-c2ccc(C#N)cc2)cc1)C(=O)O)OC[C@H](c1ccc(OCc2ccc(Cl)c(Cl)c2)cc1)O3] | 946 |
| 143 | 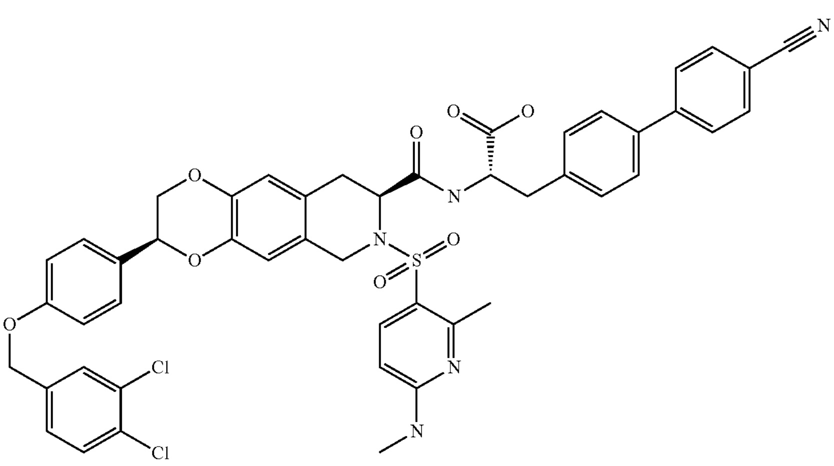 [SMILES: CNc1ccc(S(=O)(=O)N2Cc3cc4c(cc3C[C@H]2C(=O)N[C@@H](Cc2ccc(-c3ccc(C#N)cc3)cc2)C(=O)O)OC[C@H](c2ccc(OCc3ccc(Cl)c(Cl)c3)cc2)O4)c(C)n1] | 918 |

TABLE 1-continued
| Ex | Structure | LCMS (m/z) |
|---|---|---|
| 144 | 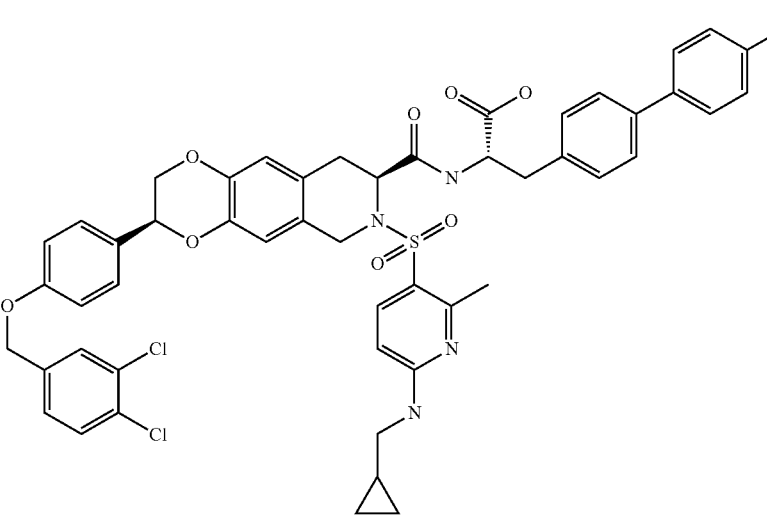 | 958 |
| 145 | 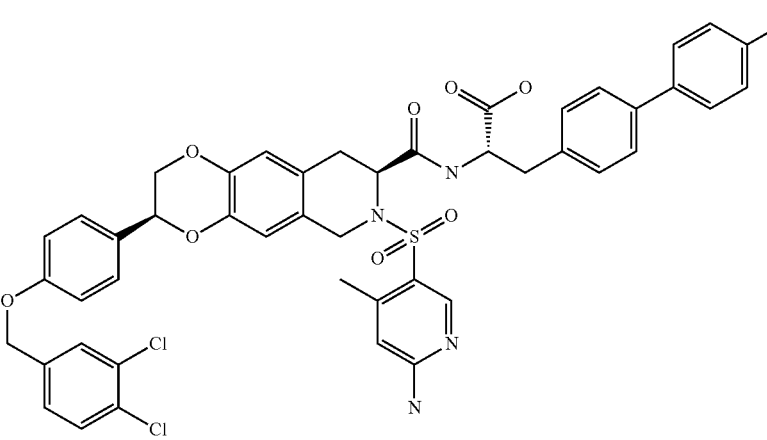 | 904 |
| 146 | 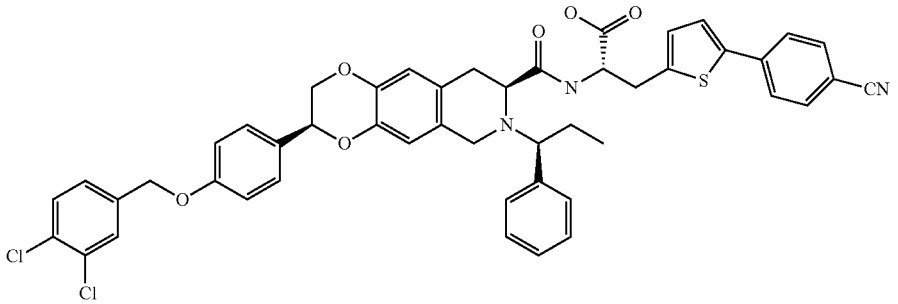 [SMILES: CC[C@@H](c1ccccc1)N1Cc2cc3c(cc2C[C@H]1C(=O)N[C@@H](Cc1ccc(-c2ccc(C#N)cc2)s1)C(=O)O)OC[C@H](c1ccc(OCc2ccc(Cl)c(Cl)c2)cc1)O3] | 861 |

TABLE 1-continued
| Ex | Structure | LCMS (m/z) |
|---|---|---|
| 147 | 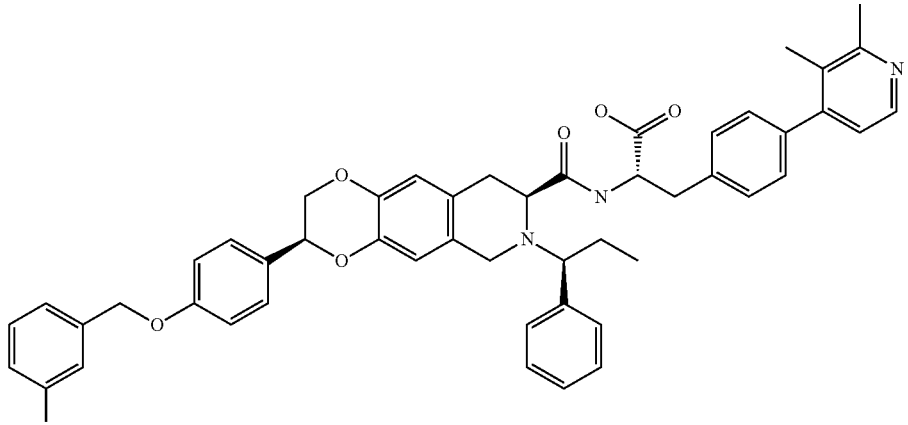 | 823 |
| 148 | 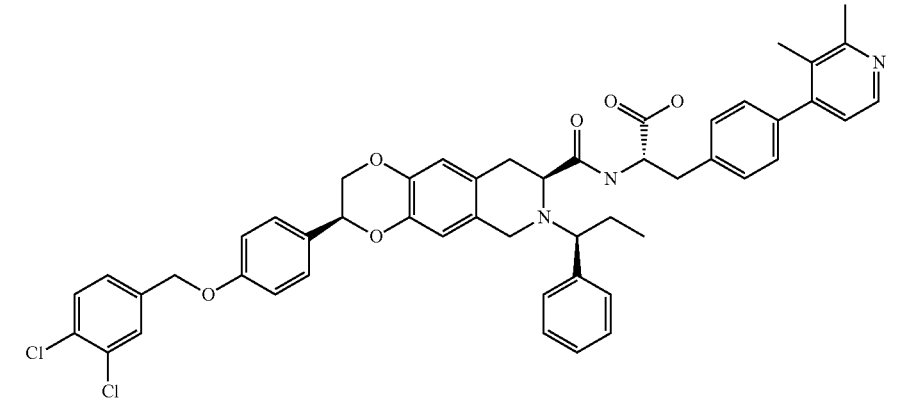 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OCc2ccc(Cl)c(Cl)c2)cc1)O3] | 823 |
| 149 | 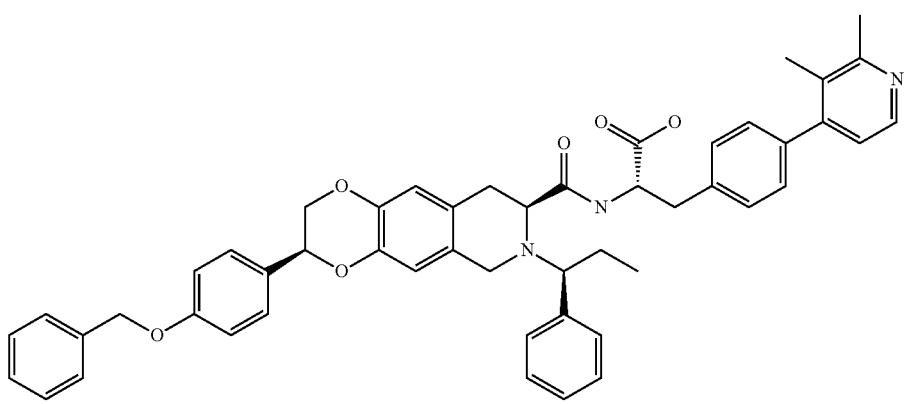 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OCc2ccccc2)cc1)O3] | 789 |

TABLE 1-continued

| Ex | Structure | LCMS (m/z) |
|---|---|---|
| 150 | 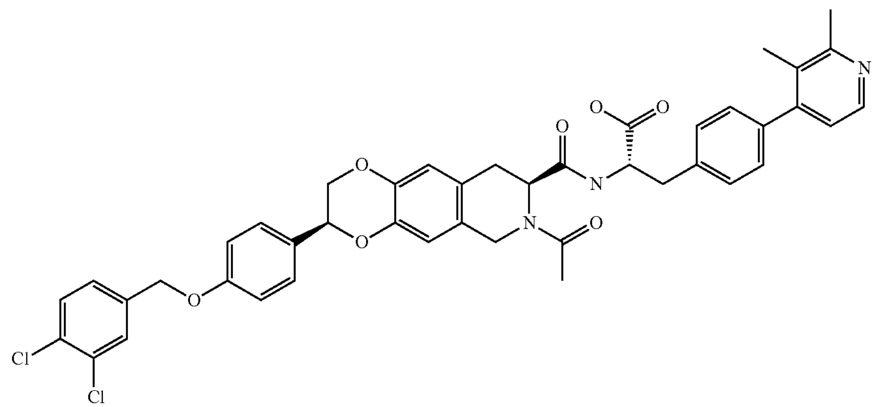 [SMILES: CC(=O)N1Cc2cc3c(cc2C[C@H]1C(=O)N[C@@H](Cc1ccc(-c2ccnc(C)c2C)cc1)C(=O)O)OC[C@H](c1ccc(OCc2ccc(Cl)c(Cl)c2)cc1)O3] | 781 |
| 151 | 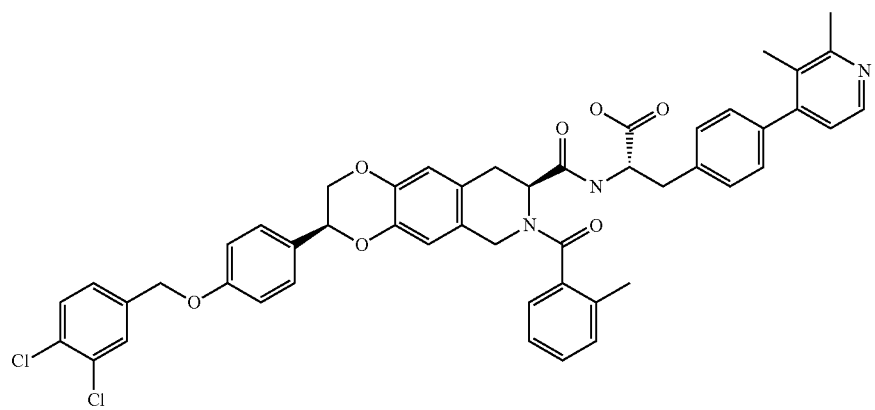 [SMILES: Cc1ccccc1C(=O)N1Cc2cc3c(cc2C[C@H]1C(=O)N[C@@H](Cc1ccc(-c2ccnc(C)c2C)cc1)C(=O)O)OC[C@H](c1ccc(OCc2ccc(Cl)c(Cl)c2)cc1)O3] | 857 |
| 152 | 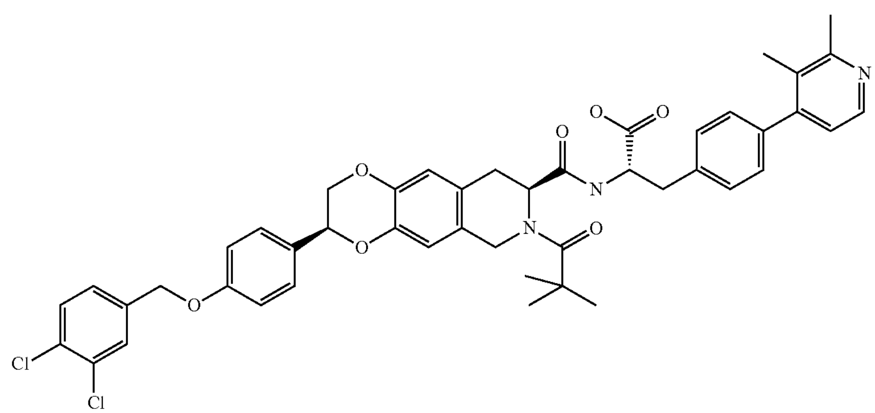 [SMILES: Cc1nccc(-c2ccc(C[C@H](NC(=O)[C@@H]3Cc4cc5c(cc4CN3C(=O)C(C)(C)C)O[C@@H](c3ccc(OCc4ccc(Cl)c(Cl)c4)cc3)CO5)C(=O)O)cc2)c1C] | 823 |
| 153 | 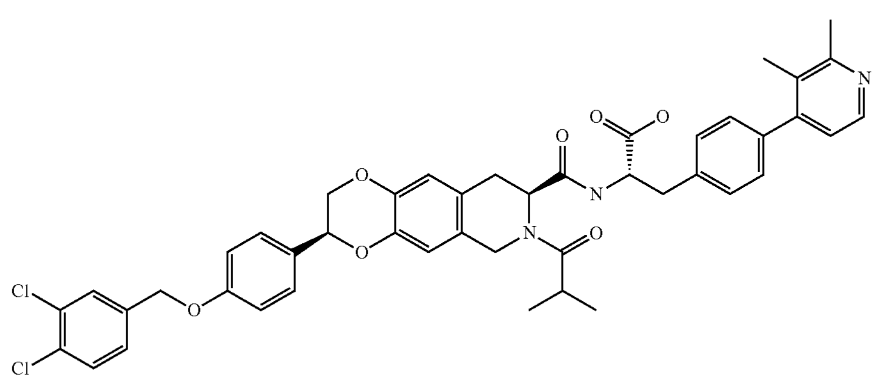 [SMILES: Cc1nccc(-c2ccc(C[C@H](NC(=O)[C@@H]3Cc4cc5c(cc4CN3C(=O)C(C)C)O[C@@H](c3ccc(OCc4ccc(Cl)c(Cl)c4)cc3)CO5)C(=O)O)cc2)c1C] | 809 |

TABLE 1-continued

| Ex | Structure | LCMS (m/z) |
|---|---|---|
| 154 | 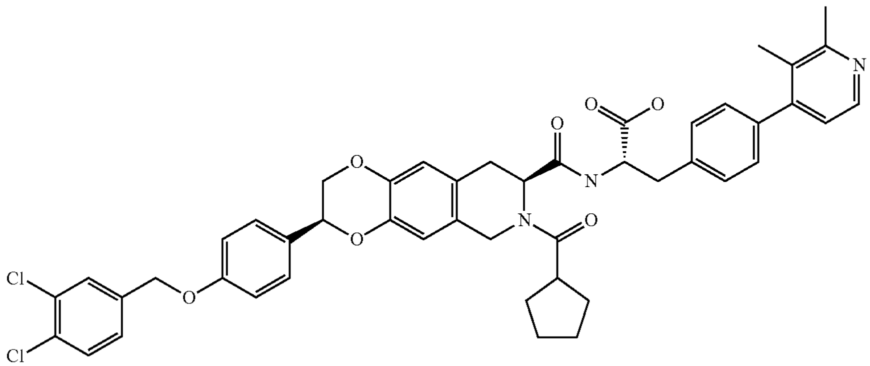 [SMILES: Cc1nccc(-c2ccc(C[C@H](NC(=O)[C@@H]3Cc4cc5c(cc4CN3C(=O)C3CCCC3)O[C@@H](c3ccc(OCc4ccc(Cl)c(Cl)c4)cc3)CO5)C(=O)O)cc2)c1C] | 835 |
| 155 | 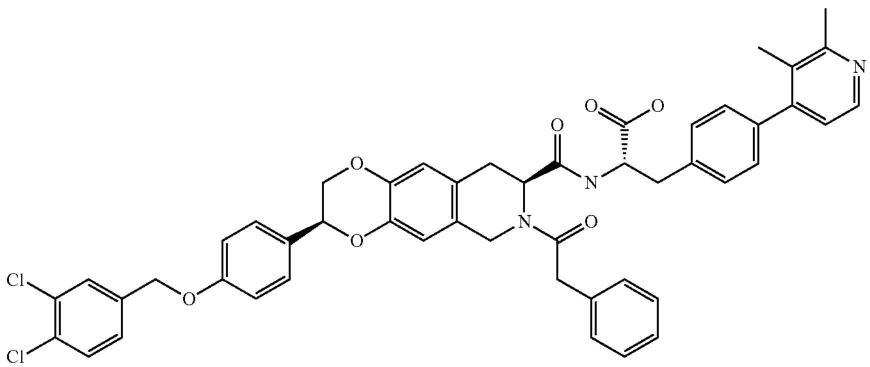 [SMILES: Cc1nccc(-c2ccc(C[C@H](NC(=O)[C@@H]3Cc4cc5c(cc4CN3C(=O)Cc3ccccc3)O[C@@H](c3ccc(OCc4ccc(Cl)c(Cl)c4)cc3)CO5)C(=O)O)cc2)c1C] | 857 |
| 156 | 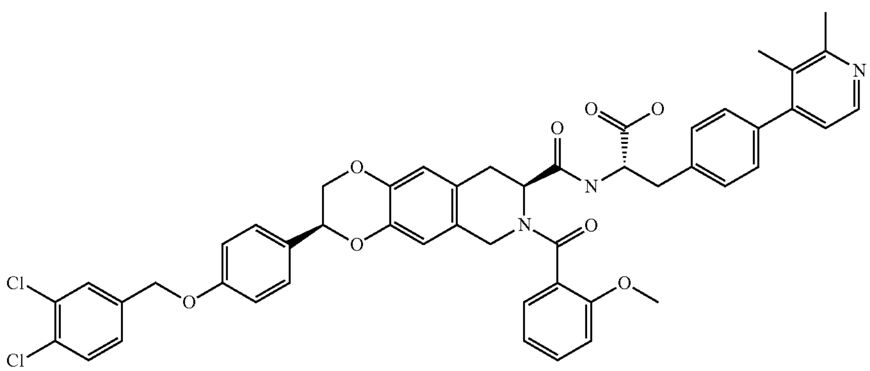 [SMILES: COc1ccccc1C(=O)N1Cc2cc3c(cc2C[C@H]1C(=O)N[C@@H](Cc1ccc(-c2ccnc(C)c2C)cc1)C(=O)O)OC[C@H](c1ccc(OCc2ccc(Cl)c(Cl)c2)cc1)O3] | 873 |
| 157 | 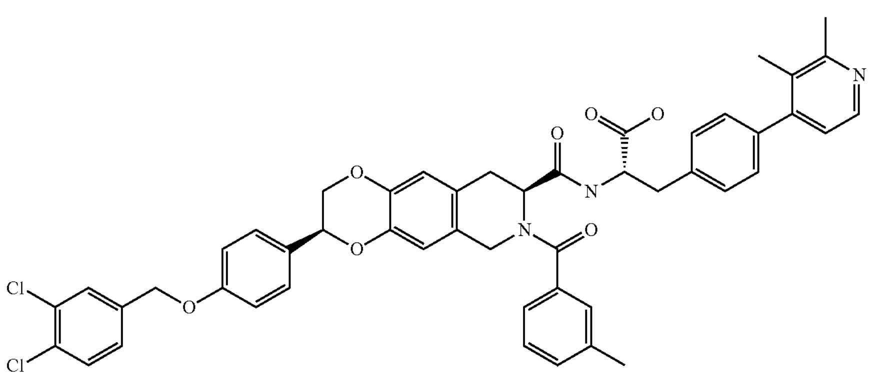 [SMILES: Cc1cccc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)c1] | 857 |

TABLE 1-continued

| Ex | Structure | LCMS (m/z) |
|---|---|---|
| 158 | 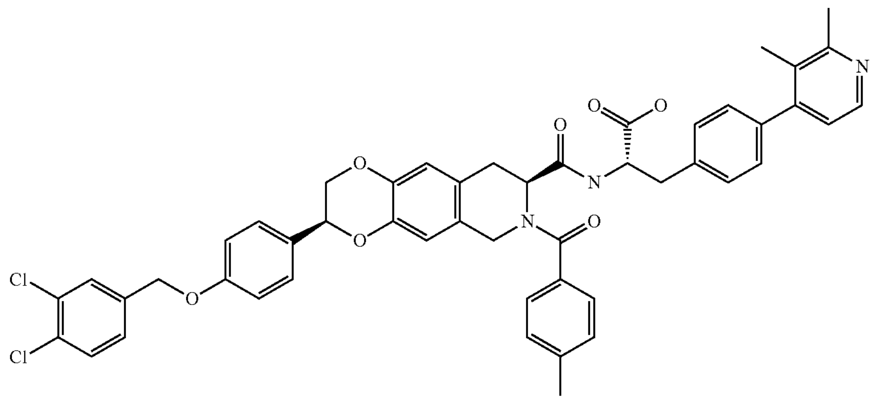 [SMILES: Cc1ccc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)cc1] | 857 |
| 159 | 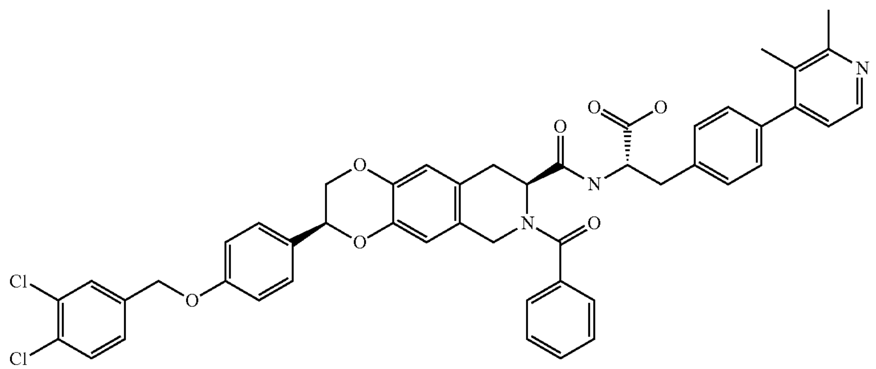 [SMILES: Cc1nccc(-c2ccc(C[C@H](NC(=O)[C@@H]3Cc4cc5c(cc4CN3C(=O)c3ccccc3)O[C@@H](c3ccc(OCc4ccc(Cl)c(Cl)c4)cc3)CO5)C(=O)O)cc2)c1C] | 843 |
| 160 | 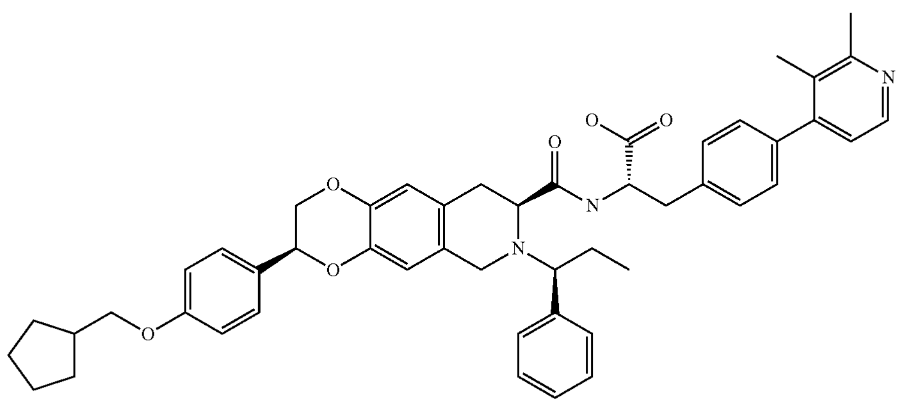 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OCC2CCCC2)cc1)O3] | 781 |
| 161 | 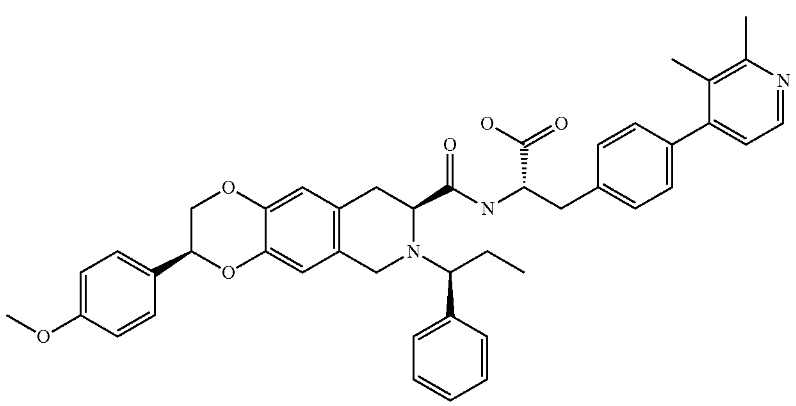 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OC)cc1)O3] | 713 |

TABLE 1-continued

| Ex | Structure | LCMS (m/z) |
|---|---|---|
| 162 | 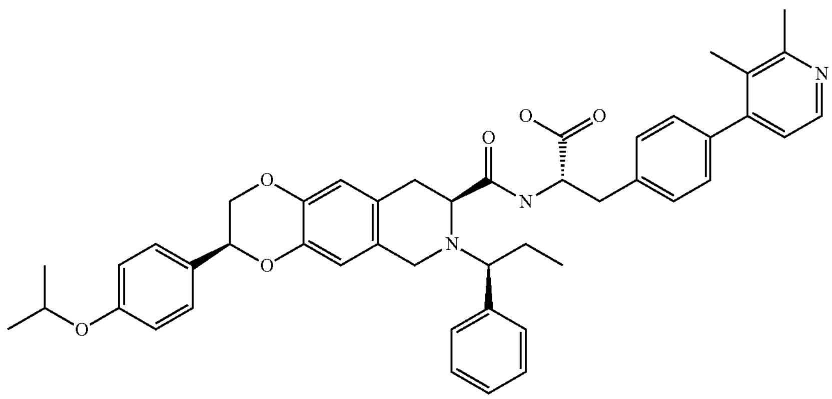 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OC(C)C)cc1)O3] | 741 |
| 163 | 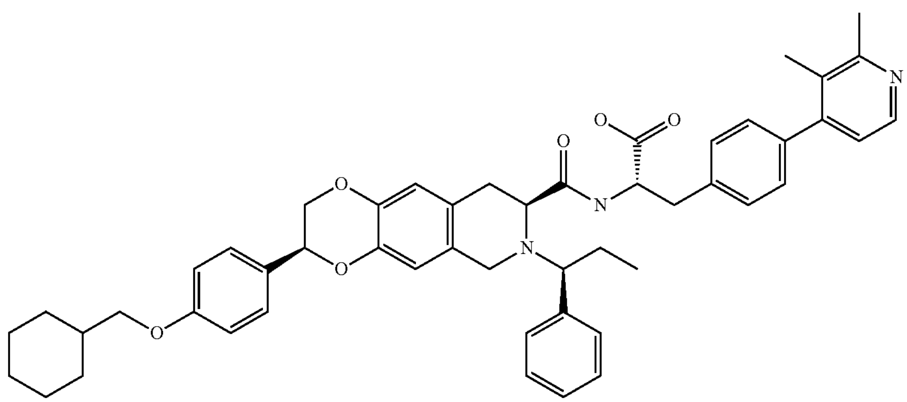 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OCC2CCCCC2)cc1)O3] | 795 |
| 164 | 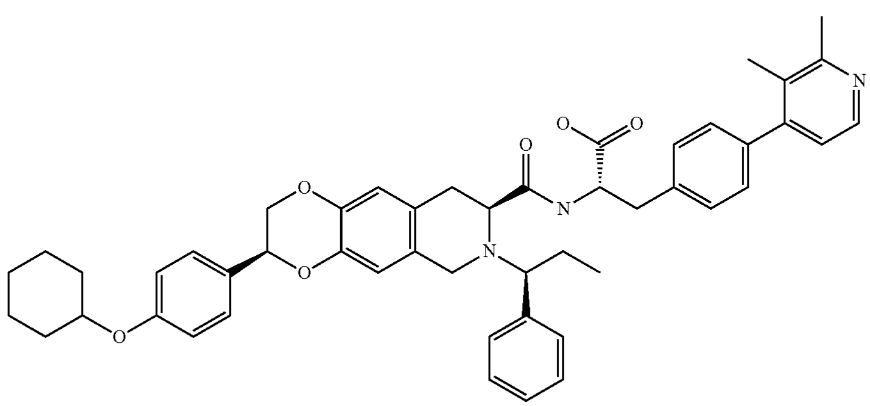 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OC2CCCCC2)cc1)O3] | 781 |
| 165 | 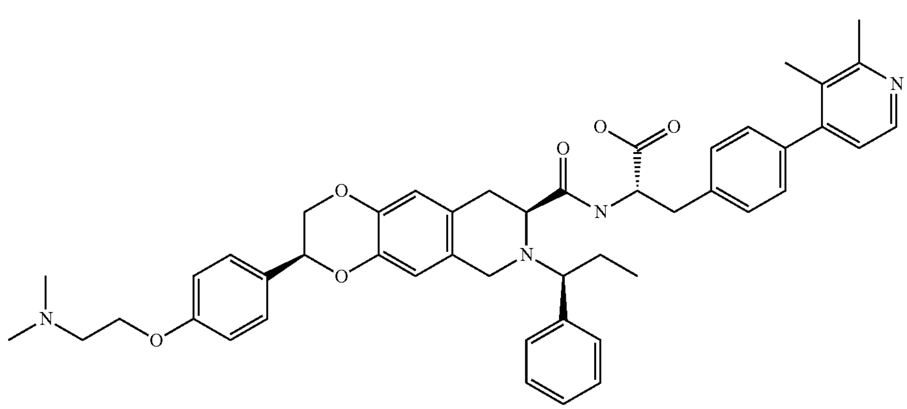 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OCCN(C)C)cc1)O3] | 770 |

TABLE 1-continued

| Ex | Structure | LCMS (m/z) |
|---|---|---|
| 166 | 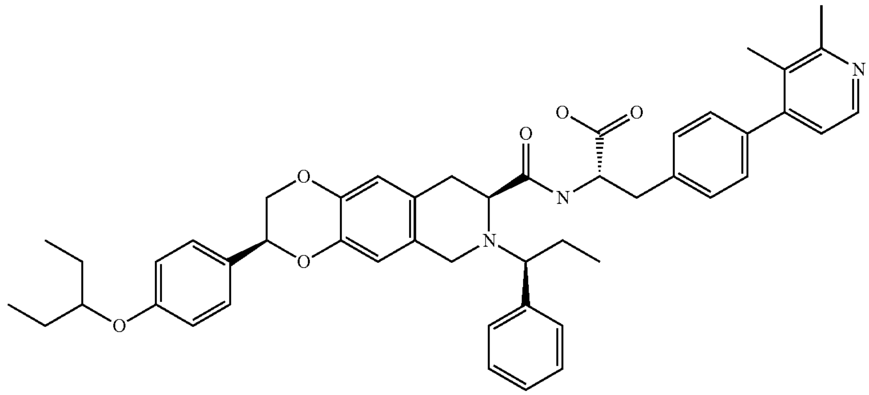 [SMILES: CCC(CC)Oc1ccc([C@H]2COc3cc4c(cc3O2)CN([C@@H](CC)c2ccccc2)[C@H](C(=O)N[C@@H](Cc2ccc(-c3ccnc(C)c3C)cc2)C(=O)O)C4)cc1] | 769 |
| 167 | 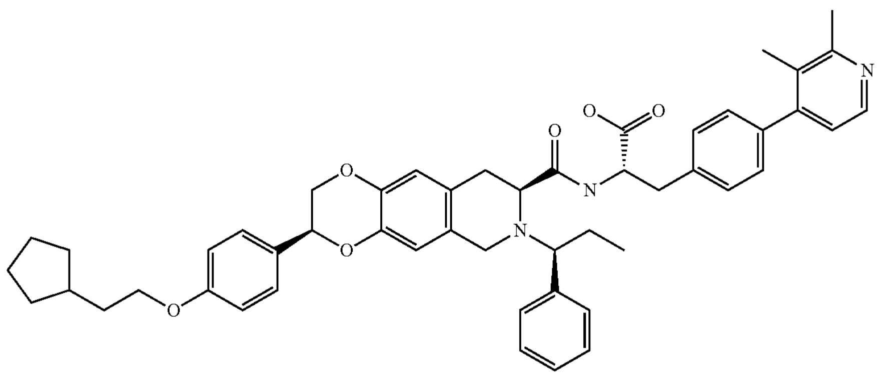 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OCCC2CCCC2)cc1)O3] | 795 |
| 168 | 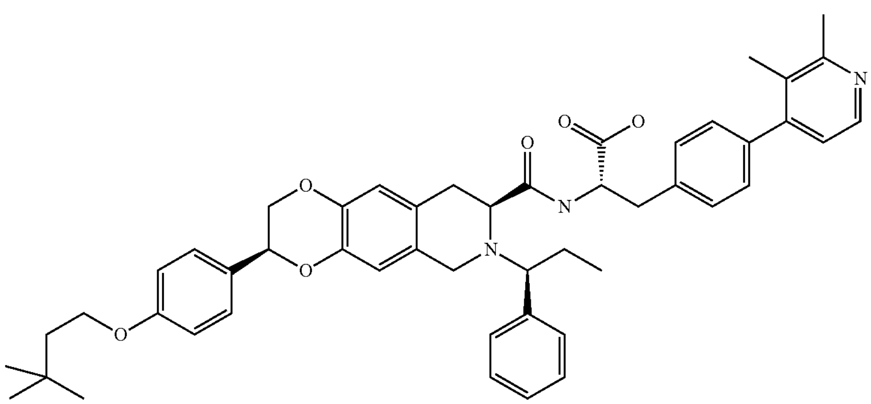 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OCCC(C)(C)C)cc1)O3] | 783 |
| 169 | 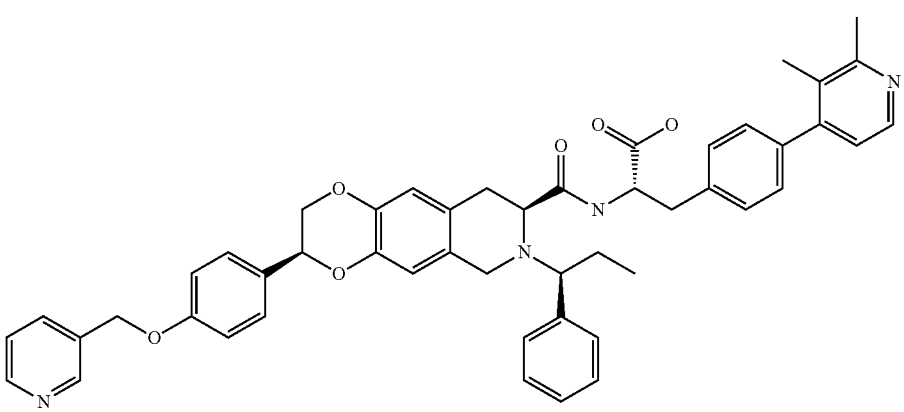 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OCc2cccnc2)cc1)O3] | 790 |

TABLE 1-continued

| Ex | Structure | LCMS (m/z) |
|---|---|---|
| 170 | 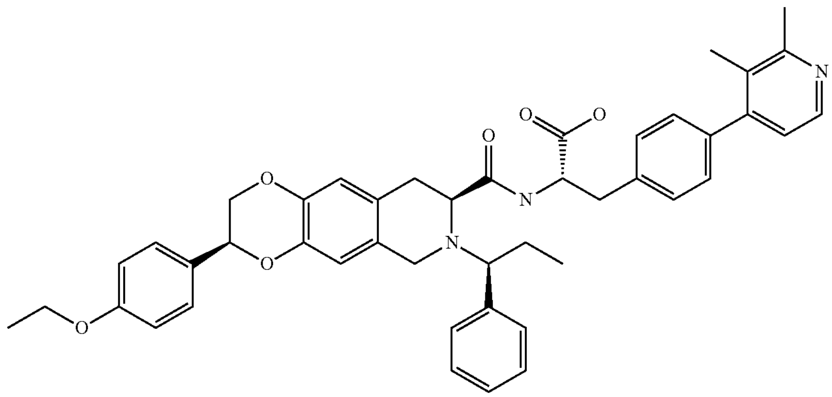 [SMILES: CCOc1ccc([C@H]2COc3cc4c(cc3O2)CN([C@@H](CC)c2ccccc2)[C@H](C(=O)N[C@@H](Cc2ccc(-c3ccnc(C)c3C)cc2)C(=O)O)C4)cc1] | 727 |
| 171 | 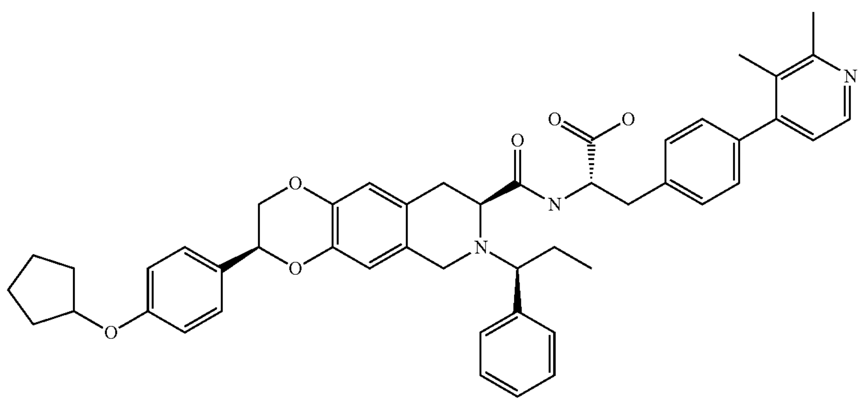 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OC2CCCC2)cc1)O3] | 767 |
| 172 | 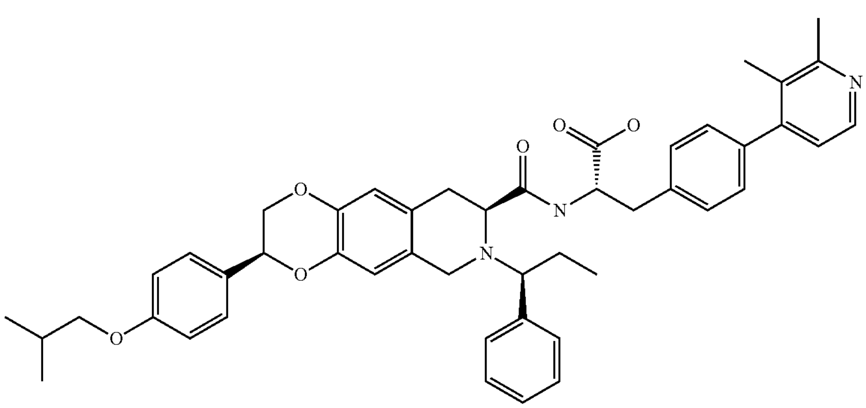 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OCC(C)C)cc1)O3] | 755 |

TABLE 1-continued

| Ex | Structure | LCMS (m/z) |
|---|---|---|
| 173 | 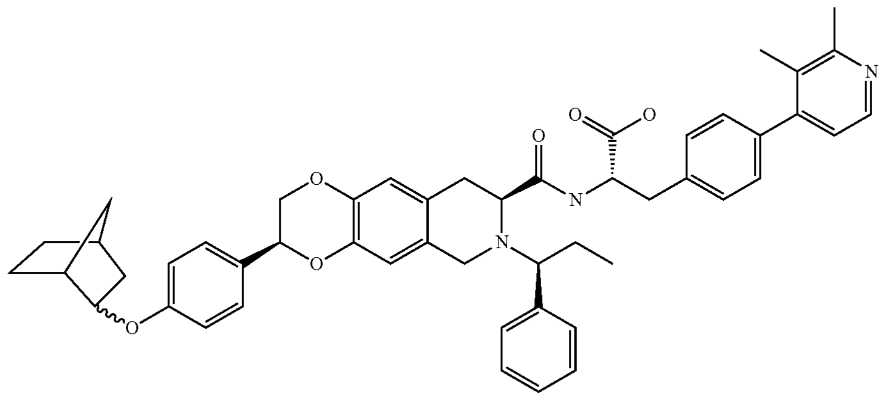 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(OC2CC4CCC2C4)cc1)O3] | 793 |
| 174 | 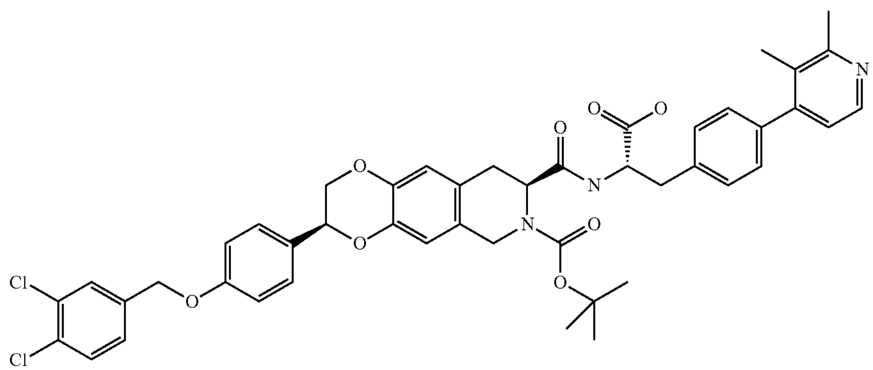 [SMILES: Cc1nccc(-c2ccc(C[C@H](NC(=O)[C@@H]3Cc4cc5c(cc4CN3C(=O)OC(C)(C)C)O[C@@H](c3ccc(OCc4ccc(Cl)c(Cl)c4)cc3)CO5)C(=O)O)cc2)c1C] | 839 |
| 175 | 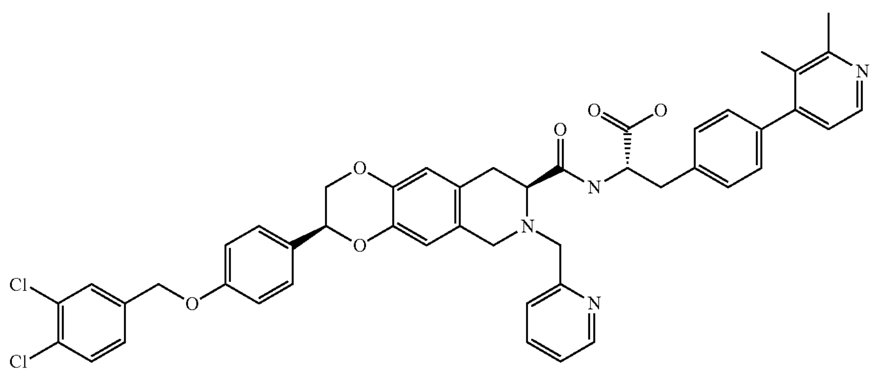 [SMILES: Cc1nccc(-c2ccc(C[C@H](NC(=O)[C@@H]3Cc4cc5c(cc4CN3Cc3ccccn3)O[C@@H](c3ccc(OCc4ccc(Cl)c(Cl)c4)cc3)CO5)C(=O)O)cc2)c1C] | 830 |
| 176 | 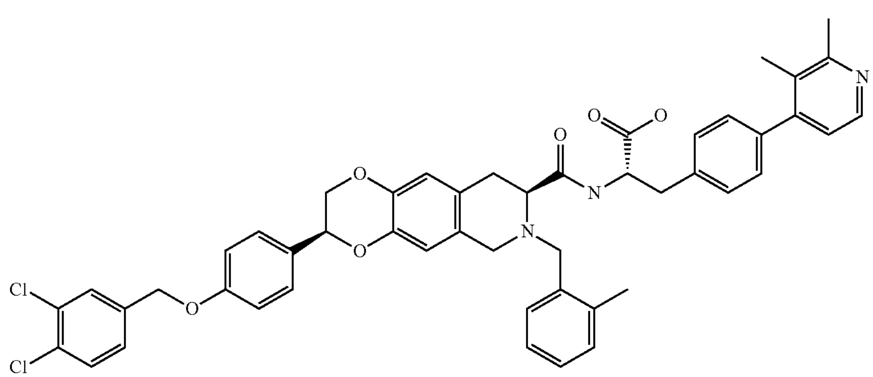 [SMILES: Cc1ccccc1CN1Cc2cc3c(cc2C[C@H]1C(=O)N[C@@H](Cc1ccc(-c2ccnc(C)c2C)cc1)C(=O)O)OC[C@H](c1ccc(OCc2ccc(Cl)c(Cl)c2)cc1)O3] | 843 |

TABLE 1-continued
| Ex | Structure | LCMS (m/z) |
|---|---|---|
| 177 | 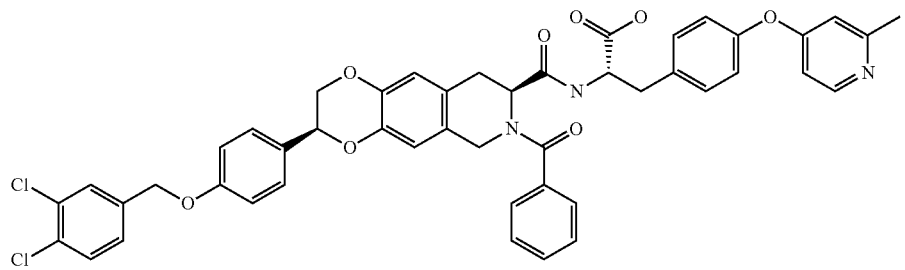 [SMILES: Cc1cc(Oc2ccc(C[C@H](NC(=O)[C@@H]3Cc4cc5c(cc4CN3C(=O)c3ccccc3)O[C@@H](c3ccc(OCc4ccc(Cl)c(Cl)c4)cc3)CO5)C(=O)O)cc2)ccn1] | 845 |
| 178 | 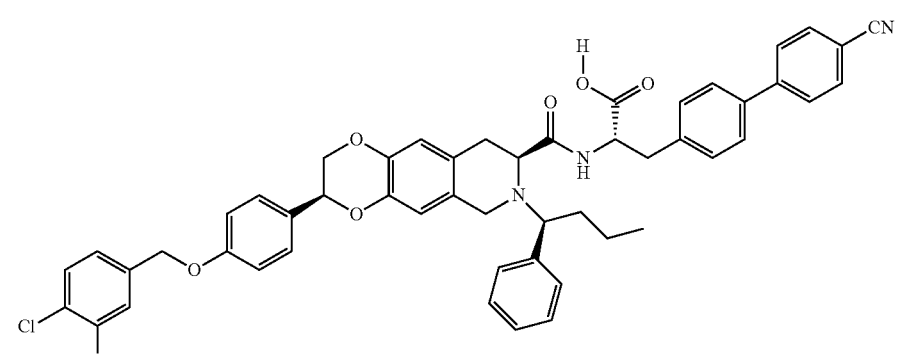 | 868 |
| 179 | 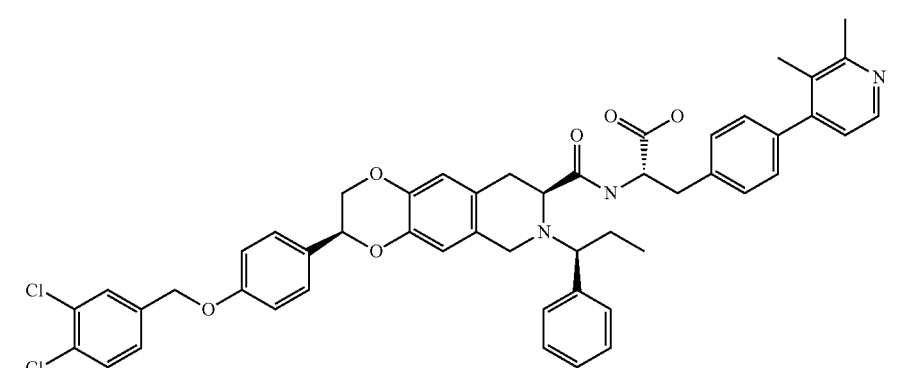 | 857 |
| 180 | 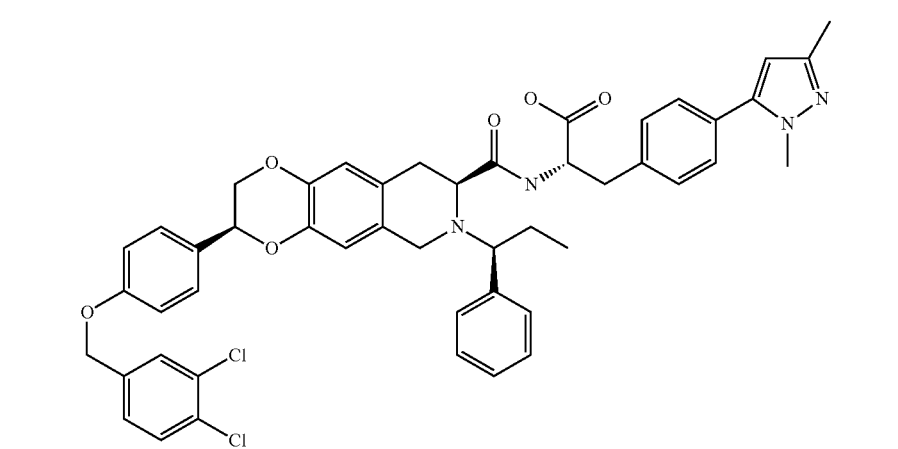 [SMILES: CC[C@@H](c1ccccc1)N1Cc2cc3c(cc2C[C@H]1C(=O)N[C@@H](Cc1ccc(-c2cc(C)nn2C)cc1)C(=O)O)OC[C@H](c1ccc(OCc2ccc(Cl)c(Cl)c2)cc1)O3] | 846 |

TABLE 1-continued

| Ex | Structure | LCMS (m/z) |
|---|---|---|
| 181 | 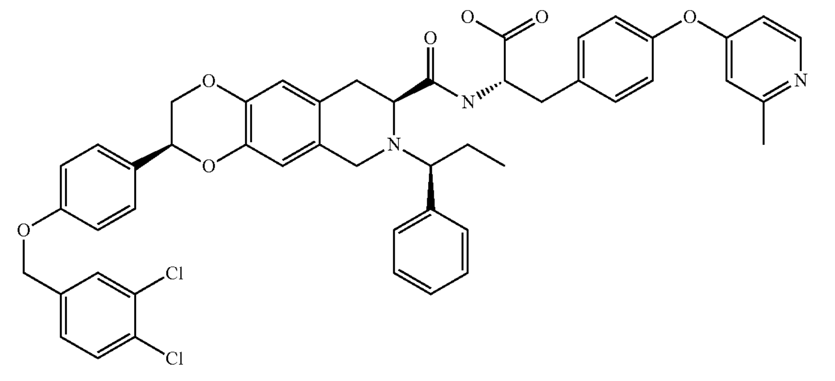 [SMILES: CC[C@@H](c1ccccc1)N1Cc2cc3c(cc2C[C@H]1C(=O)N[C@@H](Cc1ccc(Oc2ccnc(C)c2)cc1)C(=O)O)OC[C@H](c1ccc(OCc2ccc(Cl)c(Cl)c2)cc1)O3] | 859 |
| 182 | 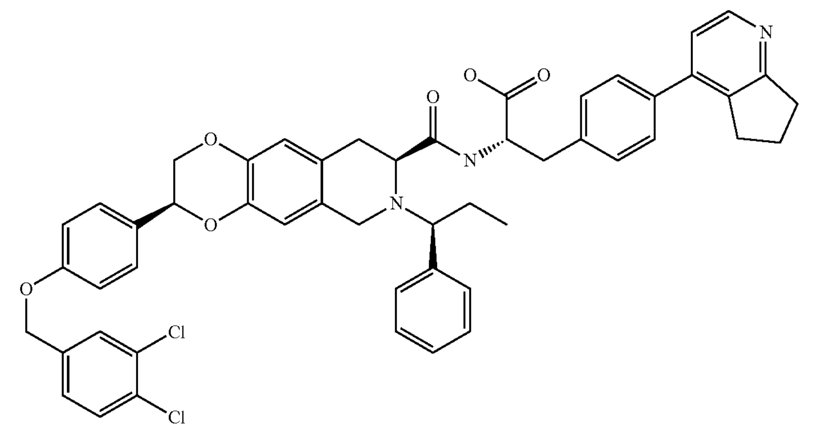 [SMILES: CC[C@@H](c1ccccc1)N1Cc2cc3c(cc2C[C@H]1C(=O)N[C@@H](Cc1ccc(-c2ccnc4c2CCC4)cc1)C(=O)O)OC[C@H](c1ccc(OCc2ccc(Cl)c(Cl)c2)cc1)O3] | 869 |
| 183 | 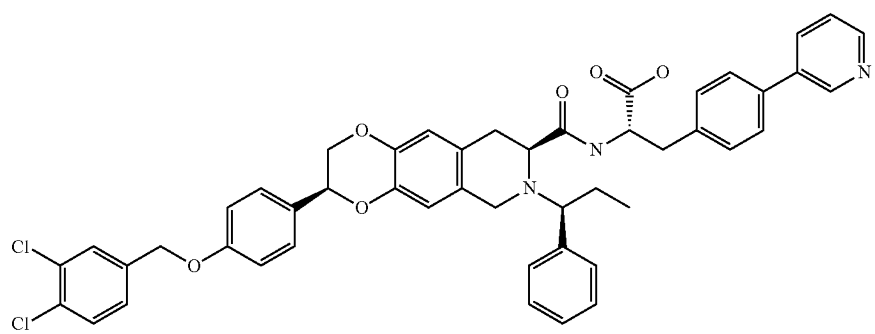 [SMILES: CC[C@@H](c1ccccc1)N1Cc2cc3c(cc2C[C@H]1C(=O)N[C@@H](Cc1ccc(-c2cccnc2)cc1)C(=O)O)OC[C@H](c1ccc(OCc2ccc(Cl)c(Cl)c2)cc1)O3] | 829 |
| 184 | 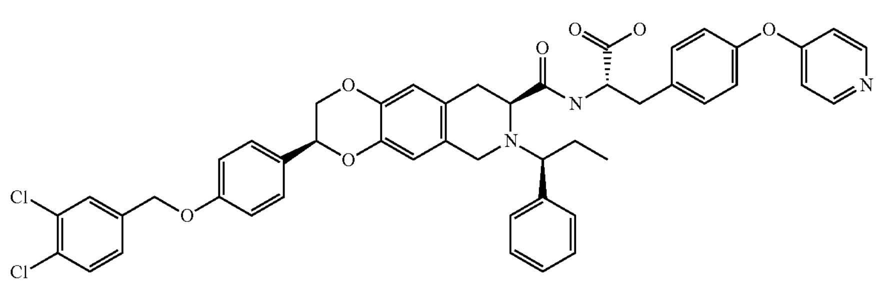 [SMILES: CC[C@@H](c1ccccc1)N1Cc2cc3c(cc2C[C@H]1C(=O)N[C@@H](Cc1ccc(Oc2ccncc2)cc1)C(=O)O)OC[C@H](c1ccc(OCc2ccc(Cl)c(Cl)c2)cc1)O3] | 845 |

TABLE 1-continued

| Ex | Structure | LCMS (m/z) |
|---|---|---|
| 185 | 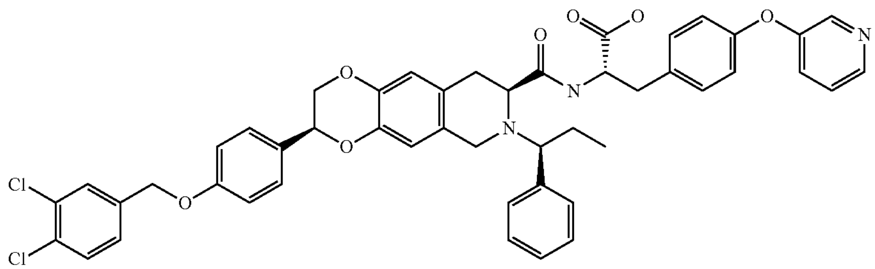 [SMILES: CC[C@@H](c1ccccc1)N1Cc2cc3c(cc2C[C@H]1C(=O)N[C@@H](Cc1ccc(Oc2cccnc2)cc1)C(=O)O)OC[C@H](c1ccc(OCc2ccc(Cl)c(Cl)c2)cc1)O3] | 845 |
| 186 | 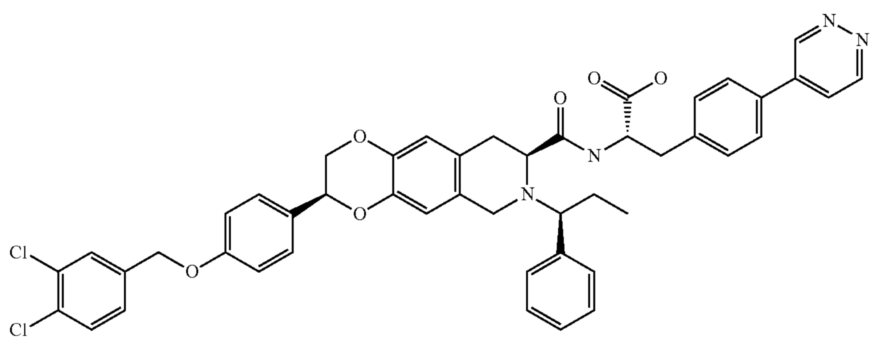 [SMILES: CC[C@@H](c1ccccc1)N1Cc2cc3c(cc2C[C@H]1C(=O)N[C@@H](Cc1ccc(-c2ccnnc2)cc1)C(=O)O)OC[C@H](c1ccc(OCc2ccc(Cl)c(Cl)c2)cc1)O3] | 830 |
| 187 | 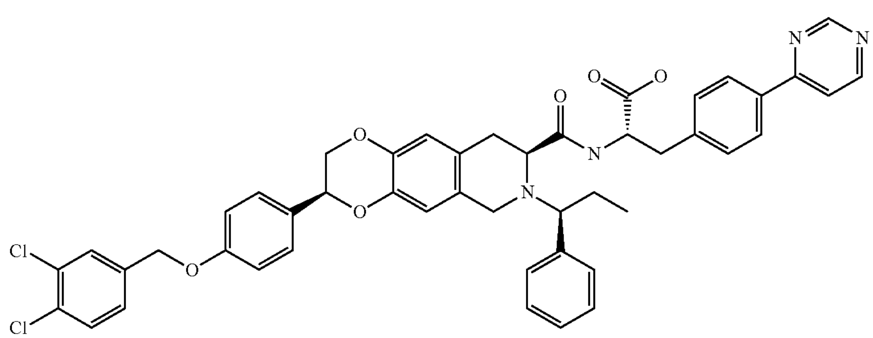 [SMILES: CC[C@@H](c1ccccc1)N1Cc2cc3c(cc2C[C@H]1C(=O)N[C@@H](Cc1ccc(-c2ccncn2)cc1)C(=O)O)OC[C@H](c1ccc(OCc2ccc(Cl)c(Cl)c2)cc1)O3] | 830 |
| 188 | 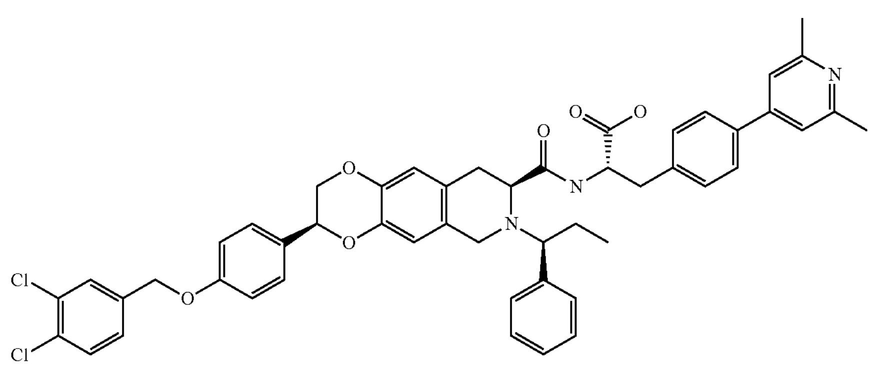 [SMILES: CC[C@@H](c1ccccc1)N1Cc2cc3c(cc2C[C@H]1C(=O)N[C@@H](Cc1ccc(-c2cc(C)nc(C)c2)cc1)C(=O)O)OC[C@H](c1ccc(OCc2ccc(Cl)c(Cl)c2)cc1)O3] | 857 |

TABLE 1-continued
| Ex | Structure | LCMS (m/z) |
|---|---|---|
| 189 | 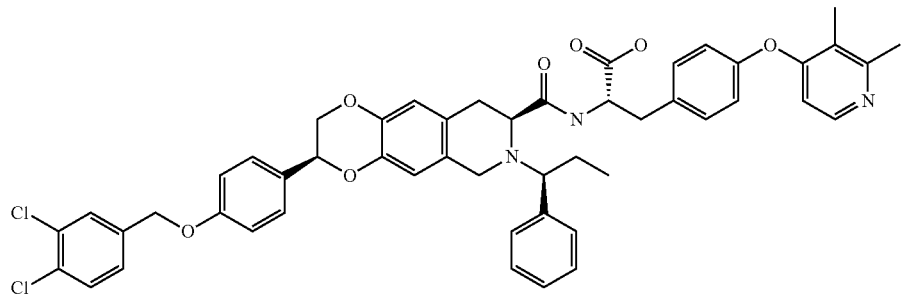 [SMILES: CC[C@@H](c1ccccc1)N1Cc2cc3c(cc2C[C@H]1C(=O)N[C@@H](Cc1ccc(Oc2ccnc(C)c2C)cc1)C(=O)O)OC[C@H](c1ccc(OCc2ccc(Cl)c(Cl)c2)cc1)O3] | 873 |
| 190 | 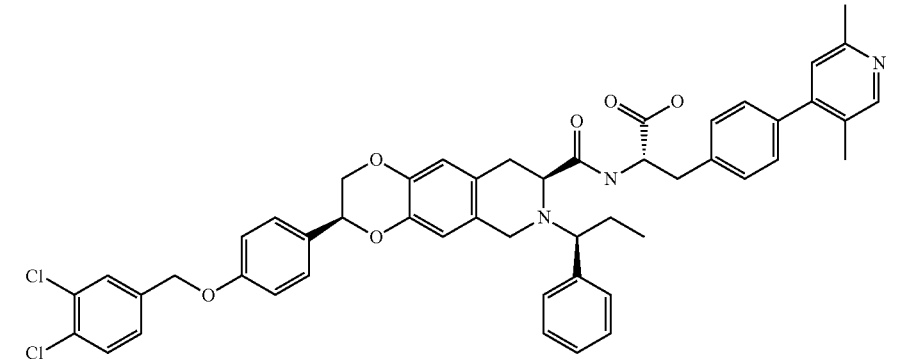 [SMILES: CC[C@@H](c1ccccc1)N1Cc2cc3c(cc2C[C@H]1C(=O)N[C@@H](Cc1ccc(-c2cc(C)ncc2C)cc1)C(=O)O)OC[C@H](c1ccc(OCc2ccc(Cl)c(Cl)c2)cc1)O3] | 857 |
| 191 | 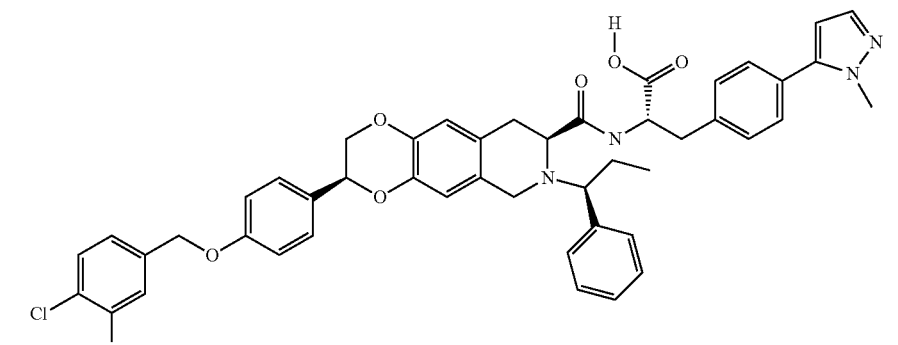 | 832 |
| 192 | 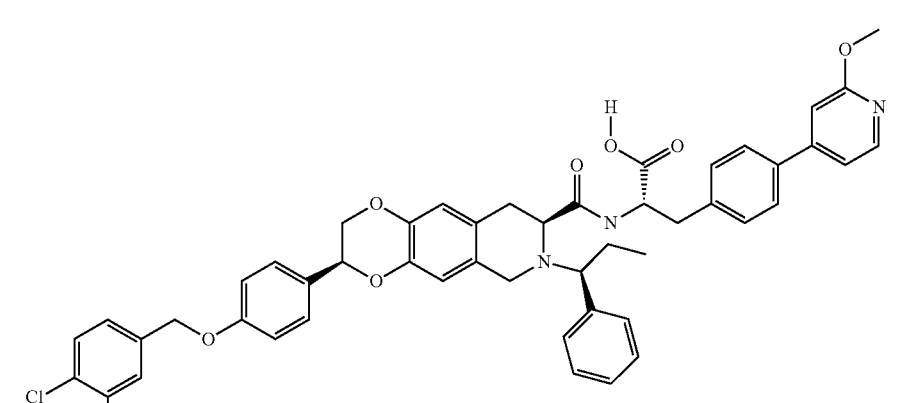 | 861 |

TABLE 1-continued

| Ex | Structure | LCMS (m/z) |
|---|---|---|
| 193 | 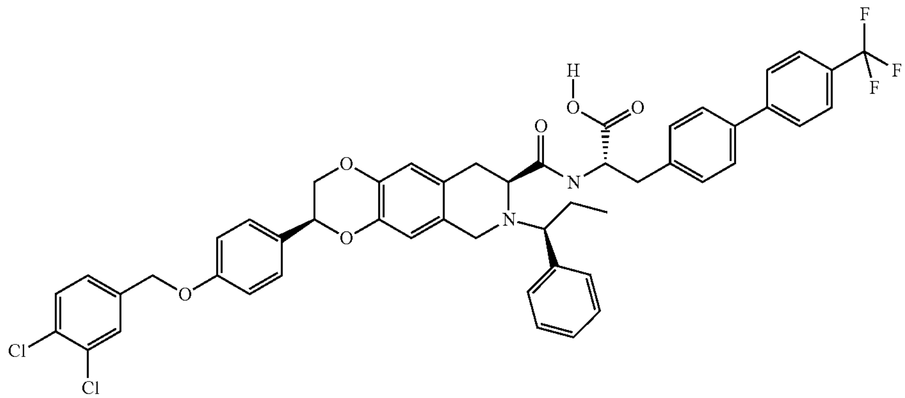 [SMILES: CC[C@@H](c1ccccc1)N1Cc2cc3c(cc2C[C@H]1C(=O)N[C@@H](Cc1ccc(-c2ccc(C(F)(F)F)cc2)cc1)C(=O)O)OC[C@H](c1ccc(OCc2ccc(Cl)c(Cl)c2)cc1)O3] | 896 |
| 194 | 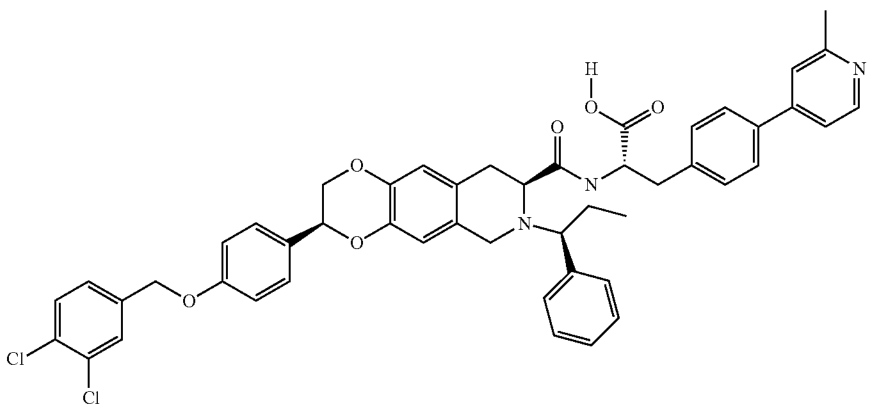 [SMILES: CC[C@@H](c1ccccc1)N1Cc2cc3c(cc2C[C@H]1C(=O)N[C@@H](Cc1ccc(-c2ccnc(C)c2)cc1)C(=O)O)OC[C@H](c1ccc(OCc2ccc(Cl)c(Cl)c2)cc1)O3] | 845 |
| 195 | 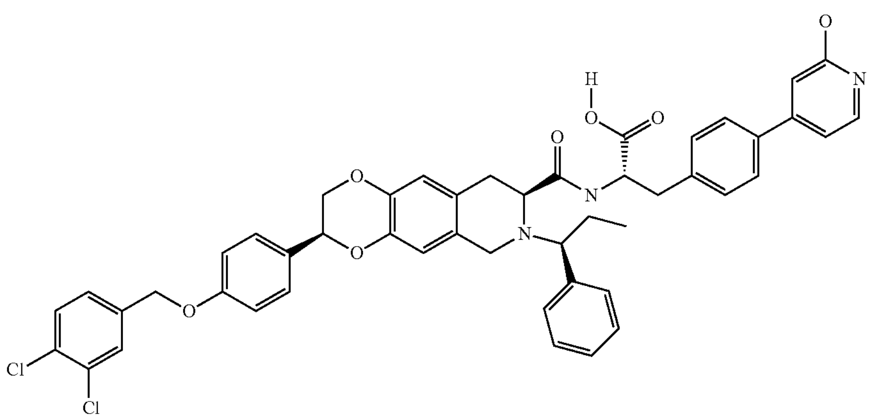 [SMILES: CC[C@@H](c1ccccc1)N1Cc2cc3c(cc2C[C@H]1C(=O)N[C@@H](Cc1ccc(-c2ccnc(O)c2)cc1)C(=O)O)OC[C@H](c1ccc(OCc2ccc(Cl)c(Cl)c2)cc1)O3] | 845 |
| 196 | 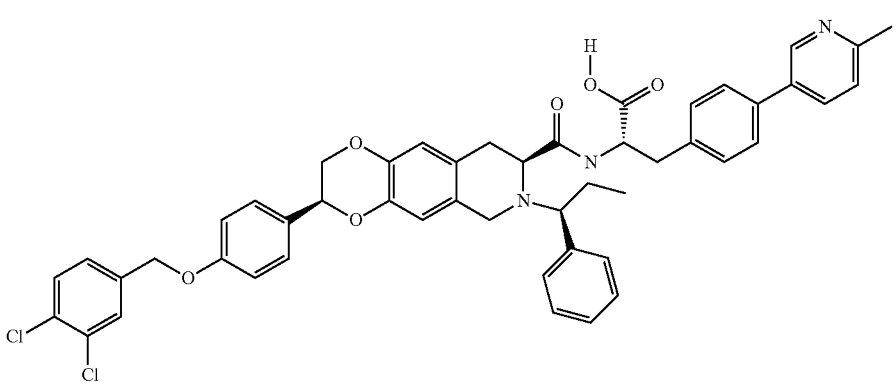 [SMILES: CC[C@@H](c1ccccc1)N1Cc2cc3c(cc2C[C@H]1C(=O)N[C@@H](Cc1ccc(-c2ccc(C)nc2)cc1)C(=O)O)OC[C@H](c1ccc(OCc2ccc(Cl)c(Cl)c2)cc1)O3] | 843 |

TABLE 1-continued

| Ex | Structure | LCMS (m/z) |
|---|---|---|
| 197 | 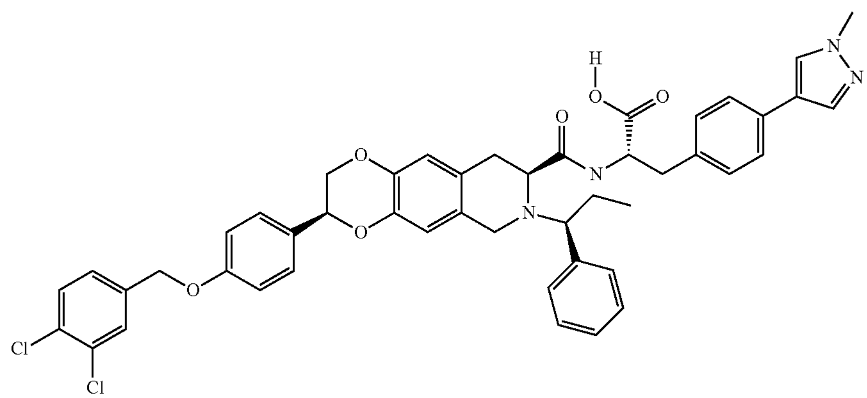 [SMILES: CC[C@@H](c1ccccc1)N1Cc2cc3c(cc2C[C@H]1C(=O)N[C@@H](Cc1ccc(-c2cnn(C)c2)cc1)C(=O)O)OC[C@H](c1ccc(OCc2ccc(Cl)c(Cl)c2)cc1)O3] | 832 |
| 198 | 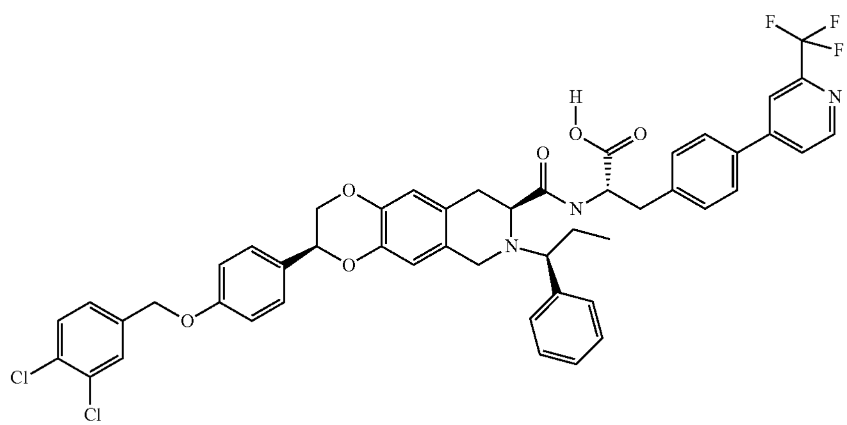 [SMILES: CC[C@@H](c1ccccc1)N1Cc2cc3c(cc2C[C@H]1C(=O)N[C@@H](Cc1ccc(-c2ccnc(C(F)(F)F)c2)cc1)C(=O)O)OC[C@H](c1ccc(OCc2ccc(Cl)c(Cl)c2)cc1)O3] | 897 |
| 199 | 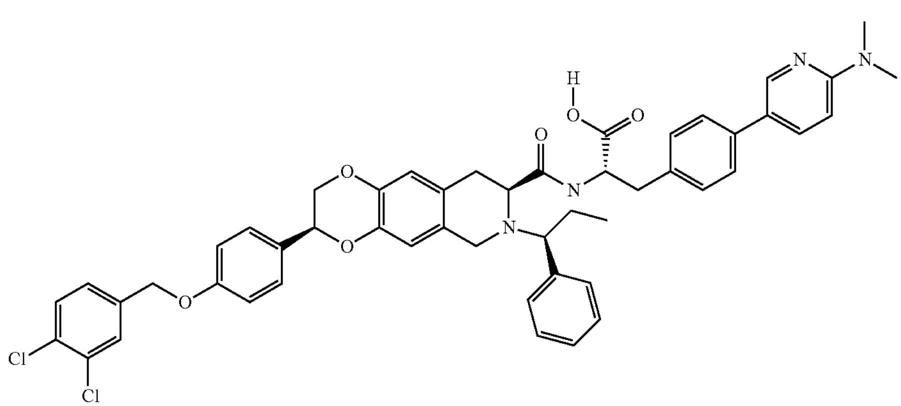 [SMILES: CC[C@@H](c1ccccc1)N1Cc2cc3c(cc2C[C@H]1C(=O)N[C@@H](Cc1ccc(-c2ccc(N(C)C)nc2)cc1)C(=O)O)OC[C@H](c1ccc(OCc2ccc(Cl)c(Cl)c2)cc1)O3] | 872 |

TABLE 1-continued
| Ex | Structure | LCMS (m/z) |
|---|---|---|
| 200 | 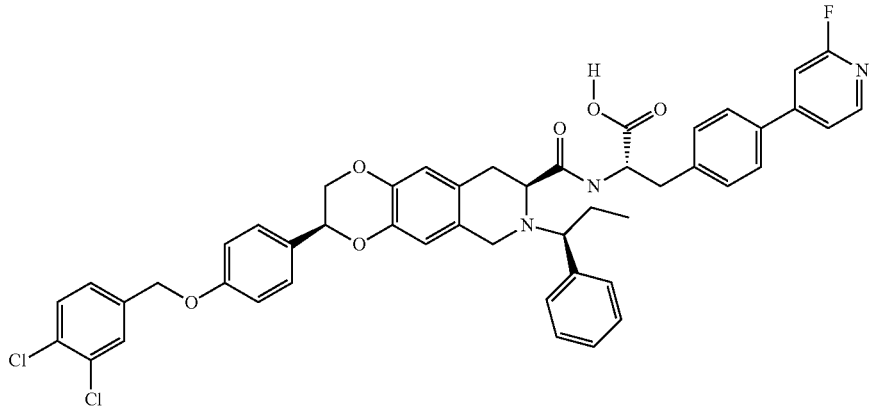 [SMILES: CC[C@@H](c1ccccc1)N1Cc2cc3c(cc2C[C@H]1C(=O)N[C@@H](Cc1ccc(-c2ccnc(F)c2)cc1)C(=O)O)OC[C@H](c1ccc(OCc2ccc(Cl)c(Cl)c2)cc1)O3] | 849 |
| 201 | 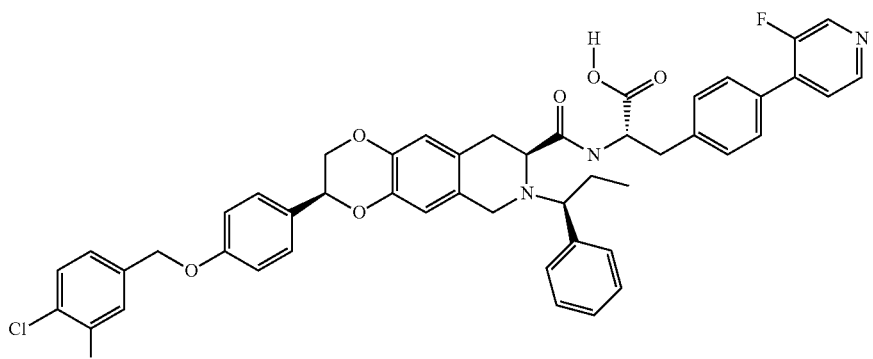 | 848 |
| 202 | 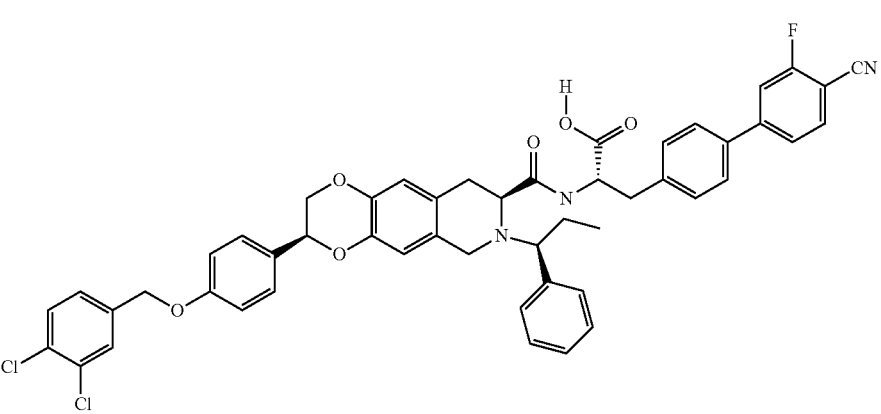 [SMILES: CC[C@@H](c1ccccc1)N1Cc2cc3c(cc2C[C@H]1C(=O)N[C@@H](Cc1ccc(-c2ccc(C#N)c(F)c2)cc1)C(=O)O)OC[C@H](c1ccc(OCc2ccc(Cl)c(Cl)c2)cc1)O3] | 874 |
| 203 | 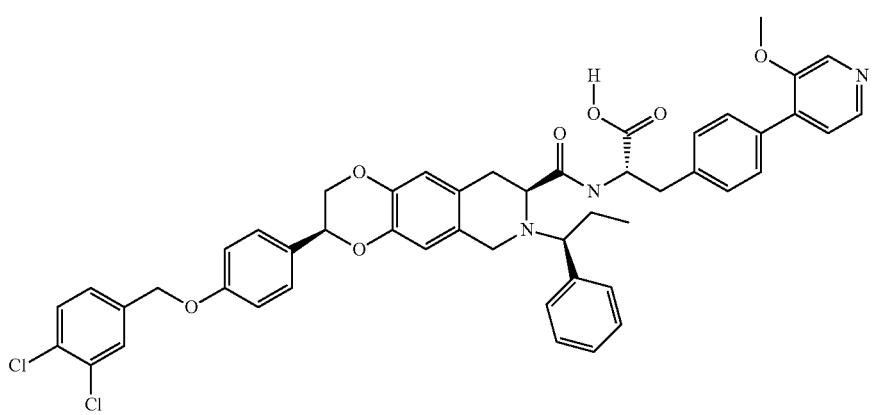 [SMILES: CC[C@@H](c1ccccc1)N1Cc2cc3c(cc2C[C@H]1C(=O)N[C@@H](Cc1ccc(-c2ccncc2OC)cc1)C(=O)O)OC[C@H](c1ccc(OCc2ccc(Cl)c(Cl)c2)cc1)O3] | 859 |

TABLE 1-continued
| Ex | Structure | LCMS (m/z) |
|---|---|---|
| 204 | 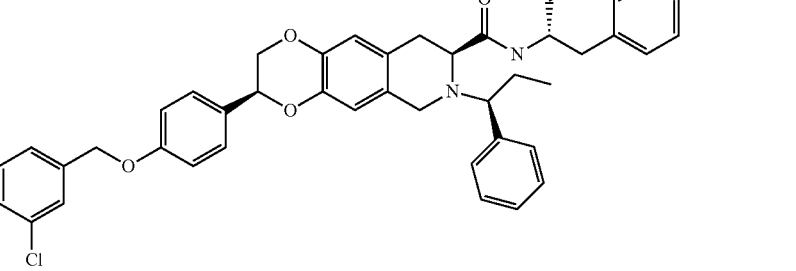 | 856 |
| 205 | 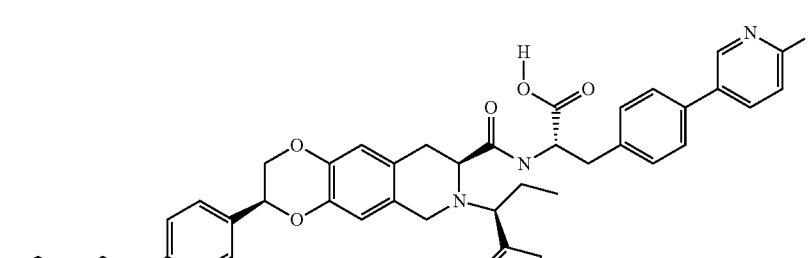 | 844 |
| 206 | 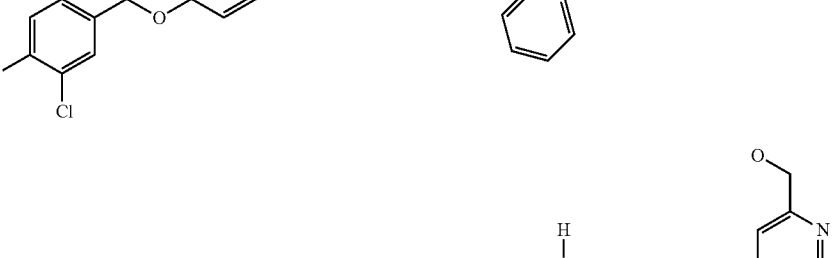 | 859 |
| 207 | 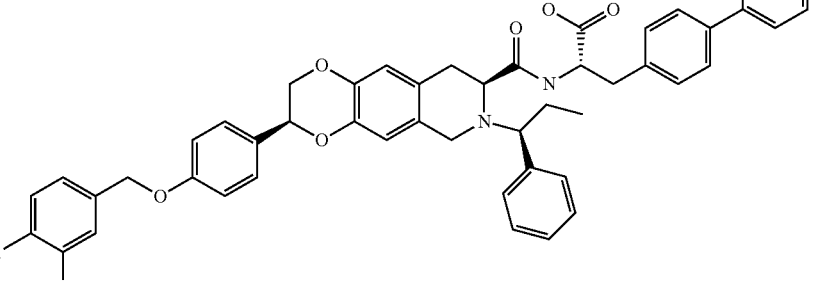 | 859 |

TABLE 1-continued

| Ex | Structure | LCMS (m/z) |
|---|---|---|
| 208 | 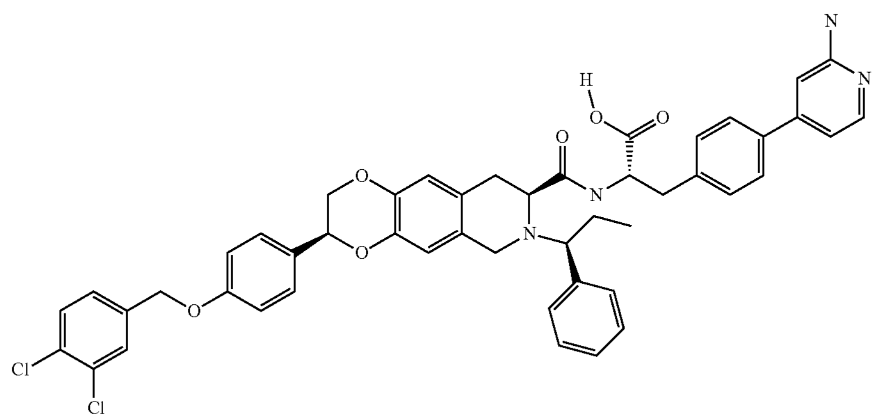 [SMILES: CC[C@@H](c1ccccc1)N1Cc2cc3c(cc2C[C@H]1C(=O)N[C@@H](Cc1ccc(-c2ccnc(N)c2)cc1)C(=O)O)OC[C@H](c1ccc(OCc2ccc(Cl)c(Cl)c2)cc1)O3] | 844 |
| 209 | 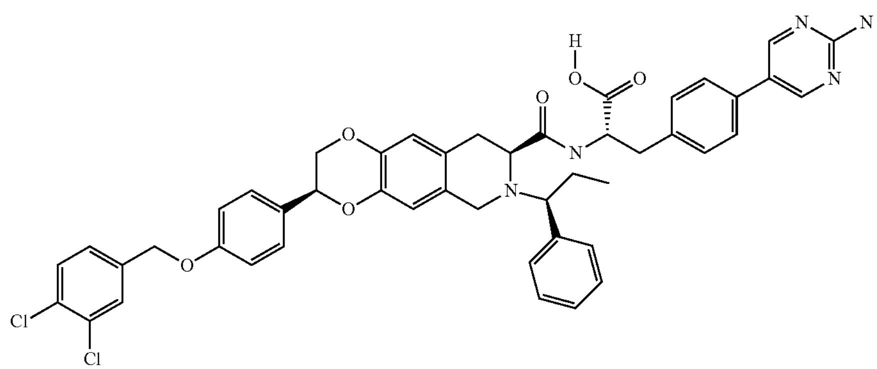 [SMILES: CC[C@@H](c1ccccc1)N1Cc2cc3c(cc2C[C@H]1C(=O)N[C@@H](Cc1ccc(-c2cnc(N)nc2)cc1)C(=O)O)OC[C@H](c1ccc(OCc2ccc(Cl)c(Cl)c2)cc1)O3] | 847 |
| 210 | 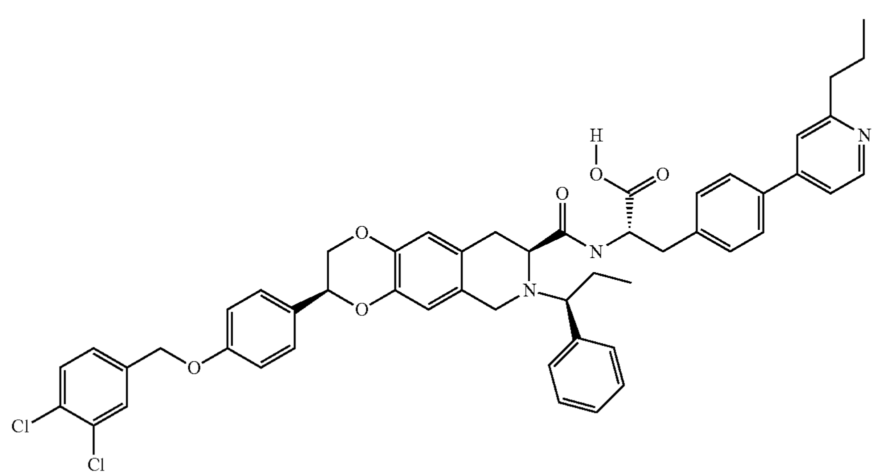 [SMILES: CCCc1cc(-c2ccc(C[C@H](NC(=O)[C@@H]3Cc4cc5c(cc4CN3[C@@H](CC)c3ccccc3)O[C@@H](c3ccc(OCc4ccc(Cl)c(Cl)c4)cc3)CO5)C(=O)O)cc2)ccn1] | 873 |

TABLE 1-continued
| Ex | Structure | LCMS (m/z) |
|---|---|---|
| 211 | 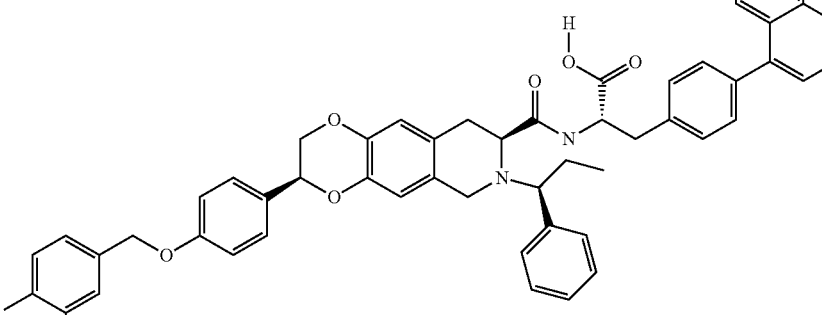 | 879 |
| 212 | 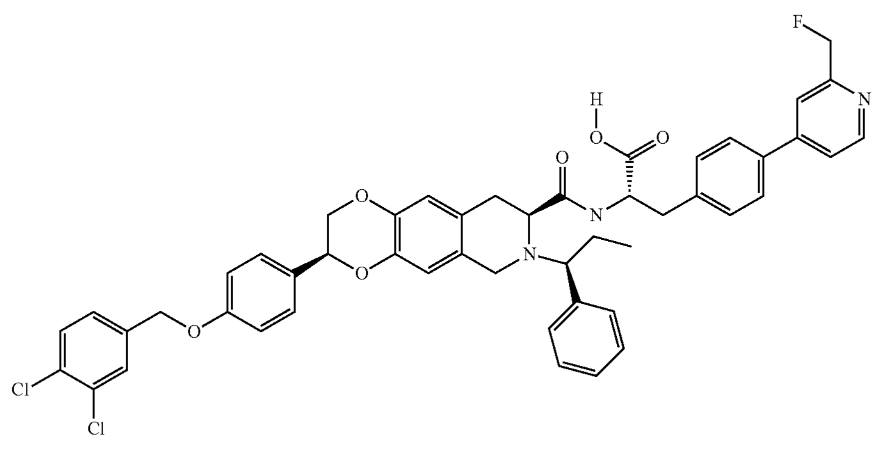 | 861 |
| 213 | 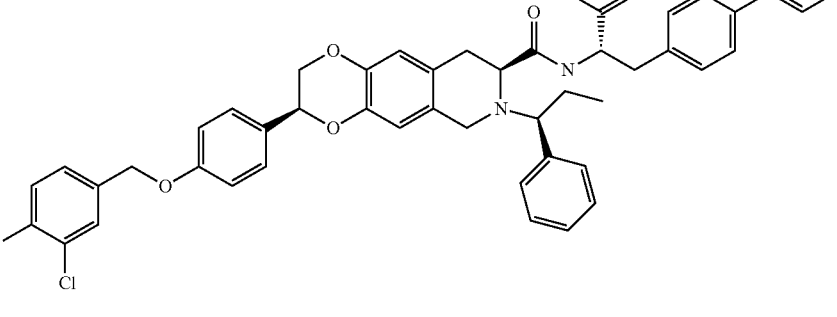 | 823 |

TABLE 1-continued

| Ex | Structure | LCMS (m/z) |
|---|---|---|
| 214 | 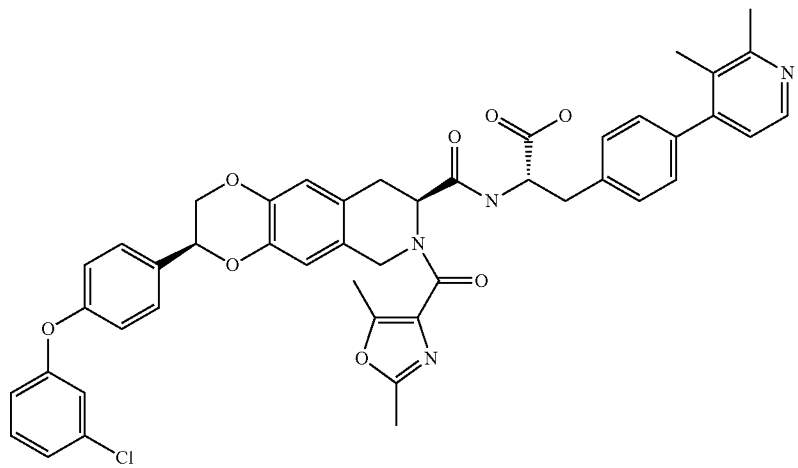 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(Oc3cccc(Cl)c3)cc2)O4)c(C)o1] | 814 |
| 215 | 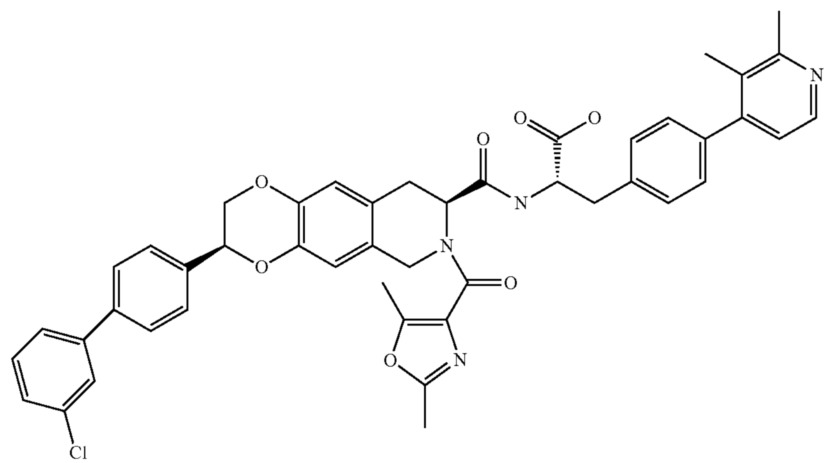 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(-c3cccc(Cl)c3)cc2)O4)c(C)o1] | 798 |
| 216 | 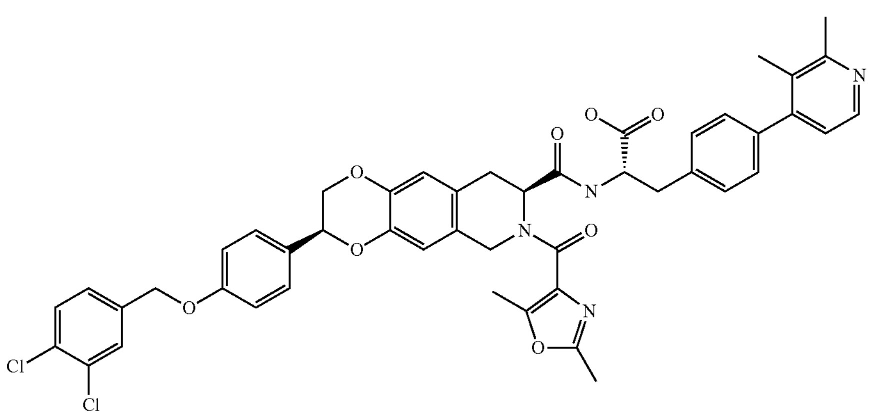 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)c(C)o1] | 862 |

TABLE 1-continued

| Ex | Structure | LCMS (m/z) |
|---|---|---|
| 217 | 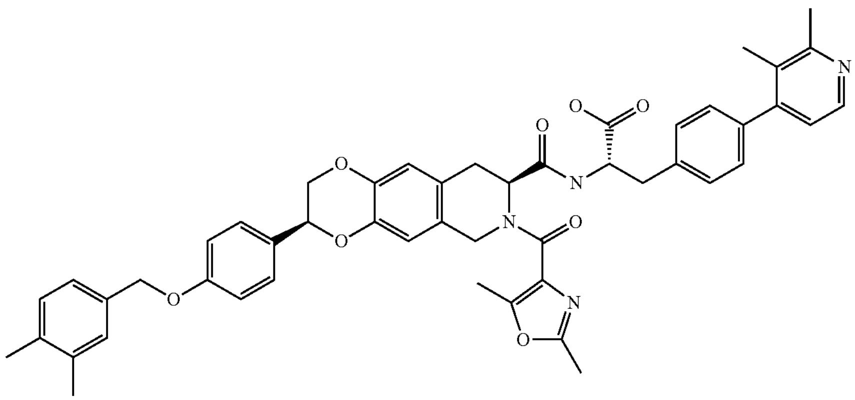 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(C)c(C)c3)cc2)O4)c(C)o1] | 822 |
| 218 | 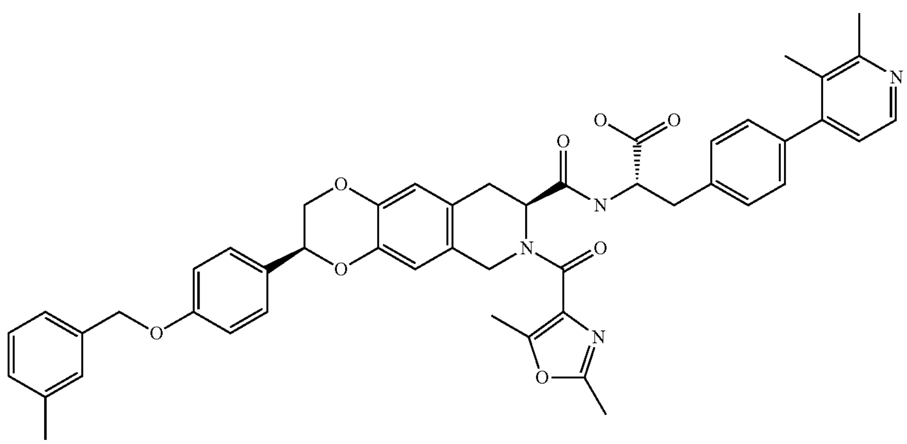 [SMILES: Cc1cccc(COc2ccc([C@H]3COc4cc5c(cc4O3)CN(C(=O)c3nc(C)oc3C)[C@H](C(=O)N[C@@H](Cc3ccc(-c4ccnc(C)c4C)cc3)C(=O)O)C5)cc2)c1] | 808 |
| 219 | 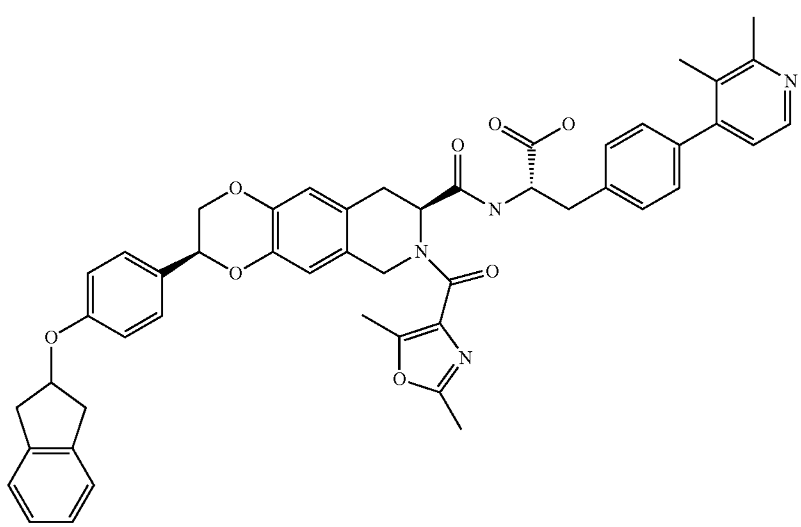 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OC3Cc5ccccc5C3)cc2)O4)c(C)o1] | 820 |

TABLE 1-continued

| Ex | Structure | LCMS (m/z) |
|---|---|---|
| 220 | 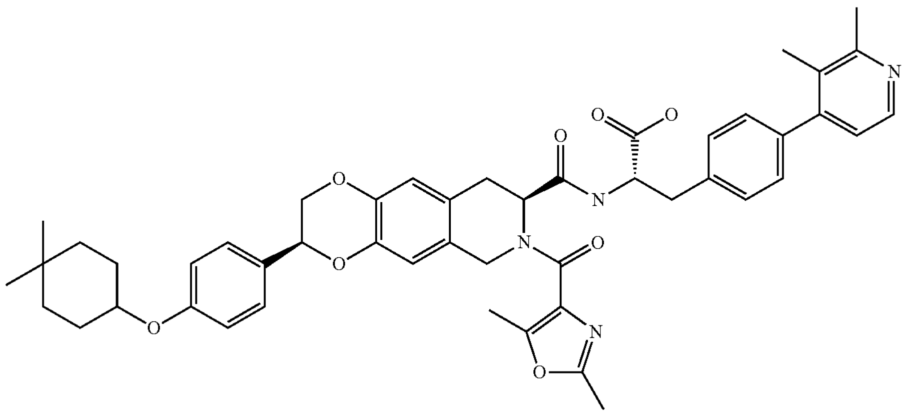 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OC3CCC(C)(C)CC3)cc2)O4)c(C)o1] | 814 |
| 221 | 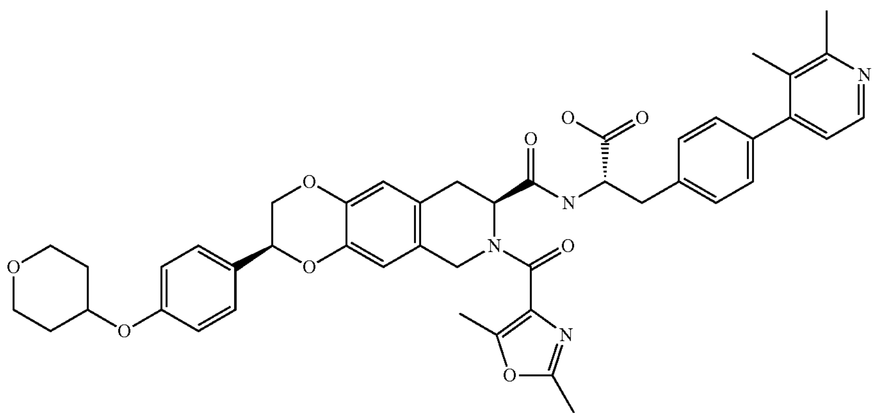 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OC3CCOCC3)cc2)O4)c(C)o1] | 788 |
| 222 | 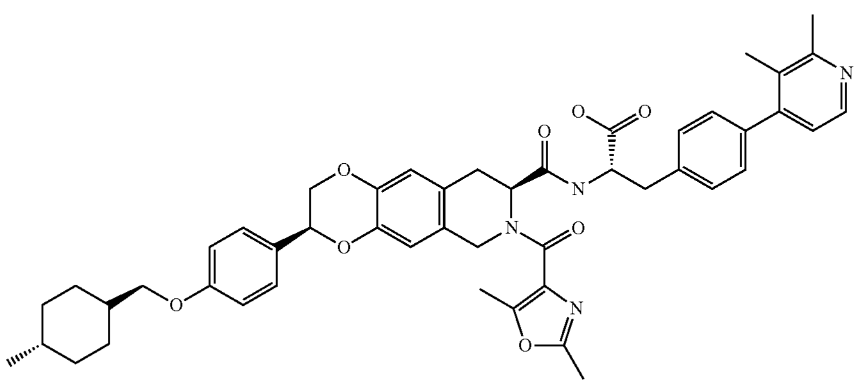 | 814 |
| 223 | 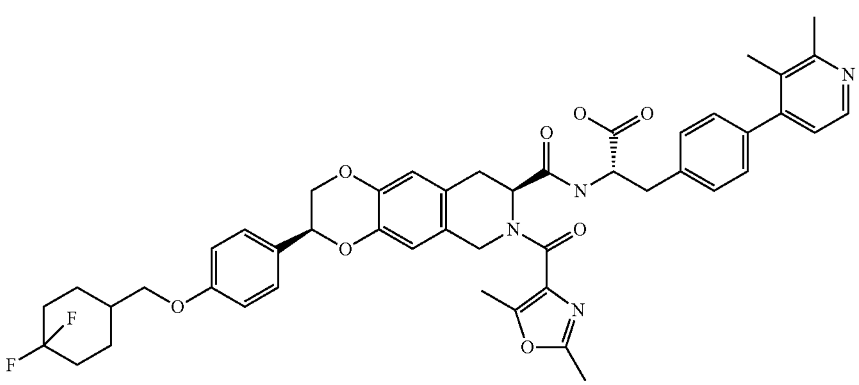 | 836 |

TABLE 1-continued

| Ex | Structure | LCMS (m/z) |
|----|-----------|------------|
| 224 | 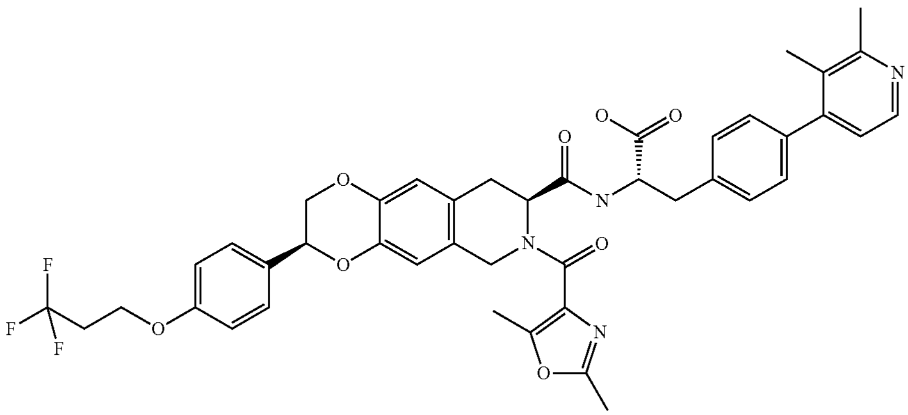 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCCC(F)(F)F)cc2)O4)c(C)o1] | 800 |
| 225 | 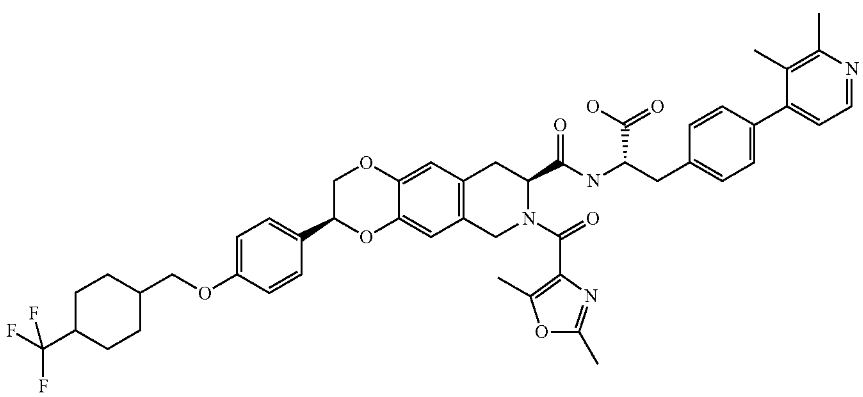 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCC3CCC(C(F)(F)F)CC3)cc2)O4)c(C)o1] | 868 |
| 226 | 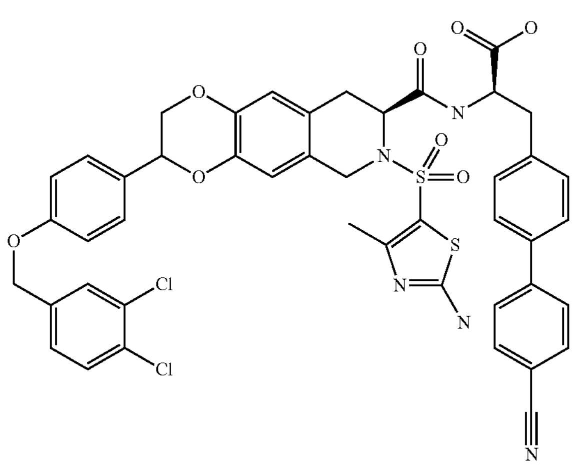 [SMILES: Cc1nc(N)sc1S(=O)(=O)N1Cc2cc3c(cc2C[C@H]1C(=O)N[C@H](Cc1ccc(-c2ccc(C#N)cc2)cc1)C(=O)O)OCC(c1ccc(OCc2ccc(Cl)c(Cl)c2)cc1)O3] | 910 |

TABLE 1-continued

| Ex | Structure | LCMS (m/z) |
|---|---|---|
| 227 | 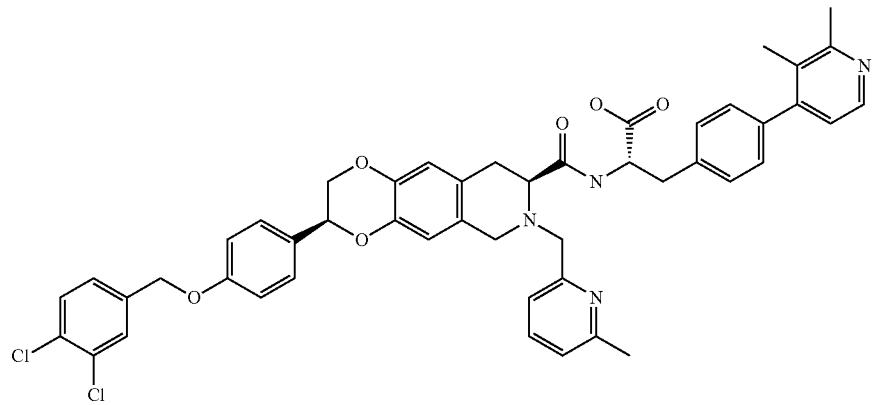 [SMILES: Cc1cccc(CN2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)n1] | 845 |
| 228 | 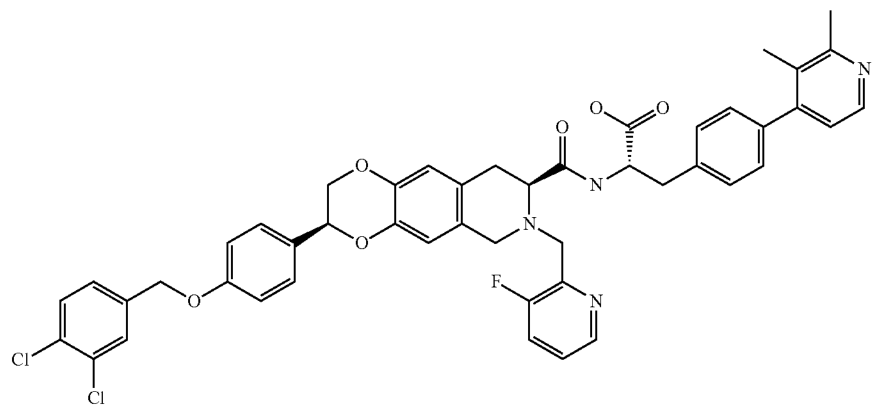 [SMILES: Cc1nccc(-c2ccc(C[C@H](NC(=O)[C@@H]3Cc4cc5c(cc4CN3Cc3ncccc3F)O[C@@H](c3ccc(OCc4ccc(Cl)c(Cl)c4)cc3)CO5)C(=O)O)cc2)c1C] | 848 |
| 229 | 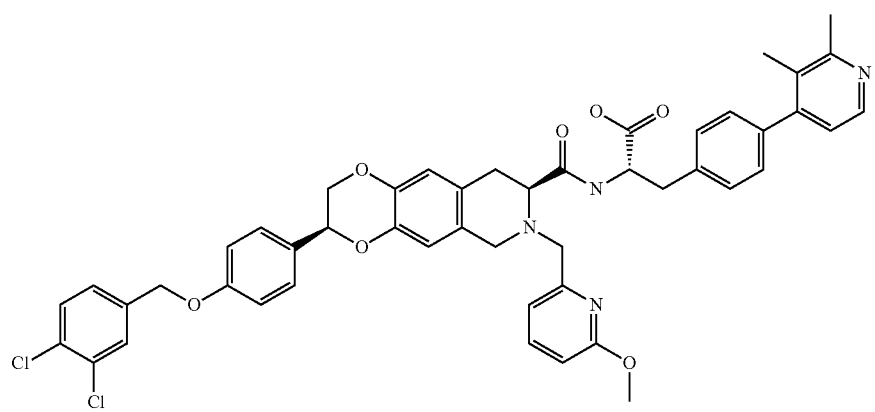 [SMILES: COc1cccc(CN2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)n1] | 860 |

TABLE 1-continued
| Ex | Structure | LCMS (m/z) |
|---|---|---|
| 230 | 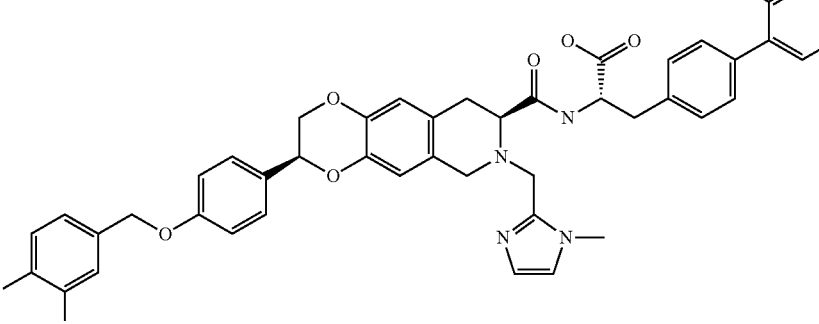 | 833 |
| 231 | 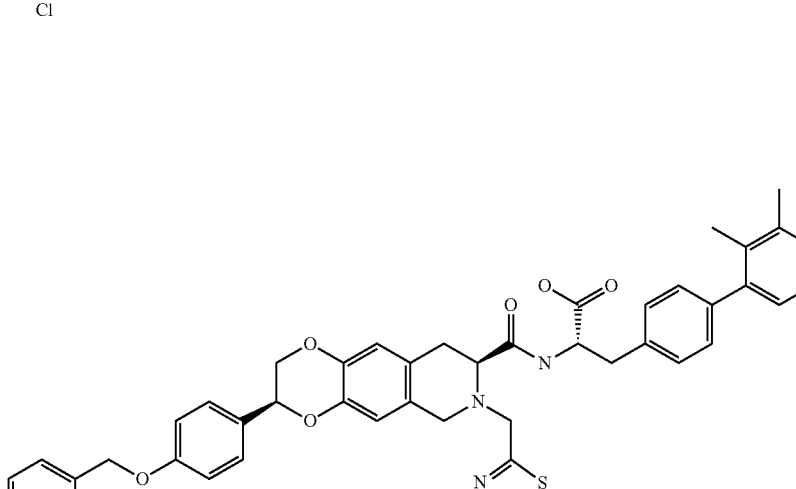 | 836 |
| 232 | 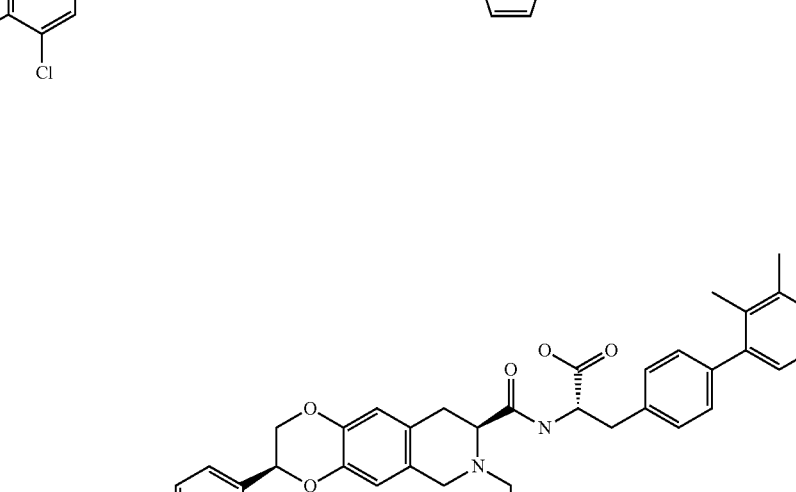 | 848 |

TABLE 1-continued

| Ex | Structure | LCMS (m/z) |
|---|---|---|
| 233 | 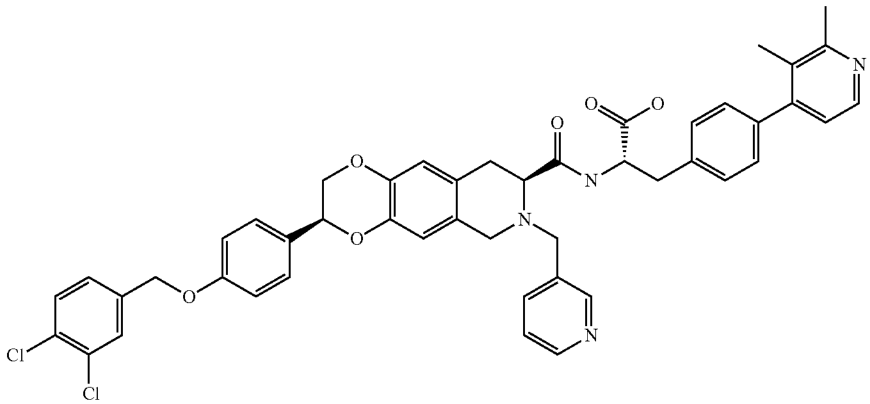 [SMILES: Cc1nccc(-c2ccc(C[C@H](NC(=O)[C@@H]3Cc4cc5c(cc4CN3Cc3cccnc3)O[C@@H](c3ccc(OCc4ccc(Cl)c(Cl)c4)cc3)CO5)C(=O)O)cc2)c1C] | 830 |
| 234 | 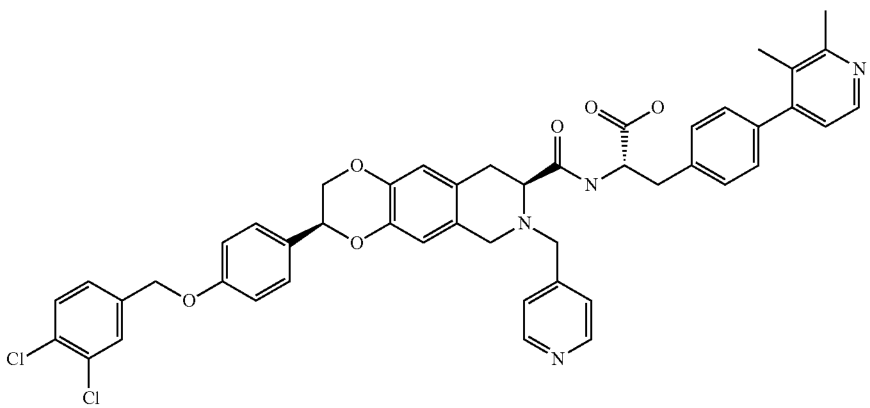 [SMILES: Cc1nccc(-c2ccc(C[C@H](NC(=O)[C@@H]3Cc4cc5c(cc4CN3Cc3ccncc3)O[C@@H](c3ccc(OCc4ccc(Cl)c(Cl)c4)cc3)CO5)C(=O)O)cc2)c1C] | 832 |
| 235 | 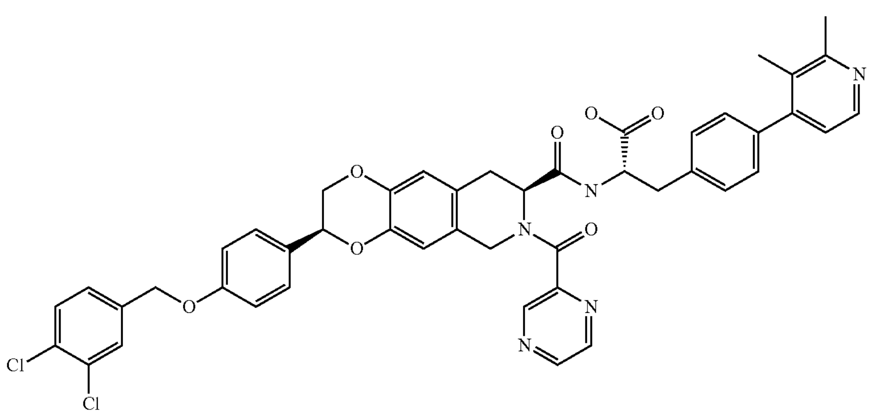 [SMILES: Cc1nccc(-c2ccc(C[C@H](NC(=O)[C@@H]3Cc4cc5c(cc4CN3C(=O)c3cnccn3)O[C@@H](c3ccc(OCc4ccc(Cl)c(Cl)c4)cc3)CO5)C(=O)O)cc2)c1C] | 847 |

TABLE 1-continued
| Ex | Structure | LCMS (m/z) |
|---|---|---|
| 236 | 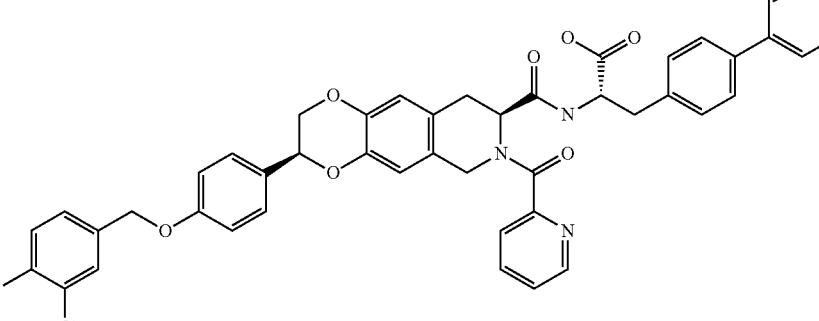 | 844 |
| 237 | 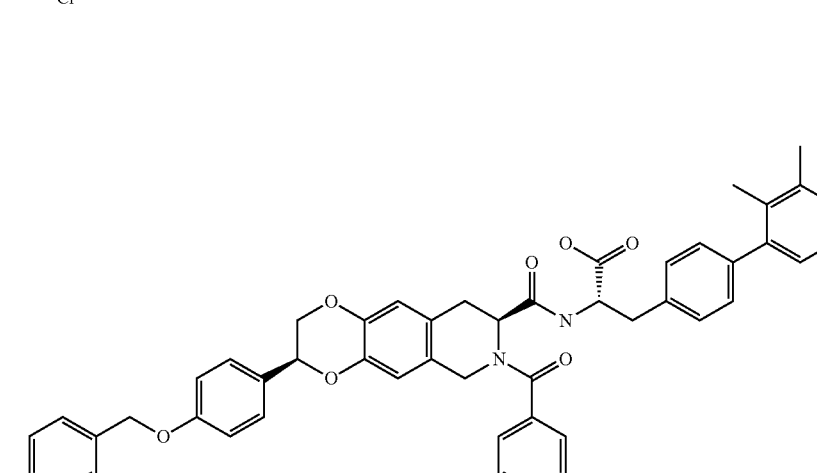 | 879 |
| 238 | 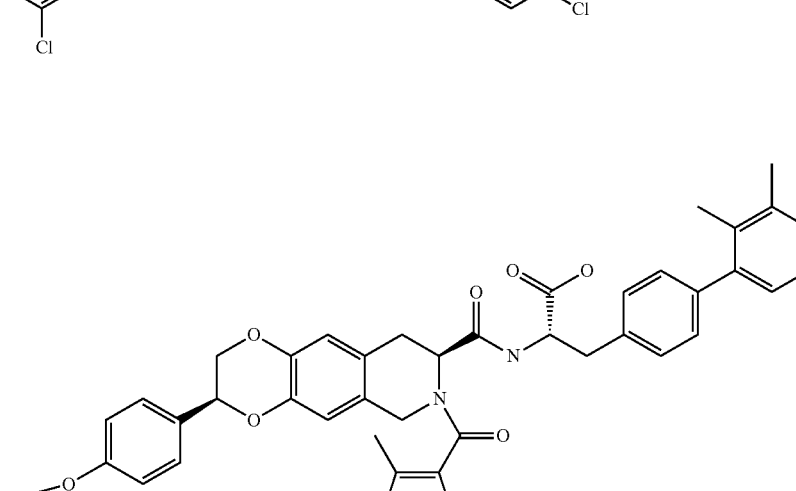 | 848. |

TABLE 1-continued
| Ex | Structure | LCMS (m/z) |
|---|---|---|
| 239 | 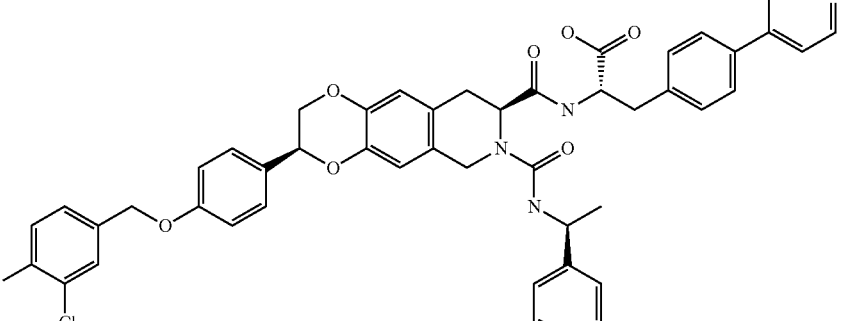 | 886 |
| 240 | 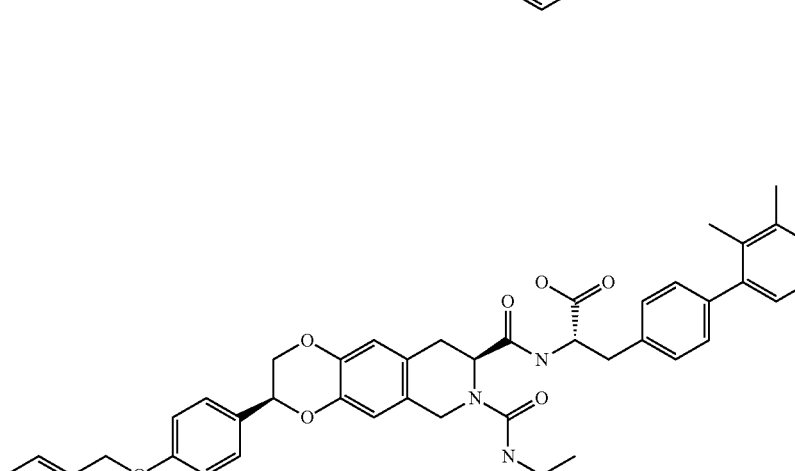 | 886 |
| 241 | 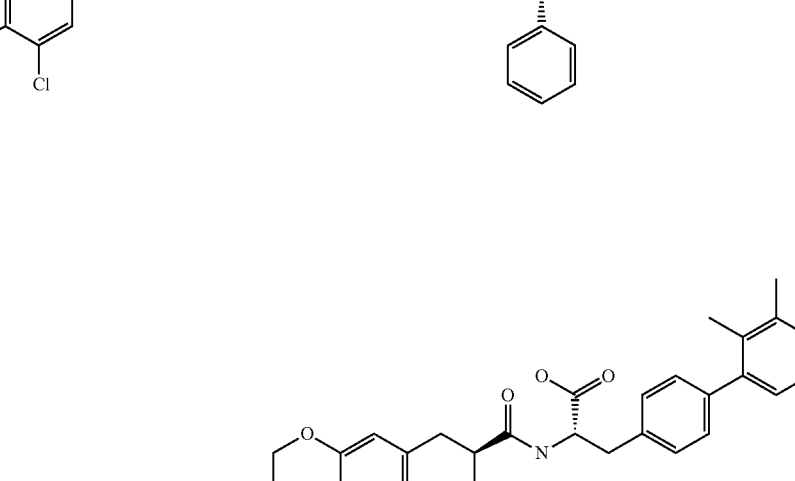 | 876 |

TABLE 1-continued

| Ex | Structure | LCMS (m/z) |
|---|---|---|
| 242 | 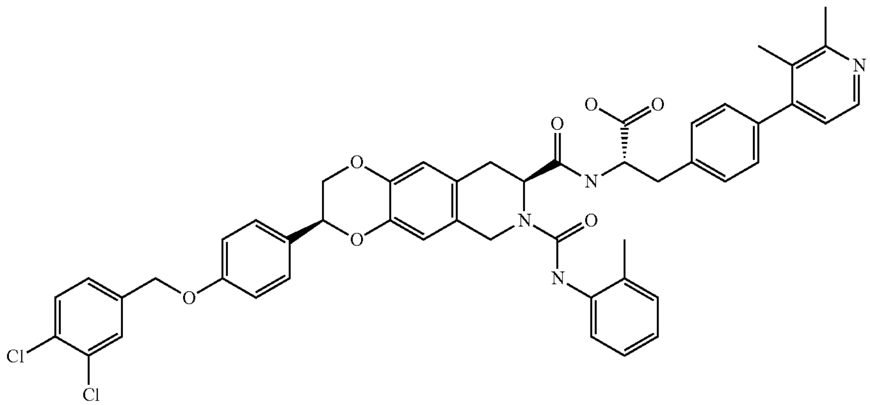 [SMILES: Cc1ccccc1NC(=O)N1Cc2cc3c(cc2C[C@H]1C(=O)N[C@@H](Cc1ccc(-c2ccnc(C)c2C)cc1)C(=O)O)OC[C@H](c1ccc(OCc2ccc(Cl)c(Cl)c2)cc1)O3] | 872 |
| 243 | 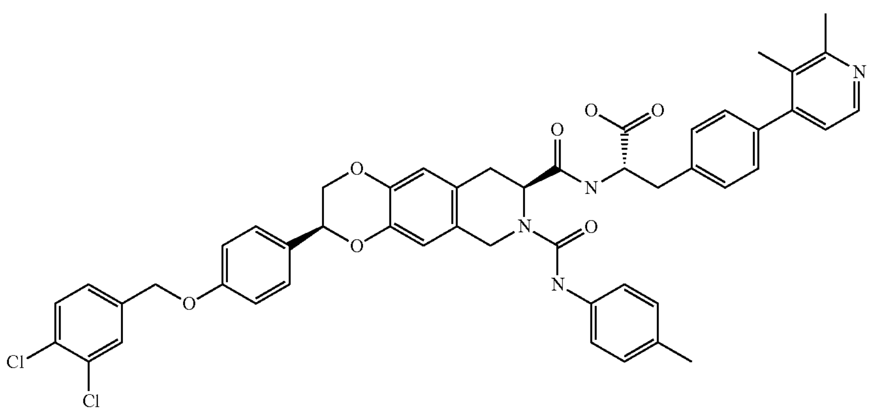 [SMILES: Cc1ccc(NC(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)cc1] | 872 |
| 244 | 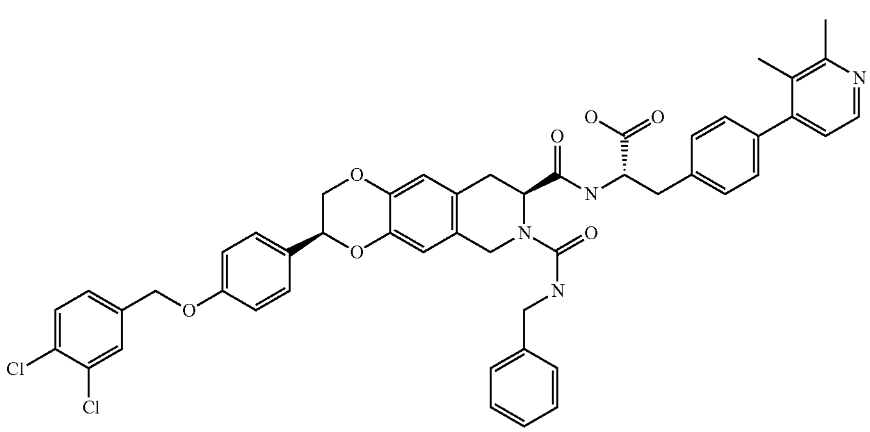 [SMILES: Cc1nccc(-c2ccc(C[C@H](NC(=O)[C@@H]3Cc4cc5c(cc4CN3C(=O)NCc3ccccc3)O[C@@H](c3ccc(OCc4ccc(Cl)c(Cl)c4)cc3)CO5)C(=O)O)cc2)c1C] | 872 |

TABLE 1-continued
| Ex | Structure | LCMS (m/z) |
|---|---|---|
| 245 | 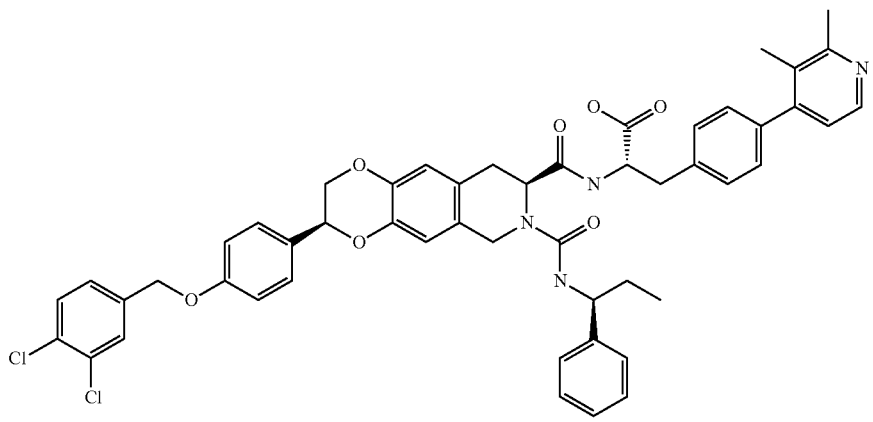 [SMILES: CC[C@H](NC(=O)N1Cc2cc3c(cc2C[C@H]1C(=O)N[C@@H](Cc1ccc(-c2ccnc(C)c2C)cc1)C(=O)O)OC[C@H](c1ccc(OCc2ccc(Cl)c(Cl)c2)cc1)O3)c1ccccc1] | 900 |
| 246 | 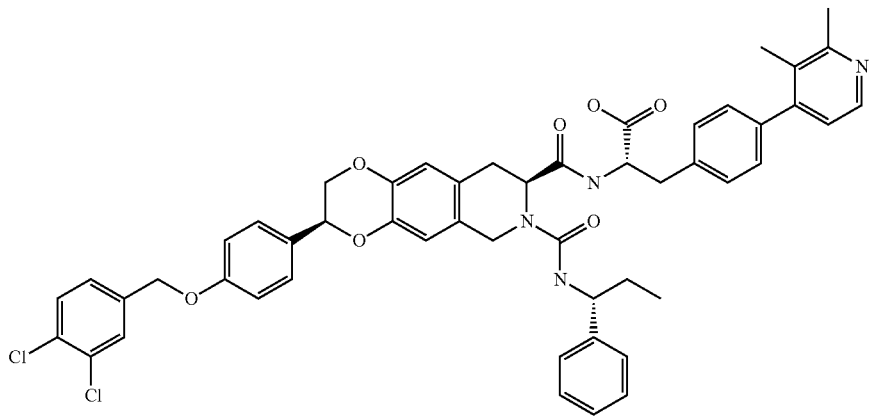 [SMILES: CC[C@@H](NC(=O)N1Cc2cc3c(cc2C[C@H]1C(=O)N[C@@H](Cc1ccc(-c2ccnc(C)c2C)cc1)C(=O)O)OC[C@H](c1ccc(OCc2ccc(Cl)c(Cl)c2)cc1)O3)c1ccccc1] | 902 |
| 247 | 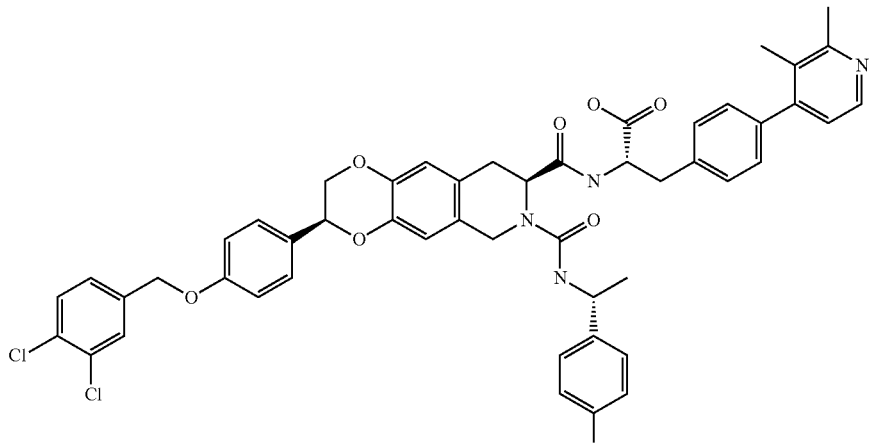 | 904 |

TABLE 1-continued

| Ex | Structure | LCMS (m/z) |
|---|---|---|
| 248 | 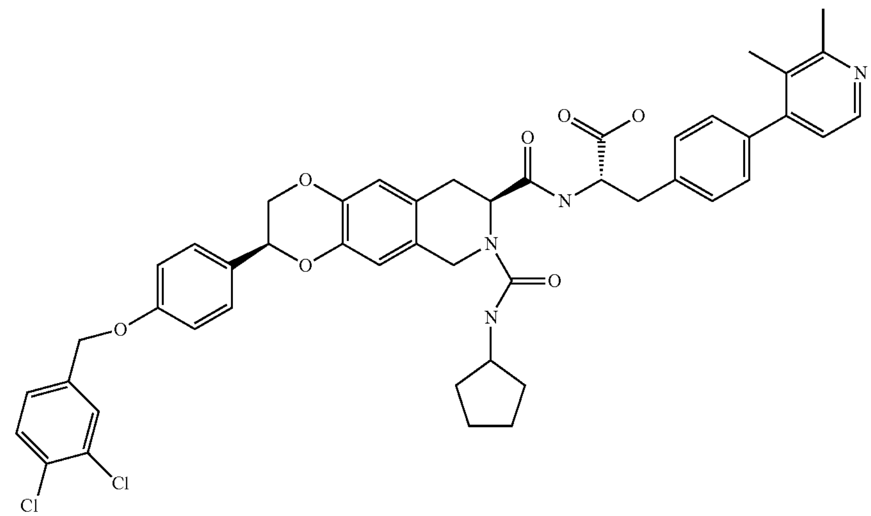 [SMILES: Cc1nccc(-c2ccc(C[C@H](NC(=O)[C@@H]3Cc4cc5c(cc4CN3C(=O)NC3CCCC3)O[C@@H](c3ccc(OCc4ccc(Cl)c(Cl)c4)cc3)CO5)C(=O)O)cc2)c1C] | 850 |
| 249 | 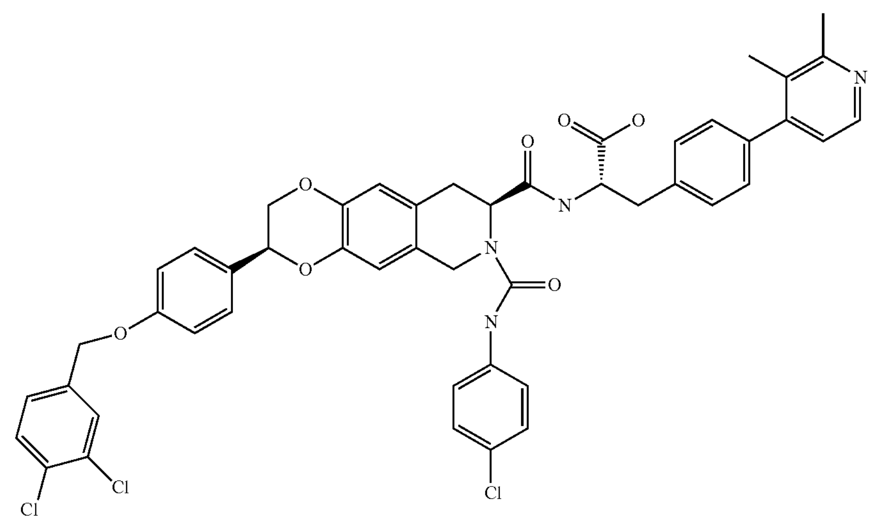 [SMILES: Cc1nccc(-c2ccc(C[C@H](NC(=O)[C@@H]3Cc4cc5c(cc4CN3C(=O)Nc3ccc(Cl)cc3)O[C@@H](c3ccc(OCc4ccc(Cl)c(Cl)c4)cc3)CO5)C(=O)O)cc2)c1C] | 894 |
| 250 | 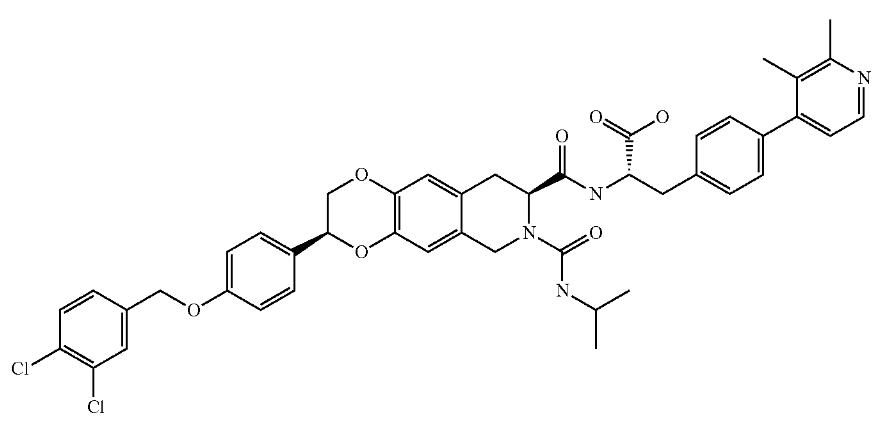 [SMILES: Cc1nccc(-c2ccc(C[C@H](NC(=O)[C@@H]3Cc4cc5c(cc4CN3C(=O)NC(C)C)O[C@@H](c3ccc(OCc4ccc(Cl)c(Cl)c4)cc3)CO5)C(=O)O)cc2)c1C] | 824 |

TABLE 1-continued

| Ex | Structure | LCMS (m/z) |
|---|---|---|
| 251 | 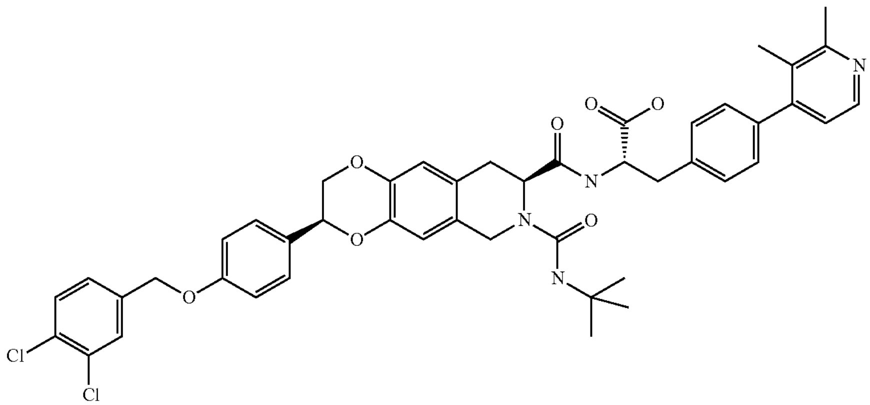 [SMILES: Cc1nccc(-c2ccc(C[C@H](NC(=O)[C@@H]3Cc4cc5c(cc4CN3C(=O)NC(C)(C)C)O[C@@H](c3ccc(OCc4ccc(Cl)c(Cl)c4)cc3)CO5)C(=O)O)cc2)c1C] | 838 |
| 252 | 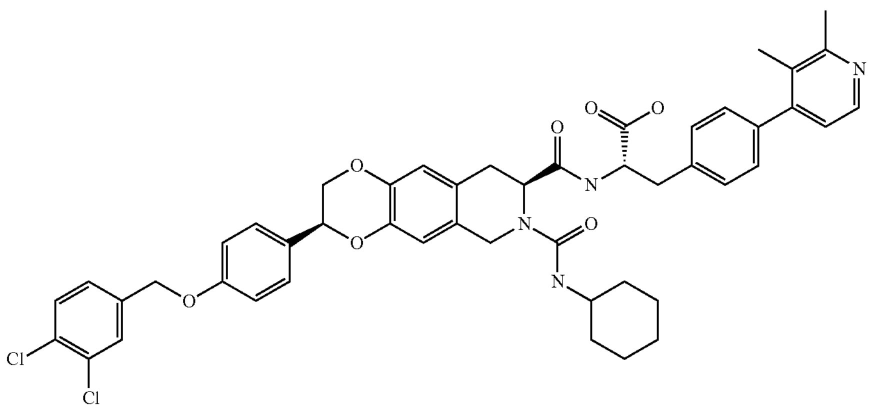 [SMILES: Cc1nccc(-c2ccc(C[C@H](NC(=O)[C@@H]3Cc4cc5c(cc4CN3C(=O)NC3CCCCC3)O[C@@H](c3ccc(OCc4ccc(Cl)c(Cl)c4)cc3)CO5)C(=O)O)cc2)c1C] | 864 |
| 253 | 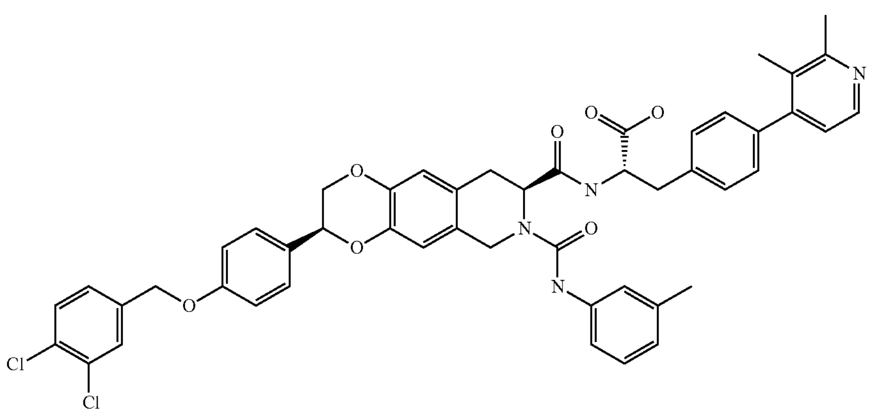 [SMILES: Cc1cccc(NC(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)c1] | 872 |

TABLE 1-continued

| Ex | Structure | LCMS (m/z) |
|----|-----------|------------|
| 254 | 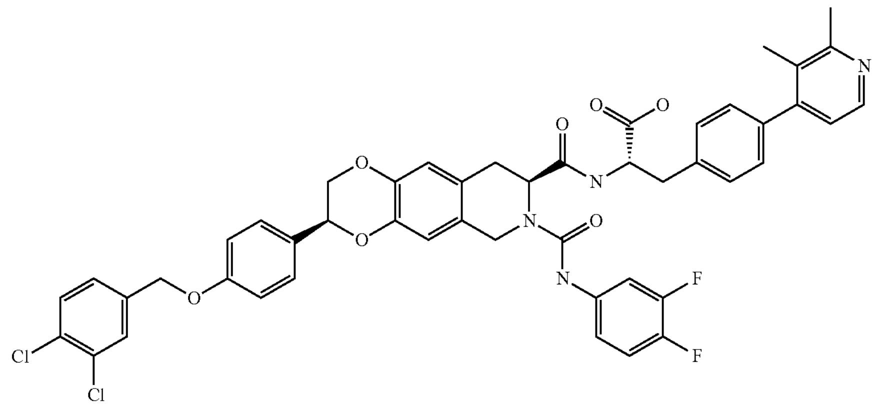 [SMILES: Cc1nccc(-c2ccc(C[C@H](NC(=O)[C@@H]3Cc4cc5c(cc4CN3C(=O)Nc3ccc(F)c(F)c3)O[C@@H](c3ccc(OCc4ccc(Cl)c(Cl)c4)cc3)CO5)C(=O)O)cc2)c1C] | 894 |
| 255 | 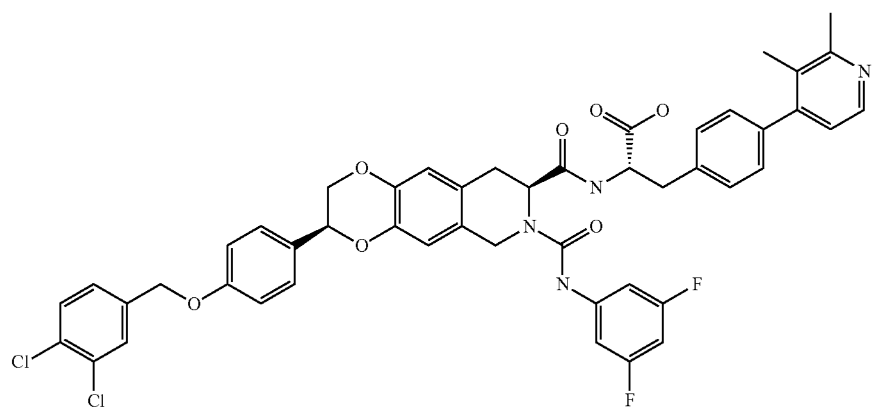 [SMILES: Cc1nccc(-c2ccc(C[C@H](NC(=O)[C@@H]3Cc4cc5c(cc4CN3C(=O)Nc3cc(F)cc(F)c3)O[C@@H](c3ccc(OCc4ccc(Cl)c(Cl)c4)cc3)CO5)C(=O)O)cc2)c1C] | 894 |
| 256 | 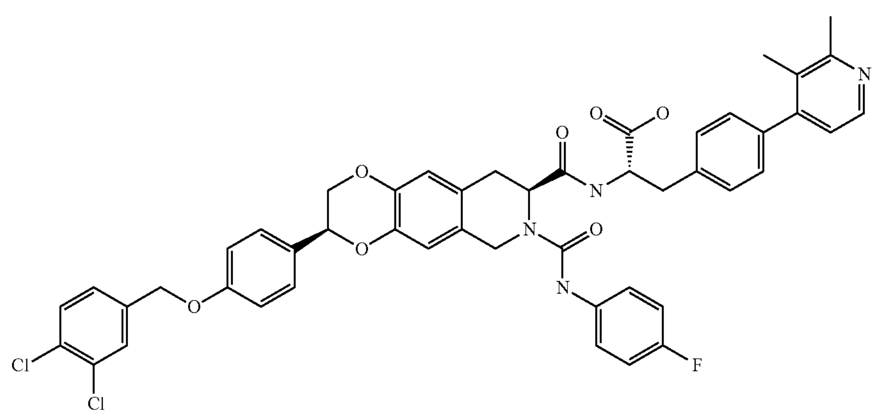 [SMILES: Cc1nccc(-c2ccc(C[C@H](NC(=O)[C@@H]3Cc4cc5c(cc4CN3C(=O)Nc3ccc(F)cc3)O[C@@H](c3ccc(OCc4ccc(Cl)c(Cl)c4)cc3)CO5)C(=O)O)cc2)c1C] | 876 |

TABLE 1-continued
| Ex | Structure | LCMS (m/z) |
|---|---|---|
| 257 | 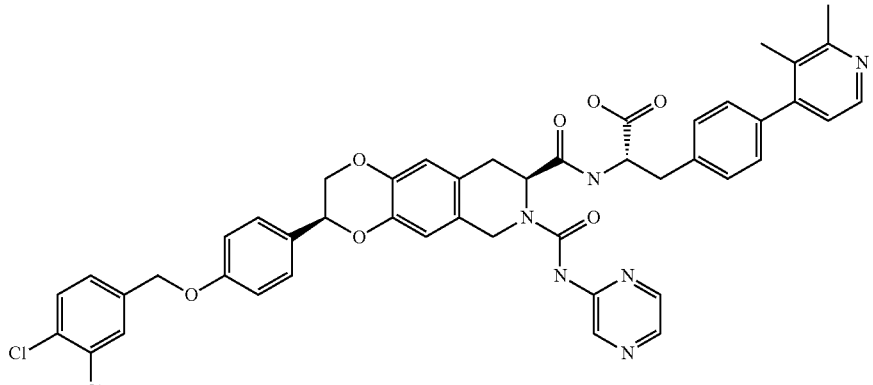 | 860 |
| 258 | 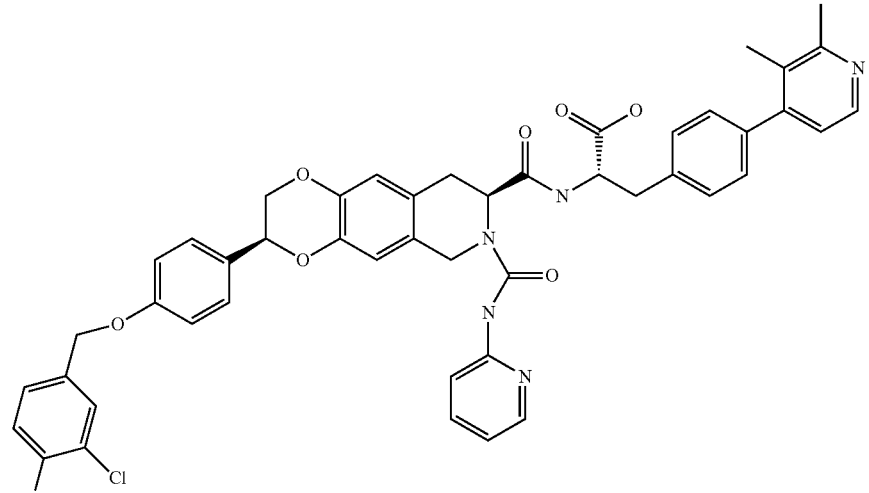 | 859 |
| 259 | 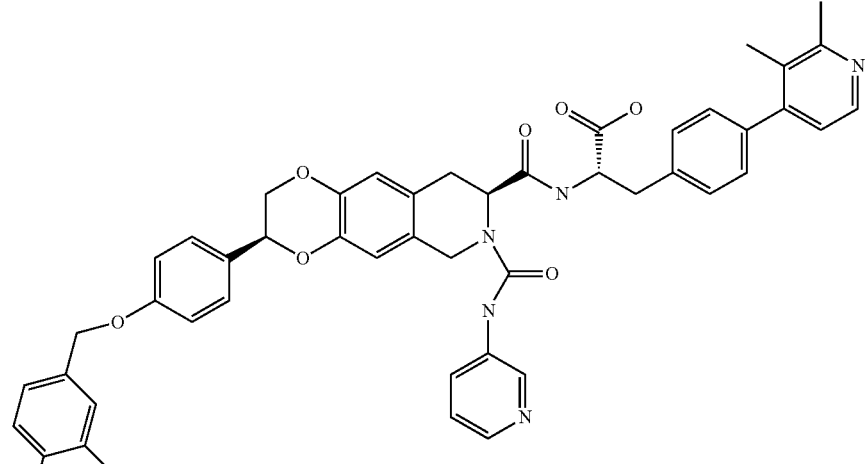 | 859 |

TABLE 1-continued

| Ex | Structure | LCMS (m/z) |
|---|---|---|
| 260 | 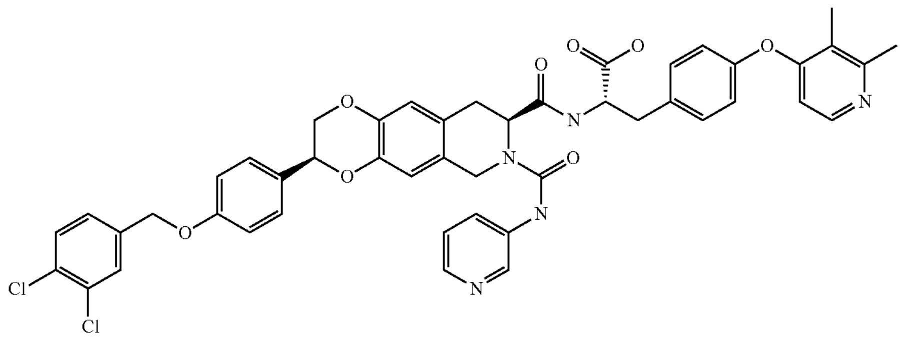 [SMILES: Cc1nccc(Oc2ccc(C[C@H](NC(=O)[C@@H]3Cc4cc5c(cc4CN3C(=O)Nc3cccnc3)O[C@@H](c3ccc(OCc4ccc(Cl)c(Cl)c4)cc3)CO5)C(=O)O)cc2)c1C] | 875 |
| 261 | 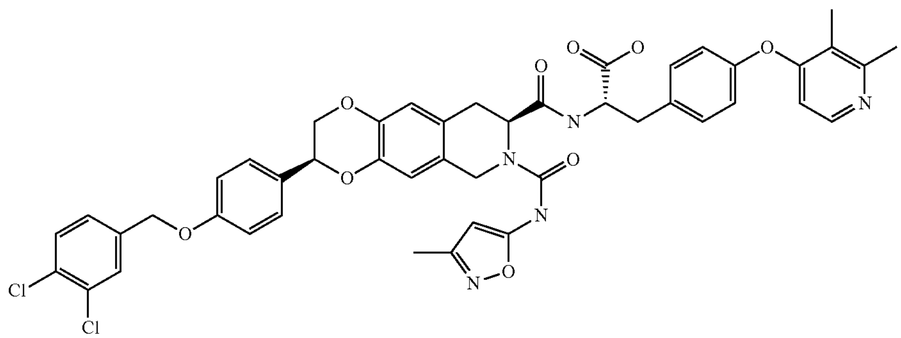 [SMILES: Cc1cc(NC(=O)N2Cc3cc4c(cc3C[C@H]2C(=O)N[C@@H](Cc2ccc(Oc3ccnc(C)c3C)cc2)C(=O)O)OC[C@H](c2ccc(OCc3ccc(Cl)c(Cl)c3)cc2)O4)on1] | 879 |
| 262 | 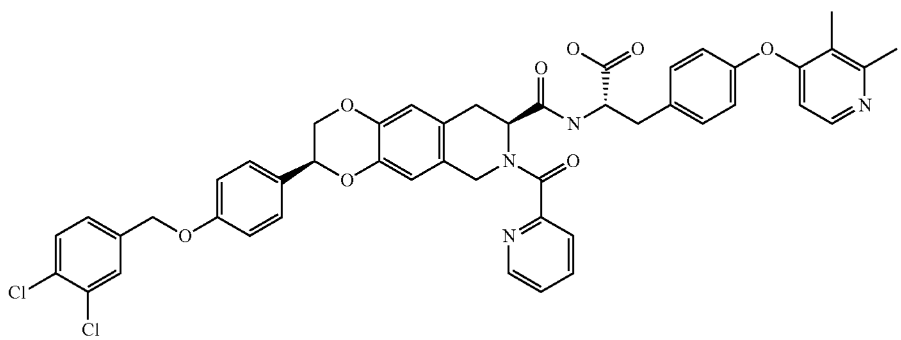 [SMILES: Cc1nccc(Oc2ccc(C[C@H](NC(=O)[C@@H]3Cc4cc5c(cc4CN3C(=O)c3ccccn3)O[C@@H](c3ccc(OCc4ccc(Cl)c(Cl)c4)cc3)CO5)C(=O)O)cc2)c1C] | 860 |
| 263 | 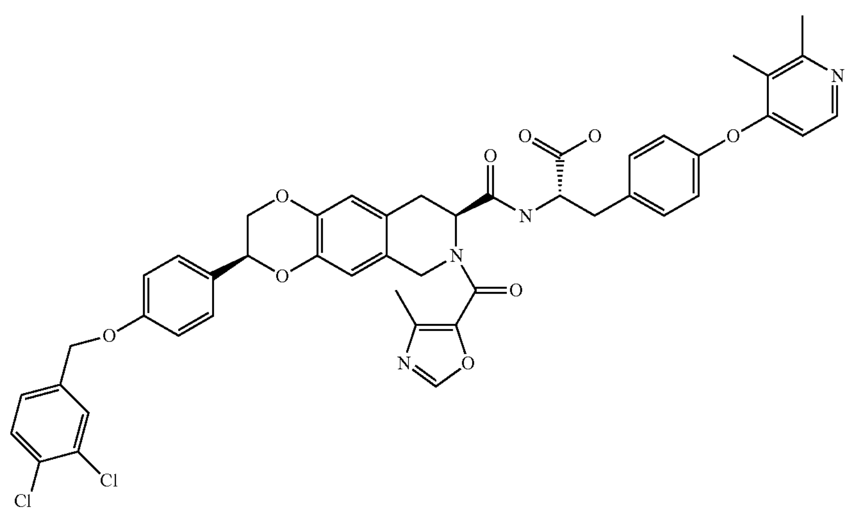 [SMILES: Cc1ncoc1C(=O)N1Cc2cc3c(cc2C[C@H]1C(=O)N[C@@H](Cc1ccc(Oc2ccnc(C)c2C)cc1)C(=O)O)OC[C@H](c1ccc(OCc2ccc(Cl)c(Cl)c2)cc1)O3] | 864 |

TABLE 1-continued

| Ex | Structure | LCMS (m/z) |
|---|---|---|
| 264 | 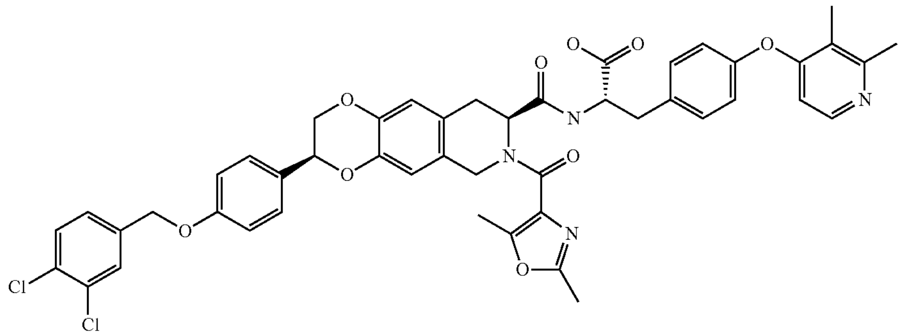 [SMILES: Cc1nc(C(=O)N2Cc3cc4c(cc3C[C@H]2C(=O)N[C@@H](Cc2ccc(Oc3ccnc(C)c3C)cc2)C(=O)O)OC[C@H](c2ccc(OCc3ccc(Cl)c(Cl)c3)cc2)O4)c(C)o1] | 878 |
| 265 | 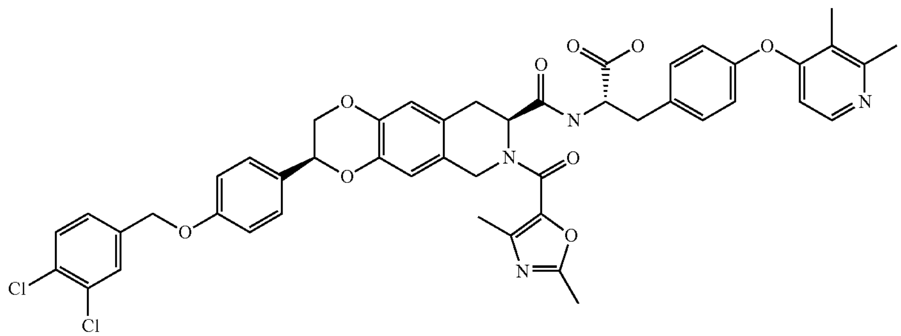 [SMILES: Cc1nc(C)c(C(=O)N2Cc3cc4c(cc3C[C@H]2C(=O)N[C@@H](Cc2ccc(Oc3ccnc(C)c3C)cc2)C(=O)O)OC[C@H](c2ccc(OCc3ccc(Cl)c(Cl)c3)cc2)O4)o1] | 878 |
| 266 | 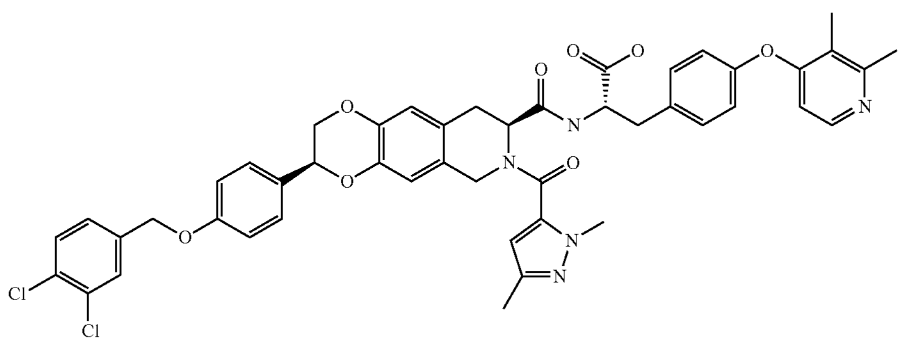 [SMILES: Cc1cc(C(=O)N2Cc3cc4c(cc3C[C@H]2C(=O)N[C@@H](Cc2ccc(Oc3ccnc(C)c3C)cc2)C(=O)O)OC[C@H](c2ccc(OCc3ccc(Cl)c(Cl)c3)cc2)O4)n(C)n1] | 877 |
| 267 | 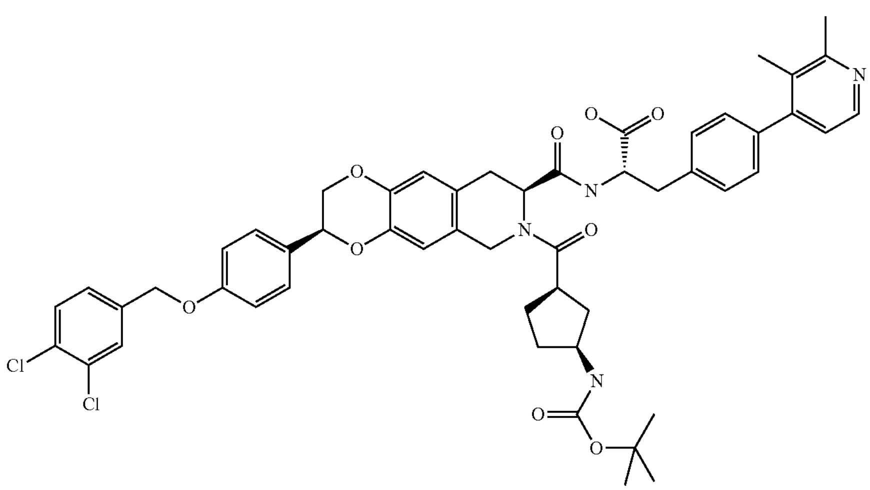 [SMILES: Cc1nccc(-c2ccc(C[C@H](NC(=O)[C@@H]3Cc4cc5c(cc4CN3C(=O)[C@@H]3CC[C@H](NC(=O)OC(C)(C)C)C3)O[C@@H](c3ccc(OCc4ccc(Cl)c(Cl)c4)cc3)CO5)C(=O)O)cc2)c1C] | 950 |

TABLE 1-continued
| Ex | Structure | LCMS (m/z) |
|---|---|---|
| 268 | 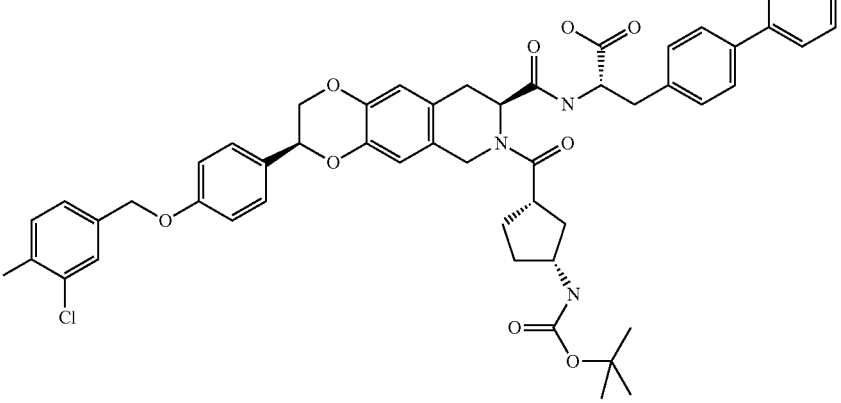 | 951 |
| 269 | 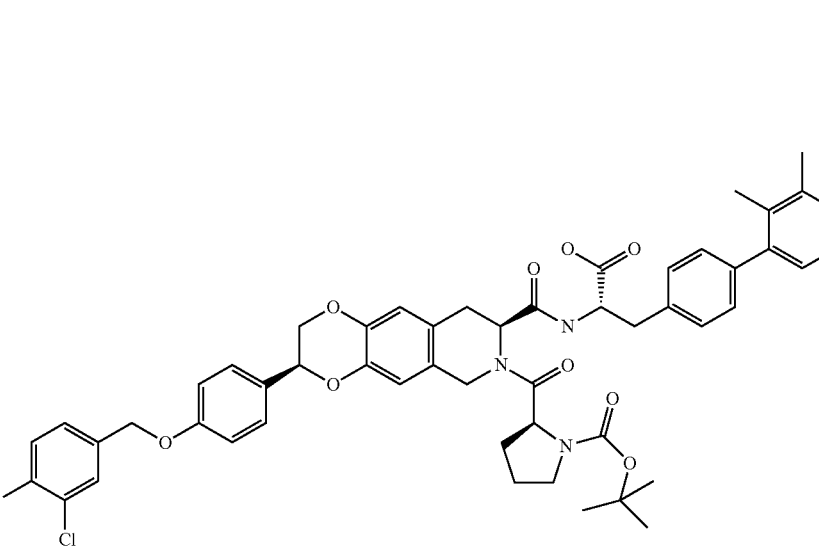 | 938 |
| 270 | 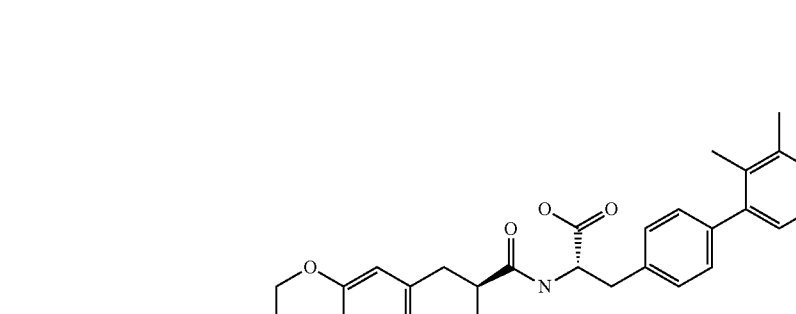 | 861 |

TABLE 1-continued

| Ex | Structure | LCMS (m/z) |
|---|---|---|
| 271 | 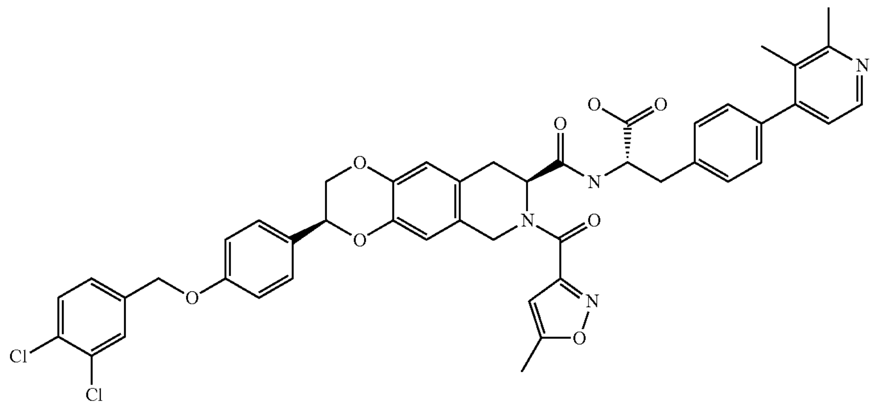 [SMILES: Cc1cc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)no1] | 848 |
| 272 | 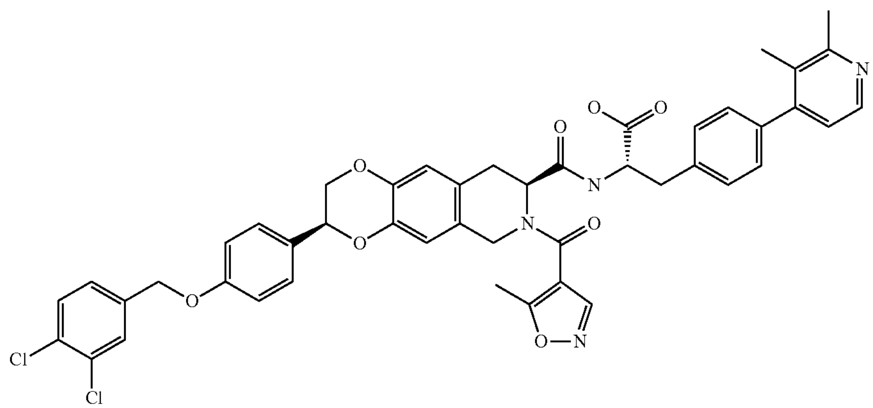 [SMILES: Cc1nccc(-c2ccc(C[C@H](NC(=O)[C@@H]3Cc4cc5c(cc4CN3C(=O)c3cnoc3C)O[C@@H](c3ccc(OCc4ccc(Cl)c(Cl)c4)cc3)CO5)C(=O)O)cc2)c1C] | 848 |
| 273 | 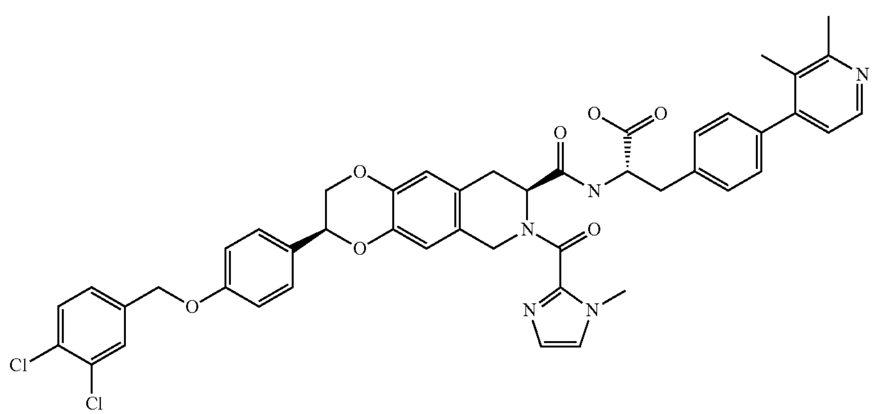 [SMILES: Cc1nccc(-c2ccc(C[C@H](NC(=O)[C@@H]3Cc4cc5c(cc4CN3C(=O)c3nccn3C)O[C@@H](c3ccc(OCc4ccc(Cl)c(Cl)c4)cc3)CO5)C(=O)O)cc2)c1C] | 848 |

TABLE 1-continued

| Ex | Structure | LCMS (m/z) |
|---|---|---|
| 274 | 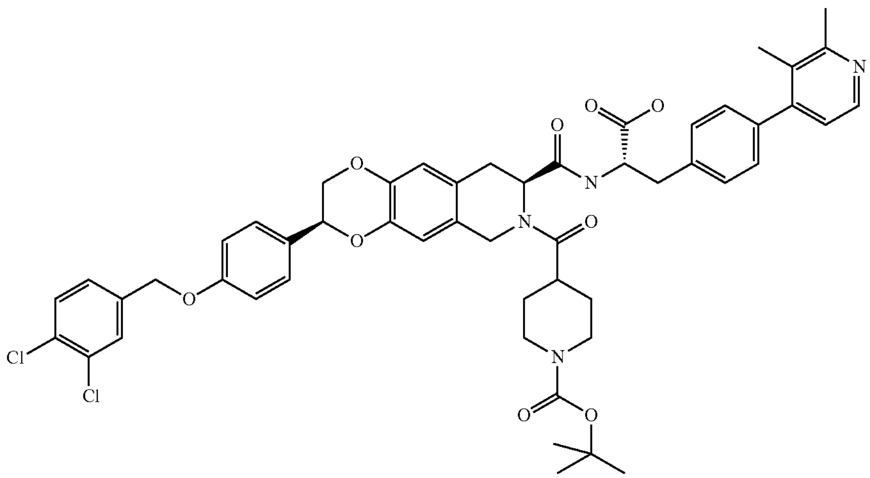 [SMILES: Cc1nccc(-c2ccc(C[C@H](NC(=O)[C@@H]3Cc4cc5c(cc4CN3C(=O)C3CCN(C(=O)OC(C)(C)C)CC3)O[C@@H](c3ccc(OCc4ccc(Cl)c(Cl)c4)cc3)CO5)C(=O)O)cc2)c1C] | 950 |
| 275 | 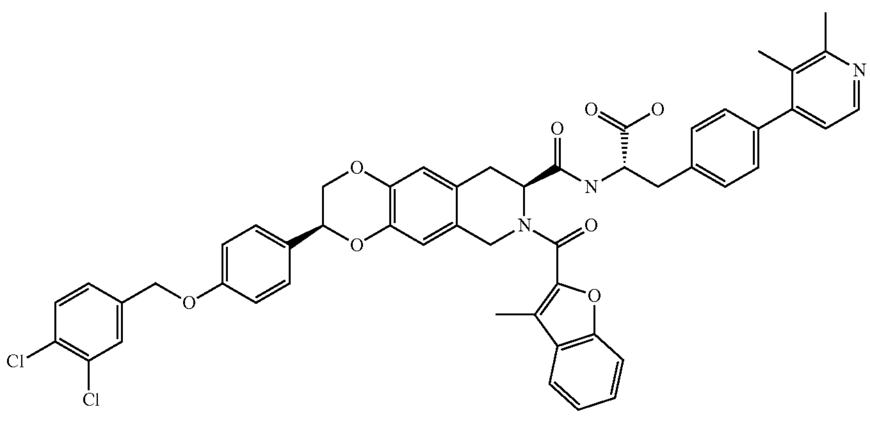 [SMILES: Cc1nccc(-c2ccc(C[C@H](NC(=O)[C@@H]3Cc4cc5c(cc4CN3C(=O)c3oc4ccccc4c3C)O[C@@H](c3ccc(OCc4ccc(Cl)c(Cl)c4)cc3)CO5)C(=O)O)cc2)c1C] | 899 |
| 276 | 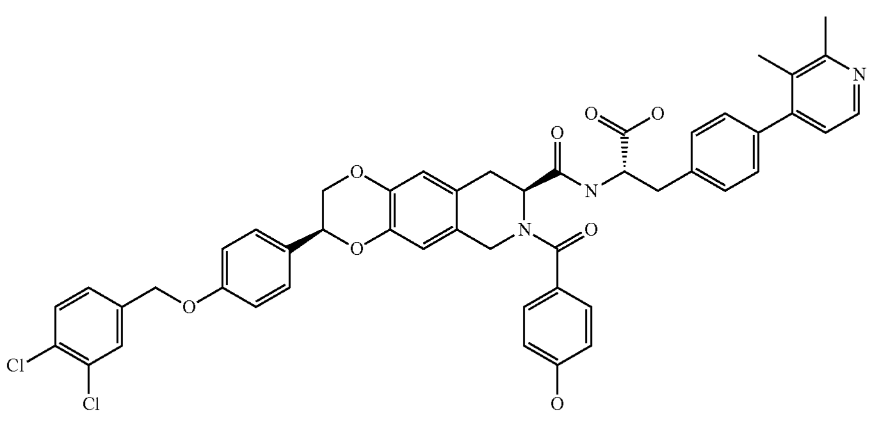 | 859 |

TABLE 1-continued
| Ex | Structure | LCMS (m/z) |
|---|---|---|
| 277 | 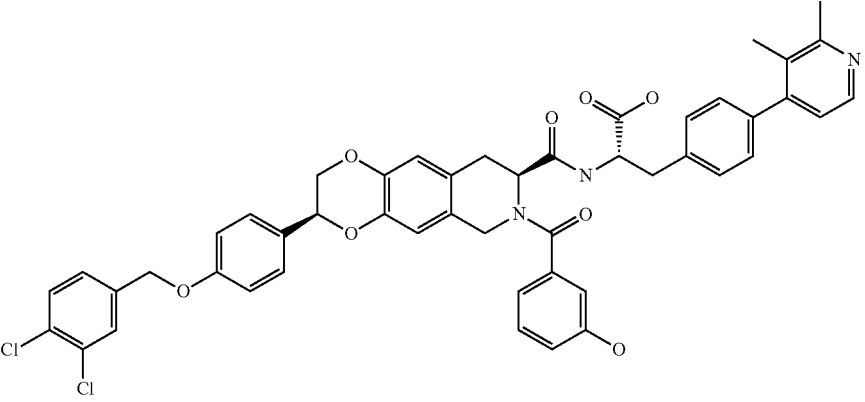 [SMILES: Cc1nccc(-c2ccc(C[C@H](NC(=O)[C@@H]3Cc4cc5c(cc4CN3C(=O)c3cccc(O)c3)O[C@@H](c3ccc(OCc4ccc(Cl)c(Cl)c4)cc3)CO5)C(=O)O)cc2)c1C] | 859 |
| 278 | 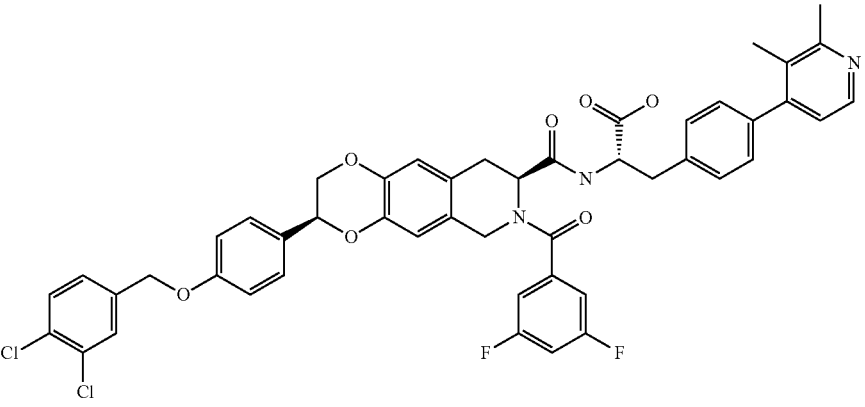 [SMILES: Cc1nccc(-c2ccc(C[C@H](NC(=O)[C@@H]3Cc4cc5c(cc4CN3C(=O)c3cc(F)cc(F)c3)O[C@@H](c3ccc(OCc4ccc(Cl)c(Cl)c4)cc3)CO5)C(=O)O)cc2)c1C] | 879 |
| 279 | 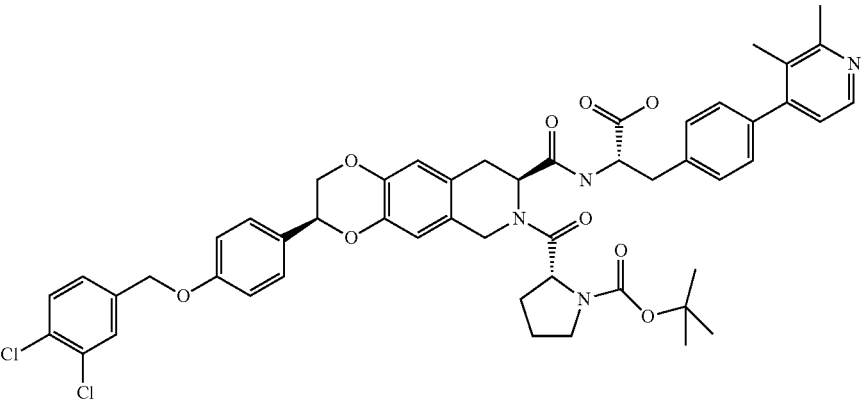 [SMILES: Cc1nccc(-c2ccc(C[C@H](NC(=O)[C@@H]3Cc4cc5c(cc4CN3C(=O)[C@H]3CCCN3C(=O)OC(C)(C)C)O[C@@H](c3ccc(OCc4ccc(Cl)c(Cl)c4)cc3)CO5)C(=O)O)cc2)c1C] | 936 |

TABLE 1-continued

| Ex | Structure | LCMS (m/z) |
|----|-----------|------------|
| 280 | 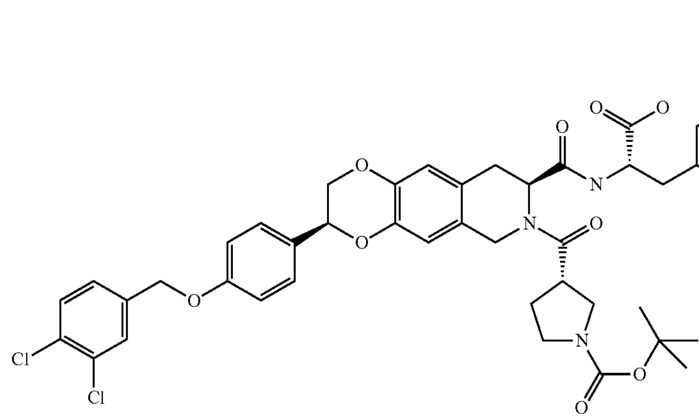 | 936 |
| 281 | 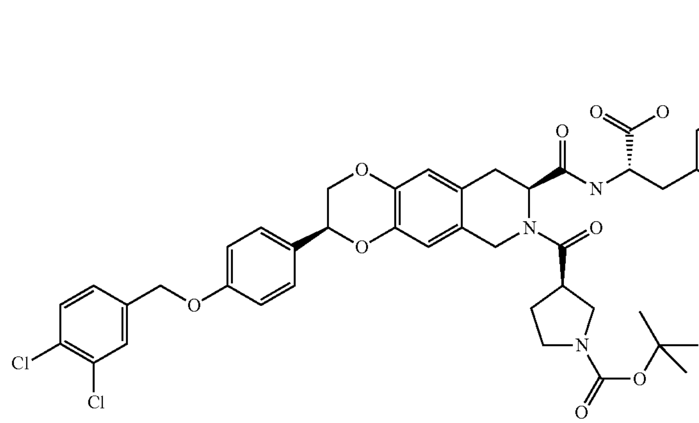 | 936 |
| 282 | 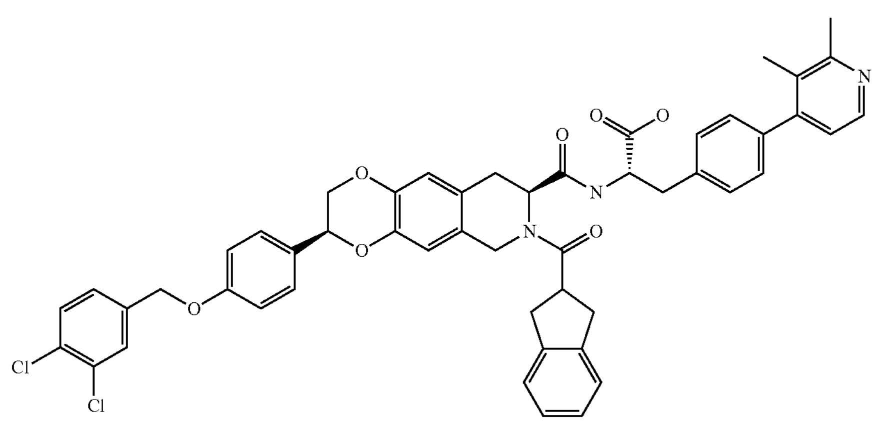 [SMILES: Cc1nccc(-c2ccc(C[C@H](NC(=O)[C@@H]3Cc4cc5c(cc4CN3C(=O)C3Cc4ccccc4C3)O[C@@H](c3ccc(OCc4ccc(Cl)c(Cl)c4)cc3)CO5)C(=O)O)cc2)c1C] | 883 |

TABLE 1-continued

| Ex | Structure | LCMS (m/z) |
|---|---|---|
| 283 | 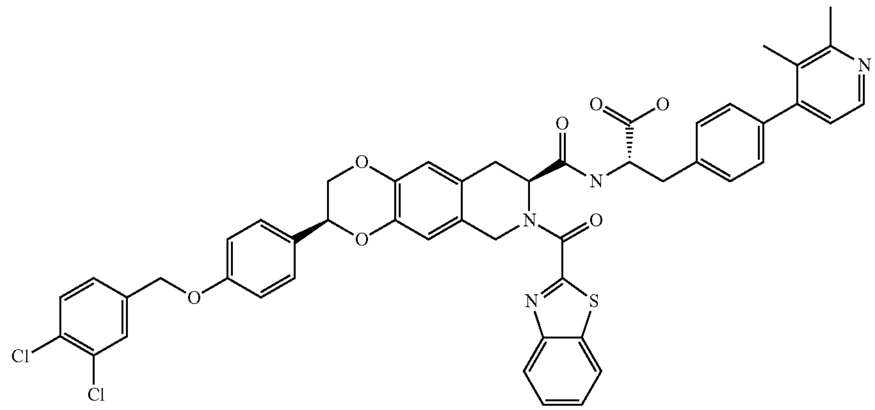 [SMILES: Cc1nccc(-c2ccc(C[C@H](NC(=O)[C@@H]3Cc4cc5c(cc4CN3C(=O)c3nc4ccccc4s3)O[C@@H](c3ccc(OCc4ccc(Cl)c(Cl)c4)cc3)CO5)C(=O)O)cc2)c1C] | 900 |
| 284 | 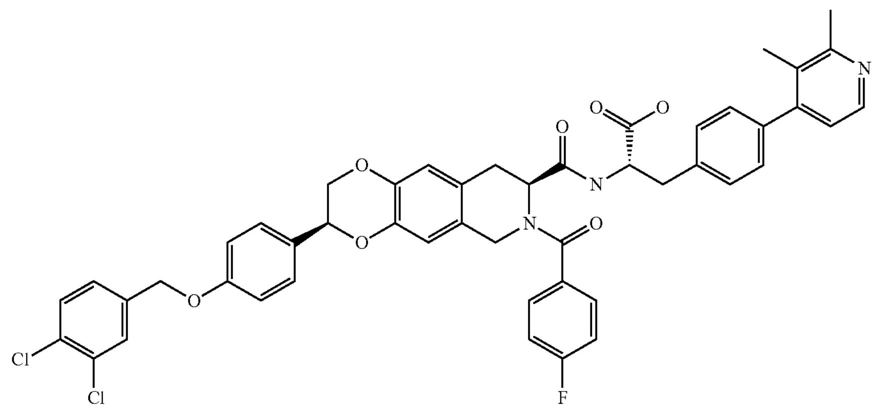 [SMILES: Cc1nccc(-c2ccc(C[C@H](NC(=O)[C@@H]3Cc4cc5c(cc4CN3C(=O)c3ccc(F)cc3)O[C@@H](c3ccc(OCc4ccc(Cl)c(Cl)c4)cc3)CO5)C(=O)O)cc2)c1C] | 861 |
| 285 | 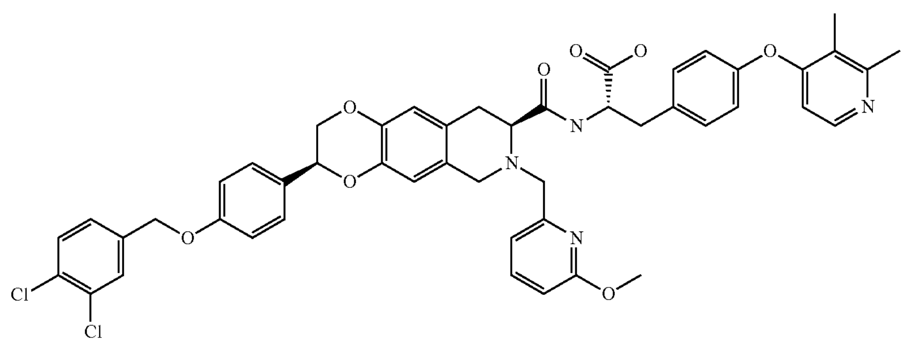 [SMILES: COc1cccc(CN2Cc3cc4c(cc3C[C@H]2C(=O)N[C@@H](Cc2ccc(Oc3ccnc(C)c3C)cc2)C(=O)O)OC[C@H](c2ccc(OCc3ccc(Cl)c(Cl)c3)cc2)O4)n1] | 876 |
| 286 | 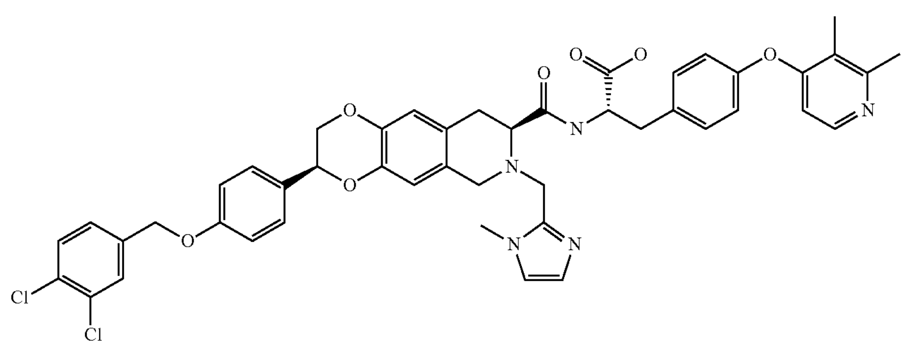 [SMILES: Cc1nccc(Oc2ccc(C[C@H](NC(=O)[C@@H]3Cc4cc5c(cc4CN3Cc3nccn3C)O[C@@H](c3ccc(OCc4ccc(Cl)c(Cl)c4)cc3)CO5)C(=O)O)cc2)c1C] | 849 |

TABLE 1-continued
| Ex | Structure | LCMS (m/z) |
|---|---|---|
| 287 | 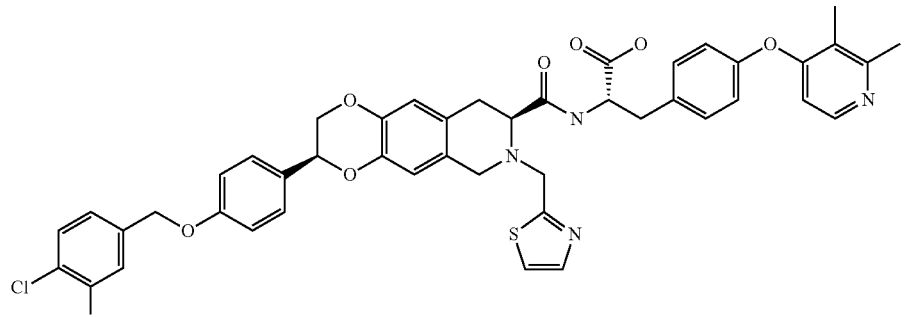 | 852 |
| 288 | 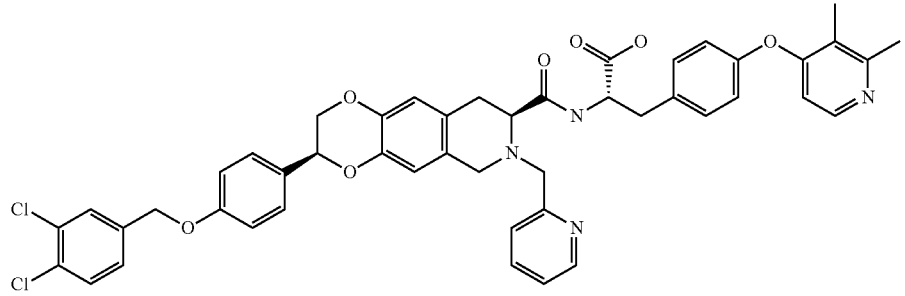 [SMILES: Cc1nccc(Oc2ccc(C[C@H](NC(=O)[C@@H]3Cc4cc5c(cc4CN3Cc3ccccn3)O[C@@H](c3ccc(OCc4ccc(Cl)c(Cl)c4)cc3)CO5)C(=O)O)cc2)c1C] | 846 |
| 289 | 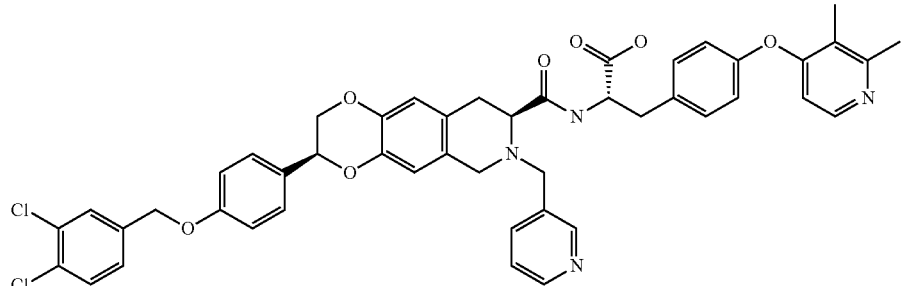 | 846 |
| 290 | 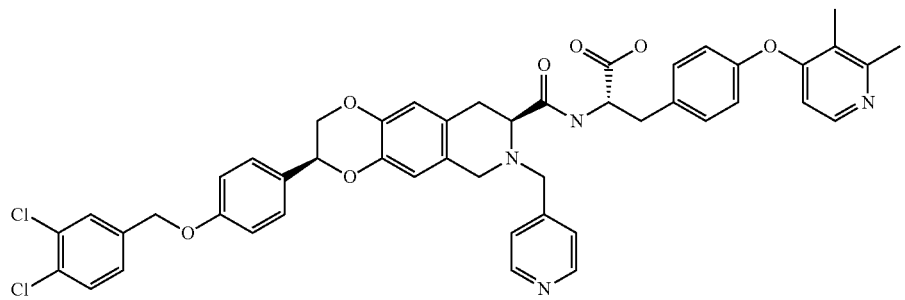 [SMILES: Cc1nccc(Oc2ccc(C[C@H](NC(=O)[C@@H]3Cc4cc5c(cc4CN3Cc3cccnc3)O[C@@H](c3ccc(OCc4ccc(Cl)c(Cl)c4)cc3)CO5)C(=O)O)cc2)c1C] | 846 |
| 291 | 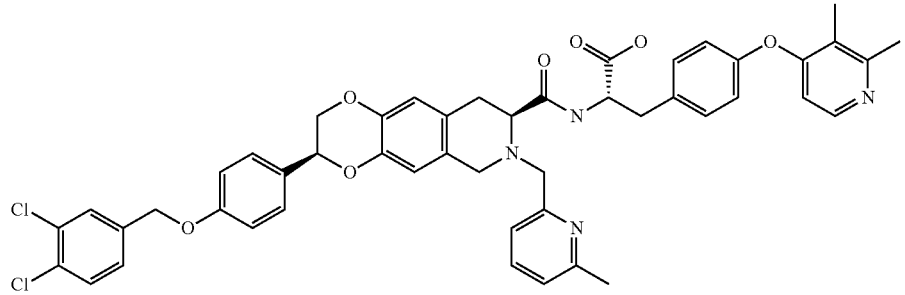 [SMILES: Cc1cccc(CN2Cc3cc4c(cc3C[C@H]2C(=O)N[C@@H](Cc2ccc(Oc3ccnc(C)c3C)cc2)C(=O)O)OC[C@H](c2ccc(OCc3ccc(Cl)c(Cl)c3)cc2)O4)n1] | 860 |

TABLE 1-continued
| Ex | Structure | LCMS (m/z) |
|---|---|---|
| 292 | 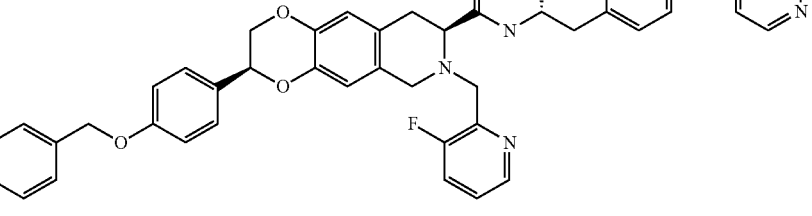 | 864 |
| 293 | 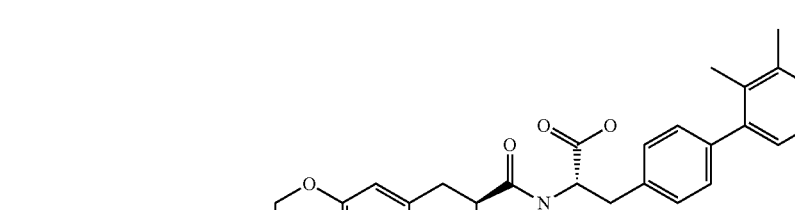 | 825 |
| 294 | 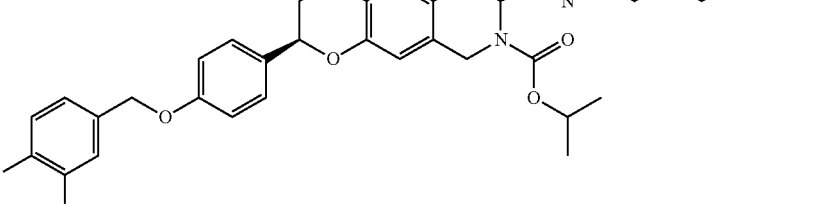 | 841 |
| 295 | 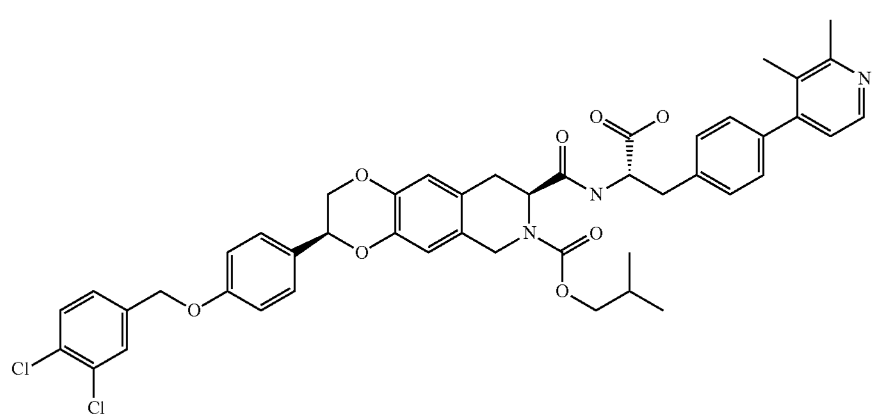 [SMILES: Cc1nccc(-c2ccc(C[C@H](NC(=O)[C@@H]3Cc4cc5c(cc4CN3C(=O)OCC(C)C)O[C@@H](c3ccc(OCc4ccc(Cl)c(Cl)c4)cc3)CO5)C(=O)O)cc2)c1C] | 839 |

TABLE 1-continued
| Ex | Structure | LCMS (m/z) |
|---|---|---|
| 296 | 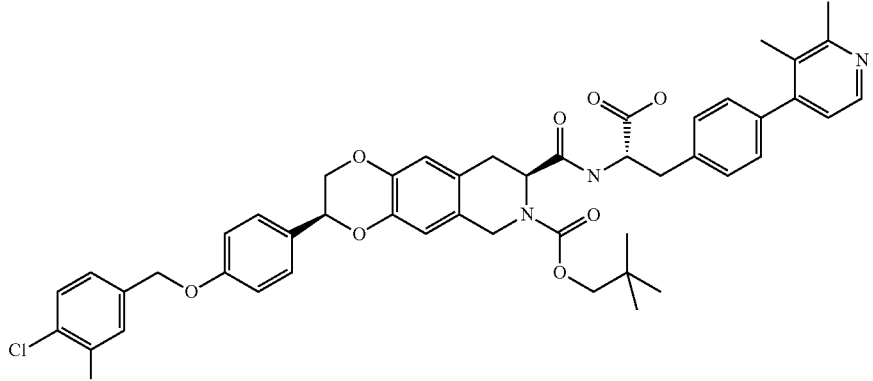 | 855 |
| 297 | 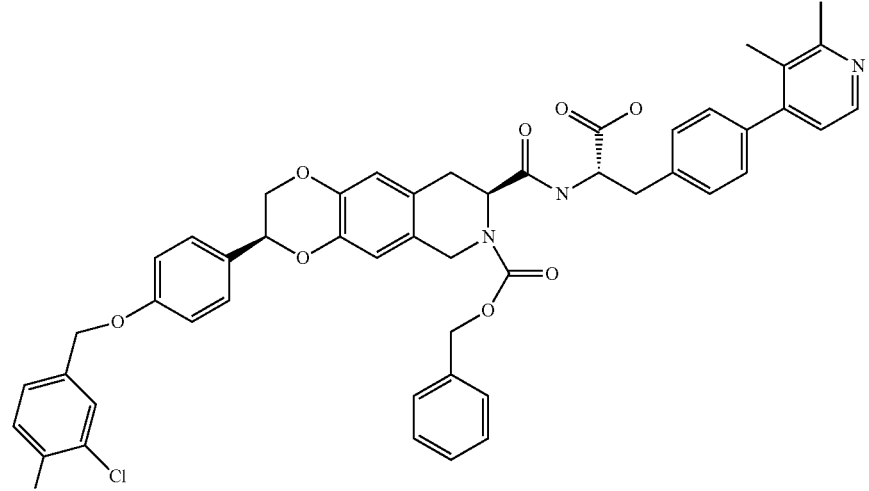 | 875 |
| 298 | 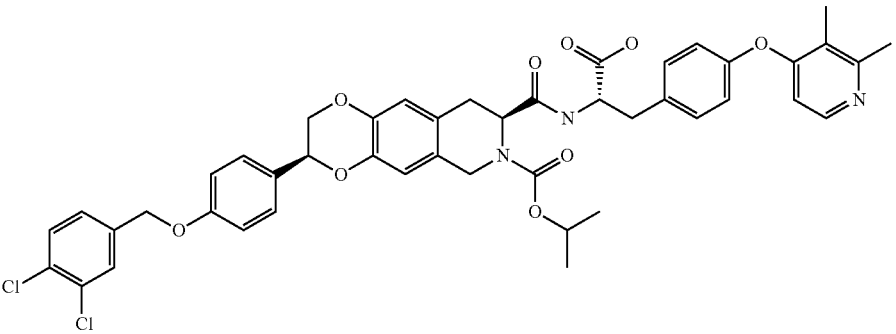 [SMILES: Cc1nccc(Oc2ccc(C[C@H](NC(=O)[C@@H]3Cc4cc5c(cc4CN3C(=O)OC(C)C)O[C@@H](c3ccc(OCc4ccc(Cl)c(Cl)c4)cc3)CO5)C(=O)O)cc2)c1C] | 841 |
| 299 | 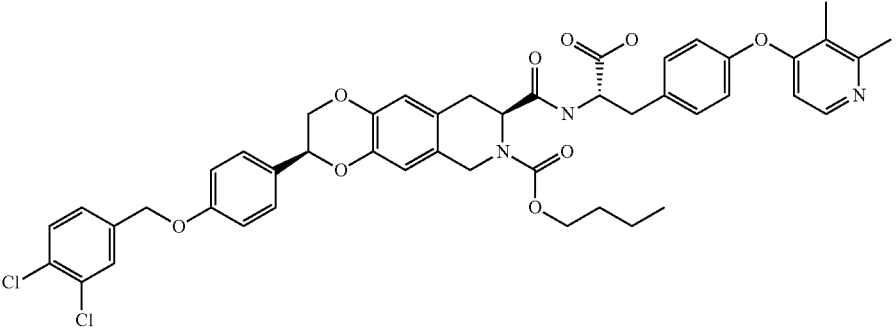 [SMILES: CCCCOC(=O)N1Cc2cc3c(cc2C[C@H]1C(=O)N[C@@H](Cc1ccc(Oc2ccnc(C)c2C)cc1)C(=O)O)OC[C@H](c1ccc(OCc2ccc(Cl)c(Cl)c2)cc1)O3] | 855 |

TABLE 1-continued

| Ex | Structure | LCMS (m/z) |
|---|---|---|
| 300 | 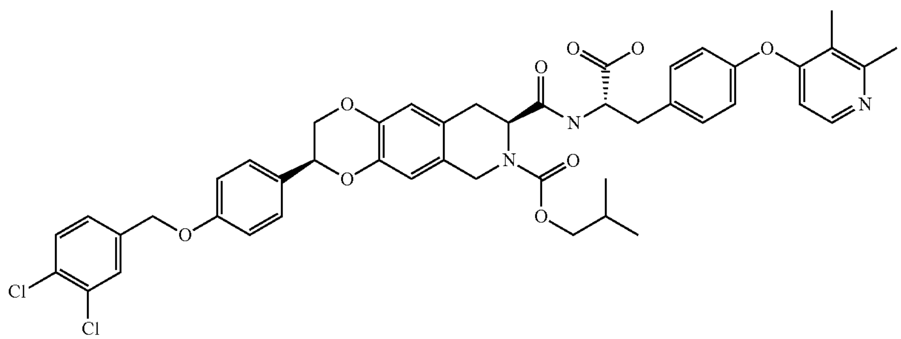 [SMILES: Cc1nccc(Oc2ccc(C[C@H](NC(=O)[C@@H]3Cc4cc5c(cc4CN3C(=O)OCC(C)C)O[C@@H](c3ccc(OCc4ccc(Cl)c(Cl)c4)cc3)CO5)C(=O)O)cc2)c1C] | 857 |
| 301 | 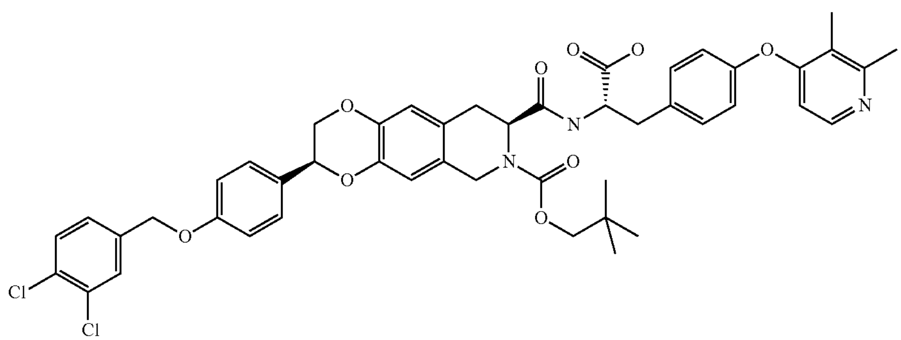 [SMILES: Cc1nccc(Oc2ccc(C[C@H](NC(=O)[C@@H]3Cc4cc5c(cc4CN3C(=O)OCC(C)(C)C)O[C@@H](c3ccc(OCc4ccc(Cl)c(Cl)c4)cc3)CO5)C(=O)O)cc2)c1C] | 869 |
| 302 | 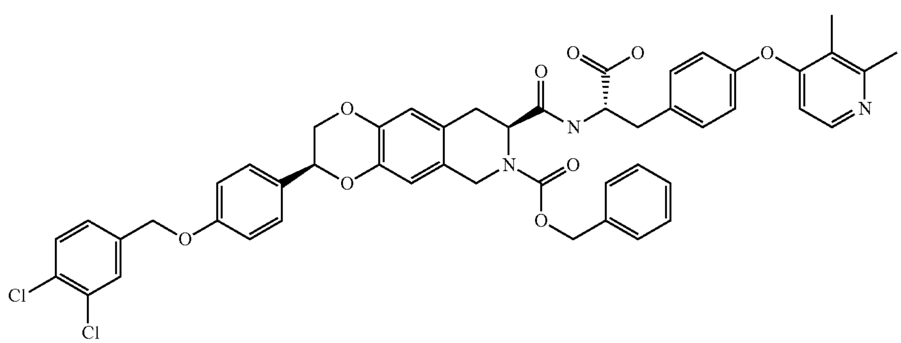 [SMILES: Cc1nccc(Oc2ccc(C[C@H](NC(=O)[C@@H]3Cc4cc5c(cc4CN3C(=O)OCc3ccccc3)O[C@@H](c3ccc(OCc4ccc(Cl)c(Cl)c4)cc3)CO5)C(=O)O)cc2)c1C] | 889 |
| 303 | 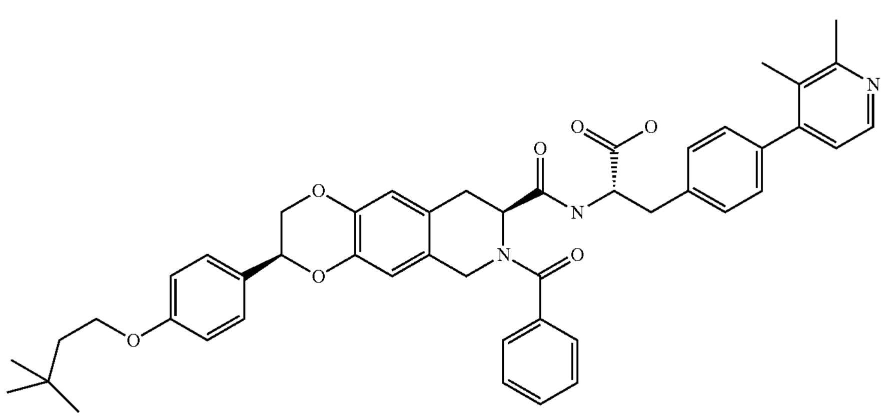 [SMILES: Cc1nccc(-c2ccc(C[C@H](NC(=O)[C@@H]3Cc4cc5c(cc4CN3C(=O)c3ccccc3)O[C@@H](c3ccc(OCCC(C)(C)C)cc3)CO5)C(=O)O)cc2)c1C] | 769 |

TABLE 1-continued

| Ex | Structure | LCMS (m/z) |
|---|---|---|
| 304 | 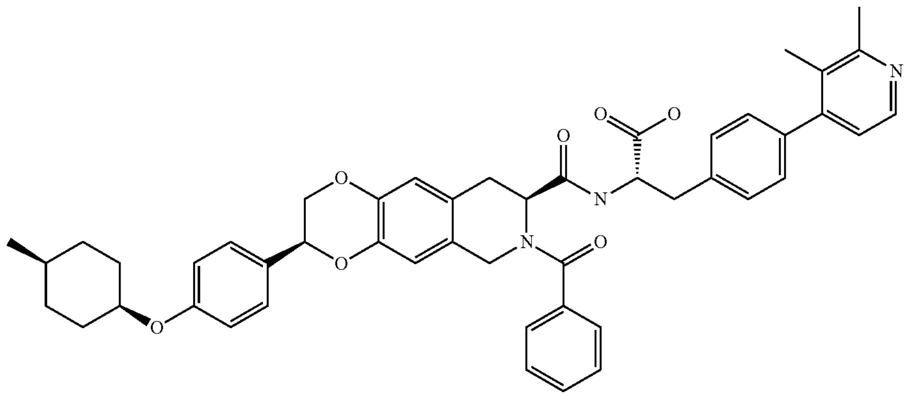 [SMILES: Cc1nccc(-c2ccc(C[C@H](NC(=O)[C@@H]3Cc4cc5c(cc4CN3C(=O)c3ccccc3)O[C@@H](c3ccc(O[C@H]4CC[C@@H](C)CC4)cc3)CO5)C(=O)O)cc2)c1C] | 781 |
| 305 | 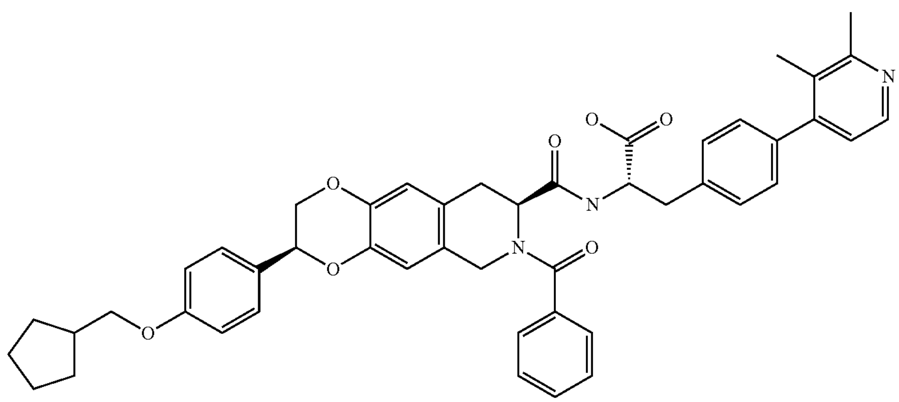 [SMILES: Cc1nccc(-c2ccc(C[C@H](NC(=O)[C@@H]3Cc4cc5c(cc4CN3C(=O)c3ccccc3)O[C@@H](c3ccc(OCC4CCCC4)cc3)CO5)C(=O)O)cc2)c1C] | 767 |
| 306 | 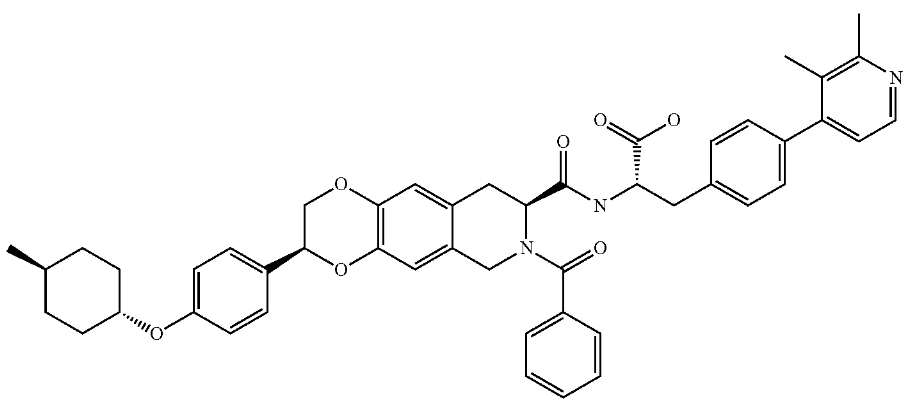 [SMILES: Cc1nccc(-c2ccc(C[C@H](NC(=O)[C@@H]3Cc4cc5c(cc4CN3C(=O)c3ccccc3)O[C@@H](c3ccc(O[C@H]4CC[C@H](C)CC4)cc3)CO5)C(=O)O)cc2)c1C] | 781 |
| 307 | (2HCl) | 850 |

TABLE 1-continued
| Ex | Structure | LCMS (m/z) |
|---|---|---|
| 308 | 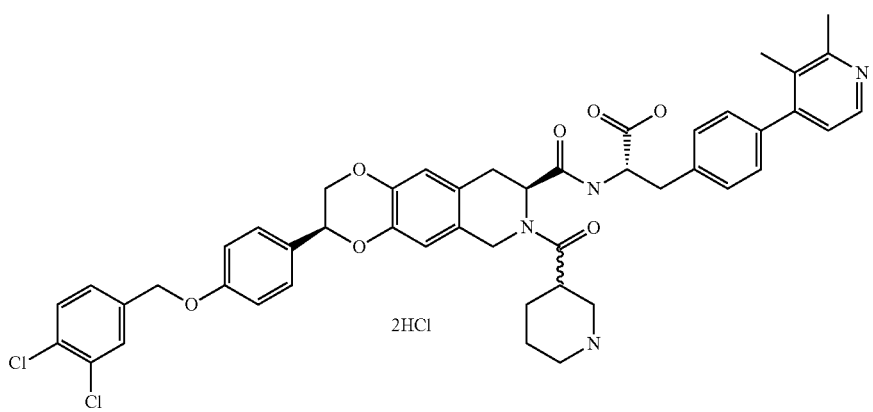 [SMILES: Cc1nccc(-c2ccc(C[C@H](NC(=O)[C@@H]3Cc4cc5c(cc4CN3C(=O)C3CCCNC3)O[C@@H](c3ccc(OCc4ccc(Cl)c(Cl)c4)cc3)CO5)C(=O)O)cc2)c1C] | 850 |
| 309 | 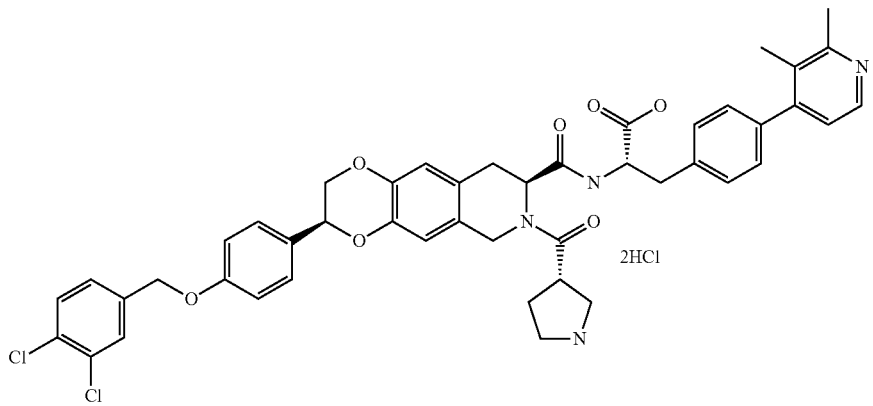 [SMILES: Cc1nccc(-c2ccc(C[C@H](NC(=O)[C@@H]3Cc4cc5c(cc4CN3C(=O)[C@H]3CCNC3)O[C@@H](c3ccc(OCc4ccc(Cl)c(Cl)c4)cc3)CO5)C(=O)O)cc2)c1C] | 836 |
| 310 | 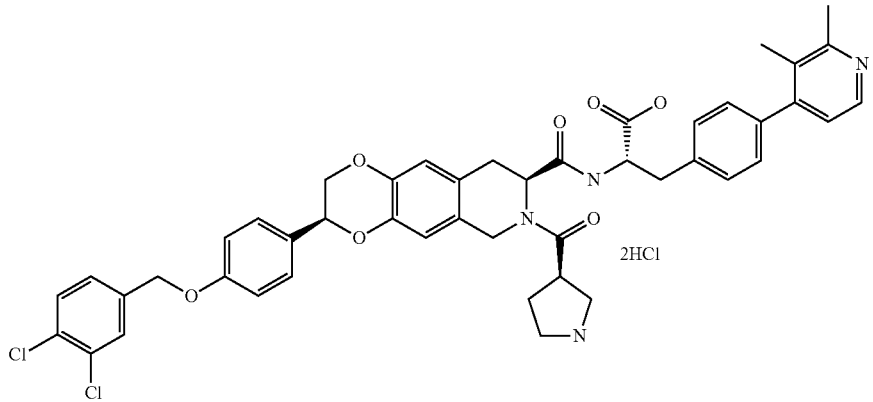 [SMILES: Cc1nccc(-c2ccc(C[C@H](NC(=O)[C@@H]3Cc4cc5c(cc4CN3C(=O)[C@@H]3CCNC3)O[C@@H](c3ccc(OCc4ccc(Cl)c(Cl)c4)cc3)CO5)C(=O)O)cc2)c1C] | 836 |

TABLE 1-continued
| Ex | Structure | LCMS (m/z) |
|---|---|---|
| 311 | 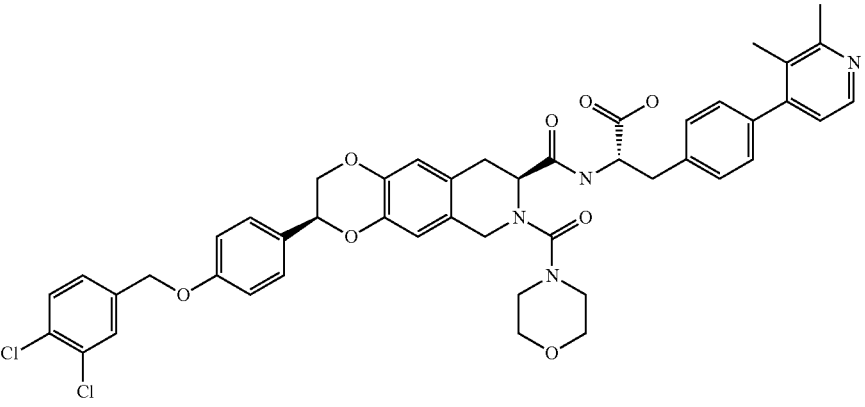 [SMILES: Cc1nccc(-c2ccc(C[C@H](NC(=O)[C@@H]3Cc4cc5c(cc4CN3C(=O)N3CCOCC3)O[C@@H](c3ccc(OCc4ccc(Cl)c(Cl)c4)cc3)CO5)C(=O)O)cc2)c1C] | 852 |
| 312 | 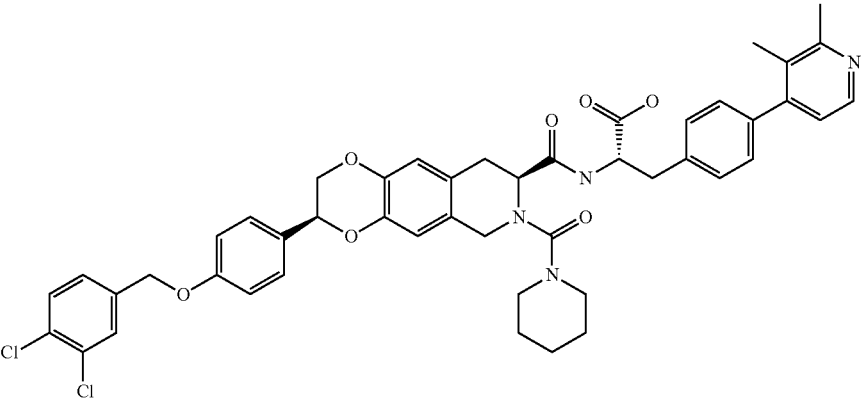 [SMILES: Cc1nccc(-c2ccc(C[C@H](NC(=O)[C@@H]3Cc4cc5c(cc4CN3C(=O)N3CCCCC3)O[C@@H](c3ccc(OCc4ccc(Cl)c(Cl)c4)cc3)CO5)C(=O)O)cc2)c1C] | 850 |
| 313 | 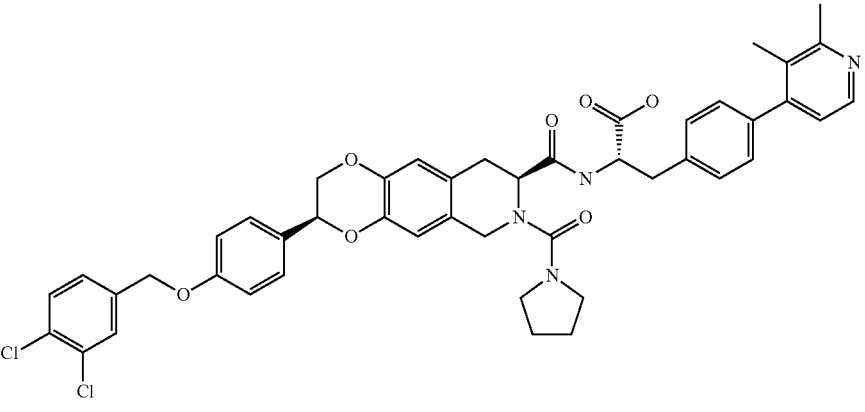 [SMILES: Cc1nccc(-c2ccc(C[C@H](NC(=O)[C@@H]3Cc4cc5c(cc4CN3C(=O)N3CCCC3)O[C@@H](c3ccc(OCc4ccc(Cl)c(Cl)c4)cc3)CO5)C(=O)O)cc2)c1C] | 836 |

TABLE 1-continued

| Ex | Structure | LCMS (m/z) |
|---|---|---|
| 314 | 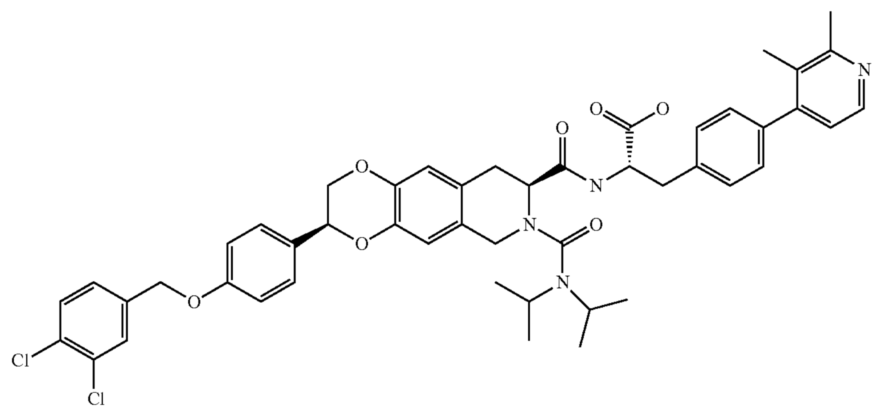 [SMILES: Cc1nccc(-c2ccc(C[C@H](NC(=O)[C@@H]3Cc4cc5c(cc4CN3C(=O)N(C(C)C)C(C)C)O[C@@H](c3ccc(OCc4ccc(Cl)c(Cl)c4)cc3)CO5)C(=O)O)cc2)c1C] | 868 |
| 315 | 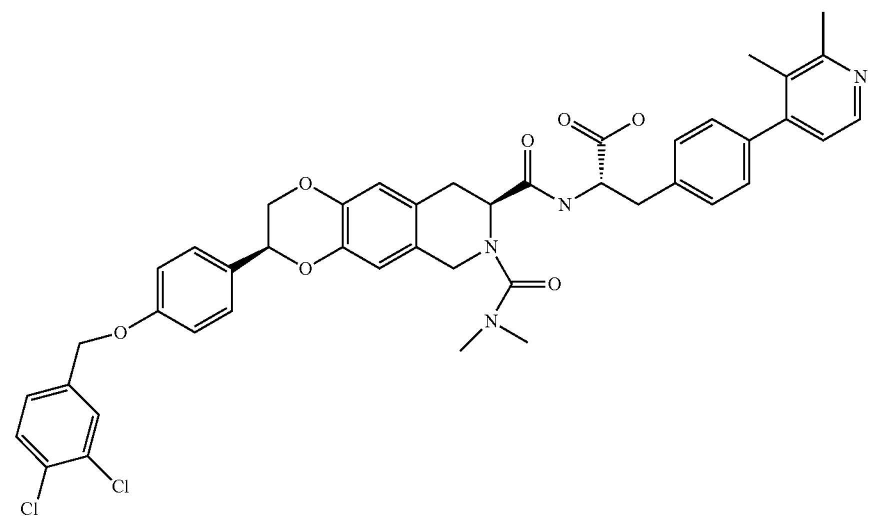 [SMILES: Cc1nccc(-c2ccc(C[C@H](NC(=O)[C@@H]3Cc4cc5c(cc4CN3C(=O)N(C)C)O[C@@H](c3ccc(OCc4ccc(Cl)c(Cl)c4)cc3)CO5)C(=O)O)cc2)c1C] | 810 |
| 316 | 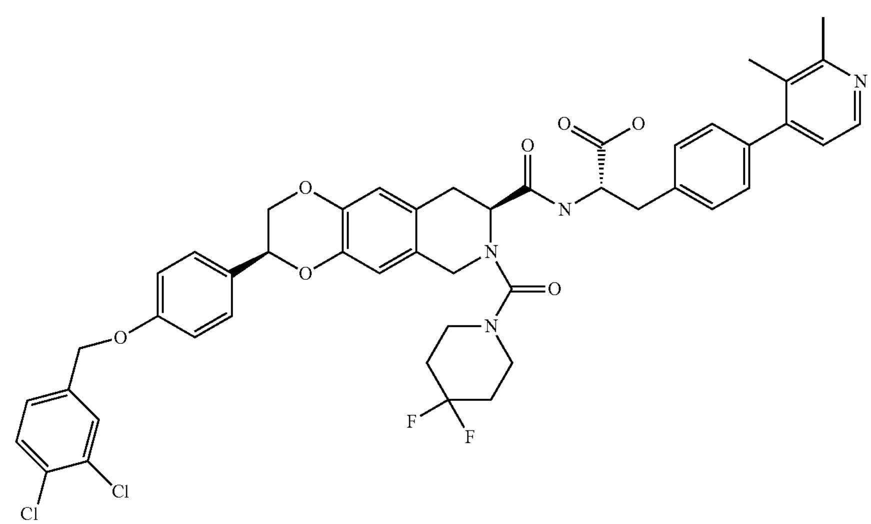 [SMILES: Cc1nccc(-c2ccc(C[C@H](NC(=O)[C@@H]3Cc4cc5c(cc4CN3C(=O)N3CCC(F)(F)CC3)O[C@@H](c3ccc(OCc4ccc(Cl)c(Cl)c4)cc3)CO5)C(=O)O)cc2)c1C] | 886 |

TABLE 1-continued

| Ex | Structure | LCMS (m/z) |
|---|---|---|
| 317 | 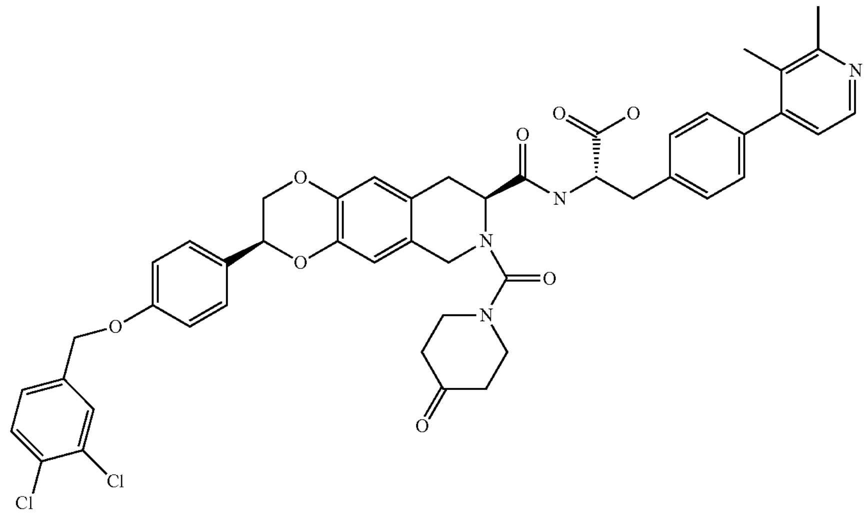 [SMILES: Cc1nccc(-c2ccc(C[C@H](NC(=O)[C@@H]3Cc4cc5c(cc4CN3C(=O)N3CCC(=O)CC3)O[C@@H](c3ccc(OCc4ccc(Cl)c(Cl)c4)cc3)CO5)C(=O)O)cc2)c1C] | 864 |
| 318 | 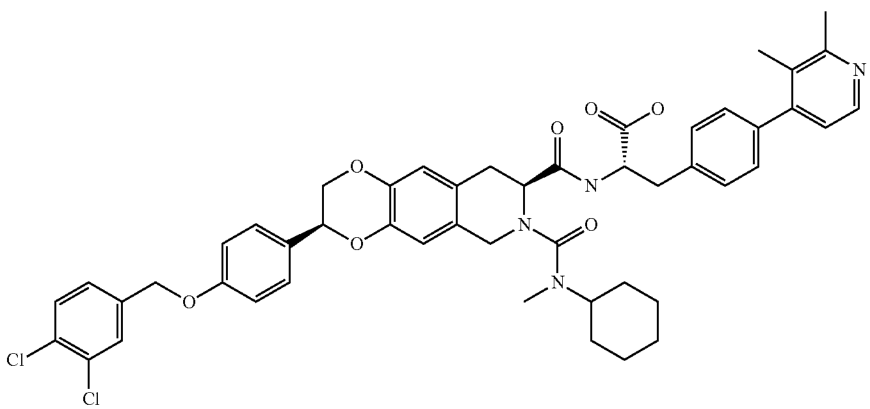 [SMILES: Cc1nccc(-c2ccc(C[C@H](NC(=O)[C@@H]3Cc4cc5c(cc4CN3C(=O)N(C)C3CCCCC3)O[C@@H](c3ccc(OCc4ccc(Cl)c(Cl)c4)cc3)CO5)C(=O)O)cc2)c1C] | 878 |
| 319 | 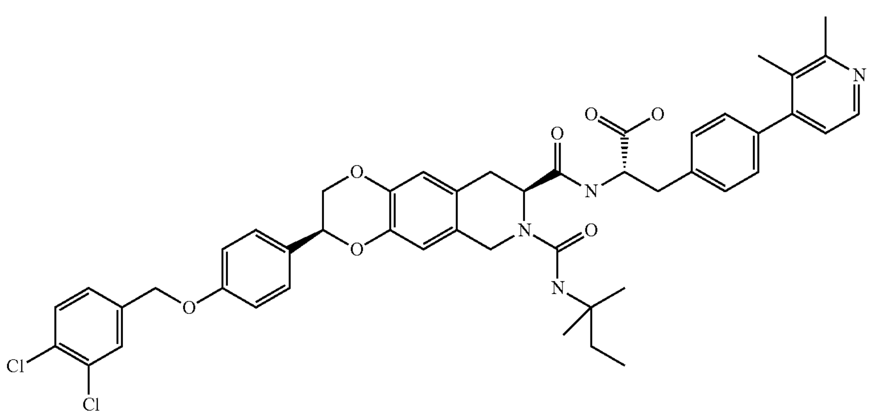 [SMILES: CCC(C)(C)NC(=O)N1Cc2cc3c(cc2C[C@H]1C(=O)N[C@@H](Cc1ccc(-c2ccnc(C)c2C)cc1)C(=O)O)OC[C@H](c1ccc(OCc2ccc(Cl)c(Cl)c2)cc1)O3] | 852 |

TABLE 1-continued
| Ex | Structure | LCMS (m/z) |
|---|---|---|
| 320 | 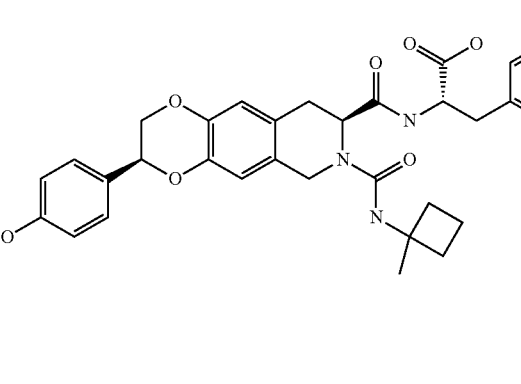 | 850 |
| 321 | 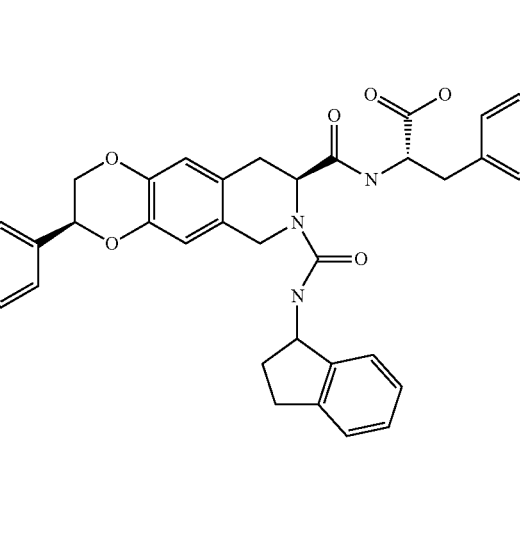 | 898 |
| 322 | 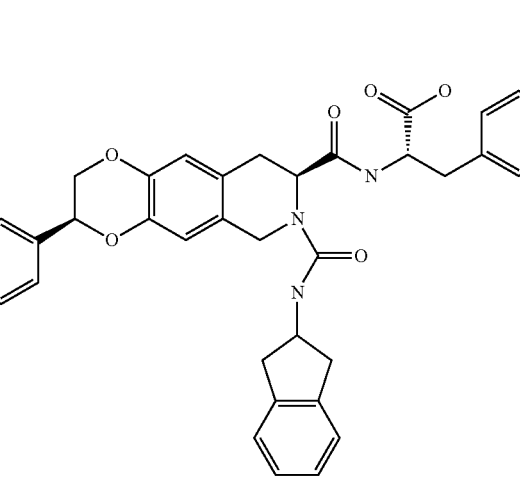 | 898 |

TABLE 1-continued

| Ex | Structure | LCMS (m/z) |
|---|---|---|
| 323 | 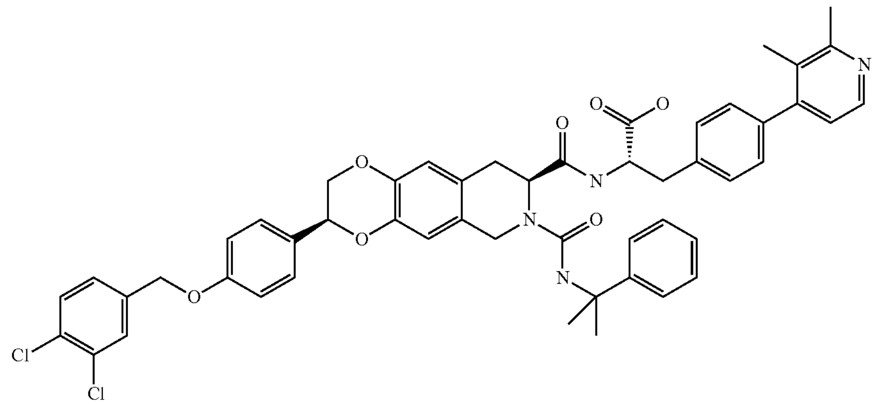 [SMILES: Cc1nccc(-c2ccc(C[C@H](NC(=O)[C@@H]3Cc4cc5c(cc4CN3C(=O)NC(C)(C)c3ccccc3)O[C@@H](c3ccc(OCc4ccc(Cl)c(Cl)c4)cc3)CO5)C(=O)O)cc2)c1C] | 900 |
| 324 | 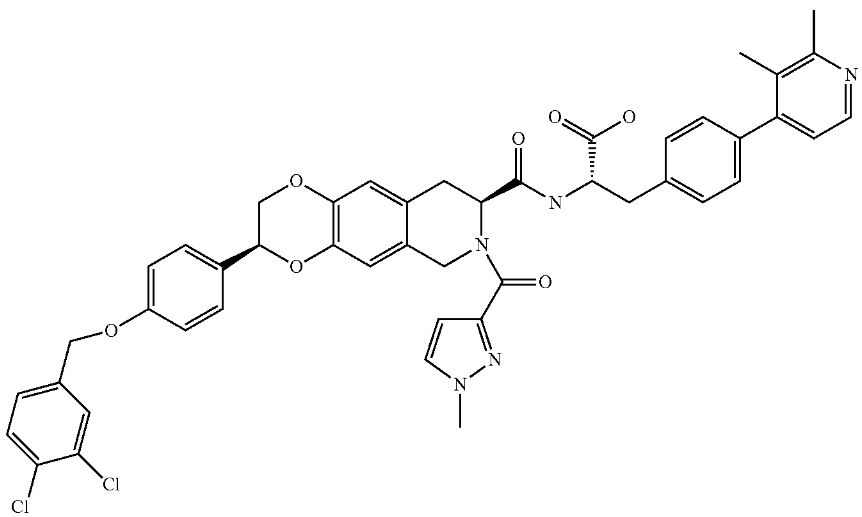 [SMILES: Cc1nccc(-c2ccc(C[C@H](NC(=O)[C@@H]3Cc4cc5c(cc4CN3C(=O)c3ccn(C)n3)O[C@@H](c3ccc(OCc4ccc(Cl)c(Cl)c4)cc3)CO5)C(=O)O)cc2)c1C] | 847 |
| 325 | 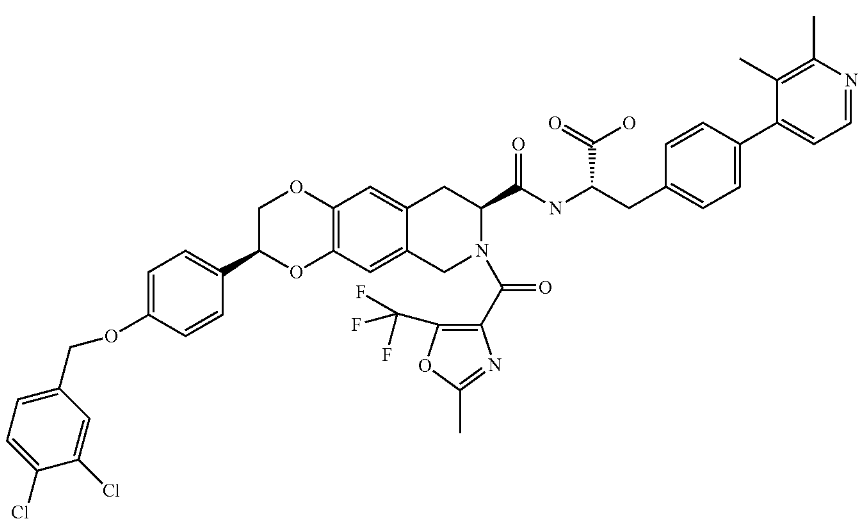 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)c(C(F)(F)F)o1] | 918 |

TABLE 1-continued

| Ex | Structure | LCMS (m/z) |
|---|---|---|
| 326 | 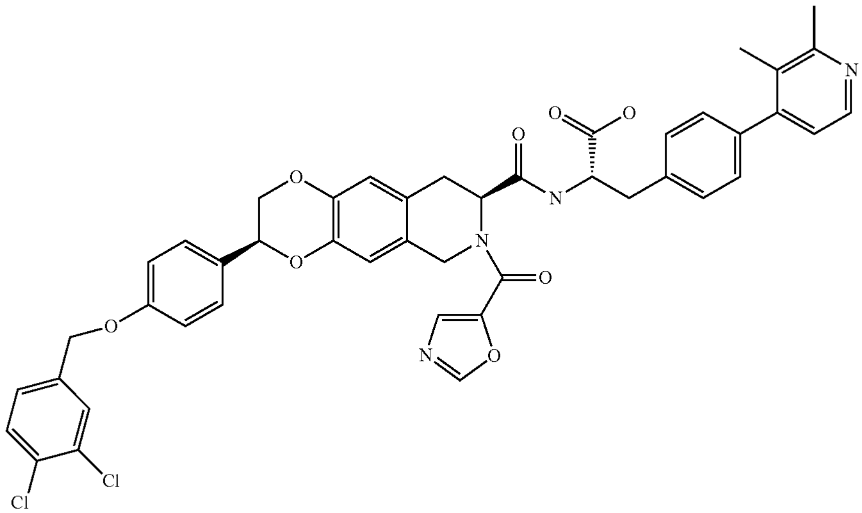 [SMILES: Cc1nccc(-c2ccc(C[C@H](NC(=O)[C@@H]3Cc4cc5c(cc4CN3C(=O)c3cnco3)O[C@@H](c3ccc(OCc4ccc(Cl)c(Cl)c4)cc3)CO5)C(=O)O)cc2)c1C] | 834 |
| 327 | 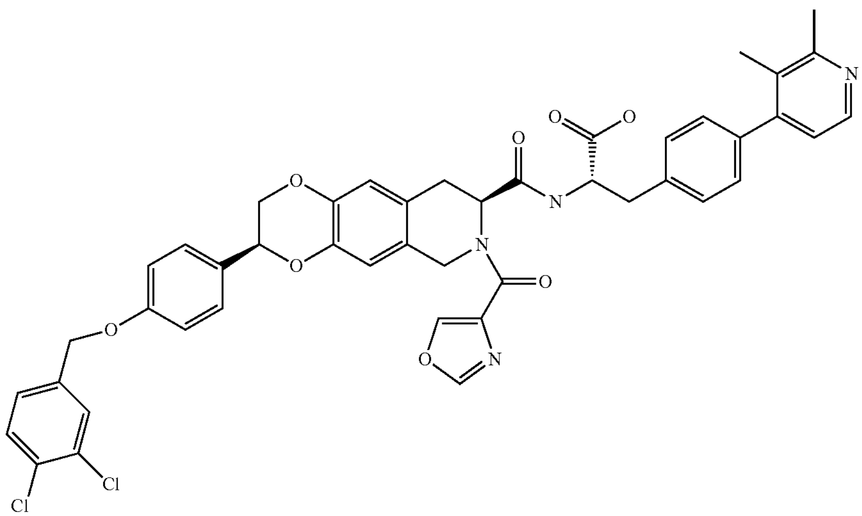 [SMILES: Cc1nccc(-c2ccc(C[C@H](NC(=O)[C@@H]3Cc4cc5c(cc4CN3C(=O)c3cocn3)O[C@@H](c3ccc(OCc4ccc(Cl)c(Cl)c4)cc3)CO5)C(=O)O)cc2)c1C] | 834 |
| 328 | 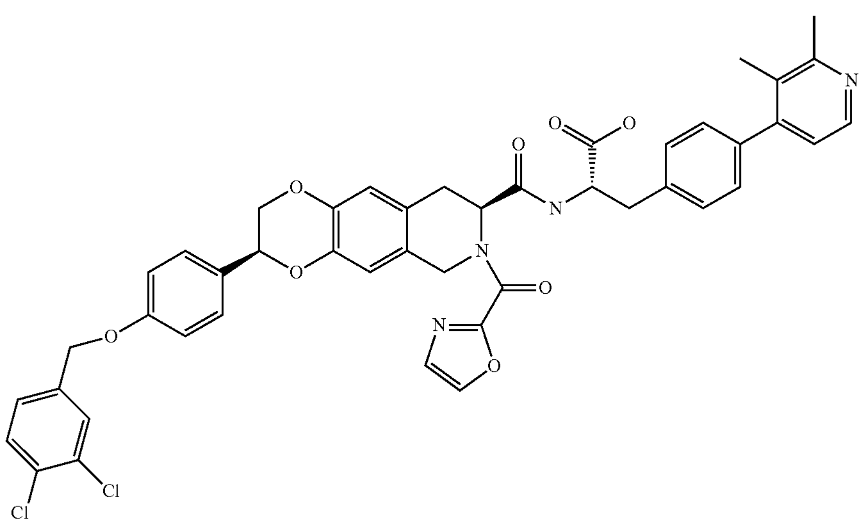 | 834 |

TABLE 1-continued
| Ex | Structure | LCMS (m/z) |
|---|---|---|
| 329 | 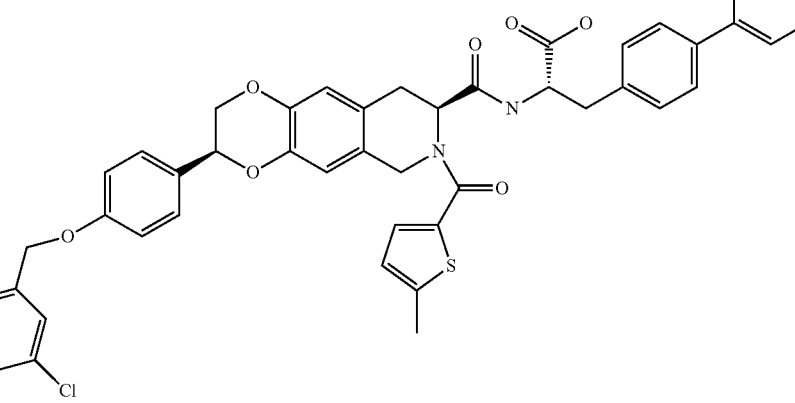 | 863 |
| 330 | 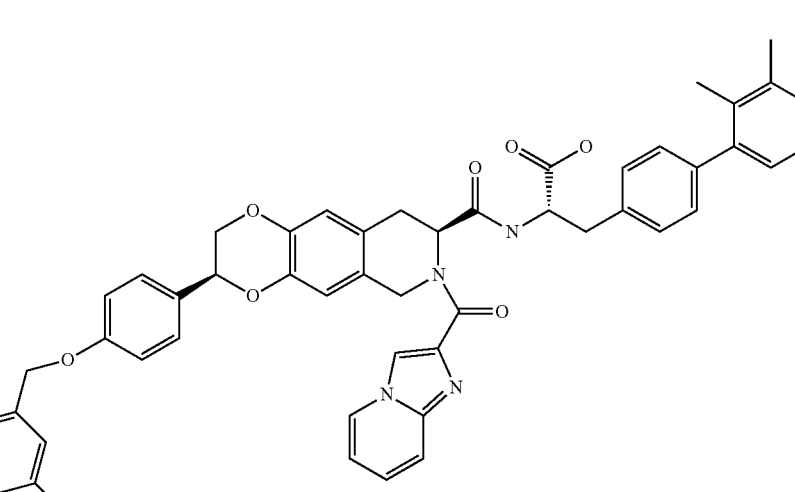 | 885 |
| 331 | 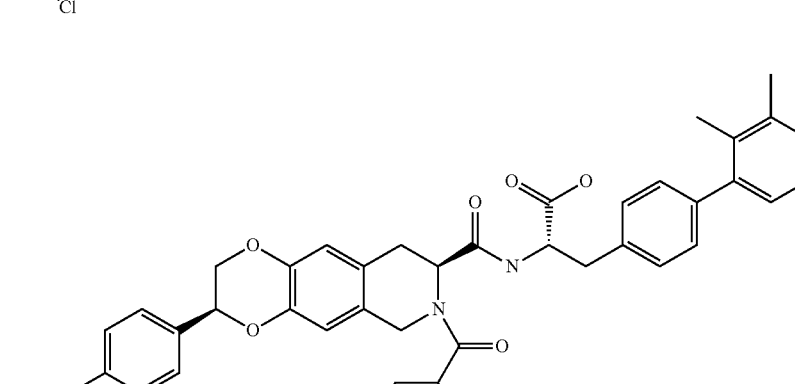 | 879 |

TABLE 1-continued

| Ex | Structure | LCMS (m/z) |
|---|---|---|
| 332 | 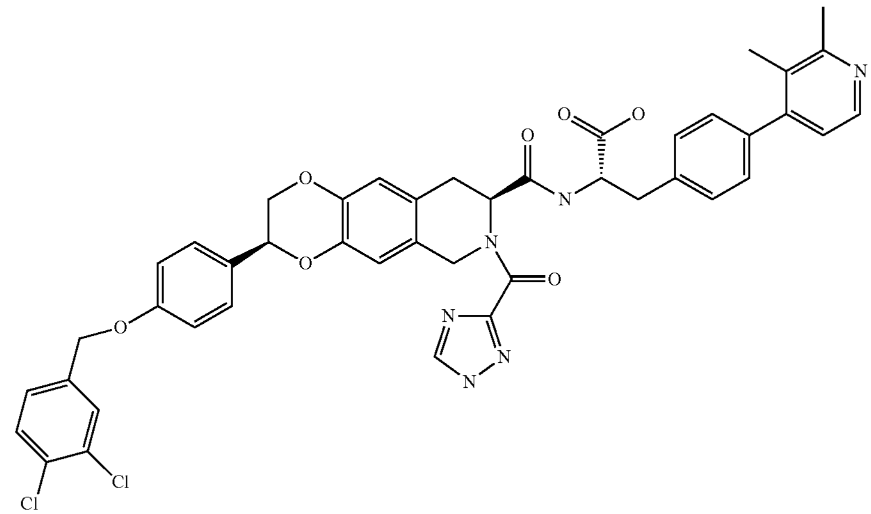 [SMILES: Cc1nccc(-c2ccc(C[C@H](NC(=O)[C@@H]3Cc4cc5c(cc4CN3C(=O)c3nc[nH]n3)O[C@@H](c3ccc(OCc4ccc(Cl)c(Cl)c4)cc3)CO5)C(=O)O)cc2)c1C] | 834 |
| 333 | 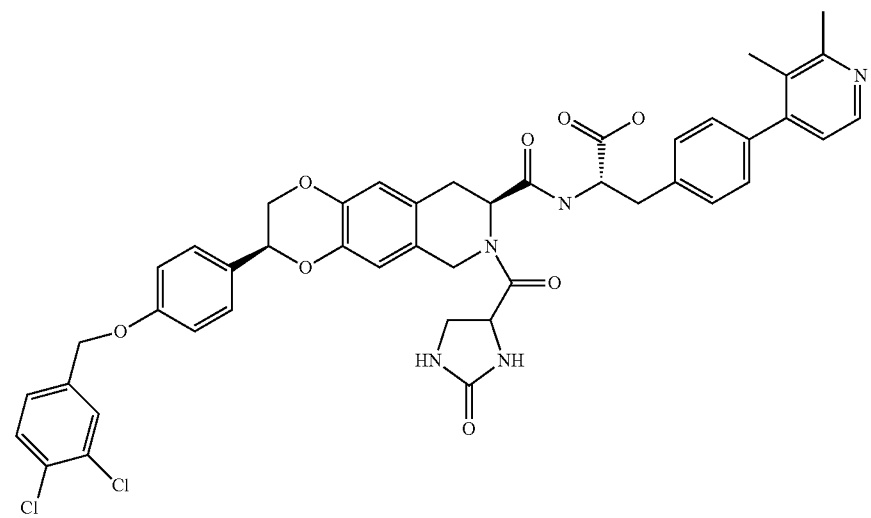 [SMILES: Cc1nccc(-c2ccc(C[C@H](NC(=O)[C@@H]3Cc4cc5c(cc4CN3C(=O)C3CNC(=O)N3)O[C@@H](c3ccc(OCc4ccc(Cl)c(Cl)c4)cc3)CO5)C(=O)O)cc2)c1C] | 851 |
| 334 | 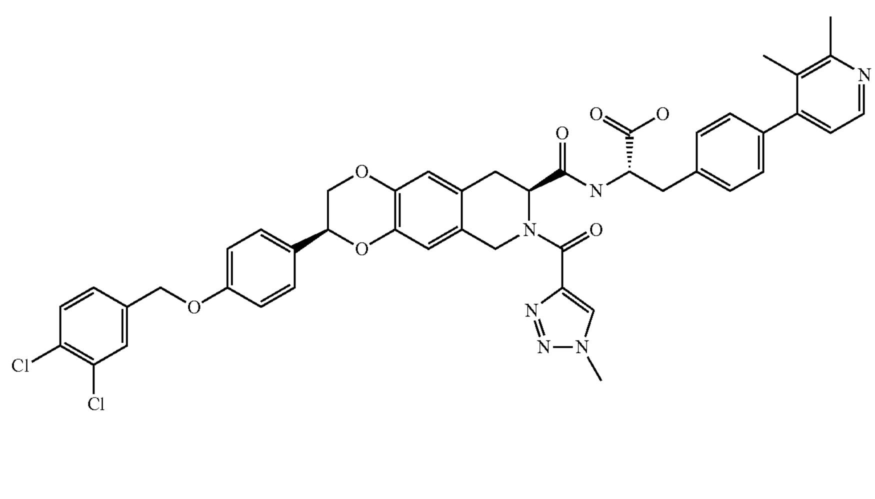 [SMILES: Cc1nccc(-c2ccc(C[C@H](NC(=O)[C@@H]3Cc4cc5c(cc4CN3C(=O)c3cn(C)nn3)O[C@@H](c3ccc(OCc4ccc(Cl)c(Cl)c4)cc3)CO5)C(=O)O)cc2)c1C] | 848 |

TABLE 1-continued

| Ex | Structure | LCMS (m/z) |
|---|---|---|
| 335 | 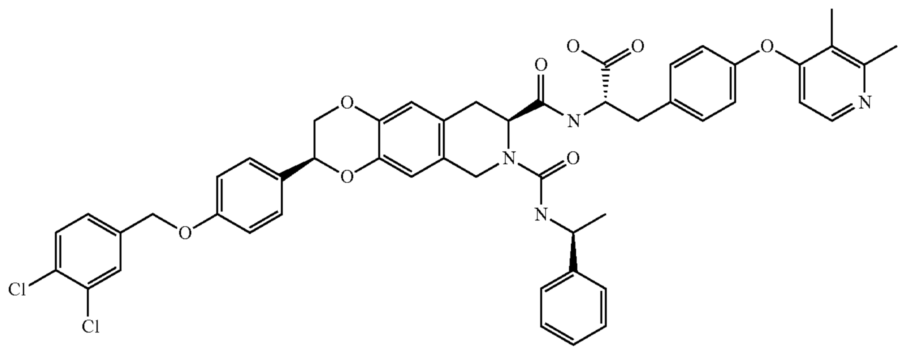 [SMILES: Cc1nccc(Oc2ccc(C[C@H](NC(=O)[C@@H]3Cc4cc5c(cc4CN3C(=O)N[C@@H](C)c3ccccc3)O[C@@H](c3ccc(OCc4ccc(Cl)c(Cl)c4)cc3)CO5)C(=O)O)cc2)c1C] | 902 |
| 336 | 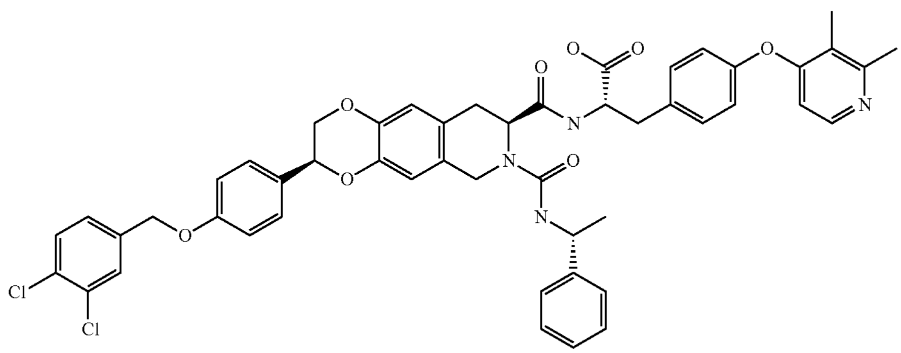 [SMILES: Cc1nccc(Oc2ccc(C[C@H](NC(=O)[C@@H]3Cc4cc5c(cc4CN3C(=O)N[C@H](C)c3ccccc3)O[C@@H](c3ccc(OCc4ccc(Cl)c(Cl)c4)cc3)CO5)C(=O)O)cc2)c1C] | 904 |
| 337 | 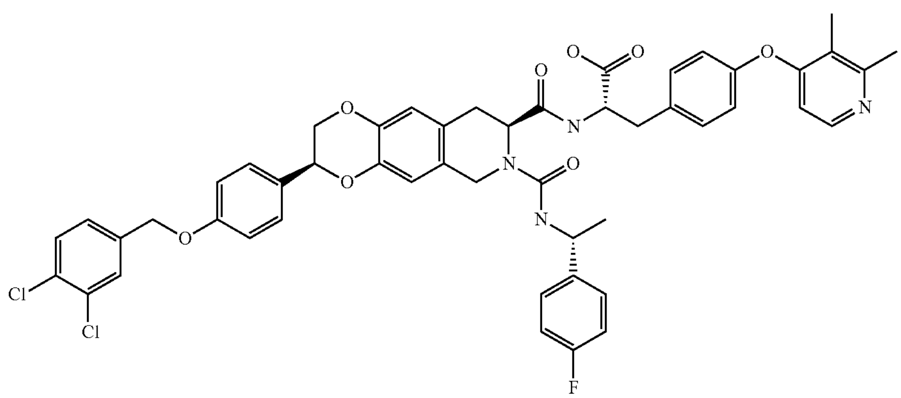 [SMILES: Cc1nccc(Oc2ccc(C[C@H](NC(=O)[C@@H]3Cc4cc5c(cc4CN3C(=O)N[C@H](C)c3ccc(F)cc3)O[C@@H](c3ccc(OCc4ccc(Cl)c(Cl)c4)cc3)CO5)C(=O)O)cc2)c1C] | 920 |
| 338 | 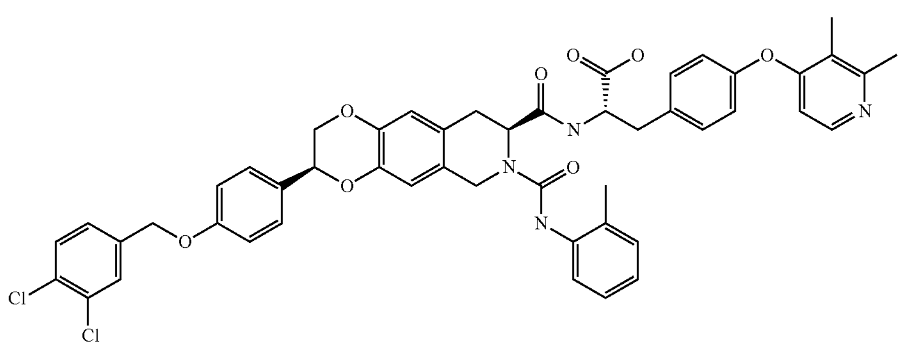 [SMILES: Cc1ccccc1NC(=O)N1Cc2cc3c(cc2C[C@H]1C(=O)N[C@@H](Cc1ccc(Oc2ccnc(C)c2C)cc1)C(=O)O)OC[C@H](c1ccc(OCc2ccc(Cl)c(Cl)c2)cc1)O3] | 888 |

TABLE 1-continued

| Ex | Structure | LCMS (m/z) |
|---|---|---|
| 339 | 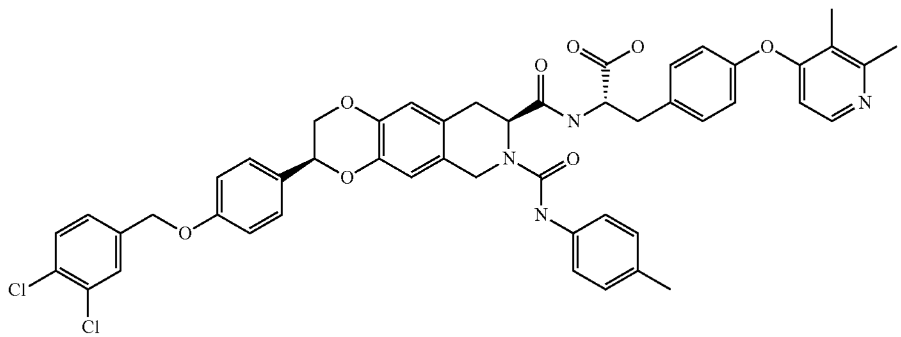 [SMILES: Cc1ccc(NC(=O)N2Cc3cc4c(cc3C[C@H]2C(=O)N[C@@H](Cc2ccc(Oc3ccnc(C)c3C)cc2)C(=O)O)OC[C@H](c2ccc(OCc3ccc(Cl)c(Cl)c3)cc2)O4)cc1] | 888 |
| 340 | 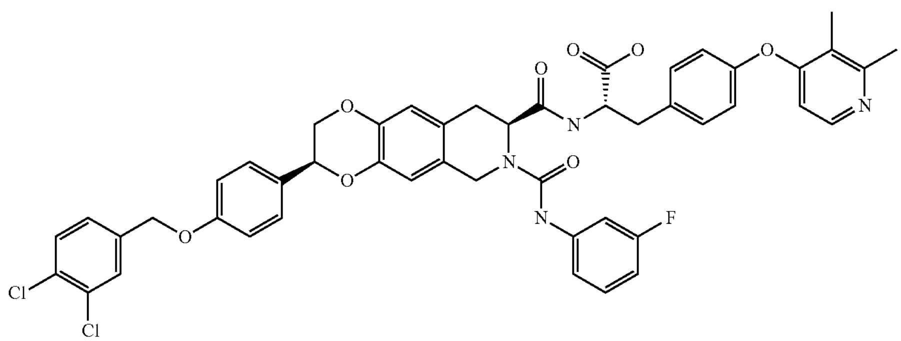 [SMILES: Cc1nccc(Oc2ccc(C[C@H](NC(=O)[C@@H]3Cc4cc5c(cc4CN3C(=O)Nc3cccc(F)c3)O[C@@H](c3ccc(OCc4ccc(Cl)c(Cl)c4)cc3)CO5)C(=O)O)cc2)c1C] | 892 |
| 341 | 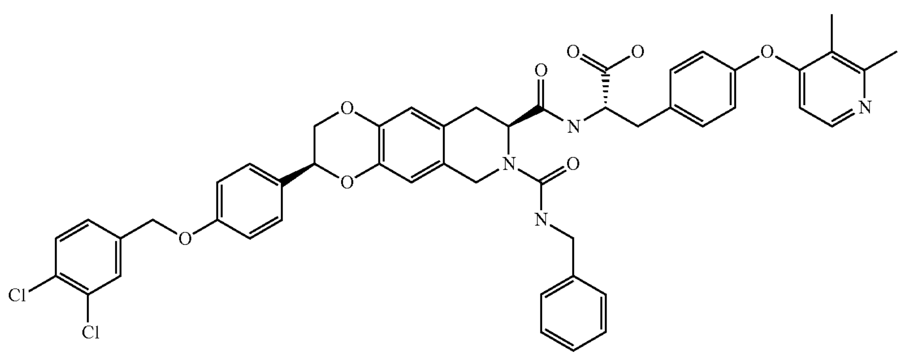 [SMILES: Cc1nccc(Oc2ccc(C[C@H](NC(=O)[C@@H]3Cc4cc5c(cc4CN3C(=O)NCc3ccccc3)O[C@@H](c3ccc(OCc4ccc(Cl)c(Cl)c4)cc3)CO5)C(=O)O)cc2)c1C] | 888 |
| 342 | 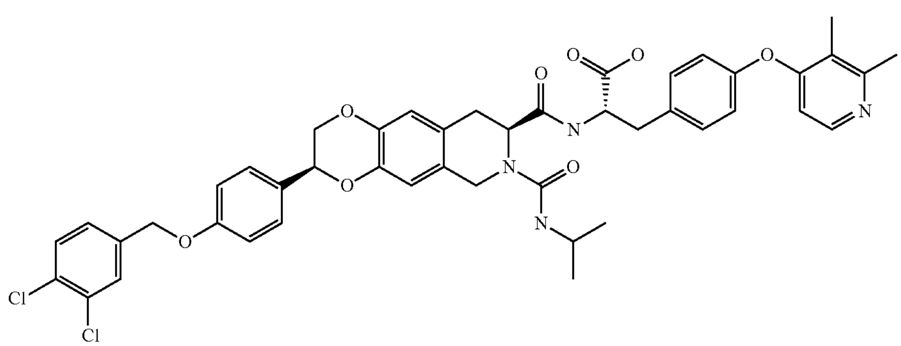 | 840 |

TABLE 1-continued

| Ex | Structure | LCMS (m/z) |
|---|---|---|
| 343 | 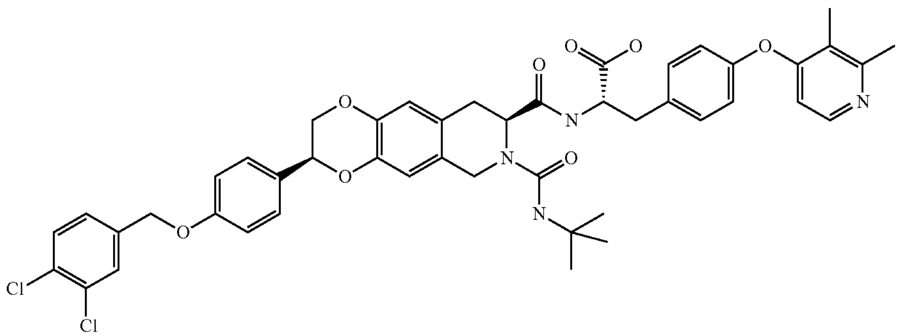 [SMILES: Cc1nccc(Oc2ccc(C[C@H](NC(=O)[C@@H]3Cc4cc5c(cc4CN3C(=O)NC(C)(C)C)O[C@@H](c3ccc(OCc4ccc(Cl)c(Cl)c4)cc3)CO5)C(=O)O)cc2)c1C] | 854 |
| 344 | 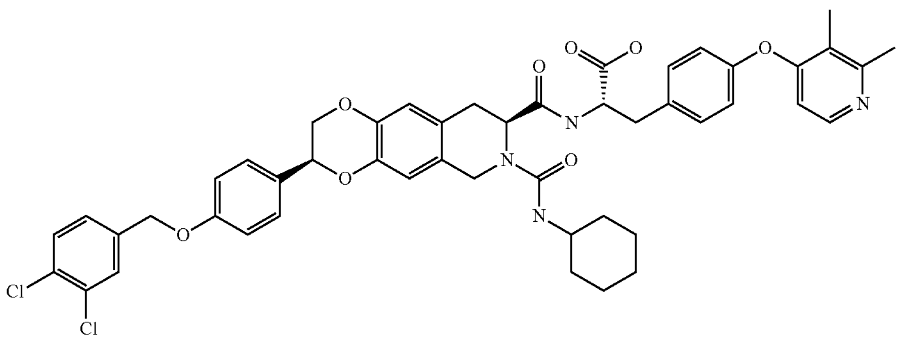 [SMILES: Cc1nccc(Oc2ccc(C[C@H](NC(=O)[C@@H]3Cc4cc5c(cc4CN3C(=O)NC3CCCCC3)O[C@@H](c3ccc(OCc4ccc(Cl)c(Cl)c4)cc3)CO5)C(=O)O)cc2)c1C] | 880 |
| 345 | 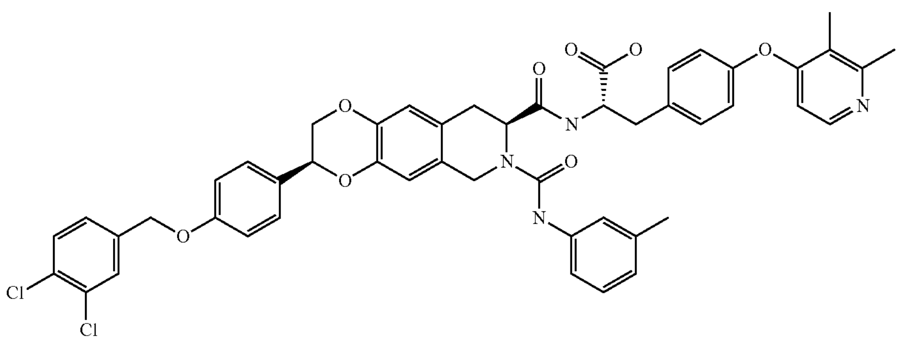 [SMILES: Cc1cccc(NC(=O)N2Cc3cc4c(cc3C[C@H]2C(=O)N[C@@H](Cc2ccc(Oc3ccnc(C)c3C)cc2)C(=O)O)OC[C@H](c2ccc(OCc3ccc(Cl)c(Cl)c3)cc2)O4)c1] | 888 |
| 346 | 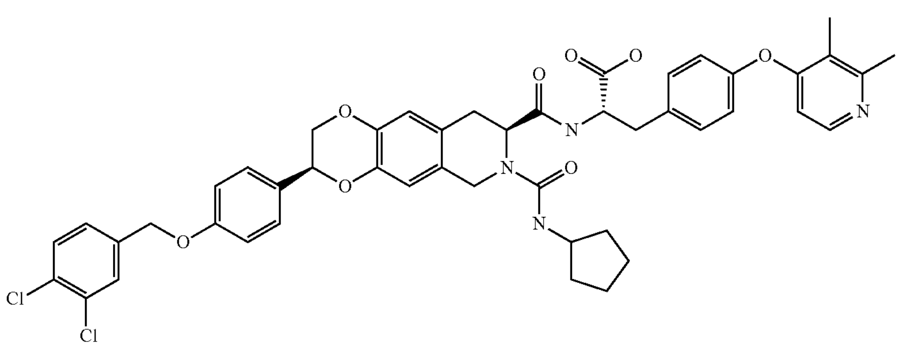 [SMILES: Cc1nccc(Oc2ccc(C[C@H](NC(=O)[C@@H]3Cc4cc5c(cc4CN3C(=O)NC3CCCC3)O[C@@H](c3ccc(OCc4ccc(Cl)c(Cl)c4)cc3)CO5)C(=O)O)cc2)c1C] | 866 |

TABLE 1-continued

| Ex | Structure | LCMS (m/z) |
|---|---|---|
| 347 | 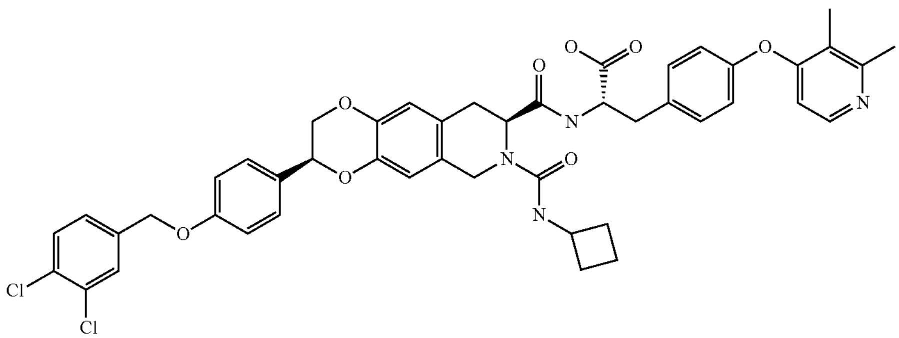 [SMILES: Cc1nccc(Oc2ccc(C[C@H](NC(=O)[C@@H]3Cc4cc5c(cc4CN3C(=O)NC3CCC3)O[C@@H](c3ccc(OCc4ccc(Cl)c(Cl)c4)cc3)CO5)C(=O)O)cc2)c1C] | 852 |
| 348 | 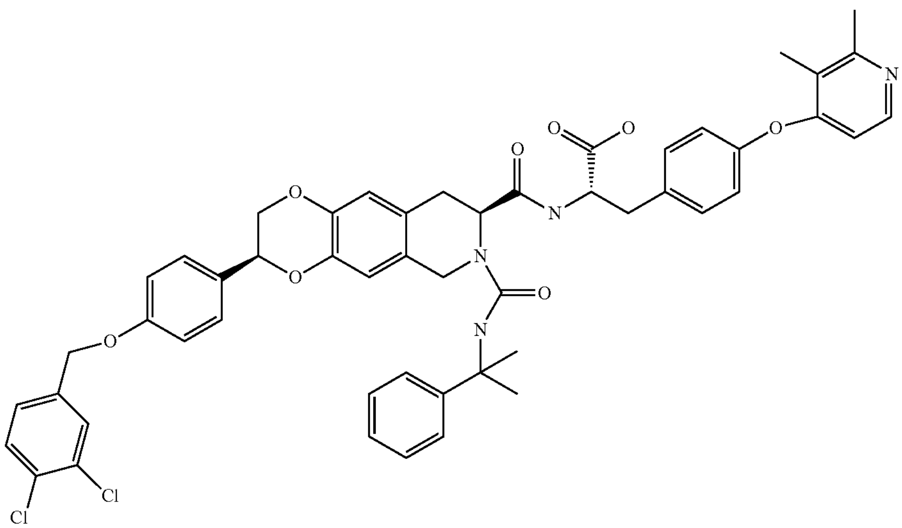 [SMILES: Cc1nccc(Oc2ccc(C[C@H](NC(=O)[C@@H]3Cc4cc5c(cc4CN3C(=O)NC(C)(C)c3ccccc3)O[C@@H](c3ccc(OCc4ccc(Cl)c(Cl)c4)cc3)CO5)C(=O)O)cc2)c1C] | 916 |
| 349 | 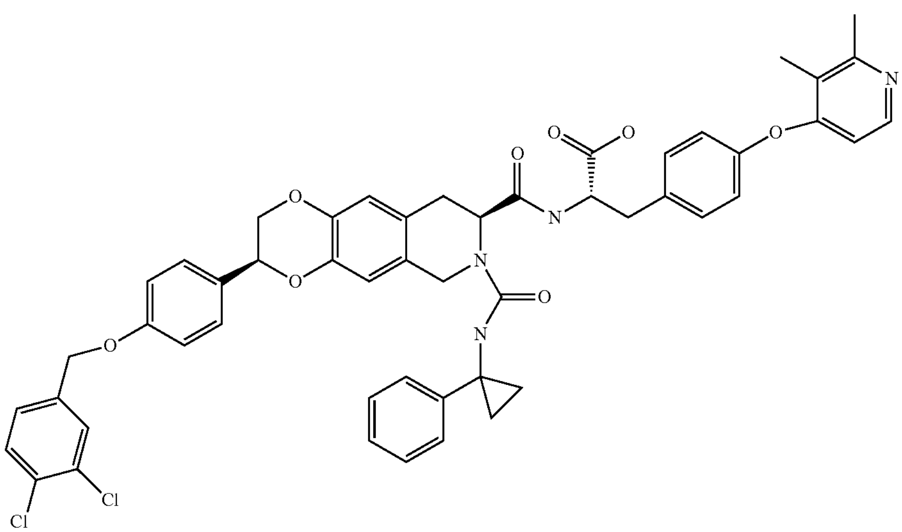 [SMILES: Cc1nccc(Oc2ccc(C[C@H](NC(=O)[C@@H]3Cc4cc5c(cc4CN3C(=O)NC3(c4ccccc4)CC3)O[C@@H](c3ccc(OCc4ccc(Cl)c(Cl)c4)cc3)CO5)C(=O)O)cc2)c1C] | 914 |

TABLE 1-continued
| Ex | Structure | LCMS (m/z) |
|---|---|---|
| 350 | 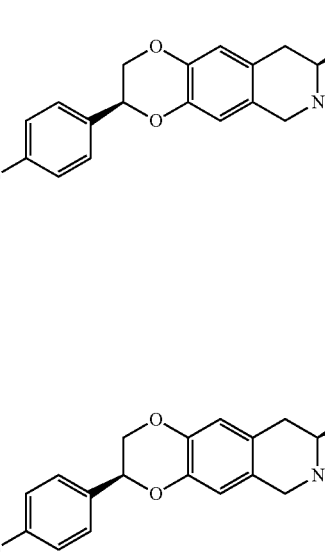 | 868 |
| 351 | 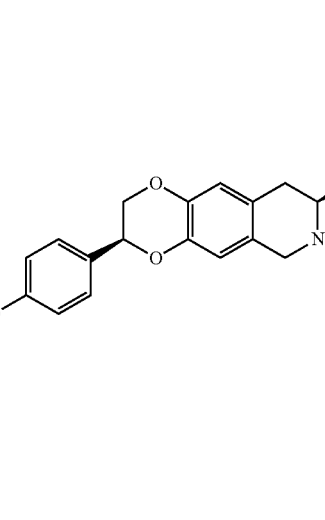 | 866 |
| 352 | 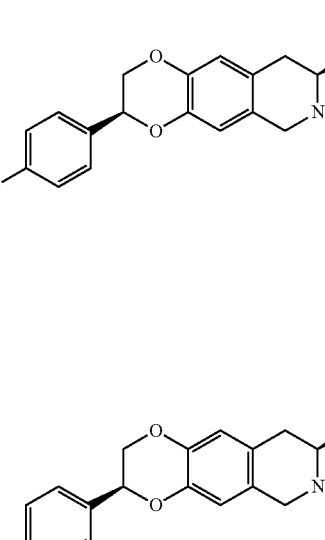 | 916 |
| 353 | 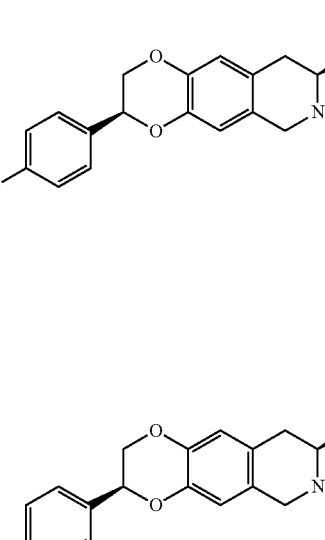 | 866 |

TABLE 1-continued
| Ex | Structure | LCMS (m/z) |
|---|---|---|
| 354 | 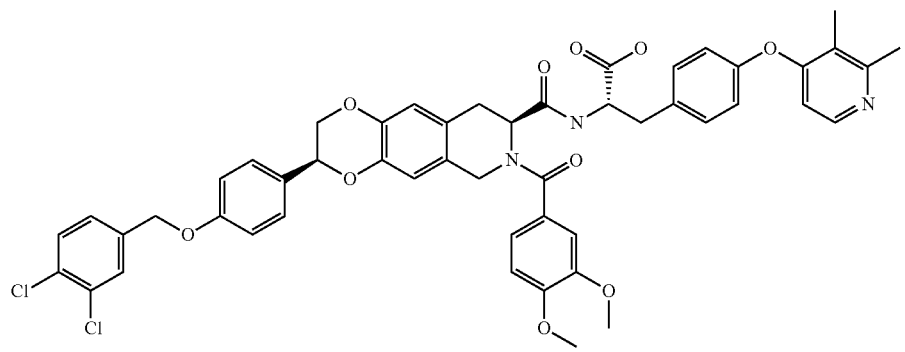 [SMILES: COc1ccc(C(=O)N2Cc3cc4c(cc3C[C@H]2C(=O)N[C@@H](Cc2ccc(Oc3ccnc(C)c3C)cc2)C(=O)O)OC[C@H](c2ccc(OCc3ccc(Cl)c(Cl)c3)cc2)O4)cc1OC] | 919 |
| 355 | 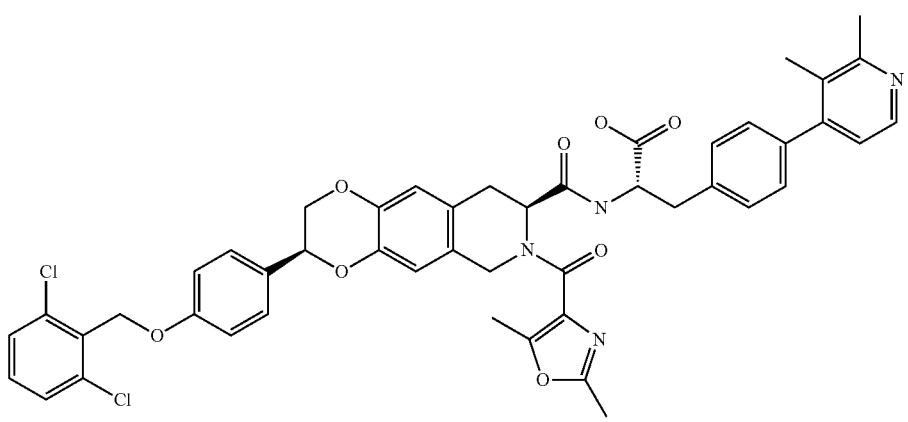 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3c(Cl)cccc3Cl)cc2)O4)c(C)o1] | 862 |
| 356 | 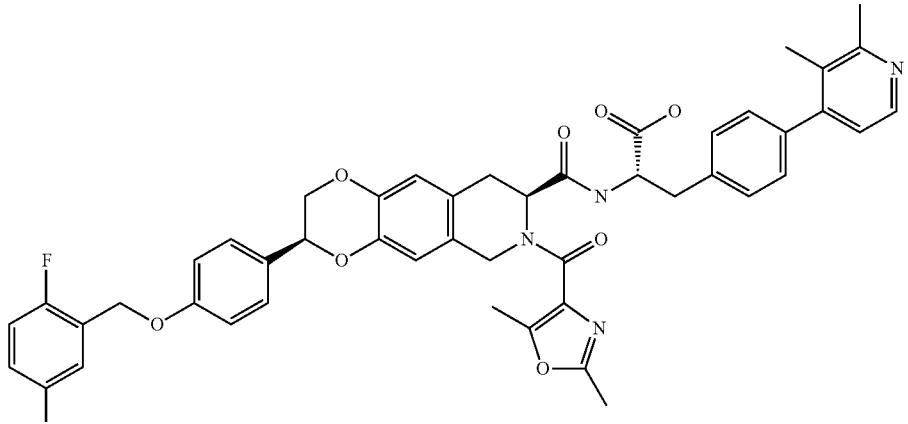 | 830 |

TABLE 1-continued

| Ex | Structure | LCMS (m/z) |
|---|---|---|
| 357 | 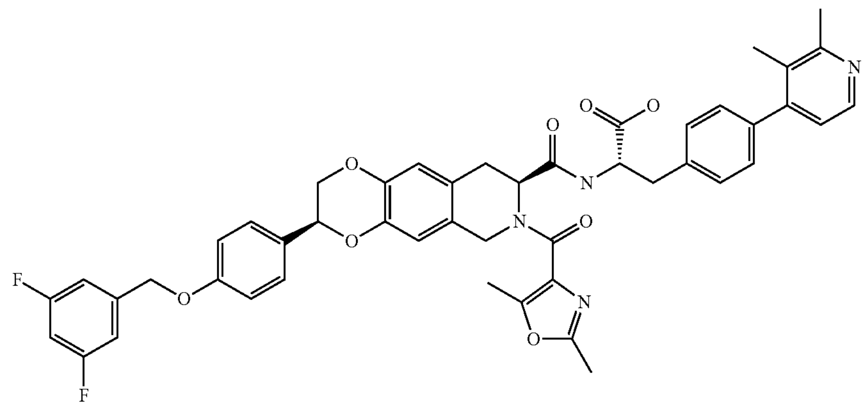 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3cc(F)cc(F)c3)cc2)O4)c(C)o1] | 830 |
| 358 | 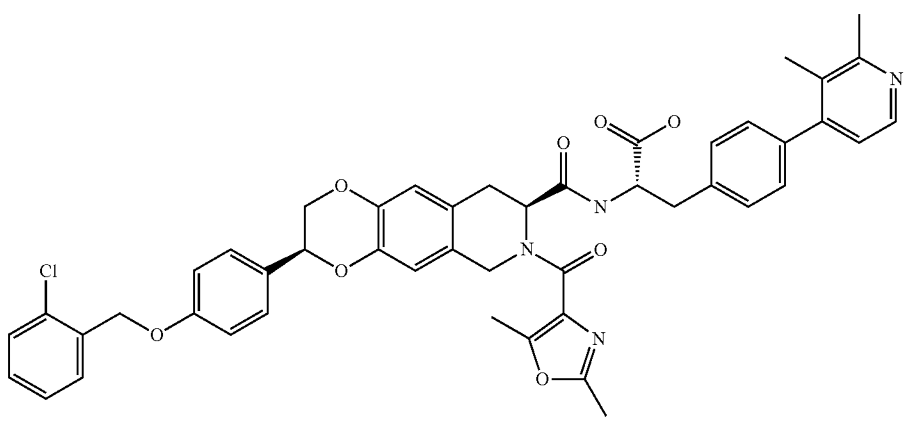 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3ccccc3Cl)cc2)O4)c(C)o1] | 828 |
| 359 | 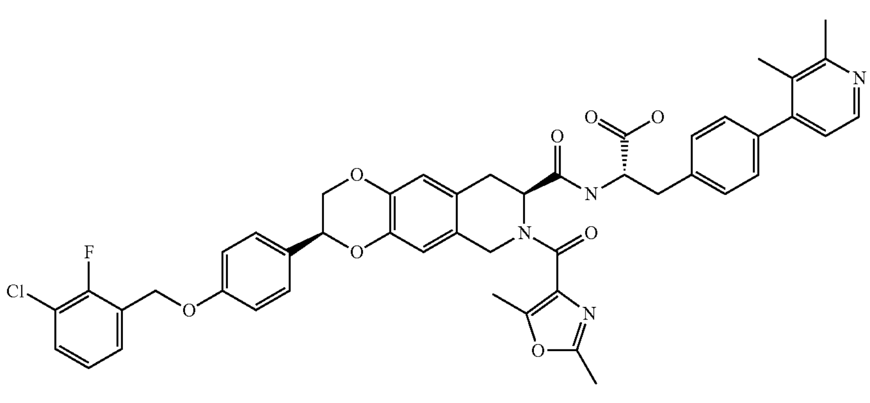 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3cccc(Cl)c3F)cc2)O4)c(C)o1] | 846 |

TABLE 1-continued
| Ex | Structure | LCMS (m/z) |
|---|---|---|
| 360 | 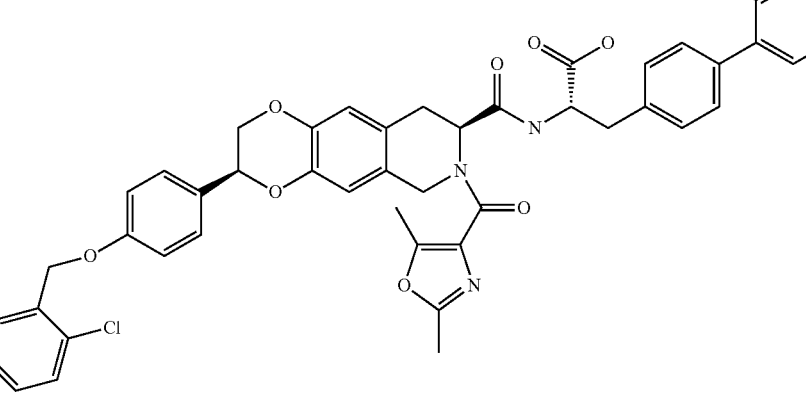 | 846 |
| 361 | 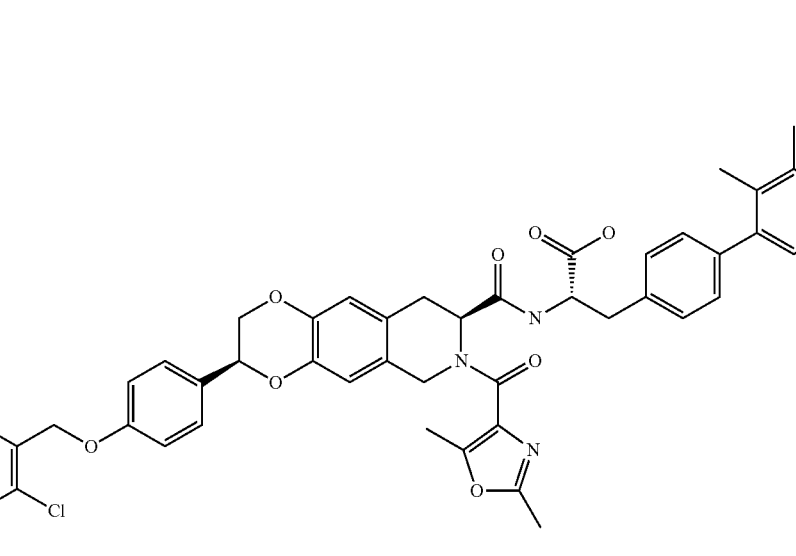 | 862 |
| 362 | 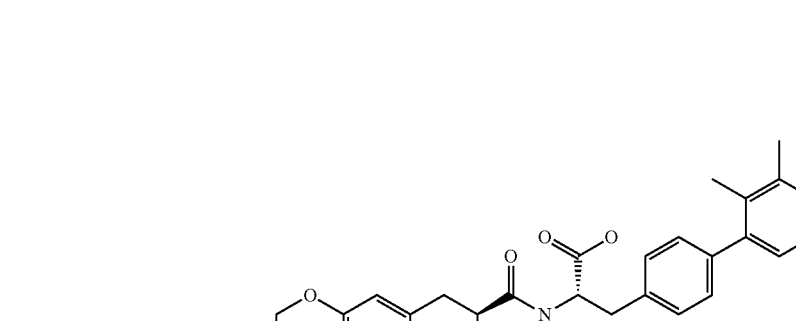 | 862 |

TABLE 1-continued

| Ex | Structure | LCMS (m/z) |
|---|---|---|
| 363 | 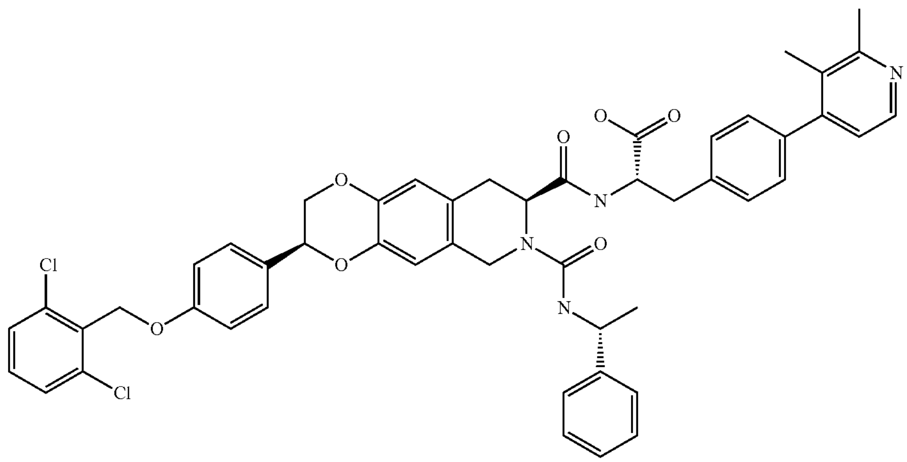 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCc4c(Cl)cccc4Cl)cc3)CO5)C(=O)O)cc2)c1C] | 886 |
| 364 | 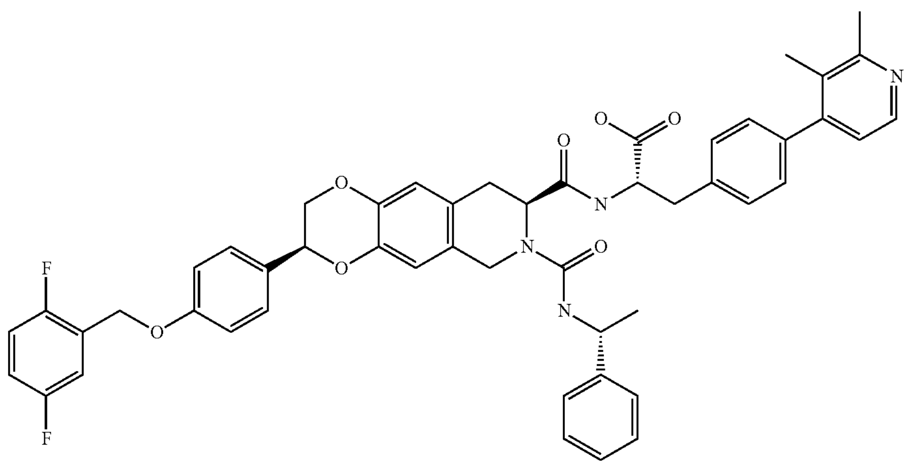 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCc4cc(F)ccc4F)cc3)CO5)C(=O)O)cc2)c1C] | 854 |
| 365 | 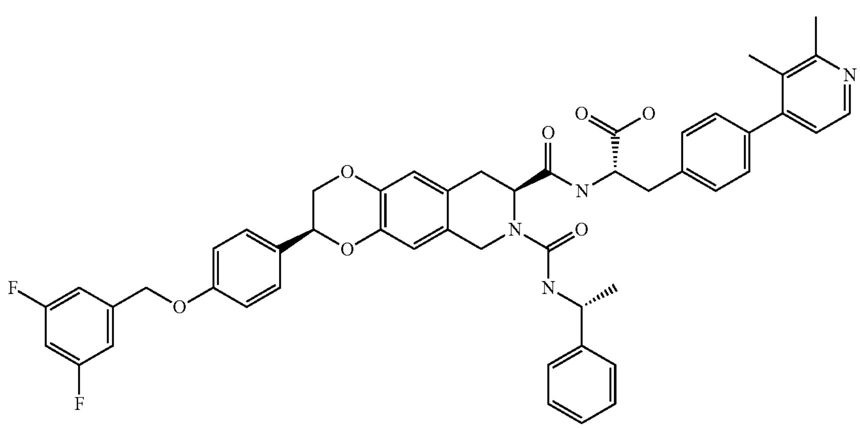 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCc4cc(F)cc(F)c4)cc3)CO5)C(=O)O)cc2)c1C] | 854 |

TABLE 1-continued

| Ex | Structure | LCMS (m/z) |
|---|---|---|
| 366 | 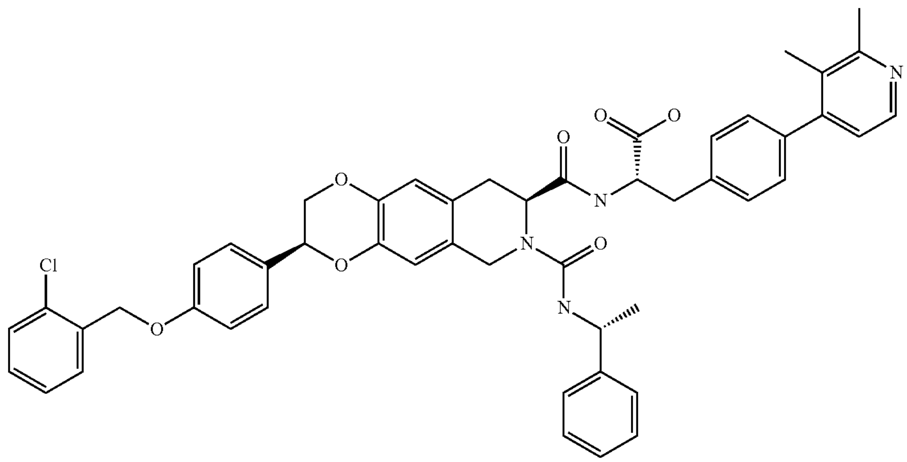 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCc4ccccc4Cl)cc3)CO5)C(=O)O)cc2)c1C] | 852 |
| 367 | 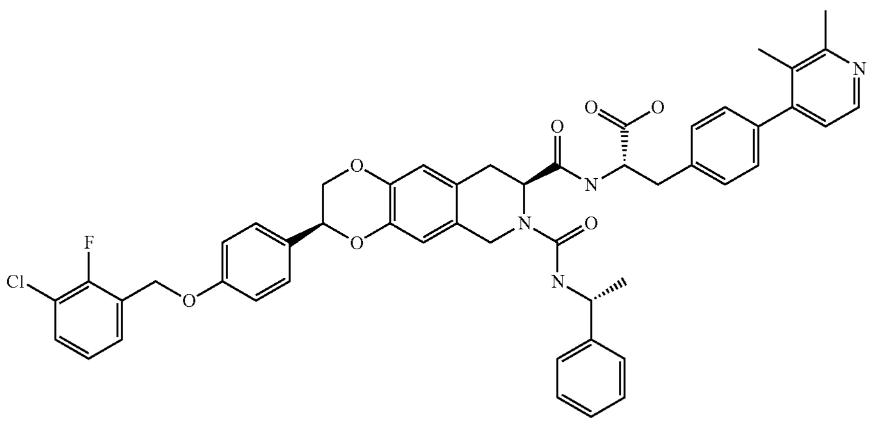 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCc4cccc(Cl)c4F)cc3)CO5)C(=O)O)cc2)c1C] | 870 |
| 368 | 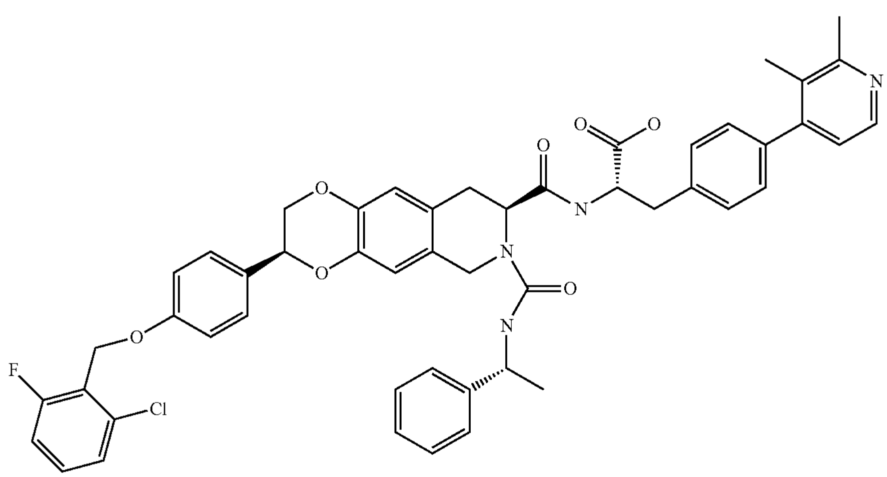 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCc4c(F)cccc4Cl)cc3)CO5)C(=O)O)cc2)c1C] | 870 |

TABLE 1-continued
| Ex | Structure | LCMS (m/z) |
|---|---|---|
| 369 | 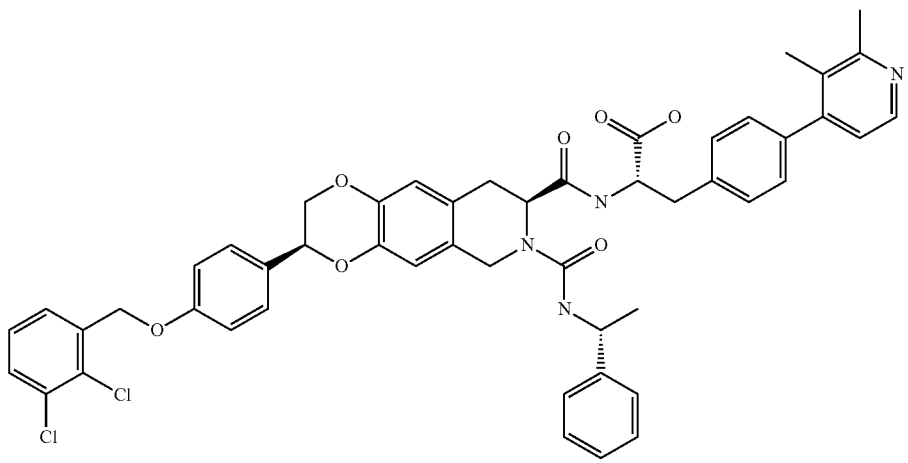 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCc4cccc(Cl)c4Cl)cc3)CO5)C(=O)O)cc2)c1C] | 886 |
| 370 | 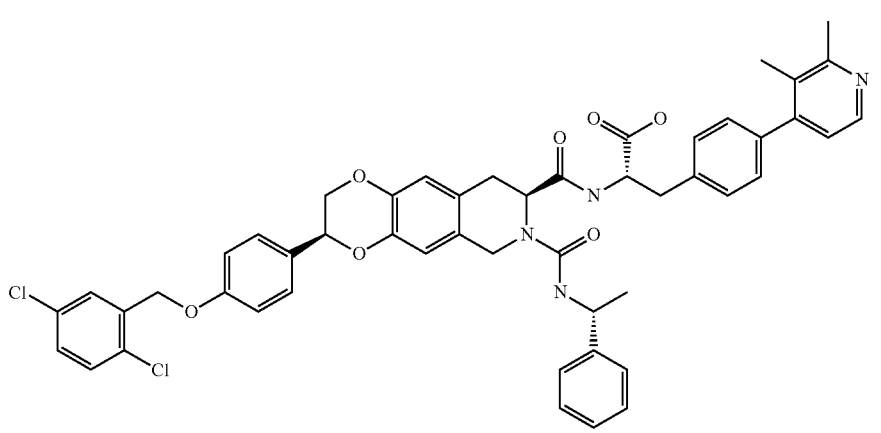 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCc4cc(Cl)ccc4Cl)cc3)CO5)C(=O)O)cc2)c1C] | 886 |
| 371 | 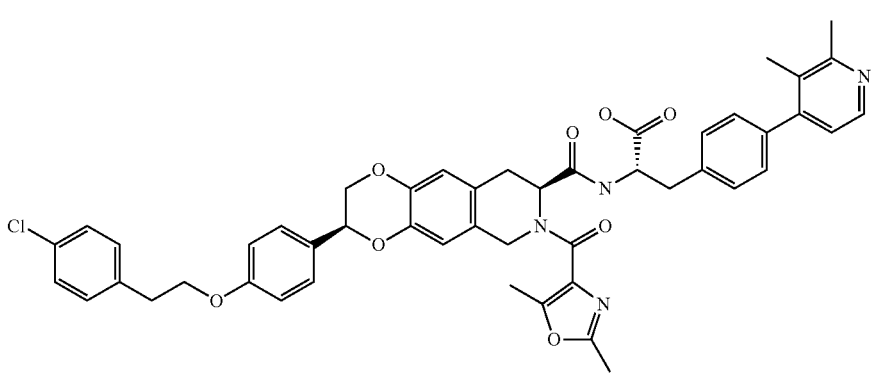 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCCc3ccc(Cl)cc3)cc2)O4)c(C)o1] | 842 |

TABLE 1-continued

| Ex | Structure | LCMS (m/z) |
|---|---|---|
| 372 | 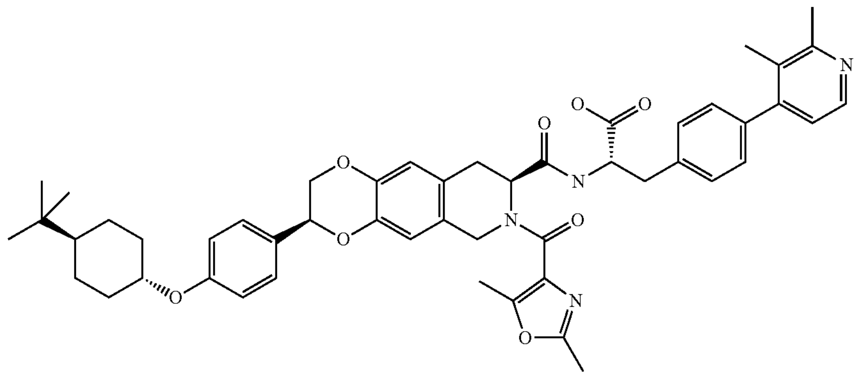 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(O[C@H]3CC[C@H](C(C)(C)C)CC3)cc2)O4)c(C)o1] | 842 |
| 373 | 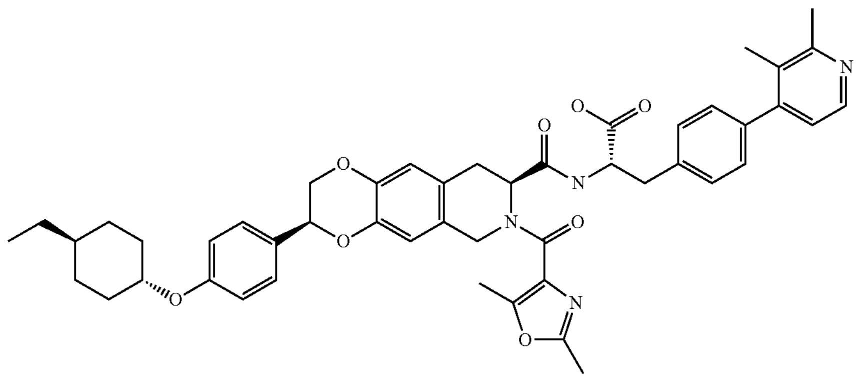 [SMILES: CC[C@H]1CC[C@H](Oc2ccc([C@H]3COc4cc5c(cc4O3)CN(C(=O)c3nc(C)oc3C)[C@H](C(=O)N[C@@H](Cc3ccc(-c4ccnc(C)c4C)cc3)C(=O)O)C5)cc2)CC1] | 814 |
| 374 | 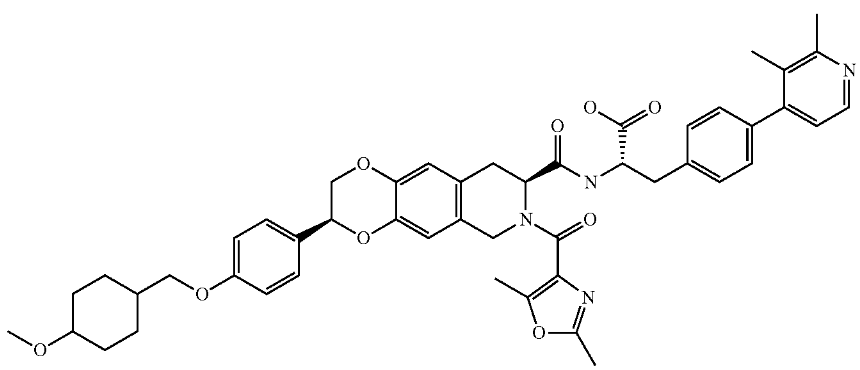 [SMILES: COC1CCC(COc2ccc([C@H]3COc4cc5c(cc4O3)CN(C(=O)c3nc(C)oc3C)[C@H](C(=O)N[C@@H](Cc3ccc(-c4ccnc(C)c4C)cc3)C(=O)O)C5)cc2)CC1] | 830 |
| 375 | 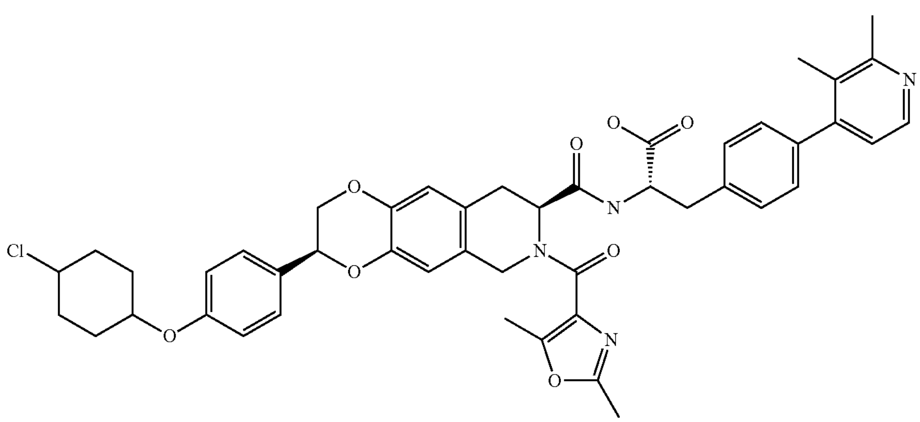 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OC3CCC(Cl)CC3)cc2)O4)c(C)o1] | 820 |

TABLE 1-continued
| Ex | Structure | LCMS (m/z) |
|---|---|---|
| 376 | 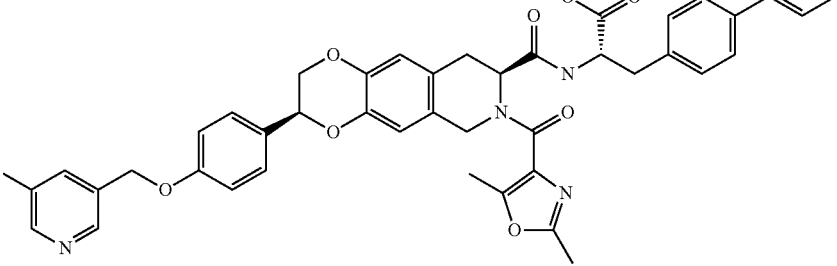 | 829 |
| 377 | 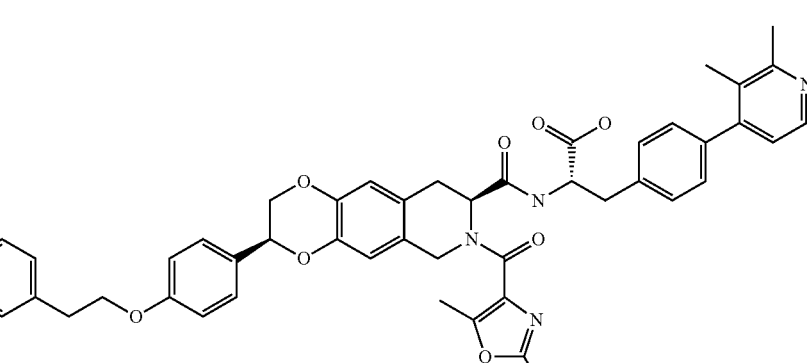 | 808 |
| 378 | 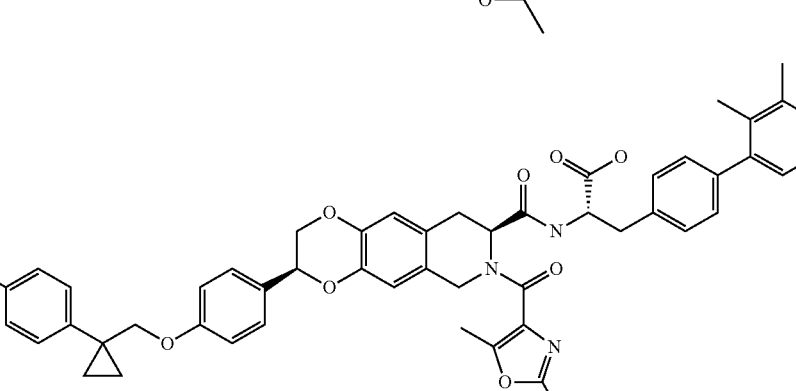 | 868 |
| 379 | 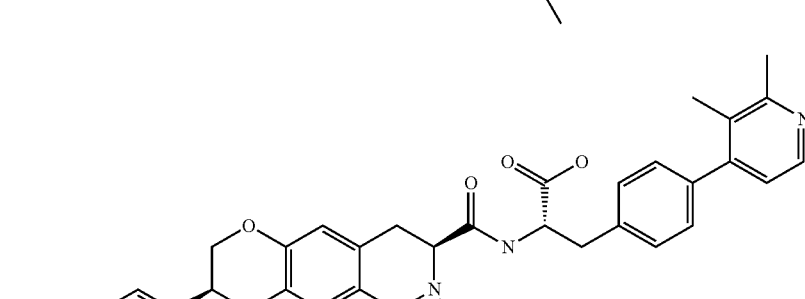 | 786 |

TABLE 1-continued
| Ex | Structure | LCMS (m/z) |
|---|---|---|
| 380 | 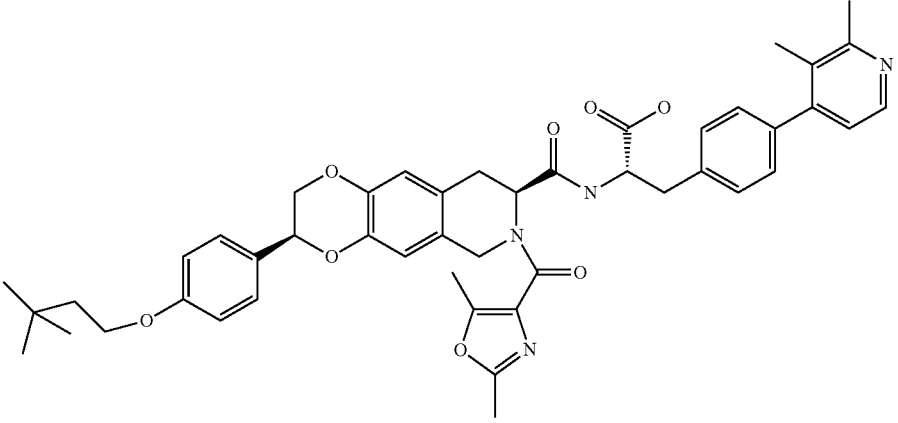 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCCC(C)(C)C)cc2)O4)c(C)o1] | 788 |
| 381 | 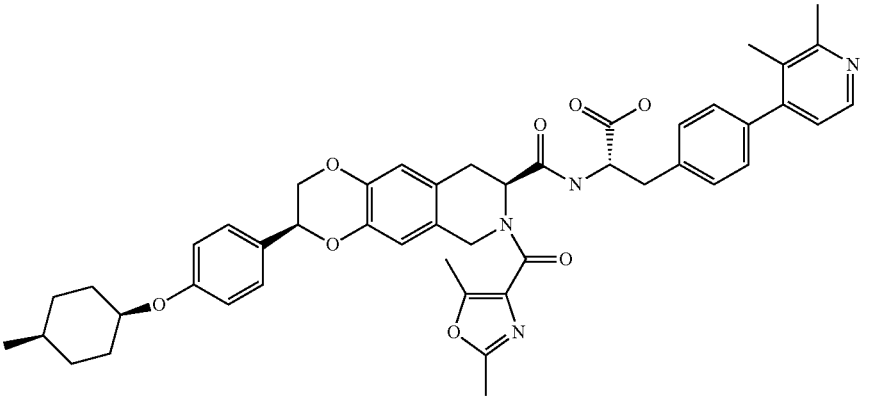 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(O[C@H]3CC[C@@H](C)CC3)cc2)O4)c(C)o1] | 800 |
| 382 | 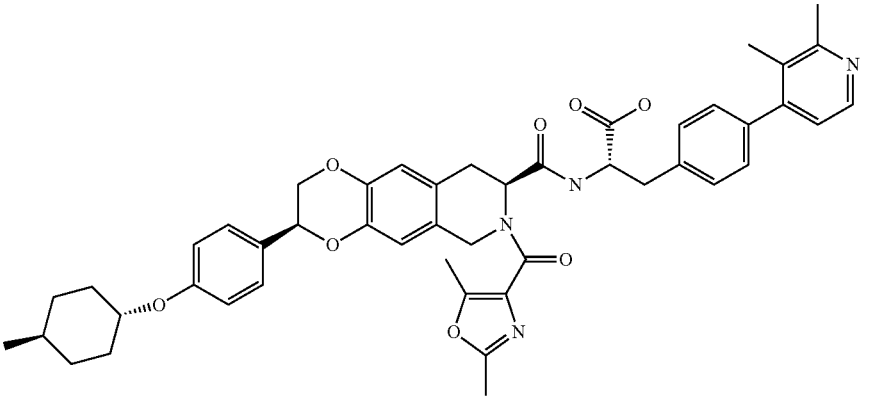 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(O[C@H]3CC[C@H](C)CC3)cc2)O4)c(C)o1] | 800 |

TABLE 1-continued

| Ex | Structure | LCMS (m/z) |
|---|---|---|
| 383 | 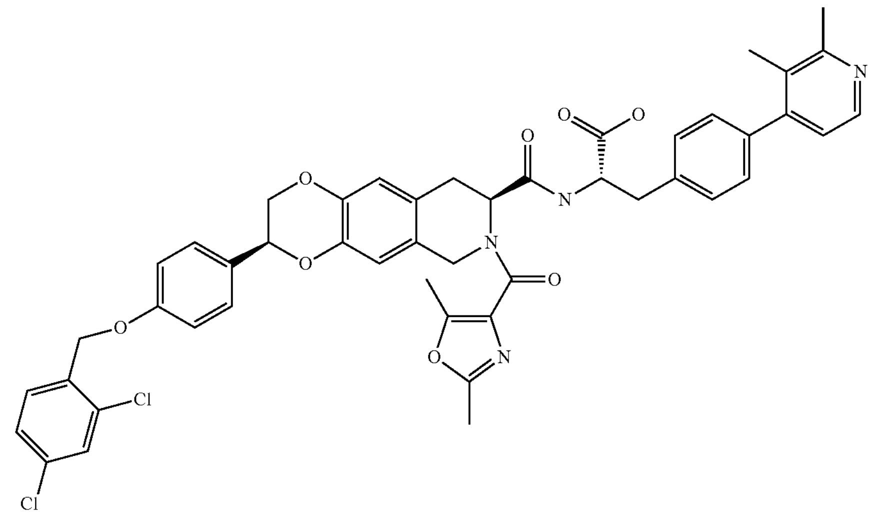 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)cc3Cl)cc2)O4)c(C)o1] | 862 |
| 384 | 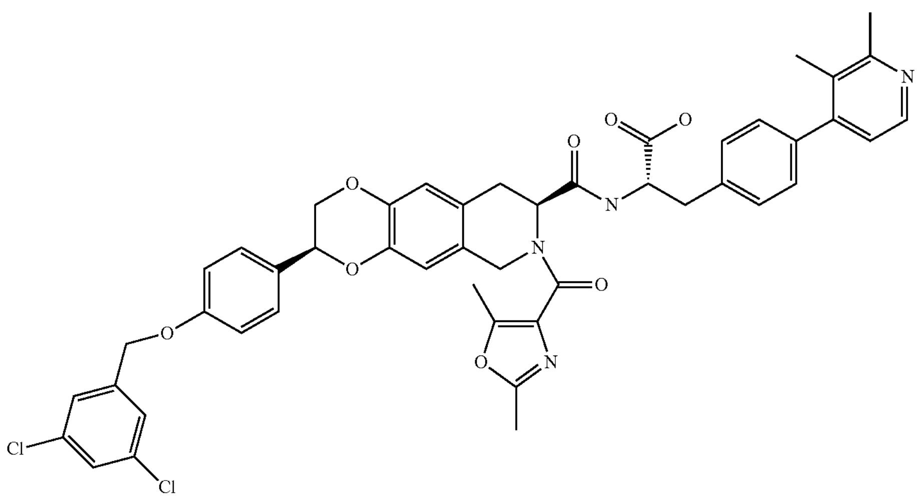 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3cc(Cl)cc(Cl)c3)cc2)O4)c(C)o1] | 862 |
| 385 | 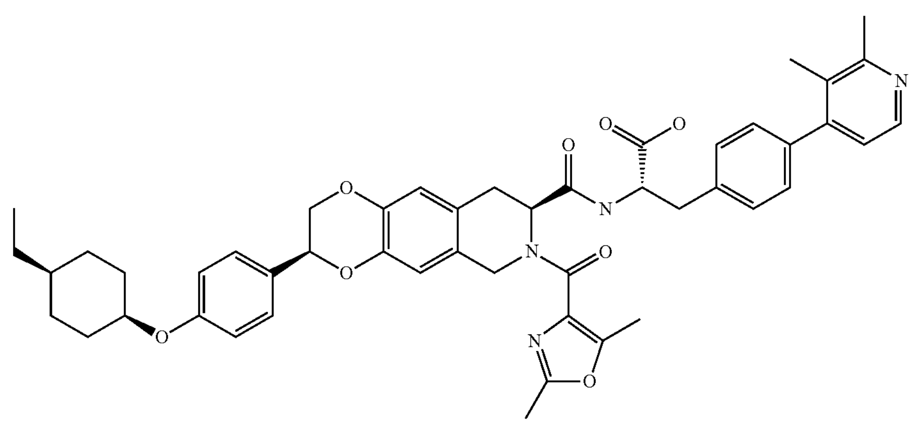 [SMILES: CC[C@H]1CC[C@@H](Oc2ccc([C@H]3COc4cc5c(cc4O3)CN(C(=O)c3nc(C)oc3C)[C@H](C(=O)N[C@@H](Cc3ccc(-c4ccnc(C)c4C)cc3)C(=O)O)C5)cc2)CC1] | 814 |

TABLE 1-continued

| Ex | Structure | LCMS (m/z) |
|---|---|---|
| 386 | 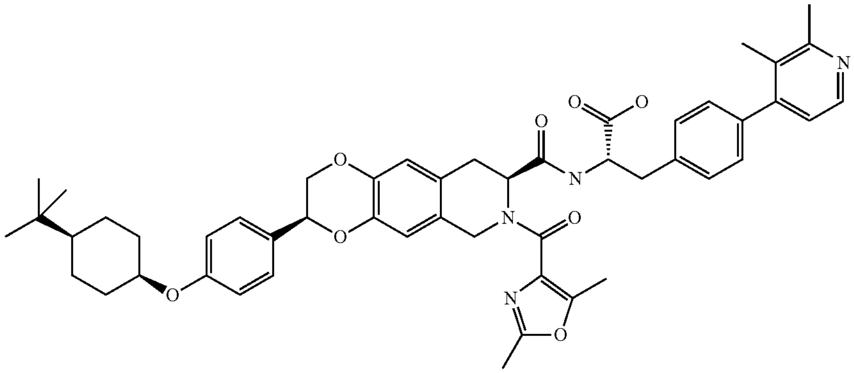 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(O[C@H]3CC[C@@H](C(C)(C)C)CC3)cc2)O4)c(C)o1] | 842 |
| 387 | 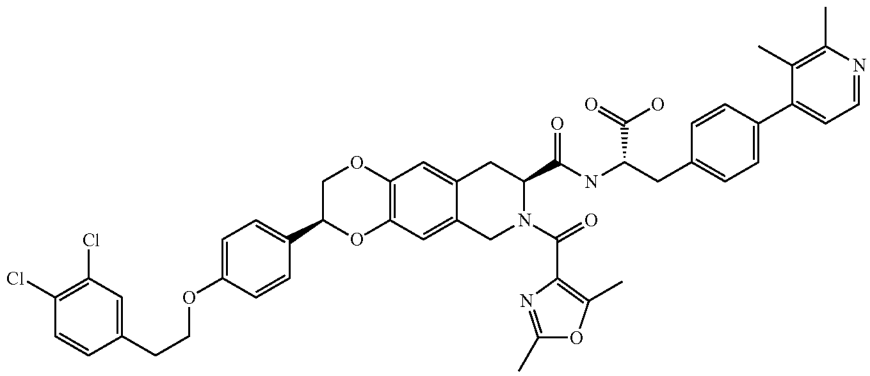 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCCc3ccc(Cl)c(Cl)c3)cc2)O4)c(C)o1] | 876 |
| 388 | 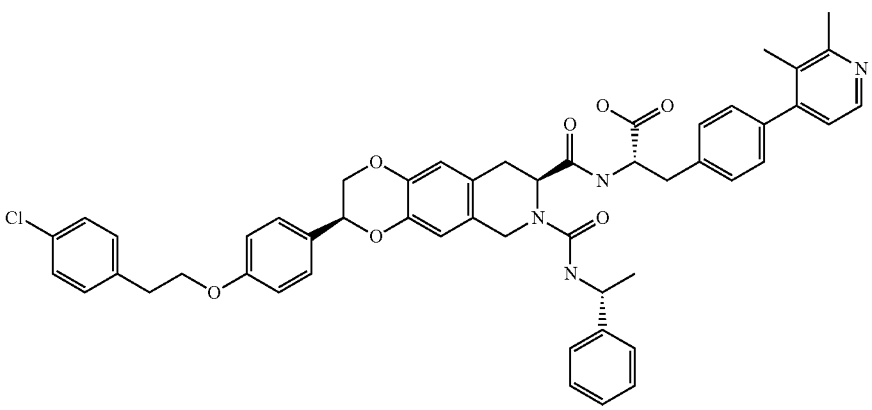 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCCc4ccc(Cl)cc4)cc3)CO5)C(=O)O)cc2)c1C] | 866 |
| 389 | 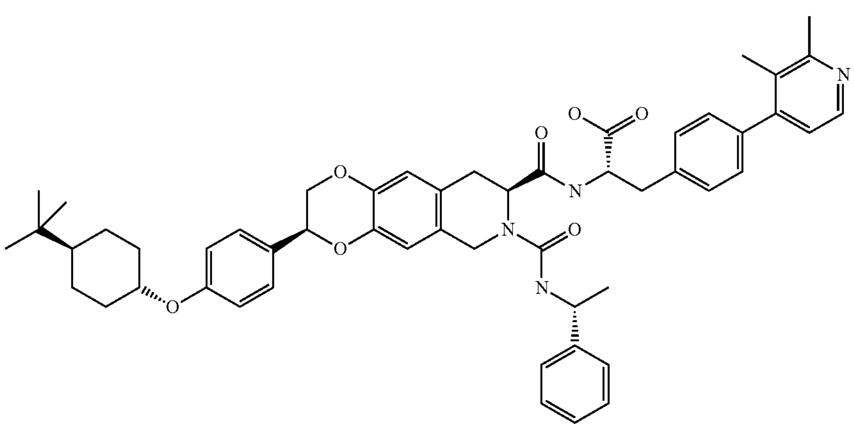 | 866 |

TABLE 1-continued

| Ex | Structure | LCMS (m/z) |
|---|---|---|
| 390 | 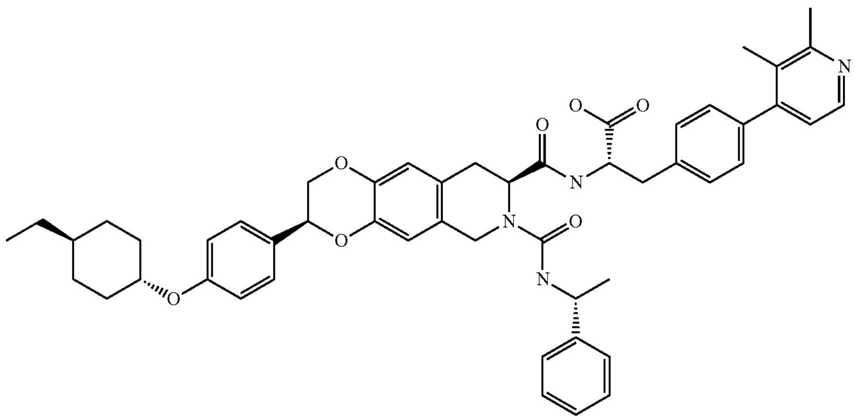 [SMILES: CC[C@H]1CC[C@H](Oc2ccc([C@H]3COc4cc5c(cc4O3)CN(C(=O)N[C@H](C)c3ccccc3)[C@H](C(=O)N[C@@H](Cc3ccc(-c4ccnc(C)c4C)cc3)C(=O)O)C5)cc2)CC1] | 838 |
| 391 | 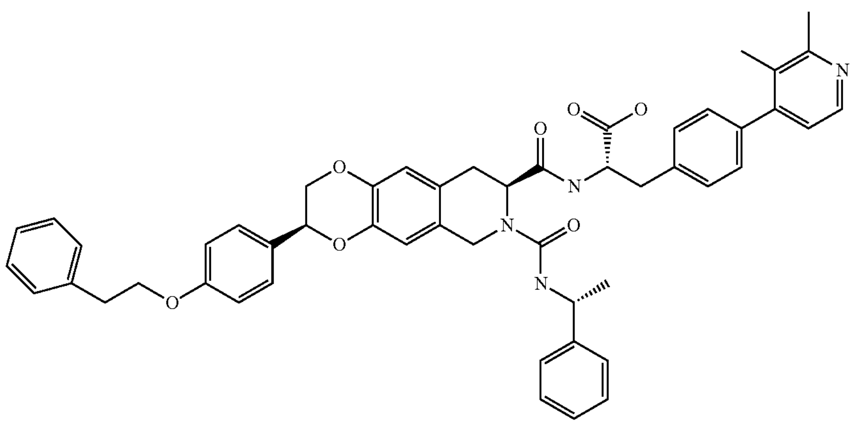 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCCc4ccccc4)cc3)CO5)C(=O)O)cc2)c1C] | 832 |
| 392 | 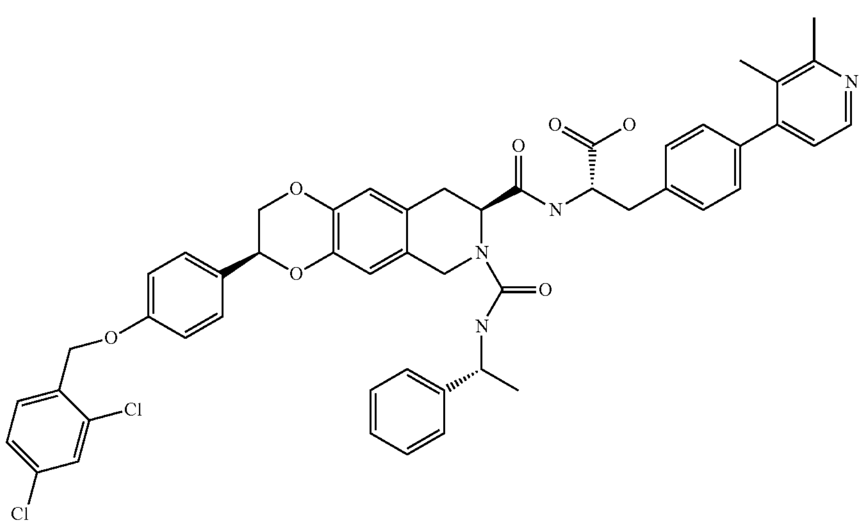 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCc4ccc(Cl)cc4Cl)cc3)CO5)C(=O)O)cc2)c1C] | 888 |

TABLE 1-continued
| Ex | Structure | LCMS (m/z) |
|---|---|---|
| 393 | 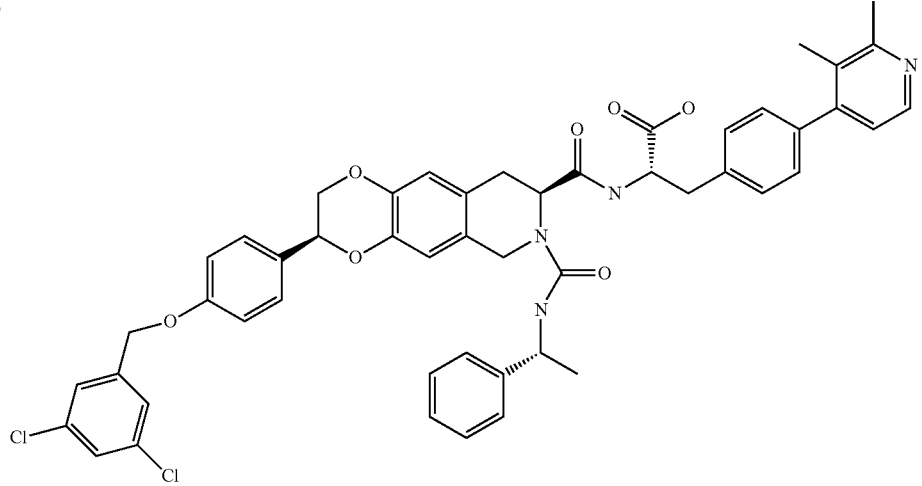 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCc4cc(Cl)cc(Cl)c4)cc3)CO5)C(=O)O)cc2)c1C] | 886 |
| 394 | 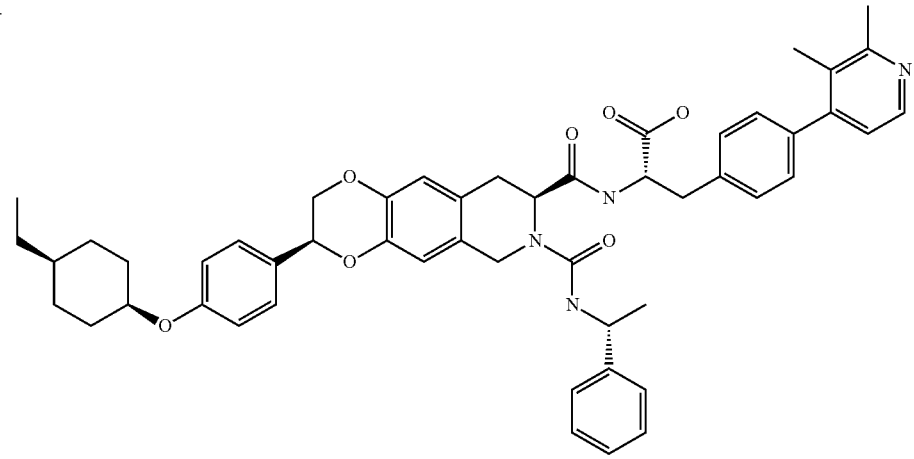 | 838 |
| 395 | 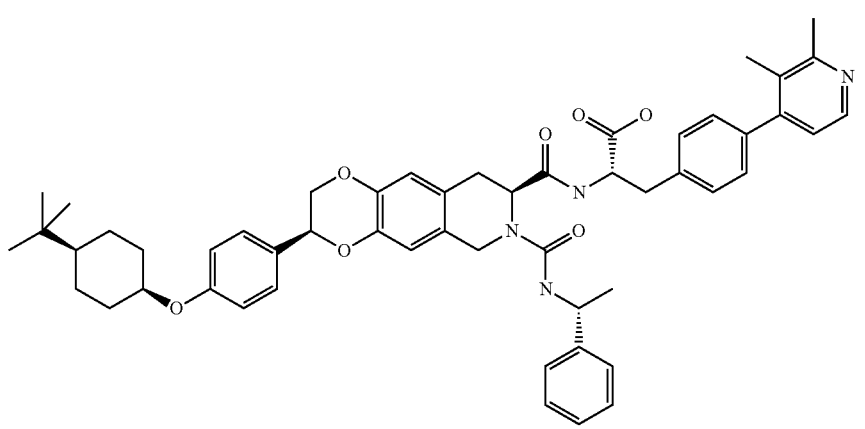 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(O[C@H]4CC[C@@H](C(C)(C)C)CC4)cc3)CO5)C(=O)O)cc2)c1C] | 866 |

TABLE 1-continued

| Ex | Structure | LCMS (m/z) |
|---|---|---|
| 396 | 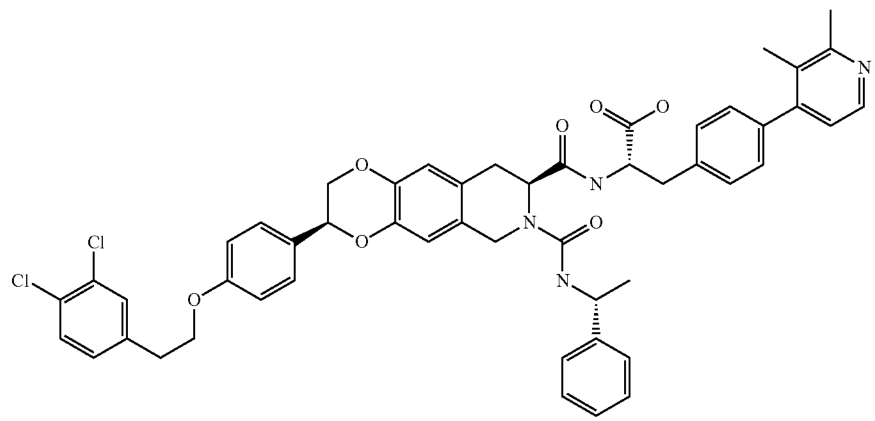 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCCc4ccc(Cl)c(Cl)c4)cc3)CO5)C(=O)O)cc2)c1C] | 900 |
| 397 | 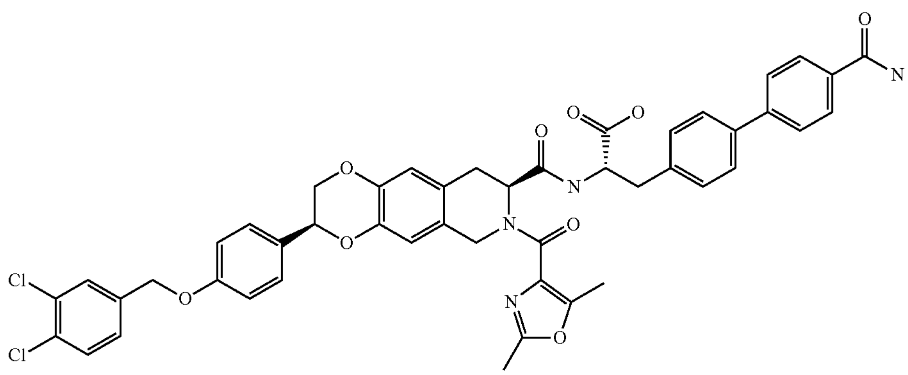 [SMILES: Cc1nc(C(=O)N2Cc3cc4c(cc3C[C@H]2C(=O)N[C@@H](Cc2ccc(-c3ccc(C(N)=O)cc3)cc2)C(=O)O)OC[C@H](c2ccc(OCc3ccc(Cl)c(Cl)c3)cc2)O4)c(C)o1] | 876 |
| 398 | 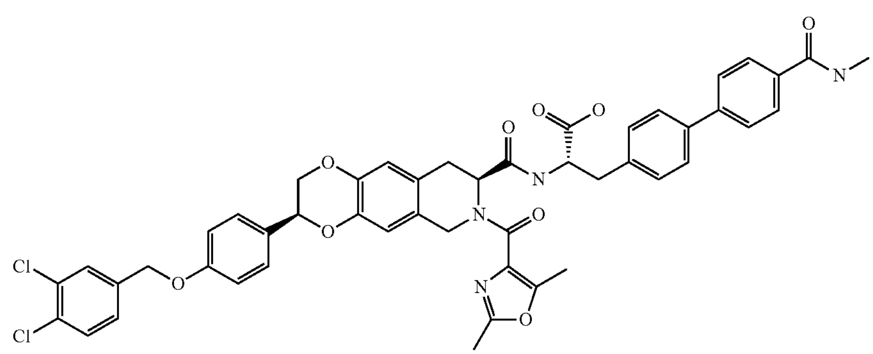 [SMILES: CNC(=O)c1ccc(-c2ccc(C[C@H](NC(=O)[C@@H]3Cc4cc5c(cc4CN3C(=O)c3nc(C)oc3C)O[C@@H](c3ccc(OCc4ccc(Cl)c(Cl)c4)cc3)CO5)C(=O)O)cc2)cc1] | 890 |
| 399 | 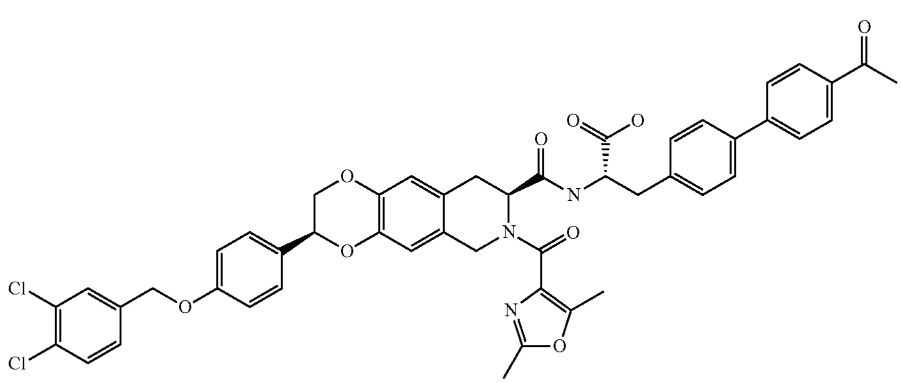 [SMILES: CC(=O)c1ccc(-c2ccc(C[C@H](NC(=O)[C@@H]3Cc4cc5c(cc4CN3C(=O)c3nc(C)oc3C)O[C@@H](c3ccc(OCc4ccc(Cl)c(Cl)c4)cc3)CO5)C(=O)O)cc2)cc1] | 875 |

| Ex | Structure | LCMS (m/z) |
|---|---|---|
| 400 | 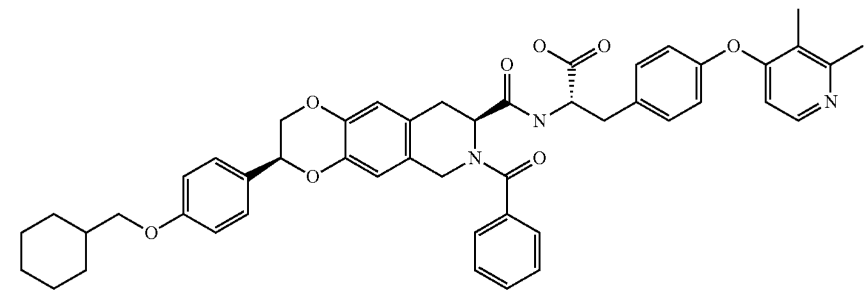 [SMILES: Cc1nccc(Oc2ccc(C[C@H](NC(=O)[C@@H]3Cc4cc5c(cc4CN3C(=O)c3ccccc3)O[C@@H](c3ccc(OCC4CCCCC4)cc3)CO5)C(=O)O)cc2)c1C] | 797 |
| 401 | 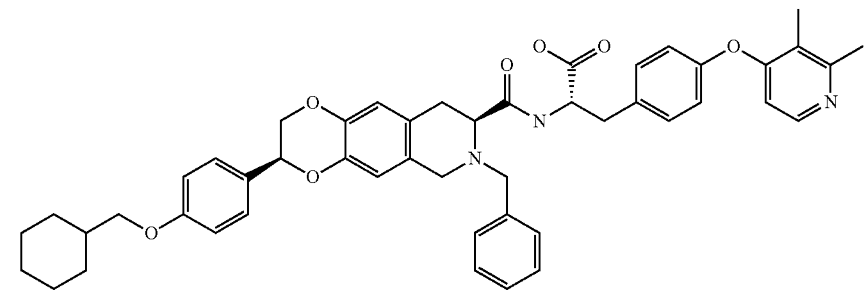 [SMILES: Cc1nccc(Oc2ccc(C[C@H](NC(=O)[C@@H]3Cc4cc5c(cc4CN3Cc3ccccc3)O[C@@H](c3ccc(OCC4CCCCC4)cc3)CO5)C(=O)O)cc2)c1C] | 783 |
| 402 | 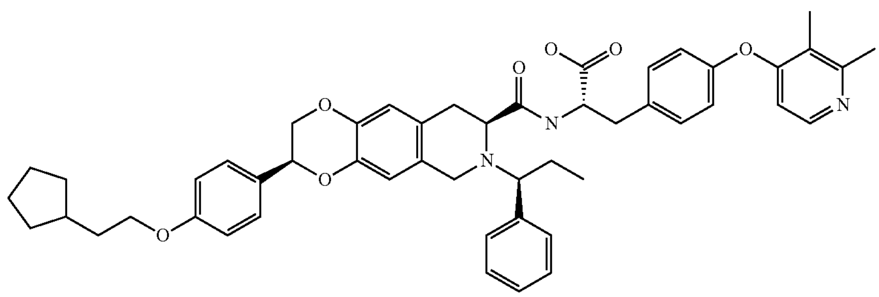 [SMILES: CC[C@@H](c1ccccc1)N1Cc2cc3c(cc2C[C@H]1C(=O)N[C@@H](Cc1ccc(Oc2ccnc(C)c2C)cc1)C(=O)O)OC[C@H](c1ccc(OCCC2CCCC2)cc1)O3] | 811 |
| 403 | 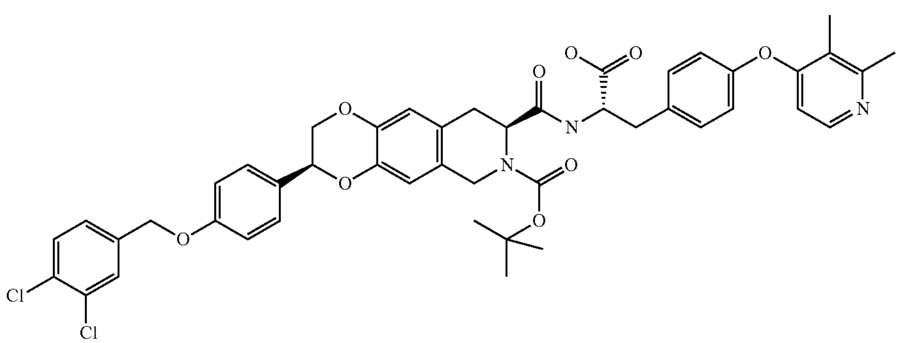 [SMILES: Cc1nccc(Oc2ccc(C[C@H](NC(=O)[C@@H]3Cc4cc5c(cc4CN3C(=O)OC(C)(C)C)O[C@@H](c3ccc(OCc4ccc(Cl)c(Cl)c4)cc3)CO5)C(=O)O)cc2)c1C] | 855 |
| 404 | 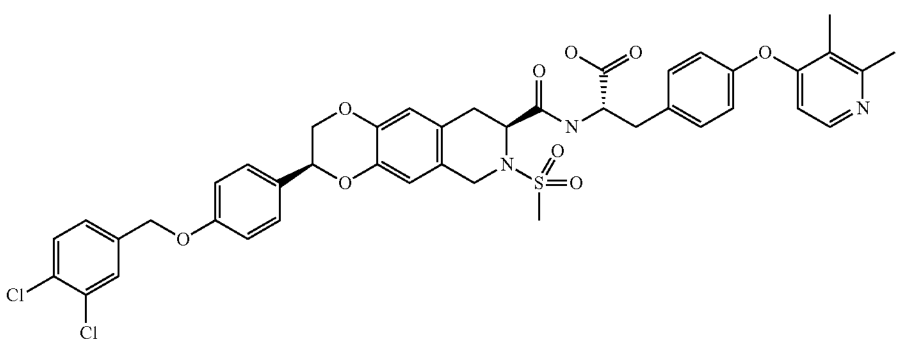 [SMILES: Cc1nccc(Oc2ccc(C[C@H](NC(=O)[C@@H]3Cc4cc5c(cc4CN3S(C)(=O)=O)O[C@@H](c3ccc(OCc4ccc(Cl)c(Cl)c4)cc3)CO5)C(=O)O)cc2)c1C] | 833 |

TABLE 1-continued

| Ex | Structure | LCMS (m/z) |
|---|---|---|
| 405 | 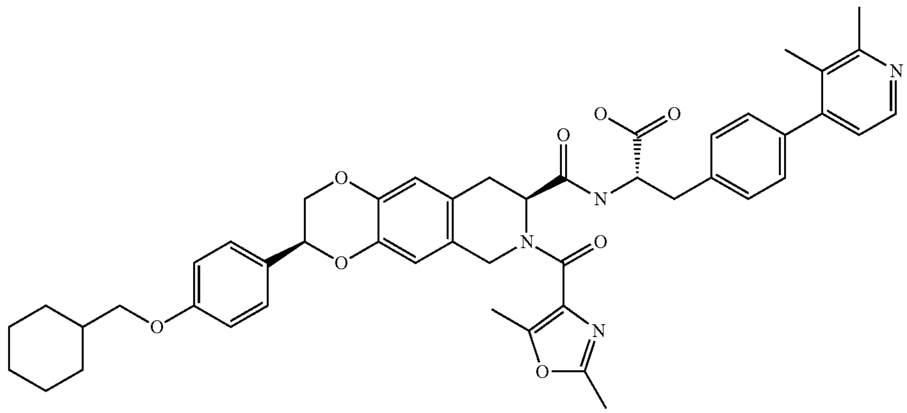 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCC3CCCCC3)cc2)O4)c(C)o1] | 800 |
| 406 | 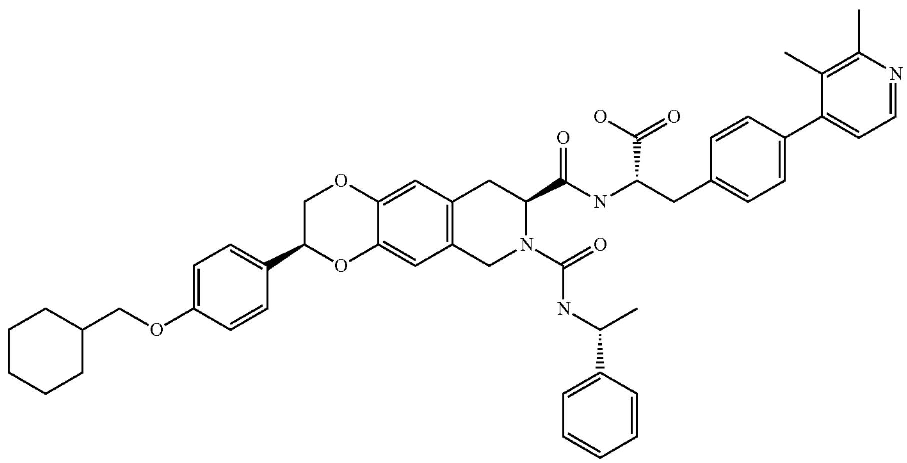 [SMILES: Cc1nccc(-c2ccc(C[C@H](NC(=O)[C@@H]3Cc4cc5c(cc4CN3C(=O)N[C@H](C)c3ccccc3)O[C@@H](c3ccc(OCC4CCCCC4)cc3)CO5)C(=O)O)cc2)c1C] | 824 |
| 407 | 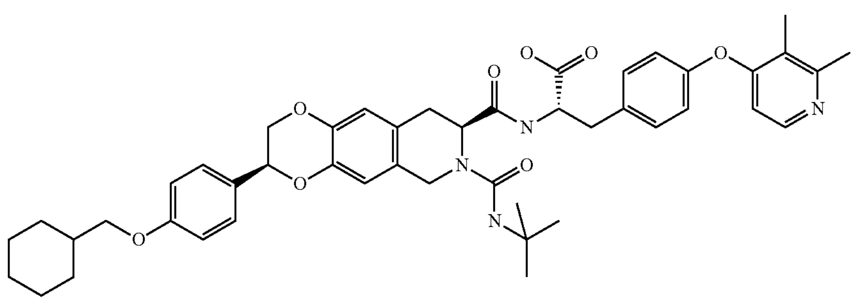 [SMILES: Cc1nccc(Oc2ccc(C[C@H](NC(=O)[C@@H]3Cc4cc5c(cc4CN3C(=O)NC(C)(C)C)O[C@@H](c3ccc(OCC4CCCCC4)cc3)CO5)C(=O)O)cc2)c1C] | 792 |
| 408 | 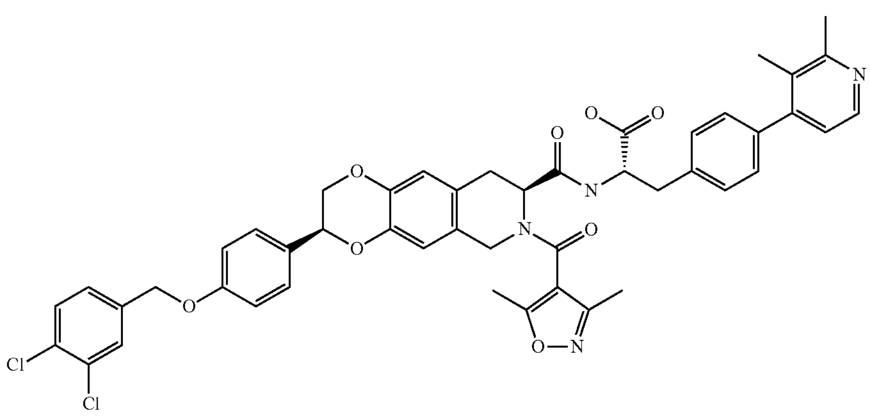 [SMILES: Cc1nccc(-c2ccc(C[C@H](NC(=O)[C@@H]3Cc4cc5c(cc4CN3C(=O)c3c(C)noc3C)O[C@@H](c3ccc(OCc4ccc(Cl)c(Cl)c4)cc3)CO5)C(=O)O)cc2)c1C] | 862 |

TABLE 1-continued

| Ex | Structure | LCMS (m/z) |
|---|---|---|
| 409 | 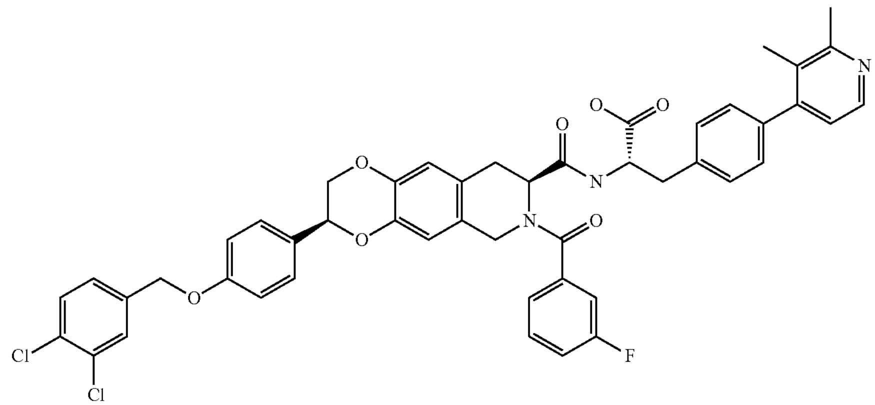 [SMILES: Cc1nccc(-c2ccc(C[C@H](NC(=O)[C@@H]3Cc4cc5c(cc4CN3C(=O)c3cccc(F)c3)O[C@@H](c3ccc(OCc4ccc(Cl)c(Cl)c4)cc3)CO5)C(=O)O)cc2)c1C] | 861 |
| 410 | 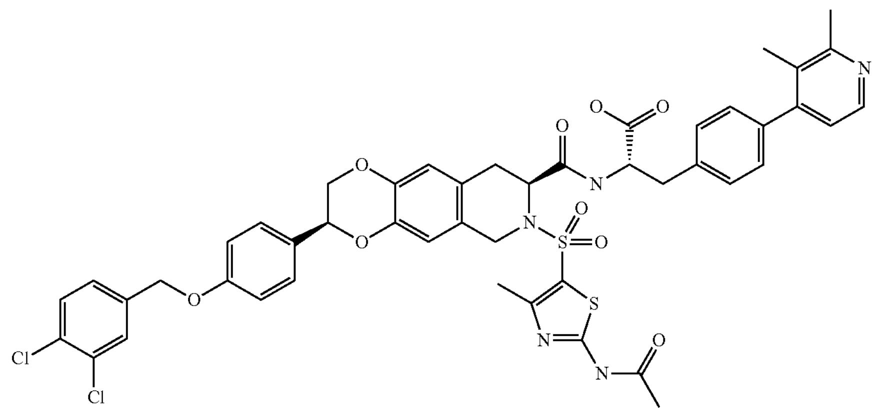 [SMILES: CC(=O)Nc1nc(C)c(S(=O)(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)s1] | 959 |
| 411 | 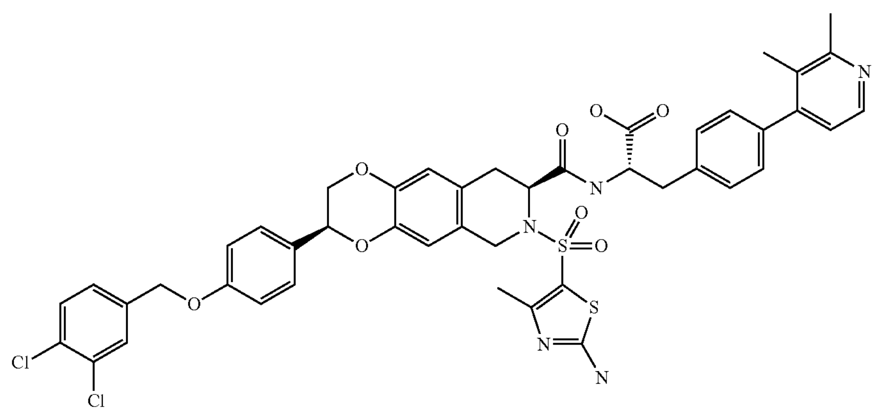 [SMILES: Cc1nc(N)sc1S(=O)(=O)N1Cc2cc3c(cc2C[C@H]1C(=O)N[C@@H](Cc1ccc(-c2ccnc(C)c2C)cc1)C(=O)O)OC[C@H](c1ccc(OCc2ccc(Cl)c(Cl)c2)cc1)O3] | 915 |
| 412 | 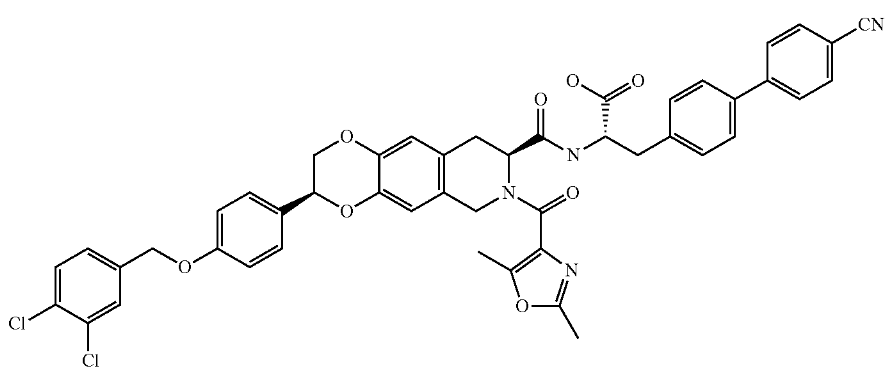 [SMILES: Cc1nc(C(=O)N2Cc3cc4c(cc3C[C@H]2C(=O)N[C@@H](Cc2ccc(-c3ccc(C#N)cc3)cc2)C(=O)O)OC[C@H](c2ccc(OCc3ccc(Cl)c(Cl)c3)cc2)O4)c(C)o1] | 860 |

TABLE 1-continued

| Ex | Structure | LCMS (m/z) |
|---|---|---|
| 413 | 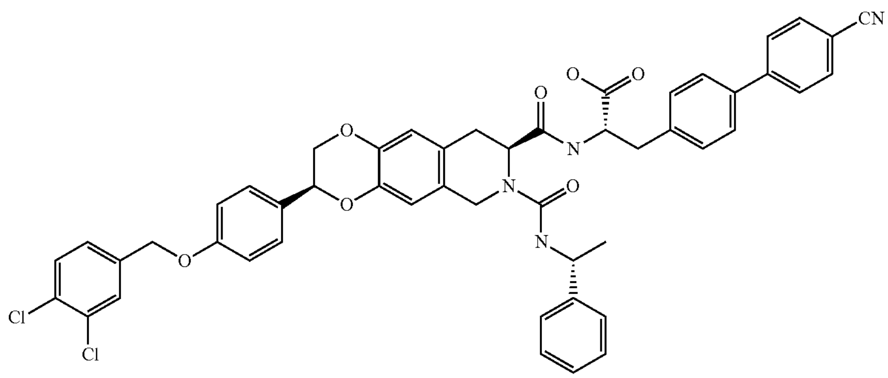 [SMILES: C[C@@H](NC(=O)N1Cc2cc3c(cc2C[C@H]1C(=O)N[C@@H](Cc1ccc(-c2ccc(C#N)cc2)cc1)C(=O)O)OC[C@H](c1ccc(OCc2ccc(Cl)c(Cl)c2)cc1)O3)c1ccccc1] | 884 |
| 414 | 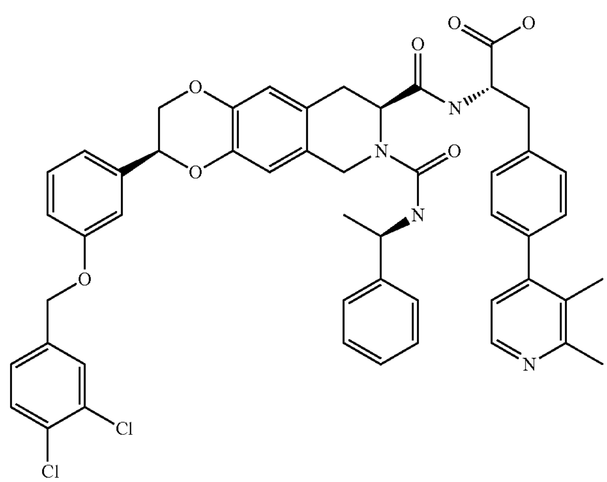 [SMILES: Cc1nccc(-c2ccc(C[C@H](NC(=O)[C@@H]3Cc4cc5c(cc4CN3C(=O)N[C@H](C)c3ccccc3)O[C@@H](c3cccc(OCc4ccc(Cl)c(Cl)c4)c3)CO5)C(=O)O)cc2)c1C] | 886 |
| 415 | 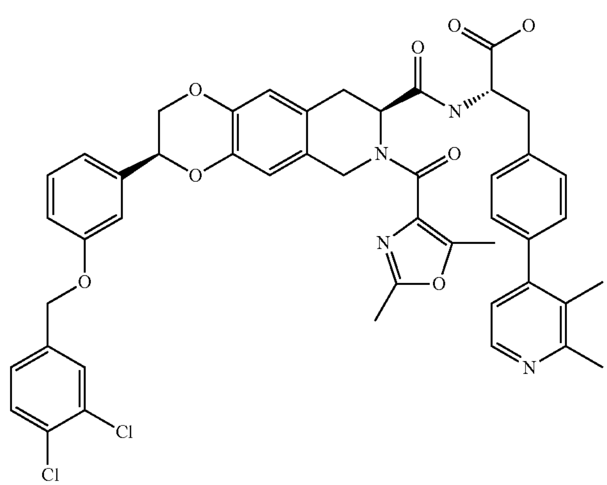 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2cccc(OCc3ccc(Cl)c(Cl)c3)c2)O4)c(C)o1] | 862 |

TABLE 1-continued
| Ex | Structure | LCMS (m/z) |
|---|---|---|
| 416 | 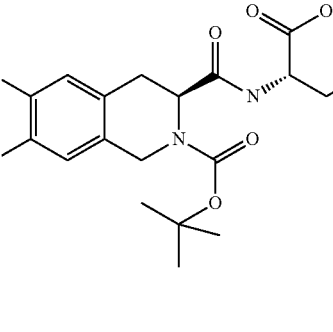 | 839 |
| 417 | 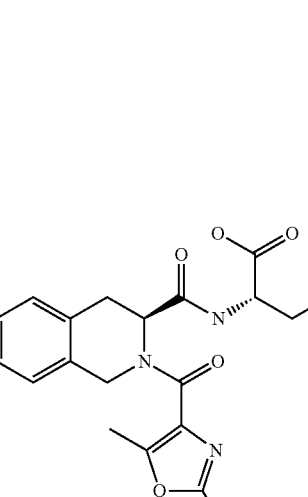 | 800 |
| 418 | 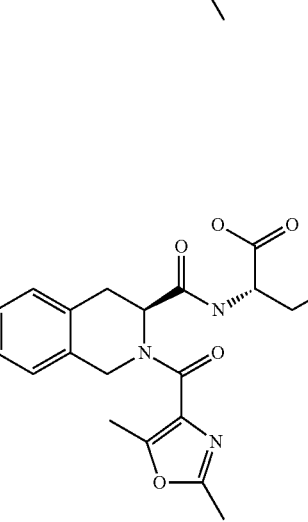 | 786 |

TABLE 1-continued

| Ex | Structure | LCMS (m/z) |
|---|---|---|
| 419 | 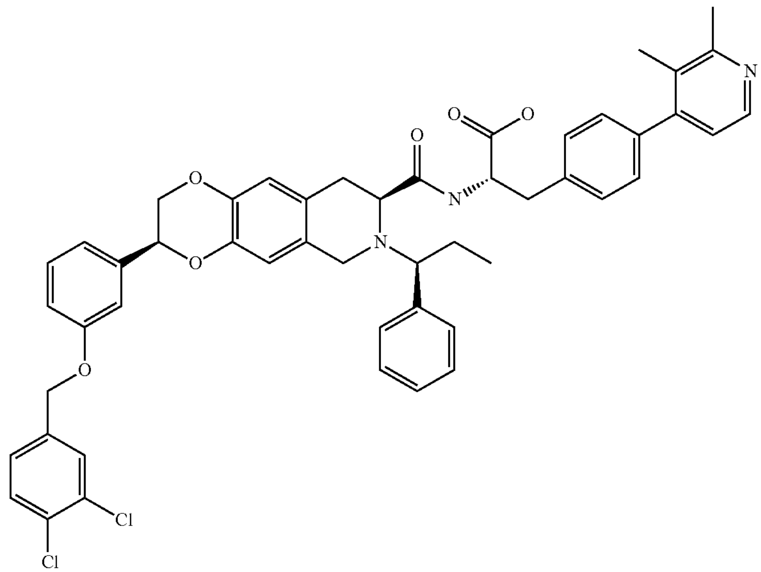 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1cccc(OCc2ccc(Cl)c(Cl)c2)c1)O3] | 857 |
| 420 | 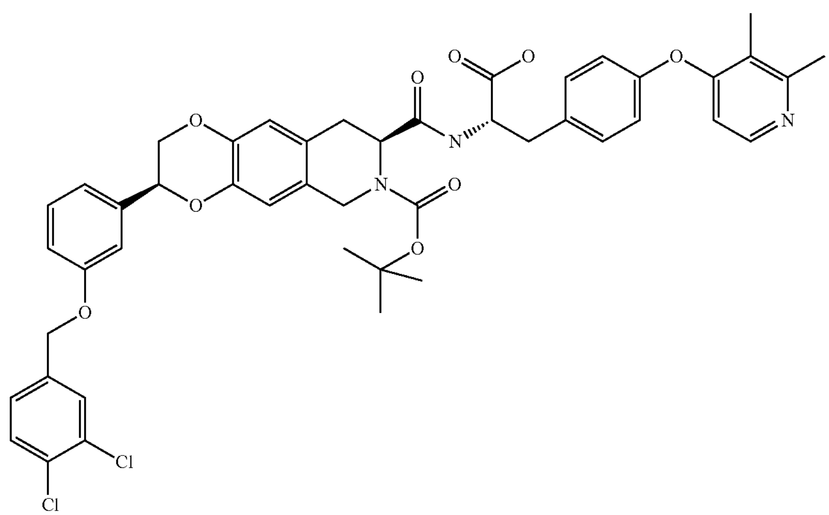 [SMILES: Cc1nccc(Oc2ccc(C[C@H](NC(=O)[C@@H]3Cc4cc5c(cc4CN3C(=O)OC(C)(C)C)O[C@@H](c3cccc(OCc4ccc(Cl)c(Cl)c4)c3)CO5)C(=O)O)cc2)c1C] | 855 |
| 421 | 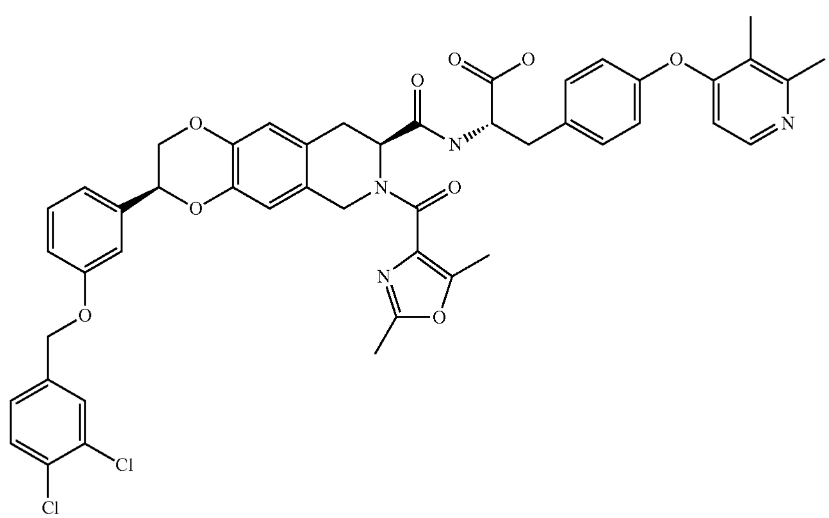 [SMILES: Cc1nc(C(=O)N2Cc3cc4c(cc3C[C@H]2C(=O)N[C@@H](Cc2ccc(Oc3ccnc(C)c3C)cc2)C(=O)O)OC[C@H](c2cccc(OCc3ccc(Cl)c(Cl)c3)c2)O4)c(C)o1] | 878 |

TABLE 1-continued

| Ex | Structure | LCMS (m/z) |
|---|---|---|
| 422 | 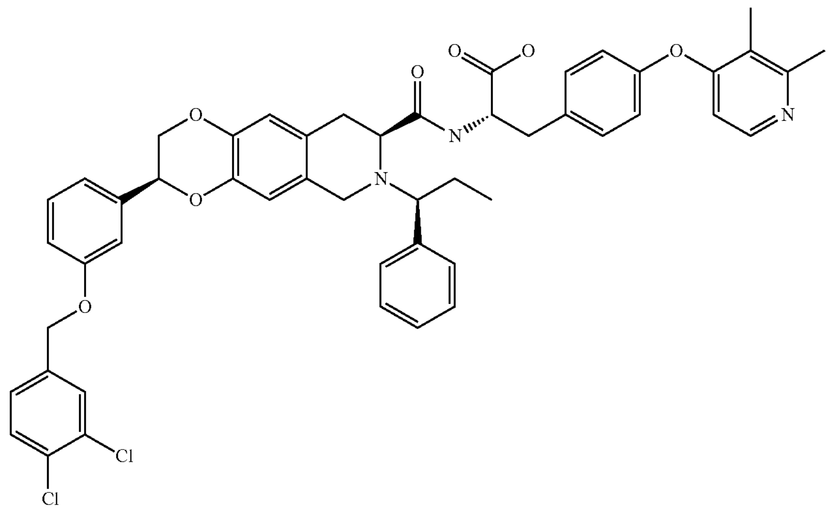 [SMILES: CC[C@@H](c1ccccc1)N1Cc2cc3c(cc2C[C@H]1C(=O)N[C@@H](Cc1ccc(Oc2ccnc(C)c2C)cc1)C(=O)O)OC[C@H](c1cccc(OCc2ccc(Cl)c(Cl)c2)c1)O3] | 873 |
| 423 | 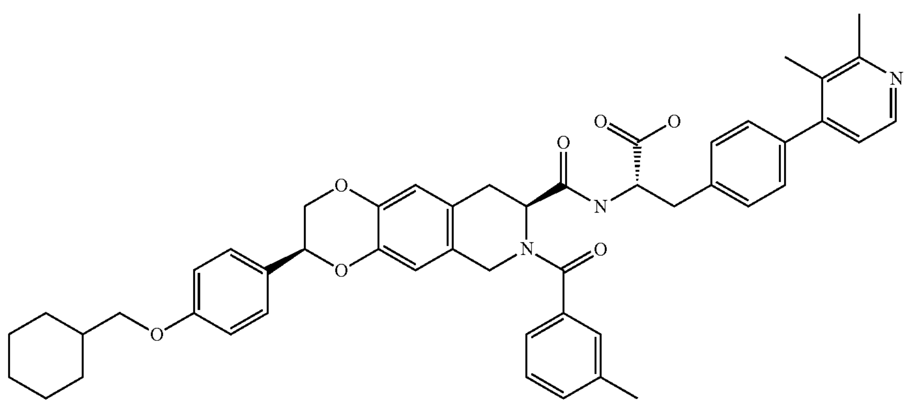 [SMILES: Cc1cccc(C(=O)N2Cc3cc4c(cc3C[C@H]2C(=O)N[C@@H](Cc2ccc(-c3ccnc(C)c3C)cc2)C(=O)O)OC[C@H](c2ccc(OCC3CCCCC3)cc2)O4)c1] | 795 |
| 424 | 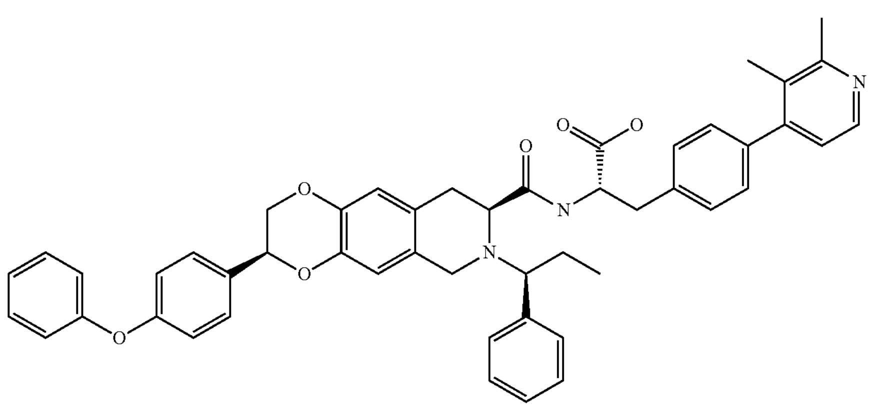 [SMILES: CC[C@@H](c1ccccc1)N1Cc2cc3c(cc2C[C@H]1C(=O)N[C@@H](Cc1ccc(-c2ccnc(C)c2C)cc1)C(=O)O)OC[C@H](c1ccc(Oc2ccccc2)cc1)O3] | 775 |

TABLE 1-continued

| Ex | Structure | LCMS (m/z) |
|---|---|---|
| 425 | 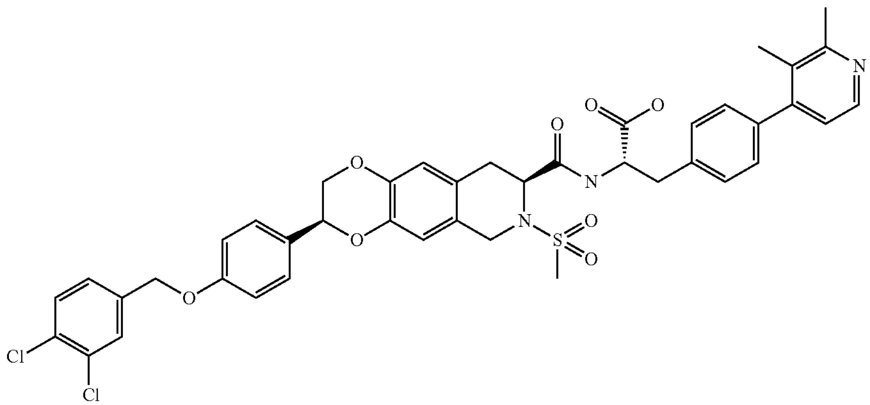 [SMILES: Cc1nccc(-c2ccc(C[C@H](NC(=O)[C@@H]3Cc4cc5c(cc4CN3S(C)(=O)=O)O[C@@H](c3ccc(OCc4ccc(Cl)c(Cl)c4)cc3)CO5)C(=O)O)cc2)c1C] | 819 |
| 426 | 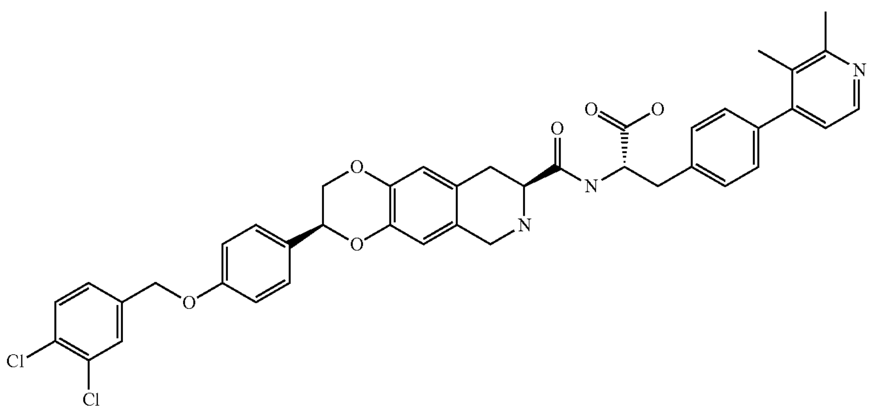 [SMILES: Cc1nccc(-c2ccc(C[C@H](NC(=O)[C@@H]3Cc4cc5c(cc4CN3)O[C@@H](c3ccc(OCc4ccc(Cl)c(Cl)c4)cc3)CO5)C(=O)O)cc2)c1C] | 741 |
| 427 | 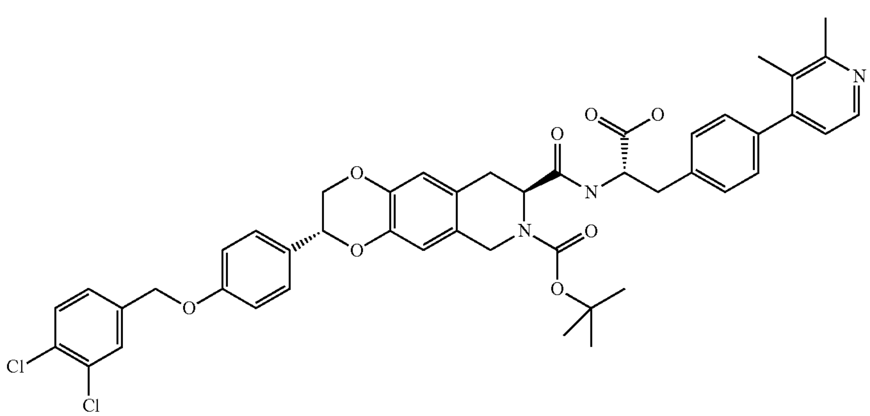 [SMILES: Cc1nccc(-c2ccc(C[C@H](NC(=O)[C@@H]3Cc4cc5c(cc4CN3C(=O)OC(C)(C)C)O[C@H](c3ccc(OCc4ccc(Cl)c(Cl)c4)cc3)CO5)C(=O)O)cc2)c1C] | 839 |

TABLE 1-continued
| Ex | Structure | LCMS (m/z) |
|---|---|---|
| 428 | 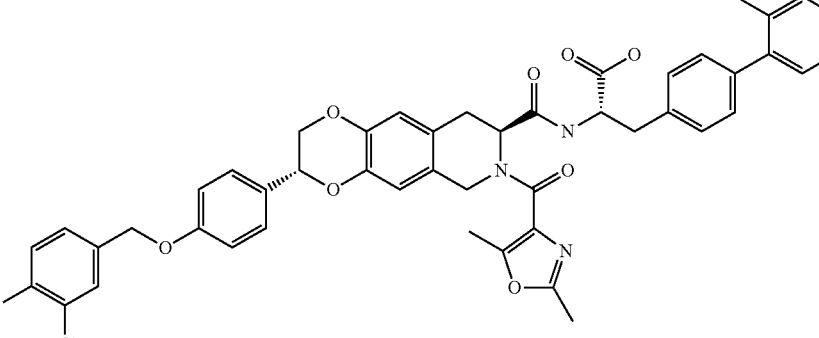 | 862 |
| 429 | 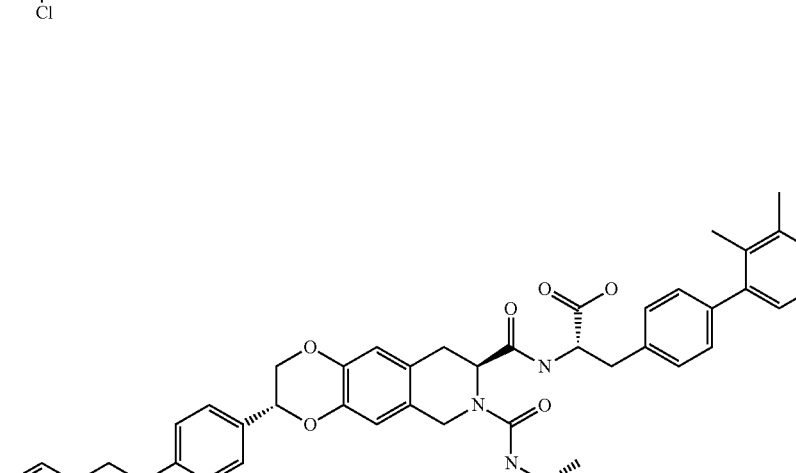 | 886 |
| 430 | 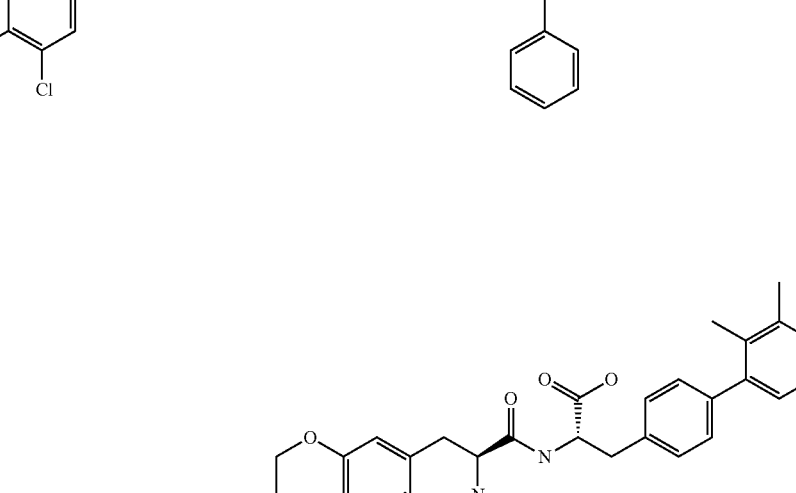 | 857 |

TABLE 1-continued

| Ex | Structure | LCMS (m/z) |
|---|---|---|
| 431 | 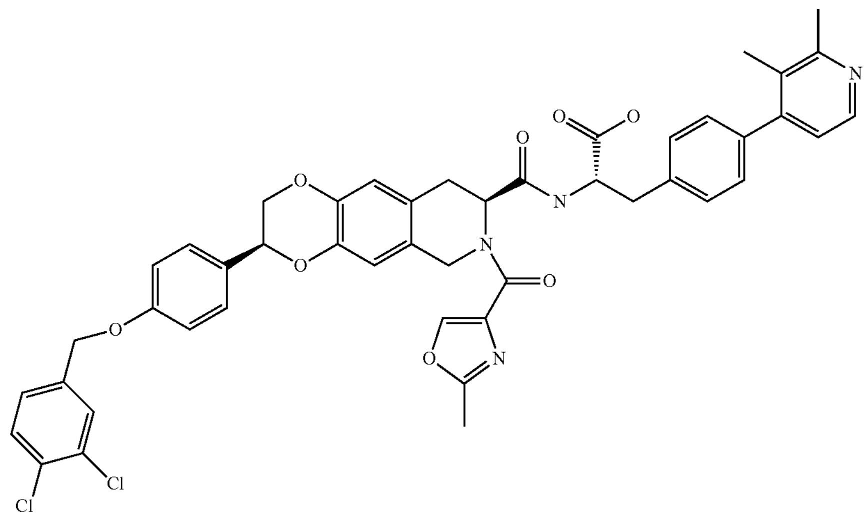 [SMILES: Cc1nc(C(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)co1] | 848 |
| 432 | 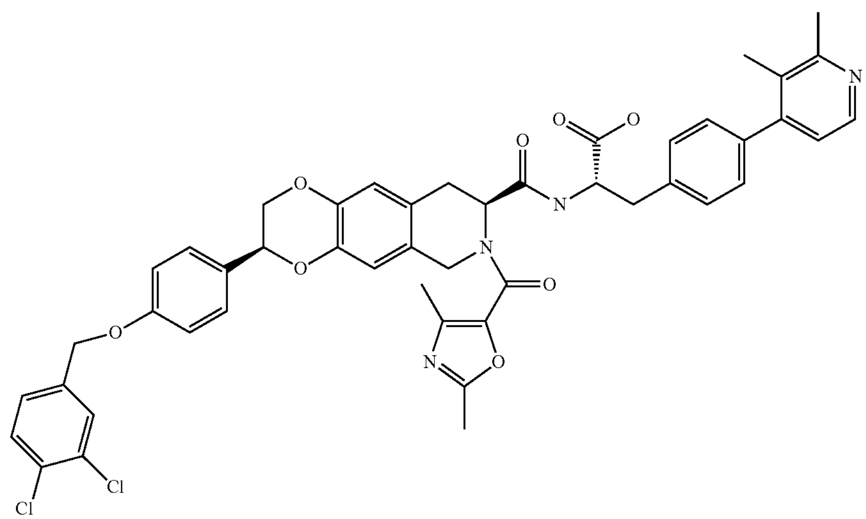 [SMILES: Cc1nc(C)c(C(=O)N2Cc3cc4c(cc3C[C@H]2C(=O)N[C@@H](Cc2ccc(-c3ccnc(C)c3C)cc2)C(=O)O)OC[C@H](c2ccc(OCc3ccc(Cl)c(Cl)c3)cc2)O4)o1] | 862 |
| 433 | 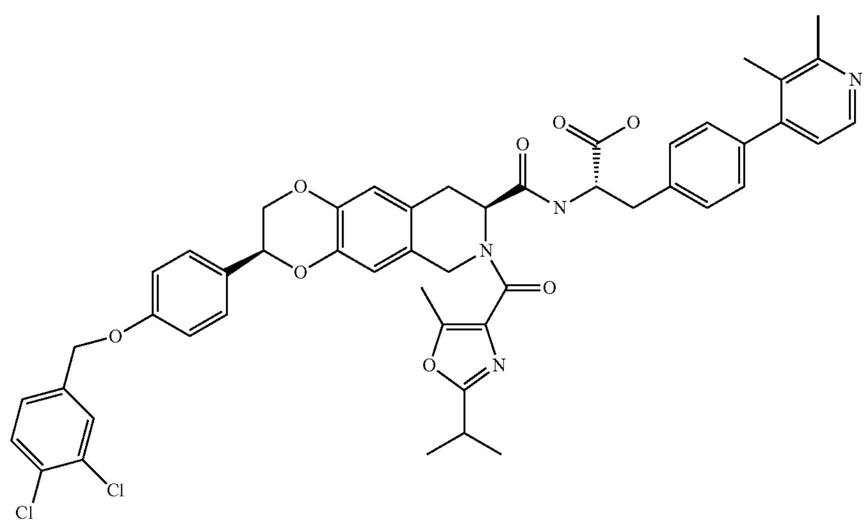 [SMILES: Cc1nccc(-c2ccc(C[C@H](NC(=O)[C@@H]3Cc4cc5c(cc4CN3C(=O)c3nc(C(C)C)oc3C)O[C@@H](c3ccc(OCc4ccc(Cl)c(Cl)c4)cc3)CO5)C(=O)O)cc2)c1C] | 892 |

TABLE 1-continued
| Ex | Structure | LCMS (m/z) |
|---|---|---|
| 434 | 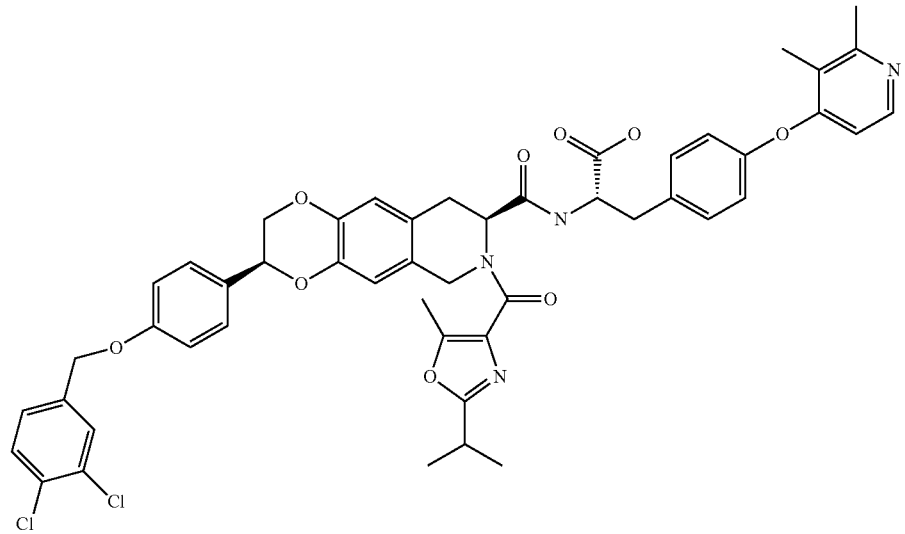 [SMILES: Cc1nccc(Oc2ccc(C[C@H](NC(=O)[C@@H]3Cc4cc5c(cc4CN3C(=O)c3nc(C(C)C)oc3C)O[C@@H](c3ccc(OCc4ccc(Cl)c(Cl)c4)cc3)CO5)C(=O)O)cc2)c1C] | 906 |
| 435 | 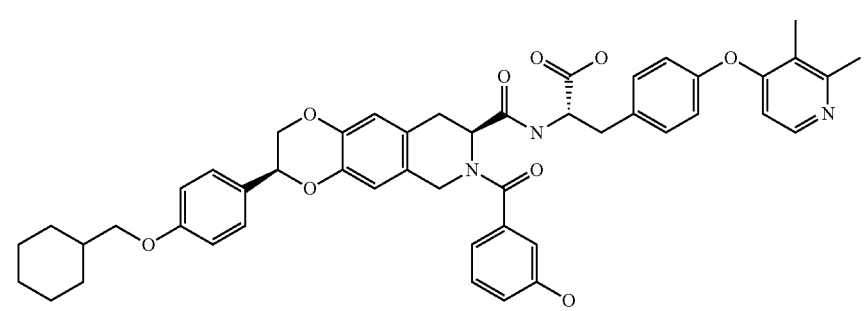 [SMILES: Cc1nccc(Oc2ccc(C[C@H](NC(=O)[C@@H]3Cc4cc5c(cc4CN3C(=O)c3cccc(O)c3)O[C@@H](c3ccc(OCC4CCCCC4)cc3)CO5)C(=O)O)cc2)c1C] | 813 |
| 436 | 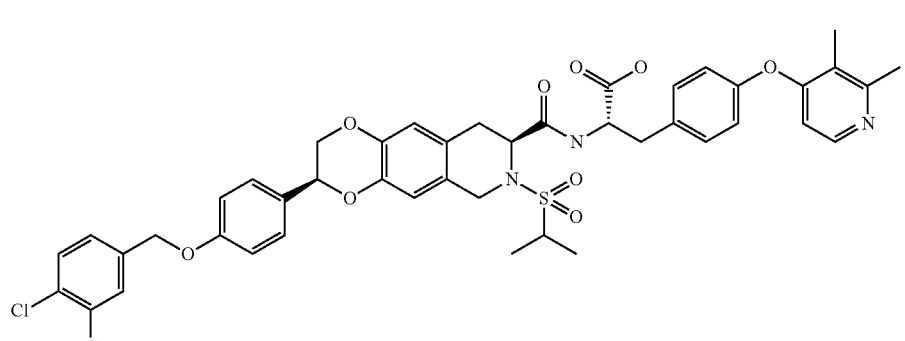 | 861 |
| 437 | 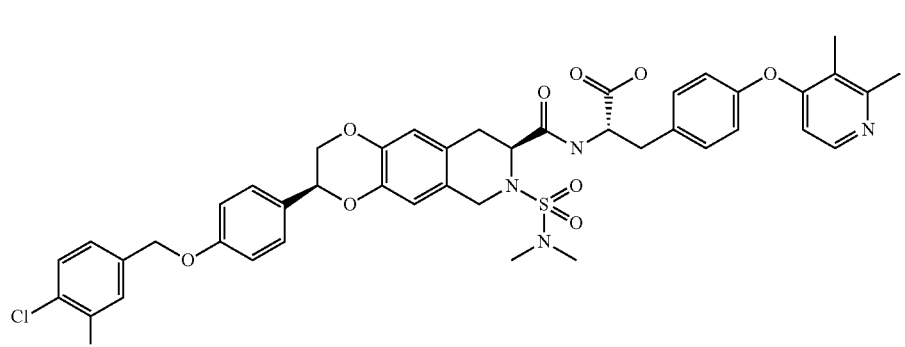 | 862 |

TABLE 1-continued

| Ex | Structure | LCMS (m/z) |
|---|---|---|
| 438 | 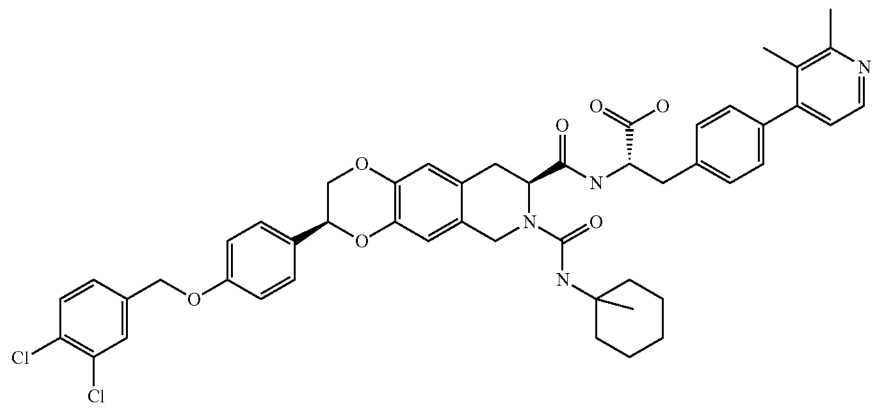 | 878 |
| 439 | 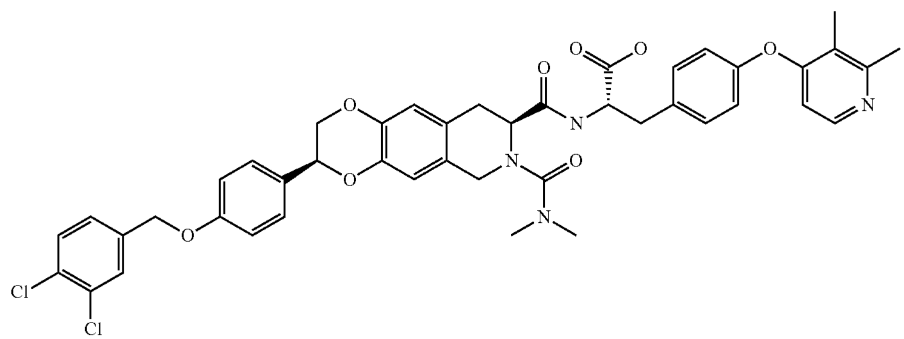 [SMILES: Cc1nccc(Oc2ccc(C[C@H](NC(=O)[C@@H]3Cc4cc5c(cc4CN3C(=O)N(C)C)O[C@@H](c3ccc(OCc4ccc(Cl)c(Cl)c4)cc3)CO5)C(=O)O)cc2)c1C] | 826 |
| 440 | 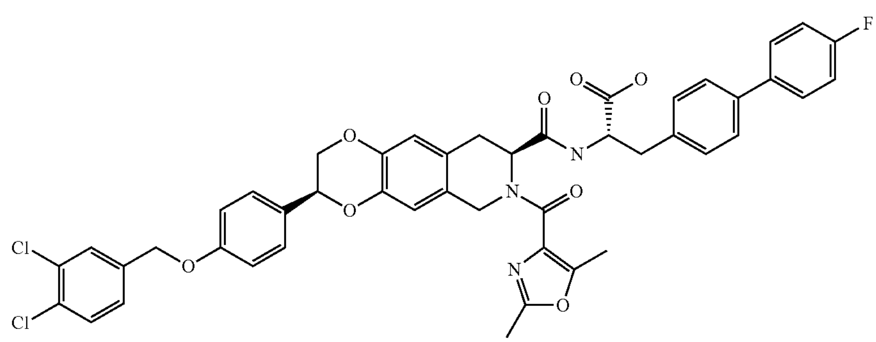 [SMILES: Cc1nc(C(=O)N2Cc3cc4c(cc3C[C@H]2C(=O)N[C@@H](Cc2ccc(-c3ccc(F)cc3)cc2)C(=O)O)OC[C@H](c2ccc(OCc3ccc(Cl)c(Cl)c3)cc2)O4)c(C)o1] | 851 |
| 441 | 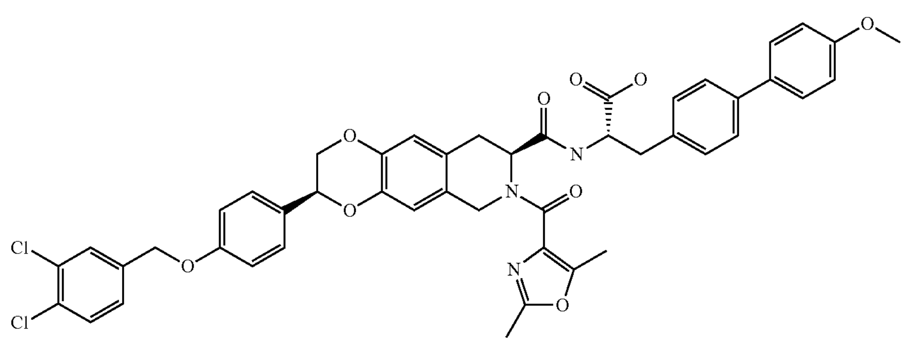 [SMILES: COc1ccc(-c2ccc(C[C@H](NC(=O)[C@@H]3Cc4cc5c(cc4CN3C(=O)c3nc(C)oc3C)O[C@@H](c3ccc(OCc4ccc(Cl)c(Cl)c4)cc3)CO5)C(=O)O)cc2)cc1] | 863 |

TABLE 1-continued

| Ex | Structure | LCMS (m/z) |
|---|---|---|
| 442 | 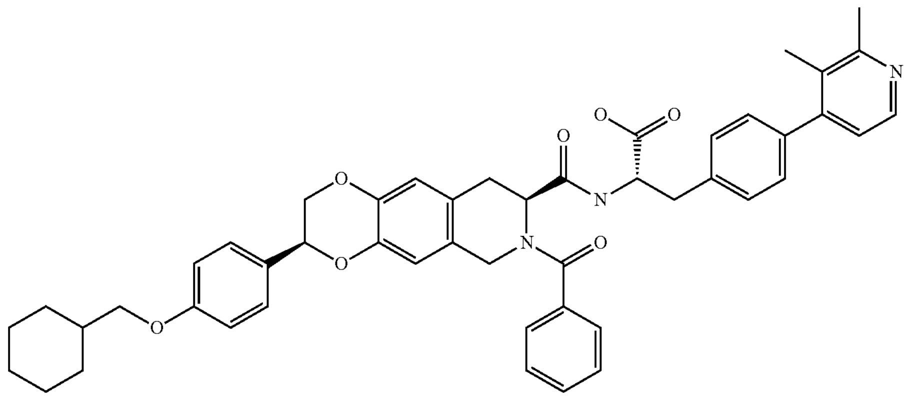 [SMILES: Cc1nccc(-c2ccc(C[C@H](NC(=O)[C@@H]3Cc4cc5c(cc4CN3C(=O)c3ccccc3)O[C@@H](c3ccc(OCC4CCCCC4)cc3)CO5)C(=O)O)cc2)c1C] | 781 |

General Synthetic Procedures

The following general procedures provide instructions for carrying out syntheses that are useful for making compounds or salts of the invention. The procedures are general in nature. Substitution of certain solvents and the like are possible, according to knowledge of the skilled artisan, as long as such substitutions would not materially affect the chemical identity of the resulting product.

The specification uses abbreviations that are commonly used by the skilled artisans. Below is a non-exhaustive list of abbreviations that appear in the synthetic examples. If an example uses an abbreviation that does not appear in the list, the abbreviation has the meaning that it would have to a skilled artisan in the relevant field.

Abbreviations
AcOH=acetic acid
CBS Reagent=Corey-Bakshi-Shibata reagent
CDI=carbonyldiimidazole
Cy=cyclohexyl
dba=dibenzylidene acetone
DBU=1,8-diazabicyclo[5.4.0]undec-7-ene
DCE=1,2-dichloroethane
DCM=dichloromethane
DIAD=diisopropylazodicarboxylate
DIEA=diisopropylethylamine
DMAP=N,N'-dimethylamino pyridine
DME=1,2-dimethoxyethane
DMF=N,N'-dimethylformamide
DMSO=dimethylsulfoxide
DPPA=diphenylphosphoryl azide
EDCl=EDC=1-ethyl-3-(3-dimethylaminopropyl)carbodiimide hydrochloride
EtOAc=EA=ethyl acetate
EtOH=ethanol
$^1$H NMR=proton NMR analysis
HBTU=2-(1H-benzotriazol-1-yl)-1,1,3,3-tetramethyluronium hexafluorophosphate
HCl=hydrochloric acid
hex=hexanes
HOBt=1-hydroxybenzotriazole
LC/MS=liquid chromatography-mass spectrometry analysis
L-DOPA=I-3,4-dihydroxyphenylalanine
MTBE=methyl tert-butyl ether
MeOH=methanol
NEt$_3$=triethylamine
NMM=N-methyl-morpholine
PPh$_3$=triphenylphosphine
Ph=phenyl
TEA=triethylamine
TBAF=tetrabutylammonium fluoride
TFA=trifluoroacetic acid
THF=tetrahydrofuran
TLC=thin layer chromatography
rt=r.t.=RT=room temperature
h=hour
min=minutes
M=molar concentration
N=normal concentration
uL=ul=microliters
eq.=eq=equiv=molar equivalents
mL=ml=milliliters
ug=micrograms
mg=milligrams
g=grams
wt=wt.=weight General Procedure A: Preparation of Amides Using HBTU To a stirring solution of a mixture of a carboxylic acid (1.0 eq) HBTU (1-2 eq) and DIEA (1-5 eq) in DMF at room temperature is added an amine (1-4 eq), and the mixture is stirred 0.5-16 h. After substantial completion of the reaction, a sufficient amount of water is added and the mixture is extracted with ethyl acetate. The combined organic layer is washed with 1 N HCl, saturated NaHCO$_3$ and brine, and then is dried over sodium sulfate. The solvent is removed under reduced pressure to yield an amide, which may be purified by column chromatography on silica gel.

General Procedure B: Methyl Ester Hydrolysis

To a solution of an ester in THF, methanol (4:1 to 1:4) and 2 N lithium hydroxide solution (2-10 eq) are added, and the resulting reaction mixture is stirred at 0° C. or at room temperature for 10-120 minutes. If started at 0° C., and the solution is then warmed to room temperature and is stirred until reaction complete. After completion of the reaction, 1N HCl is used to neutralize the base, extracted with ethyl acetate or DCM, the organic layer is washed with brine, dried over sodium sulfate, and the solvent is removed under reduced pressure to yield the product. If desired, the product may be purified via silica gel chromatography.

General Procedure C: Removal of Tert-Butyl Carbamate

To a stirred solution of the carbamate in DCM, 4 N HCl in dioxane (0.2-2× volume of DCM) are added. The reaction is stirred at room temperature for 0.5-4 hours. Solvents are removed under reduced pressure. The residue is triturated with ethyl ether (or another solvent in which the compound is insoluble) and the precipitated solid is filtered (or solvent decanted) and dried under vacuum to give an amine as a hydrochloric acid salt.

General Procedure D: Reductive Amination

To a solution of a secondary amine (1.0 eq) in dichloroethane or dichloromethane is added an aldehyde (1.0-3 eq), acetic acid (0.1-1 eq) and sodium triacetoxyborohydride or sodium cyanoborohydride (1-4 eq) and the mixture is stirred overnight. After completion of the reaction, DCM is added and the organic layer is washed with 10% $Na_2CO_3$ solution and brine, and then is dried over sodium sulfate. The solvent is removed under reduced pressure to give an amine, which may be purified by flash chromatography.

General Procedure E: Preparation of Sulfonamides

To a solution of an amine (1.0 eq) in DCM is added a sulfonyl chloride (1-3 eq), and pyridine (1-5 eq) or triethylamine (1-5 eq) and DMAP (cat. amount if required) and the mixture is stirred for 1-16 h. After completion of the reaction, ethyl acetate is added and the organic layer is washed with 1N HCl, saturated sodium bicarbonate solution and brine, and then is dried over sodium sulfate. The solvent is removed under reduced pressure to give the sulfonamide, which is purified by flash chromatography. Alternatively, after completion of the reaction, the reaction mixture is directly purified by flash chromatography.

General Procedure F: Preparation of Amides

To a solution of an amine (1.0 eq) in DCM is added an acid chloride or anhydride (1-3 eq), and pyridine (1-5 eq) or triethylamine (1-5 eq), or diisopropylethylamine (1-10 eq), and the mixture is stirred for 1-16 h. After completion of the reaction, ethyl acetate is added and the organic layer is washed with 1N HCl, saturated sodium bicarbonate solution and brine, and is then dried over sodium sulfate. The solvent is removed under reduced pressure to give an amide, which may be purified by flash chromatography. Alternatively, after completion of the reaction, the reaction mixture may be directly purified by flash chromatography.

General Procedure G: Preparation of Carbamates

To a solution of an amine (1.0 eq) in DCM is added a chloroformate (1-3 eq), and triethylamine (1-5 eq) and the mixture is stirred for 1-16 h. After completion of the reaction, ethyl acetate is added and the organic layer is washed with 1N HCl, saturated sodium bicarbonate solution and brine, and is then dried over sodium sulfate. The solvent is removed in vacuo to give a carbamate, which is purified by flash chromatography. Alternatively, after completion of the reaction, the reaction mixture may be directly purified by flash chromatography.

General Procedure H: Preparation of Ureas

To a solution of an amine (1.0 eq) in DCM, a carbamoyl chloride (1-40 eq) and triethylamine (1-10 eq) are added, and the mixture stirred for 1-40 hours. After substantial completion of the reaction, ethyl acetate is added and the organic layer is washed with 1N HCl, saturated sodium bicarbonate solution, and brine, and then dried over sodium sulfate. The solvent is removed under reduced pressure to give a urea, which is purified by flash chromatography. Alternatively, after completion of the reaction, the reaction mixture is directly purified by flash chromatography.

General Procedure I: Preparation of Ureas

To a stirred solution of an amine (1.0 eq) in THF or DCM (5 mL), DIEA (0-2 eq) is added, followed by an alkyl/aryl isocyanate (2-40 eq). The resulting solution is stirred at room temperature for 0.5-16 hours. The reaction mixture is poured into a saturated $NaHCO_3$ solution (10 mL) and extracted with ethyl acetate (2×10 mL). The combined organic layer is washed with brine (10 mL) and dried over $Na_2SO_4$, and concentrated under reduced pressure, and then purified by silica gel flash column chromatography to give a urea. Alternatively, after completion of the reaction, the reaction mixture is directly purified by flash chromatography.

General Procedure J: Alkylation of 2° Amines or Phenols

To a solution of a secondary amine (1.0 equiv.) in DMF (5 mL) is added an alkyl halide (1-5 equiv), and potassium carbonate (2-5 equiv.), and the mixture is stirred at room temperature for 2-24 h. After completion of the reaction, ethyl acetate or ether and water are added. The organic layer is washed with water or brine, and is then dried over sodium sulfate. The solvent is removed under reduced pressure to give a tertiary amine, which is purified by flash chromatography.

General Procedure K: Ether Formation Under Mitsunobu Reaction Conditions

To a solution of a phenol (1.00 mmol), an alcohol (1-4 equivalents) and triphenylphosphine or polymer-supported triphenylphosphine (1-4 equivalents) in anhydrous DCM (20 mL) is added DIAD (1-4 equivalents) at −5° C. and the reaction mixture is slowly allowed to warm up to room temperature and is stirred for 4 h. After completion of the reaction, the polymer-supported triphenylphosphine is removed from the reaction mixture and is concentrated under reduced pressure to give a product after flash chromatography on silica gel.

General Procedure L: Preparation of Amides Using EDCl Coupling

To a solution of acid (1 equiv) in dichloromethane at room temperature or at 0° C. is added HOBt (0-2 equiv.) followed by EDCl (1-5 equiv), amine (0.9-2 equiv) and NMM (0-4 equiv). The reaction mixture is stirred for 1 h. After complete conversion, the reaction mixture is diluted with DCM. The mixture is washed with water, with 1 N aqueous solution of HCl, with saturated aqueous solution of $NaHCO_3$ and then with brine. The DCM solution is dried over anhydrous $Na_2SO_4$ and concentrated by evaporation. The residue is purified by column chromatography. Alternatively, the crude mixture may be concentrated and purified by flash chromatography.

General Procedure M: Reductive Amination

To a solution of a primary amine hydrochloride (1.0 eq) in dichloroethane is added ketone (4 eq) and acetic acid (0.25 eq). The mixture is sonicated for 4 h and then sodium triacetoxyborohydride (5 eq) is added. The mixture is stirred overnight. After completion of the reaction, DCM is added and the organic layer is washed with 10% $Na_2CO_3$ solution and brine, and is dried over sodium sulfate. The solvent is removed under reduced pressure to give an amine, which may be purified by flash chromatography (9:1 to 8:2 hexanes/EtOAc).

General Procedure N: Acetamide Deprotection

To a solution of acetamine (1.0 eq) in methanol is added 4N HCl in dioxane (10.0 eq.). The mixture is heated at about 62° C. for 2-4 h. The mixture is concentrated and the residue is dissolved in DCM and the organic layer is washed with 10% $Na_2CO_3$ solution and brine, and dried over sodium sulfate. The solvent is removed under reduced pressure to give an amine, which may be purified by flash chromatography (9:1 to 7:3 hexanes/EtOAc).

General Procedure O: Alkylation of Acetamide

To a solution of acetamide (1.0 eq.) in DMF is added $K_2CO_3$ (2-6 eq) and alkyl halide (2-6 eq). The mixture is stirred at room temperature overnight. After completion of the reaction, the mixture is poured into water and is extracted with EtOAc. The organic layer is washed with water, brine, and is then dried over sodium sulfate. The solvent is removed under reduced pressure to give an alkylated acetamide, which is purified by flash chromatograpy.

General Procedure P: Alkylation of Tic Amine

To a solution of an amine (0.1 equivalents) is added an alkyl bromide (2.5 equivalents) and $NaHCO_3$ (10 equivalents). The mixture is stirred at room temperature for 2 days and then the mixture is heated at 40° C. for 2 days. The mixture is poured into water and is extracted with EtOAc (50 mL). The organic layer is washed with water (2×100 mL), brine (1×100 mL) and is dried (anhydrous $Na_2SO_4$) and concentrated to obtain an oil. The oil is purified by flash chromatography (9:1 to 8:2 hexanes/EtOAc) to obtain a solid which may contain multiple components. The solid is further purified by preparative TLC to obtain a product.

General Procedure Q: Hydrogenation of Double Bond and Debenzylation

To 1 equivalent of a dichlorobenzyloxy ester in anhydrous ethanol is added a catalytic amount of 10% palladium on activated carbon (wet). After degassing, hydrogen is introduced through a balloon. The reaction mixture is then stirred at room temperature for 0.5-2 h. The reaction mixture is then filtered through celite, and the celite cake is washed three times with ethyl acetate, and the filtrates are combined. The solvent is then removed in vacuo, and the residue is purified by flash column chromatography to give a product.

General Procedure R: Reduction of Aryl Nitro Group

To a suspension of an aryl nitro compound (1 eq) in HOAc (0.1-0.5 M), iron powder (325 mesh, 4 eq) is added and the mixture is then heated at about 120° C. under nitrogen for 3 to 4 h. At completion, the reaction mixture is diluted with water/EtOAc and the leftover iron powder is filtered and washed with EtOAc. The combined organic layer is washed with water, saturated $NaHCO_3$ and brine. The organic phase is then dried over $Na_2SO_4$, filtered, and the filtrate is concentrated and purified by silica gel chromatography to give an aniline derivative.

General Procedure S: Sonogashira Coupling

To a solution of an aryl bromide or an aryl iodide (1 eq) in anhydrous DMF (0.1-0.5 M) is added a terminal acetylene (1.2 eq) followed by tetrakis(triphenylphosphine) palladium (O) (0.05 eq), CuI (0.1 eq), and DIEA (2 eq). The reaction mixture is then heated at about 120° C. under nitrogen for 6 to 8 h. At completion, the reaction mixture is diluted with water/EtOAc, acidified with 10% citric acid, and the layers are separated. The combined organic layers are washed with water and brine, dried over $Na_2SO_4$ and filtered. The filtrate is concentrated and purified by silica gel chromatography to give an acetylene derivative.

General Procedure T: Alkylation

To a solution of phenol/thiazole (1 equivalent) in anhydrous DMF is added an alkyl or aryl halide (2 equivalents) followed by freshly ground $K_2CO_3$ (2 equivalents). The reaction mixture is heated at 100° C. under nitrogen gas for 2 h. The reaction mixture is then diluted with water/EtOAc and the layers are separated. The aqueous layer is further extracted with EtOAc, and the organic layers are combined and dried over $Na_2SO_4$. The solvent is removed in vacuo and the residue is purified by silica gel chromatography to give a product.

General Procedure U: Amination of chloropyridine

To a stirred solution of a 2-chloropyridine (1.0 eq) in dry DCM is added an excess (5-20 eq) of a primary or secondary amine. The mixture is heated with stirring to 50-80° C. for 24-48 h., and is then evaporated. The residue is dissolved in ethyl acetate and the solution is washed with 2% citric acid and water, then dried with brine and $Na_2SO_4$ and evaporated. The residue is purified by silica gel flash chromatography to give a 2-amino-pyridine product.

General Procedure V: Pictet-Spengler Reaction (S)-3-{2-[4-(3,4-Dichloro-benzyloxy)-phenyl]-2,3-dihydro-benzo[1,4]dioxin-6-yl}-2-alkylamino-propionic acid methyl ester (1.47 mmol) is dissolved in 80 mL dry dioxane, and 133 mg (4.41 mmol) paraformaldehyde and 20 mL trifluoroacetic acid are added. The reaction mixture is stirred for 12 h at room temperature, then 66 mg more paraformaldehyde is added while stirring at room temperature. After 3 h, aqueous $NaHCO_3$ is added until a pH of 7 is achieved, and then the mixture is extracted with EtOAc. The organic extract is washed with brine and dried over $Na_2SO_4$ and evaporated. The residue is purified by silica gel flash chromatography (9:1 to 8:2 hexanes/EtOAc).

General Procedure W: Alkylation of Acetamide by Mitsunobu Reaction

To a solution of an acetamide (1.0 eq.), an alcohol (2-6 eq.) and triphenylphosphine (2-6 eq.) in anhydrous THF is added DIAD (2-6 eq) at room temperature while sonication and the reaction mixture is stirred for 4 h. After completion of the reaction, the mixture is concentrated and the residue is purified by flash chromatograpy on silica to give a product.

General Procedure X: Alkyl Bromide Preparation

An alcohol (1.2 mmol) and 1 g of triphenylphosphine polystyrene (1.2 mmol/g) are taken in anhydrous dichloromethane (6 mL) and cooled to about 0° C. Then carbontetrabromide (0.4 g) is added and stirred for 1 h. Reaction is allowed to warm to room temperature and stirred for 2 h. The resin is filtered and washed with 5 mL of dichloromethane, and the filtrate is concentrated and dried in a vacuum gave a corresponding bromide, which may be used in another reaction without further purification.

General Procedure Y: Acetylation of Amino Pyridines or Amino Thiazoles

An amino pyridine or an amino thiazole (2 mmol) is taken in acetic anhydride (10 mL) and heated at 80° C. for 2-4 h. The reaction mixture is cooled to room temperature and 10 mL of MeOH is added and stirred for 1 h. All volatiles are removed by rotavapor. The residue is dried in vacuo and may be used in another reaction without further purification.

General Procedure Z: Hydrogenation of Aromatic Nitro Compounds

An aromatic nitro compound (1.0 mmol) is dissolved in THF:MeOH (1:1, 5 mL), and 30 mg of Pd—C(10% by wt) is added and stirred under a hydrogen atmosphere with a balloon for 6 h. The catalyst is filtered off and the solvent is removed under vacuum to yield an amine.

General Procedure AA: Preparation of Sulfonyl Chlorides from Anilines

To a solution of an amino-pyridine derivative (2.0 mmol) is added conc. HCl (6 mL), and then the reaction mixture is cooled to 0° C. To a solution (2 mL) of sodium nitrate (0.15 g) is added dropwise while keeping the inside temperature 0-5° C. The reaction mixture is stirred for 30 min., and cuprous chloride (5 mg) is added. A saturated solution of sulfur dioxide in water (which may be prepared by adding thionyl chloride (0.6 mL) to water (3.4 mL) over 30 min at 0° C.) is carefully added. The frothing reaction mixture is stirred for 30 min and is extracted with dichloromethane. The organic layer is washed with water, brine and dried over $Na_2SO_4$.

Solvent is removed by rotavapor and the residue is dried in vacuo. The resulting product may be used in another reaction without further purification.

General Procedure AB: Methyl Ester Hydrolysis

To a solution of ester (1 eq.) in THF-methanol (1-4 to 1-3), is added 2.5 N KOH solution (15 eq.), and the resulting reaction mixture is stirred at room temperature for 48 h. After completion of the reaction, the mixture is diluted with water and 1N HCl is used to neutralize the base and the residue is extracted with ethyl acetate. The organic layer is washed with brine, dried over sodium sulfate, and the solvent is removed under reduced pressure to give an acid.

General Procedure AC: Chiral Alkylation of Tic Amine

Step 1. Sulfonation. An amino acid methyl ester (1 eq) is dissolved in dry DCM and 4N HCl/dioxane (15 eq) is added while stirring at room temperature. After stirring for 3 h, the solvents are evaporated and the residue is evaporated again from DCM and toluene. The residue is then dissolved in 1:1 EtOAc and saturated aqueous NaHCO$_3$ and p-nitrobenzene-sulfonyl chloride (1.1 eq) are added. After stirring at room temperature for 1.5 h, the layers are separated and the organic layer is washed with water, then brine, then dried over Na$_2$SO$_4$ and then evaporated. The resulting residue may be purified by silica gel flash chromatography (9:1 to 7:3 hexanes/EtOAc) to give a product.

Step 2. Mistunobu Reaction. An amino acid benzenesulfonamide from Step 1 (1 eq) is dissolved in dry THF and 2 eq triphenylphosphine and 2 eq (R)-(+)-1-phenyl-1-propanol are added. The mixture is stirred at 0° C. for 10 min, then 2 eq DIAD are added over 2 min. The reaction is stirred at room temperature for 5 h, then is evaporated. The residue is purified by silica gel flash chromatography (9:1 to 8:2 hexanes/EtOAc) to give a product.

Step 3. De-Sulfonation. A Mitsunobu product from Step 2 (1 eq) is dissolved in dry DMF, and 3.19 eq of mercaptoacetic acid and 7.6 eq of DBU are added at room temperature. The reaction mixture is stirred for 3 h, and is then is partitioned between saturated aqueous NaHCO$_3$ and diethyl ether. The organic layer is washed successively with aqueous NaHCO$_3$, water, and brine, and then is dried with Na$_2$SO$_4$ and evaporated. The residue is purified by silica gel flash chromatography (9:1 to 8:2 hexanes/EtOAc) to give a product.

Step 4. Pictet-Spengler Reaction. A desulfonated amino acid (1 eq) from Step 3 and 2 eq paraformaldehyde are dissolved in 4:1 v/v dry dioxane and trifluoroacetic acid. The reaction mixture is stirred for 12 h at room temperature, and then 1.5 eq more paraformaldehyde is added while stirring at room temperature. After 3 h, aqueous NaHCO$_3$ is added until a pH of 7 is achieved, then the mixture is extracted with EtOAc. The organic extract is washed with brine and dried over Na$_2$SO$_4$ and evaporated. The residue is purified by silica gel flash chromatography (9:1 to 8:2 hexanes/EtOAc) to give a product.

Step 5. Hydrolysis. A Pictet-Spengler product from Step 4 (1 eq) is dissolved in 1:1 THF and MeOH and 10 eq LiOH is added. The flask is flushed with nitrogen and placed under a nitrogen balloon and stirred at 0° C. Water is then added in portions while stirring, and the reaction is stirred at room temperature for 15 h. Then, 2 eq additional LiOH and water are added to the reaction, and stirring is continued for 2 h. More water is added and stirring is continued for 30 min, then water is again added. After 1.5 h, the pH is adjusted to 7 with 10% w/v aqueous citric acid, and the mixture is extracted with EtOAc. The organic layer is washed with brine and dried over Na$_2$SO$_4$ and evaporated, to give a product.

General Procedure AD: Preparation of Isocyanates and Carbamoyl Chlorides

To a solution of primary or secondary alkyl amine (1 mmol) in 10 mL DCM, triphosgene (0.6 mmol) is added at 0° C. The mixture is stirred for 30 minutes and then triethylamine (3 mmol) is added. The mixture is stirred for an additional 20 minutes. The formation of the isocyanate or carbamoyl chloride is confirmed by reaction of a portion of the reaction mixture with 4-methoxy phenethyl amine. LCMS can be used to show the corresponding urea. The crude isocyanates or carbamoyl chlorides are used without any further purification.

Synthesis of Intermediates

In making compounds or salts of the invention, it may be useful to synthesize certain intermediate compounds. The synthetic procedures are provided exclusively for purposes of illustration. As the skilled artisan will recognize, the procedures below may not be the exclusive means by which such compounds are made. Such procedures may readily be modified or optimized, as necessary or desired.

Procedure 1

(S)-6,7-Dihydroxy-1,2,3,4-tetrahydro-isoquinoline-3-carboxylic acid methyl ester

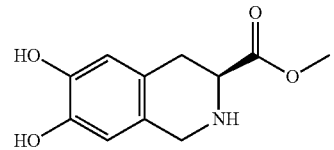 [SMILES: COC(=O)[C@@H]1Cc2cc(O)c(O)cc2CN1]

To a solution of L-DOPA (9.9 g) in 100 mL of methanol were added concentrated hydrochloric acid (20 mL) and paraformaldehyde (3 eq). The reaction mixture was heated to 100° C. and refluxed at this temperature for 16 h to give a product. The crude product was concentrated under reduced pressure then triturated with ether (2×100) to remove byproducts. After filtration, the white powder was dried under reduced pressure to give (S)-6,7-Dihydroxy-1,2,3,4-tetrahydro-isoquinoline-3-carboxylic acid methyl ester in quantitative yield. LCMS (m/z): 225.

(S)-6,7-Dihydroxy-3,4-dihydro-1H-isoquinoline-2,3-dicarboxylic acid 2-tert-butyl ester 3-methyl ester

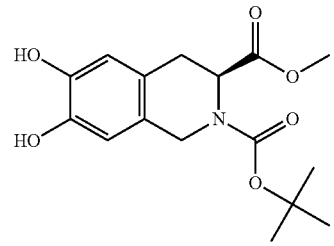 [SMILES: COC(=O)[C@@H]1Cc2cc(O)c(O)cc2CN1C(=O)OC(C)(C)C]

To a solution of (S)-6,7-dihydroxy-1,2,3,4-tetrahydro-isoquinoline-3-carboxylic acid methyl ester (4.46 g) in dioxane (100 mL) and water (50 mL) were added di-tert-butyl dicarbonate (6.6 g) and sodium bicarbonate (4.2 g). The reaction mixture was vigorously stirred at ambient temperature for 4 h. After the reaction was complete, hydrazine (10 mL, 50% solution in water) was added to this reaction mixture and stirred for 4 h to cleave carbonate. The reaction mixture was extracted with ethyl acetate (2×100 mL) then the organic extracts were combined and washed with 1N HCl (25 mL) and brine solution (50 mL) and condensed in vacuo to give desired product, (S)-6,7-dihydroxy-3,4-dihydro-1H-isoquinoline-2,3-dicarboxylic acid 2-tert-butyl ester 3-methyl ester in quantitative yield. LCMS (m/z): 324.

2-Bromo-1-[4-(3,4-dichloro-benzyloxy)-phenyl]-ethanone

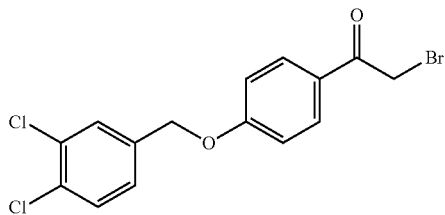 [SMILES: O=C(CBr)c1ccc(OCc2ccc(Cl)c(Cl)c2)cc1]

1-[4-(3,4-Dichloro-benzyloxy)-phenyl]-ethanone (2.92 g) was dissolved in methanol:DCM (2:1, 75 mL) and pyrolidinone hydrotribromide (7.5 g) was added and stirred at room temperature for 2.5 h. After completion of the reaction, the mixture was concentrated in vacuo and poured into saturated sodium bicarbonate solution (100 mL) and extracted with ethyl acetate (2×100 mL). The organic extracts were combined and concentrated in vacuo. Then this residue was dissolved in DCM (10 ml) and methanol (10 mL) was slowly added to this solution to precipitate the product. The colored solution was filtered through to give clear white powder product 2-bromo-1-[4-(3,4-dichloro-benzyloxy)-phenyl]-ethanone with quantitative yield (3.75 g).

$^1$H NMR (400 MHz, CDCl$_3$): 7.98 (d, 2H), 7.54 (s, 1H), 7.47 (d, 1H), 7.25 (m, 1H), 7.01 (d, 2H), 5.09 (s, 2H), and 4.40 (s, 2H).

(S)-3-[4-(3,4-Dichloro-benzyloxy)-phenyl]-3-hydroxy-2,3,8,9-tetrahydro-6H-[1,4]dioxino[2,3-g]isoquinoline-7,8-dicarboxylic acid 7-tert-butyl ester 8-methyl ester

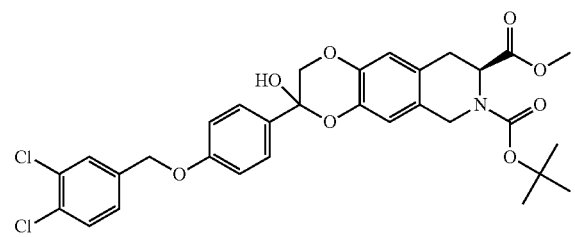 [SMILES: COC(=O)[C@@H]1Cc2cc3c(cc2CN1C(=O)OC(C)(C)C)OC(O)(c1ccc(OCc2ccc(Cl)c(Cl)c2)cc1)CO3]

6,7-Dihydroxy-3,4-dihydro-1H-isoquinoline-2,3-dicarboxylic acid 2-tert-butyl ester 3-methyl ester (0.76 g) was dissolved in anhydrous DMF (20 mL). To this solution 1-[4-(3,4-dichloro-benzyloxy)-phenyl]-ethanone (0.93 g) and potassium carbonate (0.7 g) were added and heated to 100° C. The reaction mixture was stirred at this temperature for 12 hours. After the reaction was complete, the reaction mixture was poured into water and extracted with ethyl acetate (50 mL) and washed with brine (2×50 mL), dried over (sodium sulfate) and concentrated in vacuo to give the crude product. The residue was then purified by flash column chromatography (hexanes:ethyl acetate 90:10 to 60:40) to give the desired product, (S)-3-[4-(3,4-Dichloro-benzyloxy)-phenyl]-3-hydroxy-2,3,8,9-tetrahydro-6H-[1,4]dioxino[2,3-g]isoquinoline-7,8-dicarboxylic acid 7-tert-butyl ester 8-methyl ester (0.92 g). $^1$H NMR (400 MHz, CDCl$_3$): 7.91 (d, 2H), 7.82 (d, 1H), 7.58 (d, 1H), 7.54 (d, 1H), 7.47 (m, 1H), 7.00 (m, 2H), 6.78 (m, 1H), 5.32 (s, 1H), 5.09 (s, 2H), 4.70 (m, 1H), 4.40 (m, 1H), 3.62 (s, 3H), 3.06 (m, 1H), 1.51 (s, 9H), 1.26 (m, 2H), and 0.88 (t, 2H).

(S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester

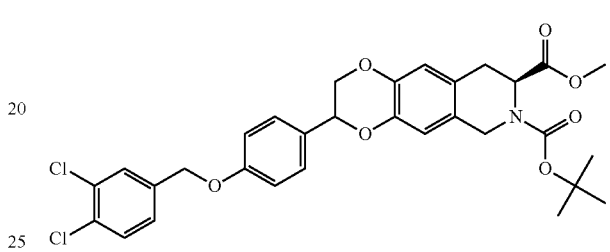

To a solution of (S)-3-[4-(3,4-Dichloro-benzyloxy)-phenyl]-3-hydroxy-2,3,8,9-tetrahydro-6H-[1,4]dioxino[2,3-g]isoquinoline-7,8-dicarboxylic acid 7-tert-butyl ester 8-methyl ester (122 mg) in DCM (10 mL) were added TFA (1 mL) and triethylsilane (3 eq) at −10° C. and the reaction mixture were stirred and allowed to warm up to room temperature within 3 h. Then the reaction mixture was concentrated in vacuo. To this residue di-tert-butyl dicarbonate (2 eq) and sodium bicarbonate (3.0 eq) were added in the presence of ethyl acetate (25 mL) and stirred at r.t. for 4 h. After t-boc protection was complete the reaction mixture was then slowly acidified with dilute HCl (25 mL, 1.0 M solution), extracted with ethyl acetate (2×25 mL). The combined organic extracts were washed with 1 N HCl (25 mL), water (25 mL) and brine (25 mL) dried over sodium sulfate, filtered, and concentrated to provide a yellow solid. The residue was then purified by silica gel chromatography (10/90 to 30/70 ethyl acetate/hexanes in 10% increments) to obtain a white solid of (S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester (73 mg).

(S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester

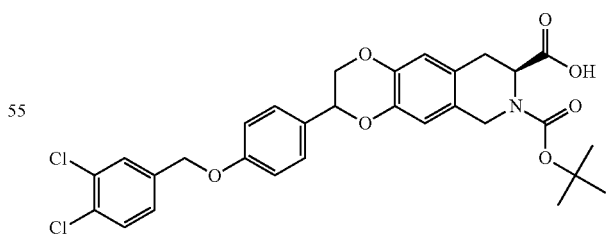

(S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester (49 mg) was prepared from (S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester (60 mg) according to General Procedure B. LCMS (m/z): 585.

(S)-8-[(S)-2-(4'-Cyano-biphenyl-4-yl)-1-methoxy-carbonyl-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid tert-butyl ester

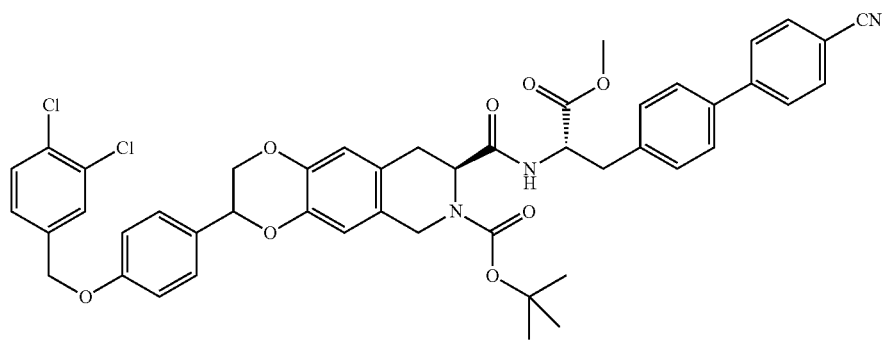 [SMILES: COC(=O)[C@H](Cc1ccc(-c2ccc(C#N)cc2)cc1)NC(=O)[C@@H]1Cc2cc3c(cc2CN1C(=O)OC(C)(C)C)OC(c1ccc(OCc2ccc(Cl)c(Cl)c2)cc1)CO3]

(S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester, HBTU and DIEA were dissolved in DMF (20 mL). (S)-2-Amino-3-(4'-cyano-biphenyl-4-yl)-propionic acid methyl ester was added and the mixture stirred at r.t. for 16 h. The reaction mixture was poured into 1 N HCl and extracted with ethyl acetate. The organic extracts were combined and washed with 1 N HCl and 10% sodium carbonate, concentrated and purified by column chromatography on silica gel (hexanes-ethyl acetate) to afford the product (4.9 g). LCMS (m/z) 851.

(S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride

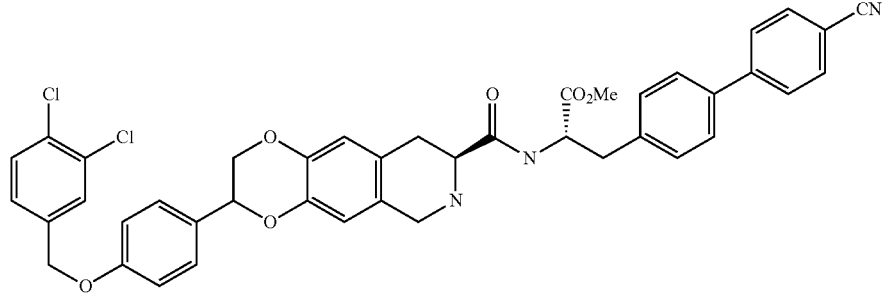

(S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride (4.0 g) was prepared from (S)-8-[(S)-2-(4'-cyano-biphenyl-4-yl)-1-methoxycarbonyl-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid tert-butyl ester (4.9 g) according to General Procedure C The residue was triturated with ethyl ether and the precipitated solid was filtered and dried under vacuum to give desired amine as hydrochloride salt. LCMS (m/z): 749.

Procedure 2

1-[4-(3,4-Dichloro-benzyloxy)-phenyl]-ethane-1,2-diol

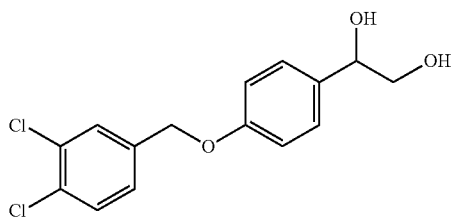 [SMILES: OCC(O)c1ccc(OCc2ccc(Cl)c(Cl)c2)cc1]

[4-(3,4-Dichloro-benzyloxy)-phenyl]-hydroxy-acetic acid methyl ester (20.46 g) was dissolved in 300 mL of anhydrous THF. The reaction mixture was cooled to 10° C. and lithium borohydride (2.0 M, 40.0 mL) in THF was added drop-wise. (Caution: vigorous gas evolution.) The reaction mixture was warmed to room temperature and stirred for 16 hours. The reaction was quenched by slow addition of 1.0 M aqueous HCl. (Caution: vigorous gas evolution.) After stirring for 2 h at room temperature, the THF was removed under reduced pressure. Water (500 mL) was added to the residue and the aqueous layer was extracted twice with 600 mL EtOAc. The combined extracts were dried over sodium sulfate, filtered, and concentrated to give of the desired diol in quantitative yield. ¹H NMR (400 MHz, CD₃COCD₃): 7.69 (s, 1H), 7.60 (d, 1H), 7.47 (dd, 1H), 7.30 (dd, 2H), 6.97 (dd, 2H), 5.13 (s, 2H), 4.65 (m, 1H), 4.24 (m, 1H), 3.78 (t, 1H), 3.40-3.60 (m, 2H).

2-(tert-Butyl-diphenyl-silanyloxy)-1-[4-(3,4-dichloro-benzyloxy)-phenyl]-ethanol

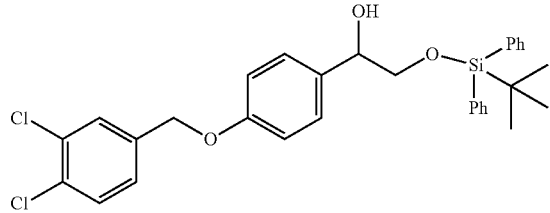 [SMILES: CC(C)(C)[Si](OCC(O)c1ccc(OCc2ccc(Cl)c(Cl)c2)cc1)(c1ccccc1)c1ccccc1]

1-[4-(3,4-Dichloro-benzyloxy)-phenyl]-ethane-1,2-diol (18.8 g), imidazole (8.17 g), and a catalytic amount of DMAP were dissolved in 60 mL of anhydrous DMF. tert-Butyldiphenylchlorosilane (18.7 mL) was added drop-wise and the mixture stirred at rt for 16 h. The reaction mixture was poured into 1 L of a mixture of water-ethyl acetate-hexanes (2:2:1) and the layers were separated. After an additional extraction with 0.5 L 3:1 EtOAc/hexanes, the organic extracts were dried over sodium sulfate and concentrated. The yellow oil was purified by silica gel flash chromatography (ethyl acetate/hexanes) to give 14.0 g of the desired product.

¹H NMR (400 MHz, CDCl₃): 7.65 (m, 4H), 7.52 (m, 1H), 7.34-7.46 (m, 7H), 7.22 (m, 3H), 6.88 (d, 2H), 5.0 (s, 2H), 4.78 (m, 1H), 3.6-3.8 (m, 2H), 3.05 (m, 1H), 1.10 (s, 9H).

(S)-3-(3-Bromo-4-{2-(tert-butyl-diphenyl-silanyloxy)-1-[4-(3,4-dichloro-benzyloxy)-phenyl]-ethoxy}-phenyl)-2-tert-butoxycarbonylamino-propionic acid methyl ester

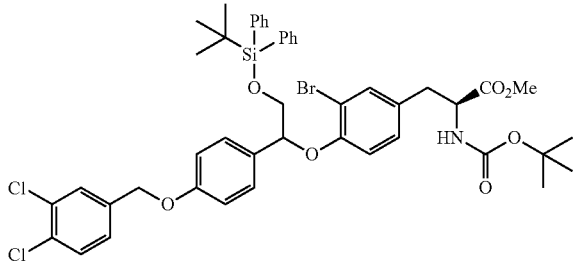 [SMILES: COC(=O)[C@H](Cc1ccc(OC(CO[Si](c2ccccc2)(c2ccccc2)C(C)(C)C)c2ccc(OCc3ccc(Cl)c(Cl)c3)cc2)c(Br)c1)NC(=O)OC(C)(C)C]

2-(tert-Butyl-diphenyl-silanyloxy)-1-[4-(3,4-dichloro-benzyloxy)-phenyl]-ethanol (11.0 g), (S)-3-(3-bromo-4-hydroxy-phenyl)-2-tert-butoxycarbonylamino-propionic acid methyl ester (7.46 g), and triphenylphosphine (7.87 g) were dissolved in 75.0 mL of anhydrous DCM and the mixture cooled to 0° C. DIAD (5.85 mL) was added drop wise to the reaction mixture. After 1 h, the cooling bath was removed and the reaction stirred overnight. Concentration gave a dark orange oil which was purified by silica gel chromatography (ethyl acetate/hexanes) to obtain the desired product. LCMS: 910.

(S)-3-(3-Bromo-4-{1-[4-(3,4-dichloro-benzyloxy)-phenyl]-2-hydroxy-ethoxy}phenyl)-2-tert-butoxycarbonylamino-propionic acid methyl ester

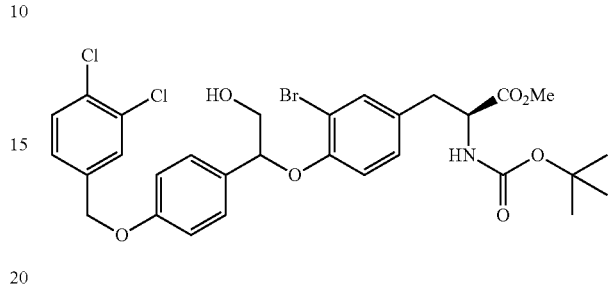

(S)-3-(3-Bromo-4-{2-(tert-butyl-diphenyl-silanyloxy)-1-[4-(3,4-dichloro-benzyloxy)-phenyl]-ethoxy}-phenyl)-2-tert-butoxycarbonylamino-propionic acid methyl ester (5.0 g) was dissolved in 10 mL of anhydrous THF. TBAF (6 mL, 1.0 M solution in THF) was added drop-wise to the reaction mixture. After 2 h, the reaction mixture was concentrated to obtain a light brown oil. The oil was purified by silica gel chromatography (ethyl acetate/hexanes) to obtain the desired product as a white fluffy solid. ¹H NMR (400 MHz, CDCl₃): 7.51 (d, 1H), 7.43 (d, 1H), 7.3 (m, 3H), 7.23 (m, 2H), 6.92 (d, 2H), 6.84 (m, 1H), 6.62 (d, 1H), 5.17 (m, 1H), 4.99 (s, 1H), 4.93 (m, 1H), 4.48 (m, 1H), 3.94 (m, 1H), 3.76 (m, 1H), 3.66 (s, 3H), 2.84-3.02 (m, 2H), 2.47 (m, 1H), 1.41 (s, 9H). LCMS: 669.

(S)-2-tert-Butoxycarbonylamino-3-{2-[4-(3,4-dichloro-benzyloxy)-phenyl]-2,3-dihydro-benzo[1,4]dioxin-6-yl}-propionic acid methyl ester

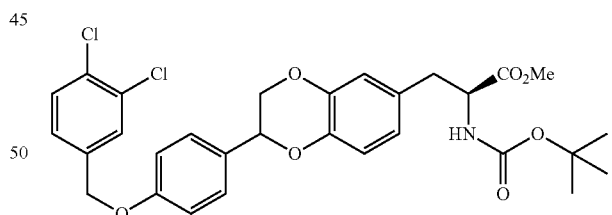

(S)-3-(3-Bromo-4-{1-[4-(3,4-dichloro-benzyloxy)-phenyl]-2-hydroxy-ethoxy}-phenyl)-2-tert-butoxycarbonylamino-propionic acid methyl ester (8.0 g), palladium acetate (224 mg), racemic 2-(di-tert-butylphosphino)1,1'-binaphthalene (480 mg), and cesium carbonate (5.86 g) were placed into a 100 mL round-bottom flask. The flask was evacuated and flushed with nitrogen twice. Anhydrous toluene (40 mL) was added and the resulting suspension was heated for 48 h at 52° C. After concentration of the reaction mixture to a brown oil, the residue was purified by silica gel chromatography (ethyl acetate/hexanes to give the desired product 10 g as a fluffy white solid. ¹H NMR (400 MHz, CDCl₃): 7.54 (d, 1H), 7.44 (d, 1H), 7.33 (m, 3H), 7.26 (m, 1H), 6.98 (m, 2H), 6.87

(d, 1H), 6.69 (d, 1H), 6.62 (dd, 1H), 5.04 (s, 2H), 4.98 (m, 1H), 4.56 (m, 1H), 4.28 (dd, 1H), 3.98 (m, 1H), 3.74 (s, 3H), 3.0 (m, 2H), 1.42 (s, 9H).

(S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester

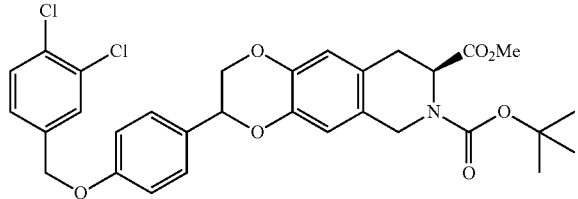 [SMILES: COC(=O)[C@@H]1Cc2cc3c(cc2CN1C(=O)OC(C)(C)C)OC(c1ccc(OCc2ccc(Cl)c(Cl)c2)cc1)CO3]

(S)-2-tert-Butoxycarbonylamino-3-{2-[4-(3,4-dichloro-benzyloxy)-phenyl]-2,3-dihydro-benzo[1,4]dioxin-6-yl}-propionic acid methyl ester (2.1 g) was deprotected according to General Procedure C. The resulting material was dissolved in dioxane (20 mL) and TFA (4 mL) and solid paraformaldehyde (300 mg) added. The reaction mixture was heated for 2 h at 60° C. and concentrated. The resulting material was dissolved in DCM and aqueous sodium bicarbonate and ditert-butyl pyrocarbonate (1.5 g) added. The layers of the reaction mixture were separated and the aqueous layer was extracted twice with 50. mL of DCM. The combined organic extracts were dried over sodium sulfate, filtered, and concentrated to provide a yellow solid. The residue was purified by silica gel chromatography (10/90 to 30/70 ethyl acetate/hexanes in 10% increments) to obtain the desired product. $^1$H NMR (400 MHz, CDCl$_3$): 7.54 (d, 1H), 7.45 (d, 1H), 7.32 (d, 2H), 7.24 (m, 2H), 6.96 (d, 2H), 6.77 (s, 1H), 6.72 (d, 2H), 5.04 (m, 1H), 5.02 (s, 2H), 4.73 (m, 1H), 4.60 (m, 1H), 4.40 (m, 1H), 4.26 (m, 1H), 3.97 (m, 1H), 3.64 (d, 3H), 3.02-3.20 (m, 2H), 1.54 and 1.44 (s, 9H).

(S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester

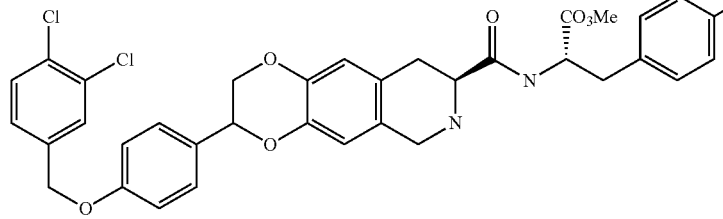

(S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester was hydrolyzed according to General Procedure B to provide (S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester. (S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester (1.17 g), EDCl (500 mg) HOBt (366 mg) and N-methylmorpholine were dissolved in DCM (6 mL). (S)-2-Amino-3-(4'-cyano-biphenyl-4-yl)-propionic acid methyl ester (632 mg) was added and the mixture stirred 2 h. The reaction mixture concentrated and purified by column chromatography on silica gel (hexanes-EtOAc) to afford the pure product (1.36 g). The resulting solid was treated with 4 N HCl in dioxane (8 mL). The reaction was stirred at room temperature for 30 min and the solvent removed under reduced pressure. The residue was triturated with ethyl ether and the precipitated solid was filtered and dried under vacuum to give desired amine as hydrochloride salt. This salt was neutralized with Na$_2$CO$_3$ solution and the residue was extracted with EtOAc. The organic layer was washed with water, brine dried and concentrated to get the free amine. This product was purified by column chromatography (DCM: EtOAc, 9:1-1:1) to get the pure amine as a mixture of diastereomers as the major product. $^1$H NMR (400 MHz, d$_6$-DMSO): 8.26 (d, 1H), 7.85 (m, 4H), 7.70 (s, 1H), 7.64 (m, 4H), 7.42 (m, 1H), 7.34 (m, 2H), 7.30 (d, 1H), 7.02 (dd, 2H), 6.60 (s, 1H), 6.56 (s, 1H), 5.13 (s, 2H), 5.06 (m, 1H), 4.60 (m, 1H), 4.31 (m, 1H), 3.96 (m, 1H), 3.66 (bs, 1H), 3.65 (s, 3H), 3.38 (m, 1H), 3.10 (m, 1H), 2.5-2.78 (m, 2H). LCMS: 749.

Procedure 3

(S)-6,7-Dihydroxy-1,2,3,4-tetrahydro-isoquinoline-3-carboxylic acid

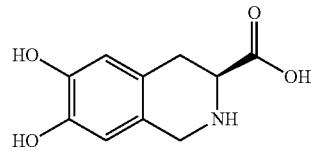 [SMILES: O=C(O)[C@@H]1Cc2cc(O)c(O)cc2CN1]

(S)-2-Amino-3-(3,4-dihydroxy-phenyl)-propionic acid (90 g) was suspended in 0.8 L water, then 18.2 mL concentrated sulfuric acid in 0.5 L additional water was added with stirring. Formaldehyde solution (136 mL, 37 wt %) was then added while stirring and the mixture was stirred 18 hours at rt. It was quenched by addition of 24.4 g NaOH in 0.5 L water, dropwise over 1 h while cooling. The resulting mixture was stored overnight at 4° C., and the solid that formed was collected by filtration, washed with hot water (70° C.), cooled again and collected by filtration. The solid was treated with 0.5 L MeOH and evaporated, then stored under vacuum overnight to give 65 g desired product. $^1$H NMR (400 MHz, MeOH-d$_4$): 6.64 (s, 1H), 6.59 (s, 1H), 4.29-4.21 (m, 3H), 3.29-3.21 (m, 1H), 3.11-3.01 (m, 1H).

(S)-6,7-Dihydroxy-1,2,3,4-tetrahydro-isoquinoline-3-carboxylic acid methyl ester

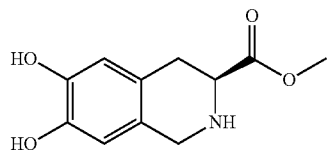 [SMILES: COC(=O)[C@@H]1Cc2cc(O)c(O)cc2CN1]

(S)-6,7-Dihydroxy-1,2,3,4-tetrahydro-isoquinoline-3-carboxylic acid (62 g), 200 mL anhydrous MeOH, and 26 mL concentrated hydrochloric acid were stirred together overnight at 70° C. The mixture was then evaporated and the residue resuspended in 500 mL acetonitrile with vigorous stirring to wash all the solid material. Stirring continued for 18 h at r.t., after which the solid product was collected by filtration, washed with 100 mL acetonitrile, and dried under vacuum overnight. Yield 77 g (quantitative). $^1$H NMR (400 MHz, MeOH-d$_4$): 6.64 (s, 1H), 6.61 (s, 1H), 4.42-4.36 (m, 1H), 4.29-4.24 (m, 2H), 3.89 (s, 3H), 3.29-3.22 (m, 1H), 3.11-3.02 (m, 1H).

(S)-6,7-Dihydroxy-3,4-dihydro-1H-isoquinoline-2,3-dicarboxylic acid 2-tert-butyl ester 3-methyl ester

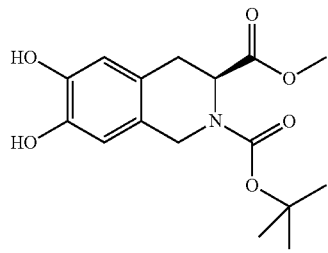 [SMILES: COC(=O)[C@@H]1Cc2cc(O)c(O)cc2CN1C(=O)OC(C)(C)C]

(S)-6,7-Dihydroxy-1,2,3,4-tetrahydro-isoquinoline-3-carboxylic acid methyl ester hydrochloride (60 g), di-t-butyl dicarbonate (61 g) and NaHCO$_3$ (46.4 g) were combined with 0.5 L each of EtOAc and water. The mixture was stirred 18 hours at r.t., then the aqueous layer was discarded. The organic layer was washed with 200 mL 1N HCl, then 200 mL of water, then was dried over Na$_2$SO$_4$ and evaporated to an oil. The oil was taken up in diethyl ether, precipitated with hexanes and collected by filtration, to give 75 g (quantitative) desired product after drying under vacuum. $^1$H NMR (400 MHz, CDCl$_3$): 6.67 (s, 1H), 6.63 (d, 1H), 6.56 (s, 1H), 5.12-5.08 and 4.73-4.69 (m, 1H), 4.56-4.48 (m, 1H), 4.42-4.30 (m, 1H), 3.67 and 3.60 (s, 3H), 3.13-2.95 (m, 2H), 1.51 and 1.46 (s, 9H).

(S)-3-[4-(3,4-Dichloro-benzyloxy)-phenyl]-3-hydroxy-2,3,8,9-tetrahydro-6H-[1,4]dioxino[2,3-g]isoquinoline-7,8-dicarboxylic acid 7-tert-butyl ester 8-methyl ester

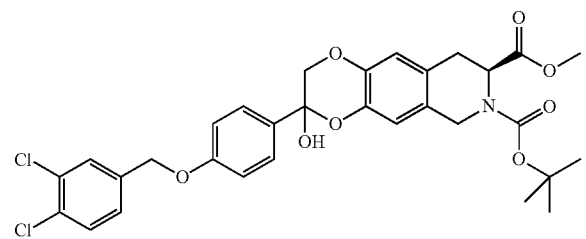 [SMILES: COC(=O)[C@@H]1Cc2cc3c(cc2CN1C(=O)OC(C)(C)C)OC(O)(c1ccc(OCc2ccc(Cl)c(Cl)c2)cc1)CO3]

(S)-6,7-Dihydroxy-3,4-dihydro-1H-isoquinoline-2,3-dicarboxylic acid 2-tert-butyl ester 3-methyl ester (30.0 g), 2-bromo-1-[4-(3,4-dichloro-benzyloxy)-phenyl]-ethanone (34.7 g), and sodium bicarbonate (7.8 g) were stirred together in 600 mL anhydrous DMF. While stirring at rt, DBU (6.95 mL) was added all at once and the mixture was stirred at rt for 18 hours. The reaction mixture was then poured into 1 L EtOAc and 500 mL water and the layers were separated. The organic layer was washed with water three times and brine once, then dried over sodium sulfate and concentrated to provide 57.8 g of orange foam which was used in the next step without further purification.

(S)-3-[4-(3,4-Dichloro-benzyloxy)-phenyl]-8,9-dihydro-6H-[1,4]dioxino[2,3-g]isoquinoline-7,8-dicarboxylic acid 7-tert-butyl ester 8-methyl ester

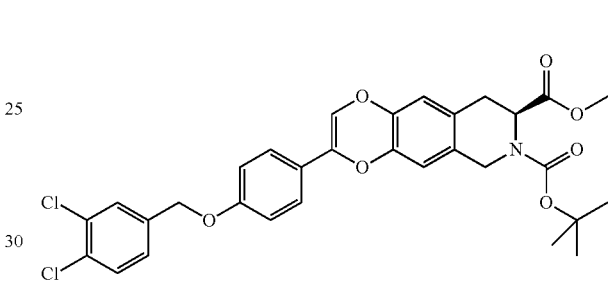

(S)-3-[4-(3,4-Dichloro-benzyloxy)-phenyl]-3-hydroxy-2,3,8,9-tetrahydro-6H-[1,4]dioxino[2,3-g]isoquinoline-7,8-dicarboxylic acid 7-tert-butyl ester 8-methyl ester (15.78 g) was dissolved in 100 mL each of anhydrous DCM and NEt$_3$ under nitrogen in a flask equipped with dropping funnel and internal thermometer. The apparatus was flushed with nitrogen, cooled to –40° C. and methanesulfonyl chloride (5.96 g) was added at a rate to maintain the internal temperature below –30° C. The reaction was allowed to warm to 10° C. over 6 hours, then was concentrated to a paste. The paste was dissolved in 1 L of a 1:1 mixture of 1M Na$_2$CO$_3$ and EtOAc and the layers were separated. The aqueous layer was extracted again with 250 mL EtOAc and the combined organic layers were washed with water, brine, and dried over sodium sulfate and concentrated. The residue was purified by silica gel flash chromatography (hexanes/EtOAc 9:1 to 7:3) to give 5.2 g of a mixture of regioisomers from the cyclization product. The desired regioisomer was isolated by trituration of the mixture with ether to separate the majority of undesired isomer as a crystalline solid. The remainder of undesired regioisomer was removed by silica gel flash chromatography (DCM/0.5% DIEA) to give 0.9 g of the desired product. $^1$H NMR (400 MHz, acetone-d$_6$): 7.71 (d, 1H), 7.61 (d, 1H), 7.52-7.46 (m, 3H), 7.05 (m, 2H), 6.78-6.69 (m, 2H), 6.62 (d, 1H), 5.19 (s, 2H), 5.03 and 4.81 (m, 1H), 4.64-4.49 (m, 1H), 4.43-4.29 (m, 1H), 3.65-3.58 (m, 3H), 3.16-2.99 (m, 2H), 1.53-1.40 (m, 9H).

333

(3S,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester and (3R,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester

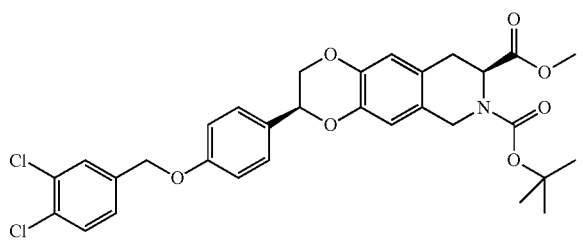

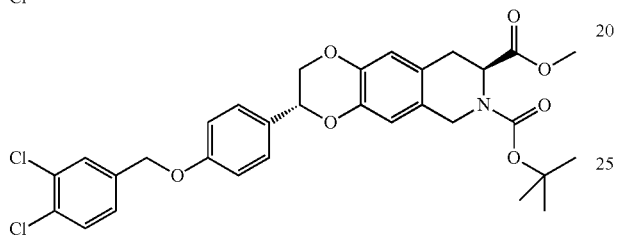

(S)-3-[4-(3,4-Dichloro-benzyloxy)-phenyl]-8,9-dihydro-6H-[1,4]dioxino[2,3-g]isoquinoline-7,8-dicarboxylic acid 7-tert-butyl ester 8-methyl ester (2.1 g) was dissolved with stirring in 30 mL EtOAc, 15 mL DCM, 2 mL MeOH, and 5 mL NEt₃. Tris(triphenylphosphine)rhodium(I) chloride (344 mg) was added and the mixture was sonicated briefly to suspend the starting material, then degassed by vacuum. The stirred was stirred under a hydrogen-filled balloon for 12 hours at rt, at which point a solution had formed. The solvents were evaporated and the residue was purified by silica gel flash chromatography (hexanes/EtOAc 9:1 to 8:2) to provide the desired product as a mixture of diastereomers. The diastereoisomers were separated by repeated silica gel flash chromatography (hexanes-MTBE 7:3) to give the faster moving diastereomer ((3S,8S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester), 1.1 g yield and the slower moving diastereomer ((3R,8S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester), 1.0 g yield (quantitative). ¹H NMR (400 MHz, benzene-d₆) faster moving diastereomer ((3S,8S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester): 7.11 (s, 4H), 6.99-6.92 (m, 2H), 6.75 (d, 1H), 6.71-6.64 (m, 2H), 5.39 and 4.80 (m, 1H), 4.76-4.62 (m, 3H), 4.29-4.23 (m, 2H), 3.86-3.80 (m, 1H), 3.59-3.51 (m, 1H), 3.17 and 3.08 (s, 3H), 3.04-2.89 (m, 1H), 2.81-2.69 (m, 1H), 1.45 and 1.42 (s, 9H); ¹H NMR (400 MHz, benzene-d₆) slower moving diastereomer ((3R,8S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester): 7.14-7.09 (m, 4H), 7.00-6.93 (m, 2H), 6.74 (d, 1H), 6.70-6.63 (m, 2H), 5.37 and 4.78 (m, 1H), 4.74-4.57 (m, 3H), 4.28-4.23 (m, 2H), 3.88-3.82 (m, 1H), 3.71-3.64 (m, 1H), 3.17 and 3.08 (s, 3H), 3.03-2.87 (m, 1H), 2.80-2.69 (m, 1H), 1.46 and 1.41 (s, 9H). LCMS: m/z 600 (M+1).

(S)-3-(4'-Cyano-biphenyl-4-yl)-2-({(3R,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride

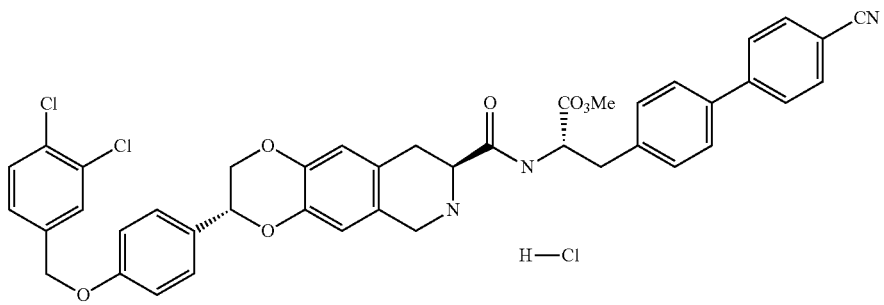

(3R,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester, (200 mg) hydrolyzed according to General Procedure B and the resulting (3R,8S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester (172 mg) was coupled with (S)-2-amino-3-(4'-cyano-biphenyl-4-yl)-propionic acid methyl ester (126 mg) according to General Procedure L to give (3R,8S)-8-[(S)-2-(4'-cyano-biphenyl-4-yl)-1-methoxycarbonyl-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid tert-butyl ester (191 mg). This intermediate (188 mg) was deprotected as described in General Procedure C to give (S)-3-(4'-cyano-biphenyl-4-yl)-2-({(3R,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride (155 mg). LCMS (m/z): 749; ¹H NMR (400 MHz, Methanol-d₆): 8.54 (d, 1H), 7.95 (s, 1H), 7.87 (d, 1H), 7.81-7.72 (m, 2H), 7.63-51 (m, 4H), 7.50-7.47 (m, 2H), 7.38-7.32 (m, 3H), 7.01 (d, 2H), 6.99 (d, 2H), 5.07 (s, 2H) 5.04-5.03 (m, 1H), 4.34-4.31 (m, 1H), 4.12-4.08 (m, 1H), 4.01-3.96 (m, 3H), 3.75 (s, 3H), 3.74-3.63 (m, 4H), 3.11-2.97 (m, 2H).

(S)-3-(4'-Cyano-biphenyl-4-yl)-2-({(3S,8S)-3-[4-(3, 4-dichloro-benzyloxy)-phenyl]-2,3,6,7,8,9-hexahydro-[1,4]dioxino[2,3-g]isoquinoline-8-carbonyl}-amino)-propionic acid methyl ester

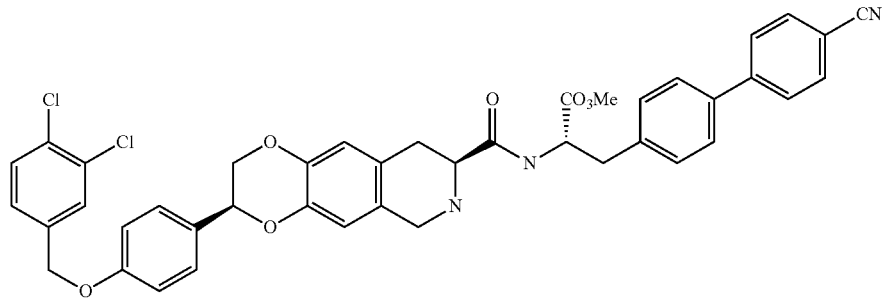

(3S,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester (708 mg) was hydrolyzed according to General Procedure B and the resulting (3S,8S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester (670 mg) was coupled with (S)-2-amino-3-(4'-cyano-biphenyl-4-yl)-propionic acid methyl ester hydrochloride (363 mg) according to General Procedure L to give (3S,8S)-8-[(S)-2-(4'-cyano-biphenyl-4-yl)-1-methoxycarbonyl-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid tert-butyl ester (750 mg). This intermediate (720 mg) was deprotected as described in General Procedure C to give (S)-3-(4'-cyano-biphenyl-4-yl)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride salt. This product was neutralized with aqueous $Na_2CO_3$ and the resulting solid was extracted with ethyl acetate (100 mL). The organic layer was washed with water, brine, dried and concentrated to furnish a white solid. The solid was purified by silica gel flash chromatography (9:1 to 1:1 DCM/EtOAc) to furnish (S)-3-(4'-cyano-biphenyl-4-yl)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (550 mg). LCMS (m/z): 748; $^1$H NMR (400 MHz, DMSO-$d_6$): 8.25 (d, 1H), 7.85 (m, 4H), 7.70 (d, 1H), 7.65 (m, 3H), 7.42 (m, 1H), 7.31 (m, 4H), 7.02 (m, 2H), 6.60 (a, 1H), 6.65 (s, 1H), 5.12 (s, 2H) 5.06-5.08 (m, 1H), 4.6 (m, 1H), 4.27 (dd, 1H), 3.96 (m, 2H), 3.65 (bs, 1H), 3.64 (s, 3H), 3.38 (m, 1H), 3.0-3.16 (m, 2H), 2.5-2.76 (m, 2H).

(S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride (S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester (mixture of diastereomers, 1.2 g) was hydrolyzed according to General Procedure B to give (S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester (quantitative) which was coupled with (S)-2-Amino-3-(4'-cyano-biphenyl-4-yl)-propionic acid methyl ester (634 mg) according to General Procedure L to give (S)-8-[(S)-2-(4'-Cyano-biphenyl-4-yl)-1-methoxycarbonyl-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid tert-butyl ester (1.58 g). This intermediate was deprotected as described in General Procedure C to give (S)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride (1.44 g). LCMS (m/z): 748.

Procedure 4

3-{2-[4-(3,4-Dichloro-benzyloxy)-phenyl]-2-oxo-ethoxy}-4-fluoro-benzonitrile

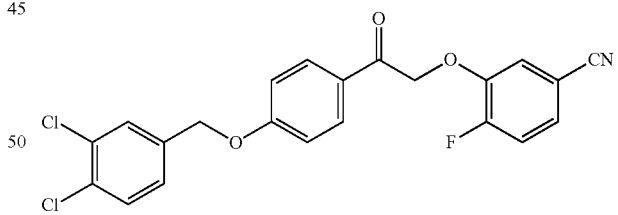

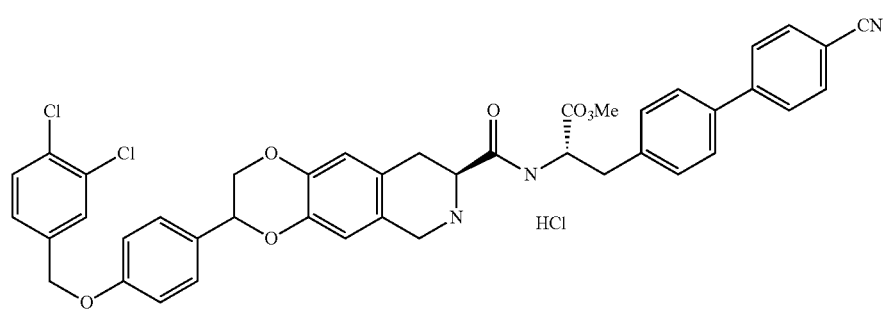

4-Fluoro-3-hydroxy-benzonitrile (15 g), 2-bromo-1-[4-(3,4-dichloro-benzyloxy)-phenyl]-ethanone (45 g), and potassium carbonate 45 g) were suspended together in 630 mL acetone with stirring. The mixture continued to stir for 18 hours, then was concentrated to dryness. The solid residue was taken up in 500 mL diethyl ether and stirred 1.5 h, then 1 L water was added and stirred vigorously an additional 3 hours. The solid product was collected by filtration and washed with 200 mL diethyl ether three times. It was then dissolved in THF, filtered to remove any remaining inorganic salt, and evaporated again to dryness. After drying under vacuum 18 h, 48 g of desired product was obtained (quantitative). $^1$H NMR (400 MHz, DMSO-$d_6$): 7.97 (d, 2H), 7.66 (d, 1H), 7.45 (m, 2H), 7.46 (m, 3H), 7.16 (d, 2H), 5.72 (s, 2H), 5.25 (s, 2H).

3-{(S)-2-[4-(3,4-Dichloro-benzyloxy)-phenyl]-2-hydroxy-ethoxy}-4-fluoro-benzonitrile

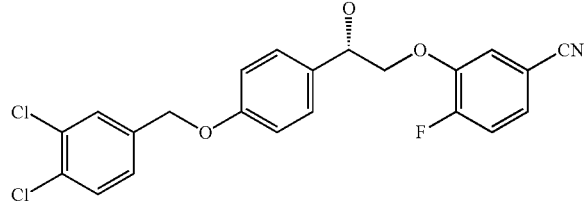 [SMILES: N#Cc1ccc(F)c(OC[C@@H](O)c2ccc(OCc3ccc(Cl)c(Cl)c3)cc2)c1]

400 mL dry THF, 93 mL of 1M (S)-CBS reagent in toluene, and 30.3 g borane-diethylaniline complex were stirred together 10 min at rt. 3-{2-[4-(3,4-dichloro-benzyloxy)-phenyl]-2-oxo-ethoxy}-4-fluoro-benzonitrile (40 g) in 1.2 L dry THF was then added through an addition funnel at rt over 10 min. The mixture stirred for 15 min, then was quenched by slow addition of 100 mL MeOH. After gas evolution ceased the mixture was evaporated to a yellow oil. The oil was dissolved in 200 mL diethyl ether, precipitated with 1.2 L of hexanes and stored 18 h at −20° C. The desired product was collected by filtration and dried under vacuum to give 28.9 g. $^1$H NMR (400 MHz, CDCl$_3$): 7.54 (d, 1H), 7.46 (d, 1H), 7.38 (m, 2H), 7.3-7.15 (m, 4H), 6.97 (m, 2H), 5.13 (m, 1H), 5.03 (s, 2H), 4.10 (m, 2H), 2.63 (d, 1H).

(S)-2-[4-(3,4-Dichloro-benzyloxy)-phenyl]-2,3-dihydro-benzo[1,4]dioxine-6-carbonitrile

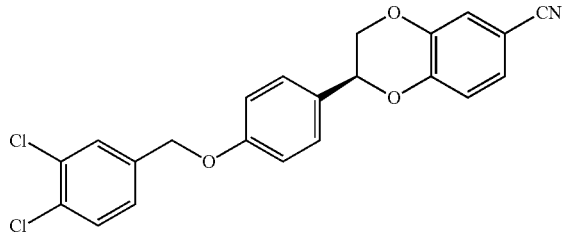 [SMILES: N#Cc1ccc2c(c1)OC[C@H](c1ccc(OCc3ccc(Cl)c(Cl)c3)cc1)O2]

3-{(S)-2-[4-(3,4-Dichloro-benzyloxy)-phenyl]-2-hydroxy-ethoxy}-4-fluoro-benzonitrile (28.9 g) was dissolved in 30 mL dry NMP and 270 mL dry diglyme under nitrogen and heated to 142° C. internal temperature. A suspension of sodium hydride (2.676 g of 60% NaH in mineral oil) in 6 mL of dry NMP and 54 mL of dry diglyme was added all at once via cannula while stirring. After 15 min the reaction was removed from heating and cooled 5 min, then poured into ice/1 L EtOAc/0.5 L 1 N HCl. The layers were separated and the organic layer washed twice with water, once with brine and dried over Na$_2$SO$_4$. The residue was purified by silica gel flash chromatography (DCM to 1:1 DCM/EtOAc) to provide 31 g of partially purified solid which was then crystallized from refluxing 3:1 MeOH/DCM, to give 15 g of desired product. $^1$H NMR (400 MHz, CDCl$_3$): 7.54 (d, 1H), 7.46 (d, 1H), 7.33 (m, 2H), 7.28-7.24 (m, 1H), 7.23 (d, 1H) 7.19 (m, 1H), 7.0 (m, 3H), 5.12 (m, 1H), 5.04 (s, 2H), 4.37 (m, 1H), 4.03 (m, 1H).

(S)-2-[4-(3,4-Dichloro-benzyloxy)-phenyl]-2,3-dihydro-benzo[1,4]dioxine-6-carbaldehyde

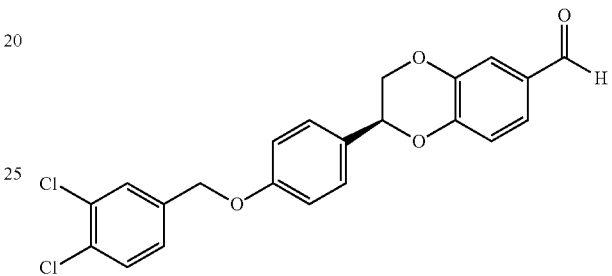

(S)-2-[4-(3,4-Dichloro-benzyloxy)-phenyl]-2,3-dihydro-benzo[1,4]dioxine-6-carbonitrile (15 g) was dissolved in 0.5 L dry toluene and cooled to 0° C. under nitrogen. 72.8 mL of a 1M solution of diisobutylaluminum hydride in toluene was added over 10 min. The reaction stirred at 0° C. for 30 min and was quenched by slow addition of 24 mL HOAc. The mixture was partitioned between 1 L water and 0.5 L EtOAc and the organic layer was washed with 0.5 L water twice, dried over brine and Na$_2$SO$_4$ and evaporated. The residue was purified by silica gel flash chromatography (DCM to 9:1 DCM/EtOAc) to give 10.94 g of desired product after drying under vacuum. $^1$H NMR (400 MHz, CDCl$_3$): 9.79 (s, 1H), 7.47 (d, 1H), 7.39 (m, 3H), 7.28 (m, 2H), 7.21-7.17 (m, 1H), 7.01 (d, 1H), 6.93 (m, 2H), 5.09 (m, 1H), 4.97 (s, 2H), 4.32 (m, 1H), 3.98 (m, 1H).

2-tert-Butoxycarbonylamino-3-{(S)-2-[4-(3,4-dichloro-benzyloxy)-phenyl]-2,3-dihydro-benzo[1,4]dioxin-6-yl}-acrylic acid methyl ester

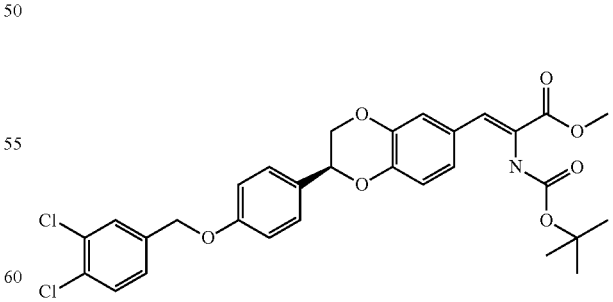

(S)-2-[4-(3,4-Dichloro-benzyloxy)-phenyl]-2,3-dihydro-benzo[1,4]dioxine-6-carbaldehyde (9.9 g) was dissolved in 80 mL dry DCM under nitrogen at rt and 7.2 mL DBU (7.33 g) was added by syringe. 7.44 g of Boc-phosphonoglycine trimethyl ester in 40 mL dry DCM was added by syringe all at once and the mixture stirred at rt for 18 h. It was then diluted with 0.5 L each of DCM and water and extracted, and the organic layer was dried with brine and Na$_2$SO$_4$ and evaporated. The residue was purified by crystallization from EtOAc/hexanes to give 12 g desired product after drying under vacuum. $^1$H NMR (400 MHz, CDCl$_3$): 7.54 (d, 1H), 7.46 (d, 1H), 7.34 (m, 2H), 7.28-7.24 (m, 1H), 7.23-7.17 (m, 2H), 7.11 (m, 1H), 6.98 (m, 2H), 6.93 (d, 1H), 5.10 (m, 1H), 5.03 (s, 2H), 4.32 (m, 1H), 4.01 (m, 1H), 3.84 (s, 3H), 1.44 (s, 9H).

(S)-2-tert-Butoxycarbonylamino-3-{(S)-2-[4-(3,4-dichloro-benzyloxy)-phenyl]-2,3-dihydro-benzo[1,4]dioxin-6-yl}-propionic acid methyl ester

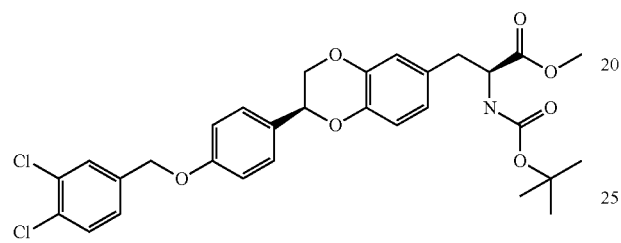

2-tert-Butoxycarbonylamino-3-{(S)-2-[4-(3,4-dichloro-benzyloxy)-phenyl]-2,3-dihydro-benzo[1,4]dioxin-6-yl}-acrylic acid methyl ester (12 g) in 1.2 L EtOAc was degassed by vacuum and flushed with hydrogen gas three times, then added 1629 mg (+)-1,2-bis((2S,5S)-2,5-diethylphospholano)benzene(cyclooctadiene)rhodium(I) trifluoromethanesulfonate. The mixture was then degassed and hydrogen flushed three times again and stirred vigorously while passing hydrogen into the reaction through a gas dispersion tube for 24 h. The solvent was then evaporated and the residue was purified by silica gel flash chromatography (hexanes to 7:3 hexanes/EtOAc) to give 10.3 g after drying. $^1$H NMR (400 MHz, acetone-d$_6$): 7.73 (d, 1H), 7.62 (d, 1H), 7.51-7.49 (m, 1H), 7.45 (m, 2H), 7.10 (m, 2H), 6.87-6.80 (m, 2H), 6.76 (m, 1H), 6.10 (d, 1H), 5.20 (s, 2H), 5.10 (m, 1H), 4.35 (m, 2H), 4.02 (m, 1H), 3.69 (s, 3H), 3.08-2.84 (m, 2H), 1.37 (s, 9H).

(3S,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester

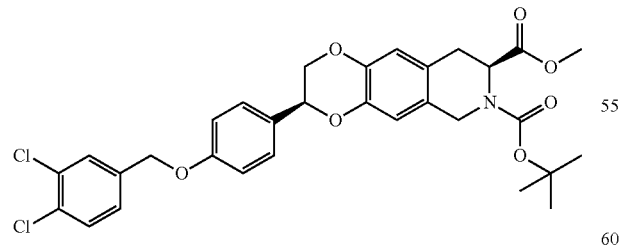

(S)-2-tert-Butoxycarbonylamino-3-{(S)-2-[4-(3,4-dichloro-benzyloxy)-phenyl]-2,3-dihydro-benzo[1,4]dioxin-6-yl}-propionic acid methyl ester (4.9 g) was dissolved in 200 mL dry DCM and stirred on 0° C. bath. 100 mL 4N HCL in dioxane was added and the mixture stirred to rt over 3 h. The solvents were evaporated and the residue was evaporated from diethyl ether 4 times. 4 g of the residue was dissolved in 250 mL dry dioxane and 462 mg paraformaldehyde was added while stirring. Then 62.5 mL trifluoroacetic acid was added and the mixture was stirred 1.5 h. The solvents were then evaporated and the residue was dissolved in 250 mL EtOAc and 250 mL saturated aqueous NaHCO$_3$, and 4.2 g di-t-butyl dicarbonate was added and stirred 18 h at rt. The layers were then separated and the organic layer was washed with brine, dried with Na$_2$SO$_4$, and evaporated. The residue was purified by silica gel flash chromatography (9:1 to 7:3 hexanes/EtOAc) to give 3.25 g after drying under vacuum. $^1$H NMR (400 MHz, acetone-d$_6$): 7.72 (d, 1H), 7.61 (d, 1H), 7.51-7.42 (m, 3H), 7.12-7.07 (m, 2H), 0.680-6.70 (m, 2H), 5.20 (s, 2H), 5.13-5.07 (m, 1H), 5.02 and 4.76 (m, 1H), 4.66-4.52 (dd, 1H), 4.42 (d, 1H), 4.36-4.30 (m, 1H), 4.01 (m, 1H), 3.64 and 3.60 (s, 3H), 3.18-3.00 (m, 2H), 1.49 and 1.43 (s, 9H).

(S)-3-{(S)-2-[4-(3,4-Dichloro-benzyloxy)-phenyl]-2,3-dihydro-benzo[1,4]dioxin-6-yl}-2-(4-nitro-benzenesulfonylamino)-propionic acid methyl ester

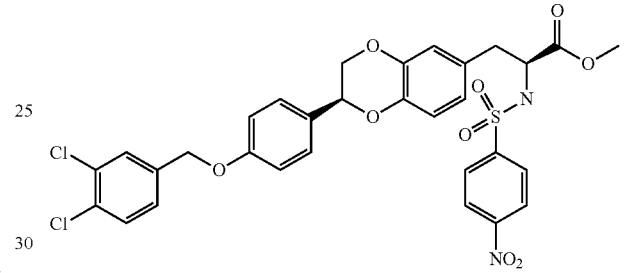

(S)-2-tert-Butoxycarbonylamino-3-{(S)-2-[4-(3,4-dichloro-benzyloxy)-phenyl]-2,3-dihydro-benzo[1,4]dioxin-6-yl}-propionic acid methyl ester (1 g) was dissolved in 20 mL dry DCM and 6.4 mL 4N HCl/dioxane was added while stirring at rt. After stirring 3 h the solvents were evaporated and the residue evaporated again from DCM and toluene. The residue was then dissolved in 20 mL EtOAc and 20 mL saturated aqueous NaHCO$_3$ and 414 mg p-nitrobenzenesulfonyl chloride was added. After stirring at rt 1.5 h the layers were separated and the organic layer was washed with water, then brine, then dried over Na$_2$SO$_4$ and evaporated. The residue was purified by silica gel flash chromatography (9:1 to 7:3 hexanes/EtOAc) to give 1.06 g desired product after drying. $^1$H NMR (400 MHz, acetone-d$_6$): 8.33 (m, 2H), 7.89 (m, 2H), 7.73 (d, 1H), 7.62 (d, 1H), 7.53-7.42 (m, 4H), 7.11 (m, 2H), 6.69-6.61 (m, 3H), 5.22 (s, 2H), 5.03 (m, 1H), 4.31 (m, 1H), 4.21 (m, 1H), 3.96 (m, 1H), 3.61 (s, 3H), 3.03 (m, 1H), 2.76 (m, 1H).

(S)-3-{(S)-2-[4-(3,4-Dichloro-benzyloxy)-phenyl]-2,3-dihydro-benzo[1,4]dioxin-6-yl}-2-[(4-nitro-benzenesulfonyl)-((S)-1-phenyl-propyl)-amino]-propionic acid methyl ester

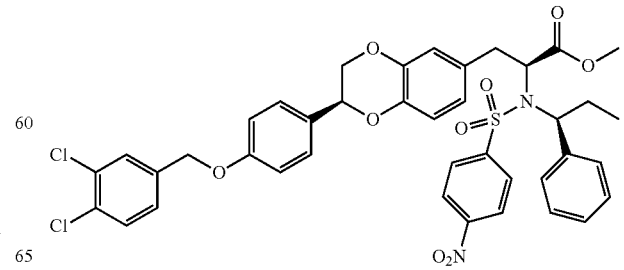

(S)-3-{(S)-2-[4-(3,4-Dichloro-benzyloxy)-phenyl]-2,3-dihydro-benzo[1,4]dioxin-6-yl}-2-(4-nitro-benzenesulfonylamino)-propionic acid methyl ester (1.6 g) was dissolved in 4 mL dry THF and 1247 mg triphenylphosphine and 650 μL (R)-(+)-1-phenyl-1-propanol were added. The mixture was stirred at 0° C. for 10 min, then 933 μL DIAD was added over 2 min. The reaction stirred at rt for 5 h, then was evaporated. The residue was purified by silica gel flash chromatography (9:1 to 8:2 hexanes/EtOAc) to give 1.8 g desired product after drying. $^1$H NMR (400 MHz, acetone-$d_6$): 8.35 (m, 2H), 7.96 (m, 2H), 7.72 (d, 1H), 7.62 (d, 1H), 7.51-7.42 (m, 3H), 7.29 (m, 5H), 7.10 (m, 2H), 6.88-6.80 (m, 3H), 5.21 (s, 2H), 5.11 (m, 1H), 4.82 (m, 1H), 4.45 (m, 1H), 4.36 (m, 1H), 4.03 (m, 1H), 3.49 (m, 1H), 3.35 (s, 3H), 3.04 (m, 1H), 2.31 (m, 1H), 1.81 (m, 1H), 0.77 (t, 3H).

(S)-3-{(S)-2-[4-(3,4-Dichloro-benzyloxy)-phenyl]-2,3-dihydro-benzo[1,4]dioxin-6-yl}-2-((S)-1-phenyl-propylamino)-propionic acid methyl ester

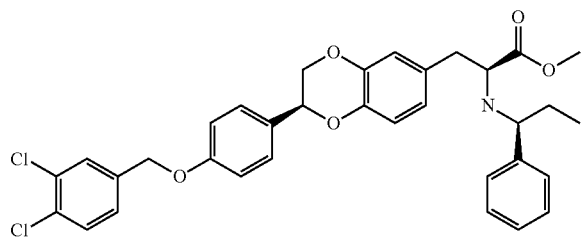 [SMILES: CC[C@H](N[C@@H](Cc1ccc2c(c1)OC[C@H](c1ccc(OCc3ccc(Cl)c(Cl)c3)cc1)O2)C(=O)OC)c1ccccc1]

(S)-3-{(S)-2-[4-(3,4-Dichloro-benzyloxy)-phenyl]-2,3-dihydro-benzo[1,4]dioxin-6-yl}-2-[(4-nitro-benzenesulfonyl)-((S)-1-phenyl-propyl)-amino]-propionic acid methyl ester (1.8 g) was dissolved in 30 mL dry DMF, then 505 μL (670 mg) mercaptoacetic acid and 2.6 mL (2.6 g) DBU were added at rt. The reaction stirred for 3 h, then was partitioned between saturated aqueous NaHCO$_3$ and diethyl ether. The organic layer was washed successively with aqueous NaHCO$_3$, water, and brine, then was dried with Na$_2$SO$_4$ and evaporated. The residue was purified by silica gel flash chromatography (9:1 to 8:2 hexanes/EtOAc) to give 893 mg desired product after drying. $^1$H NMR (400 MHz, acetone-$d_6$): 7.71 (d, 1H), 7.61 (d, 1H), 7.50-7.42 (m, 3H), 7.27-7.15 (m, 5H), 7.09 (m, 2H), 6.80 (d, 1H), 6.67 (d, 1H), 6.61 (m, 1H), 5.19 (s, 2H), 5.10 (m, 1H), 4.34 (m, 1H), 4.02 (m, 1H), 3.63 (s, 3H), 3.47 (t, 1H), 3.15 (t, 1H), 2.75 (m, 2H), 2.10 (s, 1H), 1.69-1.48 (m, 2H), 0.78 (t, 3H).

(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid methyl ester

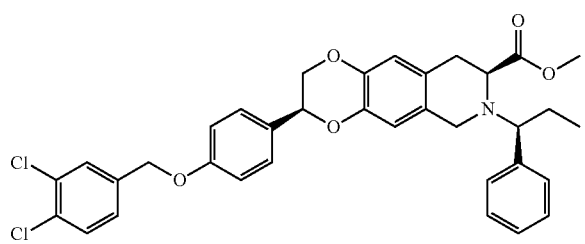 [SMILES: CC[C@@H](c1ccccc1)N1Cc2cc3c(cc2C[C@H]1C(=O)OC)OC[C@H](c1ccc(OCc2ccc(Cl)c(Cl)c2)cc1)O3]

(S)-3-{(S)-2-[4-(3,4-Dichloro-benzyloxy)-phenyl]-2,3-dihydro-benzo[1,4]dioxin-6-yl}-2-((S)-1-phenyl-propylamino)-propionic acid methyl ester (893 mg) was dissolved in 80 mL dry dioxane and 133 mg paraformaldehyde and 20 mL trifluoroacetic acid were added. The reaction stirred 12 h at rt, then 66 mg more paraformaldehyde was added while stirring at rt. After 3 h aqueous NaHCO$_3$ was added until a pH of 7 was achieved, then the mixture was extracted with EtOAc. The organic extract was washed with brine and dried over Na$_2$SO$_4$ and evaporated. The residue was purified by silica gel flash chromatography (9:1 to 8:2 hexanes/EtOAc) to give 872 mg desired product after drying. $^1$H NMR (400 MHz, acetone-$d_6$): 7.72 (d, 1H), 7.62 (d, 1H), 7.51-7.43 (m, 3H), 7.38-7.25 (m, 5H), 7.10 (m, 2H), 6.67 (s, 1H), 6.60 (s, 1H), 5.20 (s, 2H), 5.09 (m, 1H), 4.30 (m, 1H), 4.13 (m, 2H), 3.99 (m, 1H), 3.92 (m, 1H), 3.59 (m, 1H), 3.52 (s, 3H), 2.96-2.78 (m, 2H), 2.16 (m, 1H), 1.68 (m, 1H), 0.65 (t, 3H).

(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid

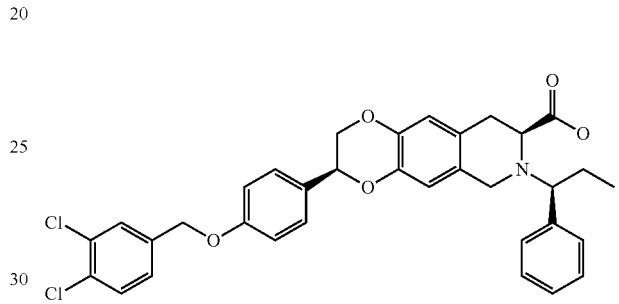

(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid methyl ester (872 mg) was dissolved in 24 mL THF and 20 mL MeOH and 591 mg LiOH was added. The flask was flushed with nitrogen and placed under a nitrogen balloon and stirred at 0° C. 12 mL water was then added in portions while stirring, then the reaction stirred at rt 15 h. 119 mg LiOH and 6 mL water were added to the reaction and stirring continued for 2 h. 4 mL water was added and stirring continued for 30 min, then 2 mL water was added. After 1.5 h the pH was adjusted to 7 with 2% w/v aqueous citric acid and the reaction extracted with EtOAc. The organic solution was washed with brine and dried over Na$_2$SO$_4$ and evaporated, to give 820 mg desired compound after drying. LCMS: m/z 605 (M+1).

4-Bromo-2,5-dimethyl-pyridine

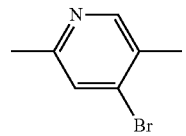

Step 1. N-oxide Formation. 5 g of 2,5-dimethyl-pyridine and 8.8 g urea-hydrogen peroxide adduct were heated together to 85° C. The mixture melted and was stirred for 18 h at 85° C. It was then cooled to rt and taken up in water-EtOAc and layers separated. The product containing aqueous layer was treated with solid NaCl and concentrated under reduced pressure and back-extracted several times with EtOAc. The back-extracted organic solution was concentrated and the product crystallized. Three crops were collected by filtration for a total of 3.73 g 2,5-dimethyl-pyridine 1-oxide. LCMS (m/z) 124.

N-oxide formation also was performed under the following conditions. To a 6,7-dihydro-5H-[1]pyrindine solution in DCM at 0° C. was added peracetic acid (3 mL, 32% in AcOH), and the reaction was slowly allowed to come to rt and stirred for 12 h. The reaction mixture was diluted with DCM (5 mL) and washed with water, aq NaHCO$_3$, brine, then dried over Na$_2$SO$_4$, filtered and concentrated to afford desired 6,7-dihydro-5H-[1]pyrindine 1-oxide (0.6 g). LCMS (m/z): 136.

Step 2. Nitration. 3.58 g of 2,5-dimethyl-pyridine 1-oxide was added to a stirring mixture of 8.25 mL concentrated HNO$_3$ and 10.5 mL concentrated H$_2$SO$_4$ at 0° C. The mixture was slowly heated to 105° C. over 3.5 h and maintained for 2 h. It was then cooled to rt, diluted with 2 volumes of water and filtered. The filtrate was extracted several times with EtOAc and the combined organic extracts were washed with brine, dried with Na$_2$SO$_4$ and concentrated under reduced pressure. The product crystallized and three crops were collected for a total of 3.6 g of 2,5-dimethyl-4-nitro-pyridine 1-oxide. LCMS (m/z) 169.

Step 3. Bromination. To a solution of 1.65 g of 2,5-dimethyl-4-nitro-pyridine 1-oxide in 50 mL dry EtOAc was added 11.1 mL PBr$_3$ at rt. The mixture was heated to reflux over 0.5 h. Reflux continued for 3 h, then cooled to rt and poured into ice and EtOAc. The resulting mixture was brought to pH 10 with addition of NaOH pellets and layers were separated. An additional EtOAc extraction was combined with the first and the organic layers were washed with brine, dried whith Na$_2$SO$_4$ and concentrated under reduced pressure. The residue was purified by column chromatography (hexanes-EtOAc) to provide 4-bromo-2,5-dimethyl-pyridine (248 mg). LCMS (m/z) 186.

A similar procedure was used to prepare 4-bromo-2,3-dimethyl-pyridine and 4-bromo-6,7-dihydro-5H-[1]pyrindine.

4-Bromo-2-ethyl-pyridine

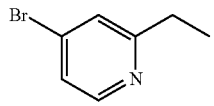

To a slurry of 4-bromopyridine (970 mg) in 17 mL of THF at −78° C. was added ethylmagnesium bromide in 3.3 mL of ether. After stirring for 10 min at −78° C., phenyl chloroformate was added dropwise. The mixture was stirred at −78° C. for 10 min, warmed to room temperature, and quenched with aqueous 20% NH$_4$Cl solution. Ether (10 mL) was added, and the organic layer was washed with 10-mL portions of water, 10% HCl, water, and brine. After drying (MgSO$_4$), the solution was concentrated to give crude dihydropyridine which was dissolved in dry toluene. To this solution, at room temperature, was added dropwise o-chloranil in glacial acetic acid. The mixture was stirred at room temperature for 18 h, cooled, and made basic with 10% NaOH. The mixture was stirred for 15 min and filtered through Celite. The dark organic layer was washed with water and then extracted with 3×20 mL of 10% HCl. The acid extracts were cooled, made basic with 20% NaOH, and extracted with DCM (3×20 mL). The combined organic extracts were washed with brine, dried (MgSO$_4$), and concentrated to yield the crude product (260 mg) as a yellow oil. The oil was purified by column chromatography to provide 4-bromo-2-ethyl-pyridine.

A similar procedure was used to prepare 4-bromo-2-isopropyl-pyridine and 4-bromo-2-propyl-pyridine.

2,3-Dimethylpyridine-4-boronic acid

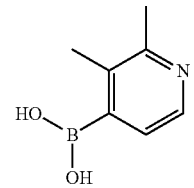

A solution of 4-bromo-2,3-dimethyl-pyridine (1.38 g) and triisopropyl borate (2.05 mL) in 4 mL dry THF and 14 mL dry toluene was strirred on a dry ice-aceton bath to an internal temperature of −65° C. and 3.56 mL n-BuLi in hexanes was added dropwise over 0.5 h. Stirring continued at −65° C. for additional 2 h, then the bath was removed the mixture allowed to warm to −20° C. Reaction was quenched by addition of 10 mL 2M HCl, then allowed to warm to rt and diluted with more THF. 5M NaOH was added until the mixture reached pH 7, layers formed and the organic layer was collected. Several more extractions with THF were done and the combined organic extracts were dried with brine and Na$_2$SO$_4$ and concentrated under reduced pressure. The product crystallized and two crops were collected, for a total of 304 mg of 2,3-dimethylpyridine-4-boronic acid. LCMS (m/z) 153.

(S)-2-Amino-3-(4'-cyano-biphenyl-4-yl)-propionic acid methyl ester -hydrochloride

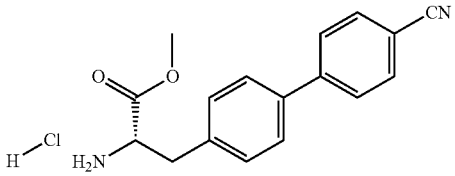

Step 1. Esterification. To a solution of (S)-3-(4-Bromo-phenyl)-2-tert-butoxycarbonylamino-propionic acid in DMF (50 mL) was added DIEA and methyl iodide. The reaction mixture stirred at rt for 2.5 h and was poured onto EtOAc and water. The organic layer was washed with 1 N HCl and 10% sodium carbonate, dried over sodium sulfate and concentrated. (S)-3-(4-Bromo-phenyl)-2-tert-butoxycarbonylamino-propionic acid methyl ester (25.1 g) was used without further purification. LCMS (m/z) 359.

Step 2. Suzuki Coupling. To a solution of (S)-3-(4-Bromo-phenyl)-2-tert-butoxycarbonylamino-propionic acid methyl ester in toluene (250 mL) was added 4-cyanobenzeneboronic acid, Pd(PPh$_3$)$_4$, and 1N Na$_2$CO$_3$ solution (105 mL). The mixture was heated at reflux for 7 h. After completion of the reaction, the aqueous layer was drained. The organic layer was washed with 10% Na$_2$CO$_3$ and 1 N HCl. The organic layer was dried over sodium sulfate and concentrated under reduced pressure to afford the crude product. The residue was then purified by column chromatography (hexanes-EtOAc)

to provide (S)-2-tert-Butoxycarbonylamino-3-(4'-cyano-biphenyl-4-yl)-propionic acid methyl ester (18.2 g). LCMS (m/z) 382.

Step 3. Removal of Tert-Butyl Carbamate. (S)-2-tert-Butoxycarbonylamino-3-(4'-cyano-biphenyl-4-yl)-propionic acid methyl ester (18.1 g) was deprotected according to General Procedure C to provide (S)-2-amino-3-(4'-cyano-biphenyl-4-yl)-propionic acid methyl ester hydrochloride (16.2 g). $^1$H NMR (400 MHz, DMSO d6): 8.71 (bs, 3H), 7.90 (m, 4H), 7.73 (d, 2H), 7.37 (d, 2H), 4.31 (t, 1H), 3.54 (s, 3H), 3.16 (m, 2H)

A similar procedure was used to prepare (S)-2-amino-3-(4'-chloro-biphenyl-4-yl)-propionic acid methyl ester; hydrochloride, (S)-2-amino-3-(4'-methoxy-biphenyl-4-yl)-propionic acid methyl ester; hydrochloride, (S)-2-amino-3-(4-pyridin-4-yl-phenyl)-propionic acid methyl ester; bis-hydrochloride, (S)-2-amino-3-(4'-methyl-biphenyl-4-yl)-propionic acid methyl ester; hydrochloride, (S)-2-amino-3-(4'-fluoro-biphenyl-4-yl)-propionic acid methyl ester; hydrochloride, (R)-2-amino-3-(4'-cyano-biphenyl-4-yl)-propionic acid methyl ester hydrochloride, (S)-2-amino-3-(4-pyridin-3-yl-phenyl)-propionic acid methyl ester dihydrochloride, (S)-2-amino-3-(3'-methyl-biphenyl-4-yl)-propionic acid methyl ester dihydrochloride, (S)-2-amino-3-[4-(2-methoxy-pyridin-4-yl)-phenyl]-propionic acid methyl ester bis hydrochloride, (S)-2-amino-3-(4'-trifluoromethyl-biphenyl-4-yl)-propionic acid methyl ester hydrochloride, (S)-2-amino-3-[4-(2-methyl-pyridin-4-yl)-phenyl]-propionic acid methyl ester bis hydrochloride, (S)-2-amino-3-[4-(2-hydroxy-pyridin-4-yl)-phenyl]-propionic acid methyl ester bis hydrochloride, (S)-2-amino-3-[4-(6-methyl-pyridin-3-yl)-phenyl]-propionic acid methyl ester bis hydrochloride, (S)-2-amino-3-[4-(2-trifluoromethyl-pyridin-4-yl)-phenyl]-propionic acid methyl ester bis hydrochloride, (S)-2-amino-3-[4-(6-dimethylamino-pyridin-3-yl)-phenyl]-propionic acid methyl ester bis hydrochloride, (S)-2-amino-3-[4-(2-fluoro-pyridin-4-yl)-phenyl]-propionic acid methyl ester bis hydrochloride, (S)-2-amino-3-[4-(3-methyl-pyridin-4-yl)-phenyl]-propionic acid methyl ester bis hydrochloride, (S)-2-amino-3-[4-(6-hydroxymethyl-pyridin-3-yl)-phenyl]-propionic acid methyl ester bis hydrochloride, (S)-2-amino-3-[4-(2,6-difluoro-pyridin-4-yl)-phenyl]-propionic acid methyl ester bis hydrochloride, (S)-2-amino-3-[4-(3-fluoro-pyridin-4-yl)-phenyl]-propionic acid methyl ester bis hydrochloride, (S)-2-amino-3-(4'-cyano-3'-fluoro-biphenyl-4-yl)-propionic acid methyl ester hydrochloride, (S)-2-amino-3-[4-(3-methoxy-pyridin-4-yl)-phenyl]-propionic acid methyl ester bis hydrochloride, (S)-2-amino-3-[4-(6-cyano-pyridin-3-yl)-phenyl]-propionic acid methyl ester bis hydrochloride, and (S)-2-amino-3-[4-(6-amino-pyridin-3-yl)-phenyl]-propionic acid methyl ester hydrochloride.

(S)-2-Amino-3-[4-(2,3-dimethyl-pyridin-4-yl)-phenyl]-propionic acid methyl ester dihydrochloride

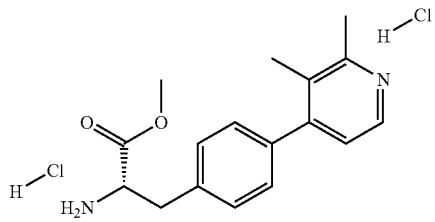

Step 1. To a solution of (S)-3-(4-bromo-phenyl)-2-tert-butoxycarbonylamino-propionic acid methyl ester (10.74 g) in DMF (200 mL) was added bis(pinacolato)diboron (15.24 g), KOAc (8.82 g), and PdCl$_2$(dppf) (2.45 g). The mixture was purged with nitrogen and stirred under nitrogen at 75° C. for 3 h. It was then cooled to rt and poured into water-EtOAc. The organic layer was washed with water and saturated brine, dried over Na$_2$SO$_4$ and concentrated under reduced pressure. The residue was purified by column chromatography (hexanes-EtOAc) to provide (S)-2-tert-butoxycarbonylamino-3-[4-(4,4,5,5-tetramethyl-[1,3,2]dioxaborolan-2-yl)-phenyl]-propionic acid methyl ester (10.26 g). LCMS (m/z) 407.

Step 2. Suzuki Coupling. To a mixture of (S)-2-tert-butoxycarbonylamino-3-[4-(4,4,5,5-tetramethyl-[1,3,2]dioxaborolan-2-yl)-phenyl]-propionic acid methyl ester (8.22 g) in 140 mL toluene and 40 mL water was added 4-bromo-2,3-dimethyl-pyridine (6.77 g), Na$_2$CO$_3$ (7.5 g), and Pd(PPh$_3$)$_4$. The mixture was purged with nitrogen and stirred under nitrogen at 80° C. for 18 h. The mixture was then cooled to rt and poured into water-EtOAc. The organic layer was washed with water and saturated brine, dried over Na$_2$SO$_4$ and concentrated under reduced pressure. The residue was purified by column chromatography (hexanes-EtOAc) to provide (S)-2-tert-butoxycarbonylamino-3-[4-(2,3-dimethyl-pyridin-4-yl)-phenyl]-propionic acid methyl ester (4.5 g). LCMS (m/z) 386.

Step 3. Removal of t-butyl Carbamate. (S)-2-tert-butoxycarbonylamino-3-[4-(2,3-dimethyl-pyridin-4-yl)-phenyl]-propionic acid methyl ester (4.5 g) was deprotected according to General Procedure C to provide (S)-2-amino-3-[4-(2,3-dimethyl-pyridin-4-yl)-phenyl]-propionic acid methyl ester dihydrochloride (4.2 g). LCMS (m/z) 286.

A similar procedure was used to prepare (S)-2-amino-3-(4-pyridazin-4-yl-phenyl)-propionic acid methyl ester dihydrochloride, (S)-2-amino-3-(4-pyrimidin-4-yl-phenyl)-propionic acid methyl ester dihydrochloride, (S)-2-amino-3-[4-(2,6-dimethyl-pyridin-4-yl)-phenyl]-propionic acid methyl ester dihydrochloride, (S)-2-amino-3-[4-(2,3-dimethyl-pyridin-4-yl)-phenyl]-propionic acid methyl ester dihydrochloride, (S)-2-amino-3-[4-(2,5-dimethyl-pyridin-4-yl)-phenyl]-propionic acid methyl ester dihydrochloride, (S)-2-amino-3-[4-(2-methyl-2H-pyrazol-3-yl)-phenyl]-propionic acid methyl ester bis hydrochloride, (S)-2-amino-3-[4-(1-methyl-1H-pyrazol-4-yl)-phenyl]-propionic acid methyl ester bis hydrochloride, (S)-2-amino-3-[4-(2-hydroxymethyl-pyridin-4-yl)-phenyl]-propionic acid methyl ester bis hydrochloride, (S)-2-amino-3-[4-(2-ethyl-pyridin-4-yl)-phenyl]-propionic acid methyl ester bis hydrochloride, (S)-2-amino-3-[4-(2-amino-pyridin-4-yl)-phenyl]-propionic acid methyl ester bis hydrochloride, (S)-2-amino-3-[4-(2-isopropyl-pyridin-4-yl)-phenyl]-propionic acid methyl ester bis hydrochloride, (S)-2-amino-3-[4-(2-amino-pyrimidin-5-yl)-phenyl]-propionic acid methyl ester bis hydrochloride, (S)-2-amino-3-[4-(2-propyl-pyridin-4-yl)-phenyl]-propionic acid methyl ester bis hydrochloride, (S)-2-amino-3-(4-quinolin-4-yl-phenyl)-propionic acid methyl ester bis hydrochloride, (S)-2-amino-3-[4-(2,5-dimethyl-2H-pyrazol-3-yl)-phenyl]-propionic acid methyl ester hydrochloride, and (S)-2-Amino-3-[4-(6,7-dihydro-5H-[1]pyrindin-4-yl)-phenyl]propionic acid methyl ester bis hydrochloride.

The biphenylalanine derivatives may also be prepared following alternative conditions for the Suzuki coupling. To a solution of (S)-2-tert-butoxycarbonylamino-3-[4-(4,4,5,5-tetramethyl-[1,3,2]dioxaborolan-2-yl)-phenyl]-propionic acid methyl ester in 2.7 mL dioxane was added heteroaryl halide, Pd$_2$(dba)$_3$ (0.01 mmol), and PCy$_3$ (0.024 mmol). Aqueous K$_3$PO$_4$ (1.27 M, 1.33 mL) was added and the mixture was purged with nitrogen and heated to 100° C. for 18 hours under nitrogen. Aqueous workup and chromatographic purification as above afforded the product in similar yield.

(S)-2-Amino-3-[4-(2,3-dimethyl-pyridin-4-yloxy)-phenyl]-propionic acid methyl ester

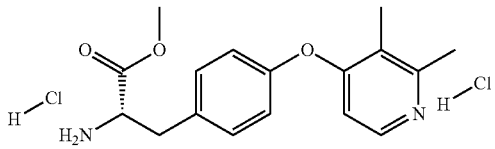

Step 1. A mixture of 304 mg of (S)-2-tert-butoxycarbonylamino-3-(4-hydroxy-phenyl)-propionic acid methyl ester, 314 mg 2,3-dimethylpyridine-4-boronic acid, 374 mg cupric acetate, and 2 grams of powdered 4 Å molecular sieves in 50 mL dry DCM and 0.75 mL TEA was stirred vigorously at rt under an $O_2$ atmosphere for 40 h. The mixture was then poured into water-EtOAc. The organic layer was washed with water and saturated brine, dried over $Na_2SO_4$ and concentrated under reduced pressure. The residue was purified by column chromatography (DCM-EtOAc) to provide (S)-2-tert-Butoxycarbonylamino-3-[4-(2,3-dimethyl-pyridin-4-yloxy)-phenyl]-propionic acid methyl ester (18 mg). LCMS (m/z) 401.

Step 2. Removal of t-butyl Carbamate. (S)-2-tert-Butoxycarbonylamino-3-[4-(2,3-dimethyl-pyridin-4-yloxy)-phenyl]-propionic acid methyl ester (18 mg) was deprotected according to General Procedure C to provide (S)-2-amino-3-[4-(2,3-dimethyl-pyridin-4-yloxy)-phenyl]-propionic acid methyl ester (16 mg). LCMS (m/z) 301.

A similar procedure was used to prepare (S)-2-amino-3-[4-(pyridin-4-yloxy)-phenyl]-propionic acid methyl ester dihydrochloride, (S)-2-amino-3-[4-(pyridin-3-yloxy)-phenyl]-propionic acid methyl ester dihydrochloride, and (S)-2-amino-3-[4-(2-methyl-pyridin-4-yloxy)-phenyl]-propionic acid methyl ester dihydrochloride.

(S)-2-Benzyloxycarbonylamino-3-(4-hydroxy-phenyl)-2-methyl-propionic acid methyl ester To a solution of (S)-2-amino-3-(4-hydroxy-phenyl)-2-methyl-propionic acid (976 mg) in methnol (50 mL) was added 4N. HCl in dioxane (1.88 mL) and the mixture was refluxed for 4 h. After the completion of the esterification, the methanol was evaporated and the residue was used as such for the next step.

To a suspension of (S)-2-amino-3-(4-hydroxy-phenyl)-2-methyl-propionic acid methyl ester hydrochloride in ethyl acetate (25 mL) was added 1N $NaHCO_3$ solution (12.5 mL) and the mixture was stirred rapidly at ambient temperature for the addition of neat benzyl chloroformate (1.01 eq.). Following addition, the reaction mixture was stirred for an additional hour; TLC and LCMS analysis showed the reaction to be complete. The mixture was partitioned and the organic phase was separated and dried over $Na_2SO_4$ and concentrated. The crude product was used directly in the subsequent reaction without purification.

(S)-2-Benzyloxycarbonylamino-2-methyl-3-(4-trifluoro-methanesulfonyloxy-phenyl)-propionic acid methyl ester To a 0° solution of the crude (S)-2-benzyloxycarbonylamino-3-(4-hydroxy-phenyl)-2-methyl-propionic acid methyl ester (440 mg) in dry DCM (13 mL) was added dry pyridine (1.5 eq.) followed by triflic anhydride (1.2 eq.). The reaction mixture was stirred at 0° C. for an additional hour at which point starting material was no longer visible by TLC or LCMS. The mixture was quenched with of saturated $NaHCO_3$ solution. The mixture was partitioned and the aqueous phase discarded. The crude product in DCM was washed with water (1×30 mL), dried over $Na_2SO_4$ and concentrated to furnish a brown oil. The crude product triflate was used as such without further purification.

(S)-2-Benzyloxycarbonylamino-3-(4'-cyano-biphenyl-4-yl)-2-methyl-propionic acid methyl ester

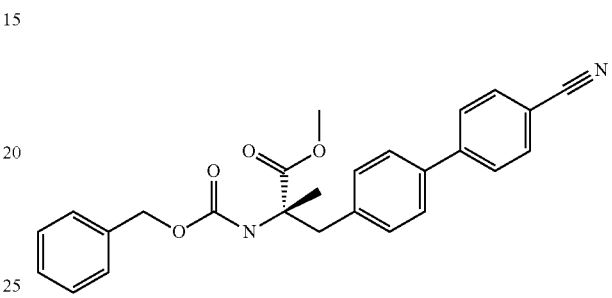

In a three necked flask, equipped with reflux condenser, was taken the crude triflate (609 mg), 4-cyanaophenyl boronic acid (226 mg), $Na_2CO_3$ (350 mg) water (1.41 mL) and totune (5 mL). The mixture was stirred and degassed with a stream of nitrogen for 45 minutes before adding Pd $(PPh_3)_4$ (30 mg). The solution was degassed for an additional 20 minutes. The mixture was heated, under nitrogen, to 85° C. for 6 h. The reaction continued until the triflate was no longer detected by TLC (50% EtOAc/hexanes, PMA char) or by LCMS. The reaction mixture was cooled to ambient temperature and partitioned. The crude product in toluene concentrated and purified by flash chromatography (7:3 hexane-EtOAc) to get a solid (488 mg). LCMS (m/z): 429. $^1$H NMR (400 MHz, CDCl$_3$): 7.72 (m, 2H), 7.64 (m, 2H), 7.39 (m, 7H), 7.06 (d, 2H), 5.52 (bs, 1H) 5.2 (d, 1H), 5.1 (d, 1H), 3.78 (s, 3 H), 3.52 (m, 2H), 3.23 (d, 2H), 1.68 (s, 3 H).

(S)-2-Amino-3-(4'-cyano-biphenyl-4-yl)-2-methyl-propionic acid methyl ester

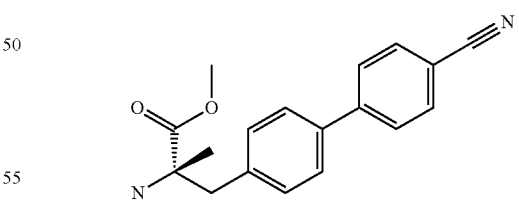

The purified cbz-protected amino acid ester (475 mg) was dissolved in cyclohexene (0.23 mL) and ethanol (10 mL). To this solution was added Pd/C (48 mg) and the mixture was degassed for 30 minutes. The mixture was heated at reflux (74-75° C.) for 4-6 hours, at which point starting material was no longer detected. The reaction mixture was cooled and filtered through celite and washed with ethyl acetate. The organic layer was concentrated and the residue was purified by flash column chromatography (gradient elution with 5-50% ethyl acetate in hexanes) afforded the purified product as a white solid. $^1$H NMR (400 MHz, CDCl$_3$): 7.72 (m, 2H), 7.66 (m, 2H), 7.52 (m, 2H), 7.28 (m, 2H), 3.73 (s, 3 H), 3.18 (d, 1H), 2.86 (d, 1H), 1.7 (bs, 2H), 1.42 (s, 3 H).

(S)-2-Amino-3-[5-(4-cyano-phenyl)-thiophen-2-yl]-propionic acid methyl ester hydrochloride

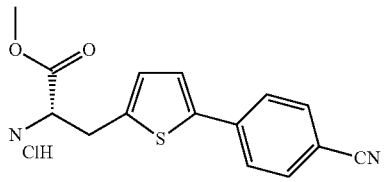 [SMILES: COC(=O)[C@@H](N)Cc1ccc(-c2ccc(C#N)cc2)s1 ; Cl]

Step 1. Esterification. To a solution of (S)-3-(5-bromo-thiophen-2-yl)-2-ter t-butoxycarbonylamino-propionic acid in DMF (50 mL) was added DIEA and methyl iodide. The reaction mixture stirred at rt for 2.5 h and was poured onto EtOAc and water. The organic layer was washed with 1 N HCl and 10% sodium carbonate, dried over sodium sulfate and concentrated to furnish (S)-3-(5-bromo-thiophen-2-yl)-2-tert-butoxycarbonylamino-propionic acid methyl ester. This product was used without further purification.

Step 2. Suzuki Coupling. To a solution of (S)-3-(5-bromo-thiophen-2-yl)-2-tert-butoxycarbonylamino-propionic acid methyl ester in toluene (10 mL) was added 4-cyanobenzeneboronic acid, Pd(PPh$_3$)$_4$, and 1N Na$_2$CO$_3$ solution (4 mL). The mixture was heated at reflux for 7 h. After completion of the reaction, the aqueous layer was drained. The organic was washed with 10% Na$_2$CO$_3$ and 1 N HCl. The organic was dried over sodium sulfate and concentrated under reduced pressure to afford the crude product. The residue was then purified by column chromatography (hexanes-EtOAc) to provide (S)-2-tert-butoxycarbonylamino-3-[5-(4-cyano-phenyl)-thiophen-2-yl]-propionic acid methyl ester.

Step 3. Removal of t-butyl Carbamate. (S)-2-tert-butoxy-carbonylamino-3-[5-(4-cyano-phenyl)-thiophen-2-yl]-propionic acid methyl ester was deprotected according to General Procedure C to provide (S)-2-amino-3-[5-(4-cyano-phenyl)-thiophen-2-yl]-propionic acid methyl ester hydrochloride. LCMS (m/z) 288.

(S)-2-tert-Butoxycarbonylamino-3-[(S)-2-(4-hydroxy-phenyl)-2,3-dihydro-benzo[1,4]dioxin-6-yl]-propionic acid methyl ester

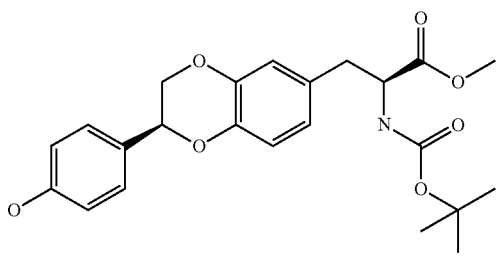 [SMILES: COC(=O)[C@H](Cc1ccc2c(c1)OC[C@H](c1ccc(O)cc1)O2)NC(=O)OC(C)(C)C]

(S)-2-tert-Butoxycarbonylamino-3-{(S)-2-[4-(3,4-dichloro-benzyloxy)-phenyl]-2,3-dihydro-benzo[1,4]dioxin-6-yl}-propionic acid methyl ester (310 mg), was subjected to hydrogenation using 10% Pd on carbon (150 mg) in methanol (20 mL), ethyl acetate (10 mL) and TEA (1 mL) as described in General Procedure Q furnished (S)-2-tert-butoxycarbonylamino-3-[(S)-2-(4-hydroxy-phenyl)-2,3-dihydro-benzo[1,4]dioxin-6-yl]-propionic acid methyl ester (240 mg). LCMS (m/z): 431.

(S)-3-[(S)-2-(4-Acetoxy-phenyl)-2,3-dihydro-benzo[1,4]dioxin-6-yl]-2-tert-butoxycarbonylamino-propionic acid methyl ester

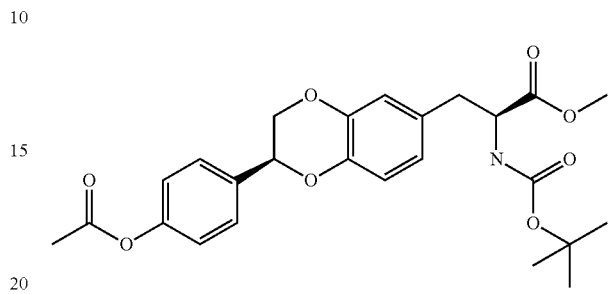

To a solution of (S)-2-tert-Butoxycarbonylamino-3-[(S)-2-(4-hydroxy-phenyl)-2,3-dihydro-benzo[1,4]dioxin-6-yl]-propionic acid methyl ester (240 mg) in DCM (10 mL) was added pyridine at 0° C. To this mixture was added acetic anhydride. The mixture was stirred for 2-3 h. After completion of the reaction, the mixture was diluted with DCM (50 mL) and was washed with water, 1N HCl and brine solution. The organic layer was dried and concentrated to get the desired product as a white solid (208 mg). LCMS (m/z): 473

(S)-3-[(S)-2-(4-Acetoxy-phenyl)-2,3-dihydro-benzo[1,4]dioxin-6-yl]-2-(4-nitro-benzenesulfonylamino)-propionic acid methyl ester

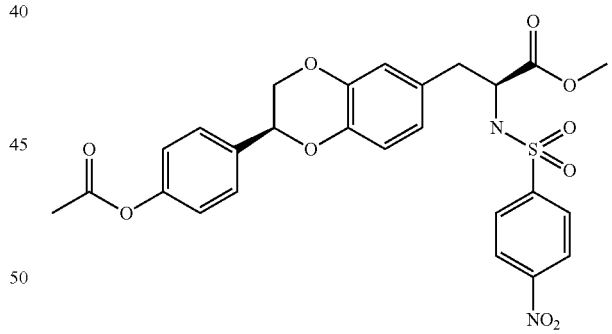

(S)-3-[(S)-2-(4-Acetoxy-phenyl)-2,3-dihydro-benzo[1,4]dioxin-6-yl]-2-tert-butoxycarbonylamino-propionic acid methyl ester (208 mg) was converted to the HCl salt of (S)-3-[(S)-2-(4-acetoxy-phenyl)-2,3-dihydro-benzo[1,4]dioxin-6-yl]-2-amino-propionic acid methyl ester according to General Procedure C. This intermediate was further reacted with 4-nitrobenzenesulfonyl chloride as described in General Procedure F to furnish (S)-3-[(S)-2-(4-acetoxy-phenyl)-2,3-dihydro-benzo[1,4]dioxin-6-yl]-2-(4-nitro-benzenesulfonylamino)-propionic acid methyl ester (230 mg). LCMS (m/z): 558.

(S)-3-[(S)-2-(4-Acetoxy-phenyl)-2,3-dihydro-benzo[1,4]dioxin-6-yl]-2-[(4-nitro-benzenesulfonyl)-((S)-1-phenyl-propyl)-amino]-propionic acid methyl ester

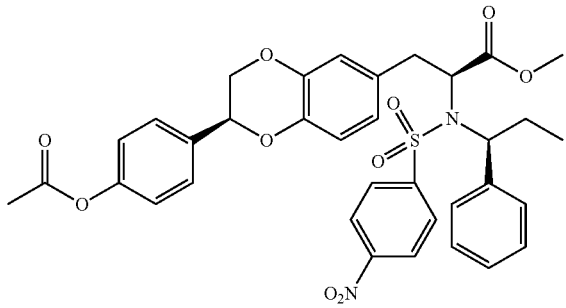 [SMILES: CC[C@@H](c1ccccc1)N([C@@H](Cc1ccc2c(c1)OC[C@H](c1ccc(OC(C)=O)cc1)O2)C(=O)OC)S(=O)(=O)c1ccc([N+](=O)[O-])cc1]

(S)-3-[(S)-2-(4-Acetoxy-phenyl)-2,3-dihydro-benzo[1,4]dioxin-6-yl]-2-(4-nitro-benzenesulfonylamino)-propionic acid methyl ester (230 mg) was dissolved in 4 mL dry THF and 262 mg triphenylphosphine and 136 mg (R)-(+)-1-phenyl-1-propanol were added. The mixture was stirred at 0° C. for 10 min, then 200 µL DIAD was added over 2 min. The reaction stirred at rt for 5 h, then was evaporated. The residue was purified by silica gel flash chromatography (9:1 to 8:2 hexanes/EtOAc) to give 270 mg desired product LCMS (m/z): 676.

(S)-3-[(S)-2-(4-Hydroxy-phenyl)-2,3-dihydro-benzo[1,4]dioxin-6-yl]-2-((S)-1-phenyl-propylamino)-propionic acid methyl ester

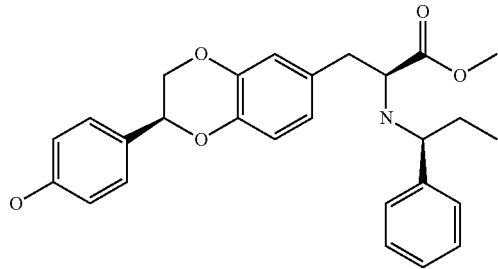 [SMILES: CC[C@H](N[C@@H](Cc1ccc2c(c1)OC[C@H](c1ccc(O)cc1)O2)C(=O)OC)c1ccccc1]

(S)-3-[(S)-2-(4-Acetoxy-phenyl)-2,3-dihydro-benzo[1,4]dioxin-6-yl]-2-[(4-nitro-benzenesulfonyl)-((S)-1-phenyl-propyl)-amino]-propionic acid methyl ester (230 mg) was dissolved in 3 mL dry DMF, then, mercaptoacetic acid and DBU were added at rt. The reaction stirred over night, and was partitioned between saturated aqueous NaHCO₃ and diethyl ether. The organic layer was washed successively with aqueous NaHCO₃, water, and brine, then was dried with Na₂SO₄ and evaporated. The residue was purified by silica gel flash chromatography (9:1 to 8:2 hexanes/EtOAc) to give 120 mg desired product. LCMS (m/z): 449.

(S)-3-[(S)-2-(4-Acetoxy-phenyl)-2,3-dihydro-benzo[1,4]dioxin-6-yl]-2-((S)-1-phenyl-propylamino)-propionic acid methyl ester

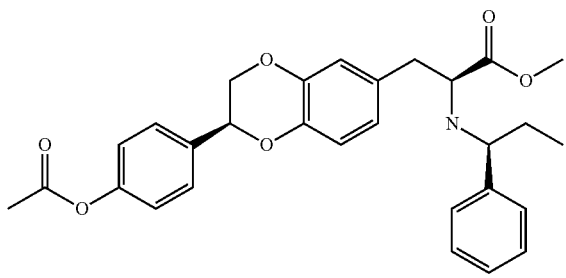 [SMILES: CC[C@H](N[C@@H](Cc1ccc2c(c1)OC[C@H](c1ccc(OC(C)=O)cc1)O2)C(=O)OC)c1ccccc1]

To a solution of (S)-3-[(S)-2-(4-hydroxy-phenyl)-2,3-dihydro-benzo[1,4]dioxin-6-yl]-2-((S)-1-phenyl-propylamino)-propionic acid methyl ester (120 mg) in DCM (3 mL) was added pyridine at 0° C. To this mixture was added acetic anhydride. The mixture was stirred for 2-3 h. After completion of the reaction, the mixture was diluted with DCM (20 mL) and was washed with water, 1N HCl and brine solution. The organic layer was dried and concentrated to get the desired product as a white solid (110 mg). LCMS (m/z): 491.

(3S,8S)-3-(4-Acetoxy-phenyl)-7-((S)-1-phenyl-propyl)-2,3,6,7,8,9-hexahydro-[1,4]dioxino[2,3-g]isoquinoline-8-carboxylic acid methyl ester

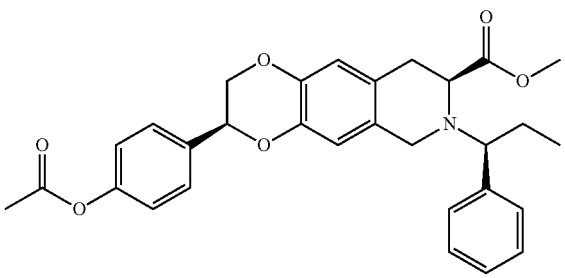 [SMILES: CC[C@@H](c1ccccc1)N1Cc2cc3c(cc2C[C@H]1C(=O)OC)OC[C@H](c1ccc(OC(C)=O)cc1)O3]

(S)-3-[(S)-2-(4-Acetoxy-phenyl)-2,3-dihydro-benzo[1,4]dioxin-6-yl]-2-((S)-1-phenyl-propylamino)-propionic acid methyl ester (110 mg) was dissolved in 32 mL dry dioxane and 20 mg paraformaldehyde and 8 mL trifluoroacetic acid were added. The reaction stirred 48 h at rt. NaHCO₃ was added until a pH of 7 was achieved, then the mixture was extracted with EtOAc. The organic extract was washed with brine and dried over Na₂SO₄ and evaporated. The residue was purified by silica gel flash chromatography (9:1 to 8:2 hexanes/EtOAc) to give 120 mg desired product. LCMS (m/z): 503.

(3S,8S)-3-(4-Hydroxy-phenyl)-7-((S)-1-phenyl-propyl)-2,3,6,7,8,9-hexahydro-[1,4]dioxino[2,3-g]isoquinoline-8-carboxylic acid methyl ester

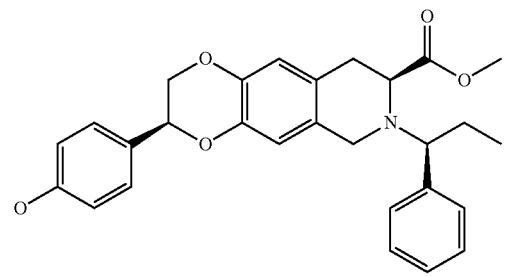 [SMILES: CC[C@@H](c1ccccc1)N1Cc2cc3c(cc2C[C@H]1C(=O)OC)OC[C@H](c1ccc(O)cc1)O3]

(3S,8S)-3-(4-Acetoxy-phenyl)-7-((S)-1-phenyl-propyl)-2,3,6,7,8,9-hexahydro-[1,4]dioxino[2,3-g]isoquinoline-8-carboxylic acid methyl ester (120 mg) was dissolved in methanol (5 mL). To this solution was added NaHCO₃ (400 mg). The mixture was stirred at rt for 2-3 h. After completion of the reaction, the mixture was poured into water (10 mL) and was extracted with EtOAc (30 mL). The organic layer was washed with water, brine, dried and concentrated to get the desired product as a white solid (110 mg) LCMS (m/z): 461.

353

(3S,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester

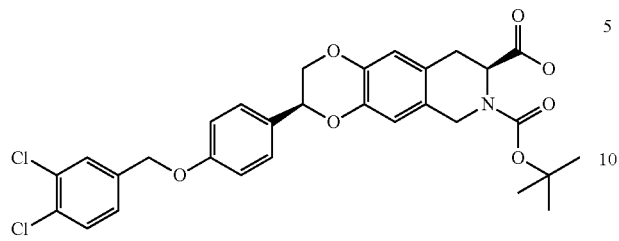

354

(3S,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester (0.40 g) was hydrolyzed according to General Procedure B to give (3S,8S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester (0.34 g) LCMS (m/z): 587.

(3S,8S)-3-[4-(3,4-Dichloro-benzyloxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester

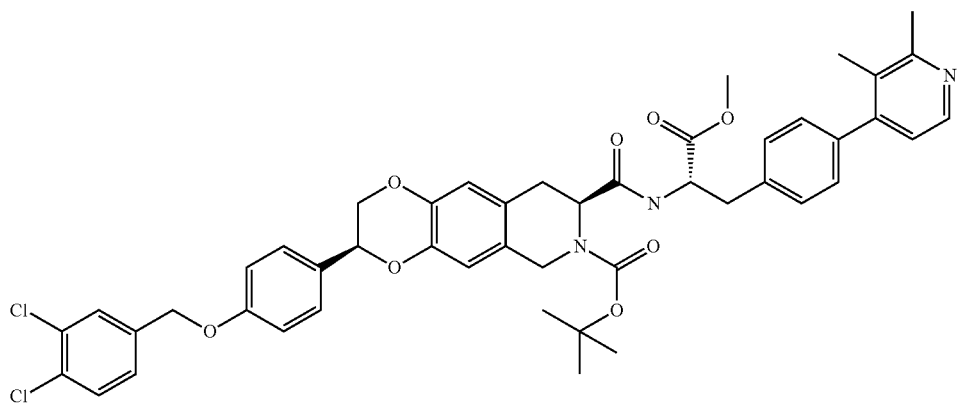 [SMILES: COC(=O)[C@H](Cc1ccc(-c2ccnc(C)c2C)cc1)NC(=O)[C@@H]1Cc2cc3c(cc2CN1C(=O)OC(C)(C)C)O[C@@H](c1ccc(OCc2ccc(Cl)c(Cl)c2)cc1)CO3]

(3S,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester (0.33 g) was coupled with (S)-2-amino-3-[4-(2,3-dimethyl-pyridin-4-yl)-phenyl]-propionic acid methyl ester bis hydrochloride (0.20 g) according to General Procedure L to provide (3S,8S)-3-[4-(3,4-dichloro-benzyloxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (0.30 g). LCMS (m/z): 853.

(S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride

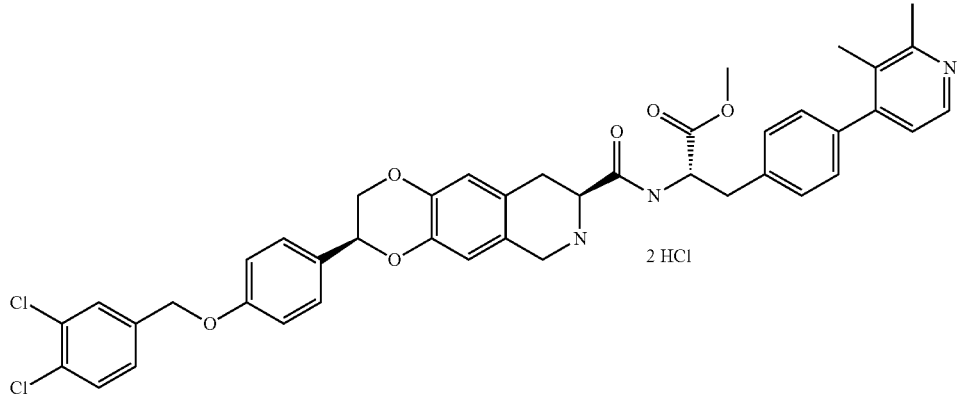 [SMILES: COC(=O)[C@H](Cc1ccc(-c2ccnc(C)c2C)cc1)NC(=O)[C@@H]1Cc2cc3c(cc2CN1)O[C@@H](c1ccc(OCc2ccc(Cl)c(Cl)c2)cc1)CO3]

(3S,8S)-3-[4-(3,4-Dichloro-benzyloxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (0.30 g) was deprotected according to General Procedure C to provide (S)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (0.288 g). LCMS (m/z): 753.

(3S,8S)-8-{(S)-2-[4-(2,3-Dimethyl-pyridin-4-yl)-phenyl]-1-methoxycarbonyl-ethylcarbamoyl}-3-(4-hydroxy-phenyl)-2,3,8,9-tetrahydro-6H-[1,4]dioxino[2,3-g]isoquinoline-7-carboxylic acid tert-butyl ester

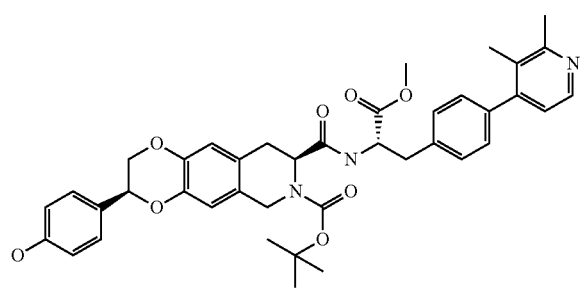 [SMILES: COC(=O)[C@H](Cc1ccc(-c2ccnc(C)c2C)cc1)NC(=O)[C@@H]1Cc2cc3c(cc2CN1C(=O)OC(C)(C)C)O[C@@H](c1ccc(O)cc1)CO3]

(3S,8S)-3-[4-(3,4-Dichloro-benzyloxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (1.0 g) was dissolved in EtOAc (4.0 mL), MeOH (12.0 mL), NEt$_3$ (0.236 g), followed by catalytic amount of 10% palladium on activated carbon (wet) was added. After degassing, hydrogen was introduced through a balloon; the reaction mixture was stirred at room temperature for 1.0 hour. The reaction mixture was then filtered through celite, the celite cake was washed three times with ethyl acetate, and the filtrates combined. The solvent was then removed in vacuo, dried under vacuum to get 0.81 g of title compound. LCMS (m/z): 695.

(5-Bromomethyl-4-methyl-thiazol-2-yl)-carbamic acid tert-butyl ester

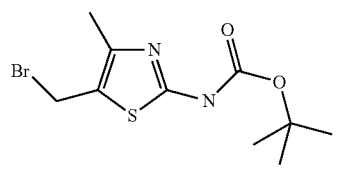 [SMILES: Cc1nc(NC(=O)OC(C)(C)C)sc1CBr]

2-tert-Butoxycarbonylamino-4-methyl-thiazole-5-carboxylic acid (0.52 g) was dissolved in THF: MeOH (2:1, 10 mL) and 2 eq of TMSCHN$_2$ (2M sln in hex) was added at RT and stirred for 6 h. All volatiles were removed in vacuum by rotavap and the residue was dried in vacuum to give 2-tert-Butoxycarbonylamino-4-methyl-thiazole-5-carboxylic acid methyl ester (0.52 g). This was used in the next reaction without further purification. 1H NMR (400 MHz, CDCl$_3$) 3.83 (s, 3H), 2.65 (s, 3H), 1.54 (s, 9H).

2-tert-Butoxycarbonylamino-4-methyl-thiazole-5-carboxylic acid methyl ester (0.5 g) was dissolved in anhydrous THF (7 mL) and cooled to 0° C. and 1 eq of Lithium aluminum hydride (2M solution in THF) was added and stirred 1 h. Reaction was slowly warmed to RT and stirred for 6 h. Reaction was cooled to 0° C. and quenched with min amount of sat. Na$_2$SO$_4$ soln. White solid was filtered and washed with ethyl acetate (5 mL), filtrate was concentrated by rotavap and residue was dired in vacuum gave (5-Hydroxymethyl-4-methyl-thiazol-2-yl)-carbamic acid tert-butyl ester (0.4 g). This was used in the next reaction without further purification. 1H NMR (400 MHz, Acetone-d6) 4.6 (s, 2H), 2.1 (s, 3H), 1.5 (s, 9H).

(5-Hydroxymethyl-4-methyl-thiazol-2-yl)-carbamic acid tert-butyl ester (0.3 g) and 1 g of triphenylphosphine polystyrene (1.2 mmol/g) were taken in anhydrous dichloromethane (6 mL) and cooled to 0° C., and carbontetrabromide (0.4 g) added. The mixture stirred for 1 h. at 0° C. room temperature for 2 h. Resin was filtered and washed with 5 mL of dichloromethane, filtrate was concentrated and dried in vacuum give (5-Bromomethyl-4-methyl-thiazol-2-yl)-carbamic acid tert-butyl ester (0.3 g). This was used in the next reaction with no further purification. 1H NMR (400 MHz, Acetone-d6) 4.9 (s, 2H), 2.45 (s, 3H), 1.55 (s, 3H).

(5-Bromomethyl-pyridin-2-yl)-carbamic acid tert-butyl ester

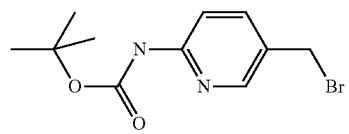 [SMILES: CC(C)(C)OC(=O)Nc1ccc(CBr)cn1]

(5-Hydroxymethyl-pyridin-2-yl)-carbamic acid tert-butyl ester (0.1 g) was converted to (5-Bromomethyl-pyridin-2-yl)-carbamic acid tert-butyl ester (0.11 g) according to General Procedure X.

4-(2-Acetylamino-thiazol-4-yl)-benzenesulfonyl chloride

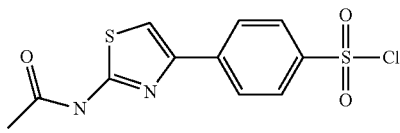 [SMILES: CC(=O)Nc1nc(-c2ccc(S(=O)(=O)Cl)cc2)cs1]

N-(4-phenyl-thiazol-2-yl)-acetamide was added to chlorosulfonic acid (5 eq) at 0° C. and allowed to warm to room temperature. The mixture was heated at 70° C. for 1 h and carefully poured into ice. The solid was filtered, washed with water and dried under vacuum to give 4-(2-acetylamino-thiazol-4-yl)-benzenesulfonyl chloride. Characterized by derivatization as N-[4-(4-Isobutylsulfamoyl-phenyl)-thiazol-2-yl]-acetamide, $^1$H NMR (400 MHz, CD$_3$OD) 8.08 (d, 2H), 7.85 (d, 2H), 7.58 (s, 1H), 2.66 (d, 2H), 2.22 (s, 3H), 1.7 (m, 1H), 0.87 (d, 6H). LCMS (m/z): 354.

N-(6-Methyl-5-nitro-pyridin-2-yl)-acetamide

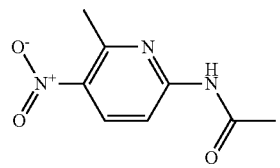

6-Methyl-5-nitro-pyridin-2-ylamine (1.0 g) was treated with acetic anhydride according to General Procedure Y to give N-(6-Methyl-5-nitro-pyridin-2-yl)-acetamide (1.2 g).

N-(5-Amino-6-methyl-pyridin-2-yl)-N-cyclobutylmethyl-acetamide

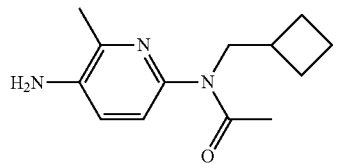 [SMILES: CC(=O)N(CC1CCC1)c1ccc(N)c(C)n1]

N-(6-Methyl-5-nitro-pyridin-2-yl)-acetamide (0.5 g) was taken in 5 mL anhydrous DMF. 3 eq of $K_2CO_3$ and 3 eq of bromomethyl-cyclobutane were added and heated at 80° C. for 24 h. Water was added to the reaction and the mixture extracted with EtOAc (2X10 mL). The organic layer was washed with water and brine and dried over $Na_2SO_4$. Solvent was concentrated and the residue was purified over silica to give N-Cyclobutylmethyl-N-(6-methyl-5-nitro-pyridin-2-yl)-acetamide LCMS (m/z): 264.

This was subjected to hydrogenation according to General Procedure to give N-(5-Amino-6-methyl-pyridin-2-yl)-N-cyclobutylmethyl-acetamide. LCMS (m/z): 234.

6-(Acetyl-cyclobutylmethyl-amino)-2-methyl-pyridine-3-sulfonyl chloride

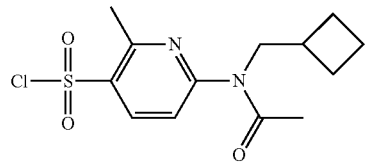 [SMILES: CC(=O)N(CC1CCC1)c1ccc(S(=O)(=O)Cl)c(C)n1]

N-(5-Amino-6-methyl-pyridin-2-yl)-N-cyclobutylmethyl-acetamide (0.23 g) was converted to 6-(Acetyl-cyclobutylmethyl-amino)-2-methyl-pyridine-3-sulfonyl chloride according to General Procedure AA (0.18 g) LCMS (m/z): 317.

6-Acetylamino-2-methyl-pyridine-3-sulfonyl chloride

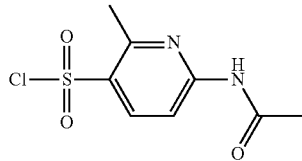

N-(6-Methyl-5-nitro-pyridin-2-yl)-acetamide (1.2 g) was reduced to N-(5-amino-6-methyl-pyridin-2-yl)-acetamide (0.9 g) according to General Procedure Z. LCMS (m/z): 166. This was converted to 6-acetylamino-2-methyl-pyridine-3-sulfonyl chloride according to General Procedure AA. LCMS (m/z): 248.

6-Isopropylamino-2-methyl-pyridine-3-sulfonyl chloride

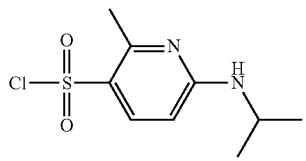

6-Chloro-2-methyl-3-nitro-pyridine (0.5 g) was treated with isopropyl amine according to General Procedure U to give isopropyl-(6-methyl-5-nitro-pyridin-2-yl)-amine LCMS (m/z): 196. This was reduced under hydrogen atmosphere according to General Procedure Z to give N*2*-Isopropyl-6-methyl-pyridine-2,5-diamine (0.35 g), LCMS (m/z): 166. This was converted to 6-isopropylamino-2-methyl-pyridine-3-sulfonyl chloride according to General Procedure AA.

2-Methyl-6-methylamino-pyridine-3-sulfonyl chloride

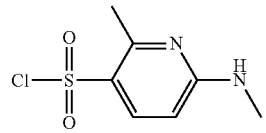

6-Chloro-2-methyl-3-nitro-pyridine (0.6 g) was treated with methyl amine according to General Procedure U to give methyl-(6-methyl-5-nitro-pyridin-2-yl)-amine LCMS (m/z): 168. This was reduced under hydrogen atmosphere according to General Procedure Z to give 6,N*2*-dimethyl-pyridine-2,5-diamine (0.35 g), LCMS (m/z): 138. This was converted to 2-methyl-6-methylamino-pyridine-3-sulfonyl chloride according to General Procedure AA.

6-(Cyclopropylmethyl-amino)-2-methyl-pyridine-3-sulfonyl chloride

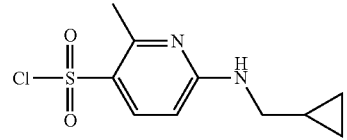 [SMILES: Cc1nc(NCC2CC2)ccc1S(=O)(=O)Cl]

6-Chloro-2-methyl-3-nitro-pyridine (0.5 g) was treated with cyclopropyl-methylamine according to General Procedure U to give methyl-(6-methyl-5-nitro-pyridin-2-yl)-amine. LCMS (m/z): 208. This was reduced under hydrogen atmosphere according to General Procedure Z to give N*2*-cyclopropylmethyl-6-methyl-pyridine-2,5-diamine (0.35 g), LCMS (m/z): 178. This was converted to 6-(cyclopropylmethyl-amino)-2-methyl-pyridine-3-sulfonyl chloride according to General Procedure AA. LCMS (m/z): 261.

6-Acetylamino-4-methyl-pyridine-3-sulfonyl chloride

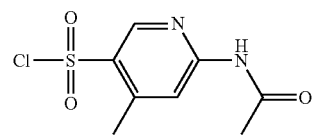

4-Methyl-5-nitro-pyridin-2-ylamine (1.0 g) was treated with acetic anhydride according to General Procedure Y to give N-(4-Methyl-5-nitro-pyridin-2-yl)-acetamide (1.1 g). LCMS (m/z): 196. N-(4-Methyl-5-nitro-pyridin-2-yl)-acetamide (0.5 g) was reduced under hydrogen atmosphere according to General Procedure Z to give N-(5-Amino-4-methyl-pyridin-2-yl)-acetamide (0.4 g), LCMS (m/z): 166. This was converted to 6-acetylamino-4-methyl-pyridine-3-sulfonyl chloride (0.35 g) according to General Procedure AA. LCMS (m/z): 249.

(S)-2-({(S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester

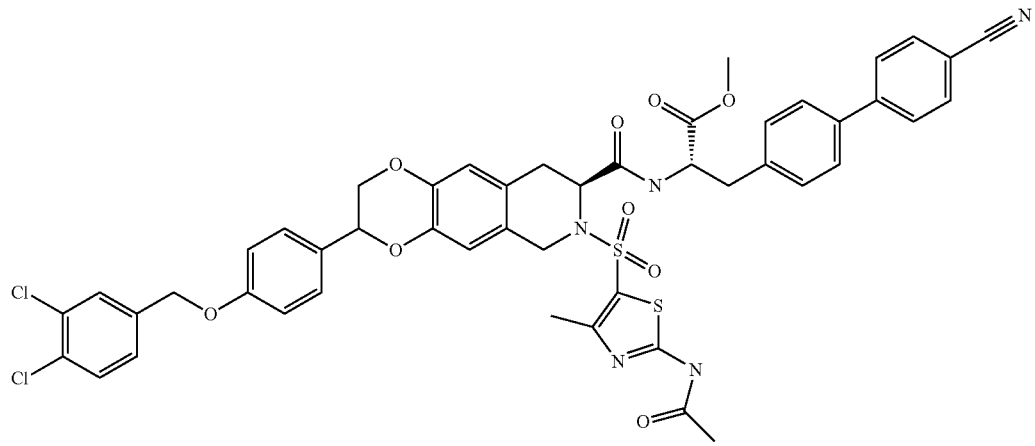 [SMILES: COC(=O)[C@H](Cc1ccc(-c2ccc(C#N)cc2)cc1)NC(=O)[C@@H]1Cc2cc3c(cc2CN1S(=O)(=O)c1sc(NC(C)=O)nc1C)OC(c1ccc(OCc2ccc(Cl)c(Cl)c2)cc1)CO3]

(S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (748 mg) was dissolved in dry DCM (5 mL). To this solution was added the thiazolesulfonyl chloride (318 mg), pyridine (260 μL) and DMAP (10 mg). The mixture was stirred for 12-14 h. Upon complete conversion, the mixture was concentrated to dryness. Fresh DCM (5 mL) was added and the solution was evaporated to dryness. The solid was purified by column, silica, DCM-EtOAc (90/10-80/20) to give the desired product as a white solid (775 mg). LCMS (m/z) 969.

(S)-2-({(S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (S)-2-({(S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (483 mg) was suspended in dry methanol (3 mL). To this solution was added 4N HCl in dioxane. The mixture was heated at 63° C. for 3-4 hours. Upon complete conversion, the mixture was concentrated to dryness. The solid was re dissolved in DCM 10 mL and was washed with Na$_2$CO$_3$ to a pH of 8. The organic layer was washed with water, brine, dried (anhydrous Na$_2$SO$_4$) and concentrated to get a white solid. The solid was purified by column chromatography (silica, DCM-EtOAc, 90/1-60/40) to get the desired product as a white solid (393 mg). LCMS (m/z) 926.

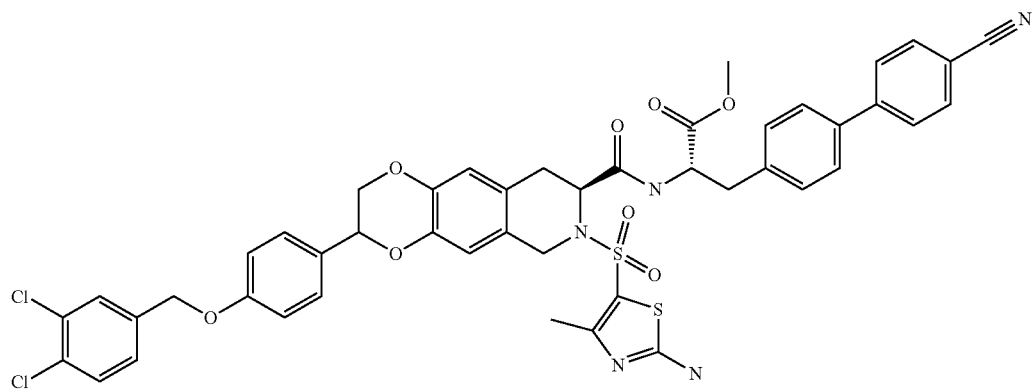 [SMILES: COC(=O)[C@H](Cc1ccc(-c2ccc(C#N)cc2)cc1)NC(=O)[C@@H]1Cc2cc3c(cc2CN1S(=O)(=O)c1sc(N)nc1C)OC(c1ccc(OCc2ccc(Cl)c(Cl)c2)cc1)CO3]

361

(S)-2-{[(3S,8S)-7-Benzoyl-3-(4-hydroxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester

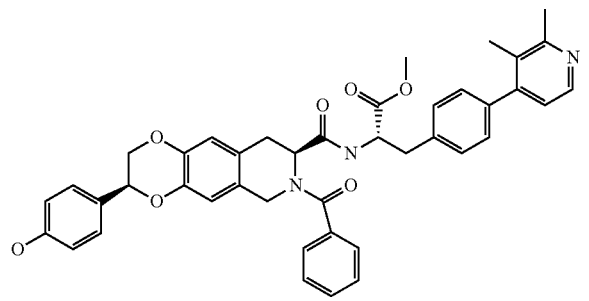 [SMILES: COC(=O)[C@H](Cc1ccc(-c2ccnc(C)c2C)cc1)NC(=O)[C@@H]1Cc2cc3c(cc2CN1C(=O)c1ccccc1)O[C@@H](c1ccc(O)cc1)CO3]

(S)-3-[2-(4-Acetoxy-phenyl)-2,3-dihydro-benzo[1,4]dioxin-6-yl]-2-tert-butoxycarbonyl-amino-propionic acid methyl ester was converted to the HCl salt of (S)-3-[2-(4-acetoxy-phenyl)-2,3-dihydro-benzo[1,4]dioxin-6-yl]-2-amino-propionic acid methyl ester according to General Procedure C. This intermediate (450 mg) dissolved in dioxane (32 mL) and TFA (8 mL). To this solution was added paraformaldehyde (60 mg) and stirred at room temperature for 6 hours.

After completion of the reaction, the mixture was poured into water (100 mL) and extracted with EtOAc. The organic layer was neutralized to a pH of 7 using NaHCO₃ and washed with water and brine, and then dried to get an oil. The oil was taken up in fresh EtOAc (200 mL) and benzoyl chloride and saturated Na₂CO₃ (20 mL) were added. The mixture was stirred for 2-3 hours and the organic layer was separated, washed dried and concentrated and purified (silica; hexanes/EtOA, 8:2 to 7:3) to get (3S,8S)-3-(4-acetoxy-phenyl)-7-benzoyl-2,3,6,7,8,9-hexahydro-[1,4]dioxino[2,3-g]isoquinoline-8-carboxylic acid methyl ester (468 mg). This ester (215 mg) was hydrolyzed according to General Procedure B to afford (3S,8S)-7-benzoyl-3-(4-hydroxy-phenyl)-2,3,6,7,8,9-hexahydro-[1,4]dioxino[2,3-g]isoquinoline-8-carboxylic acid (200 mg). LCMS (m/z) 431. This acid was coupled with (S)-2-amino-3-[4-(2,3-dimethyl-pyridin-4-yl)-phenyl]-propionic acid methyl ester bis hydrochloride according to General Procedure L gave (S)-2-{[(3S,8S)-7-Benzoyl-3-(4-hydroxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester (224 mg). LCMS (m/z): 699.

362

(3S,8S)-3-(4-Cyclohexylmethoxy-phenyl)-2,3,8,9-tetrahydro-6H-[1,4]dioxino[2,3-g]isoquinoline-7,8-dicarboxylic acid 7-tert-butyl ester

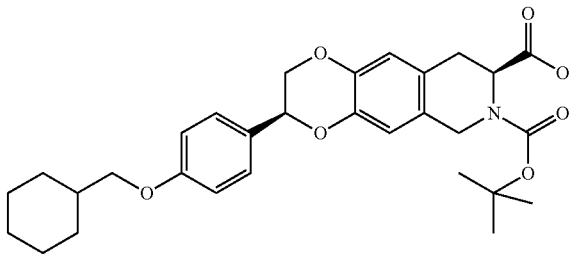 [SMILES: CC(C)(C)OC(=O)N1Cc2cc3c(cc2C[C@H]1C(=O)O)OC[C@H](c1ccc(OCC2CCCCC2)cc1)O3]

(S)-3-[2-(4-Acetoxy-phenyl)-2,3-dihydro-benzo[1,4]dioxin-6-yl]-2-tert-butoxycarbonylamino-propionic acid methyl ester was converted to the HCl salt of (S)-3-[2-(4-acetoxy-phenyl)-2,3-dihydro-benzo[1,4]dioxin-6-yl]-2-amino-propionic acid methyl ester according to General Procedure C. This intermediate (450 mg) was dissolved in dioxane (32 mL) and TFA (8 mL). To this solution was added paraformaldehyde (60 mg) and stirred at rom temperature for 6 hours. After completion of the reaction, the mixture was poured into water (100 mL) and extracted with EtOAc. The organic layer was neutralized to a pH of 7 using NaHCO₃ and washed with water and brine, and dried to get an oil. The oil was taken in fresh DCM (200 mL) and Boc anhydride and DIEA (3 mL) were added. The mixture was stirred for 2-3 h and the organic layer was separated, washed dried and concentrated and purified (silica; hexanes/EtOAc, 8:2 to 7:3) to get (3S,8S)-3-(4-acetoxy-phenyl)-2,3,8,9-tetrahydro-6H-[1,4]dioxino[2,3-g]isoquinoline-7,8-dicarboxylic acid 7-tert-butyl ester 8-methyl ester. This Boc ester (485 mg) was dissolved in methanol (20 mL). To this solution was added NaHCO₃ (2.0 g). The mixture was stirred at room temperature for 3 h. After completion of the reaction, the mixture was poured into water (200 mL) and was extracted with EtOAc (300 mL). The organic layer was washed with water, brine, dried and concentrated to get the desired product as a white solid (380 mg). This intermediate was coupled with cyclohexane methanol according to General Procedure K furnished (3S,8S)-3-(4-cyclohexylmethoxy-phenyl)-2,3,8,9-tetrahydro-6H-[1,4]dioxino[2,3-g]isoquinoline-7,8-dicarboxylic acid 7-tert-butyl ester 8-methyl ester. This ester upon hydrolysis according to General Procedure B furnished (3S,8S)-3-(4-cyclohexylmethoxy-phenyl)-2,3,8,9-tetrahydro-6H-[1,4]dioxino[2,3-g]isoquinoline-7,8-dicarboxylic acid 7-tert-butyl ester (C). LCMS (m/z): 525.

(S)-2-{[(3S,8S)-3-(4-Cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid methyl ester bis hydrochloride

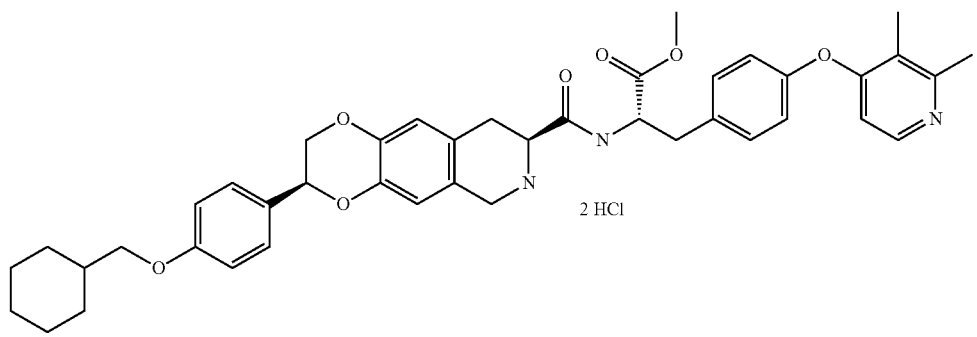 [SMILES: COC(=O)[C@H](Cc1ccc(Oc2ccnc(C)c2C)cc1)NC(=O)[C@@H]1Cc2cc3c(cc2CN1)O[C@@H](c1ccc(OCC2CCCCC2)cc1)CO3]

(3S,8S)-3-(4-Cyclohexylmethoxy-phenyl)-2,3,8,9-tetrahydro-6H-[1,4]dioxino[2,3-g]isoquinoline-7,8-dicarboxylic acid 7-tert-butyl ester was coupled with (S)-2-amino-3-[4-(2,3-dimethyl-pyridin-4-yloxy)-phenyl]-propionic acid methyl ester bis hydrochloride according to General Procedure L furnished (3S,8S)-3-(4-Cyclohexylmethoxy-phenyl)-8-{(S)-2-[4-(2,3-dimethyl-pyridin-4-yloxy)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester. This compound was converted to (S)-2-{[(3S,8S)-3-(4-cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid methyl ester bis hydrochloride according to General ProcedureC. LCMS (m/z) 707.

1-[3-(3,4-Dichloro-benzyloxy)-phenyl]-ethanone

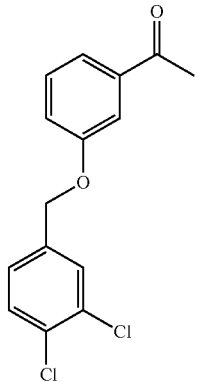 [SMILES: CC(=O)c1cccc(OCc2ccc(Cl)c(Cl)c2)c1]

To a solution of 3'-hydroxyacetophenone (19 g) in DMF (400 mL) was added $K_2CO_3$ (38.5 g) and the mixture was stirred for 3 hours at room temperature. 3,4-Dichlorobenzyl chloride (32.7 g) and potassium iodide (1.16 g) were added to the reaction mixture and stirred for 48 hours. After completion of the reaction, the mixture was poured into ice and water mixture and stirred for 15 minutes, solid was filtered and washed with water and hexanes. Solid was dissolved in DCM and precipitated by adding hexanes to get pure 1-[3-(3,4-dichloro-benzyloxy)-phenyl]-ethanone (30 g) 1H NMR (400 MHz, $CDCl_3$) 7.53-7.60 (m, 3H), 7.46 (d, 1H), 7.39 (t, 1H), 7.25-7.30 (m, 1H), 7.14-7.19 (m, 1H), 5.07 (s, 2H), 2.60 (s, 3H).

2-Bromo-1-[3-(3,4-dichloro-benzyloxy)-phenyl]-ethanone

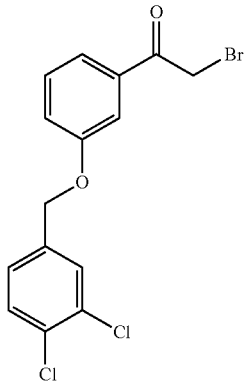 [SMILES: O=C(CBr)c1cccc(OCc2ccc(Cl)c(Cl)c2)c1]

1-[3-(3,4-Dichloro-benzyloxy)-phenyl]-ethanone (30 g) was dissolved in MeOH:DCM (2:1, 300 mL) and pyrolidone hydrotribromide (75 g) was added portion wise and stirred at room temperature for 3 hours. After completion of the reaction, the mixture was concentrated in vacuo and poured into saturated sodium bicarbonate solution (200 mL) and extracted with ethyl acetate (2×200 mL). The organic extracts were combined and washed with brine and concentrated in vacuo. Then this residue was dissolved in DCM (75 mL) and product was precipitated by slow addition of methanol (75 mL), filtered and dried in vacuum (29 g). $^1H$ NMR (400 MHz, $CDCl_3$): 7.62-7.54 (m, 3H), 7.47 (d, 1H), 7.42 (t, 1H), 7.25-7.30 (m, 1H), 7.18-7.23 (m, 1H), 5.07 (s, 2H), 4.44 (s, 2H).

3-{2-[3-(3,4-Dichloro-benzyloxy)-phenyl]-2-oxo-ethoxy}-4-fluoro-benzonitrile

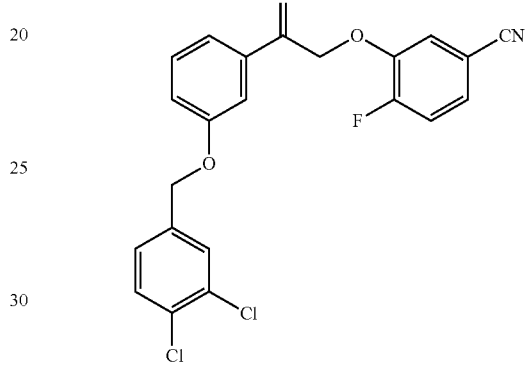

4-Fluoro-3-hydroxy-benzonitrile (7.3 g), 2-bromo-1-[3-(3,4-dichloro-benzyloxy)-phenyl]-ethanone (22 g), and potassium carbonate (24.3 g) were suspended together in 400 mL acetone with stirring. The mixture continued to stir for 8 hours, then was concentrated to dryness. The solid residue was taken up in 150 mL diethyl ether and 150 mL water and stirred 2 hours. The solid product was collected by filtration and washed with 100 mL diethyl ether two times and dried in vacuum, 20 g of desired product was obtained. $^1H$ NMR (400 MHz, DMSO-$d_6$): 7.80-7.85 (m, 1H), 7.77 (d, 1H), 7.67 (m, 1H), 7.57-7.64 (m, 2H), 7.44-7.54 (m, 4H), 7.34-7.36 (m, 1H), 5.77 (s, 2H), 5.21 (s, 2H).

3-{(S)-2-[3-(3,4-Dichloro-benzyloxy)-phenyl]-2-hydroxy-ethoxy}-4-fluoro-benzonitrile

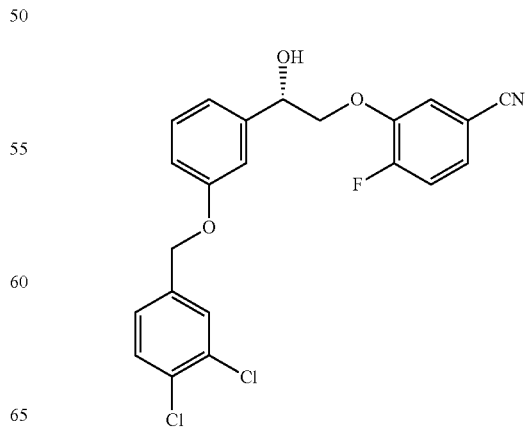

(S)-CBS reagent (46.5 mL, 1M in toluene) was added to a THF solution (200 mL) of borane-diethylaniline complex (15.16 g) were stirred together 15 min at room temperature. 3-{2-[3-(3,4-Dichloro-benzyloxy)-phenyl]-2-oxo-ethoxy}-4-fluoro-benzonitrile (20 g) in 600 mL of dry THF was then added through an addition funnel at rt over 20 minutes. The mixture was stirred for 15 minutes and then was quenched by slow addition of 60 mL MeOH. After gas evolution ceased, the mixture was evaporated and water was added to the residue and extracted with ethyl acetate. Ethyl acetate layer separated and washed with water, brine, dried (Na$_2$SO$_4$), filtered, and evaporated. The residue was purified by silicagel column (DCM; 10% EtOAc in DCM) to get pure product. $^1$H NMR (400 MHz, CDCl$_3$): 7.55 (d, 1H), 7.45 (d, 1H), 7.15-7.35 (m, 4H), 7.09 (t, 1H), 7.04 (d, 1H), 6.92 (m, 1H), 5.15 (m, 1H), 5.04 (s, 2H), 4.10 (m, 2H), 2.63 (d, 1H).

(S)-2-[3-(3,4-Dichloro-benzyloxy)-phenyl]-2,3-dihydro-benzo[1,4]dioxine-6-carbonitrile

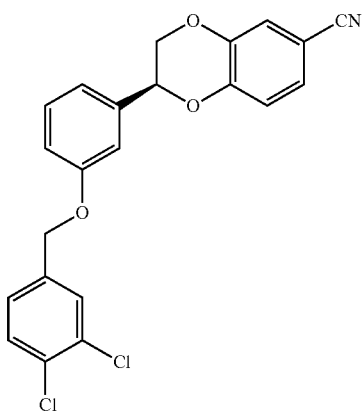 [SMILES: N#Cc1ccc2c(c1)OC[C@H](c1cccc(OCc3ccc(Cl)c(Cl)c3)c1)O2]

3-{(S)-2-[3-(3,4-Dichloro-benzyloxy)-phenyl]-2-hydroxy-ethoxy}-4-fluoro-benzonitrile (13.0 g) was dissolved in 130 mL of anhydrous NMP:diglyme (1:9) solution under nitrogen and heated to 150° C. A suspension of sodium hydride (1.2 g of 60% NaH in mineral oil) in 26 mL of anhydrous NMP:diglyme (1:9) was added all at once via cannula while stirring. After 15 minutes, the reaction was removed from heating, cooled 5 minutes, and then poured into a mixture of ice, 0.5 L EtOAc, and 0.25 L 1 N HCl. The layers were separated and the organic layer was washed with water and brine, and dried over Na$_2$SO$_4$. The residue was purified by silica gel flash chromatography (DCM to 1:1 DCM/EtOAc) to provide 8.2 g of partially purified solid which was then purified by silica gel column (1:1 DCM:hex to DCM). $^1$H NMR (400 MHz, CDCl$_3$): 7.54 (d, 1H), 7.46 (d, 1H), 7.36 (t, 1H), 7.18-7.28 (m, 3H), 6.95-7.06 (m, 4H) 5.16 (m, 1H), 5.04 (s, 2H), 4.42 (m, 1H), 4.02 (m, 1H).

(S)-2-[3-(3,4-Dichloro-benzyloxy)-phenyl]-2,3-dihydro-benzo[1,4]dioxine-6 carbaldehyde

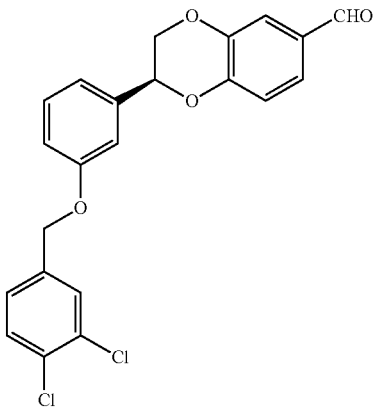 [SMILES: O=Cc1ccc2c(c1)OC[C@H](c1cccc(OCc3ccc(Cl)c(Cl)c3)c1)O2]

(S)-2-[3-(3,4-Dichloro-benzyloxy)-phenyl]-2,3-dihydro-benzo[1,4]dioxine-6-carbonitrile (2.3 g) was taken in 65 mL dry toluene and cooled to 0° C. under nitrogen. 11.0 mL of a 1M solution of diisobutylaluminum hydride in toluene was added over 5 minutes. The reaction stirred at 0° C. for 30 min and was quenched by slow addition of 6 mL HOAc. The mixture was partitioned between water (100 mL) and EtOAc (100 mL) and the organic layer was washed with 10% Na$_2$CO$_3$ solution, water, and brine, and was dried over Na$_2$SO$_4$ and evaporated. The residue was purified by silica gel plug (DCM) to give 2.1 g of desired product after drying under vacuum. $^1$H NMR (400 MHz, CDCl$_3$): 9.86 (s, 1H), 7.55 (d, 1H), 7.44-7.50 (m, 3H), 7.36 (t, 1H), 7.24-7.29 (m, 1H), 7.11 (d, 1H), 6.94-7.06 (m, 3H), 5.19 (m, 1H), 5.04 (s, 2H), 4.43 (m, 1H), 4.05 (m, 1H).

2-tert-Butoxycarbonylamino-3-{(S)-2-[3-(3,4-dichloro-benzyloxy)-phenyl]-2,3-dihydro-benzo[1,4]dioxin-6-yl}-acrylic acid methyl ester

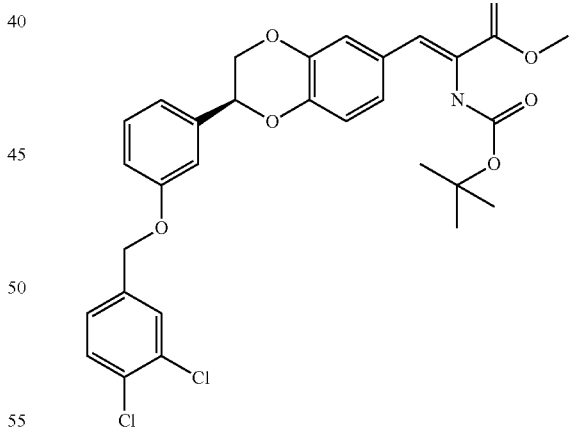

(S)-2-[3-(3,4-Dichloro-benzyloxy)-phenyl]-2,3-dihydro-benzo[1,4]dioxine-6 carbaldehyde (2.1 g) was dissolved in 8 mL dry DCM under nitrogen at rt and DBU (1.61 g) was added by syringe. A solutuion of Boc-phosphonoglycine trimethyl ester (1.58 g) in 4 mL of dry DCM was added to the reaction mixture and stirred at rt. for 12 hours. Reaction mixture was directly loaded on to silica gel column (40% hexanes in DCM to DCM) gave 1.8 g pure product. $^1$H NMR (400 MHz, CDCl$_3$): 7.55 (d, 1H), 7.46 (d, 1H), 7.32-7.38 (m, 1H), 7.18-7.28 (m, 3H), 7.10-7.15 (m, 1H), 6.94-7.06 (m, 4H), 5.13 (m, 1H), 5.03 (s, 2H), 4.36 (m, 1H), 4.01 (m, 1H), 3.84 (s, 3H), 1.44 (s, 9H). LCMS (m/z): 587.

(S)-2-tert-Butoxycarbonylamino-3-{(S)-2-[3-(3,4-dichloro-benzyloxy)-phenyl]-2,3-dihydro-benzo[1,4]dioxin-6-yl}-propionic acid methyl ester

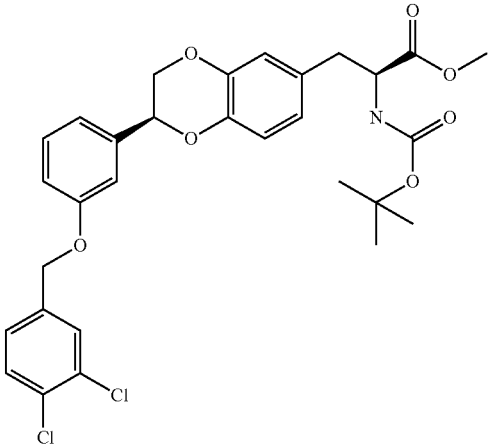 [SMILES: COC(=O)[C@H](Cc1ccc2c(c1)OC[C@H](c1cccc(OCc3ccc(Cl)c(Cl)c3)c1)O2)NC(=O)OC(C)(C)C]

(+)-1,2-bis((2S,5S)-2,5-Diethylphospholano)benzene (cyclooctadiene) rhodium(I) trifluoromethanesulfonate (0.22 g) was dissolved in 2 mL of DCM and added to a solution of 2-tert-butoxycarbonylamino-3-{(S)-2-[3-(3,4-dichloro-benzyloxy)-phenyl]-2,3-dihydro-benzo[1,4]-dioxin-6-yl}-acrylic acid methyl ester (1.8 g) in 20 mL EtOAc. The mixture was then degassed and flushed with hydrogen and stirred under hydrogen atmosphere (balloon) for 1 hour. The solvent was then evaporated and the residue was purified by silica gel flash chromatography (DCM to 5% EtOAC in DCM) to get pure product 1.7 g. $^1$H NMR (400 MHz, CDCl$_3$): 7.55 (d, 1H), 7.46 (d, 1H), 7.24-7.37 (m, 2H), 7.00-7.06 (m, 2H), 6.92-6.97 (m, 1H), 6.90 (d, 1H), 6.70 (d, 1H), 6.61-6.70 (m, 1H), 5.08 (m, 1H), 5.03 (d, 2H), 4.99 (d, 1H), 4.50-4.60 (m, 1H) 4.34 (m, 1H), 3.98 (m, 1H) 3.74 (s, 3H), 2.80-3.20 (m, 2H), 1.44 (s, 9H). LCMS (m/z): 589.

(3S,8S)-3-[3-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester

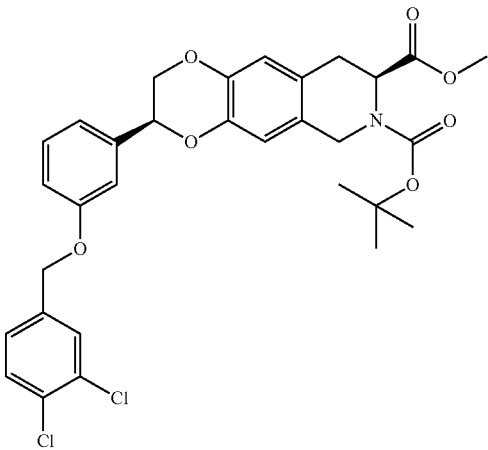 [SMILES: COC(=O)[C@@H]1Cc2cc3c(cc2CN1C(=O)OC(C)(C)C)O[C@@H](c1cccc(OCc2ccc(Cl)c(Cl)c2)c1)CO3]

(S)-2-tert-Butoxycarbonylamino-3-{(S)-2-[3-(3,4-dichloro-benzyloxy)-phenyl]-2,3-dihydro-benzo[1,4]dioxin-6-yl}-propionic acid methyl ester (1.7 g) was dissolved in 100 mL dry DCM and stirred on 0° C. bath. 10 mL of 4N HCl in dioxane was added and the mixture stirred at room temperature over 2 hours. The solvents were evaporated and the residue was evaporated from diethyl ether 2 times to get 1.5 g of residue. Then, 0.8 g of the residue was dissolved in 10 mL anhydrous dioxane, 6 mL of TFA:dioxane (1:1), and 170 mg paraformaldehyde were added while stirring. The reaction mixture was stirred at room temperature for 2 hours. The solvents were then evaporated and the residue was dissolved in 30 mL EtOAc and 10 mL of 2N Na$_2$CO$_3$ solution. Di-t-butyl dicarbonate (0.8 g) was taken in 4 mL EtOAC and added to the reaction mixture and stirred for 8 hours at room temperature. The layers were then separated and the organic layer was washed with brine, and then the solution was dried with Na$_2$SO$_4$ and evaporated. The residue was purified by silica gel flash chromatography (10% EtOAC in hexanes to 50% EtOAc in hexanes) to give 0.72 g of product. LCMS (m/z): 601.

(3S,8S)-3-[3-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester

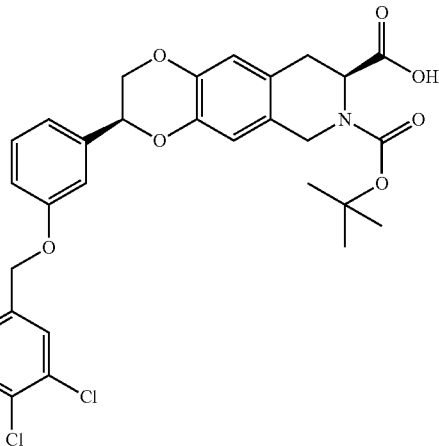

To a solution of (3S,8S)-3-[3-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester (0.72 g) in THF:MeOH (3:7, 10 mL) solution, 2 N LiOH solution (4 mL) was added and 0° C., and the resulting reaction mixture was stirred at room temperature for 10 hours. After completion of the reaction, 1N HCl (8 mL) was added to neutralize the base, extracted with ethyl acetate, organic layer was washed with water, brine, dried over sodium sulfate, and the solvent was removed under reduced pressure to afford the product (0.68 g). LCMS (m/z): 587.

(3S,8S)-3-[3-(3,4-Dichloro-benzyloxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester

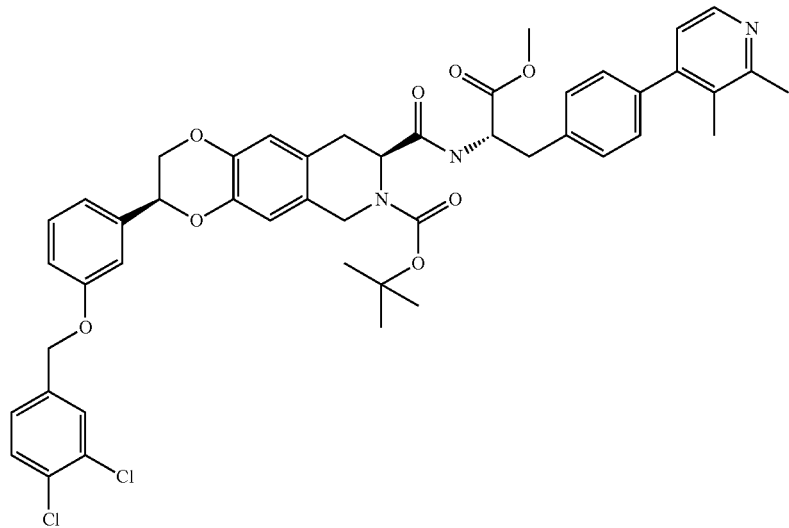 [SMILES: COC(=O)[C@H](Cc1ccc(-c2ccnc(C)c2C)cc1)NC(=O)[C@@H]1Cc2cc3c(cc2CN1C(=O)OC(C)(C)C)O[C@@H](c1cccc(OCc2ccc(Cl)c(Cl)c2)c1)CO3]

(3S,8S)-3-[3-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester (150 mg) was taken in 2 mL of anhydrous DCM and EDCl (64 mg), HOBT (47 mg) and (S)-2-amino-3-[4-(2,3-dimethyl-pyridin-4-yl)-phenyl]-propionic acid methyl ester dihydrochloride (91 mg) and stirred for 5 minutes. Reaction mixture was cooled to 0° C. and DIEA (164 mg) was added and reaction was stirred at room temperature for 2 hours. After the reaction is complete, it was purified by silica gel column chromatography (1:3 EtOAc/hexanes to 2% MeOH in 1:1 EtOAc/hexanes) (152 mg). LCMS (m/z): 853.

(S)-2-({(3S,8S)-3-[3-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester

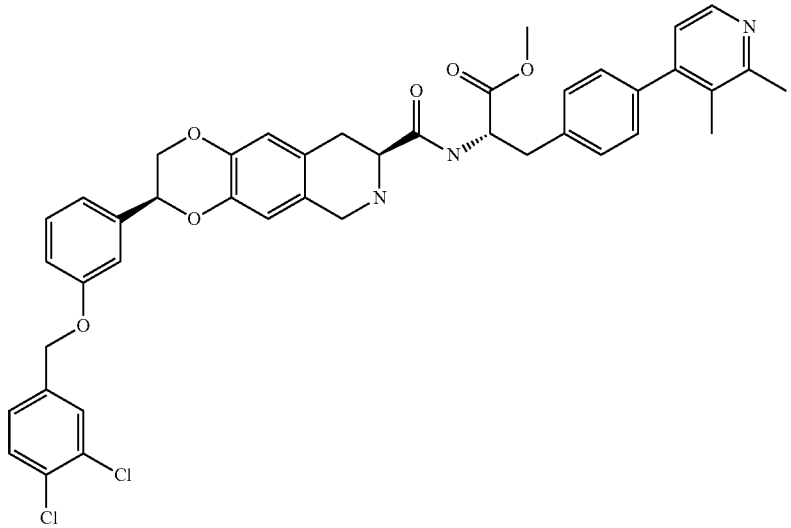 [SMILES: COC(=O)[C@H](Cc1ccc(-c2ccnc(C)c2C)cc1)NC(=O)[C@@H]1Cc2cc3c(cc2CN1)O[C@@H](c1cccc(OCc2ccc(Cl)c(Cl)c2)c1)CO3]

(3S,8S)-3-[3-(3,4-Dichloro-benzyloxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (152 mg) was taken in 3 mL anhydrous DCM and cooled 0° C., HCl (0.75 mL, 4N in dioxane) was added and stirred at room temperature for 1 hour. All volatiles are evaporated and the residue was suspended in a 2N $Na_2CO_3$ solution and then extracted with EtOAc. The ethyl acetate layer was separated and washed with brine, and then dried ($Na_2SO_4$). The solvent was evaporated (105 mg). LCMS (m/z): 753.

(3S,8S)-8-{(S)-2-[4-(2,3-Dimethyl-pyridin-4-yl)-phenyl]-1-methoxycarbonylethyl-carbamoyl}-3-(3-hydroxy-phenyl)-2,3,8,9-tetrahydro-6H-[1,4]dioxino[2,3-g]isoquinoline-7-carboxylic acid tert-butyl ester

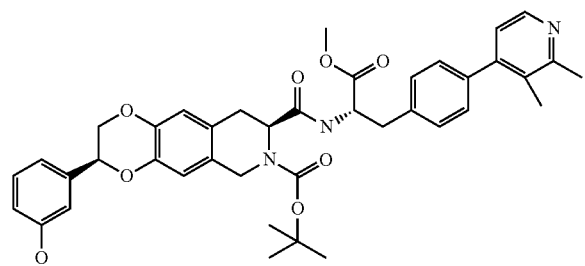 [SMILES: COC(=O)[C@H](Cc1ccc(-c2ccnc(C)c2C)cc1)NC(=O)[C@@H]1Cc2cc3c(cc2CN1C(=O)OC(C)(C)C)O[C@@H](c1cccc(O)c1)CO3]

(3S,8S)-3-[3-(3,4-Dichloro-benzyloxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (250 mg) was dissolved in 6 mL of EtOAc:MeOH (1:5) and Pd—C(30 mg, 10% by wt.) was added and stirred under a hydrogen atmosphere (balloon) for 4 hours. Triethylamine (0.3 mL) was added to the reaction mixture and stirred for 5 minutes. The catalyst was filtered and washed with MeOH. The filtrate was evaporated, and the residue was taken up in EtOAc (10 mL) and washed with water and brine, and then dried ($Na_2SO_4$), filtered, and evaporated to get (3S,8S)-8-{(S)-2-[4-(2,3-dimethyl-pyridin-4-yl)-phenyl]-1-methoxycarbonyl-ethylcarbamoyl}-3-(3-hydroxy-phenyl)-2,3,8,9-tetrahydro-6H-[1,4]dioxino-[2,3-g]isoquinoline-7-carboxylic acid tert-butyl ester (180 mg). LCMS (m/z): 695.

(S)-3-{(S)-2-[3-(3,4-Dichloro-benzyloxy)-phenyl]-2,3-dihydro-benzo[1,4]dioxin-6-yl}-2-(4-nitro-benzenesulfonylamino)-propionic acid methyl ester

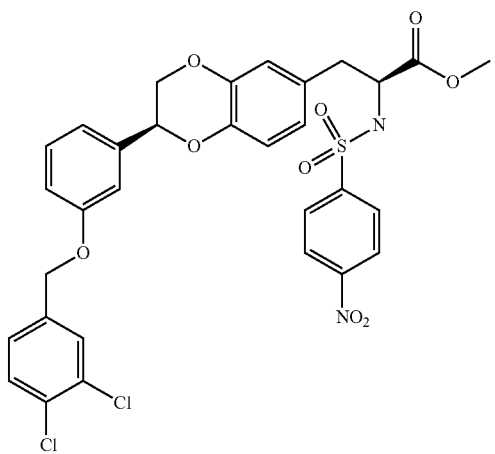 [SMILES: COC(=O)[C@H](Cc1ccc2c(c1)OC[C@H](c1cccc(OCc3ccc(Cl)c(Cl)c3)c1)O2)NS(=O)(=O)c1ccc([N+](=O)[O-])cc1]

(S)-2-Amino-3-{(S)-2-[3-(3,4-dichloro-benzyloxy)-phenyl]-2,3-dihydro benzo[1,4]dioxin-6-yl}-propionic acid methyl ester hydrochloride (0.35 g) was taken in 2 mL of EtOAc and cooled to 0° C., $NaHCO_3$ solution (1 mL) and 4-nitrobenzensulfonyl chloride (178 mg) were added and stirred for 10 minutes. Reaction was stirred at room temperature for 4 hours. EtOAc layer was seperated and washed with water and brine, and then dried ($Na_2SO_4$), filtered and evaporated. The residue was purified by silica gel column (10% EtOAc in hexanes to 50% EtOAc in hexanes) to get pure (S)-3-{(S)-2-[3-(3,4-dichloro-benzyloxy)-phenyl]-2,3-dihydro-benzo[1,4]dioxin-6-yl}-2-(4-nitro-benzenesulfonylamino)-propionic acid methyl ester (0.37 g). $^1$H NMR (400 MHz, acetone-$d_6$): 8.33 (m, 2H), 7.89 (m, 2H), 7.73 (d, 1H), 7.62 (d, 1H), 7.37-7.53 (m, 3H), 7.04-7.21 (m, 3H), 6.64-6.72 (m, 3H), 5.22 (s, 2H), 5.09 (m, 1H), 4.35 (m, 1H), 4.21 (m, 1H), 3.97 (m, 1H), 3.61 (s, 3H), 3.03 (m, 1H), 2.76 (m, 1H).

(S)-3-{(S)-2-[3-(3,4-Dichloro-benzyloxy)-phenyl]-2,3-dihydro-benzo[1,4]dioxin-6-yl}-2-((S)-1-phenyl-propylamino)-propionic acid methyl ester

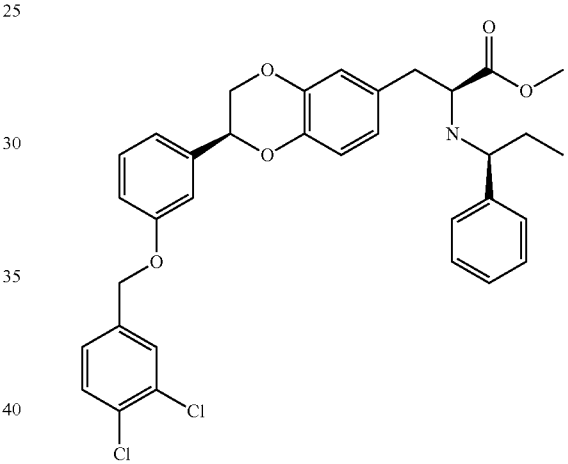

(S)-3-{(S)-2-[3-(3,4-Dichloro-benzyloxy)-phenyl]-2,3-dihydro-benzo[1,4]dioxin-6-yl}-2-(4-nitro-benzenesulfonylamino)-propionic acid methyl ester (0.37 g) was dissolved in 2 mL dry THF and triphenylphosphine (0.29 g) and (R)-(+)-1-phenyl-1-propanol (0.15 g) were added. The mixture was stirred at 0° C. for 10 min, then DIAD 933 μL (0.22 g, 1.1 mmol) was added over 2 minutes. The reaction stirred at room temperature for 5 hours, then was evaporated. The residue was purified by silica gel flash chromatography (9:1 to 7:3 hexanes/EtOAc) to give (S)-3-{(S)-2-[3-(3,4-Dichloro-benzyloxy)-phenyl]-2,3-dihydro-benzo[1,4]dioxin-6-yl}-2-[(4-nitro-benzenesulfonyl)-((S)-1-phenyl-propyl)-amino]-propionic acid methyl ester (0.42 g). This material was dissolved in DMF (0.7 mL), and then mercapto acetic acid (0.15 g) and DBU (0.48 g) were added and stirred at room temperature for 2 hours. The reaction was quenched by addition of $NaHCO_3$ solution (4 mL) and product was extracted with ether. The ether layer was washed with water and brine, and then dried ($Na_2SO_4$), filtered, and evaporated. The residue was purified by silica gel column (5% EtOAc in hexanes to 15% EtOAc in hexanes) to get pure (S)-3-{(S)-2-[3-(3,4-dichloro-benzyloxy)-phenyl]-2,3-dihydro-benzo[1,4]dioxin-6-yl}-2-((S)-1-phenyl-propylamino)-propionic acid methyl ester (0.2 g). LCMS (m/z): 607.

(3S,8S)-3-[3-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid methyl ester

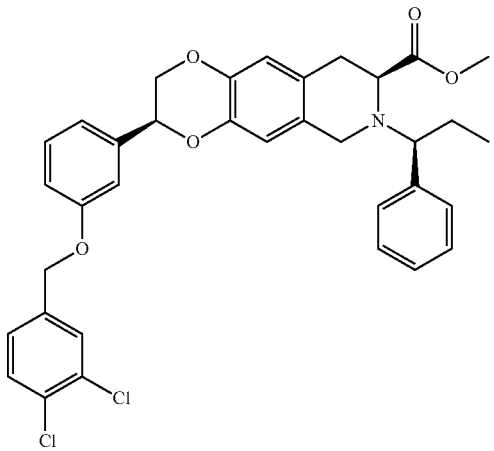 [SMILES: CC[C@@H](c1ccccc1)N1Cc2cc3c(cc2C[C@H]1C(=O)OC)OC[C@H](c1cccc(OCc2ccc(Cl)c(Cl)c2)c1)O3]

(S)-3-{(S)-2-[3-(3,4-Dichloro-benzyloxy)-phenyl]-2,3-dihydro-benzo[1,4]dioxin-6-yl}-2-((S)-1-phenyl-propylamino)-propionic acid methyl ester (0.2 g) was dissolved in 8 mL dry dioxane and cooled to 0° C.; paraformaldehyde (50 mg) and 2 mL trifluoroacetic acid were added. The reaction was stirred for 12 hours at room temperature and neutralized to pH 7 with aqueous NaHCO₃, then the mixture was extracted with EtOAc. The organic extract was washed with water and brine, and then dried over Na₂SO₄, filtered and evaporated. The residue was purified by silica gel flash chromatography (9:1 to 7:3 hexanes/EtOAc) to get (3S,8S)-3-[3-(3,4-dichloro-benzyloxy)-phenyl]-7-((S)-1-phenyl-propyl)-2,3,6,7,8,9-hexahydro-[1,4]dioxino[2,3-g]isoquinoline-8-carboxylic acid methyl ester (0.14 g). LCMS (m/z): 619.

(3S,8S)-3-[3-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid

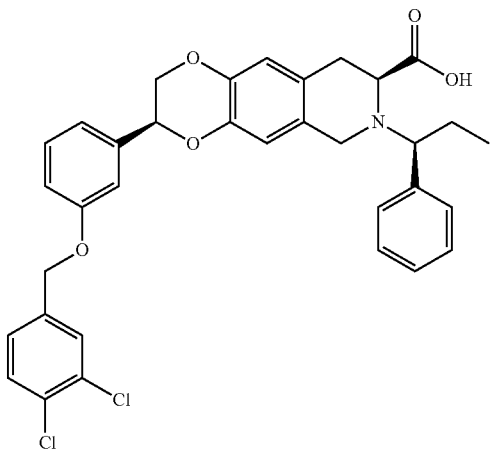 [SMILES: CC[C@@H](c1ccccc1)N1Cc2cc3c(cc2C[C@H]1C(=O)O)OC[C@H](c1cccc(OCc2ccc(Cl)c(Cl)c2)c1)O3]

(3S,8S)-3-[3-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid methyl ester (0.14 g, 0.22 mmol) was taken in 1 mL of MeOH:THF (4:1) and cooled to 0° C.; KOH (0.54 mL, 2.5 N) was added and stirred at room temperature for 12 hours. KOH (0.36 mL, 2.5 N) was added and stirred for 24 hours. Then, HCl (2.4 mL, 1 N) was added to the reaction and the product was extracted with EtOAc. The ethyl acetate layer was separated and washed with water and brine, and then dried over Na₂SO₄, filtered, and evaporated to get (3S,8S)-3-[3-(3,4-dichloro-benzyloxy)-phenyl]-7-((S)-1-phenyl-propyl)-2,3,6,7,8,9-hexahydro-[1,4]dioxino[2,3-g]isoquinoline-8-carboxylic acid (0.11 g). LCMS (m/z): 605.

(S)-2-tert-Butoxycarbonylamino-3-[4-(2,3-dimethyl-1-oxy-pyridin-4-yloxy)-phenyl]-propionic acid methyl ester

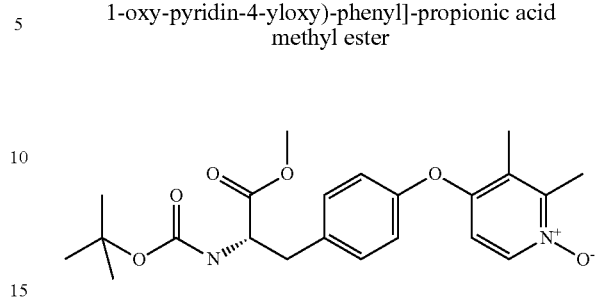

To a solution of Boc-L-Tyr-OMe (36.5 g) in anhydrous DMF (100 mL) was added potassium carbonate (34.1 g) and 4-nitro-2,3-lutidine N-oxide (13.85 g) and stirred for 7 days at room temperature. Solids were filtered from the reaction mixture and filtrate was added to water (300 mL) and acetic acid (20 mL) and stirred for 10 minutes; the product was extracted with ethyl acetate (3×200 mL). The ethyl acetate layer was separated and washed with water and brine, and then dried over Na₂SO₄, filtered, and evaporated. The residue was purified by silica gel flash chromatography (DCM to 10% MeOH in DCM) to get (S)-2-tert-butoxycarbonylamino-3-[4-(2,3-dimethyl-1-oxy-pyridin-4-yloxy)-phenyl]-propionic acid methyl ester (1.3 g). LCMS (m/z): 418.

(S)-2-tert-Butoxycarbonylamino-3-[4-(2,3-dimethyl-pyridin-4-yloxy)-phenyl]-propionic acid methyl ester

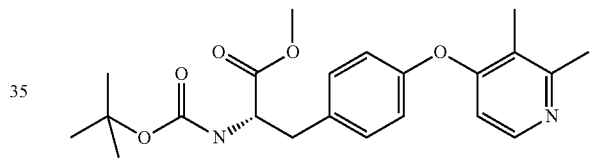

(S)-2-tert-Butoxycarbonylamino-3-[4-(2,3-dimethyl-1-oxy-pyridin-4-yloxy)-phenyl]-propionic acid methyl ester (1.3 g) was taken in acetic acid (7 mL) heated to reflux, and Zn powder (1.2 g) was added in three portions and refluxed for 1 hour. The reaction was cooled to room temperature and Zn powder was filtered and washed with ethyl acetate; the combined filtrate was evaporated. The residue was taken up in ethyl acetate (30 mL) and washed with water and brine, and then dried over Na₂SO₄, filtered, and evaporated. The residue was purified by silica gel flash chromatography (DCM to 50% EtOAc in DCM) to get (S)-2-tert-butoxycarbonylamino-3-[4-(2,3-dimethyl-pyridin-4-yloxy)-phenyl]-propionic acid methyl ester (0.9 g). LCMS (m/z): 402.

(S)-2-Amino-3-[4-(2,3-dimethyl-pyridin-4-yloxy)-phenyl]-propionic acid methyl ester dihydrochloride

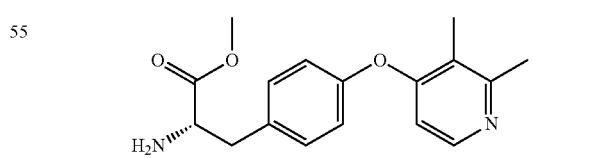

(S)-2-tert-Butoxycarbonylamino-3-[4-(2,3-dimethyl-pyridin-4-yloxy)-phenyl]-propionic acid methyl ester (0.2 g) was taken in 4 mL of DCM and cooled to 0° C. and HCl (1 mL, 4N in dioxane) was added and reaction was stirred at room temperature for 2 hours. All volatiles were evaporated and residue was triturated with DCM/hexanes (0.17 g). LCMS (m/z): 302.

(3S,8S)-3-[3-(3,4-Dichloro-benzyloxy)-phenyl]-8-{(S)-2-[4-(2,3-dimethyl-pyridin-4-yloxy)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester

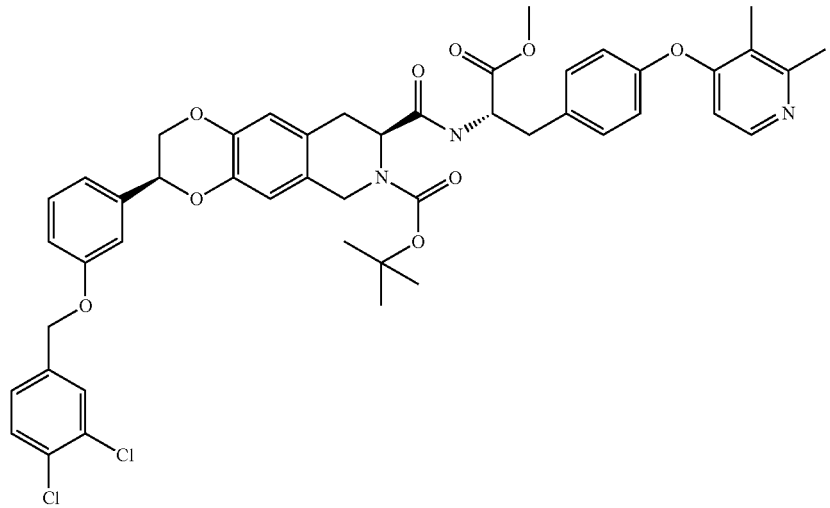

(3S,8S)-3-[3-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester (80 mg) was taken up in 2 mL of anhydrous DCM and EDCl (34 mg), HOBT (25 mg) and (S)-2-amino-3-[4-(2,3-dimethyl-pyridin-4-yloxy)-phenyl]-propionic acid methyl ester dihydrochloride (50 mg) were added and stirred for 5 minutes. The reaction mixture was cooled to 0° C. and DIEA (85 mg) was added and reaction was stirred at room temperature for 2 hours. After the reaction was complete, it was purified by column chromatography (silica gel; 1:3 ethyl acetate/hexanes to 4% MeOH in 1:1 ethyl acetate/hexanes) (70 mg). LCMS (m/z): 869.

(3S,8S)-3-(4-Cyclohexylmethoxy-phenyl)-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (3S,8S)-3-(4-Cyclohexylmethoxy-phenyl)-2,3,8,9-tetrahydro-6H-[1,4]dioxino[2,3-g]isoquinoline-7,8-dicarboxylic acid 7-tert-butyl ester (72 mg), EDCl (33 mg), HOBt (24 mg), and (S)-2-amino-3-[4-(2,3-dimethyl-pyridin-4-yl)-phenyl]-propionic acid methyl ester bis hydrochloride (59 mg) were suspended in 3 mL DCM and NMM (0.067 mL) added. The mixture was stirred at room temperature for 3 hours and the mixture was directly purified over silica (hexanes to 1:1 hexanes/EtOAc to 1:1 hexanes/EtOAc+1% MeOH) to give (3S,8S)-3-(4-cyclohexylmethoxy-phenyl)-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (86 mg). LCMS: (m/z) 791.

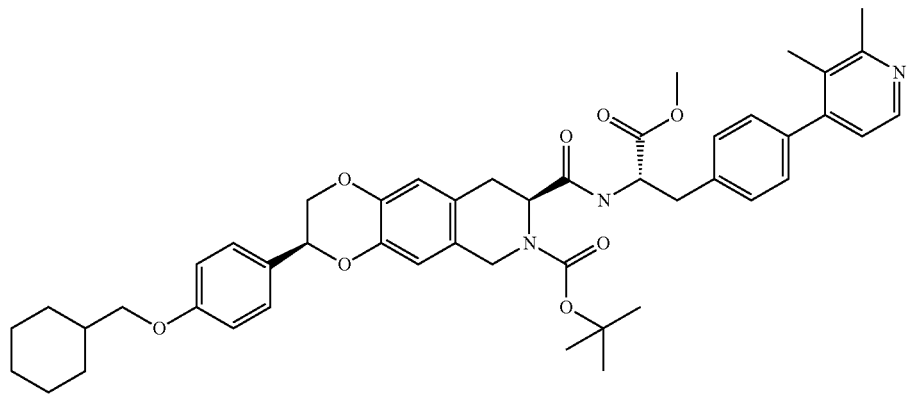 [SMILES: COC(=O)[C@H](Cc1ccc(-c2ccnc(C)c2C)cc1)NC(=O)[C@@H]1Cc2cc3c(cc2CN1C(=O)OC(C)(C)C)O[C@@H](c1ccc(OCC2CCCCC2)cc1)CO3]

(S)-2-{[(3S,8S)-3-(4-Cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester bis hydrochloride

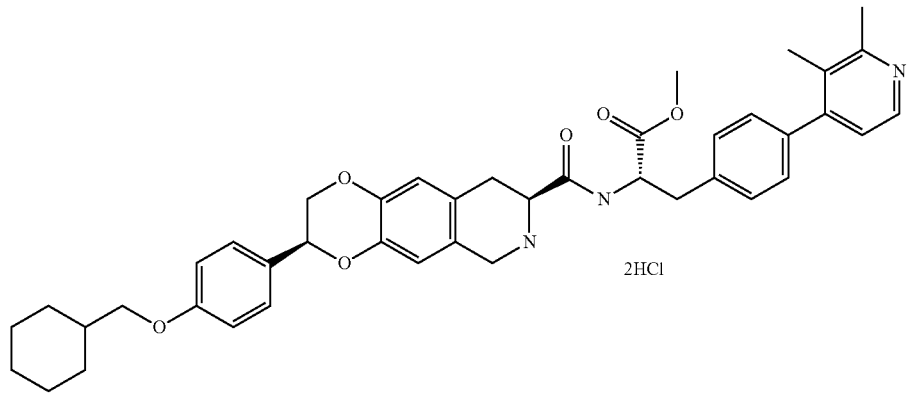 [SMILES: COC(=O)[C@H](Cc1ccc(-c2ccnc(C)c2C)cc1)NC(=O)[C@@H]1Cc2cc3c(cc2CN1)O[C@@H](c1ccc(OCC2CCCCC2)cc1)CO3]

(3S,8S)-3-(4-Cyclohexylmethoxy-phenyl)-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (86 mg) was dissolved in 3 mL DCM and 3 mL 4 N HCl (dioxane) was added. The mixture stirred at room temperature for 3 hours, and the mixture was concentrated. DCM was added and the mixture was again concentrated. The solid was triturated with diethyl ether and dried under vacuum to provide (S)-2-{[(3S,8S)-3-(4-cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester bis hydrochloride (71 mg). LCMS: (m/z) 691.

3-{(R)-2-[4-(3,4-Dichloro-benzyloxy)-phenyl]-2-hydroxy-ethoxy}-4-fluoro-benzonitrile

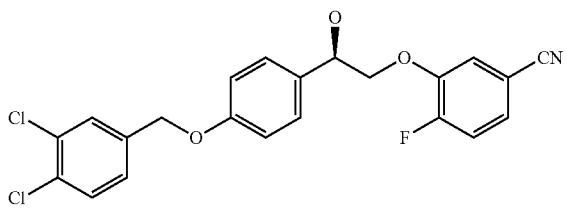 [SMILES: N#Cc1ccc(F)c(OC[C@H](O)c2ccc(OCc3ccc(Cl)c(Cl)c3)cc2)c1]

100 mL dry THF, 75 mL of 1M (R)-CBS reagent in toluene, and 26.7 mL borane-diethylaniline complex were stirred together 20 min at room temperature. 3-{2-[4-(3,4-Dichloro-benzyloxy)-phenyl]-2-oxo-ethoxy}-4-fluoro-benzonitrile (31.7 g) in 700 mL dry THF was then added through an addition funnel at rt over 30 minutes. The mixture stirred for 30 min, then was quenched by slow addition of 100 mL MeOH. After gas evolution ceased the mixture was evaporated to a yellow oil. The oil was dissolved in 200 mL ethyl acetate and washed with water and brine. The organic layer was dried over sodium sulfate and concentrated. The residue was stirred with hexanes and the hexanes layer removed. The resulting residue was purified over silica gel (DCM). $^1$H NMR (400 MHz, CDCl$_3$): 7.54 (d, 1H), 7.46 (d, 1H), 7.38 (m, 2H), 7.3-7.15 (m, 4H), 6.97 (m, 2H), 5.13 (m, 1H), 5.03 (s, 2H), 4.10 (m, 2H), 2.64 (d, 1H).

(R)-2-[4-(3,4-Dichloro-benzyloxy)-phenyl]-2,3-dihydro-benzo[1,4]dioxine-6-carbonitrile

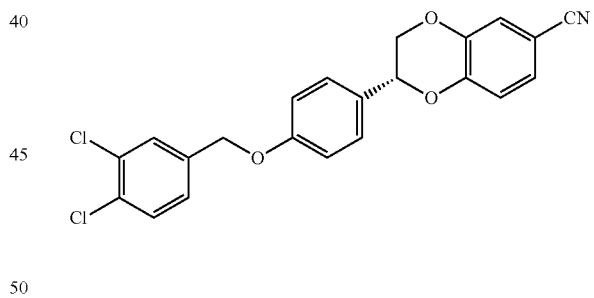

3-{(R)-2-[4-(3,4-Dichloro-benzyloxy)-phenyl]-2-hydroxy-ethoxy}-4-fluoro-benzonitrile (10.2 g) was dissolved in 108 mL NMP-diglyme (1:9) under nitrogen and heated to 150° C. internal temperature. A suspension of sodium hydride (1130 mg of 60% NaH in mineral oil) in 10 mL NMP-diglyme (1:9) was added all at once via syringe while stirring. After 2 minutes, the reaction was removed from heating and cooled, then poured onto saturated ammonium chloride and EtOAc. The layers were separated and the organic layer washed 3 times with 1 N HCl and dried over Na$_2$SO$_4$. The residue was purified by silica gel flash chromatography (DCM-hexanes 1:1 to DCM). The residue was crystallized from refluxing MeOH/DCM (about 3:1), to give 5.2 g of desired product. $^1$H NMR (400 MHz, CDCl$_3$): 7.53 (d, 1H), 7.45 (d, 1H), 7.34 (m, 2H), 7.27-7.24 (m, 1H), 7.22 (d, 1H) 7.18 (m, 1H), 7.0 (m, 3H), 5.12 (m, 1H), 5.04 (s, 2H), 4.37 (m, 1H), 4.03 (m, 1H).

(R)-2-[4-(3,4-Dichloro-benzyloxy)-phenyl]-2,3-dihydro-benzo[1,4]dioxine-6-carbaldehyde

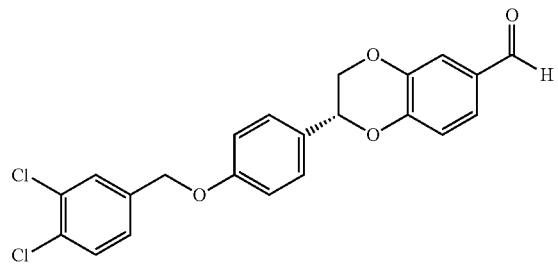 [SMILES: O=Cc1ccc2c(c1)OC[C@@H](c1ccc(OCc3ccc(Cl)c(Cl)c3)cc1)O2]

(R)-2-[4-(3,4-Dichloro-benzyloxy)-phenyl]-2,3-dihydro-benzo[1,4]dioxine-6-carbonitrile (5.2 g) was dissolved in 200 mL dry toluene and cooled to 0° C. under nitrogen. 25.2 mL of a 1M solution of diisobutylaluminum hydride in toluene was added over 10 min. The reaction stirred at 0° C. for 10 minutes, and was quenched by slow addition of 20 mL HOAc. 300 mL of water was added and the mixture stirred at room temperature for 2 hours. The aqueous layer was drained on the organic layer washed 3 times with 10% sodium carbonate. The organic layer was dried over Na$_2$SO$_4$ and evaporated. The residue was purified by silica gel flash chromatography (hexanes to 8:2 hexanes/EtOAc) to give 5.0 g of product. $^1$H NMR (400 MHz, CDCl$_3$): 9.85 (s, 1H), 7.54 (d, 1H), 7.4 (m, 3H), 7.35 (m, 2H), 7.25 (m, 1H), 7.07 (d, 1H), 7.0 (m, 2H), 5.15 (m, 1H), 5.04 (s, 2H), 4.38 (m, 1H), 4.05 (m, 1H).

2-tert-Butoxycarbonylamino-3-{(R)-2-[4-(3,4-dichloro-benzyloxy)-phenyl]-2,3-dihydro-benzo[1,4]dioxin-6-yl}-acrylic acid methyl ester

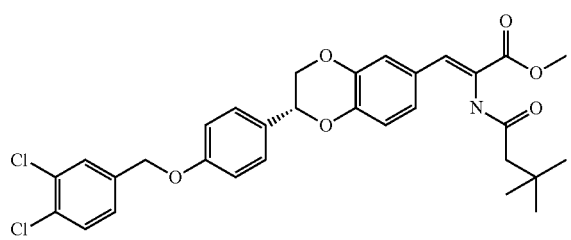 [SMILES: COC(=O)/C(=C/c1ccc2c(c1)OC[C@@H](c1ccc(OCc3ccc(Cl)c(Cl)c3)cc1)O2)NC(=O)CC(C)(C)C]

(R)-2-[4-(3,4-Dichloro-benzyloxy)-phenyl]-2,3-dihydro-benzo[1,4]dioxine-6-carbaldehyde (5.0 g) was dissolved in 25 mL dry DCM under nitrogen at rt and 3.6 mL DBU was added by syringe. 3.8 g of Boc-phosphonoglycine trimethyl ester in 10 mL dry DCM was added by syringe dropwise and the mixture stirred at rt for 14 hours. The residue was purified over silica (hexanes to 8:2 hexanes/EtOAc) 4.9 g desired product after drying under vacuum. $^1$H NMR (400 MHz, CDCl$_3$): 7.54 (d, 1H), 7.46 (d, 1H), 7.35 (m, 2H), 7.27 (m, 1H), 7.22-7.19 (m, 2H), 7.11 (m, 1H), 6.98 (m, 2H), 6.93 (d, 1H), 5.10 (m, 1H), 5.04 (s, 2H), 4.32 (m, 1H), 4.02 (m, 1H), 3.84 (s, 3H), 1.44 (s, 9H).

(S)-2-tert-Butoxycarbonylamino-3-{(R)-2-[4-(3,4-dichloro-benzyloxy)-phenyl]-2,3-dihydro-benzo[1,4]dioxin-6-yl}-propionic acid methyl ester

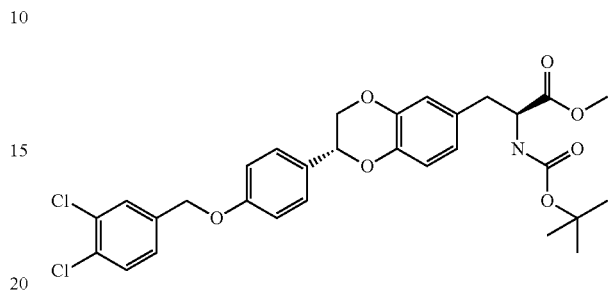

2-tert-Butoxycarbonylamino-3-{(R)-2-[4-(3,4-dichloro-benzyloxy)-phenyl]-2,3-dihydro-benzo[1,4]dioxin-6-yl}-acrylic acid methyl ester (4.9 g) was suspended in 300 mL EtOAc. 400 mg (+)-1,2-bis((2S,5S)-2,5-diethylphospholano)benzene(cyclooctadiene)rhodium(I) trifluoromethanesulfonate in 30 mL DCM was added. The mixture was then degassed and a hydrogen balloon was added. The mixture was stirred at room temperature for 2 hours and the solvent was evaporated. The residue was purified by silica gel flash chromatography (hexanes to 8:2 hexanes/EtOAc) to give 4.8 g after drying. $^1$H NMR (400 MHz, CDCl$_3$): 7.54 (d, 1H), 7.46 (d, 1H), 7.34 (m, 2H), 7.24-7.28 (m, 1H), 6.98 (m, 2H), 6.87 (d, 1H), 6.69 (d, 1H), 6.62 (m, 1H), 5.07-4.96 (m, 4H), 4.54 (m, 1H), 4.30 (m, 1H), 4.0 (m, 1H), 3.74 (s, 3H), 3.0 (m, 2H), 1.43 (s, 9H).

(S)-2-Amino-3-{(R)-2-[4-(3,4-dichloro-benzyloxy)-phenyl]-2,3-dihydro-benzo[1,4]dioxin-6-yl}-propionic acid methyl ester hydrochloride

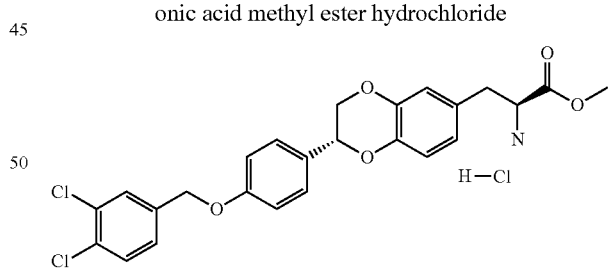

(S)-2-tert-Butoxycarbonylamino-3-{(R)-2-[4-(3,4-dichloro-benzyloxy)-phenyl]-2,3-dihydro-benzo[1,4]dioxin-6-yl}-propionic acid methyl ester (3.0 g) was dissolved in 60 mL DCM. 25 mL of 4N HCl (in dioxane) was added and the mixture stirred at room temperature for 2.5 hours. The mixture was concentrated and DCM added and mixture concentrated again. The resulting solid was dried under vacuum to provide 2.6 g. LCMS: m/z 489.

381

(3R,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester

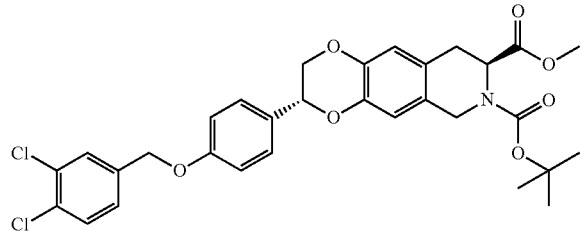 [SMILES: COC(=O)[C@@H]1Cc2cc3c(cc2CN1C(=O)OC(C)(C)C)O[C@H](c1ccc(OCc2ccc(Cl)c(Cl)c2)cc1)CO3]

(S)-2-Amino-3-{(R)-2-[4-(3,4-dichloro-benzyloxy)-phenyl]-2,3-dihydro-benzo[1,4]dioxin-6-yl}-propionic acid methyl ester hydrochloride (1.4 g) was dissolved in 100 mL dry dioxane and 160 mg paraformaldehyde was added while stirring. Then 25 mL trifluoroacetic acid was added and the mixture was stirred for 4 hours. The mixture was diluted with EtOAc and neutralized with 10% sodium carbonate. Saturated sodium bicarbonate was added to the organic layer and 1.2 g di-t-butyl dicarbonate was added and stirred 6 hours at room temperature. The layers were then separated and the organic layer was dried with $Na_2SO_4$, and evaporated. The residue was purified by silica gel flash chromatography (hexanes to 7:3 hexanes/EtOAc) to give 1.0 g after drying under vacuum. LCMS: m/z 601.

382

(3R,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester

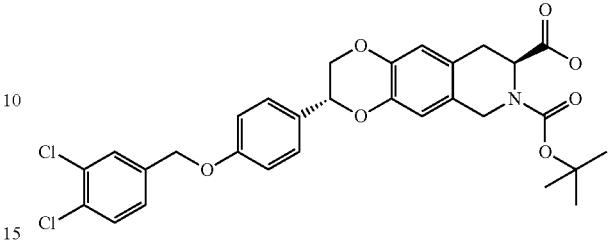

(3R,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester (1.0 g) was dissolved in 60 mL of THF-MeOH (1:4) and the mixture cooled on an ice bath. 2 N aqueous LiOH (5 eq.) was added and the mixture was stirred on ice for 15 minutes and then at room temperature for 14 hours. The pH of the mixture was adjusted to about 2 with 1N HCl and extracted with EtOAc. The organic layer was washed with brine, dried over sodium sulfate and concentrated. DCM was added and mixture was again concentrated (900 mg). LCMS: m/z 587.

(3R,8S)-3-[4-(3,4-Dichloro-benzyloxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester

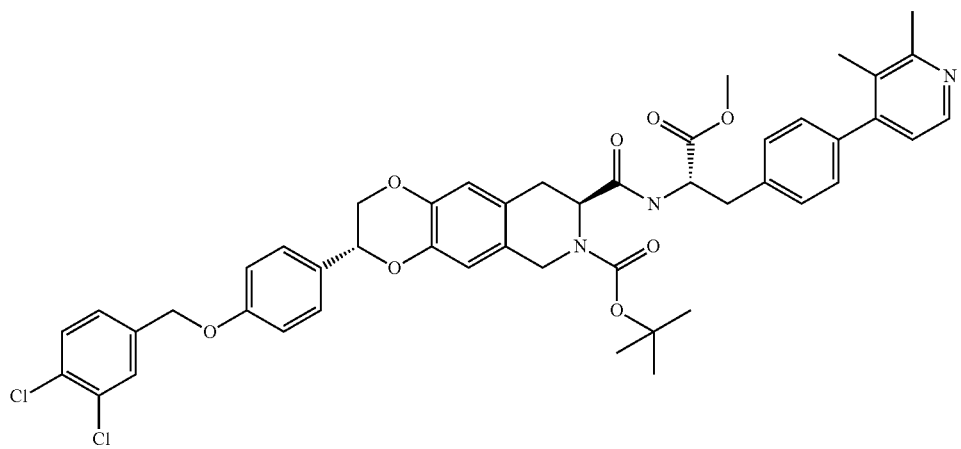 [SMILES: COC(=O)[C@H](Cc1ccc(-c2ccnc(C)c2C)cc1)NC(=O)[C@@H]1Cc2cc3c(cc2CN1C(=O)OC(C)(C)C)O[C@H](c1ccc(OCc2ccc(Cl)c(Cl)c2)cc1)CO3]

(3R,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester (260 mg), (S)-2-amino-3-[4-(2,3-dimethyl-pyridin-4-yl)-phenyl]-propionic acid methyl ester bis hydrochloride (190 mg), EDC (106 mg), and HOBt (78 mg) were suspended in 2 mL DCM and NMM (0.214 mL) added. The resulting mixture stirred at room temperature for 4 hours and loaded directly onto silica. The residue was purified by silica gel flash chromatography (hexanes to 1:1 hexanes/EtOAc to 1:1 hexanes/EtOAc+1% MeOH) to give 320 mg after drying under vacuum. LCMS: m/z 853.

(S)-2-({(3R,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester

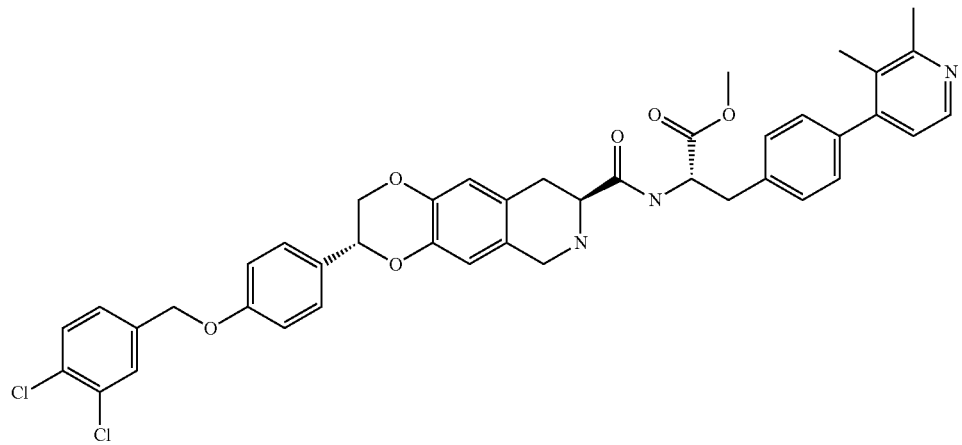 [SMILES: COC(=O)[C@H](Cc1ccc(-c2ccnc(C)c2C)cc1)NC(=O)[C@@H]1Cc2cc3c(cc2CN1)O[C@H](c1ccc(OCc2ccc(Cl)c(Cl)c2)cc1)CO3]

(3R,8S)-3-[4-(3,4-Dichloro-benzyloxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]-isoquinoline-7-carboxylic acid tert-butyl ester (300 mg) was dissolved in 15 mL DCM and 7.5 mL 4N HCl (in dioxane) added. The reaction was stirred at room temperature for 2.5 hours, DCM was added and mixture was concentrated. The solid was suspended in EtOAc-THF (9:1) and washed with a 10% sodium carbonate solution. The organic layer was washed with brine, nd dried over sodium sulfate and concentrated. DCM added and the mixture concentrated to provide 0.2 g of the product. LCMS: m/z 753.

(S)-3-{(R)-2-[4-(3,4-Dichloro-benzyloxy)-phenyl]-2,3-dihydro-benzo[1,4]dioxin-6-yl}-2-(4-nitro-benzenesulfonylamino)-propionic acid methyl ester

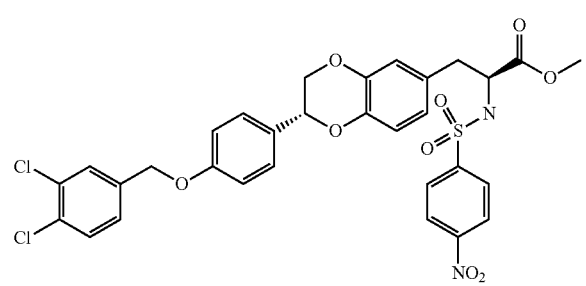 [SMILES: COC(=O)[C@H](Cc1ccc2c(c1)OC[C@@H](c1ccc(OCc3ccc(Cl)c(Cl)c3)cc1)O2)NS(=O)(=O)c1ccc([N+](=O)[O-])cc1]

(S)-2-Amino-3-{(R)-2-[4-(3,4-dichloro-benzyloxy)-phenyl]-2,3-dihydro-benzo[1,4]dioxin-6-yl}-propionic acid methyl ester hydrochloride (1.2 g) was dissolved in 100 mL EtOAc and 100 mL saturated aqueous $NaHCO_3$ and 1.0 g p-nitrobenzenesulfonyl chloride was added. After stirring at room temperature for 2 hours, the layers were separated and the organic layer was dried over $Na_2SO_4$ and evaporated. The residue was purified by silica gel flash chromatography (hexanes to 7:3 hexanes/EtOAc) to give 1.7 g desired product after drying. $^1$H NMR (400 MHz, 8.27 (m, 2H), 7.89 (m, 2H), 7.54 (d, 1H), 7.45 (d, 1H), 7.35 (m, 2H), 7.28-7.24 (m, 1H), 7.20 (m, 2H), 6.81 (m, 1H), 6.56 (m, 2H) 5.26 (m, 1H), 5.02 (s, 2H), 4.99 (m, 1H), 4.26 (m, 2H), 3.95 (m, 1H), 3.66 (s, 3H), 3.05-2.85 (m, 2H).

(S)-3-{(R)-2-[4-(3,4-Dichloro-benzyloxy)-phenyl]-2,3-dihydro-benzo[1,4]dioxin-6-yl}-2-((S)-1-phenyl-propylamino)-propionic acid methyl ester

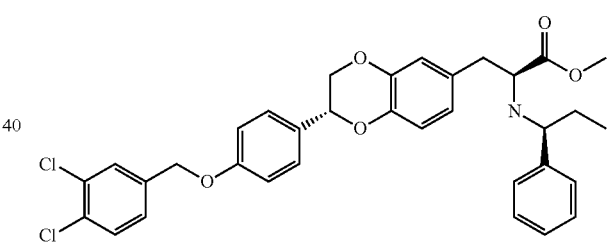

(S)-3-{(R)-2-[4-(3,4-Dichloro-benzyloxy)-phenyl]-2,3-dihydro-benzo[1,4]dioxin-6-yl}-2-(4-nitro-benzenesulfonylamino)-propionic acid methyl ester (1.7 g) was dissolved in 10 mL dry THF and 1320 mg triphenylphosphine and 691 µL (R)-(+)-1-phenyl-1-propanol were added. The mixture was stirred at 0° C. for 10 minutes, then 992 µL DIAD was added dropwise. The reaction was stirred at room temperature for 3 hours and was evaporated. The residue was purified by silica gel flash chromatography (hexanes to 8:2 hexanes/EtOAc). The resulting residue was dissolved in 20 mL dry DMF, then 526 µL mercaptoacetic acid and 2.5 mL DBU were added at room temperature. The reaction was stirred for 30 minutes and was partitioned between saturated aqueous $NaHCO_3$ and diethyl ether. The aqueous layer was washed again with diethyl ether and the organic layers were combined. The organic layer was washed with aqueous $NaHCO_3$, dried over $Na_2SO_4$ and evaporated. The residue was purified by silica gel flash chromatography (hexanes to 8:2 hexanes/EtOAc (first column)) and (hexanes to 1:1 DCM-hexanes to DCM to 9:1 DCM-EtOAc (second column)) to give 1.05 g of the product after drying.

¹H NMR (400 MHz, CDCl₃): 7.54 (d, 1H), 7.45 (d, 1H), 7.35 (m, 2H), 7.27-7.19 (m, 4H), 7.12 (m, 2H), 6.98 (m, 2H), 6.83 (d, 1H), 6.66 (d, 1H), 6.58 (m, 1H), 5.12-5.08 (m, 3H), 4.30 (m, 1H), 4.00 (m, 1H), 3.66 (s, 3H), 3.42 (m, 1H), 3.23 (m, 1H), 2.77 (m, 2H), 1.7-1.5 (m, 2H), 0.78 (t, 3H). LCMS: m/z 607.

(3R,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid methyl ester

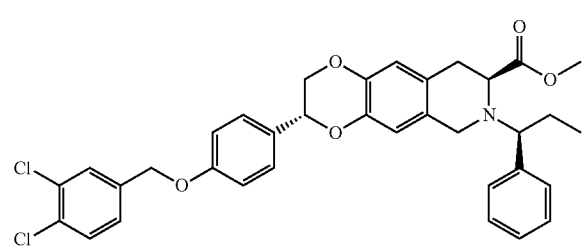 [SMILES: CC[C@@H](c1ccccc1)N1Cc2cc3c(cc2C[C@H]1C(=O)OC)OC[C@@H](c1ccc(OCc2ccc(Cl)c(Cl)c2)cc1)O3]

(S)-3-{(R)-2-[4-(3,4-Dichloro-benzyloxy)-phenyl]-2,3-dihydro-benzo[1,4]dioxin-6-yl}-2-((S)-1-phenyl-propylamino)-propionic acid methyl ester (1.0 g) was dissolved in 37 mL dry dioxane and 149 mg paraformaldehyde added. 30 mL dry dioxane and 17 mL trifluoroacetic acid were mixed, cooled on ice and added to the reaction mixture. The reaction was stirred for 20 hours at room temperature and diluted with EtOAc. The oranic layer was washed with 10% sodium, dried over Na₂SO₄ and evaporated. The residue was purified by silica gel flash chromatography (DCM+0.2% TEA) to give 934 mg of product after drying. ¹H NMR (400 MHz, acetone-d₆): 7.71 (d, 1H), 7.61 (d, 1H), 7.50-7.41 (m, 3H), 7.38-7.26 (m, 5H), 7.09 (m, 2H), 6.67 (s, 1H), 6.60 (s, 1H), 5.19 (s, 2H), 5.10 (m, 1H), 4.32 (m, 1H), 4.12 (m, 2H), 4.01 (m, 1H), 3.92 (m, 1H), 3.59 (m, 1H), 3.51 (s, 3H), 2.97-2.78 (m, 2H), 2.16 (m, 1H), 1.68 (m, 1H), 0.66 (t, 3H).

(3R,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid

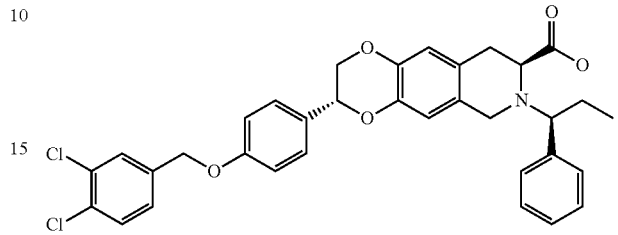

(3R,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid methyl ester (934 mg) was dissolved in 120 mL of THF-MeOH (1-4) and 9 mL KOH was added over 1 hour. The resulting mixture stirred at room temperature for 4 days. The pH was adjusted to about 7 with 1 N HCl and brine and EtOAc added. The organic solution was dried over Na₂SO₄ and evaporated. The residue was purified by silica gel flash chromatography (DCM-MeOH 99.5:0.5 to DCM-MeOH 95:5) to give 0.502 g of product after drying. LCMS: m/z 605.

(S)-2-({(3S,8S)-3-[4-(3,4-Dichloro-benzyloxy)-phenyl]-2,3,6,7,8,9-hexahydro-[1,4]dioxino-[2,3-g]isoquinoline-8-carbonyl}-amino)-3-[4-(2,3-dimethyl-pyridin-4-yl)-phenyl]-propionic acid methyl ester

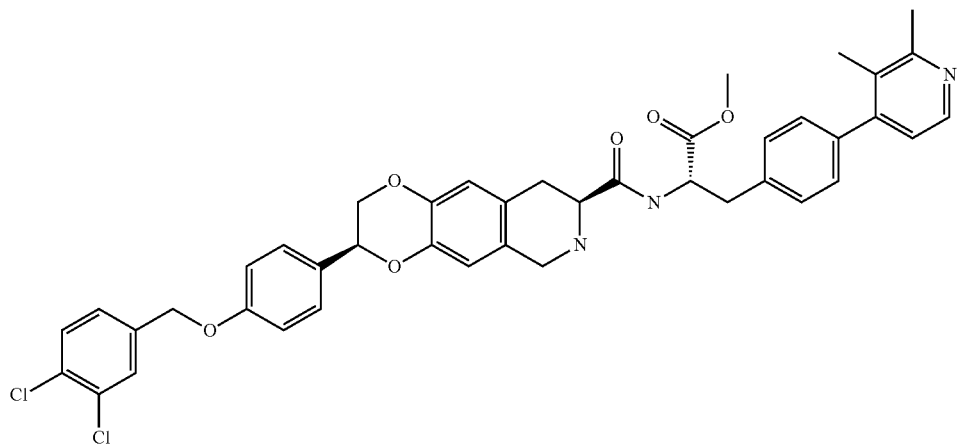 [SMILES: COC(=O)[C@H](Cc1ccc(-c2ccnc(C)c2C)cc1)NC(=O)[C@@H]1Cc2cc3c(cc2CN1)O[C@@H](c1ccc(OCc2ccc(Cl)c(Cl)c2)cc1)CO3]

(S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (245 mg) was dissolved in DCM and the resulting solution was washed with aqueous Na₂CO₃. The organic layer was dried and evaporated to provide 208 mg of (S)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester. LCMS (m/z): 753.

(S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester bis hydrochloride

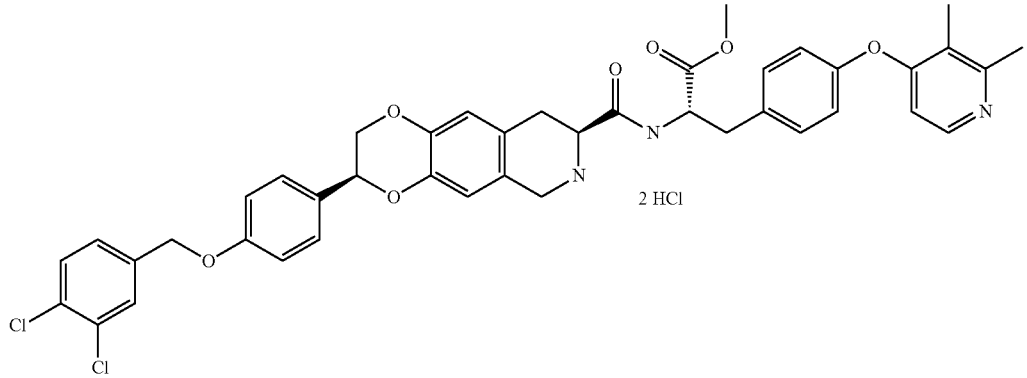 [SMILES: COC(=O)[C@H](Cc1ccc(Oc2ccnc(C)c2C)cc1)NC(=O)[C@@H]1Cc2cc3c(cc2CN1)O[C@@H](c1ccc(OCc2ccc(Cl)c(Cl)c2)cc1)CO3]

(3S,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester (0.56 g) was coupled with (S)-2-amino-3-[4-(2,3-dimethyl-pyridin-4-yloxy)-phenyl]-propionic acid methyl ester according to General Procedure L to provide 432 mg of product, which was deprotected according to General Procedure C to provide 349 mg of (S)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester bis hydrochloride (349 mg). The free base was generated by taking 224 mg of the bis-HCl salt up in DCM and washing with aqueous $Na_2CO_3$, drying the organic layer and evaporation to provide 215 mg of (S)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester. LCMS (m/z): 769.

EXAMPLES

Example 1

(S)-2-({(S)-7-Benzoyl-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid The title compound (23 mg) was prepared from (S)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride (38 mg) according to General Procedures F and B. LCMS (m/z): 841.

The compounds identified in Examples 2-27, below, were prepared using synthetic procedures analogous to those used for the synthesis of the compound of Example 1.

Example 2

(S)-3-(4'-Cyano-biphenyl-4-yl)-2-{[(S)-3-[4-(3,4-dichloro-benzyloxy)-phenyl]-7-(2-fluoro-benzoyl)-2,3,6,7,8,9-hexahydro-[1,4]dioxino[2,3-g]isoquinoline-8-carbonyl]-amino}-propionic acid

Example 3

(S)-3-(4'-Cyano-biphenyl-4-yl)-2-{[(S)-3-[4-(3,4-dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-propionic acid

Example 4

(S)-2-({(S)-7-(2-Cyano-benzoyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid

Example 5

(S)-3-(4'-Cyano-biphenyl-4-yl)-2-{[(S)-3-[4-(3,4-dichloro-benzyloxy)-phenyl]-7-(2-methyl-benzoyl)-2,3,6,7,8,9-hexahydro-[1,4]dioxino[2,3-g]isoquinoline-8-carbonyl]-amino}-propionic acid

Example 6

(S)-3-(4'-Cyano-biphenyl-4-yl)-2-{[(S)-3-[4-(3,4-dichloro-benzyloxy)-phenyl]-7-(furan-2-carbonyl)-2,3,6,7,8,9-hexahydro-[1,4]dioxino[2,3-g]isoquinoline-8-carbonyl]-amino}-propionic acid

Example 7

(S)-3-(4'-Cyano-biphenyl-4-yl)-2-{[(S)-3-[4-(3,4-dichloro-benzyloxy)-phenyl]-7-(thiophene-2-carbonyl)-2,3,6,7,8,9-hexahydro-[1,4]dioxino[2,3-g]isoquinoline-8-carbonyl]-amino}-propionic acid

Example 8

(S)-3-(4'-Cyano-biphenyl-4-yl)-2-({(S)-7-cyclobutanecarbonyl-3-[4-(3,4-dichloro-benzyloxy)-phenyl]-2,3,6,7,8,9-hexahydro-[1,4]dioxino[2,3-g]isoquinoline-8-carbonyl}-amino)-propionic acid

Example 9

(S)-2-({(S)-7-(2-Chloro-benzoyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid

Example 10

(S)-3-(4'-Cyano-biphenyl-4-yl)-2-({(S)-7-cyclohexanecarbonyl-3-[4-(3,4-dichloro-benzyloxy)-phenyl]-2,3,6,7,8,9-hexahydro-[1,4]dioxino[2,3-g]isoquinoline-8-carbonyl}-amino)-propionic acid

Example 11

(S)-3-(4'-Cyano-biphenyl-4-yl)-2-{[(S)-3-[4-(3,4-dichloro-benzyloxy)-phenyl]-7-(tetrahydro-pyran-4-carbonyl)-2,3,6,7,8,9-hexahydro-[1,4]dioxino[2,3-g]isoquinoline-8-carbonyl]-amino}-propionic acid

Example 12

(S)-3-(4'-Cyano-biphenyl-4-yl)-2-{[(S)-3-[4-(3,4-dichloro-benzyloxy)-phenyl]-7-(3-methyl-benzoyl)-2,3,6,7,8,9-hexahydro-[1,4]dioxino[2,3-g]isoquinoline-8-carbonyl]-amino}-propionic acid

Example 13

(S)-3-(4'-Cyano-biphenyl-4-yl)-2-{[(S)-3-[4-(3,4-dichloro-benzyloxy)-phenyl]-7-(4-methyl-benzoyl)-2,3,6,7,8,9-hexahydro-[1,4]dioxino[2,3-g]isoquinoline-8-carbonyl]-amino}-propionic acid

Example 14

(S)-3-(4'-Cyano-biphenyl-4-yl)-2-{[(S)-3-[4-(3,4-dichloro-benzyloxy)-phenyl]-7-(4-fluoro-benzoyl)-2,3,6,7,8,9-hexahydro-[1,4]dioxino[2,3-g]isoquinoline-8-carbonyl]-amino}-propionic acid

Example 15

(S)-3-(4'-Cyano-biphenyl-4-yl)-2-{[(S)-3-[4-(3,4-dichloro-benzyloxy)-phenyl]-7-(2-trifluoromethyl-benzoyl)-2,3,6,7,8,9-hexahydro-[1,4]dioxino[2,3-g]isoquinoline-8-carbonyl]-amino}-propionic acid

Example 16

(S)-3-(4'-Cyano-biphenyl-4-yl)-2-{[(S)-3-[4-(3,4-dichloro-benzyloxy)-phenyl]-7-(2-methanesulfonyl-benzoyl)-2,3,6,7,8,9-hexahydro-[1,4]dioxino[2,3-g]isoquinoline-8-carbonyl]-amino}-propionic acid

Example 17

(S)-3-(4'-Cyano-biphenyl-4-yl)-2-{[(S)-3-[4-(3,4-dichloro-benzyloxy)-phenyl]-7-(pyridine-2-carbonyl)-2,3,6,7,8,9-hexahydro-[1,4]dioxino[2,3-g]isoquinoline-8-carbonyl]-amino}-propionic acid

Example 18

(S)-3-(4'-Cyano-biphenyl-4-yl)-2-{[(S)-3-[4-(3,4-dichloro-benzyloxy)-phenyl]-7-(pyrazine-2-carbonyl)-2,3,6,7,8,9-hexahydro-[1,4]dioxino[2,3-g]isoquinoline-8-carbonyl]-amino}-propionic acid

Example 19

(S)-3-(4'-Cyano-biphenyl-4-yl)-2-{[(S)-3-[4-(3,4-dichloro-benzyloxy)-phenyl]-7-(3-phenyl-propynoyl)-2,3,6,7,8,9-hexahydro-[1,4]dioxino[2,3-g]isoquinoline-8-carbonyl]-amino}-propionic acid

Example 20

(S)-3-(4'-Cyano-biphenyl-4-yl)-2-{[(S)-3-[4-(3,4-dichloro-benzyloxy)-phenyl]-7-(thiazole-4-carbonyl)-2,3,6,7,8,9-hexahydro-[1,4]dioxino[2,3-g]isoquinoline-8-carbonyl]-amino}-propionic acid

Example 21

(S)-3-(4'-Cyano-biphenyl-4-yl)-2-{[(S)-3-[4-(3,4-dichloro-benzyloxy)-phenyl]-7-(2,4-dimethyl-thiazole-5-carbonyl)-2,3,6,7,8,9-hexahydro-[1,4]dioxino[2,3-g]isoquinoline-8-carbonyl]-amino}-propionic acid

Example 22

(S)-3-(4'-Cyano-biphenyl-4-yl)-2-{[(S)-3-[4-(3,4-dichloro-benzyloxy)-phenyl]-7-(tetrahydro-furan-3-carbonyl)-2,3,6,7,8,9-hexahydro-[1,4]dioxino[2,3-g]isoquinoline-8-carbonyl]-amino}-propionic acid

Example 23

(S)-3-(4'-Cyano-biphenyl-4-yl)-2-({(S)-7-cyclopentanecarbonyl-3-[4-(3,4-dichloro-benzyloxy)-phenyl]-2,3,6,7,8,9-hexahydro-[1,4]dioxino[2,3-g]isoquinoline-8-carbonyl}-amino)-propionic acid

Example 24

(S)-3-(4'-Cyano-biphenyl-4-yl)-2-{[(S)-3-[4-(3,4-dichloro-benzyloxy)-phenyl]-7-(tetrahydro-furan-2-carbonyl)-2,3,6,7,8,9-hexahydro-[1,4]dioxino[2,3-g]isoquinoline-8-carbonyl]-amino}-propionic acid

Example 25

(S)-3-(4'-Cyano-biphenyl-4-yl)-2-{[(S)-3-[4-(3,4-dichloro-benzyloxy)-phenyl]-7-(3-methyl-butyryl)-2,3,6,7,8,9-hexahydro-[1,4]dioxino[2,3-g]isoquinoline-8-carbonyl]-amino}-propionic acid

Example 26

(S)-3-(4'-Cyano-biphenyl-4-yl)-2-{[(S)-3-[4-(3,4-dichloro-benzyloxy)-phenyl]-7-(2-methyl-2H-pyrazole-3-carbonyl)-2,3,6,7,8,9-hexahydro-[1,4]dioxino[2,3-g]isoquinoline-8-carbonyl]-amino}-propionic acid

Example 27

(S)-3-(4'-Cyano-biphenyl-4-yl)-2-{[(S)-3-[4-(3,4-dichloro-benzyloxy)-phenyl]-7-(furan-3-carbonyl)-2,3,6,7,8,9-hexahydro-[1,4]dioxino[2,3-g]isoquinoline-8-carbonyl]-amino}-propionic acid

Example 28

(S)-3-(4'-Cyano-biphenyl-4-yl)-2-({(S)-3-[4-(3,4-dichloro-benzyloxy)-phenyl]-7-pyridin-2-ylmethyl-2,3,6,7,8,9-hexahydro-[1,4]dioxino[2,3-g]isoquinoline-8-carbonyl}-amino)-propionic acid (S)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (40 mg) was treated with pyridine-2-carbaldehyde according to General Procedure D to give (S)-3-(4'-cyano-biphenyl-4-yl)-2-({(S)-3-[4-(3,4-dichloro-benzyloxy)-phenyl]-7-pyridin-2-ylmethyl-2,3,6,7,8,9-hexahydro-[1,4]dioxino[2,3-g]isoquinoline-8-carbonyl}-amino)-propionic acid methyl ester (42 mg). LCMS (m/z): 842. The methyl ester (25 mg) was hydrolyzed according to General Procedure B to give the title compound (20 mg). LCMS (m/z): 827.

The compounds identified in Examples 29-42, below, were prepared using synthetic procedures analogous to those used for the synthesis of the compound of Example 28.

Example 29

(S)-3-(4'-Cyano-biphenyl-4-yl)-2-({(S)-3-[4-(3,4-dichloro-benzyloxy)-phenyl]-7-thiophen-2-ylmethyl-2,3,6,7,8,9-hexahydro-[1,4]dioxino[2,3-g]isoquinoline-8-carbonyl}-amino)-propionic acid

Example 30

(S)-3-(4'-Cyano-biphenyl-4-yl)-2-({(S)-3-[4-(3,4-dichloro-benzyloxy)-phenyl]-7-furan-2-ylmethyl-2,3,6,7,8,9-hexahydro-[1,4]dioxino[2,3-g]isoquinoline-8-carbonyl}-amino)-propionic acid

Example 31

(S)-2-({(S)-7-(2-Cyano-benzyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid

Example 32

(S)-2-({(S)-7-(2-Chloro-6-fluoro-benzyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid

Example 33

(S)-3-(4'-Cyano-biphenyl-4-yl)-2-{[(S)-3-[4-(3,4-dichloro-benzyloxy)-phenyl]-7-(2-fluoro-6-methoxy-benzyl)-2,3,6,7,8,9-hexahydro-[1,4]dioxino[2,3-g]isoquinoline-8-carbonyl]-amino}-propionic acid

Example 34

(S)-3-(4'-Cyano-biphenyl-4-yl)-2-({(S)-3-[4-(3,4-dichloro-benzyloxy)-phenyl]-7-oxazol-2-ylmethyl-2,3,6,7,8,9-hexahydro-[1,4]dioxino[2,3-g]isoquinoline-8-carbonyl}-amino)-propionic acid

Example 35

(S)-3-(4'-Cyano-biphenyl-4-yl)-2-{[(S)-3-[4-(3,4-dichloro-benzyloxy)-phenyl]-7-(2-hydroxy-benzyl)-2,3,6,7,8,9-hexahydro-[1,4]dioxino[2,3-g]isoquinoline-8-carbonyl]-amino}-propionic acid

Example 36

(S)-2-({(S)-7-(2-Chloro-benzyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid

Example 37

(S)-3-(4'-Cyano-biphenyl-4-yl)-2-{[(S)-3-[4-(3,4-dichloro-benzyloxy)-phenyl]-7-(2-methyl-benzyl)-2,3,6,7,8,9-hexahydro-[1,4]dioxino[2,3-g]isoquinoline-8-carbonyl]-amino}-propionic acid

Example 38

2-{(S)-8-[(S)-1-Carboxy-2-(4'-cyano-biphenyl-4-yl)-ethylcarbamoyl]-3-[4-(3,4-dichloro-benzyloxy)-phenyl]-2,3,8,9-tetrahydro-6H-[1,4]dioxino[2,3-g]isoquinolin-7-ylmethyl}-benzoic acid

Example 39

(S)-2-({(S)-7-Benzyl-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid

Example 40

(S)-3-(4'-Cyano-biphenyl-4-yl)-2-{[(S)-3-[4-(3,4-dichloro-benzyloxy)-phenyl]-7-(1-methyl-1H-imidazol-2-ylmethyl)-2,3,6,7,8,9-hexahydro-[1,4]dioxino[2,3-g]isoquinoline-8-carbonyl]-amino}-propionic acid

Example 41

(S)-3-(4'-Cyano-biphenyl-4-yl)-2-{[(S)-3-[4-(3,4-dichloro-benzyloxy)-phenyl]-7-(tetrahydro-pyran-4-ylmethyl)-2,3,6,7,8,9-hexahydro-[1,4]dioxino[2,3-g]isoquinoline-8-carbonyl]-amino}-propionic acid

Example 42

(S)-3-(4'-Cyano-biphenyl-4-yl)-2-({(S)-3-[4-(3,4-dichloro-benzyloxy)-phenyl]-7-ethyl-2,3,6,7,8,9-hexahydro-[1,4]dioxino[2,3-g]isoquinoline-8-carbonyl}-amino)-propionic acid

Example 43

(S)-8-[(S)-1-Carboxy-2-(4'-cyano-biphenyl-4-yl)-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid isopropyl ester The title compound (12 mg) was prepared from (S)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride (40 mg) according to General Procedures G and B. LCMS (m/z): 823.

The compounds identified in Examples 44-47, below, were prepared using synthetic procedures analogous to those used for the synthesis of the compound of Example 43.

Example 44

(S)-8-[(S)-1-Carboxy-2-(4'-cyano-biphenyl-4-yl)-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid 2,2-dimethyl-propyl ester

Example 45

(S)-8-[(S)-1-Carboxy-2-(4'-cyano-biphenyl-4-yl)-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid but-2-ynyl ester

Example 46

(S)-8-[(S)-1-Carboxy-2-(4'-cyano-biphenyl-4-yl)-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid tert-butyl ester

Example 47

(S)-8-[(S)-1-Carboxy-2-(4'-cyano-biphenyl-4-yl)-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid tetrahydro-pyran-4-yl ester

Example 48

(S)-2-({(S)-7-tert-Butylcarbamoyl-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid The title compound (19 mg) was prepared from (S)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride (40 mg) according to General Procedures I and B. LCMS (m/z): 837.

Example 49

(S)-2-({(S)-7-Benzenesulfonyl-3-[4-(3,4-dichloro-benzyloxy)-phenyl]-2,3,6,7,8,9-hexa hydro-[1,4]dioxino[2,3-g]isoquinoline-8-carbonyl}-amino)-3-(4'-cyano-biphenyl-4-yl)-propionic acid The title compound (21 mg) was prepared from (S)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride (40 mg) according to General Procedures E and B. LCMS (m/z): 879.

Example 50

(S)-2-({(3S,8S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-3-(4'-Cyano-biphenyl-4-yl)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (510 mg) was reacted with 2-acetylamino-4-methyl-thiazole-5-sulfonyl chloride to yield (S)-2-({(3S,8S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (526 mg) according to General Procedure E. The title compound (32 mg) was prepared by the hydrolysis of (S)-2-({(3S,8S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (LCMS m/z=968) (40 mg) according to General Procedure B. LCMS (m/z): 952.

Example 51

1H-4-oxa-1,6-diaza-anthracene-7-carbonyl}-amino)-3-(4'-cyano-biphenyl-4-yl)-(S)-2-({(S)-6-Benzoyl-3-[4-(3,4-dichloro-benzyloxy)-phenyl]-2,3,5,6,7,8-hexahydro-propionic acid Step 1. Preparation of (S)-7-hydroxy-1,2,3,4-tetrahydro-isoquinoline-3-carboxylic acid methyl ester hydrochloride To a solution of (S)-7-hydroxy-1,2,3,4-tetrahydro-isoquinoline-3-carboxylic acid (19.3 g) in 100 mL MeOH was added hydrochloric acid (100 mL, 4M solution in dioxane) at room temperature and the reaction mixture was heated to reflux and stirred at 70° C. for 16 hours. After completion of the reaction, the reaction mixture was concentrated in vacuo to give (S)-7-hydroxy-1,2,3,4-tetrahydro-isoquinoline-3-carboxylic acid methyl ester hydrochloride salt. The product was used in a subsequent step without further purification.

Step 2. Preparation of ((5)-7-hydroxy-6-nitro-3,4-dihydro-1H-isoquinoline-2,3-dicarboxylic acid 2-tert-butyl ester 3-methyl ester To a solution of (S)-7-hydroxy-1,2,3,4-tetrahydro-isoquinoline-3-carboxylic acid methyl ester hydrochloride (23.35 g) in TFA (100 mL) was slowly added sodium nitrite (2.0 eq.) at 0° C., then stirred and slowly warmed to room temperature. After completion of the reaction, excess TFA was removed and to this residue di-tert-butyl dicarbonate (2 eq.) and sodium bicarbonate (3.0 eq.) were added in the presence of ethyl acetate (300 mL). After t-boc protection was complete, the reaction mixture was treated with hydrazine hydrate (20 mL, 33% solution in water) to cleave the carbonate. The reaction mixture was stirred at room temperature for 2 hours, then this mixture was slowly acidified with dilute HCl (500 mL, 1.0 M solution), extracted with ethyl acetate (3×200 mL). Then, the organics were combined and washed with HCl (2×100 mL), water (1×100 mL) and brine (1×100 mL), and dried over sodium sulfate and concentrated in vacuo to give the both nitrated regioisomers (6- and 8-nitro substituted analogs). The regioisomers (S)-7-hydroxy-6-nitro-3,4-dihydro-1H-isoquinoline-2,3-dicarboxylic acid 2-tert-butyl ester 3-methyl ester and (S)-7-hydroxy-8-nitro-3,4-dihydro-1H-isoquinoline-2,3-dicarboxylic acid 2-tert-butyl ester 3-methyl ester isomers were separated with silica gel chromatography using hexanes/ethyl acetate (from 90:10 to 70:30) as an eluent system.

Step 3. Preparation of (S)-6-amino-7-hydroxy-3,4-dihydro-1H-isoquinoline-2,3-dicarboxylic acid 2-tert-butyl ester 3-methyl ester To a stirred solution of the nitro derivative (3.42 g) in methanol (50 mL) was added Pd—C (342 mg, 10% on activated carbon) and the resulting reaction mixture was subjected to hydrogenation (balloon pressure). The reaction mixture was stirred under hydrogen balloon at room temperature for 16 hours. The catalyst was filtered off through a pad of celite and the celite pad was washed with an ethyl acetate/methanol mixture (1:1, 25 mL). The combined filtrate was concentrated under reduced pressure. The resulting residue, (S)-6-amino-7-hydroxy-3,4-dihydro-1H-isoquinoline-2,3-dicarboxylic acid 2-tert-butyl ester 3-methyl ester was used in the next step without further purification.

Step 4. Preparation of [4-(3,4-dichloro-benzyloxy)-phenyl]-oxo-acetaldehyde

To a solution of (4-hydroxy-phenyl)-oxo-acetaldehyde (756 mg) in dry DMF (10 mL) were added 3,4-dichlorobenzylbromide (1.2 g) and potassium carbonate (1.03 g). After 4 hours, the reaction mixture was poured into water (100 mL) and extracted with ethyl acetate (2×50 mL). The organic extracts were then combined and washed with brine (2×50 mL) and a saturated sodium bicarbonate solution (2×50 mL). The organic layer was dried over sodium sulfate and concentrated under reduced pressure to give [4-(3,4-dichloro-benzyloxy)-phenyl]-oxo-acetaldehyde (1.3 g).

Step 5. Preparation of (S)-3-[4-(3,4-Dichloro-benzyloxy)-phenyl]-1,2,3,5,7,8-hexahydro-4-oxa-1,6-diaza-anthracene-6,7-dicarboxylic acid 6-tert-butyl ester 7-methyl ester

[4-(3,4-Dichloro-benzyloxy)-phenyl]-oxo-acetaldehyde (616 mg) was dissolved in DCE (25 mL), and (S)-6-amino-7-hydroxy-3,4-dihydro-1H-isoquinoline-2,3-dicarboxylic acid 2-tert-butyl ester 3-methyl ester (644 mg) and sodium triacetoxyborohydride (520 mg) were added. The mixture was stirred overnight at room temperature. DCM (50 mL) was added to the reaction mixture and poured into water (25 mL). The organic layer was washed with 10% Na$_2$CO$_3$ solution and brine, and dried over sodium sulfate. The solvent was removed under reduced pressure and the residue was purified by flash chromatography (hexanes/ethyl acetate from 90:10 to 70:30) to give (S)-3-[4-(3,4-Dichloro-benzyloxy)-phenyl]-1,2,3,5,7,8-hexahydro-4-oxa-1,6-diaza-anthracene-6,7-dicarboxylic acid 6-tert-butyl ester 7-methyl ester (855 mg).

Step 6. Preparation of (S)-3-[4-(3,4-dichloro-benzyloxy)-phenyl]-1,2,3,5,7,8-hexahydro-4-oxa-1,6-diaza-anthracene-6,7-dicarboxylic acid 6-tert-butyl ester (S)-3-[4-(3,4-Dichloro-benzyloxy)-phenyl]-1,2,3,5,7,8-hexahydro-4-oxa-1,6-diaza-anthracene- 6,7-dicarboxylic acid 6-tert-butyl ester 7-methyl ester (598 mg) was dissolved in THF/methanol (4:1). 2 N Lithium hydroxide (1 mL) was added, and the resulting reaction mixture was stirred at room temperature for 4 hours. Excess 1N HCl was added and the mixture extracted with ethyl acetate. The organic layer was washed with brine, dried over sodium sulfate, and the solvent was removed under reduced pressure to give the product in substantially pure form (0.56 g).

Step 7. Preparation of (S)-7-[(S)-2-(4'-Cyano-biphenyl-4-yl)-1-methoxycarbonyl-ethylcarbamoyl]-3-[4-(3,4-dichloro-benzyloxy)-phenyl]-1,2,3,5,7,8-hexahydro-4-oxa-1,6-diaza-anthracene-6-carboxylic acid tert-butyl ester To a stirring solution of (S)-3-[4-(3,4-Dichloro-benzyloxy)-phenyl]-1,2,3,5,7,8-hexahydro-4-oxa-1,6-diaza-anthracene-6,7-dicarboxylic acid 6-tert-butyl ester (146 mg), HBTU (95 mg) and DIEA (0.088 mL) in DMF (5 mL), was added (S)-2-amino-3-(4'-cyano-biphenyl-4-yl)-propionic acid methyl ester (79 mg). After 4 hours a sufficient amount of water was added and the mixture extracted with ethyl acetate. The organic layer was washed with 1 N HCl, saturated NaHCO$_3$ and brine, and dried over sodium sulfate. The solvent was removed under reduced pressure to provide the crude amide. The residue was purified by column chromatography on silica gel (with an eluent of hexanes/ethyl acetate from 80:20 to 60:40) to give the product (169 mg).

Step 8. Preparation of (S)-3-(4'-Cyano-biphenyl-4-yl)-2-({(S)-3-[4-(3,4-dichloro-benzyloxy)-phenyl]-2,3,5,6,7,8-hexahydro-1H-4-oxa-1,6-diaza-anthracene-7-carbonyl}-amino)-propionic acid methyl ester bis hydrochloride A solution of (S)-7-[(S)-2-(4'-Cyano-biphenyl-4-yl)-1-methoxycarbonyl-ethylcarbamoyl]-3-[4-(3,4-dichloro-benzyloxy)-phenyl]-1,2,3,5,7,8-hexahydro-4-oxa-1,6-diaza-anthracene-6-carboxylic acid tert-butyl ester (85 mg) in DCM (5 mL) was treated with 4 N HCl in dioxane (0.2 mL). The reaction stirred at room temperature for 30 minutes, and the solvents were removed under reduced pressure. The residue was triturated with ethyl ether and the precipitated solid was filtered and dried under vacuum to give desired amine as the bis hydrochloride salt.

Step 9. Preparation of the Title Compound

The title compound (26 mg) was prepared from (S)-3-(4'-cyano-biphenyl-4-yl)-2-({(S)-3-[4-(3,4-dichloro-benzyloxy)-phenyl]-2,3,5,6,7,8-hexahydro-1H-4-oxa-1,6-diaza-anthracene-7-carbonyl}-amino)-propionic acid methyl ester bis hydrochloride (41 mg) according to General Procedures A and B. LCMS (m/z): 840.

Example 52

(S)-2-({(S)-6-Benzoyl-3-[4-(3,4-dichloro-benzyloxy)-phenyl]-1-methyl-2,3,5,6,7,8-hexahydro-1H-4-oxa-1,6-diaza-anthracene-7-carbonyl}-amino)-3-(4'-cyano-biphenyl-4-yl)-propionic acid Step 1. Preparation of (S)-7-hydroxy-1,2,3,4-tetrahydro-isoquinoline-3-carboxylic acid methyl ester hydrochloride To a solution of (S)-7-hydroxy-1,2,3,4-tetrahydro-isoquinoline-3-carboxylic acid (19.3 g) in 100 mL MeOH was added hydrochloric acid (100 mL, 4M solution in dioxane) at room temperature, and the reaction mixture was heated to reflux and stirred at 70° C. for 16 hours. After completion of the reaction, the reaction mixture was concentrated in vacuo to give (S)-7-hydroxy-1,2,3,4-tetrahydro-isoquinoline-3-carboxylic acid methyl ester hydrochloride salt with quantitative yield. The product was used in the next step without further purification.

Step 2. Preparation of ((S)-7-hydroxy-6-nitro-3,4-dihydro-1H-isoquinoline-2,3-dicarboxylic acid 2-tert-butyl ester 3-methyl ester To a solution of (S)-7-hydroxy-1,2,3,4-tetrahydro-isoquinoline-3-carboxylic acid methyl ester hydrochloride (23.35 g) in TFA (100 mL), was slowly added sodium nitrite (2.0 eq.) at 0° C., then stirred and slowly warmed to room temperature. After completion of the reaction, excess TFA was removed and to this residue di-tert-butyl dicarbonate (2 eq.) and sodium bicarbonate (3.0 eq.) were added in the presence of ethyl acetate (300 mL). After t-boc protection was complete, the reaction mixture was treated with hydrazine hydrate (20 mL, 33% solution in water) to cleave the carbonate. The reaction mixture was stirred at room temperature for 2 hours, then this mixture was slowly acidified with dilute HCl (500 mL, 1.0 M solution), extracted with ethyl acetate (3×200 mL), the organics were combined and washed with HCl (2×100 mL), water (1×100 mL) and brine (1×100 mL), dried over sodium sulfate and concentrated in vacuo to give the both nitrated regioisomers (6- and 8-nitro substituted analogs). The regioisomers ((S)-7-hydroxy-6-nitro-3,4-dihydro-1H-isoquinoline-2,3-dicarboxylic acid 2-tert-butyl ester 3-methyl ester and (S)-7-hydroxy-8-nitro-3,4-dihydro-1H-isoquinoline-2,3-dicarboxylic acid 2-tert-butyl ester 3-methyl ester isomers) were separated with silica gel chromatography using hexanes/ethyl acetate (from 90:10 to 70:30) as an eluent system.

Step 3. Preparation of (S)-6-Amino-7-hydroxy-3,4-dihydro-1H-isoquinoline-2,3-dicarboxylic acid 2-tert-butyl ester 3-methyl ester To a stirred solution of the nitro derivative (3.42 g) in methanol (50 mL) was added Pd—C (342 mg, 10% on activated carbon) and the resultant reaction mixture was subjected to hydrogenation (balloon pressure). The reaction mixture was stirred under hydrogen balloon at room temperature for 16 hours. The catalyst was filter off through a pad of celite and the celite pad was washed with ethyl acetate-methanol mixture (1:1, 25 mL). The combined filtrate was concentrated under reduced pressure. The resulting residue, (S)-6-Amino-7-hydroxy-3,4-dihydro-1H-isoquinoline-2,3-dicarboxylic acid 2-tert-butyl ester 3-methyl ester was used in the next step without further purification.

Step 4. Preparation of [4-(3,4-Dichloro-benzyloxy)-phenyl]-oxo-acetaldehyde

To a solution of (4-hydroxy-phenyl)-oxo-acetaldehyde (756 mg) in dry DMF (10 mL) were added 3,4-dichlorobenzylbromide (1.2 g) and potassium carbonate (1.03 g). After 4 hours, the reaction mixture was poured into water (100 mL) and extracted with ethyl acetate (2×50 mL). The organic extracts were combined and washed with brine (2×50 mL) and saturated sodium bicarbonate solution (2×50 mL). The organic layer was dried over sodium sulfate and concentrated under reduced pressure to give [4-(3,4-dichloro-benzyloxy)-phenyl]-oxo-acetaldehyde (1.3 g).

Step 5. Preparation of (S)-3-[4-(3,4-Dichloro-benzyloxy)-phenyl]-1,2,3,5,7,8-hexahydro-4-oxa-1,6-diaza-anthracene-6,7-dicarboxylic acid 6-tert-butyl ester 7-methyl ester

[4-(3,4-Dichloro-benzyloxy)-phenyl]-oxo-acetaldehyde (616 mg) was dissolved in DCE (25 mL) and sodium triacetoxyborohydride (520 mg) and (S)-6-amino-7-hydroxy-3,4-dihydro-1H-isoquinoline-2,3-dicarboxylic acid 2-tert-butyl ester 3-methyl ester (644 mg). The mixture was stirred overnight at room temperature. DCM (50 mL) was added to the reaction mixture and poured into water (25 mL). The organic layer was washed with 10% $Na_2CO_3$ solution and brine, and dried over sodium sulfate. The solvent was removed under reduced pressure and the residue purified by flash chromatography (hexanes/ethyl acetate from 90:10 to 70:30) to afford (S)-3-[4-(3,4-Dichloro-benzyloxy)-phenyl]-1,2,3,5,7,8-hexahydro-4-oxa-1,6-diaza-anthracene-6,7-dicarboxylic acid 6-tert-butyl ester 7-methyl ester (855 mg).

Step 6. Preparation of (S)-3-[4-(3,4-Dichloro-benzyloxy)-phenyl]-1-methyl-1,2,3,5,7,8-hexahydro-4-oxa-1,6-diaza-anthracene-6,7-dicarboxylic acid 6-tert-butyl ester 7-methyl ester To a solution of (S)-3-[4-(3,4-dichloro-benzyloxy)-phenyl]-1,2,3,5,7,8-hexahydro-4-oxa-1,6-diaza-anthracene-6,7-dicarboxylic acid 6-tert-butyl ester 7-methyl ester (298 mg) in THF/DCE (30 mL, 2:1) was added paraformaldehyde (90 mg, 4 eq.) and sodium triacetoxyborohydride (208 mg) and the mixture stirred 4 hours. DCM was added to the mixture and the organic washed with 10% $Na_2CO_3$ solution and brine. The organic was dried over sodium sulfate and the solvent removed under reduced pressure to afford the crude amine. The residue was purified by flash chromatography (hexanes/ethyl acetate from 80:20 to 60:40) to provide the product (277 mg).

Step 7. Preparation of (S)-3-[4-(3,4-Dichloro-benzyloxy)-phenyl]-1-methyl-1,2,3,5,7,8-hexahydro-4-oxa-1,6-diaza-anthracene-6,7-dicarboxylic acid 6-tert-butyl ester (S)-3-[4-(3,4-Dichloro-benzyloxy)-phenyl]-1-methyl-1,2,3,5,7,8-hexahydro-4-oxa-1,6-diaza-anthracene-6,7-dicarboxylic acid 6-tert-butyl ester 7-methyl ester was dissolved in THF:methanol (4:1). 2 N lithium hydroxide (0.5 mL) was added and the resulting reaction mixture was stirred at room temperature for 4 hours. Excess 1N HCl was added and the mixture extracted with ethyl acetate. The organic layer was washed with brine, dried over sodium sulfate, and the solvent was removed under reduced pressure to afford the product in pure form (122 mg).

Step 8. Preparation of (S)-7-[(S)-2-(4'-Cyano-biphenyl-4-yl)-1-methoxycarbonyl-ethylcarbamoyl]-3-[4-(3,4-dichloro-benzyloxy)-phenyl]-1-methyl-1,2,3,5,7,8-hexahydro-4-oxa-1,6-diaza-anthracene-6-carboxylic acid tert-butyl ester To a stirring solution of (S)-3-[4-(3,4-dichloro-benzyloxy)-phenyl]-1-methyl-1,2,3,5,7,8-hexahydro-4-oxa-1,6-diaza-anthracene-6,7-dicarboxylic acid 6-tert-butyl ester, HBTU (95 mg) and DIEA in DMF (5 mL) was added (S)-2- amino-3-(4'-cyano-biphenyl-4-yl)-propionic acid methyl ester (79 mg). After 4 hours a sufficient amount of water was added and the mixture was extracted with ethyl acetate. The organic was washed with 1 N HCl, saturated NaHCO$_3$ and brine, and dried over sodium sulfate. The solvent was removed under reduced pressure to provide the crude amide. The residue was purified by column chromatography on silica gel (hexanes/ethyl acetate from 80:20 to 60:40) to afford the product (180 mg).

Step 9. Preparation of (S)-3-(4'-Cyano-biphenyl-4-yl)-2-({(S)-3-[4-(3,4-dichloro-benzyloxy)-phenyl]-1-methyl-2,3,5,6,7,8-hexahydro-1H-4-oxa-1,6-diaza-anthracene-7-carbonyl}-amino)-propionic acid methyl ester bis hydrochloride A solution of (S)-7-[(S)-2-(4'-cyano-biphenyl-4-yl)-1-methoxycarbonyl-ethylcarbamoyl]-3-[4-(3,4-dichloro-benzyloxy)-phenyl]-1-methyl-1,2,3,5,7,8-hexahydro-4-oxa-1,6-diaza-anthracene-6-carboxylic acid tert-butyl ester (86 mg) in DCM (5 mL) was treated with 4 N HCl in dioxane (0.2 mL). The reaction mixture was stirred at room temperature for 30 min and the solvents were removed under reduced pressure. The residue was triturated with ethyl ether and the precipitated solid was filtered and dried under vacuum to give desired amine as the bis-hydrochloride salt in quantitative yield.

Step 10. Preparation of the Title Compound

The title compound (33 mg) was prepared from (S)-3-(4'-Cyano-biphenyl-4-yl)-2-({(S)-3-[4-(3,4-dichloro-benzyloxy)-phenyl]-1-methyl-2,3,5,6,7,8-hexahydro-1H-4-oxa-1,6-diaza-anthracene-7-carbonyl}-amino)-propionic acid methyl ester bis hydrochloride (43 mg) according to General Procedures F and B. LCMS (m/z): 851.

Example 53

(S)-2-({(S)-1-Acetyl-6-benzoyl-3-[4-(3,4-dichloro-benzyloxy)-phenyl]-2,3,5,6,7,8-hexahydro-1H-4-oxa-1,6-diaza-anthracene-7-carbonyl}-amino)-3-(4'-cyano-biphenyl-4-yl)-propionic acid Step 1. Preparation of (S)-7-hydroxy-1,2,3,4-tetrahydro-isoquinoline-3-carboxylic acid methyl ester hydrochloride To a solution of (S)-7-hydroxy-1,2,3,4-tetrahydro-isoquinoline-3-carboxylic acid (19.3 g) in 100 mL MeOH was added hydrochloric acid (100 mL, 4M solution in dioxane) at room temperature and the reaction mixture was heated to reflux and stirred at 70° C. for 16 hours. After completion of the reaction the reaction mixture was concentrated in vacuo to give (S)-7-hydroxy-1,2,3,4-tetrahydro-isoquinoline-3-carboxylic acid methyl ester hydrochloride salt with quantitative yield. The product was used in the next step without further purification.

Step 2. Preparation of ((S)-7-hydroxy-6-nitro-3,4-dihydro-1H-isoquinoline-2,3-dicarboxylic acid 2-tert-butyl ester 3-methyl ester To a solution of (S)-7-hydroxy-1,2,3,4-tetrahydro-isoquinoline-3-carboxylic acid methyl ester hydrochloride (23.35 g) in TFA (100 mL) was slowly added sodium nitrite (2.0 eq.) at 0° C., then stirred and slowly warmed to room temperature. After completion of the reaction, excess TFA was removed and to this residue di-tert-butyl dicarbonate (2 eq.) and sodium bicarbonate (3.0 eq.) were added in the presence of ethyl acetate (300 mL). After t-boc protection was complete, the reaction mixture was treated with hydrazine hydrate (20 mL, 33% solution in water) to cleave the carbonate. The reaction mixture was stirred at room temperature for 2 hours, then this mixture was slowly acidified with dilute HCl (500 mL, 1.0 M solution), extracted with ethyl acetate (3×200 mL), the organics were combined and washed with HCl (2×100 mL), water (1×100 mL) and brine (1×100 mL), dried over sodium sulfate and concentrated in vacuo to give the both nitrated regioisomers (6- and 8-Nitro substituted analogs). The regioisomers (S)-7-hydroxy-6-nitro-3,4-dihydro-1H-isoquinoline-2,3-dicarboxylic acid 2-tert-butyl ester 3-methyl ester and (S)-7-hydroxy-8-nitro-3,4-dihydro-1H-isoquinoline-2,3-dicarboxylic acid 2-tert-butyl ester 3-methyl ester isomers were carefully separated with silica gel chromatography using hexanes/ethyl acetate (from 90:10 to 70:30) as an eluent system.

Step 3. Preparation of (S)-6-amino-7-hydroxy-3,4-dihydro-1H-isoquinoline-2,3-dicarboxylic acid 2-tert-butyl ester 3-methyl ester To a stirred solution of the nitro derivative (3.42 g) in methanol (50 mL) was added Pd—C (342 mg, 10% on activated carbon) and the resulting reaction mixture was subjected to hydrogenation (balloon pressure). The reaction mixture was stirred under hydrogen balloon at room temperature for 16 hours. The catalyst was filter off through a pad of celite and the celite pad was washed ethyl acetate-methanol mixture (1:1, 25 mL). The combined filtrate was concentrated under reduced pressure. The resulting residue, (S)-6-amino-7-hydroxy-3,4-dihydro-1H-isoquinoline-2,3-dicarboxylic acid 2-tert-butyl ester 3-methyl ester was used in the next step without further purification.

Step 4. Preparation of [4-(3,4-dichloro-benzyloxy)-phenyl]-oxo-acetaldehyde

To a solution of (4-hydroxy-phenyl)-oxo-acetaldehyde (756 mg) in dry DMF (10 mL) was added 3,4-dichlorobenzylbromide (1.2 g) and potassium carbonate (1.03 g). After 4 hours, the reaction mixture was poured into water (100 mL) and extracted with ethyl acetate (2×50 mL). The organic extracts were combined and washed with brine (2×50 mL) and saturated sodium bicarbonate solution (2×50 mL). The organic layer was dried over sodium sulfate and concentrated under reduced pressure to give [4-(3,4-dichloro-benzyloxy)-phenyl]-oxo-acetaldehyde (1.3 g).

Step 5. Preparation of (S)-3-[4-(3,4-dichloro-benzyloxy)-phenyl]-1,2,3,5,7,8-hexahydro-4-oxa-1,6-diaza-anthracene-6,7-dicarboxylic acid 6-tert-butyl ester 7-methyl ester

[4-(3,4-Dichloro-benzyloxy)-phenyl]-oxo-acetaldehyde (616 mg) was dissolved in DCE (25 mL) and sodium triacetoxyborohydride (520 mg) and (S)-6-Amino-7-hydroxy-3,4-dihydro-1H-isoquinoline-2,3-dicarboxylic acid 2-tert-butyl ester 3-methyl ester (644 mg) The mixture was stirred overnight at room temperature. DCM (50 mL) was added to the reaction mixture and poured into water (25 mL). The organic layer was washed with 10% Na$_2$CO$_3$ solution and brine, and dried over sodium sulfate. The solvent was removed under reduced pressure and the residue purified by flash chromatography (hexanes/ethyl acetate from 90:10 to 70:30) to give (S)-3-[4-(3,4-Dichloro-benzyloxy)-phenyl]-1,2,3,5,7,8-hexahydro-4-oxa-1,6-diaza-anthracene-6,7-dicarboxylic acid 6-tert-butyl ester 7-methyl ester (855 mg).

Step 6. Preparation of (S)-3-[4-(3,4-dichloro-benzyloxy)-phenyl]-1,2,3,5,7,8-hexahydro-4-oxa-1,6-diaza-anthracene-6,7-dicarboxylic acid 6-tert-butyl ester (S)-3-[4-(3,4-Dichloro-benzyloxy)-phenyl]-1,2,3,5,7,8-hexahydro-4-oxa-1,6-diaza-anthracene-6,7-dicarboxylic acid 6-tert-butyl ester 7-methyl ester (598 mg) was dissolved in THF-methanol (4:1). 2 N Lithium hydroxide (1 mL) was added and the resulting reaction mixture was stirred at room temperature for 4 hours. Excess 1N HCl was added and the mixture extracted with ethyl acetate. The organic layer was washed with brine, dried over sodium sulfate, and the solvent was removed under reduced pressure to afford the product in pure form (0.56 g).

Step 7. Preparation of (S)-7-[(S)-2-(4'-cyano-biphenyl-4-yl)-1-methoxycarbonyl-ethylcarbamoyl]3-[4-(3,4-dichloro-benzyloxy)-phenyl]-1,2,3,5,7,8-hexahydro-4-oxa-1,6-diaza-anthracene-6-carboxylic acid tert-butyl ester To a stirring solution of (S)-3-[4-(3,4-dichloro-benzyloxy)-phenyl]-1,2,3,5,7,8-hexahydro-4-oxa-1,6-diaza-anthracene-6,7-dicarboxylic acid 6-tert-butyl ester (146 mg), HBTU (95 mg) and DIEA in DMF (5 mL) was added (S)-2-amino-3-(4'-cyano-biphenyl-4-yl)-propionic acid methyl ester (79 mg). After 4 hours, a sufficient amount of water was added and the mixture extracted with ethyl acetate. The organic layer was washed with 1 N HCl, saturated NaHCO$_3$ and brine, and dried over sodium sulfate. The solvent was removed under reduced pressure to provide the crude amide. The residue was purified by column chromatography on silica gel (hexanes/ethyl acetate from 80:20 to 60:40) to give the product (169 mg).

Step 8. Preparation of (S)-1-acetyl-7-[(S)-2-(4'-cyano-biphenyl-4-yl)-1-methoxycarbonyl-ethylcarbamoyl]-3-[4-(3,4-dichloro-benzyloxy)-phenyl]-1,2,3,5,7,8-hexahydro-4-oxa-1,6-diaza-anthracene-6-carboxylic acid tert-butyl ester A solution of (S)-7-[(S)-2-(4'-cyano-biphenyl-4-yl)-1-methoxycarbonyl-ethylcarbamoyl]-3-[4-(3,4-dichloro-benzyloxy)-phenyl]-1,2,3,5,7,8-hexahydro-4-oxa-1,6-diaza-anthracene-6-carboxylic acid tert-butyl ester (85 mg) in DCM (5 mL) at 0° C. was treated with acetyl chloride, and triethylamine. The mixture was allowed to slowly warm to room temperature. After 3 hours, ethyl acetate was added and the organic layer was washed with 1N HCl. The organic layer was washed saturated sodium bicarbonate solution and brine, and dried over sodium sulfate. The solvent was removed under reduced pressure to give the crude amide. The residue was purified by flash chromatography (using hexanes/ethyl acetate, from 70:30 to 55:45, as an eluent) to give the product (76 mg).

Step 9. Preparation of (S)-2-({(S)-1-Acetyl-3-[4-(3,4-dichloro-benzyloxy)-phenyl]-2,3,5,6,7,8-hexahydro-1H-4-oxa-1,6-diaza-anthracene-7-carbonyl}-amino)-3-(4'-cyano-biphenyl-4-yl)-propionic acid methyl ester hydrochloride A solution of (S)-1-acetyl-7-[(S)-2-(4'-cyano-biphenyl-4-yl)-1-methoxycarbonyl-ethylcarbamoyl]-3-[4-(3,4-dichloro-benzyloxy)-phenyl]-1,2,3,5,7,8-hexahydro-4-oxa-1,6-diaza-anthracene-6-carboxylic acid tert-butyl ester (88 mg) in DCM (0.5 mL) was treated with 4 N HCl in dioxane (0.2 mL). The reaction was stirred at room temperature for 30 minutes and the solvents were removed under reduced pressure. The residue was triturated with ethyl ether and the precipitated solid was filtered and dried under vacuum to give desired amine as the hydrochloride salt.

Step 10. Preparation of the Title Compound

The title compound (29 mg) was prepared from (S)-2-({(S)-1-Acetyl-3-[4-(3,4-dichloro-benzyloxy)-phenyl]-2,3,5,6,7,8-hexahydro-1H-4-oxa-1,6-diaza-anthracene-7-carbonyl}-amino)-3-(4'-cyano-biphenyl-4-yl)-propionic acid methyl ester hydrochloride (44 mg) according to General Procedures F and B. LCMS (m/z): 881.

Example 54

(S)-2-({(S)-7-(2-Amino-4-methyl-thiazole-5-sulfonyl)-3-[4-(3,4-dichloro-benzoylamino)-phenyl]-2,3,6,7,8,9-hexahydro-[1,4]dioxino[2,3-g]isoquinoline-8-carbonyl}-amino)-3-(4'-cyano-biphenyl-4-yl)-propionic acid Step 1. Preparation of (S)-3-(4-Nitro-phenyl)-8,9-dihydro-6H-[1,4]dioxino[2,3-g]isoquinoline-7,8-dicarboxylic acid 7-tert-butyl ester 8-methyl ester (S)-6,7-Dihydroxy-3,4-dihydro-1H-isoquinoline-2,3-dicarboxylic acid 2-tert-butyl ester 3-methyl ester (3.3 g) and potassium carbonate (2 g) were stirred together in a flask containing 25 mL anhydrous acetone at room temperature under nitrogen atmosphere. After 15 minutes, 2-bromo-1-(4-nitro-phenyl)-ethanone (3.2 g) was added and the mixture was stirred at 60-80° C. for 6 hours. The reaction mixture was diluted with 50 mL of water and 100 mL of ethyl acetate and the layers were separated. The organic layer was washed with water three times and brine once, dried over sodium sulfate and concentrated to provide (S)-3-hydroxy-3-(4-nitro-phenyl)-2,3,8,9-tetrahydro-6H-[1,4]dioxino[2,3-g]isoquinoline-7,8-dicarboxylic acid 7-tert-butyl ester 8-methyl ester (3.1 g), and was dissolved in 25 mL of 1:1 ratio of anhydrous triethylamine and dichloromethane under nitrogen atmosphere. The reaction mixture was cooled to −76 to −40° C. and methanesulfonyl chloride (1.9 g) was added dropwise to maintain internal temperature below -30 to −40° C. The reaction mixture was allowed to warm to room temperature gradually (8-10 hours) and was quenched with 1M sodium carbonate solution (10 mL) and extracted with dichloromethane three times (3×25 mL). The organic layers were washed with water, brine and dried over sodium sulfate and concentrated under reduced pressure. The residue was purified by silica column chromatography and eluted with 7:3 hexanes/EtOAc to give a regioisomeric mixture of (S)-3-(4-Nitro-phenyl)-8,9-dihydro-6H-[1,4]dioxino[2,3-g]isoquinoline-7,8-dicarboxylic acid 7-tert-butyl ester 8-methyl ester (2.0 g). LCMS: (m/z) 469, $^1$H NMR (400 MHz, Acetone-d$_6$): 8.12 (d, 1H), 7.61 (d, 1H), 7.15 (m, 1H), 6.78-6.69 (m, 1H), 5.01-511 (m, 1H), 4.94-4.87 (m, 1H), 4.91-4.81 (m, 1H), 4.64-4.49 (m, 1H), 4.43-4.29 (m, 1H), 3.65-3.58 (m, 3H), 3.18-2.99 (m, 2H), 1.53-1.40 (m, 9H).

Step 2. Preparation of (S)-3-[4-(3,4-Dichloro-benzoylamino)-phenyl]-2,3,8,9-tetrahydro-6H-[1,4]dioxino[2,3-g]isoquinoline-7,8-dicarboxylic acid 7-tert-butyl ester 8-methyl ester (S)-3-(4-Nitro-phenyl)-8,9-dihydro-6H-[1,4]dioxino[2,3-g]isoquinoline-7,8-dicarboxylic acid 7-tert-butyl ester 8-methyl ester (235 mg) was reduced according to General Procedure R to provide (S)-3-(4-amino-phenyl)-8,9-dihydro-6-H-[1,4]dioxino[2,3-g]isoquinoline-7,8-dicarboxylic acid 7-tert-butyl ester 8-methyl ester (160 mg). This was reacted with 3,4-dichlorobenzoyl chloride (152 mg) to give a regioisomeric mixture of (S)-3-[4-(3,4-dichloro-benzoylamino)-phenyl]-8,9-dihydro-6H-[1,4]-dioxino[2,3-g]iso-quinoline-7,8-dicarboxylic acid 7-tert-butyl ester 8-methyl ester (151 mg).

The desired regioisomer was isolated from undesired isomer by repeated silica gel flash column chromatography (hexanes/EtOAc 8:2 to 7:3) and required bottom spot (desired isomer) was treated with activated palladium according to General Procedure Q to give (S)-3-[4-(3,4-dichloro-benzoylamino)-phenyl]-2,3,8,9-tetrahydro-6H-[1,4]dioxino[2,3-g]isoquinoline-7,8-dicarboxylic acid 7-tert-butyl ester 8-methyl ester (26 mg). $^1$H NMR (400 MHz, Acetone-$d_6$): 9.69 (d, 1H), 8.07 (d, 1H), 7.88-7.86 (m, 1H), 7.85-7.77 (m, 1H), 7.62-7.61 (m, 1H), 7.60-7.59 (m, 1H), 7.49-7.47 (m, 1H), 7.39-7.37 (m, 1H), 6.69-6.59 (m, 1H), 5.04-5.02 (m, 1H), 4.65-4.48 (m, 1H), 4.35-4.29 (m, 1H), 4.28-4.26 (m, 1H), 4.19-4.16 (m, 1H), 3.93-3.91 (m, 1H), 3.68-3.65 (m, 1H), 3.54-3.47 (m, 3H), 3.02-2.95 (m, 2H), 1.43-1.33 (m, 9H).

Step 3. Preparation of (S)-2-({(S)-7-(2-Amino-4-methyl-thiazole-5-sulfonyl)-3-[4-(3,4-dichloro-benzoylamino)-phenyl]-2,3,6,7,8,9-hexahydro-[1,4]dioxino[2,3-g]isoquinoline-8-carbonyl}-amino)-3-(4'-cyano-biphenyl-4-yl)-propionic acid Boc-protected amine ester (25 mg) was hydrolyzed according to General Procedure B to provide (S)-3-[4-(3,4-Dichloro-benzoylamino)-phenyl]-2,3,8,9-tetrahydro-6H-[1,4]dioxino[2,3-g]isoquinoline-7,8-dicarboxylic acid 7-tert-butyl ester (19 mg), which was coupled with (S)-2-amino-3-(4'-cyano-biphenyl-4-yl)-propionic acid methyl ester (14 mg) according to General Procedure A to give (S)-8-[(S)-2-(4'-Cyano-biphenyl-4-yl)-1-methoxycarbonyl-ethylcarbamoyl]-3-[4-(3,4-dichloro-benzoylamino)-phenyl]-2,3,8,9-tetrahydro-6H-[1,4]dioxino[2,3-g]isoquinoline-7-carboxylic acid tert-butyl ester (16 mg). This (15 mg) was treated as described in General Procedure C to give (S)-3-(4'-cyano-biphenyl-4-yl)-2-({(S)-3-[4-(3,4-dichloro-benzoylamino)-phenyl]-2,3,6,7,8,9-hexahydro-[1,4]dioxino[2,3-g]isoquinoline-8-carbonyl}-amino)-propionic acid methyl ester hydrochloride salt (10 mg).

The methyl ester hydrochloride (10 mg) was reacted with 2-acetylamino-4-methyl thiazole-5-sulfonyl chloride (7 mg) according to General Procedure E. The resulting (S)-2-({(S)-7-(2-Acetylamino-4-methyl-thiazole-5-sulfonyl)-3-[4-(3,4-dichloro-benzoylamino)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (8 mg) was hydrolyzed according to General Procedures N and B to give the title compound. LCMS: (m/z) 924.

Example 55

(S)-3-(4'-Cyano-biphenyl-4-yl)-2-({(S)-7-[2-(cyclobutanecarbonyl-amino)-4-methyl-thiazole-5-sulfonyl]-3-[4-(3,4-dichloro-benzyloxy)-phenyl]-2,3,6,7,8,9-hexahydro[1,4]dioxino[2,3-g]isoquinoline-8-carbonyl}-amino)-propionic acid The title compound (12 mg) was prepared from (S)-2-({(S)-7-(2-Amino-4-methyl-thiazole-5-sulfonyl)-3-[4-(3,4-dichloro-benzyloxy)-phenyl]-2,3,6,7,8,9 -hexahydro-[1,4] dioxino[2,3-g]isoquinoline-8-carbonyl}-amino)-3-(4'-cyano-biphenyl-4-yl)-propionic acid methyl ester (23 mg) according to General Procedures F and B. LCMS: (m/z) 993.

Example 56

(S)-3-(4'-Cyano-biphenyl-4-yl)-2-({(S)-7-[2-(cyclopropanecarbonyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid The title compound (11 mg) was prepared from (S)-2-({(S)-7-(2-amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (23 mg) according to General Procedures F and B. LCMS: (m/z) 979.

Example 57

(S)-2-({(S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-biphenyl-4-yl-propionic acid (S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester (59 mg) was coupled with (S)-2-amino-3-biphenyl-4-yl-propionic acid methyl ester (31 mg) according to General Procedure A. The resulting Boc-protected amine was treated as described in General Procedure C to give (S)-3-Biphenyl-4-yl-2-({(S)-3-[4-(3,4-dichloro-benzyloxy)-phenyl]-2,3,6,7,8,9-hexahydro-[1,4]dioxino-[2,3-g]isoquinoline-8-carbonyl}-amino)-propionic acid methyl ester hydrochloride salt (43 mg).

The methyl ester hydrochloride salt (36 mg) was reacted with 2-acetylamino-4-methyl thiazole-5-sulfonyl chloride (26 mg) according to General Procedure E. The resulting (S)-2-({(S)-7-(2-acetylamino-4-methyl-thiazole-5-sulfonyl)-3-[4-(3,4-dichloro-benzyloxy)-phenyl-]-2,3,6,7,8,9-hexahydro-[1,4]dioxino[2,3-g]isoquinoline-8-carbonyl}-amino)-3-biphenyl-4-yl-propionic acid methyl ester (32 mg) was hydrolyzed according to General Procedures N and B to give the title compound (14 mg). LCMS: (m/z) 887.

Example 58

(S)-2-({(S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-5-(4-cyano-phenyl)-pent-4-ynoic acid (S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester (59 mg) was coupled with (S)-propargyl-glycinemethylester hydrochloride (20 mg) according to General Procedure A. The resulting (S)-3-[4-(3,4-dichloro-benzyloxy)-phenyl]-8-((S)-1-methoxycarbonyl-but-3-ynylcarbamoyl)-2,3,8,9-tetrahydro-6H-[1,4]dioxino[2,3-g]isoquinoline-7-carboxylic acid tert-butyl ester (26 mg) was reacted with 4-iodobenzonitrile (7 mg) according to General Procedure S to give (S)-8-[(S)-4-(4-cyano-phenyl)-1 methoxycarbonyl-but-3-ynylcarbamoyl]-3-[4-(3,4-dichlorobenzyloxy)-phenyl]-2,3,8,9-tetrahydro-6H-[1,4]dioxino[2,3-g]isoquinoline-7-carboxylic acid tert-butyl ester (12 mg).

The Boc-protected amine ester was treated as described in General Procedure C and resulting methylester hydrochloride salt (11 mg) was reacted with 2-acetylamino-4-methyl thiazole-5-sulfonyl chloride (8 mg) according to General Procedure E to obtain (S)-2-({(S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-5-(4-cyano-phenyl)-pent-4-ynoic acid methyl ester (10 mg). This was hydrolyzed according to General Procedures N and B to give the title compound. LCMS: (m/z) 860.

Example 59

(S)-2-({(3R,8S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (3R,8S)-3-[4-(3,4-Dichloro-benzyloxy)-phenyl]-2,3,8,9-tetrahydro-6H-[1,4]dioxino[2,3-g]isoquinoline-7,8-dicarboxylic acid 7-tert-butyl ester 8-methyl ester (200 mg) was hydrolyzed according to General Procedure B. The resulting (3R,8S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester (172 mg) was coupled with (S)-2-amino-3-(4'-cyano-biphenyl-4-yl)-propionic acid methyl ester (126 mg) according to General Procedure A to give (3R,8S)-8-[(S)-2-(4'-cyano-biphenyl-4-yl)-1-methoxycarbonyl-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid tert-butyl ester (191 mg). Boc-cyano-biphenyl ester (188 mg) was treated as described in General Procedure C to give (S)-3-(4'-cyano-biphenyl-4-yl)-2-({(3R,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride salt (155 mg). LCMS: (m/z) 749; $^1$H NMR (400 MHz, Methanol-d$_6$): 8.54 (d, 1H), 7.95 (s, 1H), 7.87 (d, 1H), 7.81-7.72 (m, 2H), 7.63-51 (m, 4H), 7.50-7.47 (m, 2H), 7.38-7.32 (m, 3H), 7.01 (d, 2H), 6.99 (d, 2H), 5.07 (s, 2H) 5.04-5.03 (m, 1H), 4.34-4.31 (m, 1H), 4.12-4.08 (m, 1H), 4.01-3.96 (m, 3H), 3.75 (s, 3H), 3.74-3.63 (m, 4H), 3.11-2.97 (m, 2H).

(S)-3-(4'-Cyano-biphenyl-4-yl)-2-({(3R,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (94 mg) was reacted with 2-acetylamino-4-methyl thiazole-5-sulfonyl chloride (64 mg) according to General Procedure E to obtain (S)-2-({(3R,8S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (16 mg). This was hydrolyzed according to General Procedure B to give the title compound (11 mg). LCMS: (m/z) 955. $^1$H NMR (400 MHz, DMSO-d$_6$): 7.80-7.75 (m, 4H), 7.71 (d, 1H), 7.66-7.64 (m, 3H), 7.54 (d, 2H), 7.45 (d, 1H), 7.32 (d, 2H), 7.10 (d, 1H), 7.04-7.02 (m, 2H), 6.72 (s, 1H), 6.63 (s, 1H), 5.57-5.56 (m, 2H), 5.53-5.52 (m, 1H), 5.14 (s, 2H) 5.02-4.99 (m, 1H), 4.55-4.53 (m, 1H), 4.35-4.29 (m, 1H), 4.27-4.20 (m, 3H), 3.94-3.89 (m, 1H), 3.74-3.70 (m, 2H), 2.95-2.92 (m, 1H), 2.48 (s, 3H).

Example 60

(S)-2-({(3R,8S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-2-({(3R,8S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (29 mg) was prepared from (S)-2-({(3R,8S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (49 mg) following General Procedure N. LCMS: (m/z) 924.

The title compound (14 mg) was prepared from (S)-2-({(3R,8S)-7-(2-amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (20 mg) according to General Procedure B. LCMS: (m/z) 912. $^1$H NMR (400 MHz, DMSO-d$_6$): 7.76-7.64 (m, 4H), 7.45 (d, 1H), 7.44 (d, 2H), 7.43 (d, 2H), 7.38 (d, 2H), 7.04 (d, 2H), 6.90 (d, 2H), 6.72 (s, 1H), 6.69 (s, 1H), 5.14 (s, 2H), 5.0-4.98 (m 1H), 4.40-4.39 (m, 1 H), 4.30-4.13 (m 3H), 4.08-3.95 (m, 2H), 3.10-3.0 (m, 1 H), 2.68-2.63 (m, 4 H), 2.22 (s, 3 H).

Example 61

(S)-3-(4'-Cyano-biphenyl-4-yl)-2-{[(3R,8S)-3-[4-(3,4-dichloro-benzyloxy)-phenyl]-7-(4-methyl-2-methylamino-thiazole-5-sulfonyl)-2,3,6,7,8,9-hexahydro-[1,4]dioxino[2,3-g]isoquinoline-8-carbonyl]-amino}-propionic acid (S)-2-({(3R,8S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (49 mg) was reacted with methyl iodide (15 mg) according to General Procedure T to obtain (S)-2-({(3R,8S)-7-[2-(acetyl-methyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester. This was hydrolyzed according to General Procedures N and B to give the title compound (11 mg). LCMS: (m/z) 924.

Example 62

(S)-3-(4'-Cyano-biphenyl-4-yl)-2-{[(3R,8S)-3-[4-(3,4-dichloro-benzyloxy)-phenyl]-7-(2-ethylamino-4-methyl-thiazole-5-sulfonyl)-2,3,6,7,8,9-hexahydro-[1,4]dioxino[2,3-g]isoquinoline-8-carbonyl]-amino}-propionic acid (S)-2-({(3R,8S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (49 mg) was reacted with ethyl iodide (16 mg) according to General Procedure T to obtain (S)-2-({(3R,8S)-7-[2-(acetyl-ethyl-amino)-4-methyl-thiazole-5-sulfonyl]-3-[4-(3,4-dichloro-benzyloxy)-phenyl]-2,3,6,7,8,9-hexahydro-[1,4]

dioxino[2,3-g]isoquinoline-8-carbonyl}-amino)-3-(4'-cyano-biphenyl-4-yl)-propionic acid methyl ester. This was hydrolyzed according to General Procedures N and B to give the title compound (17 mg). LCMS: (m/z) 938.

Example 63

(S)-2-{[(S)-3-[4-(3-Chloro-4-methyl-benzyloxy)-phenyl]-7-(2-ethylamino-4-methyl-thiazole-5-sulfonyl)-2,3,6,7,8,9-hexahydro-[1,4]dioxino[2,3-g]isoquinoline-8-carbonyl]-amino}-3-(4'-cyano-biphenyl-4-yl)-propionic acid (S)-2-({(S)-7-(2-Acetylamino-4-methyl-thiazole-5-sulfonyl)-3-[4-(3-chloro-4-methyl-benzyloxy)-phenyl]-2,3,6,7,8,9-hexahydro-[1,4]-dioxino-[2,3-g]isoquinoline-8-carbonyl}-amino)-3-(4'-cyano-biphenyl-4-yl)-propionic acid methyl ester (24 mg) was reacted with bromoethane (6 mg) according to General Procedure T to obtain (S)-2-({(S)-7-[2-(Acetyl-ethyl-amino)-4-methyl-thiazole-5-sulfonyl]-3-[4-(3-chloro-4-methyl-benzyloxy)-phenyl]2,3,6,7,8,9-hexahydro-[1,4]-dioxino-[2,3g]-isoquinoline-8-carbonyl}-amino)-3-(4'-cyano-biphenyl-4-yl)-propionic acid methyl ester. This was hydrolyzed according to General Procedures N and B to give the title compound (9 mg). LCMS: (m/z) 918.

Example 64

(S)-2-({(S)-3-[4-(3-Chloro-4-methyl-benzyloxy)-phenyl]-7-[2-(cyclopentylmethyl-amino)-4-methyl-thiazole-5-sulfonyl]-2,3,6,7,8,9-hexahydro-[1,4]dioxino[2,3g]isoquinoline-8-carbonyl}-amino)-3-(4'-cyano-biphenyl-4-yl)-propionic acid (S)-2-({(S)-7-(2-Acetylamino-4-methyl-thiazole-5-sulfonyl)-3-[4-(3-chloro-4-methyl-benzyloxy)-phenyl]-2,3,6,7,8,9-hexahydro-[1,4]-dioxino-[2,3-g]isoquinoline-8-carbonyl}-amino)-3-(4'-cyano-biphenyl-4-yl)-propionic acid methyl ester (24 mg) was reacted with iodomethyl cyclopentane (11 mg) according to General Procedure T to obtain (S)-2-({(S)-7-[2-(Acetyl-cyclopentylmethyl-amino)-4-methyl-thiazole-5-sulfonyl]-3-[4-(3-chloro-4-methyl-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester. This was hydrolyzed according to General Procedures N and B to give the title compound. LCMS: (m/z) 972.

Example 65

(S)-2-({(S)-7-(2-Amino-4-methyl-thiazole-5-sulfonyl)-3-[4-(3-chloro-4-methyl-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-3-(4-Hydroxy-phenyl)-2,3,8,9-tetrahydro-6H-[1,4]dioxin-[2,3-g]isoquinoline-7,8-dicarboxylic acid 7-tert-butyl ester 8-methyl ester (55 mg) was reacted with 3 chloro-4-methylbenzylchloride (32 mg) according to General Procedure T to give O-3-chloro-4-methylester ((S)-3-[4-(3-chloro-4-methyl-benzyloxy)-phenyl]-2,3,8,9-tetrahydro-6H-[1,4]dioxino[2,3-g]isoquinoline-7,8-dicarboxylic acid 7-tert-butyl ester 8-methyl ester). The Boc-4-cyano-biphenyl coupled product is formed from ester according to General Procedures B and A. The Boc-protected amine was treated as described in General Procedure C to give the amine hydrochloride ((S)-2-({(S)-3-[4-(3-Chloro-4-methyl-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester hydrochloride) (16 mg).

(S)-2-({(S)-3-[4-(3-Chloro-4-methyl-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester hydrochloride (15 mg) was reacted with 2-acetylamino-4-methyl thiazole-5-sulfonyl chloride (11 mg) according to General Procedure E to give (S)-2-({(S)-7-(2-acetylamino-4-methyl-thiazole-5-sulfonyl)-3-[4-(3-chloro-4-methyl-benzyloxy)-phenyl]-2,3,6,7,8,9-hexahydro[1,4]dioxino[2,3-g]isoquinoline-8-carbonyl}-amino)-3-(4'-cyano-biphenyl-4-yl)propionic acid methyl ester (11 mg), which was hydrolyzed according to General Procedures N and B to give the title compound (5 mg). LCMS: (m/z) 893.

Example 66

(S)-2-({(S)-7-(2-Amino-4-methyl-thiazole-5-sulfonyl)-3-[4-(3,4-dimethyl-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-3-(4-Hydroxy-phenyl)-2,3,8,9-tetrahydro-6H-[1,4]dioxin-[2,3-g]isoquinoline-7,8-dicarboxylic acid 7-tert-butyl ester 8-methyl ester (55 mg) was reacted with 3,4-dimethyl-benzylchloride (28 mg) according to General Procedure T to give O-3,4-dimethyl-ester ((S)-3-[4-(3,4-dimethyl-benzyloxy)-phenyl]-2,3,8,9-tetrahydro-6H-[1,4]dioxino[2,3-g]isoquinoline-7,8-dicarboxylic acid 7-tert-butyl ester 8-methyl ester). The Boc-4-cyano-biphenyl coupled product is formed from the ester according to General Procedures B and A. The Boc-protected amine was treated according to General Procedure C to give the amine hydrochloride ((S)-3-(4'-cyano-biphenyl-4-yl)-2-({(S)-3-[4-(3,4-dimethyl-benzyloxy)-phenyl]-2,3,6,7,8,9-hexahydro-[1,4]dioxino-[2,3-g]isoquinoline-8-carbonyl}-amino)-propionic acid methyl ester hydrochloride) (12 mg).

(S)-3-(4'-Cyano-biphenyl-4-yl)-2-({(S)-3-[4-(3,4-dimethyl-benzyloxy)-phenyl]-2,3,6,7,8,9-hexahydro-[1,4]dioxino[2,3-g]isoquinoline-8-carbonyl}-amino)-propionic acid methyl ester hydrochloride (11 mg) was reacted with 2-acetylamino-4-methyl thiazole-5-sulfonyl chloride (9 mg) according to General Procedure E to give (S)-2-({(S)-7-(2-acetylamino-4-methyl-thiazole-5-sulfonyl)-3-[4-(3,4-dimethyl-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (10 mg). This was hydrolyzed according to General Procedures N and B to give the title compound (3 mg). LCMS: (m/z) 870.

Example 67

(S)-2-{[(S)-7-(2-Amino-4-methyl-thiazole-5-sulfonyl)-3-(4-ethoxy-phenyl)-2,3,6,7,8,9-hexahydro-[1,4]dioxino[2,3-g]isoquinoline-8-carbonyl]-amino}-3-(4'-cyano-biphenyl-4-yl)-propionic acid (S)-3-[4-(3,4-Dichloro-benzyloxy)-phenyl]-8,9-dihydro-6H-[1,4]dioxino-[2,3-g]isoquinoline-7,8-dicarboxylicacid 7-tert-butyl ester 8-methyl ester (299 mg) was reduced and debezylated according to General Procedure Q to give (S)-3-(4-Hydroxy-phenyl)-2,3,8,9-tetrahydro-6H-[1,4]dioxin-[2,3-g]isoquinoline-7,8-dicarboxylic acid 7-tert-butyl ester 8-methyl ester (55 mg). This was reacted with bromoethane (21 mg) according to General Procedure T to give an O-ethyl-ester. The Boc-4-cyano-biphenyl coupled product was formed from ester according to General Procedures B and A. The Boc-protected amine was treated as described in General Procedure C to give the amine hydrochloride (21 mg).

(S)-3-(4'-Cyano-biphenyl-4-yl)-2-{[(S)-3-(4-ethoxy-phenyl)-2,3,6,7,8,9-hexahydro-[1,4]dioxino[2,3-g]isoquinoline-8-carbonyl]-amino}-propionic acid methyl ester hydrochloride (18 mg) was reacted with 2-acetylamino-4-methyl thiazole-5-sulfonyl chloride (11 mg) according to General Procedure E to give (S)-2-{[(S)-7-(2-acetylamino-4-methyl-thiazole-5-sulfonyl)-3-(4-ethoxy-phenyl)-2,3,6,7,8,9-hexahydro-[1,4]dioxino[2,3-g]isoquinoline-8-carbonyl]-amino}-3-(4'-cyano-biphenyl-4-yl)-propionic acid methyl ester (17 mg). This was hydrolyzed according to General Procedures N and B to give the title compound (5 mg). LCMS: (m/z) 783.

Example 68

(S)-2-{[(S)-7-(2-Amino-4-methyl-thiazole-5-sulfonyl)-3-(4-benzyloxy-phenyl)-2,3,6,7,8,9-hexahydro-[1,4]dioxino[2,3-g]isoquinoline-8-carbonyl]-amino}-3-(4'-cyano-biphenyl-4-yl)-propionic acid (S)-3-(4-Hydroxy-phenyl)-2,3,8,9-tetrahydro-6H-[1,4]-dioxin-[2,3-g]isoquinoline-7,8-dicarboxylic acid 7-tert-butyl ester 8-methyl ester (55 mg) was reacted with benzylbromide (32 mg) according to General Procedure T to give O-benzyl-ester ((S)-3-(4-benzyloxy-phenyl)-2,3,8,9-tetrahydro-6H [1,4]dioxino[2,3g]iso-quinoline-7,8-dicarboxylic acid 7-tert-butyl ester 8-methyl ester). The Boc-4-cyano-biphenyl coupled product was formed from ester according to General Procedures B and A. The Boc-protected amine was treated as described in General Procedure C to give the amine hydrochloride ((S)-2-{[(S)-3-(4-Benzyloxy-phenyl)-2,3,6,7,8,9-hexahydro-[1,4]dioxino-[2,3g]-isoquinoline-8-carbonyl]-amino}-3-(4'-cyano-biphenyl-4-yl)-propionic acid methyl ester hydrochloride) (20 mg).

(S)-2-{[(S)-3-(4-Benzyloxy-phenyl)-2,3,6,7,8,9-hexahydro-[1,4]dioxino-[2,3g]-isoquinoline-8-carbonyl]-amino}-3-(4'-cyano-biphenyl-4-yl)-propionic acid methyl ester hydrochloride was reacted with 2-acetylamino-4-methyl thiazole-5-sulfonyl chloride according to General Procedure E. The resulting (S)-2-{[(S)-7-(2-Acetylamino-4-methyl-thiazole-5-sulfonyl)-3-(4-benzyloxy-phenyl)-2,3,6,7,8,9-hexahydro-[1,4]dioxino[2,3-g]isoquinoline-8-carbonyl]-amino}-3-(4'-cyano-biphenyl-4-yl)-propionic acid methyl ester (18 mg) was hydrolyzed according to General Procedures N and B to the title compound (5 mg). LCMS (m/z) 843.

Example 69

(S)-2-{[(S)-7-(2-Amino-4-methyl-thiazole-5-sulfonyl)-3-(4-cyclopentylmethoxy-phenyl)-2,3,6,7,8,9-hexahydro-[1,4]dioxino[2,3-g]isoquinoline-8-carbonyl]-amino}-3-(4'-cyano-biphenyl-4-yl)-propionic acid (S)-3-(4-Hydroxy-phenyl)-2,3,8,9-tetrahydro-6H-[1,4]di-oxin-[2,3-g]isoquinoline-7,8-dicarboxylic acid 7-tert-butyl ester 8-methyl ester (55 mg) was reacted with iodomethyl-cyclopentane (38 mg) according to General Procedure T to give O-cyclopentyl-ester ((S)-3-(4-cyclopentylmethoxy-phenyl)-2,3,8,9-tetrahydro-6H-[1,4]dioxino[2,3-g]isoquinoline-7,8-dicarboxylic acid 7-tert-butyl ester 8-methyl ester). The Boc-4-cyano-biphenyl coupled product was formed from ester according to General Procedures B and A. The Boc-protected amine was treated according to General Procedure C to give an amine hydrochloride ((S)-3-(4'-cyano-biphenyl-4-yl)-2-{[(S)-3-(4-cyclopentylmethoxy-phenyl)-2,3,6,7,8,9-hexahydro-[1,4]dioxino[2,3-g]isoquinoline-8-carbonyl]-amino}-propionic acid methylester hydrochloride) (21 mg).

(S)-3-(4'-Cyano-biphenyl-4-yl)-2-{[(S)-3-(4-cyclopentylmethoxy-phenyl)-2,3,6,7,8,9-hexahydro-[1,4]dioxino[2,3-g]isoquinoline-8-carbonyl]-amino}-propionic acid methyl-ester hydrochloride (18 mg) was reacted with 2-acetylamino-4-methyl thiazole-5-sulfonyl chloride (11 mg) according to General Procedure E to give (S)-2-{[(S)-7-(2-acetylamino-4-methyl-thiazole-5-sulfonyl)-3-(4-cyclopentylmethoxy-phenyl)-2,3,6,7,8,9-hexahydro-[1,4]dioxino[2,3-g]isoquinoline-8-carbonyl]-amino}-3-(4'-cyano-biphenyl-4-yl)-propionic acid methyl ester (17 mg). This was hydrolyzed according to General Procedures N and B to give the title compound (4.5 mg). LCMS: (m/z) 835.

Example 70

(S)-3-(4'-Cyano-biphenyl-4-yl)-2-({(S)-3-[4-(3,4-dichloro-benzyloxy)-phenyl]-7-[4-methyl-2-(2,2,2-trifluoro-acetylamino)-thiazole-5-sulfonyl]-2,3,6,7,8,9-hexahydro-[1,4]dioxino[2,3-g]isoquinoline-8-carbonyl}-amino)-propionic acid The title compound (16 mg) was prepared from (S)-2-({(S)-7-(2-Amino-4-methyl-thiazole-5-sulfonyl)-3-[4-(3,4-dichloro-benzyloxy)-phenyl]-2,3,6,7,8,9-hexahydro-[1,4] dioxino[2,3-g]isoquinoline-8-carbonyl}-amino)-3-(4'-cyano-biphenyl-4-yl)-propionic acid methyl ester (30 mg) and trifluoroacetic anhydride according to General Procedures F and B. LCMS (m/z): 1007.

Example 71

(S)-3-(4'-Cyano-biphenyl-4-yl)-2-[((S)-3-[4-(3,4-dichloro-benzyloxy)-phenyl]-7-{4-methyl-2-[((S)-pyrrolidine-2-carbonyl)-amino]-thiazole-5-sulfonyl}-2,3,6,7,8,9-hexahydro-[1,4]dioxino[2,3-g] isoquinoline-8-carbonylamino]-propionic acid The title compound (18 mg) was prepared from (S)-2-({(S)-7-(2-Amino-4-methyl-thiazole-5-sulfonyl)-3-[4-(3,4-dichloro-benzyloxy)-phenyl]-2,3,6,7,8,9-hexahydro-[1,4] dioxino[2,3-g]isoquinoline-8-carbonyl}-amino)-3-(4'-cyano-biphenyl-4-yl)-propionic acid methyl ester and boc-L-proline according to General Procedures L, C, and B. LCMS (m/z): 1008.

Example 72

(S)-3-(4'-Cyano-biphenyl-4-yl)-2-{[(3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-propionic acid The title compound (193 mg) was prepared from (3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carboxylic acid (272 mg) and (S)-2-amino-3-(4'-cyano-biphenyl-4-yl)-propionic acid methyl ester hydrochloride according to General Procedures L and B. LCMS (m/z): 853.

Example 73

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-(4-pyridin-4-yl-phenyl)-propionic acid The title compound (19 mg) was prepared from (3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carboxylic acid (30 mg) and (S)-2-amino-3-(4-pyridin-4-yl-phenyl)-propionic acid methyl ester hydrochloride according to General Procedures L and B. LCMS (m/z): 829.

Example 74

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-(4'-fluoro-biphenyl-4-yl)-propionic acid The title compound (14 mg) was prepared from (3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carboxylic acid (30 mg) and (S)-2-amino-3-(4'-fluoro-biphenyl-4-yl)-propionic acid methyl ester hydrochloride according to General Procedures L and B. LCMS (m/z): 846.

Example 75

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-(4'-methoxy-biphenyl-4-yl)-propionic acid The title compound (16 mg) was prepared from (3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carboxylic acid (30 mg) and (S)-2-amino-3-(4'-methoxy-biphenyl-4-yl)-propionic acid methyl ester hydrochloride according to General Procedures L and B. LCMS (m/z): 858.

Example 76

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-(4'-methyl-biphenyl-4-yl)-propionic acid The title compound (19 mg) was prepared from (3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carboxylic acid (30 mg) and (S)-2-amino-3-(4'-methyl-biphenyl-4-yl)-propionic acid methyl ester hydrochloride according to General Procedures L and B. LCMS (m/z): 842.

Example 77

(S)-3-(4'-Chloro-biphenyl-4-yl)-2-{[(3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-propionic acid The title compound (16 mg) was prepared from (3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carboxylic acid (30 mg) and (S)-2-amino-3-(4'-chloro-biphenyl-4-yl)-propionic acid methyl ester hydrochloride according to General Procedures L and B. LCMS (m/z): 862.

Example 78

(S)-3-(4'-Cyano-biphenyl-4-yl)-2-({(S)-7-(6-cyclopentylamino-2-methyl-pyridine-3-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid The title compound (4 mg) was prepared from (S)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (79 mg) with 6-chloro-pyridine-3-sulfonyl chloride and cyclopentylamine according to General Procedures E, U and B in order. LCMS (m/z): 974.

Example 79

(S)-3-(4'-Cyano-biphenyl-4-yl)-2-({(S)-3-[4-(3,4-dichloro-benzyloxy)-phenyl]-7-isopropyl-2,3,6,7,8,9-hexahydro-[1,4]dioxino[2,3-g]isoquinoline-8-carbonyl}-amino)-propionic acid (S)-2-amino-3-{2-[4-(3,4-dichloro-benzyloxy)-phenyl]-2,3-dihydro-benzo[1,4]dioxin-6-yl}-propionic acid methyl ester hydrochloride (105 mg) was converted to (S)-3-{2-[4-(3,4-dichloro-benzyloxy)-phenyl]-2,3-dihydro-benzo[1,4]dioxin-6-yl}-2-isopropylamino-propionic acid methyl ester according to General Procedure M. This ester (150 mg) was converted to (S)-3-[4-(3,4-dichloro-benzyloxy)-phenyl]-7-isopropyl-2,3,6,7,8,9-hexahydro-[1,4]dioxino[2,3-g]isoquinoline-8-carboxylic acid methyl ester according to General Procedure V. This compound (70 mg) upon hydrolysis followed by amide coupling according to General Procedures B and L gave ((S)-3-(4'-cyano-biphenyl-4-yl)-2-({(S)-3-[4-(3,4-dichloro-benzyloxy)-phenyl]-7-isopropyl-2,3,6,7,8,9-hexahydro-[1,4]dioxino[2,3-g]isoquinoline-8-carbonyl}-amino)-propionic acid methyl ester LCMS (m/z)=792. This ester (25 mg), on hydrolysis according to General Procedure B, gave the title compound (20 mg). LCMS (m/z): 777.

Example 80

(S)-2-({(3S,8S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (S)-2-({(3S,8S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (340 mg) was converted to the title compound (282 mg)

using General Procedure N. LCMS (m/z): 926. $^1$H NMR (400 MHz, Acetone-d$_6$): 7.83 (m, 4H), 7.71 (d, 1H), 7.65 (m, 3H), 7.48 (m, 2H), 7.36 (m, 2H), 7.11 (d, 1H), 7.06 (s, 1H), 7.0 (m, 2H), 6.77 (s, 1H), 6.69 (s, 1H), 5.18 (s, 2H) 5.09 (m, 1H), 4.71 (m, 1H), 4.56 (m, 1H), 4.31 (m, 3H), 3.93 (m, 1H), 3.68 (s, 3H), 3.04-3.18 (m, 2H), 2.82 (m, 1H), 2.34 (s, 3H).

Example 81

(S)-2-({(3S,8S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-2-({(3S,8S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (50 mg), upon hydrolysis according to General Procedure B, gave the title compound (42 mg). LCMS (m/z): 910. $^1$H NMR (400 MHz, DMSO-d$_6$): 12.9 (bs, 1H), 8.06 (d, 1H), 7.83 (m, 4H), 7.71 (d, 1H), 7.64 (d, 2 H), 7.59 (d, 2 H), 7.44 (m, 2 H), 7.30 (d, 2 H), 7.16 (d, 2 H), 6.98 (d, 2 H), 6.74 (s, 1 H), 6.63 (s, 1 H), 5.12 (s, 2H) 5.07 (m, 1H), 4.49 (m, 1 H), 4.38 (m, 1H), 4.30 (m, 3 H), 3.91 (m, 1 H), 2.74-3.08 (m, 4 H), 2.47 (s, 3 H).

Example 82

(S)-3-(4'-Cyano-biphenyl-4-yl)-2-({(S)-7-[2-(cyclopentanecarbonyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid (S)-2-({(S)-7-(2-amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (30 mg) was reacted with cyclopentanecarbonyl chloride according to General Procedure F to furnish (S)-3-(4'-cyano-biphenyl-4-yl)-2-({(S)-7-[2-(cyclopentanecarbonyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester. This ester (25 mg), upon hydrolysis according to General Procedure B, gave the title compound (21 mg). LCMS (m/z): 1009.

Example 83

4-(5-{(S)-8-[(S)-1-Carboxy-2-(4'-cyano-biphenyl-4-yl)-ethylcarbamoyl]-3-[4-(3,4-dichloro-benzyloxy)-phenyl]-2,3,8,9-tetrahydro-6H-[1,4]dioxino[2,3-g]isoquinoline-7-sulfonyl}-4-methyl-thiazol-2-ylcarbamoyl)-piperidine-1-carboxylic acid tert-butyl ester To a solution of piperidine-1,4-dicarboxylic acid mono-tert-butyl ester (75 mg) was added EDCl (31 mg) in 1:1 mixture of DCM/THF (4 mL), and the reaction mixture was stirred at room temperature for 15 minutes. To this solution was added (S)-2-({(S)-7-(2-amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (30 mg) and the mixture was heated at 50° C. for 24 hours. The mixture was concentrated and the residue was purified by flash chromatography to furnish 4-(5-{(S)-8-((S)-2-(4'-cyano-biphenyl-4-yl-1-methoxycarbonyl-ethylcarbamoyl)-3-[4-(3,4-dichloro-benzyloxy)-phenyl]-2,3,8,9-tetrahydro-6H-[1,4]dioxino[2,3-g]isoquinoline-7-sulfonyl}-4-methyl-thiazol-2-ylcarbamoyl)-piperidine-1-carboxylic acid tert-butyl ester. This ester (30 mg), upon hydrolysis according to General Procedure B, gave the title compound (24 mg). LCMS (m/z): 1023.

Example 84

((S)-3-(4'-Cyano-biphenyl-4-yl)-2-({(S)-3-[4-(3,4-dichloro-benzyloxy)-phenyl]-7-[2-(3-ethyl-ureido)-5-methyl-thiazole-4-sulfonyl]-2,3,6,7,8,9-hexahydro-[1,4]dioxino[2,3-g]isoquinoline-8-carbonyl}-amino)-propionic acid (S)-2-({(S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (50 mg) was reacted with ethyl isocyanate to give (S)-3-(4'-cyano-biphenyl-4-yl)-2-({(S)-3-[4-(3,4-dichloro-benzyloxy)-phenyl]-7-[2-(3-ethyl-ureido)-5-methyl-thiazole-4-sulfonyl]-2,3,6,7,8,9-hexahydro-[1,4]dioxino[2,3-g]isoquinoline-8-carbonyl}-amino)-propionic acid methyl ester according to General Procedure I. This product (20 mg) was hydrolyzed according to General Procedure B to give the title compound. LCMS (m/z): 983.

Example 85

(S)-3-(4'-Cyano-biphenyl-4-yl)-2-{[(3S,8S)-3-[4-(3,4-dichloro-benzyloxy)-phenyl]-7-(4-methyl-2-methylamino-thiazole-5-sulfonyl)-2,3,6,7,8,9-hexahydro-[1,4]dioxino[2,3-g]isoquinoline-8-carbonyl]-amino}-propionic acid (S)-2-({(3S,8S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (29 mg) was reacted with methyl iodide and K$_2$CO$_3$ in DMF to give (S)-2-({(3S,8S)-7-[2-(acetyl-methyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (LCMS (m/z): 982) according to General Procedure O. This product (26 mg) was hydrolyzed according to General Procedure B to furnish the title compound (22 mg). LCMS (m/z): 0.924.

The compounds identified in Examples 86-92, below, were prepared using synthetic procedures analogous to those used for the synthesis of the compound of Example 85.

Example 86

(S)-3-(4'-Cyano-biphenyl-4-yl)-2-{[(3S,8S)-3-[4-(3,4-dichloro-benzyloxy)-phenyl]-7-(2-ethylamino-4-methyl-thiazole-5-sulfonyl)-2,3,6,7,8,9-hexahydro-[1,4]dioxino[2,3-g]isoquinoline-8-carbonyl]-amino}-propionic acid

Example 87

(S)-3-(4'-Cyano-biphenyl-4-yl)-2-{[(S)-3-[4-(3,4-dichloro-benzyloxy)-phenyl]-7-(4-methyl-2-propylamino-thiazole-5-sulfonyl)-2,3,6,7,8,9-hexahydro-[1,4]dioxino[2,3-g]isoquinoline-8-carbonyl]-amino}-propionic acid

Example 88

(S)-3-(4'-Cyano-biphenyl-4-yl)-2-({(S)-7-[2-(cyclopropylmethyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid

Example 89

(S)-3-(4'-Cyano-biphenyl-4-yl)-2-({(3S,8S)-7-[2-(cyclohexylmethyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid

Example 90

(S)-3-(4'-Cyano-biphenyl-4-yl)-2-({(3S,8S)-7-[2-(cyclopentylmethyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid

Example 91

(S)-3-(4'-Cyano-biphenyl-4-yl)-2-{[(3S,8S)-3-[4-(3,4-dichloro-benzyloxy)-phenyl]-7-(2-isobutylamino-4-methyl-thiazole-5-sulfonyl)-2,3,6,7,8,9-hexahydro-[1,4]dioxino[2,3-g]isoquinoline-8-carbonyl]-amino}-propionic acid

Example 92

(S)-3-(4'-Cyano-biphenyl-4-yl)-2-({(3S,8S)-3-[4-(3,4-dichloro-benzyloxy)-phenyl]-7-[2-(2-methoxy-ethylamino)-4-methyl-thiazole-5-sulfonyl]-2,3,6,7,8,9-hexahydro-[1,4]dioxino[2,3-g]isoquinoline-8-carbonyl}-amino)-propionic acid

Example 93

(S)-3-(4'-Cyano-biphenyl-4-yl)-2-{[(S)-3-[4-(3,4-dichloro-benzyloxy)-phenyl]-7-(4-methyl-2-morpholin-4-yl-thiazole-5-sulfonyl)-2,3,6,7,8,9-hexahydro-[1,4]dioxino[2,3-g]isoquinoline-8-carbonyl]-amino}-propionic acid (S)-2-({(S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (30 mg) was reacted with 1-bromo-2-(2-bromo-ethoxy)-ethane and $K_2CO_3$ in DMF according to General Procedure O to give (S)-2-({(S)-7-{2-[2-(2-acetyl-2-bromo-ethoxy)-ethylamino]-4-methyl-thiazole-5-sulfonyl}-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester. This product was deacylated according to General Procedure N to give (S)-2-({(S)-7-{2-[2-(2-bromo-ethoxy)-ethylamino]-4-methyl-thiazole-5-sulfonyl}-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester. This intermediate was cyclized using $K_2CO_3$ in DMF at 50° C. to give (S)-3-(4'-cyano-biphenyl-4-yl)-2-{[(S)-3-[4-(3,4-dichloro-benzyloxy)-phenyl]-7-(4-methyl-2-morpholin-4-yl-thiazole-5-sulfonyl)-2,3,6,7,8,9-hexahydro-[1,4]dioxino[2,3-g]isoquinoline-8-carbonyl]-amino}-propionic acid methyl ester (16 mg) (LCMS (m/z): 997). This ester, upon hydrolysis according to General Procedure B, gave the title compound (12 mg). LCMS (m/z): 984.

Example 94

(S)-2-({(S)-7-(2-Acetylamino-5-methyl-thiazole-4-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (130 mg) was reacted with 2-acetylamino-5-methyl-thiazole-4-sulfonyl chloride (54 mg) to furnish (S)-2-({(S)-7-(2-acetylamino-5-methyl-thiazole-4-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (LCMS m/z: 965) according to General Procedure E. The title compound (16 mg) was prepared by the hydrolysis of (S)-2-({(S)-7-(2-acetylamino-5-methyl-thiazole-4-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (20 mg) using General Procedure B. LCMS (m/z): 952.

Example 95

(S)-2-({(S)-7-(2-Amino-5-methyl-thiazole-4-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-2-({(S)-7-(2-Acetylamino-5-methyl-thiazole-4-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (40 mg) was converted to (S)-2-({(S)-7-(2-amino-5-methyl-thiazole-4-sulfonyl)-3-[4-(3,4-dichloro-benzyloxy)-phenyl]-2,3,6,7,8,9-hexahydro-[1,4]-dioxino[2,3-g]isoquinoline-8-carbonyl}-amino)-3-(4'-cyano-biphenyl-4-yl)-propionic acid methyl ester (28 mg) using General Procedure N. The title compound (24 mg) was prepared by the hydrolysis of (S)-2-({(S)-7-(2-amino-5-methyl-thiazole-4-sulfonyl)-

3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (28 mg) using General Procedure B. LCMS (m/z): 912.

Example 96

(S)-3-(4'-Cyano-biphenyl-4-yl)-2-{[(S)-3-[4-(3,4-dichloro-benzyloxy)-phenyl]-7-(2-ethylamino-5-methyl-thiazole-4-sulfonyl)-2,3,6,7,8,9-hexahydro-[1,4]dioxino[2,3-g]isoquinoline-8-carbonyl]-amino}-propionic acid (S)-2-({(S)-7-(2-Acetylamino-5-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (40 mg) was reacted with iodoethane and $K_2CO_3$ in DMF to give (S)-2-({(S)-7-[2-(acetyl-ethyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester according to General Procedure O. This product (18 mg) was hydrolysed according to General Procedure B to give the title compound (14 mg). LCMS (m/z): 940.

Example 97

(S)-3-(4'-Cyano-biphenyl-4-yl)-2-{[(S)-3-[4-(3,4-dichloro-benzyloxy)-phenyl]-7-((S)-1-phenyl-ethylcarbamoyl)-2,3,6,7,8,9-hexahydro-[1,4]dioxino[2,3-g]isoquinoline-8-carbonyl]-amino}-propionic acid (S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (25 mg) was reacted with (S)-1-isocyanato-ethyl)-benzene (25 mg) to give (S)-3-(4'-cyano-biphenyl-4-yl)-2-{[(S)-3-[4-(3,4-dichloro-benzyloxy)-phenyl]-7-((S)-1-phenyl-ethylcarbamoyl)-2,3,6,7,8,9-hexahydro-[1,4]dioxino[2,3-g]isoquinoline-8-carbonyl]-amino}-propionic acid methyl ester according to General Procedure I. This product (25 mg) was hydrolyzed according to General Procedure B to give the title compound (20 mg). LCMS (m/z): 882.

Example 98

(S)-3-(4'-Cyano-biphenyl-4-yl)-2-{[(3S,8S)-3-[4-(3,4-dichloro-benzyloxy)-phenyl]-7-(2-methoxy-4-methyl-benzenesulfonyl)-2,3,6,7,8,9-hexahydro-[1,4]dioxino[2,3-g]isoquinoline-8-carbonyl]-amino}-propionic acid (S)-3-(4'-Cyano-biphenyl-4-yl)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (25 mg) was reacted with 2-methoxy-4-methylbenzenesulfonyl chloride to afford (S)-3-(4'-cyano-biphenyl-4-yl)-2-{[(3S,8S)-3-[4-(3,4-dichloro-benzyloxy)-phenyl]-7-(2-methoxy-4-methyl-benzenesulfonyl)-2,3,6,7,8,9-hexahydro-[1,4]dioxino[2,3-g]isoquinoline-8-carbonyl]-amino}-propionic acid methyl ester according to General Procedure E. This product (20 mg) was hydrolyzed according to General Procedure B to give the title compound (16 mg). LCMS (m/z): 0.919.

Example 99

(S)-3-(4'-Cyano-biphenyl-4-yl)-2-{[(3S,8S)-3-[4-(3,4-dichloro-benzyloxy)-phenyl]-7-(2-nitro-benzenesulfonyl)-2,3,6,7,8,9-hexahydro-[1,4]dioxino[2,3-g]isoquinoline-8-carbonyl]-amino}-propionic acid (S)-3-(4'-Cyano-biphenyl-4-yl)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (25 mg) was reacted with 2-nitro-benzenesulfonyl chloride to give (S)-3-(4'-cyano-biphenyl-4-yl)-2-{[(3S,8S)-3-[4-(3,4-dichloro-benzyloxy)-phenyl]-7-(2-nitro-benzenesulfonyl)-2,3,6,7,8,9-hexahydro-[1,4]dioxino[2,3-g]isoquinoline-8-carbonyl]-amino}-propionic acid methyl ester according to General Procedure E. This product (21 mg) was hydrolyzed according to General Procedure B to give the title compound (16 mg). LCMS (m/z): 919.

Example 100

(S)-3-(4'-Cyano-biphenyl-4-yl)-2-{[(3S,8S)-3-[4-(3,4-dichloro-benzyloxy)-phenyl]-7-(4-methoxy-2-nitro-benzenesulfonyl)-2,3,6,7,8,9-hexahydro-[1,4]dioxino[2,3-g]isoquinoline-8-carbonyl]-amino}-propionic acid (S)-3-(4'-Cyano-biphenyl-4-yl)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (20 mg) was reacted with 4-methoxy-2-nitro-benzenesulfonyl chloride to give (S)-3-(4'-cyano-biphenyl-4-yl)-2-{[(3S,8S)-3-[4-(3,4-dichloro-benzyloxy)-phenyl]-7-(4-methoxy-2-nitro-benzenesulfonyl)-2,3,6,7,8,9-hexahydro-[1,4]dioxino[2,3-g]isoquinoline-8-carbonyl]-amino}-propionic acid methyl ester according to General Procedure E. This product (5 mg) was hydrolyzed according to General Procedure B to give the title compound (4 mg). LCMS (m/z): 951.

Example 101

(S)-3-(4'-Cyano-biphenyl-4-yl)-2-{[(3S,8S)-3-[4-(3,4-dichloro-benzyloxy)-phenyl]-7-(1-phenyl-propyl)-2,3,6,7,8,9-hexahydro-[1,4]dioxino[2,3-g]isoquinoline-8-carbonyl]-amino}-propionic acid (S)-3-(4'-Cyano-biphenyl-4-yl)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester was reacted with 1-(bromo-propyl)-benzene and $NaHCO_3$ in DMF according to General Procedure P to give (S)-3-(4'-cyano-biphenyl-4-yl)-2-{[(3S,8S)-3-[4-(3,4-dichloro-benzyloxy)-phenyl]-7-(1-phenyl-propyl)-2,3,6,7,8,9-hexahydro-[1,4]dioxino[2,3-g]isoquinoline-8-carbonyl]-amino}-propionic acid methyl ester. This product (12 mg), upon hydrolysis according to General Procedure B, gave the title compound (8 mg). LCMS (m/z): 854.

Example 102

(S)-3-(4'-Cyano-biphenyl-4-yl)-2-{[(3R,8S)-3-[4-(3,4-dichloro-benzyloxy)-phenyl]-7-(1-phenyl-propyl)-2,3,6,7,8,9-hexahydro-[1,4]dioxino[2,3-g]isoquinoline-8-carbonyl]-amino}-propionic acid (S)-3-(4'-Cyano-biphenyl-4-yl)-2-({(3R,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester was reacted with 1-(bromo-propyl)-benzene and $NaHCO_3$ in DMF according to General Procedure P to give (S)-3-(4'-cyano-biphenyl-4-yl)-2-{[(3R,8S)-3-[4-(3,4-dichloro-benzyloxy)-phenyl]-7-(1-phenyl-propyl)-2,3,6,7,8,9-hexahydro-[1,4]dioxino[2,3-g]isoquinoline-8-carbonyl]-amino}-propionic acid methyl ester. This product, upon hydrolysis according to General Procedure B, gave the title compound (6 mg). LCMS (m/z): 852.

Example 103

(S)-2-({(S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-2-methyl-propionic acid (S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester (100 mg) was coupled with (S)-2-amino-3-(4'-cyano-biphenyl-4-yl)-2-methyl-propionic acid methyl ester (50 mg) according to General Procedure L to give (S)-8-[(S)-2-(4'-Cyano-biphenyl-4-yl)-1-methoxycarbonyl-1-methyl-ethyl-carbamoyl]-3-[4-(3,4-dichloro-benzyloxy)-phenyl]-2,3,8,9-tetrahydro-6H-[1,4]dioxino[2,3-g]-isoquinoline-7-carboxylic acid tert-butyl ester (106 mg). This intermediate was deprotected according to General Procedure C to give (S)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-2-methyl-propionic acid methyl ester hydrochloride. This compound (40 mg) was further reacted with 2-acetylamino-4-methyl-thiazole-5-sulfonyl chloride to give (S)-2-({(S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-2-methyl-propionic acid methyl ester according to General Procedure E. This product (25 mg) was hydrolyzed according to General Procedure B to give the title. LCMS (m/z): 966.

Example 104

(S)-2-({(S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-2-methyl-propionic acid (S)-2-({(S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-2-methyl-propionic acid methyl ester was converted to (S)-2-({(S)-7-(2-amino-4-methyl-thiazole-5-sulfonyl)-3-[4-(3,4-dichloro-benzyloxy)-phenyl]-2,3,6,7,8,9-hexahydro-[1,4]-dioxino[2,3-g]isoquinoline-8-carbonyl}-amino)-3-(4'-cyano-biphenyl-4-yl)-2-methyl-propionic acid methyl ester according to General Procedure N. This ester, upon hydrolysis according to General Procedure B, gave the title compound. LCMS (m/z): 927.

Example 105

(S)-3-(4'-Cyano-biphenyl-4-yl)-2-({(S)-7-[2-(cyclobutylmethyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid (S)-2-({(S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (30 mg) was reacted with bromomethyl cyclobutane and K₂CO₃ in DMF afforded (S)-2-({(S)-7-[2-(acetyl-cyclobutylmethyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester according to General Procedure O. This product (20 mg) was hydrolyzed according to General Procedure B to give the title compound. LCMS (m/z): 979.

Example 106

(S)-3-(4'-Cyano-biphenyl-4-yl)-2-({(S)-7-(2-cyclobutylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid (S)-2-({(S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (50 mg) was reacted with cyclobutanol according to General Procedure W to give (S)-2-({(S)-7-[2-(acetyl-cyclobutyl-amino)-4-methyl-thiazole-5-sulfonyl]-3-[4-(3,4-dichloro-benzyloxy)-phenyl]-2,3,6,7,8,9-hexahydro-[1,4]dioxino[2,3-g]-isoquinoline-8-carbonyl}-amino)-3-(4'-cyano-biphenyl-4-yl)-propionic acid methyl ester. This product (16 mg) was hydrolyzed according to General Procedure B to give the title compound. LCMS (m/z): 964.

The compounds identified in Examples 107-110, below, were prepared using synthetic procedures analogous to those used for the synthesis of the compound of Example 106.

Example 107

(S)-3-(4'-Cyano-biphenyl-4-yl)-2-{[(S)-3-[4-(3,4-dichloro-benzyloxy)-phenyl]-7-(2-isopropylamino-4-methyl-thiazole-5-sulfonyl)-2,3,6,7,8,9-hexahydro-[1,4]dioxino[2,3-g]isoquinoline-8-carbonyl]-amino}-propionic acid

Example 108

(S)-3-(4'-Cyano-biphenyl-4-yl)-2-({(S)-7-(2-cyclopentylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid

Example 109

(S)-2-({(S)-7-(2-Butylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid

Example 110

(S)-3-(4'-Cyano-biphenyl-4-yl)-2-({(S)-3-[4-(3,4-dichloro-benzyloxy)-phenyl]-7-[4-methyl-2-(3-methyl-butylamino)-thiazole-5-sulfonyl]-2,3,6,7,8,9-hexahydro-[1,4]dioxino[2,3-g]isoquinoline-8-carbonyl}-amino)-propionic acid

Example 111

(S)-2-({(S)-7-(4-Acetylamino-2-methyl-benzenesulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (20 mg) was reacted with 4-acetylamino-2-methyl-benzenesulfonyl chloride to give (S)-2-({(S)-7-(4- acetylamino-2-methyl-benzenesulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester according to General Procedure E. The title compound was prepared by the hydrolysis of (S)-2-({(S)-7-(4-acetylamino-4-methyl-benzenesulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (8 mg) according to General Procedure B. LCMS (m/z): 945.

Example 112

(S)-3-(4'-Cyano-biphenyl-4-yl)-2-{[(S)-3-[4-(3,4-dichloro-benzyloxy)-phenyl]-7-(6-morpholin-4-yl-pyridine-3-sulfonyl)-2,3,6,7,8,9-hexahydro-[1,4]dioxino[2,3-g]isoquinoline-8-carbonyl]-amino}-propionic acid (S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (20 mg) was reacted with 4-morpholin-4-yl-benzenesulfonyl chloride to give (S)-3-(4'-cyano-biphenyl-4-yl)-2-{[(S)-3-[4-(3,4-dichloro-benzyloxy)-phenyl]-7-(6-morpholin-4-yl-pyridine-3-sulfonyl)-2,3,6,7,8,9-hexahydro-[1,4]dioxino[2,3-g]isoquinoline-8-carbonyl]-amino}-propionic acid methyl ester according to General Procedure E. The title compound was prepared by the hydrolysis of (S)-3-(4'-cyano-biphenyl-4-yl)-2-{[(S)-3-[4-(3,4-dichloro-benzyloxy)-phenyl]-7-(6-morpholin-4-yl-pyridine-3-sulfonyl)-2,3,6,7,8,9-hexahydro-[1,4]dioxino[2,3-g]isoquinoline-8-carbonyl]-amino}-propionic acid methyl ester using general the procedure B. LCMS (m/z): 961.

Example 113

(S)-3-(4'-Cyano-biphenyl-4-yl)-2-({(S)-3-[4-(3,4-dichloro-benzyloxy)-phenyl]-7-[2-(3,3-dimethyl-butylamino)-4-methyl-thiazole-5-sulfonyl]-2,3,6,7,8,9-hexahydro-[1,4]dioxino[2,3-g]isoquinoline-8-carbonyl}-amino)-propionic acid (S)-2-({(S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (30 mg) was reacted with 1-bromo-3,3-dimethyl-butane and $K_2CO_3$ in DMF afforded (S)-2-({(S)-7-[2-(acetyl-3,3-dimethyl-butyl-amino)-5-methyl-thiazole-4-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester according to General Procedure O. This product (10 mg) was hydrolysed according to General Procedure B to give the title compound. LCMS (m/z): 996.

Example 114

(S)-3-(4'-Cyano-biphenyl-4-yl)-2-{[(S)-3-[4-(3,4-dichloro-benzyloxy)-phenyl]-7-(2-isobutyrylamino-4-methyl-thiazole-5-sulfonyl)-2,3,6,7,8,9-hexahydro-[1,4]dioxino[2,3-g]isoquinoline-8-carbonyl]-amino}-propionic acid (S)-2-({(S)-7-(2-amino-4-methyl-thiazole-5-sulfonyl)-3-[4-(3,4-dichloro-benzyloxy)-phenyl]-2,3,6,7,8,9- hexahydro-[1,4]dioxino[2,3-g]isoquinoline-8-carbonyl}-amino)-3-(4'-cyano-biphenyl-4-yl)-propionic acid methyl ester (30 mg) was reacted with isobutyryl chloride according to General Procedure F to give (S)-3-(4'-cyano-biphenyl-4-yl)-2-({(S)-7-[2-(isobutyrylamino)-4-methyl-thiazole-5-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester. This ester, upon hydrolysis according to General Procedure B, gave the title compound. LCMS (m/z): 980.

Example 115

(S)-2-({(S)-7-(4-Acetylamino-benzenesulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (32 mg) was reacted with 4-acetylamino-benzenesulfonyl chloride to give (S)-2-({(S)-7-(4-acetylamino-benzenesulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester according to General Procedure E. This product (20 mg) was hydrolysed according to General Procedure B to give the title compound (3 mg). LCMS (m/z): 931.

Example 116

(S)-3-(4'-Cyano-biphenyl-4-yl)-2-{[(S)-3-[4-(3,4-dichloro-benzyloxy)-phenyl]-7-(5-methyl-isoxazol-4-ylmethyl)-2,3,6,7,8,9-hexahydro-[1,4]dioxino[2,3-g]isoquinoline-8-carbonyl]-amino}-propionic acid The title compound was prepared from (S)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride (25 mg) according to General Procedures D and B. LCMS (m/z): 830.

Example 117

(S)-3-(4'-Cyano-biphenyl-4-yl)-2-{[(S)-3-[4-(3,4-dichloro-benzyloxy)-phenyl]-7-(3,5-dimethyl-isoxazol-4-ylmethyl)-2,3,6,7,8,9-hexahydro-[1,4]dioxino[2,3-g]isoquinoline-8-carbonyl]-amino}-propionic acid The title compound (11 mg) was prepared from (S)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride (25 mg) according to General Procedures D and B. LCMS (m/z): 844.

Example 118

(S)-2-({(S)-7-(2-Amino-benzothiazole-6-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-3-(4'-Cyano-biphenyl-4-yl)-2-({(S)-3-[4-(3,4-dichloro-benzyloxy)-phenyl]-2,3,6,7,8,9- hexahydro-[1,4]

dioxino[2,3-g]isoquinoline-8-carbonyl}-amino)-propionic acid methyl ester (25 mg) was reacted with (6-chlorosulfonyl-benzothiazol-2-yl)-carbamic acid tert-butyl ester to give (S)-2-({(S)-7-(2-tert-butoxycarbonylamino-benzothiazole-6-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester according to General Procedure E. This product (25 mg) was deprotected and hydrolysed according to General Procedure C and B to give the title compound. LCMS (m/z): 947.

Example 119

(S)-2-{[(S)-3-[4-(3,4-Dichloro-benzyloxy)-phenyl]-7-(2-ethylamino-4-methyl-thiazole-5-sulfonyl)-2,3,6,7,8,9-hexahydro-[1,4]dioxino[2,3-g]isoquinoline-8-carbonyl]-amino}-3-(4'-fluoro-biphenyl-4-yl)-propionic acid (S)-3-[4-(3,4-dichloro-benzyloxy)-phenyl]-2,3,8,9-tetrahydro-6H-[1,4]dioxino[2,3-g]-isoquinoline-7,8-dicarboxylic acid 7-tert-butyl ester (50 mg) was coupled with (S)-2-amino-3-(4'-fluoro-biphenyl-4-yl)-propionic acid methyl ester hydrochloride (29 mg) according to General Procedure L to give (S)-3-[4-(3,4-dichloro-benzyloxy)-phenyl]-8-[(S)-2-(4'-fluoro-biphenyl-4-yl)-1-methoxycarbonyl-ethylcarbamoyl]-2,3,8,9-tetrahydro-6H-[1,4]dioxino[2,3-g]isoquinoline-7-carboxylic acid tert-butyl ester (52 mg). This intermediate was deprotected as described in General Procedure C to give (S)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-fluoro-biphenyl-4-yl)-propionic acid methyl esterhydrochloride. This compound was further reacted with 2-acetylamino-4-methyl-thiazole-5-sulfonyl chloride to furnish (S)-2-({(S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-fluoro-biphenyl-4-yl)-propionic acid methyl ester as described in General Procedure E. This compound, upon reaction with ethyl iodide and K$_2$CO$_3$ in DMF, gave (S)-2-({(S)-7-[2-(acetyl-ethyl-amino)-5-methyl-thiazole-4-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-fluoro-biphenyl-4-yl)-propionic acid methyl ester according to General Procedure O. This product (15 mg) was hydrolyzed according to General Procedure B to furnish the title compound. LCMS (m/z): 934.

Example 120

(S)-3-(4'-Chloro-biphenyl-4-yl)-2-{[(S)-3-[4-(3,4-dichloro-benzyloxy)-phenyl]-7-(2-ethylamino-4-methyl-thiazole-5-sulfonyl)-2,3,6,7,8,9-hexahydro-[1,4]dioxino[2,3-g]isoquinoline-8-carbonyl]-amino}-propionic acid (S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester (50 mg) was coupled with (S)-2-amino-3-(4'-chloro-biphenyl-4-yl)-propionic acid methyl ester hydrochloride (31 mg) according to General Procedure L to give (S)-8-[(S)-2-(4'-chloro-biphenyl-4-yl)-1-methoxycarbonyl-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid tert-butyl ester (39 mg). This intermediate was deprotected as described in General Procedure C to give (S)-3-(4'-chloro-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride salt. This compound was further reacted with 2-acetylamino-4-methyl-thiazole-5-sulfonyl chloride to furnish (S)-2-({(S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-chloro-biphenyl-4-yl)-propionic acid methyl ester according to General Procedure E. This compound, upon reaction with ethyl iodide and K$_2$CO$_3$ in DMF, gave (S)-2-({(S)-7-[2-(acetyl-ethyl-amino)-5-methyl-thiazole-4-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-chloro-biphenyl-4-yl)-propionic acid methyl ester according to General Procedure O. This product (15 mg) was hydrolyzed according to General Procedure B to give the title compound. LCMS (m/z): 950.

Example 121

(S)-3-(4'-Cyano-biphenyl-4-yl)-2-{[(S)-3-[4-(3,4-dichloro-benzyloxy)-phenyl]-7-(1-methyl-1H-pyrazol-3-ylmethyl)-2,3,6,7,8,9-hexahydro-[1,4]dioxino[2,3-g]isoquinoline-8-carbonyl]-amino}-propionic acid (S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (35 mg) was treated with 1-methyl-1H-pyrazole-3-carbaldehyde according to General Procedure D to give (S)-3-(4'-Cyano-biphenyl-4-yl)-2-{[(S)-3-[4-(3,4-dichloro-benzyloxy)-phenyl]-7-(1-methyl-1H-pyrazol-3-yl-methyl)-2,3,6,7,8,9-hexahydro-[1,4]dioxino[2,3-g]isoquinoline-8-carbonyl]-amino}-propionic acid methyl ester (25 mg). This was hydrolyzed according to General Procedure B to give the title compound (21 mg). LCMS (m/z): 830.

Example 122

(S)-2-({(S)-7-(2-Amino-4-methyl-thiazol-5-ylmethyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-2-({(S)-7-(2-Amino-4-methyl-thiazol-5-ylmethyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (20 mg) was hydrolyzed according to General Procedure B to give the title compound (17 mg). LCMS (m/z) 862.

Example 123

(S)-3-(4'-Cyano-biphenyl-4-yl)-2-({(S)-3-[4-(3,4-dichloro-benzyloxy)-phenyl]-7-pyridin-4-ylmethyl-2,3,6,7,8,9-hexahydro-[1,4]dioxino[2,3-g]isoquinoline-8-carbonyl}-amino)-propionic acid (S)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (50 mg) was alkylated with (5-Bromomethyl-4-methyl-thiazol-2-yl)-carbamic acid tert-butyl ester (3 eq.) and NaHCO₃ (10 eq.) according to General Procedure P to give the title compound (45 mg).

Example 124

(S)-2-({(S)-7-(6-Amino-pyridin-3-ylmethyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-2-({(S)-7-(6-Amino-pyridin-3-ylmethyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (25 mg) was hydrolyzed according to General Procedure B to give the title compound (19 mg).

Example 125

(S)-3-(4'-Cyano-biphenyl-4-yl)-2-{[(3S,8S)-3-[4-(3,4-dichloro-benzyloxy)-phenyl]-7-((R)-1-phenyl-propyl)-2,3,6,7,8,9-hexahydro-[1,4]dioxino[2,3-g]isoquinoline-8-carbonyl]-amino}-propionic acid (S)-2-tert-Butoxycarbonylamino-3-{(S)-2-[4-(3,4-dichloro-benzyloxy)-phenyl]-2,3-dihydro-benzo[1,4]dioxin-6-yl}-propionic acid methyl ester was treated with HCl according to General Procedure C and followed by aqueous NaHCO3 wash to give (S)-2-amino-3-{(S)-2-[4-(3,4-dichloro-benzyloxy)-phenyl]-2,3-dihydro-benzo[1,4]dioxin-6-yl}-propionic acid methyl ester. This was subjected to alkylation with (1-bromo-propyl)-benzene according to General Procedure P. Resulting product was purified on silica gel to give (S)-3-{(S)-2-[4-(3,4-dichloro-benzyloxy)-phenyl]-2,3-dihydro-benzo[1,4]dioxin-6-yl}-2-((R)-1-phenyl-propylamino)-propionic acid methyl ester (slower moving diastereomer). LCMS (m/z): 606. 1H NMR (400 MHz, Acetone-d6) 7.72 (d, 1H), 7.62 (d, 1H), 7.48 (m, 1H) 7.44 (d, 2H), 7.3 (m, 4H), 7.22 (m, 1H) 7.10 (d, 1H) 6.8 (d, 1H) 6.74 (d, 1H) 6.68 (m, 1H) 5.2 (s, 2H) 5.1 (m, 1H) 4.35 (m, 1H) 4.0 (m. 1H) 3.56 (t, 1H) 3.45 (s, 3H) 3.40 (t, 1H) 3.15 (s, 3H) 2.9 (m, 2H) 1.74 (m, 1H) 1.56 (m, 1H) 0.75 (t, 3H).

(S)-3-{(S)-2-[4-(3,4-Dichloro-benzyloxy)-phenyl]-2,3-dihydro-benzo[1,4]dioxin-6-yl}-2-((R)-1-phenyl-propylamino)-propionic acid methyl ester (0.165 g) was treated with formaldehyde according to General Procedure V to give (3S,8S)-3-[4-(3,4-Dichloro-benzyloxy)-phenyl]-7-((R)-1-phenyl-propyl)-2,3,6,7,8,9-hexahydro-[1,4]dioxino[2,3-g]isoquinoline-8-carboxylic acid methyl ester (0.13 g). This was treated with LiOH in THF:MeOH (1:3) according to General Procedure B to give (3S,8S)-3-[4-(3,4-Dichloro-benzyloxy)-phenyl]-7-((R)-1-phenyl-propyl)-2,3,6,7,8,9-hexahydro-[1,4]dioxino[2,3-g]isoquinoline-8-carboxylic acid (75 mg). LCMS (m/z): 604

(3S,8S)-3-[4-(3,4-Dichloro-benzyloxy)-phenyl]-7-((R)-1-phenyl-propyl)-2,3,6,7,8,9-hexahydro-[1,4]dioxino[2,3-g]isoquinoline-8-carboxylic acid (75 mg) was coupled with (S)-2-amino-3-(4'-cyano-biphenyl-4-yl)-propionic acid methyl ester according to General Procedure L to give (S)-3-(4'-cyano-biphenyl-4-yl)-2-{[(3S,8S)-3-[4-(3,4-dichloro-benzyloxy)-phenyl]-7-((R)-1-phenyl-propyl)-2,3,6,7,8,9-hexahydro-[1,4]dioxino[2,3-g]isoquinoline-8-carbonyl]-amino}-propionic acid methyl ester (30 mg). LCMS (m/z): 866.

(S)-3-(4'-Cyano-biphenyl-4-yl)-2-{[(3S,8S)-3-[4-(3,4-dichloro-benzyloxy)-phenyl]-7-((R)-1-phenyl-propyl)-2,3,6,7,8,9-hexahydro-[1,4]dioxino[2,3-g]isoquinoline-8-carbonyl]-amino}-propionic acid methyl ester (25 mg)) was hydrolyzed according to General Procedure B to give the title compound (21 mg). LCMS (m/z): 852.

Example 126

(S)-2-({(S)-7-(2-Amino-4-methyl-thiazole-5-carbonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid 2-tert-Butoxycarbonylamino-4-methyl-thiazole-5-carboxylic acid (1 eq) and TFFH (1 eq) were taken in 2 mL anhydrous THF and stirred for 10 min. (S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (50 mg) and DIEA (3 eq) were added to the reaction mixture and stirred for 1 hour. Reaction mixture was diluted with EtOAc (5 mL), washed with water and brine and dried over Na₂SO₄. The solvent was removed by rotavap and the residue was purified by silicagel column to give (S)-2-({(S)-7-(2-tert-butoxycarbonylamino-4-methyl-thiazole-5-carbonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (42 mg). Treatment with HCl according to General Procedure C followed by NaHCO₃ wash gave (S)-2-({(S)-7-(2-Amino-4-methyl-thiazole-5-carbonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (35 mg).

(S)-2-({(S)-7-(2-Amino-4-methyl-thiazole-5-carbonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (25 mg) was hydrolyzed according to General Procedure B to give the title compound (18 mg). LCMS (m/z): 876.

Example 127

(S)-3-(4'-Cyano-biphenyl-4-yl)-2-{[(S)-3-[4-(3,4-dichloro-benzyloxy)-phenyl]-7-(2-methoxy-benzenesulfonyl)-2,3,6,7,8,9-hexahydro-[1,4]dioxino[2,3-g]isoquinoline-8-carbonyl]-amino}-propionic acid (S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (40 mg) was treated with 2-methoxy-benzenesulfonyl chloride according to General Procedure E to give (S)-3-(4'-cyano-biphenyl-4-yl)-2-{[(S)-3-[4-(3,4-dichloro-benzyloxy)-phenyl]-7-(2-methoxy-benzenesulfonyl)-2,3,6,7,8,9-hexahydro-[1,4]dioxino[2,3-g]isoquinoline-8-carbonyl]-amino}-propionic acid methyl ester. This (26 mg) was hydrolyzed according to General Procedure B to give the title compound (23 mg). LCMS (m/z): 906.

The compounds identified in Examples 128-130, below, were prepared using synthetic procedures analogous to those used for the synthesis of the compound of Example 127.

Example 128

(S)-3-(4'-Cyano-biphenyl-4-yl)-2-{[(S)-3-[4-(3,4-dichloro-benzyloxy)-phenyl]-7-(3,5-dimethyl-isoxazole-4-sulfonyl)-2,3,6,7,8,9-hexahydro-[1,4]dioxino[2,3-g]isoquinoline-8-carbonyl]-amino}-propionic acid

Example 129

(S)-2-({(S)-7-(2-Acetylamino-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid

Example 130

(S)-3-(4'-Cyano-biphenyl-4-yl)-2-{[(S)-3-[4-(3,4-dichloro-benzyloxy)-phenyl]-7-(2,4-dimethyl-thiazole-5-sulfonyl)-2,3,6,7,8,9-hexahydro-[1,4]dioxino[2,3-g]isoquinoline-8-carbonyl]-amino}-propionic acid

Example 131

(S)-2-({(S)-7-(2-Amino-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (48 mg) was treated with 2-acetylaminothiazole-5-sulfonyl chloride according to General Procedure E to give (S)-2-({(S)-7-(2-Acetylamino-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester.

(S)-2-({(S)-7-(2-Acetylamino-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester was treated with HCl according to General Procedure N to give (S)-2-({(S)-7-(2-Amino-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester.

(S)-2-({(S)-7-(2-Amino-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (25 mg)) was hydrolysed according to General Procedure B to give the title compound (20 mg). LCMS (m/z) 897.

Example 132

(S)-3-(4'-Cyano-biphenyl-4-yl)-2-{[(S)-3-[4-(3,4-dichloro-benzyloxy)-phenyl]-7-(4-methyl-2-propionylamino-thiazole-5-sulfonyl)-2,3,6,7,8,9-hexahydro-[1,4]dioxino[2,3g]isoquinoline-8-carbonyl]-amino}-propionic acid (S)-2-({(S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (30 mg) treated with propionyl chloride according to General Procedure F to give (S)-3-(4'-cyano-biphenyl-4-yl)-2-{[(S)-3-[4-(3,4-dichloro-benzyloxy)-phenyl]-7-(4-methyl-2-propionylamino-thiazole-5-sulfonyl)-2,3,6,7,8,9-hexahydro-[1,4]dioxino-[2,3-g]isoquinoline-8-carbonyl]-amino}-propionic acid methyl ester (19 mg).

(S)-3-(4'-Cyano-biphenyl-4-yl)-2-{[(S)-3-[4-(3,4-dichloro-benzyloxy)-phenyl]-7-(4-methyl-2-propionylamino-thiazole-5-sulfonyl)-2,3,6,7,8,9-hexahydro-[1,4]dioxino[2,3-g]isoquinoline-8-carbonyl]-amino}-propionic acid methyl ester (19 mg) was hydrolyzed according to General Procedure B to give the title compound (16 mg). LCMS (m/z): 967.

Example 133

(S)-3-(4'-Cyano-biphenyl-4-yl)-2-{[(S)-3-[4-(3,4-dichloro-benzyloxy)-phenyl]-7-(2-methyl-6-morpholin-4-yl-pyridine-3-sulfonyl)-2,3,6,7,8,9-hexahydro-[1,4]dioxino[2,3-g]isoquinoline-8-carbonyl]-amino}-propionic acid (S)-2-({(S)-7-(6-Chloro-2-methyl-pyridine-3-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (80 mg) was prepared from (S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (80 mg) and 6-Chloro-2-methyl-pyridine-3-sulfonyl chloride (29 mg) according to General Procedure E (except that the 1 N HCl wash was omitted). LCMS (m/z) 937.

(S)-2-({(S)-7-(6-Chloro-2-methyl-pyridine-3-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (30 mg) was treated with morpholine according to General Procedure U to give (S)-3-(4'-Cyano-biphenyl-4-yl)-2-{[(S)-3-[4-(3,4-dichloro-benzyloxy)-phenyl]-7-(2-methyl-6-morpholin-4-yl-pyridine-3-sulfonyl)-2,3,6,7,8,9-hexahydro-[1,4]dioxino[2,3-g]isoquinoline-8-carbonyl]amino}-propionic acid methyl ester (24 mg).

(S)-3-(4'-Cyano-biphenyl-4-yl)-2-{[(S)-3-[4-(3,4-dichloro-benzyloxy)-phenyl]-7-(2-methyl-6-morpholin-4-yl-pyridine-3-sulfonyl)-2,3,6,7,8,9-hexahydro-[1,4]dioxino[2,3-g]isoquinoline-8-carbonyl]-amino}-propionic acid methyl ester (24 mg) was hydrolysed according to General Procedure B to give the title compound (21 mg). LCMS (m/z): 975.

The compounds identified in Examples 134-137, below, were prepared using synthetic procedures analogous to those used for the synthesis of the compound of Example 133.

Example 134

(S)-3-(4'-Cyano-biphenyl-4-yl)-2-{[(S)-3-[4-(3,4-dichloro-benzyloxy)-phenyl]-7-(2-methyl-6-pyrrolidin-1-yl-pyridine-3-sulfonyl)-2,3,6,7,8,9-hexahydro-[1,4]dioxino[2,3-g]isoquinoline-8-carbonyl]-amino}-propionic acid

Example 135

(S)-3-(4'-Cyano-biphenyl-4-yl)-2-{[(S)-3-[4-(3,4-dichloro-benzyloxy)-phenyl]-7-(6-ethylamino-2-methyl-pyridine-3-sulfonyl)-2,3,6,7,8,9-hexahydro-[1,4]dioxino[2,3-g]isoquinoline-8-carbonyl]-amino}-propionic acid

Example 136

(S)-3-(4'-Cyano-biphenyl-4-yl)-2-({(S)-3-[4-(3,4-dichloro-benzyloxy)-phenyl]-7-[6-(2-methoxy-ethylamino)-2-methyl-pyridine-3-sulfonyl]-2,3,6,7,8,9-hexahydro-[1,4]dioxino[2,3-g]isoquinoline-8-carbonyl}-amino)-propionic acid

Example 137

(S)-3-(4'-Cyano-biphenyl-4-yl)-2-{[(S)-3-[4-(3,4-dichloro-benzyloxy)-phenyl]-7-(6-isobutylamino-2-methyl-pyridine-3-sulfonyl)-2,3,6,7,8,9-hexahydro-[1,4]dioxino[2,3-g]isoquinoline-8-carbonyl]-amino}-propionic acid

Example 138

(S)-2-({(S)-7-[4-(2-Acetylamino-thiazol-4-yl)-benzenesulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-3-(4'-Cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester was treated with 4-(2-acetylamino-thiazol-4-yl)-benzenesulfonyl chloride according to General Procedure E to give (S)-2-({(S)-7-[4-(2-acetylamino-thiazol-4-yl)-benzenesulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester.

(S)-2-({(S)-7-[4-(2-Acetylamino-thiazol-4-yl)-benzenesulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (25 mg) was hydrolysed according to General Procedure B to give the title compound (22 mg). LCMS (m/z): 1014.

Example 139

(S)-2-({(S)-7-[4-(2-Amino-thiazol-4-yl)-benzenesulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-2-({(S)-7-[4-(2-Acetylamino-thiazol-4-yl)-benzenesulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester (30 mg) was treated with HCl according to General Procedure N to give (S)-2-({(S)-7-[4-(2-Amino-thiazol-4-yl)-benzenesulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester. This was hydrolyzed according to General Procedure B to give the title compound (20 mg). LCMS (m/z): 972.

Example 140

(S)-3-(4'-Cyano-biphenyl-4-yl)-2-({(3S,8S)-7-[6-(cyclobutylmethyl-amino)-2-methyl-pyridine-3-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid (S)-3-(4'-Cyano-biphenyl-4-yl)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (40 mg) was treated with 6-(acetyl-cyclobutylmethyl-amino)-2-methyl-pyridine-3-sulfonyl chloride according to General Procedure E to give (S)-2-({(3S,8S)-7-[6-(acetyl-cyclobutylmethyl-amino)-2-methyl-pyridine-3-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester. HCl treatment according General Procedure N gave (S)-3-(4'-cyano-biphenyl-4-yl)-2-({(3S,8S)-7-[6-(cyclobutylmethyl-amino)-2-methyl-pyridine-3-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (27 mg).

(S)-3-(4'-Cyano-biphenyl-4-yl)-2-({(3S,8S)-7-[6-(cyclobutylmethyl-amino)-2-methyl-pyridine-3-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (25 mg) was hydrolysed according to General Procedure B to give the title compound (22 mg). LCMS (m/z): 972.

The compounds identified in Examples 141-145, below, were prepared using synthetic procedures analogous to those used for the synthesis of the compound of Example 140.

Example 141

(S)-2-({(3S,8S)-7-(6-Amino-2-methyl-pyridine-3-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid

Example 142

(S)-3-(4'-Cyano-biphenyl-4-yl)-2-{[(3S,8S)-3-[4-(3,4-dichloro-benzyloxy)-phenyl]-7-(6-isopropylamino-2-methyl-pyridine-3-sulfonyl)-2,3,6,7,8,9-hexahydro-[1,4]dioxino[2,3-g]isoquinoline-8-carbonyl]-amino}-propionic acid

Example 143

(S)-3-(4'-Cyano-biphenyl-4-yl)-2-{[(3S,8S)-3-[4-(3,4-dichloro-benzyloxy)-phenyl]-7-(2-methyl-6-methylamino-pyridine-3-sulfonyl)-2,3,6,7,8,9-hexahydro-[1,4]dioxino[2,3-g]isoquinoline-8-carbonyl]-amino}-propionic acid

Example 144

(S)-3-(4'-Cyano-biphenyl-4-yl)-2-({(3S,8S)-7-[6-(cyclopropylmethyl-amino)-2-methyl-pyridine-3-sulfonyl]-3-[4-(3,4-dichloro-benzyloxy)-phenyl]-2,3,6,7,8,9-hexahydro-[1,4]dioxino[2,3-g]isoquinoline-8-carbonyl}-amino)-propionic acid

Example 145

(S)-2-({(3S,8S)-7-(6-Amino-4-methyl-pyridine-3-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid

Example 146

(S)-3-[5-(4-Cyano-phenyl)-thiophen-2-yl]-2-{[(3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-propionic acid (3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid (30 mg) was coupled with (S)-2-amino-3-[5-(4-cyano-phenyl)-thiophen-2-yl]-propionic acid methyl ester hydrochloride according to General Procedure L. The resulting ester (25 mg) was hydrolyzed according to General Procedure B to give the title compound (22 mg). LCMS (m/z): 861.

Example 147

(S)-2-{[(3S,8S)-3-[4-(3-Chloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3S,8S)-3-(4-Hydroxy-phenyl)-7-((S)-1-phenyl-propyl)-2,3,6,7,8,9-hexahydro-[1,4]dioxino[2,3-g]isoquinoline-8-carboxylic acid methyl ester (20 mg) was reacted with 3-chloro-benzyl bromide according to General Procedure J and the resulting ester was hydrolyzed according to General Procedure AB to provide (3S,8S)-3-[4-(3-chloro-benzyloxy)-phenyl]-7-((S)-1-phenyl-propyl)-2,3,6,7,8,9-hexahydro-[1,4]dioxino[2,3-g]isoquinoline-8-carboxylic acid (20 mg). The title compound (18 mg) was prepared from (3S,8S)-3-[4-(3-chloro-benzyloxy)-phenyl]-7-((S)-1-phenyl-propyl)-2,3,6,7,8,9-hexahydro-[1,4]dioxino[2,3-g]isoquinoline-8-carboxylic acid (20 mg) and (S)-2-amino-3-[4-(2,3-dimethyl-pyridin-4-yl)-phenyl]-propionic acid methyl ester bis hydrochloride according to General Procedures L and B. LCMS (m/z): 823.

The compounds identified in Examples 148 and 149 were prepared using synthetic procedures analogous to those used for the synthesis of the compound of Example 147.

Example 148

(S)-2-{[(3S,8S)-3-[4-(4-Chloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 149

(S)-2-{[(3S,8S)-3-(4-Benzyloxy-phenyl)-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 150

(S)-2-({(3S,8S)-7-Acetyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (25 mg) was acylated with acetyl chloride according to General Procedure F. The resulting compound was hydrolyzed according to General Procedure B to give the title compound (15 mg). LCMS (m/z): 781.

The compounds identified in Examples 151-159, below, were prepared using synthetic procedures analogous to those used for the synthesis of the compound of Example 150.

Example 151

(S)-2-{[(3S,8S)-3-[4-(3,4-Dichloro-benzyloxy)-phenyl]-7-(2-methyl-benzoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 152

(S)-2-{[(3S,8S)-3-[4-(3,4-Dichloro-benzyloxy)-phenyl]-7-(2,2-dimethyl-propionyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 153

(S)-2-({(3S,8S)-3-[4-(3,4-Dichloro-benzyloxy)-phenyl]-7-isobutyryl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 154

(S)-2-({(3S,8S)-7-Cyclopentanecarbonyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 155

(S)-2-({(3S,8S)-3-[4-(3,4-Dichloro-benzyloxy)-phenyl]-7-phenylacetyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 156

(S)-2-{[(3S,8S)-3-[4-(3,4-Dichloro-benzyloxy)-phenyl]-7-(2-methyl-benzoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 157

(S)-2-{[(3S,8S)-3-[4-(3,4-Dichloro-benzyloxy)-phenyl]-7-(3-methyl-benzoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 158

(S)-2-{[(3S,8S)-3-[4-(3,4-Dichloro-benzyloxy)-phenyl]-7-(4-methyl-benzoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 159

(S)-2-({(3S,8S)-7-Benzoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-l)-dimethyl-pyridin-4-y phenyl]-propionic acid

Example 160

(S)-2-{[(3S,8S)-3-(4-Cyclopentylmethoxy-phenyl)-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3S,8S)-3-(4-Hydroxy-phenyl)-7-((S)-1-phenyl-propyl)-2,3,6,7,8,9-hexahydro-[1,4]dioxino[2,3-g]isoquinoline-8-carboxylic acid methyl ester (20 mg) was reacted with cyclopentylmethanol according to General Procedure K and the resulting ester was hydrolyzed according to General Procedure AB to provide (3S,8S)-3-(4-cyclopentylmethoxy-phenyl)-7-((S)-1-phenyl-propyl)-2,3,6,7,8,9-hexahydro-[1,4]dioxino[2,3-g]isoquinoline-8-carboxylic acid (18 mg). The title compound (17 mg) was prepared from (3S,8S)-3-(4-cyclopentylmethoxy-phenyl)-7-((S)-1-phenyl-propyl)-2,3,6,7,8,9-hexahydro-[1,4]dioxino[2,3-g]isoquinoline-8-carboxylic acid (18 mg) and (S)-2-amino-3-[4-(2,3-dimethyl-pyridin-4-yl)-phenyl]-propionic acid methyl ester bis hydrochloride according to General Procedures L and B. LCMS (m/z): 781.

The compounds identified in Examples 161-173, below, were prepared using synthetic procedures analogous to those used for the synthesis of the compound of Example 160.

Example 161

(S)-3-[4-(2,3-Dimethyl-pyridin-4-yl)-phenyl]-2-{[(3S,8S)-3-(4-methoxy-phenyl)-7-((S)-1-phenyl-propyl)-2,3,6,7,8,9-hexahydro-[1,4]dioxino[2,3-g]isoquinoline-8-carbonyl]-amino}-propionic acid

Example 162

(S)-3-[4-(2,3-Dimethyl-pyridin-4-yl)-phenyl]-2-{[(3S,8S)-3-(4-isopropoxy-phenyl)-7-((S)-1-phenyl-propyl)-2,3,6,7,8,9-hexahydro-[1,4]dioxino[2,3-g]isoquinoline-8-carbonyl]-amino}-propionic acid

Example 163

(S)-2-{[(3S,8S)-3-(4-Cyclohexylmethoxy-phenyl)-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 164

(S)-2-{[(3S,8S)-3-(4-Cyclohexyloxy-phenyl)-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 165

(S)-2-{[(3S,8S)-3-[4-(2-Dimethylamino-ethoxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 166

(S)-3-[4-(2,3-Dimethyl-pyridin-4-yl)-phenyl]-2-{[(3S,8S)-3-[4-(1-ethyl-propoxy)-phenyl]-7-((S)-1-phenyl-propyl)-2,3,6,7,8,9-hexahydro-[1,4]dioxino[2,3-g]isoquinoline-8-carbonyl]-amino}-propionic acid

Example 167

(S)-2-{[(3S,8S)-3-[4-(2-Cyclopentyl-ethoxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-5 phenyl]-propionic acid

Example 168

(S)-2-{[(3S,8S)-3-[4-(3,3-Dimethyl-butoxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 169

(S)-3-[4-(2,3-Dimethyl-pyridin-4-yl)-phenyl]-2-({(3S,8S)-7-((S)-1-phenyl-propyl)-3-[4-(pyridin-3-ylmethoxy)-phenyl]-2,3,6,7,8,9-hexahydro-[1,4]dioxino[2,3-g]isoquinoline-8-carbonyl}-amino)-propionic acid

Example 170

(S)-3-[4-(2,3-Dimethyl-pyridin-4-yl)-phenyl]-2-{[(3S,8S)-3-(4-ethoxy-phenyl)-7-((S)-1-phenyl-propyl)-2,3,6,7,8,9-hexahydro-[1,4]dioxino[2,3-g]isoquinoline-8-carbonyl]-amino}-propionic acid

Example 171

(S)-2-{[(3S,8S)-3-(4-Cyclopentyloxy-phenyl)-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 172

(S)-3-[4-(2,3-Dimethyl-pyridin-4-yl)-phenyl]-2-{[(3S,8S)-3-(4-isobutoxy-phenyl)-7-((S)-1-phenyl-propyl)-2,3,6,7,8,9-hexahydro-[1,4]dioxino[2,3-g]isoquinoline-8-carbonyl]-amino}-propionic acid

Example 173

(S)-2-{[(3S,8S)-3-[4-(Bicyclo[2.2.1]hept-2-yloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 174

(3S,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid tert-butyl ester The title compound (17 mg) was prepared from (S)-2-tert-butoxycarbonylamino-3-{(S)-2-[4-(3,4-dichloro-benzyloxy)-phenyl]-2,3-dihydro-benzo[1,4]dioxin-6-yl}-propionic acid methyl ester, which was deprotected according to General Procedure C, subjected to General Procedure V, then reprotected. Hydrolysis followed General Procedure B and the resulting acid and (S)-2-amino-3-[4-(2,3-dimethyl-pyridin-4-yl)-phenyl]-propionic acid methyl ester dihydrochloride were reacted according to General Procedures L and B. LCMS (m/z): 839.

Example 175

(S)-2-({(3S,8S)-3-[4-(3,4-Dichloro-benzyloxy)-phenyl]-7-pyridin-2-ylmethyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid The title compound (13 mg) was prepared from (S)-2-tert-butoxycarbonylamino-3-{(S)-2-[4-(3,4-dichloro-benzyloxy)-phenyl]-2,3-dihydro-benzo[1,4]dioxin-6-yl}-propionic acid methyl ester, which was deprotected according to General Procedure C, subjected to General Procedure V, then reprotected. Hydrolysis followed General Procedure B and the resulting acid and (S)-2-amino-3-[4-(2,3-dimethyl-pyridin-4-yl)-phenyl]-propionic acid methyl ester dihydrochloride were reacted according to General Procedures L and C. The amine was treated with 2-pyridinecarboxaldehyde, then hydrolyzed according to General Procedures D and B. LCMS (m/z): 830.

Example 176

(S)-2-{[(3S,8S)-3-[4-(3,4-Dichloro-benzyloxy)-phenyl]-7-(2-methyl-benzyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid The title compound (7 mg) was prepared from (S)-2-tert-butoxycarbonylamino-3-{(S)-2-[4-(3,4-dichloro-benzyloxy)-phenyl]-2,3-dihydro-benzo[1,4]dioxin-6-yl}-propionic acid methyl ester, which was deprotected according to General Procedure C, subjected to General Procedure V, then reprotected. Hydrolysis followed General Procedure B and the resulting acid and (S)-2-amino-3-[4-(2,3-dimethyl-pyridin-4-yl)-phenyl]-propionic acid methyl ester dihydrochloride were reacted according to General Procedures L and C. The amine was treated with o-tolualdehyde, then hydrolyzed according to General Procedures D and B. LCMS (m/z): 843.

Example 177

(S)-2-({(3S,8S)-7-Benzoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2-methyl-pyridin-4-yloxy)-phenyl]-propionic acid The title compound (24 mg) was prepared from (S)-2-tert-butoxycarbonylamino-3-{(S)-2-[4-(3,4-dichloro-benzyloxy)-phenyl]-2,3-dihydro-benzo[1,4]dioxin-6-yl}-propionic acid methyl ester, which was deprotected according to General Procedure C, subjected to General Procedure V, then acylated with benzoyl chloride according to General Procedure F. Hydrolysis followed General Procedure B and the resulting acid and (S)-2-amino-3-[4-(2-methyl-pyridin-4-yloxy)-phenyl]-propionic acid methyl ester dihydrochloride were reacted according to General Procedures L and B. LCMS (m/z): 845.

Example 178

(S)-3-(4'-Cyano-biphenyl-4-yl)-2-{[(3S,8S)-3-[4-(3,4-dichloro-benzyloxy)-phenyl]-7-((S)-1-phenyl-butyl)-2,3,6,7,8,9-hexahydro-[1,4]dioxino[2,3-g]isoquinoline-8-carbonyl]-amino}-propionic acid (3S,8S)-3-[4-(3,4-Dichloro-benzyloxy)-phenyl]-7-((S)-1-phenyl-butyl)-2,3,6,7,8,9-hexahydro-[1,4]dioxino[2,3-g]isoquinoline-8-carboxylic acid methyl ester was synthesized from (S)-2-tert-butoxycarbonylamino-3-{(S)-2-[4-(3,4-dichloro-benzyloxy)-phenyl]-2,3-dihydro-benzo[1,4]dioxin-6-yl}-propionic acid methyl ester and (R)-1-phenyl-butane-1-ol according to General Procedure AC. This ester was converted to (3S,8S)-3-[4-(3,4-dichloro-benzyloxy)-phenyl]-7-((S)-1-phenyl-butyl)-2,3,6,7,8,9-hexahydro-[1,4]dioxino[2,3-g]isoquinoline-8-carboxylic acid according to General Procedure AB.

The title compound was prepared from (3S,8S)-3-[4-(3,4-dichloro-benzyloxy)-phenyl]-7-((S)-1-phenyl-butyl)-2,3,6,7,8,9-hexahydro-[1,4]dioxino[2,3-g]isoquinoline-8-carboxylic acid and (S)-2-amino-3-(4'-cyano-biphenyl-4-yl)-propionic acid methyl ester hydrochloride according to General Procedures L and B. LCMS (m/z): 868.

Example 179

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid The title compound (110 mg) was prepared from (3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carboxylic acid and (S)-2-amino-3-[4-(2,3-dimethyl-pyridin-4-yl)-phenyl]-propionic acid methyl ester dihydrochloride according to General Procedures L and B. LCMS (m/z): 857. $^1$H NMR (400 MHz, acetone-$d_6$): 8.18 (d, 1H), 7.86 (d, 1H), 7.59 (d, 1H), 7.49 (d, 1H), 7.36 (dd, 1H), 7.23-7.18 (m, 4H), 7.15 (m, 1H), 7.11-7.07 (m, 4H), 6.86 (d, 1H), 6.78-6.72 (m, 4H), 6.61 (s, 1H), 6.52 (s, 1H), 5.03 (s, 2H), 4.93 (dd, 1H), 4.72 (m, 1H), 4.14 (dd, 1H), 3.67 (dd, 1H), 3.54 (dd, 1H), 3.45 (d, 1H), 3.39 (dd, 1H), 3.23 (d, 1H), 3.03 (dd, 1H), 2.89-2.79 (m, 2H), 2.66 (dd, 1H), 2.38 (s, 3H), 2.02 (s, 3H), 1.87-1.75 (m, 1H), 1.72-1.61 (m, 1H), 0.48 (t, 3H).

The compounds identified in Examples 180-211, below, were prepared using synthetic procedures analogous to those used for the synthesis of the compound of Example 179.

Example 180

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,5-dimethyl-2H-pyrazol-3-yl)-phenyl]-propionic acid

Example 181

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2-methyl-pyridin-4-yloxy)-phenyl]-propionic acid

Example 182

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(6,7-dihydro-5H-[1]pyrindin-4-yl)-phenyl]-propionic acid

Example 183

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-(4-pyridin-3-yl-phenyl)-propionic acid

Example 185

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(pyridin-3-yloxy)-phenyl]-propionic acid

Example 186

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-(4-pyridazin-4-yl-phenyl)-propionic acid

Example 187

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-(4-pyrimidin-4-yl-phenyl)-propionic acid

Example 188

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,6-dimethyl-pyridin-4-yl)-phenyl]-propionic acid

Example 189

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 190

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,5-dimethyl-pyridin-4-yl)-phenyl]-propionic acid

Example 191

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2-methyl-2H-pyrazol-3-yl)-phenyl]-propionic acid

Example 192

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2-methoxy-pyridin-4-yl)-phenyl]-propionic acid

Example 193

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-(4'-trifluoromethyl-biphenyl-4-yl)-propionic acid

Example 194

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2-methyl-pyridin-4-yl)-phenyl]-propionic acid

Example 195

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2-hydroxy-pyridin-4-yl)-phenyl]-propionic acid

Example 196

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(6-methyl-pyridin-3-yl)-phenyl]-propionic acid

Example 197

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(1-methyl-1H-pyrazol-4-yl)-phenyl]-propionic acid

Example 198

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2-trifluoromethyl-pyridin-4-yl)-phenyl]-propionic acid

Example 199

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(6-dimethylamino-pyridin-3-yl)-phenyl]-propionic acid

Example 200

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2-fluoro-pyridin-4-yl)-phenyl]-propionic acid

Example 201

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(3-fluoro-pyridin-4-yl)-phenyl]-propionic acid

Example 202

(S)-3-(4'-Cyano-3'-fluoro-biphenyl-4-yl)-2-{[(3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-propionic acid

Example 203

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(3-methoxy-pyridin-4-yl)-phenyl]-propionic acid

Example 204

(S)-3-[4-(6-Cyano-pyridin-3-yl)-phenyl]-2-{[(3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-propionic acid

Example 205

(S)-3-[4-(6-Amino-pyridin-3-yl)-phenyl]-2-{[(3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-propionic acid

Example 206

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2-hydroxymethyl-pyridin-4-yl)-phenyl]-propionic acid

Example 207

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2-ethyl-pyridin-4-yl)-phenyl]-propionic acid

Example 208

(S)-3-[4-(2-Amino-pyridin-4-yl)-phenyl]-2-{[(3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-propionic acid

Example 209

(S)-3-[4-(2-Amino-pyrimidin-5-yl)-phenyl]-2-{[(3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-propionic acid

Example 210

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2-propyl-pyridin-4-yl)-phenyl]-propionic acid

Example 211

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-(4-quinolin-4-yl-phenyl)-propionic acid

Example 212

(S)-2-{[(3S,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2-fluoromethyl-pyridin-4-yl)-phenyl]-propionic acid (S)-2-tert-Butoxycarbonylamino-3-[4-(2-hydroxymethyl-pyridin-4-yl)-phenyl]-propionic acid methyl ester was dissolved in DCM and cooled to 0° C. Methoxyethyl-DAST was added dropwise and the reaction mixture was allowed to warm to room temperature. After the reaction was complete, it was quenched with a 10% NaOH solution. The mixture was extracted 3 times with DCM and the organic concentrated in vacuo. The resulting residue was purified over silica (80:20 hexanes/EtOAc). The material was treated with 4N HCl in dioxane and precipitated from DCM-hexanes to provide (S)-2-amino-3-[4-(2-fluoromethyl-pyridin-4-yl)-phenyl]-propionic acid methyl ester bis hydrochloride salt.

The title compound was prepared from (3S,8S)-3-[4-(3,4-dichloro-benzyloxy)-phenyl]-7-((S)-1-phenyl-propyl)-2,3,6,7,8,9-hexahydro-[1,4]dioxino[2,3-g]isoquinoline -8-carboxylic acid and (S)-2-amino-3-[4-(2-fluoromethyl-pyridin-4-yl)-phenyl]-propionic acid methyl ester bis hydrochloride according to General Procedures L and B. LCMS (m/z): 861.

Example 213

(S)-2-{[(3S,8S)-3-[4-(3,4-Dichloro-benzyloxy)-phenyl]-7-(1-ethyl-2-methyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid The title compound (15 mg) was prepared from (S)-2-tert-butoxycarbonylamino-3-{(S)-2-[4-(3,4-dichloro-benzyloxy)-phenyl]-2,3-dihydro-benzo[1,4]dioxin-6-yl}-propionic acid methyl ester, which was deprotected according to General Procedure C, then treated with 2-methyl-3-pentanone according to General Procedure M. The reductive amination product was subjected to General Procedures V and B in succession, then the resulting acid and (S)-2-amino-3-[4-(2,3-dimethyl-pyridin-4-yl)-phenyl]-propionic acid methyl ester dihydrochloride were reacted according to General Procedures L and B. LCMS (m/z): 823.

Example 214

(S)-2-{[(3S,8S)-3-[4-(3-chloro-phenoxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3S,8S)-8-{(S)-2-[4-(2,3-Dimethyl-pyridin-4-yl)-phenyl]-1-methoxycarbonyl-ethylcarbamoyl}-3-(4-hydroxy-phenyl)-2,3,8,9-tetrahydro-6H-[1,4]dioxino[2,3g]isoquinoline-7-carboxylic acid tert-butyl (0.1 g), 3-chlorophenylboronic acid (0.0337 g), cupric acetate (0.39 g), and 1 gram of powdered 4 Å molecular sieves in 5 mL dry DCM and 0.1 mL TEA was stirred vigorously at room temperature overnight. The reaction mixture was then filtered through celite, the celite cake was washed three times with DCM, and the filtrates combined. The solvent was then removed in vacuo, and purified by column chromatography using 2% MeOH and 1:1 hexane and ethyl acetate as an eluents to give 50 mg of (3S,8S)-3-[4-(3-chloro-phenoxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester which was deprotected according to General Procedure C to provide (S)-2-({(3S,8S)-3-[4-(3-chloro-phenoxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (0.035 g).

(S)-2-({(3S,8S)-3-[4-(3-Chloro-phenoxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (0.035 g), 2,5-dimethyl-oxazole-4-carboxylic acid (0.014 g), HBTU (0.038 g) in DCM (3.0 mL), DIEA (0.026 g) was added. The reaction mixture was stirred at r.t for 2.0 h, poured on to a silica gel column chromatography and eluted with 1% MeOH, 1:1 hexanes/EtOAc to provide (S)-2-{[(3S,8S)-3-[4-(3-Chloro-phenoxy)-phenyl]-7-(2,5-dimethyl-oxazole-4-carbonyl)-2,3,6,7,8,9-hexahydro-[1,4]dioxino[2,3g]iso-quinoline-8-carbonyl]-amino}-3-[4-(2,3-dimethyl-pyridin-4-yl)-phenyl]-propionic acid methyl etser (0.020 g).

(S)-2-{[(3S,8S)-3-[4-(3-Chloro-phenoxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl etser (0.020 g) dissolved in THF (0.3 mL) and MeOH (0.3 mL) and 0.3 mL of 2.0 N LiOH was added at 0° C. and stirred at that temperature for 30 minutes. The pH was adjusted to 6-7, and the mixture was extracted with EtOAc, dried with (Na₂SO₄), and evaporated and dried under vacuum to get the title compound (0.015 g). LCMS (m/z): 814.

Example 215

(S)-2-{[(3S,8S)-3-(3'-Chloro-biphenyl-4-yl)-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3S,8S)-8-{(S)-2-[4-(2,3-Dimethyl-pyridin-4-yl)-phenyl]-1-methoxycarbonyl-ethylcarbamoyl}-3-(4-hydroxy-phenyl)-2,3,8,9-tetrahydro-6H-[1,4]dioxino[2,3g]iso-quinoline-7-carboxylic acid tert-butyl (0.1 g) and trufluoromethanesulfonic anhydride (0.077 g) were dissolved in DCM (3.0 mL). To this stirring solution at 0° C., pyridine (0.1 mL) was added drop-wise and stirred at room temperature for 30 minutes. Solvents were evaporated and the compound was purified by column chromatography (1 MeOH, 1:1 hexane and EA) to get (3S,8S)-8-{(S)-2-[4-(2,3-dimethyl-pyridin-4-yl)-phenyl]-1-methoxycarbonyl-ethyl-carbamoyl}-3-(4-trifluoromethanesulfonyloxy-phenyl)-2,3,8,9-tetrahydro-6H-[1,4]dioxino-[2,3-g]isoquinoline-7-carboxylic acid tert-butyl ester (0.075 g).

To a solution of (3S,8S)-8-{(S)-2-[4-(2,3-Dimethyl-pyridin-4-yl)-phenyl]-1-methoxycarbonyl-ethylcarbamoyl}-3-(4-trifluoromethanesulfonyloxy-phenyl)-2,3,8,9-tetrahydro-6H-[1,4]dioxino[2,3-g]isoquinoline-7-carboxylic acid tert-butyl ester (0.075 g) in toluene (4.0 mL) was added 3-chlorophenylboronic acid (0.0337 g), Pd(PPh₃)₄ (0.0052 g), and Na₂CO₃ (24 mg in 1.0 mL H₂O). The mixture was heated at 90° C. for 3.0 hours. After completion of the reaction, the aqueous layer was drained. The organic layer was poured on to a silica gel column chromatography and eluted with 1% MeOH, 1:1 hexanes/EtOAc to provide (3S,8S)-3-(3'-Chloro-biphenyl-4-yl)-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (0.039 g) which was deprotected according to General Procedure C to provide (S)-2-{[(3S,8S)-3-(3'-Chloro-biphenyl-4-yl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester bis hydrochloride (0.025 g).

(S)-2-{[(3S,8S)-3-(3'-Chloro-biphenyl-4-yl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester bis hydrochloride (0.025 g), 2,5-dimethyl-oxazole-4-carboxylic acid (0.010 g), HBTU (0.027 g) in DCM (3.0 mL), DIEA (0.019 g) was added. The reaction mixture was stirred at room temperature for 2.0 hours, poured onto a silica gel column and eluted with 1% MeOH, 1:1 hexanes-EtOAc to provide (S)-2-{[(3S,8S)-3-(3'-Chloro-biphenyl-4-yl)-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester (0.0139 g).

(S)-2-{[(3S,8S)-3-(3'-Chloro-biphenyl-4-yl)-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester (0.0139 g) was dissolved in THF (0.3 mL) and MeOH (0.3 mL) and 0.3 mL of 2.0 N LiOH was added at 0° C. and stirred at that temperature for 30 min. pH was adjusted to 6-7, extracted with EtOAc, dried (Na₂SO₄), evaporated the solvents and dried under vacco to get the title compound. LCMS (m/z): 798.

Example 216

(S)-2-{[(3S,8S)-3-[4-(3,4-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (25 mg) was converted to (S)-2-{[(3S,8S)-3-[4-(3,4-dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester according to General Procedure F. The resulting compound was hydrolyzed according to General Procedure B to give the title compound (15 mg). LCMS (m/z): 862.

Example 217

(S)-2-{[(3S,8S)-3-[4-(3,4-Dimethyl-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3S,8S)-8-{(S)-2-[4-(2,3-Dimethyl-pyridin-4-yl)-phenyl]-1-methoxycarbonyl-ethyl-carbamoyl}-3-(4-hydroxy-phenyl)-2,3,8,9-tetrahydro-6H-[1,4]dioxino[2,3-g]isoquinoline-7-carboxylic acid tert-butyl ester (30 mg) was dissolved in DMF and 3,4-dimethylbenzyl bromide (2 equiv) and potassium carbonate (3 eq.) added. The reaction mixture was stirred at room temperature and was poured onto EtOAc and water. The organic layer was dried over sodium sulfate and concentrated. The mixture was purified over silica (hexanes; 1:1 hexanes/EtOAc; 1:1 hexanes/EtOAc+1% MeOH). The resulting compound was dissolved in 2 mL DCM and 1 mL 4N HCl (dioxane) was added. The mixture was stirred at room temperature for 1.5 hours and was concentrated. The residue was suspended in DCM. TEA (3 eq.) was added and the mixture used in the following reaction sequence. In a separate vial, EDC (3 eq.) and 2,5-dimethyl-oxazole-4-carboxylic acid (6 eq.) were dissolved in DCM and stirred for 40 minutes. This solution was added to the above mixture and stirred for 12 hours. The reaction mixture was directly purified over silica (hexanes; 1:1 hexanes/EtOAc; 1:1 hexanes/EtOAc+1% MeOH; 1:1 hexanes/EtOAc+2% MeOH; 1:1 hexanes/EtOAc+3% MeOH). The resulting compound was hydrolyzed according to General Procedure B to give the title compound. LCMS (m/z): 822.

Example 218

(S)-2-({(3S,8S)-7-(2,5-Dimethyl-oxazole-4-carbonyl)-3-[4-(3-methyl-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)phenyl]-propionic acid (3S,8S)-8-{(S)-2-[4-(2,3-Dimethyl-pyridin-4-yl)-phenyl]-1-methoxycarbonyl-ethyl-carbamoyl}-3-(4-hydroxy-phenyl)-2,3,8,9-tetrahydro-6H-[1,4]dioxino[2,3-g]isoquinoline-7-carboxylic acid tert-butyl ester (30 mg) was dissolved in DMF and 3-methylbenzyl bromide (2 eq.) and potassium carbonate (3 eq.) added. The reaction mixture was stirred at room temperature and was then poured onto EtOAc and water. The organic layer was dried over sodium sulfate and concentrated. The mixture was purified over silica (hexanes; 1:1 hexanes EtOAc; 1:1 hexanes EtOAc+1% MeOH). The resulting compound was dissolved in 2 mL DCM and 1 mL 4N HCl (dioxane) was added. The mixture stirred at room temperature for 1.5 hours and was concentrated. The residue was suspended in DCM, TEA (3 eq.) added and the mixture used in the following reaction sequence. In a separate vial EDC (3 eq.) and 2,5-dimethyl-oxazole-4-carboxylic acid (6 eq.) were dissolved in DCM and stirred 40 minutes. This solution was added to the above mixture stirred 12 hours. The reaction mixture was directly purified over silica (hexanes; 1:1 hexanes/EtOAc; 1:1 hexanes EtOAc+1% MeOH; 1:1 hexanes EtOAc+2% MeOH; 1:1 hexanes EtOAc+3% MeOH). The resulting compound was hydrolyzed according to General Procedure B to give the title compound. LCMS (m/z): 808.

Example 219

(S)-2-({(3S,8S)-7-(2,5-Dimethyl-oxazole-4-carbonyl)-3-[4-(indan-2-yloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)phenyl]-propionic acid (3S,8S)-8-{(S)-2-[4-(2,3-Dimethyl-pyridin-4-yl)-phenyl]-1-methoxycarbonyl-ethyl-carbamoyl}-3-(4-hydroxy-phenyl)-2,3,8,9-tetrahydro-6H-[1,4]dioxino[2,3g]isoquinoline-7-carboxylic acid tert-butyl ester (30 mg) was dissolved in DCM and indan-2-ol (5 eq.), triphenyl phosphine (5 eq.) and DIAD (4.6 eq.) added at 0° C. The reaction mixture stirred at room temperature for 16 hours and was directly purified over silica (hexanes; 1:1 hexanes/EtOAc; 1:1 hexanes EtOAc+1% MeOH). The resulting compound was dissolved in 2 mL DCM and 1 mL 4N HCl (dioxane) was added. The mixture stirred at room temperature for 1.5 hours and was concentrated. The residue was suspended in DCM, TEA (3 eq.) was added and the mixture was concentrated. In a separate vial, EDC (3 eq.) and 2,5-dimethyl-oxazole-4-carboxylic acid (6 eq.) were dissolved in DCM and stirred for 40 minutes. This solution was added to the above mixture and stirred for 16 hours. The reaction mixture was directly purified over silica (hexanes; 1:1 hexanes/EtOAc; 1:1 hexanes EtOAc+1% MeOH). This compound was dissolved in THF (0.3 mL) and MeOH (0.3 mL) and 0.3 mL of 2.0 N LiOH was added at 0° C. and stirred at that temperature for 30 minutes. Then, pH was adjusted to 6-7, and the mixture was extracted with EtOAc, dried (Na$_2$SO$_4$), and evaporated and dried under vacuum to give the title compound (0.008 g) LCMS (m/z) 820.

The compounds identified in Examples 220-224, below, were prepared using synthetic procedures analogous to those used for the synthesis of the compound of Example 219.

Example 220

(S)-2-{[(3S,8S)-3-[4-(4,4-Dimethyl-cyclohexyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 221

(S)-2-({(3S,8S)-7-(2,5-Dimethyl-oxazole-4-carbonyl)-3-[4-(tetrahydro-pyran-4-yloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 222

(S)-2-({(3S,8S)-7-(2,5-Dimethyl-oxazole-4-carbonyl)-3-[4-(trans-4-methyl-cyclohexyl-methoxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 223

(S)-2-{[(3S,8S)-3-[4-(4,4-Difluoro-cyclohexyl-methoxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]propionic acid

Example 224

(S)-2-({(3S,8S)-7-(2,5-Dimethyl-oxazole-4-carbonyl)-3-[4-(3,3,3-trifluoro-propoxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 225

(S)-2-({(3S,8S)-7-(2,5-Dimethyl-oxazole-4-carbonyl)-3-[4-(4-trifluoromethyl-cyclohexylmethoxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid (3S,8S)-8-{(S)-1-Carboxy-2-[4-(2,3-dimethyl-pyridin-4-yl)-phenyl]-ethyl-carbamoyl}-3-(4-hydroxy-phenyl)-2,3,8,9-tetrahydro-6H-[1,4]dioxino[2,3-g]isoquinoline-7-carboxylic acid tert-butyl ester was coupled with (4-trifluoromethyl-cyclohexyl)-methanol according to the General Procedure K. The resulting product was converted to (S)-2-({(3S,8S)-7-(2,5-dimethyl-oxazole-4-carbonyl)-3-[4-(4-trifluoromethyl-cyclohexyl-methoxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester according to General Procedure C, then the residue was suspended in DCM. TEA (3 eq.) added and the mixture was concentrated. In a separate vial, EDC (3 eq.) and 2,5-dimethyl-oxazole-4-carboxylic acid (6 eq.) were dissolved in DCM and stirred for 40 minutes. This solution was added to the above mixture and stirred for 16 hours. The reaction mixture was directly purified over silica (hexanes; 1:1 hexanes/EtOAc; 1:1 hexanes EtOAc+1% MeOH). This ester was hydrolyzed according to General Procedure B to give the title compound. LCMS (m/z): 868.

Example 226

(R)-2-({(S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid (S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester (75 mg) was coupled with (R)-2-amino-3-(4'-cyano-biphenyl-4-yl)-propionic acid methyl ester hydrochloride (43 mg) according to General Procedure L to give (S)-8-[(R)-2-(4'-cyano-biphenyl-4-yl)-1-methoxycarbonyl-ethylcarbamoyl]-3-[4-(3,4-dichloro-benzyloxy)-phenyl]-2,3,8,9-tetrahydro-6H-[1,4]dioxino[2,3-g]isoquinoline-7-carboxylic acid tert-butyl ester (88 mg). This intermediate was deprotected according to General Procedure C to give (R)-3-(4'-cyano-biphenyl-4-yl)-2-({(S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester hydrochloride. This compound (100 mg) was further reacted with 2-acetylamino-4-methyl-thiazole-5-sulfonyl chloride to give (R)-2-({(S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-(4'-cyano-biphenyl-4-yl)-propionic acid methyl ester according to General Procedure E. This product (69 mg) was deacylated followed by hydrolysis according to General Procedures N and B to give the title compound. LCMS (m/z): 910.

Example 227

(S)-2-{[(3S,8S)-3-[4-(3,4-Dichloro-benzyloxy)-phenyl]-7-(6-methyl-pyridin-2-ylmethyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester dihydrochloride (30 mg) was reacted with 6-methyl-pyridine-2-carbaldehyde according to General Procedure D. The reaction mixture was directly purified over silica (hexanes to 1:1 hexanes EtOAc to 1:1 hexanes EtOAc+1% MeOH to 1:1 hexanes EtOAc+2% MeOH up to 1:1 hexanes EtOAc+5% MeOH) to give (S)-2-{[(3S,8S)-3-[4-(3,4-dichloro-benzyloxy)-phenyl]-7-(6-methyl-pyridin-2-ylmethyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester. This ester was hydrolyzed according to General Procedure B to give the title compound (15 mg). LCMS (m/z): 845.

The compounds identified in Examples 228-234, below, were prepared using synthetic procedures analogous to those used for the synthesis of the compound of Example 227.

Example 228

(S)-2-{[(3S,8S)-3-[4-(3,4-Dichloro-benzyloxy)-phenyl]-7-(3-fluoro-pyridin-2-ylmethyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 229

(S)-2-{[(3S,8S)-3-[4-(3,4-Dichloro-benzyloxy)-phenyl]-7-(6-methoxy-pyridin-2-ylmethyl)-2,3,6,7,8,9-hexahydro-[1,4]dioxino[2,3-g]isoquinoline-8-carbonyl]-amino}-3-[4-(2,3-dimethyl-pyridin-4-yl)phenyl]-propionic acid Example 230

(S)-2-{[(3S,8S)-3-[4-(3,4-Dichloro-benzyloxy)-phenyl]-7-(1-methyl-1H-imidazol-2-ylmethyl)-2,3,6,7,8,9-hexahydro-[1,4]dioxino[2,3-g]isoquinoline-8-carbonyl]-amino}-3-[4-(2,3-dimethyl-pyridin-4-yl)phenyl]-propionic acid Example 231

(S)-2-({(3S,8S)-3-[4-(3,4-Dichloro-benzyloxy)-phenyl]-7-thiazol-2-ylmethyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid Example 232

(S)-2-{[(3S,8S)-3-[4-(3,4-Dichloro-benzyloxy)-phenyl]-7-(2,5-dimethyl-oxazol-4-ylmethyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 233

(S)-2-({(3S,8S)-3-[4-(3,4-Dichloro-benzyloxy)-phenyl]-7-pyridin-3-ylmethyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid Example 234

(S)-2-({(3S,8S)-3-[4-(3,4-Dichloro-benzyloxy)-phenyl]-7-pyridin-4-ylmethyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid Example 235

(S)-2-{[(3S,8S)-3-[4-(3,4-Dichloro-benzyloxy)-phenyl]-7-(pyrazine-2-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester dihydrochloride (25 mg)

was reacted with pyrazine-2-carbonyl chloride according to General Procedure F. The reaction mixture was directly purified over silica (heaxnes to 1:1 hexanes EtOAc to 1:1 hexanes EtOAc+1% MeOH to 1:1 hexanes EtOAc+2% MeOH to 1:1 hexanes EtOAc+4% MeOH). to give (S)-2-{[(3S,8S)-3-[4-(3,4-dichloro-benzyloxy)-phenyl]-7-(pyrazine-2-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester. This ester was hydrolyzed according to General Procedure B to give the title compound (12 mg). LCMS (m/z): 847.

The compounds identified in Examples 236-238, below, were prepared using synthetic procedures analogous to those used for the synthesis of the compound of Example 235.

Example 236

(S)-2-{[(3S,8S)-3-[4-(3,4-Dichloro-benzyloxy)-phenyl]-7-(pyridine-2-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 237

(S)-2-({(3S,8S)-7-(3-Chloro-benzoyl)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid Example 238

(S)-2-{[(3S,8S)-3-[4-(3,4-Dichloro-benzyloxy)-phenyl]-7-(4-methyl-oxazole-5-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 239

(S)-2-{[(3S,8S)-3-[4-(3,4-Dichloro-benzyloxy)-phenyl]-7-((S)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid To a solution of (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester in DCM was added (S)-1-isocyanato-ethyl)-benzene (5 equiv) and the reaction was stirred at rt for 1 hour. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+3% MeOH). The resulting compound was hydrolyzed according to General Procedure B to give the title compound. LCMS (m/z): 886.

The compounds identified in Examples 240-256, below, were prepared using synthetic procedures analogous to those used for the synthesis of the compound of Example 239.

Example 240

(S)-2-{[(3S,8S)-3-[4-(3,4-Dichloro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 241

(S)-2-{[(3S,8S)-3-[4-(3,4-Dichloro-benzyloxy)-phenyl]-7-(3-fluoro-phenylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 242

(S)-2-({(3S,8S)-3-[4-(3,4-Dichloro-benzyloxy)-phenyl]-7-o-tolylcarbamoyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid Example 243

(S)-2-({(3S,8S)-3-[4-(3,4-Dichloro-benzyloxy)-phenyl]-7-p-tolylcarbamoyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid Example 244

(S)-2-({(3S,8S)-7-Benzylcarbamoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid Example 245

(S)-2-{[(3S,8S)-3-[4-(3,4-Dichloro-benzyloxy)-phenyl]-7-((S)-1-phenyl-propylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 246

(S)-2-{[(3S,8S)-3-[4-(3,4-Dichloro-benzyloxy)-phenyl]-7-((R)-1-phenyl-Propylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 247

(S)-2-({(3S,8S)-3-[4-(3,4-Dichloro-benzyloxy)-phenyl]-7-[(R)-1-(4-fluoro-phenyl)-ethylcarbamoyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 248

(S)-2-({(3S,8S)-7-Cyclopentylcarbamoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 249

(S)-2-({(3S,8S)-7-(4-chloro-phenylcarbamoyl)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 250

(S)-2-({(3S,8S)-3-[4-(3,4-Dichloro-benzyloxy)-phenyl]-7-isopropylcarbamoyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 251

(S)-2-({(3S,8S)-7-tert-Butylcarbamoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 252

(S)-2-({(3S,8S)-7-Cyclohexylcarbamoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 253

(S)-2-({(3S,8S)-3-[4-(3,4-Dichloro-benzyloxy)-phenyl]-7-m-tolylcarbamoyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 254

(S)-2-{[(3S,8S)-3-[4-(3,4-Dichloro-benzyloxy)-phenyl]-7-(3,4-difluoro-phenylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 255

(S)-2-{[(3S,8S)-3-[4-(3,4-Dichloro-benzyloxy)-phenyl]-7-(3,5-difluoro-phenylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 256

(S)-2-{[(3S,8S)-3-[4-(3,4-Dichloro-benzyloxy)-phenyl]-7-(4-fluoro-phenylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 257

(S)-2-{[(3S,8S)-3-[4-(3,4-Dichloro-benzyloxy)-phenyl]-7-(pyrazin-2-ylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid To a solution of pyrazin-2-ylamine in DCE (2 mL) were added CDI and DMAP (3 mg). The mixture was heated at 60° C. for 1 hour and cooled. To this solution was added a solution of (S)-2-({(3S,8S)-3-[4-(3,4-dichloro-benzyloxy)-phenyl]-2,3,6,7,8,9-hexahydro[1,4]dioxino[2,3-g]isoquinoline-8-carbonyl}-amino)-3-[4-(2,3-dimethyl-pyridin-4-yl)phenyl]-propionic acid methyl ester (0.040 mmol, 30 mg) in 1 mL DCE. The mixture was heated at 60° C. for 1 hour and cooled. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+5% MeOH). The resulting compound was hydrolyzed according to General Procedure B to give the title compound. LCMS (m/z): 860.

The compounds identified in Examples 258-259, below, were prepared using synthetic procedures analogous to those used for the synthesis of the compound of Example 257.

Example 258

(S)-2-{[(3S,8S)-3-[4-(3,4-dichloro-benzyloxy)-phenyl]-7-(pyridin-2-ylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 259

(S)-2-{[(3S,8S)-3-[4-(3,4-Dichloro-benzyloxy)-phenyl]-7-(pyridin-3-ylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 260

(S)-2-{[(3S,8S)-3-[4-(3,4-Dichloro-benzyloxy)-phenyl]-7-(pyridin-3-ylcarbamoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid Pyridine-3-ylamine was stirred at 60° C. with 1 eq CDI and a catalytic amount of DMAP in DCE for 1 h, then cooled. A solution of (S)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester (1 eq) in DCE was added and stirred at 60° C. for 1 hour. The reaction mixture was cooled, then directly purified by flash chromatography. The resulting compound was hydrolyzed according to General Procedure B to give the title compound (3 mg). LCMS (m/z) 875.

Example 261

(S)-2-{[(3S,8S)-3-[4-(3,4-Dichloro-benzyloxy)-phenyl]-7-(3-methyl-isoxazol-5-ylcarbamoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid 3-Methyl-isoxazol-5-ylamine was stirred at 60° C. with 1 eq CDI and a catalytic amount of DMAP in DCE for 1 hour, then cooled. A solution of (S)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester (1 eq) in DCE was added and stirred at 60° C. for 1 hour. The reaction mixture was cooled, then directly purified by flash chromatography. The resulting compound was hydrolyzed according to General Procedure B to give the title compound (4 mg). LCMS (m/z) 879.

Example 262

(S)-2-{[(3S,8S)-3-[4-(3,4-Dichloro-benzyloxy)-phenyl]-7-(pyridine-2-carbonyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester dihydrochloride (25 mg) was reacted with pyridine-2-carbonyl chloride according to General Procedure F. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+5% MeOH) to give (S)-2-{[(3S,8S)-3-[4-(3,4-dichloro-benzyloxy)-phenyl]-7-(pyridine-2-carbonyl)-2,3,6,7,8,9 hexahydro-[1,4]dioxino[2,3-g]-isoquinoline-8-carbonyl]-amino}-3-[4-(2,3-dimethyl-pyridin-4-yloxy)-phenyl]-propionic acid methyl ester. This ester was hydrolyzed according to General Procedure B to give the title compound (8 mg). LCMS (m/z): 860.

The compounds identified in Examples 263-266, below, were prepared using synthetic procedures analogous to those used for the synthesis of the compound of Example 262.

Example 263

(S)-2-{[(3S,8S)-3-[4-(3,4-Dichloro-benzyloxy)-phenyl]-7-(4-methyl-oxazole-5-carbonyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 264

(S)-2-{[(3S,8S)-3-[4-(3,4-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 265

(S)-2-{[(3S,8S)-3-[4-(3,4-Dichloro-benzyloxy)-phenyl]-7-(2,4-dimethyl-oxazole-5-carbonyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 266

(S)-2-{[(3S,8S)-3-[4-(3,4-Dichloro-benzyloxy)-phenyl]-7-(2,5-dimethyl-2H-pyrazole-3-carbonyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 267

(S)-2-({(3S,8S)-7-((1R,3S)-3-tert. Butoxycarbonylamino-cyclopentanecarbonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid EDC (3 eq.) and (1R,3S)-3-tert-butoxycarbonylamino-cyclopentanecarboxylic acid (6 eq.) were dissolved in DCM and stirred for 40 minutes. To this solution was added (S)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester (25 mg) and stirred for 12 hours. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+3% MeOH). The resulting compound was hydrolyzed according to General Procedure B to give the title compound. LCMS (m/z): 950.

The compounds identified in Examples 268-284, below, were prepared using synthetic procedures analogous to those used for the synthesis of the compound of Example 267.

Example 268

(S)-2-({(3S,8S)-7-((1S,3R)-3-tert. Butoxycarbonylamino-cyclopentanecarbonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 269

(S)-2-{(3S,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carbonyl}-pyrrolidine-1-carboxylic acid tert.butyl ester

Example 270

(S)-2-{[(3S,8S)-3-[4-(3,4-Dichloro-benzyloxy)-phenyl]-7-(2,5-dimethyl-2H-pyrazole-3-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionoc acid

Example 271

(S)-2-{[(3S,8S)-3-[4-(3,4-Dichloro-benzyloxy)-phenyl]-7-(5-methyl-isoxazole-3-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 272

(S)-2-{[(3S,8S)-3-[4-(3,4-Dichloro-benzyloxy)-phenyl]-7-(5-methyl-isoxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 273

(S)-2-{[(3S,8S)-3-[4-(3,4-Dichloro-benzyloxy)-phenyl]-7-(1-methyl-1H-imidazole-2-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 274

4-{(3S,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carbonyl}-piperidine-1-carboxyl is acid tert-butyl ester

Example 275

(S)-2-{[(3S,8S)-3-[4-(3,4-Dichloro-benzyloxy)-phenyl]-7-(3-methyl-benzofuran-2-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 276

(S)-2-{[(3S,8S)-3-[4-(3,4-Dichloro-benzyloxy)-phenyl]-7-(4-hydroxy-benzoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 277

(S)-2-{[(3S,8S)-3-[4-(3,4-Dichloro-benzyloxy)-phenyl]-7-(3-hydroxy-benzoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 278

(S)-2-{[(3S,8S)-3-[4-(3,4-Dichloro-benzyloxy)-phenyl]-7-(3,5-difluoro-benzoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 279

(R)-2-{(3S,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carbonyl}-pyrrolidine-1-carboxylic acid tert-butyl ester

Example 280

(S)-3-{(3S,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carbonyl}-pyrrolidine-1-carboxylic acid tert-butyl ester

Example 281

(R)-3-{(3S,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carbonyl}-pyrrolidine-1-carboxylic acid tert-butyl ester

Example 282

(S)-2-{[(3S,8S)-3-[4-(3,4-Dichloro-benzyloxy)-phenyl]-7-(indane-2-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 283

(S)-2-({(3S,8S)-7-(Benzothiazole-2-carbonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 284

(S)-2-{[(3S,8S)-3-[4-(3,4-Dichloro-benzyloxy)-phenyl]-7-(4-fluoro-benzoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 285

(S)-2-{[(3S,8S)-3-[4-(3,4-Dichloro-benzyloxy)-phenyl]-7-(6-methoxy-pyridin-2-ylmethyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester bis hydrochloride (30 mg) was reductively aminated with 6-methoxy-pyridine-2-carbaldehyde according to General Procedure D (with excess of aldehyde). The resulting compound was hydrolyzed according to General Procedure B to give the title compound (20 mg). LCMS (m/z): 876.

The compounds identified in Examples 286-292, below, were prepared using synthetic procedures analogous to those used for the synthesis of the compound of Example 285.

Example 286

(S)-2-{[(3S,8S)-3-[4-(3,4-Dichloro-benzyloxy)-phenyl]-7-(1-methyl-1H-imidazol-2-ylmethyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 287

(S)-2-({(3S,8S)-3-[4-(3,4-Dichloro-benzyloxy)-phenyl]-7-thiazol-2-ylmethyl-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 288

(S)-2-({(3S,8S)-3-[4-(3,4-Dichloro-benzyloxy)-phenyl]-7-pyridin-2-ylmethyl-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 289

(S)-2-({(3S,8S)-3-[4-(3,4-Dichloro-benzyloxy)-phenyl]-7-pyridin-3-ylmethyl-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 290

(S)-2-({(3S,8S)-3-[4-(3,4-Dichloro-benzyloxy)-phenyl]-7-pyridin-4-ylmethyl-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 291

(S)-2-{[(3S,8S)-3-[4-(3,4-Dichloro-benzyloxy)-phenyl]-7-(6-methyl-pyridin-2-ylmethyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 292

(S)-2-{[(3S,8S)-3-[4-(3,4-Dichloro-benzyloxy)-phenyl]-7-(3-fluoro-pyridin-2-ylmethyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 293

(3S,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid isopropyl ester (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (25 mg) was reacted with isopropyl chloroformate according to General Procedure G (with excess of chloroformate). The resulting compound was hydrolyzed according to General Procedure B to give the title compound (7 mg). LCMS (m/z): 825.

The compounds identified in Examples 294-297, below, were prepared using synthetic procedures analogous to those used for the synthesis of the compound of Example 293.

Example 294

(3S,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid butyl ester

Example 295

(3S,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid isobutyl ester

Example 296

(3S,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid 2,2-dimethyl-propyl ester

Example 297

(3S,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid benzyl ester

Example 298

(3S,8S)-8-{(S)-1-Carboxy-2-[4-(2,3-dimethyl-pyridin-4-yloxy)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid isopropyl ester (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester bis hydrochloride (25 mg) was reacted with isopropyl chloroformate according to General Procedure G (with excess of chloroformate). The resulting compound was hydrolyzed according to General Procedure B to give the title compound (4 mg). LCMS (m/z): 841.

The compounds identified in Examples 299-302, below, were prepared using synthetic procedures analogous to those used for the synthesis of the compound of Example 298.

Example 299

(3S,8S)-8-{(S)-1-Carboxy-2-[4-(2,3-dimethyl-pyridin-4-yloxy)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid butyl ester

Example 300

(3S,8S)-8-{(S)-1-Carboxy-2-[4-(2,3-dimethyl-pyridin-4-yloxy)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid isobutyl ester

Example 301

(3S,8S)-8-{(S)-1-Carboxy-2-[4-(2,3-dimethyl-pyridin-4-yloxy)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid 2,2-dimethyl-propyl ester

Example 302

(3S,8S)-8-{(S)-1-Carboxy-2-[4-(2,3-dimethyl-pyridin-4-yloxy)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid benzyl ester

Example 303

(S)-2-({(3S,8S)-7-Benzoyl-3-[4-(3,3-dimethyl-butoxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid (S)-2-{[(3S,8S)-7-Benzoyl-3-(4-hydroxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester (18 mg) was dissolved in DCM, triphenyl phosphine (5.9 eq.). 3,3-Dimethyl-butan-1-ol (excess) added and mixture cooled on ice. DIAD (5.1 eq.) was added and the reaction mixture stirred on ice for 10 minutes and rt for 16 hours. The reaction mixture was directly purified over silica (DCM-EtOAc 8:2 to DCM-EtOAc 6:4). The resulting residue was hydrolyzed according to General Procedure B and purified over silica (DCM to DCM+1% MeOH to DCM+7% MeOH) to give the title compound (11 mg). LCMS (m/z): 769.

The compounds identified in Examples 304-306, below, were prepared using synthetic procedures analogous to those used for the synthesis of the compound of Example 303.

Example 304

(S)-2-({(3S,8S)-7-Benzoyl-3-[4-(cis-4-methyl-cyclohexyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 305

(S)-2-{[(3S,8S)-7-Benzoyl-3-(4-cyclopentylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 306

(S)-2-({(3S,8S)-7-Benzoyl-3-[4-(trans-4-methyl-cyclohexyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 307

(S)-2-{[(3S,8S)-3-[4-(3,4-Dichloro-benzyloxy)-phenyl]-7-(piperidine-2-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid bis hydrochloride (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (25 mg) was suspended in DCM, 0.1 mL DIEA added and mixture concentrated to provide a solid. In a separate vial, EDC (35 mg) and piperidine-1,2-dicarboxylic acid mono-tert-butyl ester (83 mg) were dissolved in DCM and stirred 15 min. This solution was added to the solid and mixture stirred for 4 hours. The reaction mixture was directly purified over silica (hexanes to 1:1 hexanes EtOAc to 1:1 hexanes EtOAc+2% MeOH). The resulting compound was hydrolyzed (2 mg removed before deprotection) and deprotected according to General Procedures B and C to provide the title compound (10 mg). LCMS (m/z): 850.

The compounds identified in Examples 308-310, below, were prepared using synthetic procedures analogous to those used for the synthesis of the compound of Example 307.

Example 308

(S)-2-{[(3S,8S)-3-[4-(3,4-Dichloro-benzyloxy)-phenyl]-7-(piperidine-3-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid bis hydrochloride

Example 309

(S)-2-{[(3S,8S)-3-[4-(3,4-Dichloro-benzyloxy)-phenyl]-7-((S)-pyrrolidine-3-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid bis hydrochloride

Example 310

(S)-2-{[(3S,8S)-3-[4-(3,4-Dichloro-benzyloxy)-phenyl]-7-((R)-pyrrolidine-3-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid bis hydrochloride

Example 311

(S)-2-{[(3S,8S)-3-[4-(3,4-Dichloro-benzyloxy)-phenyl]-7-(morpholine-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (21 mg) was reacted with morpholine-4-carbonyl chloride according to General Procedure H. The resulting compound was hydrolyzed according to General Procedure B to give the title compound (11 mg). LCMS (m/z): 852.

The compounds identified in Examples 312-315, below, were prepared using synthetic procedures analogous to those used for the synthesis of the compound of Example 311.

Example 312

(S)-2-{[(3S,8S)-3-[4-(3,4-Dichloro-benzyloxy)-phenyl]-7-(piperidine-1-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 313

(S)-2-{[(3S,8S)-3-[4-(3,4-Dichloro-benzyloxy)-phenyl]-7-(pyrrolidine-1-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 314

(S)-2-({(3S,8S)-3-[4-(3,4-Dichloro-benzyloxy)-phenyl]-7-diisopropylcarbamoyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 315

(S)-2-({(3S,8S)-3-[4-(3,4-Dichloro-benzyloxy)-phenyl]-7-dimethylcarbamoyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 316

(S)-2-{[(3S,8S)-3-[4-(3,4-Dichloro-benzyloxy)-phenyl]-7-(4,4-difluoro-piperidine-1-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester (30 mg) in DCM (3 mL), 4,4-difluoro-piperidine-1-carbonyl chloride (5.0 eq, prepared according to General Procedure AD) according to General Procedure H and purified over silica (hexanes to 1:1 hexanes EtOAc to 1:1 hexanes EtOAc+1% MeOH). The resulting compound was hydrolyzed according to General Procedure B to give the title compound (8 mg). LCMS (m/z) 886.

The compounds identified in Examples 317-318, below, were prepared using synthetic procedures analogous to those used for the synthesis of the compound of Example 316.

Example 317

(S)-2-{[(3S,8S)-3-[4-(3,4-Dichloro-benzyloxy)-phenyl]-7-(4-oxo-piperidine-1-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 318

(S)-2-({(3S,8S)-7-(Cyclohexyl-methyl-carbamoyl)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 319

(S)-2-{[(3S,8S)-3-[4-(3,4-Dichloro-benzyloxy)-phenyl]-7-(1,1-dimethyl-propylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester (20 mg) was reacted with 2-isocyanato-2-methyl-butane (prepared according to General Procedure AD) according to General Procedure I (with excess of isocyanate). The resulting compound was hydrolyzed according to General Procedure B to give the title compound (7 mg). LCMS (m/z): 852.

The compounds identified in Examples 320-323, below, were prepared using synthetic procedures analogous to those used for the synthesis of the compound of Example 319.

Example 320

(S)-2-{[(3S,8S)-3-[4-(3,4-Dichloro-benzyloxy)-phenyl]-7-(1-methyl-cyclobutylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 321

(S)-2-{[(3S,8S)-3-[4-(3,4-dichloro-benzyloxy)-phenyl]-7-(indan-1-ylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 322

(S)-2-{[(3S,8S)-3-[4-(3,4-dichloro-benzyloxy)-phenyl]-7-(indan-2-ylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 323

(S)-2-{[(3S,8S)-3-[4-(3,4-Dichloro-benzyloxy)-phenyl]-7-(1-methyl-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 324

(S)-2-{[(3S,8S)-3-[4-(3,4-Dichloro-benzyloxy)-phenyl]-7-(1-methyl-1H-pyrazole-3-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester (30 mg) was reacted with 1-methyl-1H-pyrazole-3-carboxylic acid in DCM (3.0 mL) according to General Procedure A and directly purified over silica (hexanes to 1:1 hexanes EtOAc to 1:1 hexanes EtOAc+1% MeOH). The resulting compound was hydrolyzed according to General Procedure B to give the title compound (15 mg). LCMS (m/z): 847.

The compounds identified in Examples 325-334, below, were prepared using synthetic procedures analogous to those used for the synthesis of the compound of Example 324.

Example 325

(S)-2-{[(3S,8S)-3-[4-(3,4-Dichloro-benzyloxy)-phenyl]-7-(2-methyl-5-trifluoromethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 326

(S)-2-{[(3S,8S)-3-[4-(3,4-dichloro-benzyloxy)-phenyl]-7-(oxazole-5-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 327

(S)-2-{[(3S,8S)-3-[4-(3,4-dichloro-benzyloxy)-phenyl]-7-(oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 328

(S)-2-{[(3S,8S)-3-[4-(3,4-dichloro-benzyloxy)-phenyl]-7-(oxazole-2-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 329

(S)-2-{[(3S,8S)-3-[4-(3,4-dichloro-benzyloxy)-phenyl]-7-(5-methyl-thiophene-2-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 330

(S)-2-{[(3S,8S)-3-[4-(3,4-Dichloro-benzyloxy)-phenyl]-7-(imidazo[1,2-a]pyridine-2-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 331

(S)-2-{[(3S,8S)-3-[4-(3,4-Dichloro-benzyloxy)-phenyl]-7-(3,4-difluoro-benzoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 332

(S)-2-{[(3S,8S)-3-[4-(3,4-Dichloro-benzyloxy)-phenyl]-7-(1H-[1,2,4]triazole-3-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 333

(S)-2-{[(3S,8S)-3-[4-(3,4-Dichloro-benzyloxy)-phenyl]-7-(2-oxo-imidazolidine-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 334

(S)-2-{[(3S,8S)-3-[4-(3,4-Dichloro-benzyloxy)-phenyl]-7-(1-methyl-1H-[1,2,3]triazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 335

(S)-2-{[(3S,8S)-3-[4-(3,4-Dichloro-benzyloxy)-phenyl]-7-((S)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester was reacted with (S)-1-isocyanato-ethyl-benzene according to General Procedure I to give (S)-2-{[(3S,8S)-3-[4-(3,4-dichloro-benzyloxy)-phenyl]-7-((S)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid methyl ester. This ester was hydrolyzed according to General Procedure B to give the title compound (15 mg). LCMS (m/z): 902.

The compounds identified in Examples 336-346, below, were prepared using synthetic procedures analogous to those used for the synthesis of the compound of Example 335.

Example 336

(S)-2-{[(3S,8S)-3-[4-(3,4-Dichloro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 337

(S)-2-({(3S,8S)-3-[4-(3,4-Dichloro-benzyloxy)-phenyl]-7-[(R)-1-(4-fluoro-phenyl)-ethylcarbamoyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 338

(S)-2-({(3S,8S)-3-[4-(3,4-Dichloro-benzyloxy)-phenyl]-7-o-tolylcarbamoyl-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 339

(S)-2-({(3S,8S)-3-[4-(3,4-Dichloro-benzyloxy)-phenyl]-7-p-tolylcarbamoyl-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 340

(S)-2-{[(3S,8S)-3-[4-(3,4-Dichloro-benzyloxy)-phenyl]-7-(3-fluoro-phenylcarbamoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 341

(S)-2-({(3S,8S)-7-Benzylcarbamoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 342

(S)-2-({(3S,8S)-3-[4-(3,4-Dichloro-benzyloxy)-phenyl]-7-isopropylcarbamoyl-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 343

(S)-2-({(3S,8S)-7-tert-Butylcarbamoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 344

(S)-2-({(3S,8S)-7-Cyclohexylcarbamoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 345

(S)-2-({(3S,8S)-3-[4-(3,4-Dichloro-benzyloxy)-phenyl]-7-m-tolylcarbamoyl-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 346

(S)-2-({(3S,8S)-7-Cyclopentylcarbamoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid

Example 347

(S)-2-({(3S,8S)-7-Cyclobutylcarbamoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester (30 mg) was reacted with Isocyanato-cyclobutane according to General Procedure AD and I to give (S)-2-({(3S,8S)-7-cyclobutylcarbamoyl-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester. This ester was hydrolyzed according to General Procedure B to give the title compound (12 mg). LCMS (m/z): 852.

The compounds identified in Examples 348-352, below, were prepared using synthetic procedures analogous to those used for the synthesis of the compound of Example 347.

Example 348

(S)-2-{[(3S,8S)-3-[4-(3,4-Dichloro-benzyloxy)-phenyl]-7-(1-methyl-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 349

(S)-2-{[(3S,8S)-3-[4-(3,4-Dichloro-benzyloxy)-phenyl]-7-(1-phenyl-cyclopropylcarbamoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 350

(S)-2-{[(3S,8S)-3-[4-(3,4-Dichloro-benzyloxy)-phenyl]-7-(1,1-dimethyl-propylcarbamoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 351

(S)-2-{[(3S,8S)-3-[4-(3,4-Dichloro-benzyloxy)-phenyl]-7-(1-methyl-cyclobutylcarbamoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 352

(S)-2-{[(3S,8S)-3-[4-(3,4-Dichloro-benzyloxy)-phenyl]-7-(4,4-difluoro-cyclohexylcarbamoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid

Example 353

(S)-2-{[(3S,8S)-3-[4-(3,4-Dichloro-benzyloxy)-phenyl]-7-(2-methyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid EDC (5 eq.) and 2-methyl-oxazole-4-carboxylic acid (10 equiv) were dissolved in DCM and stirred 40 min. To this solution was added (S)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester and stirred for 12 h. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+3% MeOH). The resulting compound was hydrolyzed according to General Procedure B to give the title compound (12 mg). LCMS (m/z): 866.

Example 354

(S)-2-{[(3S,8S)-3-[4-(3,4-Dichloro-benzyloxy)-phenyl]-7-(3,4-dimethoxy-benzoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid 3,4-Dimethoxybenzoic acid (1 eq.) was stirred in dry DCM with 0.5 eq EDCl at RT for 1 h. (S)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester in dry DCM (10 eq benzoic acid relative to amine) was added and the resulting mixture stirred 16 h, then directly purified by flash chromatography. The resulting compound was hydrolyzed according to General Procedure B to give the title compound (5 mg). LCMS (m/z) 919.

Example 355

(S)-2-{[(3S,8S)-3-[4-(2,6-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)phenyl]-propionic acid (3S,8S)-8-{(S)-2-[4-(2,3-Dimethyl-pyridin-4-yl)-phenyl]-1-methoxycarbonyl-ethylcarbamoyl}-3-(4-hydroxyphenyl)-2,3,8,9-tetrahydro-6H-[1,4]dioxino[2,3-g]isoquinoline-7-carboxylic acid tert-butyl ester was dissolved in DMF and 2,6-dichlorobenzyl bromide (2 eq.) and potassium carbonate (3 eq.) were added. The reaction mixture stirred at room temperature and was poured onto EtOAc and water. The organic layer was dried over sodium sulfate and concentrated. The mixture was purified over silica (hexanes to 1:1 hexanes EtOAc to 1:1 hexanes EtOAc+1% MeOH). The resulting compound was dissolved in 2 mL DCM and 1 mL 4N HCl (dioxane) was added. The mixture was stirred at room temperature for 1.5 hours and was concentrated. The residue was suspended in DCM, TEA (3 eq.) added and the mixture used in the following reaction sequence. In a separate vial EDC (3 eq.) and 2,5-dimethyl-oxazole-4-carboxylic acid (6 eq.) were dissolved in DCM and stirred 40 minutes. This solution was added to the above mixture stirred for 12 hours. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+3% MeOH). The resulting compound was hydrolyzed according to General Procedure B to give the title compound (6 mg). LCMS (m/z): 862.

The compounds identified in Examples 356-362, below, were prepared using synthetic procedures analogous to those used for the synthesis of the compound of Example 355.

Example 356

(S)-2-{[(3S,8S)-3-[4-(2,5-Difluoro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 357

(S)-2-{[(3S,8S)-3-[4-(3,5-Difluoro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]propionic acid

Example 358

(S)-2-{[(3S,8S)-3-[4-(2-Chloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]propionic acid

Example 359

(S)-2-{[(3S,8S)-3-[4-(3-Chloro-2-fluoro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)phenyl]-propionic acid

Example 360

(S)-2-{[(3S,8S)-3-[4-(2-Chloro-6-fluoro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)phenyl]-propionic acid

Example 361

(S)-2-{[(3S,8S)-3-[4-(2,3-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)phenyl]-propionic acid

Example 362

(S)-2-{[(3S,8S)-3-[4-(2,5-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 363

(S)-2-{[(3S,8S)-3-[4-(2,6-Dichloro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3S,8S)-8-{(S)-2-[4-(2,3-Dimethyl-pyridin-4-yl)-phenyl]-1-methoxycarbonyl-ethyl-carbamoyl}-3-(4-hydroxy-phenyl)-2,3,8,9-tetrahydro-6H-[1,4]dioxino[2,3-g]isoquinoline-7-carboxylic acid tert-butyl ester was dissolved in DMF and 2,6-dichlorobenzyl bromide (2 eq.) and potassium carbonate (3 eq.) was added. The reaction mixture was stirred at room temperature and was poured onto EtOAc and water. The organic layer was dried over sodium sulfate and concentrated. The mixture was purified over silica (hexanes to 1:1 hexanes EtOAc to 1:1 hexanes EtOAc+1% MeOH). The resulting compound was dissolved in 2 mL DCM and 1 mL 4N HCl (dioxane) was added. The mixture stirred at room temperature for 1.5 hours and was concentrated. The residue was suspended in DCM, TEA (3 eq.) added and the mixture used in the following reaction sequence. ((R)-1-isocyanato-ethyl)-benzene (5 eq.) was added and the reaction was stirred at room temperature for 1 hour. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+3% MeOH). The resulting compound was hydrolyzed according to General Procedure B to give the title compound (5 mg). LCMS (m/z): 886.

The compounds identified in Examples 364-370, below, were prepared using synthetic procedures analogous to those used for the synthesis of the compound of Example 363.

Example 364

(S)-2-{[(3S,8S)-3-[4-(2,5-Difluoro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 365

(S)-2-{[(3S,8S)-3-[4-(3,5-Difluoro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 366

(S)-2-{[(3S,8S)-3-[4-(2-Chloro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 367

(S)-2-{[(3S,8S)-3-[4-(3-Chloro-2-fluoro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 368

(S)-2-{[(3S,8S)-3-[4-(2-chloro-6-fluoro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 369

(S)-2-{[(3S,8S)-3-[4-(2,3-Dichloro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 370

(S)-2-{[(3S,8S)-3-[4-(2,5-Dichloro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 371

(S)-2-{[(3S,8S)-3-{4-[2-(4-Chloro-phenyl)-ethoxy]-phenyl}-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3S,8S)-8-{(S)-2-[4-(2,3-Dimethyl-pyridin-4-yl)-phenyl]-1-methoxycarbonyl-ethylcarbamoyl}-3-(4-hydroxy-phenyl)-2,3,8,9-tetrahydro-6H-[1,4]dioxino[2,3-g]isoquinoline-7-carboxylic acid tert-butyl ester (30 mg) was dissolved in DCM and 2(4-chloro-phenyl)-ethanol (5 equiv), triphenyl phosphine (5 eq.) and DIAD (4.5 eq.) added. The reaction mixture stirred at room temperature and was directly purified over silica (hexanes to 1:1 hexanes EtOAc to 1:1 hexanes EtOAc+1% MeOH). The resulting compound was dissolved in 2 mL DCM and 1 mL 4N HCl (dioxane) added. The mixture stirred at room temperature for 1.5 hours and was concentrated. The residue was suspended in DCM, TEA (3 eq.) added the mixture used in the following reaction sequence. In a separate vial EDC (3 eq.) and 2,5-dimethyl-oxazole-4-carboxylic acid (6 eq.) were dissolved in DCM and stirred 40 minutes. This solution was added to the above mixture stirred 12 hours. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+3% MeOH). The resulting compound was hydrolyzed according to General Procedure B to give the title compound. LCMS (m/z): 842.

The compounds identified in Examples 372-387, below, were prepared using synthetic procedures analogous to those used for the synthesis of the compound of Example 371.

Example 372

(S)-2-{[(3S,8S)-3-[4-(trans-4-tert-Butyl-cyclohexyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 373

(S)-2-({(3S,8S)-7-(2,5-Dimethyl-oxazole-4-carbonyl)-3-[-4-(trans-4-ethyl-cyclohexyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid Example 374

(S)-2-({(3S,8S)-7-(2,5-Dimethyl-oxazole-4-carbonyl)-3-[4-(4-methoxy-cyclohexylmethoxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid Example 375

(S)-2-{[(3S,8S)-3-[4-(4-Chloro-cyclohexyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 376

(S)-2-{[(3S,8S)-3-[4-(5-Chloro-pyridin-3-yl-methoxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 377

(S)-2-{[(3S,8S)-7-(2,5-Dimethyl-oxazole-4-carbonyl)-3-(4-phenethyloxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 378

(S)-2-{[(3S,8S)-3-{4-[1-(4-Chloro-phenyl)-cyclopropylmethoxy]-phenyl}-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 379

(S)-2-{[(3S,8S)-3-(4-cyclopentylmethoxy-phenyl)-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 380

(S)-2-{[(3S,8S)-3-[4-(3,3-dimethyl-butoxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 381

(S)-2-({(3S,8S)-7-(2,5-Dimethyl-oxazole-4-carbonyl)-3-[4-(cis-4-methyl-cyclohexyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid Example 382

(S)-2-({(3S,8S)-7-(2,5-Dimethyl-oxazole-4-carbonyl)-3-[4-(trans-4-methyl-cyclohexyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid Example 383

(S)-2-{[(3S,8S)-3-[4-(2,4-dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid Example 384

(S)-2-{[(3S,8S)-3-[4-(3,5-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 385

(S)-2-({(3S,8S)-7-(2,5-Dimethyl-oxazole-4-carbonyl)-3-[4-(cis-4-ethyl-cyclohexyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid

Example 386

(S)-2-{[(3S,8S)-3-[4-(cis-4-tert-Butyl-cyclohexyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 387

(S)-2-{[(3S,8S)-3-{4-[2-(3,4-Dichloro-phenyl)-ethoxy]-phenyl}-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 388

(S)-2-{[(3S,8S)-3-{4-[2-(4-Chloro-phenyl)-ethoxy]-phenyl}-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3S,8S)-8-{(S)-2-[4-(2,3-Dimethyl-pyridin-4-yl)-phenyl]-1-methoxycarbonyl-ethyl-carbamoyl}-3-(4-hydroxy-phenyl)-2,3,8,9-tetrahydro-6H-[1,4]dioxino[2,3-g]isoquinoline-7-carboxylic acid tert-butyl ester (30 mg) was dissolved in DCM and 2(4-chloro-phenyl)-ethanol (5 equiv), triphenyl phosphine (5 eq.) and DIAD (4.5 eq.) added. The reaction mixture stirred at room temperature and was directly purified over silica (hexanes to 1:1 hexanes EtOAc to 1:1 hexanes EtOAc+1% MeOH). The resulting compound was dissolved in 2 mL DCM and 1 mL 4N HCl (dioxane) was added. The mixture was stirred at room temperature for 1.5 hours and was concentrated. The residue was suspended in DCM, and TEA (3 eq.) was added to the mixture used in the following reaction sequence. ((R)-1-isocyanato-ethyl)-benzene (5 eq.) was added and reaction stirred at room temperature for 1 hour. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+3% MeOH). The resulting compound was hydrolyzed according to General Procedure B to give the title compound. LCMS (m/z): 866.

The compounds identified in Examples 389-396, below, were prepared using synthetic procedures analogous to those used for the synthesis of the compound of Example 388.

Example 389

(S)-2-{[(3S,8S)-3-[4-(trans-4-tert-Butyl-cyclohexyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 390

(S)-3-[4-(2,3-Dimethyl-pyridin-4-yl)-phenyl]-2-{[(3S,8S)-3-[4-(trans-4-ethyl-cyclohexyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-propionic acid

Example 391

(S)-3-[4-(2,3-Dimethyl-pyridin-4-yl)-phenyl]-2-{[(3S,8S)-3-(4-phenethyloxy-phenyl)-7-((R)-1-phenyl-ethylcarbamoyl)-2,3,6,7,8,9-hexahydro-[1,4]dioxino[2,3-g]isoquinoline-8-carbonyl]-amino}-propionic acid

Example 392

(S)-2-{[(3S,8S)-3-[4-(2,4-dichloro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 393

(S)-2-{[(3S,8S)-3-[4-(3,5-dichloro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 394

(S)-3-[4-(2,3-Dimethyl-pyridin-4-yl)-phenyl]-2-{[(3S,8S)-3-[4-(cis-4-ethyl-cyclohexyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-propionic acid

Example 395

(S)-2-{[(3S,8S)-3-[4-(cis-4-tert-Butyl-cyclohexyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 396

(S)-2-{[(3S,8S)-3-{4-[2-(3,4-Dichloro-phenyl)-ethoxy]-phenyl}-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid

Example 397

(S)-3-(4'-Carbamoyl-biphenyl-4-yl)-2-{[(3S,8S)-3-[4-(3,4-dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-propionic acid (S)-3-(4-Bromo-phenyl)-2-tert-butoxycarbonylamino-propionic acid methyl ester and 4-carbamoylphenyl boronic acid (2 eq.) were coupled in 7:2 toluene-H$_2$O with Na$_2$CO$_3$ (3 eq.) and Pd(PPh$_3$)$_4$ (0.1 eq.). After heating for 4 hours at 80° C., the reaction mixture was purified by flash chromatography to provide (S)-2-tert-butoxycarbonylamino-3-(4'-carbamoyl-biphenyl-4-yl)-propionic acid methyl ester. The product was deprotected according to General Procedure C to provide an amine-HCl salt, which was coupled with (3S,8S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester according to General Procedure L. The product was deprotected according to General Procedure C to provide an amine-HCl salt, which was treated with excess NEt$_3$ in DCM to produce a free amine. The free amine was coupled with 2,5-dimethyloxazole-4-carboxylic acid (2 eq.) in dry DCM with HBTU (2.2 eq.) and NEt$_3$ (3 eq.). After reacting for 2 hours at room temperature, the reaction mixture was purified by flash chromatography to provide the product, which was hydrolyzed acording to general procedure B to give the title compound (11 mg). LCMS (m/z) 876.

The compounds identified in Examples 398-399, below, were prepared using synthetic procedures analogous to those used for the synthesis of the compound of Example 397.

Example 398

(S)-2-{[(3S,8S)-3-[4-(3,4-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-(4'-methylcarbamoyl-biphenyl-4-yl)-propionic acid

Example 399

(S)-3-(4'-Acetyl-biphenyl-4-yl)-2-{[(3S,8S)-3-[4-(3,4-dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-propionic acid

Example 400

(S)-2-{[(3S,8S)-7-Benzoyl-3-(4-cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid (S)-2-{[(3S,8S)-3-(4-Cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid methyl ester di hydrochloride (19 mg) was dissolved in 1:1 EtOAc and saturated aqueous NaHCO$_3$ and benzoyl chloride (3 eq.) added. After stirring at room temperature for 1 hour, the layers were separated and the organic layer was dried over Na$_2$SO$_4$ and evaporated. The residue was purified over silica (hexanes to 8:2 hexanes-EtOAc to 6:4 hexanes-EtOAc to 6:4 hexanes-EtOAc+2% MeOH to DCM+3% MeOH). The resulting compound was hydrolyzed according to General Procedure B to give the title compound (20 mg). LCMS (m/z): 797.

Example 401

(S)-2-{[(3S,8S)-7-Benzyl-3-(4-cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid (S)-2-{[(3S,8S)-3-(4-Cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid methyl ester di-hydrochloride (19 mg) was reacted with benzaldehyde according to General Procedure D. The reaction mixture was directly purified over silica (hexanes to 1:1 hexanes EtOAc to 1:1 hexanes EtOAc+1% MeOH to 1:1 hexanes EtOAc+2% MeOH upto 1:1 hexanes EtOAc+5% MeOH) to give (S)-2-{[(3S,8S)-7-benzyl-3-(4-cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid methyl ester. This ester was hydrolyzed according to General Procedure B to give the title compound (14 mg). LCMS (m/z): 783.

Example 402

(S)-2-{[(3S,8S)-3-[4-(2-Cyclopentyl-ethoxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid (S)-3-(4-Hydroxy-phenyl)-7-((S)-1-phenyl-propyl)-2,3,6,7,8,9-hexahydro-[1,4]dioxino[2,3-g]isoquinoline-8-carboxylic acid methyl ester (20 mg) was dissolved in DCM and cyclopentane-ethanol (5 eq.), triphenyl phosphine (5 eq.) and DIAD (4.5 eq.) added. The reaction mixture stirred at room temperature and was directly purified over silica (hexanes to 9:1 hexanes EtOAc to 7:3 hexanes EtOAc). This ester was hydrolyzed according to General Procedure AB to give (3S,8S)-3-[4-(2-cyclopentyl-ethoxy)-phenyl]-7-((S)-1-phenyl-propyl)-2,3,6,7,8,9-hexahydro-[1,4]dioxino[2,3-g]isoquinoline-8-carboxylic acid. This acid was coupled with (S)-2-amino-3-[4-(2,3-dimethyl-pyridin-4-yloxy)-phenyl]-propionic acid methyl ester di hydrochloride according to General Procedure L to give (S)-2-{[(3S,8S)-3-[4-(2-cyclopentyl-ethoxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid methyl ester. This ester was hydrolyzed according to General Procedure B to give the title compound (5 mg). LCMS (m/z): 811.

Example 403

(3S,8S)-8-{(S)-1-Carboxy-2-[4-(2,3-dimethyl-pyridin-4-yloxy)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid tert-butyl ester (3S,8S)-3-[4-(3,4-Dichloro-benzyloxy)-phenyl]-8-{(S)-2-[4-(2,3-dimethyl-pyridin-4-yloxy)-phenyl]-1- methoxycarbonyl-ethylcarbamoyl}-2,3,8,9-tetrahydro-6H-[1,4]dioxino[2,3-g]isoquinoline-7-carboxylic acid tert-bubutyl ester (10 mg) was hydrolyzed according to General Procedure B to give the title compound (5 mg). LCMS (m/z): 855.

Example 404

(S)-2-({(3S,8S)-3-[4-(3,4-Dichloro-benzyloxy)-phenyl]-7-methanesulfonyl-2,3,6,7,8,9-hexahydro-[1,4] dioxino[2,3-g]isoquinoline-8-carbonyl}-amino)-3-[4-(2,3-dimethyl-pyridin-4-yloxy)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester dihydrochloride (25 mg) was reacted with methane-sulfonyl chloride according to General Procedure E. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+5% MeOH) to give (S)-2-({(3S,8S)-3-[4-(3,4-dichloro-benzyloxy)-phenyl]-7-methanesulfonyl-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl.ester. This ester was hydrolyzed according to General Procedure B to give the title compound (12 mg). LCMS (m/z): 833.

Example 405

(S)-2-{[(3S,8S)-3-(4-Cyclohexylmethoxy-phenyl)-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-{[(3S,8S)-3-(4-Cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester dihydrochloride (25 mg) was reacted with 2,5-dimethyl-oxazole-4-carbonyl chloride according to General Procedure F to give (S)-2-{[(3S,8S)-3-(4-Cyclohexylmethoxy-phenyl)-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester (20 mg). This ester was hydrolyzed according to General Procedure B to give the title compound. LCMS (m/z): 800.

Example 406

(S)-2-{[(3S,8S)-3-(4-Cyclohexylmethoxy-phenyl)-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid To a solution of (S)-2-{[(3S,8S)-3-(4-cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester in DCM was added ((R)-1-isocyanato-ethyl)-benzene (5 eq.) and the reaction was stirred at room temperature for 1 hour. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+3% MeOH). The resulting compound was hydrolyzed according to General Procedure B to give the title compound. LCMS (m/z): 824.

Example 407

(S)-2-{[(3S,8S)-7-tert-Butylcarbamoyl-3-(4-cyclohexylmethoxy-phenyl)-2,3,6,7,8,9-hexahydro-[1,4] dioxino[2,3-g]isoquinoline-8-carbonyl]-amino}-3-[4-(2,3-dimethyl-pyridin-4-yloxy)-phenyl]-propionic acid To a solution of (S)-2-{[(3S,8S)-3-(4-cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid methyl ester (25 mg) in DCM was added 2-isocyanato-2-methyl-propane (5 eq.) and the reaction stirred was at room temperature for 1 hour. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+3% MeOH). The resulting compound was hydrolyzed according to General Procedure B to give the title compound. LCMS (m/z): 792.

Example 408

(S)-2-{[(3S,8S)-3-[4-(3,4-Dichloro-benzyloxy)-phenyl]-7-(3,5-dimethyl-isoxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexa hydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (25 mg) was dissolved in 1:1 EtOAc and saturated aqueous NaHCO₃ and 3,5-dimethyl-isoxazole-4-carbonyl chloride (3 eq.) were added. After stirring at room temperature for 1 hour, the layers were separated and the organic layer was dried over Na₂SO₄ and evaporated. The residue was purified by over silica (hexanes to 8:2 hexanes-EtOAc to 6:4 hexanes-EtOAc to 6:4 hexanes-EtOAc+2% MeOH to DCM+3% MeOH). The resulting compound was hydrolyzed according to General Procedure B to give the title compound (16 mg). LCMS (m/z): 862.

Example 409

(S)-2-{[(3S,8S)-3-[4-(3,4-Dichloro-benzyloxy)-phenyl]-7-(3-fluoro-benzoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexa hydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (25 mg) was dissolved in 1:1 EtOAc and saturated aqueous NaHCO₃ and 3-fluorobenzoyl chloride (3 eq.) were added. After stirring at room temperature for 1 hour, the layers were separated and the organic layer was dried over Na₂SO₄ and evaporated. The residue was purified by over silica (hexanes to 8:2 hexanes-EtOAc to 6:4 hexanes-EtOAc to 6:4 hexanes-EtOAc+2% MeOH to DCM+3% MeOH). The resulting compound

Example 410

(S)-2-({(3S,8S)-7-(2-Acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexa hydro-[1,4]dioxino[2,3-g]isoquinoline-8-carbonyl}-amino)-3-[4-(2,3-dim ethyl-pyridin-4-yl)-phenyl]-propionic acid methyl ester (60 mg) was reacted with 2-acetylamino-4-methyl-thiazole-5-sulfonyl chloride to give (S)-2-({(3S,8S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester according to General Procedure E. This ester (12 mg) was hydrolyzed according to General Procedure B to give the title compound (10 mg). LCMS (m/z): 959.

Example 411

(S)-2-({(3S,8S)-7-(2-Amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid (S)-2-({(3S,8S)-7-(2-acetylamino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)phenyl]-propionic acid methyl ester was converted to (S)-2-({(3S,8S)-7-(2-amino-4-methyl-thiazole-5-sulfonyl)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester according to General Procedure N. This ester (20 mg) was hydrolyzed according to General Procedure B to give the title compound (17 mg). LCMS (m/z): 915.

Example 412

(S)-3-(4'-Cyano-biphenyl-4-yl)-2-{[(3S,8S)-3-[4-(3,4-dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-propionic acid EDC (3 eq.) and 2,5-dimethyl-oxazole-4-carboxylic acid (6 eq.) were dissolved in DCM and stirred 40 minutes. To this solution was added (S)-3-(4'-cyano-biphenyl-4-yl)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (20 mg) and stirred for 12 hours. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+3% MeOH). The resulting compound was hydrolyzed according to General Procedure B to give the title compound (22 mg). LCMS (m/z): 860.

Example 413

(S)-3-(4'-Cyano-biphenyl-4-yl)-2-{[(3S,8S)-3-[4-(3,4-dichloro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-propionic acid To a solution of (S)-3-(4'-Cyano-biphenyl-4-yl)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-propionic acid methyl ester (20 mg) was added ((R)-1-isocyanato-ethyl)-benzene (5 equiv) and the reaction stirred at room temperature for 1 hour. The reaction mixture was directly purified over silica (hexanes to 1:1 hexanes EtOAc to 1:1 hexanes EtOAc+1% MeOH to 1:1 hexanes EtOAc+2% MeOH to 1:1 hexanes EtOAc+3% MeOH). The resulting compound was hydrolyzed according to General Procedure B to give the title compound (26 mg). LCMS (m/z): 884.

Example 414

(S)-2-{[(3S,8S)-3-[3-(3,4-Dichloro-benzyloxy)-phenyl]-7-((R)-1-phenyl ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (R)-(+)-α-Methylbenzyl isocyanate (5 mg) was added to a solution of (S)-2-({(3S,8S)-3-[3-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester (20 mg) in 0.5 mL DCM and stirred for 1 h at room temperature. The reaction mixture was directly loaded onto a silica gel column (1:1 EtOAc/hexanes to 6% MeOH in 1:1 EtOAc/hexanes) to isolate the desired product (16 mg).

(S)-2-{[(3S,8S)-3-[3-(3,4-Dichloro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester (16 mg) was hydrolyzed according to General Procedure B to give the title compound (14 mg). LCMS (m/z): 886.

Example 415

(S)-2-{[(3S,8S)-3-[3-(3,4-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid 2,5-Dimethyl-oxazole-4-carboxylic acid (5 mg) and EDCl (8 mg), HOBT (6 mg) were taken up in 1 mL of anhydrous DCM and stirred for 5 min. DIEA (10 mg) and (S)-2-({(3S,8S)-3-[3-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester (20 mg in 0.5 mL DCM) were added to the reaction mixture and stirred for 6 hours. After completion of the reaction, it was loaded onto a silica gel column (1:3 EtOAc/hexanes to 5% MeOH in 1:1 EtOAc/hexanes) to get pure compound (17 mg), which was hydrolyzed according to General Procedure B to give the title compound (13 mg). LCMS (m/z): 862.

(page start) was hydrolyzed according to General Procedure B to give the title compound (15 mg). LCMS (m/z): 861.

Example 416

(3S,8S)-8-{(S)-1-Carboxy-2-[4-(2,3-dimethyl-pyridin-4-yl)-phenyl]-ethylcarbamoyl}-3-[3-(3,4-dichloro-benzyloxy)-phenyl]-2,3,8,9-tetrahydro-6H-[1,4]dioxino[2,3 g]isoquinoline-7-carboxylic acid tert-butyl ester (3S,8S)-3-[3-(3,4-Dichloro-benzyloxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (15 mg) was hydrolysed according to General Procedure B to give the title compound (12 mg). LCMS (m/z): 839.

Example 417

(S)-2-{[(3S,8S)-3-(3-Cyclohexylmethoxy-phenyl)-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3S,8S)-8-{(S)-2-[4-(2,3-Dimethyl-pyridin-4-yl)-phenyl]-1-methoxycarbonyl-ethylcarbamoyl}-3-(3-hydroxy-phenyl)-2,3,8,9-tetrahydro-6H-[1,4]dioxino[2,3-g]isoquinoline-7-carboxylic acid tert-butyl ester (25 mg), cyclohexyl methanol (12 mg), triphenyl phosphine (38 mg) were taken in 1 mL of anhydrous DCM and cooled to 0° C. Diisobutyl azodicarboxylate (22 mg) was added and reaction was warmed to room temperature and stirred for 4 hours. After the completion, reaction was loaded onto a silica gel column (1:1 EtOAc:hexanes to 4% MeOH in 1:1 EtOAc:hexanes) gave (3S,8S)-3-(3-cyclohexylmethoxy-phenyl)-8-{(S)-2-[4-(2,3-dimethyl-pyridin-4-yl)-phenyl]-1-methoxycarbonyl-ethyl-carbamoyl}-2,3,8,9-tetrahydro-6H-[1,4]dioxino[2,3-g]isoquinoline-7-carboxylic acid tert-butyl ester (27 mg). This was taken in 2 mL anhydrous DCM and cooled 0° C., HCl (0.5 mL, 4N in dioxane) was added and stirred at room temperature for 1 hour. All volatiles were evaporated and the residue was precipitated from DCM/hexanes to get (S)-2-{[(3S,8S)-3-(3-cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester dihydrochloride (25 mg).

2,5-Dimethyl-oxazole-4-carboxylic acid (6 mg) was taken in 1 mL of anhydrous DCM and EDCl (9 mg), HOBT (7 mg) and (S)-2-{[(3S,8S)-3-(3-cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester dihydrochloride (25 mg) and stirred for 5 minutes. The reaction mixture was cooled to 0° C. and DIEA (25 mg) was added and reaction was stirred at room temperature for 2 hours. After the reaction was complete, it was loaded onto a silica gel column (1:3 EtOAc/hexanes to 4% MeOH in 1:1 EtOAc/hexanes) to get pure (S)-2-{[(3S,8S)-3-(3-cyclohexylmethoxy-phenyl)-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester (22 mg). This product was hydrolyzed according to General Procedure B to the title compound (17 mg). LCMS (m/z): 800.

Example 418

(S)-2-{[(3S,8S)-3-(3-Cyclopentylmethoxy-phenyl)-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3S,8S)-8-{(S)-2-[4-(2,3-Dimethyl-pyridin-4-yl)-phenyl]-1-methoxycarbonyl-ethyl-carbamoyl}-3-(3-hydroxy-phenyl)-2,3,8,9-tetrahydro-6H-[1,4]dioxino[2,3-g]isoquinoline-7-carboxylic acid tert-butyl ester (25 mg), cyclopentyl methanol (11 mg), triphenyl phosphine (38 mg) were taken in 1 mL of anhydrous DCM and cooled to 0° C. Diisobutyl azodicarboxylate (22 mg) was added and reaction was warmed to room temperature and stirred for 4 hours. After the completion of the reaction, the reaction mixture was loaded onto a silica gel column (1:1 EtOAc:hexanes to 4% MeOH in 1:1 EtOAc:hexanes) to give (3S,8S)-3-(3-cyclopentyl-methoxy-phenyl)-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (24 mg). This was taken up in 2 mL anhydrous DCM and cooled 0° C., HCl (0.5 mL, 4N in dioxane) was added and stirred at room temperature for 1 hour. All volatiles are evaporated and residue was precipitated from DCM/hexanes to get (S)-2-{[(3S,8S)-3-(3-cyclopentyl-methoxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester dihydrochloride (22 mg).

2,5-Dimethyl-oxazole-4-carboxylic acid (6 mg) was taken in 1 mL of anhydrous DCM and EDCl (9 mg), HOBT (7 mg) and (S)-2-{[(3S,8S)-3-(3-cyclopentylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester dihydrochloride (22 mg) and stirred for 5 minutes. The reaction mixture was cooled to 0° C. and DIEA (25 mg) was added and reaction was stirred at room temperature for 2 hours. After the reaction completed, the reaction mixture was loaded onto a silica gel column (1:3 EtOAc:hexanes to 4% MeOH in 1:1 EtOAc:hexanes) to get purified (S)-2-{[(3S,8S)-3-(3-cyclopentyloxy-phenyl)-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester (20 mg). This was hydrolyzed according to General Procedure B to get the title compound (16 mg). LCMS (m/z): 786.

Example 419

(S)-2-{[(3S,8S)-3-[3-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3S,8S)-3-[3-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid (25 mg), EDCl (10 mg), HOBT (8 mg) and (S)-2-amino-3-[4-(2,3-dimethyl-pyridin-4-yl)-phenyl]-propionic acid methyl ester dihydrochloride (15 mg) were taken up in 1 mL of anhydrous DCM and stirred for 5 minutes. The reaction mixture was cooled to 0° C. and DIEA (21 mg) was added and reaction was stirred at room temperature for 2 hours. After the reaction was complete, the mixture was loaded onto a silica gel column (1:3 EtOAc: hexanes to 4% MeOH in 1:1 EtOAc:hexanes) to get purified (S)-2-{[(3S,8S)-3-[3-(3,4-dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester (23 mg). This was hydrolysed according to General Procedure B to give the title compound (20 mg). LCMS (m/z): 857.

Example 420

(3S,8S)-8-{(S)-1-Carboxy-2-[4-(2,3-dimethyl-pyridin-4-yloxy)-phenyl]-ethylcarbamoyl}-3-[3-(3,4-dichloro-benzyloxy)-phenyl]-2,3,8,9-tetrahydro-6H-[1,4]dioxino[2,3-g]isoquinoline-7-carboxylic acid tert-butyl ester (3S,8S)-3-[3-(3,4-Dichloro-benzyloxy)-phenyl]-8-{(S)-2-[4-(2,3-dimethyl-pyridin-4-yloxy)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (20 mg) was hydrolyzed according to General Procedure B to give the title compound (16 mg). LCMS (m/z): 855.

Example 421

(S)-2-{[(3S,8S)-3-[3-(3,4-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid (3S,8S)-3-[3-(3,4-Dichloro-benzyloxy)-phenyl]-8-{(S)-2-[4-(2,3-dimethyl-pyridin-4-yloxy)-phenyl]-1-methoxycarbonyl-ethylcarbamoyl}-2,3,8,9-tetrahydro-6H-[1,4]dioxino[2,3-g]-isoquinoline-7-carboxylic acid tert-butyl ester (50 mg) was taken in 2 mL of DCM and cooled to 0° C., HCl (0.5 mL, 4N in dioxane) was added and stirred at room temperature for 2 hours. All volatiles were evaporated and residue was washed with hexanes and dried under vacuum to get (S)-2-({(3S,8S)-3-[3-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester dihydrochloride (46 mg).

2,5-Dimethyl-oxazole-4-carboxylic acid (6 mg) was taken in 1 mL of anhydrous DCM and EDCl (9 mg), HOBT (7 mg) and (S)-2-({(3S,8S)-3-[3-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester dihydrochloride (25 mg) and stirred for 5 minutes. The reaction mixture was cooled to 0° C. and DIEA (25 mg) was added and reaction was stirred at room temperature for 2 hours. After the reaction was complete, the reaction mixture was loaded onto a silica gel column (1:3 EtOAc:hexanes to 4% MeOH in 1:1 EtOAc:hexanes) to get purified (S)-2-{[(3S,8S)-3-[3-(3,4-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid methyl ester (23 mg). This was hydrolyzed according to General Procedure B to give the title compound (19 mg). LCMS (m/z): 878.

Example 422

(S)-2-{[(3S,8S)-3-[3-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid (3S,8S)-3-[3-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid (25 mg), EDCl (10 mg), HOBT (8 mg) and (S)-2-amino-3-[4-(2,3-dimethyl-pyridin-4-yloxy)-phenyl]-propionic acid methyl ester (16 mg) were taken up in 1 mL of anhydrous DCM and stirred for 5 minutes. The reaction mixture was cooled to 0° C. and DIEA (21 mg) was added and reaction was stirred at room temperature for 2 hours. After the reaction was complete, the reaction mixture was loaded on a silica gel column (1:3 EtOAc:hexanes to 4% MeOH in 1:1 EtOAc:hexanes) to get purified (S)-2-{[(3S,8S)-3-[3-(3,4-dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid methyl ester (22 mg). This was hydrolyzed according to General Procedure B to give the title compound (18 mg). LCMS (m/z): 873.

Example 423

(S)-2-{[(3S,8S)-3-(4-Cyclohexylmethoxy-phenyl)-7-(3-methyl-benzoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-{[(3S,8S)-3-(4-cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester bis hydrochloride (20 mg) was dissolved in 1:1 EtOAc and saturated aqueous NaHCO₃ and 3-methylbenzoyl chloride (3 eq) added. After stirring at room temperature 1 hour, the layers were separated and the organic layer was dried over Na₂SO₄ and evaporated. The residue was purified by over silica (hexanes to 8:2 hexanes-EtOAc to 6:4 hexanes-EtOAc to 6:4 hexanes-EtOAc+2% MeOH to DCM+3% MeOH). The resulting compound was hydrolyzed according to General Procedure B to give the title compound (15 mg). LCMS (m/z): 795.

Example 424

(S)-3-[4-(2,3-Dimethyl-pyridin-4-yl)-phenyl]-2-{[(3S,8S)-3-(4-phenoxy-phenyl)-7-((S)-1-phenyl-propyl)-2,3,6,7,8,9-hexahydro-[1,4]dioxino[2,3-g]isoquinoline-8-carbonyl]-amino}-propionic acid (S)-3-(4-Hydroxy-phenyl)-7-((S)-1-phenyl-propyl)-2,3,6,7,8,9-hexahydro-[1,4]dioxino[2,3-g]isoquinoline-8-carboxylic acid methyl ester (30 mg), Cu(OAc)₂, (25 mg), phenyl boronic acid (32 mg) and molecular sieves suspended in 5 mL DCM. TEA (0.064 mL) added, reaction flushed with oxygen and stirred at room temperature for 20 hours. The resulting mixture poured onto EtOAc and 10% sodium carbonate. Organic layer washed 3 times with 10% sodium carbonate, dried over sodium sulfate and concentrated. Residue purified over silica (hexanes to 9:1 hexanes/EtOAc) to give (3S,8S)-3-(4-phenoxy-phenyl)-7-((S)-1-phenyl-propyl)-2,3,6,7,8,9-hexahydro-[1,4]dioxino[2,3-g]isoquinoline-8-carboxylic acid methyl ester (22 mg). LCMS (m/z): 537.

(3S,8S)-3-(4-Phenoxy-phenyl)-7-((S)-1-phenyl-propyl)-2,3,6,7,8,9-hexahydro-[1,4]dioxino[2,3-g]isoquinoline-8-carboxylic acid methyl ester (22 mg) was dissolved in 2 mL of MeOH-THF (3-1), mixture cooled to 0° C., and KOH (15 equiv, 2.5 N aqueous solution) added. The resulting mixture stirred at 0° C. for 10 minutes then at room temperature for 40 hours. The pH was then adjusted to about 7 with 1 N HCl and EtOAc and brine added. The organic portion was dried over sodium sulfate and concentrated to give the corresponding acid (20 mg).

(3S,8S)-3-(4-Phenoxy-phenyl)-7-((S)-1-phenyl-propyl)-2,3,6,7,8,9-hexahydro-[1,4]dioxino[2,3-g]isoquinoline-8-carboxylic acid (10 mg), (S)-2-amino-3-[4-(2,3-dimethyl-pyridin-4-yl)-phenyl]-propionic acid methyl ester bis hydrochloride (8 mg), EDC (5 mg), and HOBt (3 mg) were suspended in 5 mL DCM and NMM (0.009 mL) added. The reaction mixture was stirred at room temperature for 6 hours and directly purified over silica (hexanes to 1:1 hexanes EtOAc to 1:1 hexanes EtOAc+1% MeOH). The resulting compound was hydrolyzed according to General Procedure B to give the title compound (9 mg). LCMS (m/z): 775.

Example 425

(S)-2-({(3S,8S)-3-[4-(3,4-Dichloro-benzyloxy)-phenyl]-7-methanesulfonyl-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (25 mg) was reacted with methanesulfonyl chloride according to General Procedure E (with excess of sulfonyl chloride). The resulting compound was hydrolyzed according to General Procedure B to give the title compound (14 mg) LCMS (m/z): 819.

Example 426

(S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester bis hydrochloride (20 mg) was hydrolyzed according to General Procedure B to give the title compound (12 mg). LCMS (m/z): 741.

Example 427

(3R,8S)-8-{(S)-1-Carboxy-2-[4-(2,3-dimethyl-pyridin-4-yl)-phenyl]-ethylcarbamoyl}-3-[4-(3,4-dichloro-benzyloxy)-phenyl]-2,3,8,9-tetrahydro-6H-[1,4]dioxino[2,3-g]isoquinoline-7-carboxylic acid tert-butyl ester (3R,8S)-3-[4-(3,4-Dichloro-benzyloxy)-phenyl]-8-{(S)-2-[4-(2,3-dimethyl-pyridin-4-yl)-phenyl]-1-methoxycarbonyl-ethylcarbamoyl}-2,3,8,9-tetrahydro-6H-[1,4]dioxino[2,3-g]isoquinoline-7-carboxylic acid tert-butyl ester (20 mg) hydrolyzed according to General Procedure B to give the title compound (14 mg). LCMS (m/z): 839.

Example 428

(S)-2-{[(3R,8S)-3-[4-(3,4-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3R,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester (35 mg) was dissolved in 2 mL DCM. In a separate vial EDC (5 equiv) and 2,5-dimethyl-oxazole-4-carboxylic acid (10 equiv) were dissolved in DCM and stirred 40 min. This solution was added to the above mixture stirred 4 hours. The reaction mixture was directly purified over silica (hexanes to 1:1 hexanes EtOAc to 1:1 hexanes EtOAc+2% MeOH). The resulting compound was hydrolyzed according to General Procedures B to give the title compound (10 mg). LCMS (m/z): 862.

Example 429

(S)-2-{[(3R,8S)-3-[4-(3,4-Dichloro-benzyloxy)-phenyl]-7-((R)-1-phenyl-ethylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3R,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester (35 mg) was dissolved in 2 mL DCM and ((R)-1-isocyanato-ethyl)-benzene (5 equiv) added and reaction stirred at room temperature for 2 hours. The reaction mixture was directly purified over silica (hexanes to 1:1 hexanes EtOAc to 1:1 hexanes EtOAc+2% MeOH). The resulting compound was hydrolyzed according to General Procedures B to give the title compound (28 mg). LCMS (m/z): 886.

Example 430

(S)-2-{[(3R,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (3R,8S)-3-[4-(3,4-Dichloro-benzyloxy)-phenyl]-7-((S)-1-phenyl-propyl)-2,3,6,7,8,9-hexahydro-[1,4]dioxino[2,3-g]isoquinoline-8-carboxylic acid (300 mg) (S)-2-amino-3-[4-(2,3-dimethyl-pyridin-4-yl)-phenyl]-propionic acid methyl ester bis hydrochloride (213 mg), EDC (119 mg), and HOBt (87 mg) were suspended in 5 mL DCM and NMM (0.240 mL) added. The resulting mixture stirred at room temperature for 12 hours and loaded directly onto silica. The residue was purified by silica gel flash chromatography (hexanes to 1:1 hexanes/EtOAc to 1:1 hexanes/EtOAc+1% MeOH). The resulting compound (330 mg) was dissolved in 8 mL of THF-MeOH (4-1) and cooled on ice. LiOH (2N aq. soln, 5 equiv) was added and the mixture stirred on ice for 1.5 hours. The pH of the mixture was adjusted to about 7 with 1 N HCl and EtOAc and brine added. The organic was dried over sodium sulfate and concentrated to about 5 mL volume where a precipitate formed. The solid was filtered, washed with EtOAc and dried under vacuum to provide 181 mg of the title compound. LCMS (m/z): 857. $^1$H NMR (400 MHz, dmso-$d_6$): 13.0 (s, 1H), 8.18 (d, 1H), 7.94 (d, 1H), 7.73-7.62 (m, 2H), 7.43 (m, 1H), 7.24-7.18 (m, 7H), 7.16 (d, 2H), 7.02-6.94 (m, 4H), 6.88 (d, 1H), 6.66 (s, 1H), 6.48 (s, 1H), 5.13 (s, 2H), 4.91 (m, 1H), 4.55 (m, 1H), 4.25 (m, 1H), 3.90 (m, 1H), 3.40-3.56 (m, 3H), 3.18 (d, 1H), 3.03 (m, 1H), 2.93 (m, 1H), 2.78 (m, 1H), 2.65 (m, 1H), 2.40 (s, 3H), 2.24 (s, 3H), 1.85 (m, 1H), 1.67 (m, 1H), 0.52 (t, 3H).

Example 431

(S)-2-{[(3S,8S)-3-[4-(3,4-Dichloro-benzyloxy)-phenyl]-7-(2-methyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid To a stirring solution of 2-methyl-oxazole-4-carboxylic acid (30 mg) in DCM (2.0 mL), oxalyl chloride (3.0 eq) was added at room temperature. The reaction mixture was stirred for 30 minutes. Solvents were evaporated and dried under vacuo to afford 2-methyl-oxazole-4-carbonyl chloride.

(S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester (30 mg) was reacted with 2-methyl-oxazole-4-carbonyl chloride (prepared above) according to General Procedure F and purified over silica (hexanes to 1:1 hexanes EtOAc to 1:1 hexanes EtOAc+1% MeOH). The resulting compound was hydrolyzed according to General Procedure B to give the title compound (10 mg). LCMS (m/z): 848.

Example 432

(S)-2-{[(3S,8S)-3-[4-(3,4-Dichloro-benzyloxy)-phenyl]-7-(2,4-dimethyl-oxazole-5-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid To a stirring solution of 2,4-dimethyl-oxazole-5-carboxylic acid (30 mg) in DCM (2.0 mL), oxalyl chloride (3.0 eq) was added at room temperature. The reaction mixture was stirred for 30 minutes. Solvents were evaporated and dried under vacuo to afford 2,4-dimethyl-oxazole-5-carbonyl chloride.

(S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester (30 mg) was reacted with 2,4-dimethyl-oxazole-5-carbonyl chloride (prepared above) according to General Procedure F and purified over silica (hexanes to 1:1 hexanes EtOAc to 1:1 hexanes EtOAc+1% MeOH). The resulting compound was hydrolyzed according to General Procedure B to give the title compound (9 mg). LCMS (m/z): 862.

Example 433

(S)-2-{[(3S,8S)-3-[4-(3,4-Dichloro-benzyloxy)-phenyl]-7-(2-isopropyl-5-methyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester (30 mg) was reacted with 2-isopropyl-5-methyl-oxazole-4-carboxylic acid (according to a procedure in *Synthesis*, Vol. 10, pp. 1569-71 (2005)) in DCM (3.0 mL) according to General Procedure A and directly purified over silica (hexanes to 1:1 hexanes EtOAc to 1:1 hexanes EtOAc+1% MeOH). The resulting compound was hydrolyzed according to General Procedure B to give the title compound (8 mg). LCMS (m/z) 892.

Example 434

(S)-2-{[(3S,8S)-3-[4-(3,4-Dichloro-benzyloxy)-phenyl]-7-(2-isopropyl-5-methyl-oxazole-4-carbonyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester (30 mg) was reacted with 2-isopropyl-5-methyl-oxazole-4-carboxylic acid (according to a procedure in *Synthesis*, Vol. 10, pp. 1569-71 (2005)) in DCM (3.0 mL) according to General Procedure A and directly purified over silica (hexanes to 1:1 hexanes EtOAc to 1:1 hexanes EtOAc+1% MeOH). The resulting compound was hydrolyzed according to General Procedure B to give the title compound (8.5 mg). LCMS (m/z) 906.

Example 435

(S)-2-{[(3S,8S)-3-(4-Cyclohexylmethoxy-phenyl)-7-(3-hydroxy-benzoyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid (S)-2-{[(3S,8S)-3-(4-Cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid methyl ester bis hydrochloride and excess acetic acid 3-chlorocarbonyl-phenyl ester were reacted in a biphasic mixture of EtOAc and saturated aqueous NaHCO$_3$. The resulting compound was hydrolyzed according to General Procedure B to give the title compound (15 mg). LCMS (m/z) 813.

Example 436

(S)-2-{[(3S,8S)-3-[4-(3,4-Dichloro-benzyloxy)-phenyl]-7-(propane-2-sulfonyl)-2,3,6,7,8,9-hexahydro-[1,4]dioxino[2,3-g]isoquinoline-8-carbonyl]-amino}-3-[4-(2,3-dimethyl-pyridin-4-yloxy)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester bis hydrochloride was coupled with propane-2-sulfonyl chloride according to General Procedure E. The resulting compound was hydrolyzed according to General Procedure B to give the title compound (3 mg). LCMS (m/z) 861.

Example 437

(S)-2-({(3S,8S)-3-[4-(3,4-Dichloro-benzyloxy)-phenyl]-7-dimethylsulfamoyl-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester bis hydrochloride was coupled with N,N-dimethylsulfamoyl chloride according to General Procedure E. The resulting compound was hydrolyzed according to General Procedure B to give the title compound (9 mg). LCMS (m/z) 862.

Example 438

(S)-2-{[(3S,8S)-3-[4-(3,4-Dichloro-benzyloxy)-phenyl]-7-(1-methyl-cyclohexylcarbamoyl)-2,3,6,7,8,9-hexahydro-[1,4]dioxino[2,3-g]isoquinoline-8-carbonyl]-amino}-3-[4-(2,3-dimethyl-pyridin-4-yl)phenyl]-propionic acid 1-Methylcyclohexanecarboxylic acid was heated at 120° C. with 1 eq DPPA and 1.2 eq NEt$_3$ for 1 hour, then evaporated to dryness. The residue containing crude isocyanate was coupled with (S)-2-({(3S,8S)-3-[4-(3,4-dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yl)-phenyl]-propionic acid methyl ester according to General Procedure I. The resulting compound was hydrolyzed according to General Procedure B to give the title compound (11 mg). LCMS (m/z) 878.

Example 439

(S)-2-({(3S,8S)-3-[4-(3,4-Dichloro-benzyloxy)-phenyl]-7-dimethylcarbamoyl-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid (S)-2-({(3S,8S)-3-[4-(3,4-Dichloro-benzyloxy)-phenyl]-2,3,6,7,8,9-hexahydro-[1,4]dioxino[2,3-g]isoquinoline-8-carbonyl}-amino)-3-[4-(2,3-dimethyl-pyridin-4-yloxy)-phenyl]-propionic acid methyl ester bis hydrochloride was coupled with N,N-dimethylcarbamyl chloride according to General Procedure H. The resulting compound was hydrolyzed according to General Procedure B to give the title compound (11 mg). LCMS (m/z): 826.

Example 440

(S)-2-{[(3S,8S)-3-[4-(3,4-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-(4'-fluoro-biphenyl-4-yl)-propionic acid (S)-2-amino-3-(4'-fluoro-biphenyl-4-yl)-propionic acid methyl ester hydrochloride was coupled with (3S,8S)-3-[4-(3,4-dichloro-benzyloxy)-phenyl]-2,3,8,9-tetrahydro-6H-[1,4]dioxino[2,3-g]isoquinoline-7,8-dicarboxylic acid 7-tert-butyl ester according to General Procedure L. The product was deprotected according to General Procedure C to provide amine-HCl salt, which was treated with excess NEt$_3$ in DCM to produce the free amine. The free amine was coupled with 2,5-dimethyloxazole-4-carboxylic acid (2 eq) in dry DCM with HBTU (2.2 eq) and NEt$_3$ (3 eq). After 2 hour reaction at RT the reaction mixture was purified by flash chromatography to provide the product, which was hydrolyzed according to general procedure B to give the title compound (6 mg). LCMS (m/z): 851.

Example 441

(S)-2-{[(3S,8S)-3-[4-(3,4-Dichloro-benzyloxy)-phenyl]-7-(2,5-dimethyl-oxazole-4-carbonyl)-2,3,6,7,8,9-hexahydro-[1,4]dioxino[2,3-g]isoquinoline-8-carbonyl]-amino}-3-(4'-methoxy-biphenyl-4-yl)-propionic acid (S)-2-amino-3-(4'-methoxy-biphenyl-4-yl)-propionic acid methyl ester hydrochloride was coupled with (3S,8S)-3-[4-(3,4-dichloro-benzyloxy)-phenyl]-2,3,8,9-tetrahydro-6H-[1,4]dioxino-[2,3-g]isoquinoline-7,8-dicarboxylic acid 7-tert-butyl ester according to General Procedure L. The product was deprotected according to General Procedure C to provide amine-HCl salt, which was treated with excess NEt$_3$ in DCM to produce the free amine. The free amine was coupled with 2,5-dimethyloxazole-4-carboxylic acid (2 eq) in dry DCM with HBTU (2.2 eq) and NEt$_3$ (3 eq). After 2 hour reaction at RT the reaction mixture was purified by flash chromatography to provide the product, which was hydrolyzed according to General Procedure B to give the title compound (21 mg). LCMS (m/z): 863.

Example 442

(S)-2-{[(3S,8S)-7-Benzoyl-3-(4-cyclohexylmethoxyphenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid (S)-2-{[(3S,8S)-3-(4-Cyclohexylmethoxy-phenyl)-2,3,6,7,8,9-hexahydro-[1,4]dioxino[2,3-g]isoquinoline-8-carbonyl]-amino}-3-[4-(2,3-dimethyl-pyridin-4-yl)-phenyl]-propionic acid methyl ester di hydrochloride was dissolved in 1:1 EtOAc and saturated aqueous NaHCO$_3$ and benzoyl chloride (3 eq) added. After stirring at room temperature for 1 hour, the layers were separated and the organic layer was dried over Na$_2$SO$_4$ and evaporated. The residue was purified over silica (hexanes to 8:2 hexanes-EtOAc to 6:4 hexanes-EtOAc to 6:4 hexanes-EtOAc+2% MeOH to DCM+3% MeOH). The resulting compound was hydrolyzed according to General Procedure B to give the title compound (17 mg). LCMS (m/z): 781.

Uses of GLP-1R Aqonists

Compounds that function as GLP-1R agonists are potentially useful in treating diseases, disorders, or conditions in which modulation of the human GLP-1 receptor is beneficial. Such diseases, disorders, or conditions include, but are not limited to: metabolic syndrome, glucose intolerance, hyperglycaemia, dyslipidemia, diabetes mellitus type 1, diabetes mellitus type 2, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders where activation of the GLP-1 receptor is beneficial, and complications resulting from or associated with diabetes, including, but not limited to, neuropathy, retinopathy, nephropathy, and impaired wound healing. The compounds of Formula (I), or pharmaceutically acceptable salts thereof, may therefore be useful in the treatment of one or more of these diseases.

Pharmaceutical Compositions

In one embodiment, the present invention provides a pharmaceutical composition comprising the compound of Formula (I), or pharmaceutically acceptable salts thereof. In another embodiment, the present invention provides a pharmaceutical composition comprising a compound of any one of embodiments 1 to 308 (recited above). In another embodiment, the pharmaceutical composition comprises a compound of any one of embodiments 1 to 308 and a pharmaceutically acceptable carrier, excipient, diluent, or a mixture thereof.

In an embodiment, the pharmaceutical compositions containing a compound of Formula (I), or pharmaceutically acceptable salts thereof, may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or *acacia*; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release. In another embodiment, formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

In another embodiment, the composition may comprise an aqueous suspension. Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum *acacia*; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Also, oily suspensions may be formulated by suspending the active ingredient in a vegetable oil, for example *arachis* oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or *arachis* oil, or a mineral oil, for example a liquid paraffin, or a mixture thereof. Suitable emulsifying agents may be naturally-occurring gums, for example gum *acacia* or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

In another embodiment, the pharmaceutical compositions of the present invention may comprise a syrup or elixir. Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The pharmaceutical compositions of the present invention may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

In an embodiment, for topical use, creams, ointments, jellies, solutions of suspensions, etc., containing the compounds of the invention may be employed. For the purpose of this application, topical applications shall include mouth washes and gargles. In an embodiment, the compounds of Formula (I) or pharmaceutically acceptable salts thereof may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Pharmaceutically-acceptable salts of compounds of Formula (I), where a basic or acidic group is present in the structure, are also included within the scope of the invention. The term "pharmaceutically acceptable salts" refers to salts of the compounds of this invention which are not biologically or otherwise undesirable and are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

Thus, in another embodiment, the invention provides a pharmaceutical composition comprising a compound of Formula (I), or a pharmaceutically acceptable salt thereof, and one or more pharmaceutically acceptable carriers, excipients, or diluents. In another embodiment, the invention provides a pharmaceutical composition comprising a compound of any one of embodiments 1 to 308 and one or more pharmaceutically acceptable carriers, excipients, or diluents.

In another embodiment, the present invention provides a compound of Formula (I), or pharmaceutically acceptable salt thereof, for use in medicine. In another embodiment, the invention provides a compound of any one of embodiments 1 to 308 for use in medicine.

The present invention further provides for the use of a compound of Formula (I), or a pharmaceutically acceptable salt thereof, in combination with one or more medically effective active compounds for simultaneous, subsequent, or sequential administration. The invention also provides for the use of a compound of any one of embodiments 1 to 308 in combination with one or more medically effective active compounds for simultaneous, subsequent, or sequential administration.

Examples of such medically effective active ingredients include, but are not limited to, antidiabetics, antiobesity agents, antihypertensive agents, antiatherosclerotic agent, a lipid lowering agent, and agents for the treatment and/or prevention of complications resulting from or associated with diabetes including but not limited to neuropathy, retinopathy, nephropathy, impaired wound healing, and the like. Further examples of such medically effective active ingredients also include, but are not limited to, infertility agents, agents for treating polycystic ovary syndrome, agents for treating growth disorders, agents for treating frailty, agents for treating arthritis, agents for preventing allograft rejection in transplantation, agents for treating autoimmune diseases, anti-AIDS agents, anti-osteoporosis agents, agents for treating immunomodulatory diseases, antithrombotic agents, agents for the treatment of cardiovascular disease, antibiotic agents, anti-psychotic agents, agents for treating chronic inflammatory bowel disease or syndrome and/or agents for treating anorexia nervosa.

Examples of suitable anti-diabetic agents for use in combination with the compounds of the present invention include biguanides (e.g., metformin or phenformin), glucosidase inhibitors (e.g., acarbose or miglitol), insulins (including insulin secretagogues or insulin sensitizers), meglitinides (e.g., repaglinide, and nateglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), DPP-IV inhibitors, and SGLT2 inhibitors.

Examples of other suitable glucagon-like peptide-1 compounds that may be used in combination with the compounds of the present invention include GLP-1(1-36) amide, GLP-1 (7-36) amide and GLP-1(7-37).

Examples of suitable hypolipidemic/lipid lowering agents that may be used in combination with the compounds of the present invention include one or more MTP inhibitors, HMG CoA reductase inhibitors, squalene synthetase inhibitors, fibric acid derivatives, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors, and/or nicotinic acid and derivatives thereof.

The HMG CoA reductase inhibitors which may be employed in combination with one or more compounds or salts of the present invention include mevastatin and related compounds, lovastatin (mevinolin) and related compounds, pravastatin and related compounds, simvastatin and related compounds, atorvastatin, fluvastatin, cerivastatin, and atavastatin.

Examples of fibric acid derivatives which may be employed in combination with one or more compounds of the present invention include fenofibrate, gemfibrozil, clofibrate, bezafibrate, ciprofibrate, clinofibrate, probucol and the like.

Examples of suitable anti-hypertensive agents for use in combination with the compounds of the present invention include beta adrenergic blockers (e.g., alprenolol, atenolol, timolol, pindolol propranolol and metoprolol), calcium channel blockers (L-type and T-type; e.g. nicardipine, isradipine, nimodipine, diltiazem, felodipine, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril, benazepril), AT-1 receptor antagonists (e.g., losartan, irbesartan, valsartan), ET receptor antagonists (e.g., sitaxsentan and atrsentan), Dual ET/AII antagonist, neutral endopeptidase (NEP) inhibitors, vasopepsidase inhibitors (dual NEP-ACE inhibitors) (e.g., omapatrilat and gemopatrilat), and nitrates.

Examples of anti-obesity agents that may be used in combination with the compounds of the present invention include a NPY receptor antagonist, a MCH antagonist, a GHSR antagonist, a CRH antagonist, a beta 3 adrenergic agonist, a lipase inhibitor (orlistat), a serotonin (and dopamine) reuptake inhibitor (sibutramine, topiramate or axokine), a thyroid receptor beta drug and/or an anorectic agent (dexamphetamine, amphetamine, phentermine, phenylpropanolamine or mazindol).

Examples of anti-psychotic agents which may be optionally employed in combination with compounds of the present invention include clozapine, haloperidol, olanzapine and aripiprazole.

In one embodiment, the invention provides a pharmaceutical composition comprising a compound of any one of embodiments 1 to 308 and at least one other medically effective active ingredient selected from an antidiabetic agent, a glucagon-like peptide compound, a lipid-lowering agent, an HMG CoA reductase inhibitor, a fibric acid derivative, an antihypertensive agent, an antiathersclerotic agent, an antiobesity agent, an antipsychotic agent, an agent for the treatment of diabetic neuropathy, an agent for the treatment of diabetic retinopathy, an agent for the treatment of diabetic nephropathy, and an agent for the treatment of impaired wound healing. In another embodiment, the invention provides for the use of a compound of any one of embodiments 1 to 308 in combination with at least one other medically effective active ingredient selected from an antidiabetic agent, a glucagon-like peptide compound, a lipid-lowering agent, an HMG CoA reductase inhibitor, a fibric acid derivative, an antihypertensive agent, an antiathersclerotic agent, an antiobesity agent, an antipsychotic agent, an agent for the treatment of diabetic neuropathy, an agent for the treatment of diabetic retinopathy, an agent for the treatment of diabetic nephropathy, and an agent for the treatment of impaired wound healing, for simultaneous, subsequent, or sequential administration.

Medical Uses and Methods of Treatment

A compound of Formula (I) or pharmaceutically acceptable salt thereof, or a pharmaceutical composition comprising a compound of Formula (I) or a pharmaceutically acceptable salt thereof may be used for the treatment of metabolic syndrome, glucose intolerance, hyperglycaemia, dyslipidemia, diabetes mellitus type 1, diabetes mellitus type 2, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders where activation of the GLP-1 receptor is beneficial, and complications resulting from or associated with diabetes, including, but not limited to, neuropathy, retinopathy, nephropathy, and impaired wound healing.

In one embodiment, the invention provides a method of treatment comprising administering a compound of any one of embodiments 1 to 308 to a human. In another embodiment, the invention provides a method of treatment comprising administering at least 0.1 milligrams of a compound of any one of embodiments 1 to 308 to a human.

In another embodiment, the invention provides a method of treatment comprising administering a compound of any one of embodiments 1 to 308 to a human, so as to treat at least one disorder selected from metabolic syndrome, glucose intolerance, hyperglycaemia, dyslipidemia, diabetes mellitus type 1, diabetes mellitus type 2, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders where activation of the GLP-1 receptor is beneficial, and complications resulting from or associated with diabetes, including, but not limited to, neuropathy, retinopathy, nephropathy, and impaired wound healing. In another embodiment, the invention provides a method of treatment comprising administering a compound of any one of embodiments 1 to 308 to a human, so as to treat diabetes mellitus type 2.

In another embodiment, the invention provides a compound of any one of embodiments 1 to 308 for use in medicine. In another embodiment, the invention provides a compound of any one of embodiments 1 to 308 for use in the treatment of at least one disorder selected from metabolic syndrome, glucose intolerance, hyperglycaemia, dyslipidemia, diabetes mellitus type 1, diabetes mellitus type 2, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders where activation of the GLP-1 receptor is beneficial, and complications resulting from or associated with diabetes, including, but not limited to, neuropathy, retinopathy, nephropathy, and impaired wound healing. In another embodiment, the invention provides a compound of any one of embodiments 1 to 308 for use in the treatment of diabetes mellitus type 2. In another embodiment, the invention provides a compound of any one of embodiments 1 to 308 for use in the prevention of at least one disorder selected from metabolic syndrome, glucose intolerance, hyperglycaemia, dyslipidemia, diabetes mellitus type 1, diabetes mellitus type 2, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders where activation of the GLP-1 receptor is beneficial, and complications resulting from or associated with diabetes, including, but not limited to, neuropathy, retinopathy, nephropathy, and impaired wound healing. In another embodiment, the invention provides a compound of any one of embodiments 1 to 308 for use in the prevention of diabetes mellitus type 2.

In another embodiment, the invention provides for the use of a compound of any one of embodiments 1 to 308 for the preparation of a medicament. In another embodiment, the invention provides for the use of a compound of any one of embodiments 1 to 308 for the preparation of a medicament for the treatment of at least one disorder selected from metabolic syndrome, glucose intolerance, hyperglycaemia, dyslipidemia, diabetes mellitus type 1, diabetes mellitus type 2, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders where activation of the GLP-1 receptor is beneficial, and complications resulting from or associated with diabetes, including, but not limited to, neuropathy, retinopathy, nephropathy, and impaired wound healing. In another embodiment, the invention provides for the use of a compound of any one of embodiments 1 to 308 for the preparation of a medicament for the treatment of diabetes mellitus type 2.

In another embodiment, the present invention provides a method for modulating the human GLP-1 receptor. In one embodiment, the invention provides a method for treating diabetes mellitus type 2 comprising: administering a compound of any one of embodiments 1 to 308 to a human, so as to modulate the human GLP-1 receptor. In a further embodiment, the invention provides a compound of any one of embodiments 1 to 308 for use in the modulation of the human GLP-1 receptor. In a further embodiment, the invention provides for the use of a compound of any one of embodiments 1 to 308 for the preparation of a medicament for modulating the human GLP-1 receptor.

In another embodiment, the present invention provides a method for the inhibition of intestinal motility comprising administering to a human a compound of any one of embodiments 1 to 308 or a pharmaceutical composition comprising a compound of any one of embodiments 1 to 308. In a further embodiment, the invention provides a compound of any one of embodiments 1 to 308 for use in inhibiting intestinal motility. In a further embodiment, the invention provides for the use of a compound of any one of embodiments 1 to 308 for the preparation of a medicament for inhibiting intestinal motility.

In another embodiment, the present invention provides a method for lowering blood glucose in a human comprising administering to a human a compound of any one of embodiments 1 to 308 or a pharmaceutical composition comprising a compound of any one of embodiments 1 to 308. In a further embodiment, the invention provides a compound of any one of embodiments 1 to 308 for use in lowering blood glucose in a human. In a further embodiment, the invention provides for the use of a compound of any one of embodiments 1 to 308 for the preparation of a medicament for lowering blood glucose in a human.

In another embodiment, the present invention provides a method for delaying or preventing the progression from IGT to Type 2 diabetes comprising administering to a human a compound of any one of embodiments 1 to 308 or a pharmaceutical composition comprising a compound of any one of embodiments 1 to 308. In a further embodiment, the invention provides a compound of any one of embodiments 1 to 308 for use in delaying or preventing the progression from IGT to Type 2 diabetes. In a further embodiment, the invention provides for the use of a compound of any one of embodiments 1 to 308 for the preparation of a medicament for delaying or preventing the progression from IGT to Type 2 diabetes.

In another embodiment, the present invention provides a method for delaying or preventing the progression from non-insulin requiring Type 2 diabetes to insulin requiring Type 2 diabetes comprising administering to a human a compound of any one of embodiments 1 to 308 or a pharmaceutical composition comprising a compound of any one of embodiments 1 to 308. In a further embodiment, the invention provides a compound of any one of embodiments 1 to 308 for use in delaying or preventing the progression from non-insulin requiring Type 2 diabetes to insulin requiring Type 2 diabetes. In a further embodiment, the invention provides for the use of a compound of any one of embodiments 1 to 308 for the preparation of a medicament for delaying or preventing the progression from non-insulin requiring Type 2 diabetes to insulin requiring Type 2 diabetes.

In another embodiment, the present invention provides a method for delaying or preventing Type 1 diabetes comprising administering to a human a compound of any one of embodiments 1 to 308 or a pharmaceutical composition comprising a compound of any one of embodiments 1 to 308. In a further embodiment, the invention provides a compound of any one of embodiments 1 to 308 for use in delaying or preventing Type 1 diabetes. In a further embodiment, the invention provides for the use of a compound of any one of embodiments 1 to 308 for the preparation of a medicament for delaying or preventing Type 1 diabetes.

In another embodiment, the present invention provides a method for enhancing glucose-dependent insulin secretion by a human pancreatic beta-cell comprising administering to a human a compound of any one of embodiments 1 to 308 or a pharmaceutical composition comprising a compound of any one of embodiments 1 to 308. In a further embodiment, the invention provides a compound of any one of embodiments 1 to 308 for use in enhancing glucose-dependent insulin secretion by a human pancreatic beta-cell. In a further embodiment, the invention provides for the use of a compound of any one of embodiments 1 to 308 for the preparation of a medicament for enhancing glucose-dependent insulin secretion by a human pancreatic beta-cell.

In another embodiment, the present invention provides a method for suppressing glucagon secretion in a human comprising administering to a human a compound of any one of embodiments 1 to 308 or a pharmaceutical composition comprising a compound of any one of embodiments 1 to 308. In a further embodiment, the invention provides a compound of any one of embodiments 1 to 308 for use in suppressing glucagon secretion in a human. In a further embodiment, the invention provides for the use of a compound of any one of embodiments 1 to 308 for the preparation of a medicament for suppressing glucagon secretion in a human.

In another embodiment, the present invention provides a method for slowing gastric emptying comprising administering to a human a compound of any one of embodiments 1 to 308 or a pharmaceutical composition comprising a compound of any one of embodiments 1 to 308. In a further embodiment, the invention provides a compound of any one of embodiments 1 to 308 for use in slowing gastric emptying. In a further embodiment, the invention provides for the use of a compound of any one of embodiments 1 to 308 for the preparation of a medicament for slowing gastric emptying.

In another embodiment, the present invention provides a method for reducing food intake in a human comprising administering to a human a compound of any one of embodiments 1 to 308 or a pharmaceutical composition comprising a compound of any one of embodiments 1 to 308. In a further embodiment, the invention provides a compound of any one of embodiments 1 to 308 for use in reducing food intake in a human. In a further embodiment, the invention provides for the use of a compound of any one of embodiments 1 to 308 for the preparation of a medicament for reducing food intake in a human.

In another embodiment, the present invention provides a method for appetite regulation or treatment of an energy expenditure disorder such as eating disorders, e.g., bulimia, and other conditions where a weight reduction is required comprising administering to a human a compound of any one of embodiments 1 to 308 or a pharmaceutical composition comprising a compound of any one of embodiments 1 to 308. In a further embodiment, the invention provides a compound of any one of embodiments 1 to 308 for use in regulating appetite or treating an energy expenditure disorder such as eating disorders, e.g., bulimia, and other conditions where a weight reduction is required. In a further embodiment, the invention provides for the use of a compound of any one of embodiments 1 to 308 for the preparation of a medicament for regulating appetite or treating an energy expenditure disorder such as eating disorders, e.g., bulimia, and other conditions where a weight reduction is required.

In an embodiment, a therapeutically effective amount may be administered.

In each of the methods or uses described above, a compound of any of embodiments 1 to 308 may be administered to a subject as part of a pharmaceutically composition, as described above.

Biological Assay

The efficacy of GLP-1 receptor agonists was studied in a cAMP functional assay using HEK-293 Cells expressing the cloned human GLP-1 receptor. GLP-1-expressing cells (10,000-20,000 cells per 0.1 mL) were plated in 96-well plates in Dulbecco's modified eagles media (DMEM) containing 10% fetal bovine serum, 2 mg/mL G418 and penicillin-streptomycin. Following overnight incubation of cells, media was removed, and compounds (at concentrations ranging from 0.0001 to 100 µM) were added to monolayer cells in Iscove's modified dulbecco's medium (IMDM), 100 µM RO 20-1724 PDE inhibitor, 0.1% BSA, 2% DMSO in a final volume of 100 µL, and incubated for 30 min at 37° C. 95%$O_2$, 5% $CO_2$ in a humidified incubator. Alternatively, cells were harvested and combined with compounds in suspension using the buffer and protocol described above. cAMP was quantified using a homogenous time-resolved fluorescence detection system (cAMP dynamic, CIS bio International). GLP-1 typically produced cAMP dose response curves with $EC_{50}$ values ranging from 0.2 µM-5 µM, typically ranging from about 0.5 µM to about 2 µM. Table 2 shows the mean $EC_{50}$ (in nM) for selected Examples, particularly those that exhibited a mean $EC_{50}$ below 400-500 nM. The numbers of the Examples correspond to the Examples from Table 1 and the experimental descriptions, above.

The specificity of GLP-1 agonists for GLP-1 receptor was confirmed by performing the assay with vector-control mock cells which lack the cloned human GLP-1 receptor for representative compounds. All compounds tested were devoid of cAMP accumulation in the mock-transfected cell lines.

TABLE 2

| Examples | Mean $EC_{50}$ (nM) |
|---|---|
| 27 | 843 |
| 31 | 657 |
| 40 | 310 |
| 51 | 410 |
| 53 | 380 |
| 55 | 360 |
| 60 | 109 |
| 61 | 73 |
| 62 | 328 |
| 63 | 277 |
| 65 | 434 |
| 70 | 259 |
| 71 | 477 |
| 72 | 480 |
| 73 | 76 |
| 81 | 326 |
| 85 | 263 |
| 86 | 249 |
| 87 | 67 |
| 88 | 75 |
| 92 | 156 |
| 95 | 462 |
| 96 | 185 |
| 98 | 377 |
| 105 | 321 |
| 108 | 70 |
| 109 | 298 |
| 110 | 356 |
| 111 | 44 |
| 112 | 48 |
| 114 | 232 |
| 115 | 163 |
| 119 | 131 |
| 120 | 264 |

TABLE 2-continued

| Examples | Mean $EC_{50}$ (nM) |
|---|---|
| 126 | 312 |
| 128 | 178 |
| 130 | 111 |
| 132 | 214 |
| 133 | 54 |
| 135 | 284 |
| 136 | 50 |
| 138 | 241 |
| 139 | 85 |
| 141 | 315 |
| 142 | 263 |
| 144 | 245 |
| 147 | 5 |
| 148 | 13 |
| 149 | 26 |
| 150 | 372 |
| 151 | 18 |
| 152 | 80 |
| 153 | 327 |
| 154 | 108 |
| 155 | 525 |
| 156 | 93 |
| 157 | 34 |
| 158 | 146 |
| 159 | 19 |
| 160 | 62 |
| 161 | 117 |
| 162 | 56 |
| 163 | 113 |
| 164 | 62 |
| 165 | 396 |
| 166 | 22 |
| 167 | 174 |
| 168 | 114 |
| 169 | 116 |
| 170 | 538 |
| 171 | 118 |
| 172 | 132 |
| 173 | 145 |
| 174 | 153 |
| 175 | 5 |
| 176 | 4 |
| 177 | 150 |
| 178 | 306 |
| 179 | 5 |
| 180 | 3 |
| 181 | 16 |
| 182 | 29 |
| 184 | 74 |
| 185 | 119 |
| 186 | 256 |
| 188 | 14 |
| 189 | 31 |
| 190 | 11 |
| 191 | 66 |
| 194 | 20 |
| 195 | 138 |
| 196 | 127 |
| 197 | 262 |
| 200 | 222 |
| 204 | 154 |
| 206 | 61 |
| 207 | 13 |
| 208 | 72 |
| 210 | 83 |
| 211 | 21 |
| 212 | 34 |
| 216 | 17 |
| 217 | 24 |
| 222 | 75 |
| 223 | 176 |
| 225 | 183 |
| 228 | 22 |
| 229 | 76 |
| 230 | 18 |
| 231 | 39 |
| 232 | 133 |
| 235 | 166 |

TABLE 2-continued

| Examples | Mean $EC_{50}$ (nM) |
|---|---|
| 236 | 56 |
| 237 | 22 |
| 238 | 146 |
| 239 | 82 |
| 240 | 56 |
| 243 | 92 |
| 245 | 203 |
| 246 | 126 |
| 247 | 175 |
| 248 | 187 |
| 249 | 96 |
| 250 | 171 |
| 251 | 144 |
| 252 | 99 |
| 253 | 85 |
| 254 | 186 |
| 255 | 317 |
| 257 | 348 |
| 258 | 251 |
| 263 | 187 |
| 265 | 95 |
| 266 | 132 |
| 270 | 142 |
| 271 | 102 |
| 274 | 2 |
| 275 | 172 |
| 277 | 143 |
| 278 | 45 |
| 279 | 15 |
| 280 | 165 |
| 281 | 5 |
| 282 | 198 |
| 293 | 261 |
| 294 | 64 |
| 295 | 137 |
| 296 | 87 |
| 297 | 23 |
| 299 | 263 |
| 300 | 311 |
| 302 | 182 |
| 303 | 141 |
| 305 | 200 |
| 306 | 103 |
| 311 | 74 |
| 312 | 32 |
| 313 | 73 |
| 314 | 73 |
| 319 | 183 |
| 320 | 45 |
| 323 | 178 |
| 324 | 126 |
| 325 | 42 |
| 329 | 81 |
| 332 | 66 |
| 333 | 195 |
| 335 | 115 |
| 336 | 115 |
| 337 | 145 |
| 338 | 377 |
| 342 | 204 |
| 343 | 124 |
| 344 | 271 |
| 345 | 255 |
| 347 | 315 |
| 348 | 262 |
| 350 | 212 |
| 351 | 109 |
| 352 | 338 |
| 353 | 177 |
| 355 | 45 |
| 356 | 57 |
| 357 | 19 |
| 359 | 117 |
| 360 | 297 |
| 361 | 89 |
| 362 | 12 |
| 365 | 95 |
| 369 | 112 |

TABLE 2-continued

| Examples | Mean $EC_{50}$ (nM) |
|---|---|
| 370 | 62 |
| 371 | 36 |
| 372 | 64 |
| 373 | 187 |
| 375 | 50 |
| 376 | 38 |
| 377 | 49 |
| 378 | 282 |
| 379 | 152 |
| 380 | 213 |
| 381 | 313 |
| 382 | 106 |
| 383 | 138 |
| 384 | 26 |
| 386 | 269 |
| 387 | 34 |
| 388 | 179 |
| 389 | 191 |
| 392 | 133 |
| 393 | 74 |
| 396 | 156 |
| 403 | 138 |
| 405 | 213 |
| 409 | 24 |
| 410 | 24 |
| 411 | 9 |
| 412 | 156 |
| 413 | 288 |
| 414 | 191 |
| 415 | 75 |
| 419 | 90 |
| 422 | 8 |
| 424 | 203 |
| 425 | 267 |
| 427 | 84 |
| 428 | 22 |
| 429 | 32 |
| 430 | 12 |
| 431 | 31 |
| 432 | 21 |
| 436 | 320 |
| 438 | 37 |
| 440 | 387 |
| 442 | 208 |

While the invention has been described and illustrated with reference to certain embodiments thereof, those skilled in the art will appreciate that various changes, modifications and substitutions can be made therein without departing from the spirit and scope of the invention. Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Moreover, all compounds that are recited in the written description are contemplated as possibilities for any of the recited methods, processes, compositions, and/or compounds as appear in the written description and the appended claims.

We claim:
1. A compound of the formula:

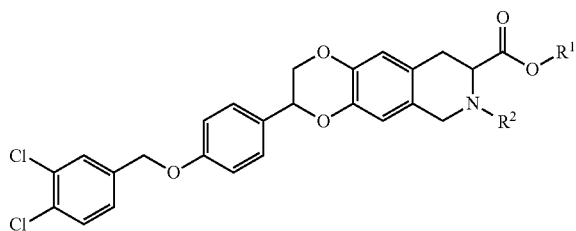

wherein
$R^1$ is hydrogen or methyl, and
$R^2$ is —$CO_2$-tert-butyl, or -1-(phenyl)-propyl.

2. The compound of claim 1, wherein $R^2$ is —(R)-1-phenyl-propyl.

3. The compound of claim 1, wherein $R^2$ is —(S)-1-phenyl-propyl.

4. A compound of the formula:

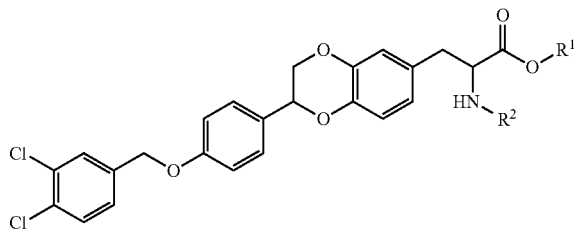

wherein
$R^1$ is methyl, and
$R^2$ is hydrogen or —$CO_2$-tert-butyl.

5. A compound of the formula:

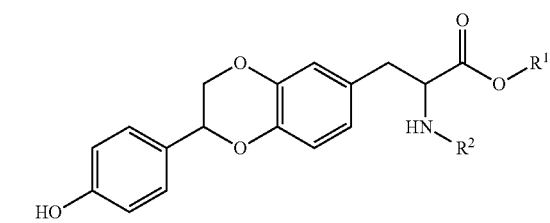

wherein
$R^1$ is methyl, and
$R^2$ is —$CO_2$-tert-butyl or -1-(phenyl)-propyl.

6. The compound of claim 5, wherein $R^2$ is —(R)-1-phenyl-propyl.

7. The compound of claim 5, wherein $R^2$ is —(S)-1-phenyl-propyl.

8. A compound of the formula:

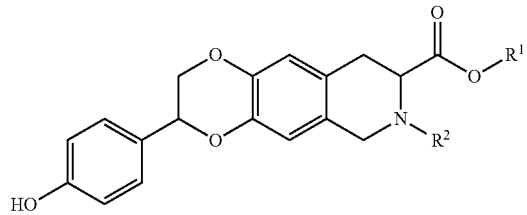

wherein
$R^1$ is methyl, and
$R^2$ is -1-(phenyl)-propyl.

9. The compound of claim 8, wherein $R^2$ is —(R)-1-phenyl-propyl.

10. The compound of claim 8, wherein $R^2$ is —(S)-1-phenyl-propyl.

11. A compound of the formula:

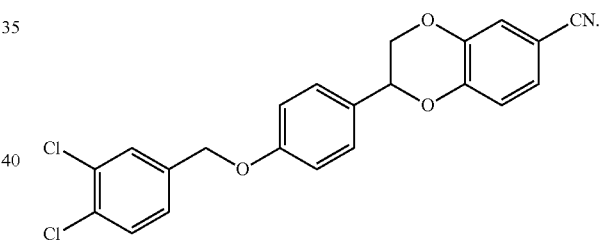

* * * * *